US012116580B2

(12) United States Patent
Zhao et al.

(10) Patent No.: US 12,116,580 B2
(45) Date of Patent: Oct. 15, 2024

(54) GENETIC TOOLBOX FOR METABOLIC ENGINEERING OF NON-CONVENTIONAL YEAST

(71) Applicant: THE BOARD OF TRUSTEES OF THE UNIVERSITY OF ILLINOIS, Urbana, IL (US)

(72) Inventors: Huimin Zhao, Champaign, IL (US); Mingfeng Cao, Urbana, IL (US); Vinh Tran, Urbana, IL (US); Zia Fatma, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 650 days.

(21) Appl. No.: 17/180,741

(22) Filed: Feb. 20, 2021

(65) Prior Publication Data

US 2021/0348175 A1    Nov. 11, 2021

Related U.S. Application Data

(60) Provisional application No. 62/979,798, filed on Feb. 21, 2020.

(51) Int. Cl.
*C12N 9/22* (2006.01)
*C12N 15/11* (2006.01)
*C12N 15/81* (2006.01)

(52) U.S. Cl.
CPC ............. *C12N 15/815* (2013.01); *C12N 9/22* (2013.01); *C12N 15/11* (2013.01); *C12N 2320/50* (2013.01)

(58) Field of Classification Search
None
See application file for complete search history.

(56) References Cited

U.S. PATENT DOCUMENTS

2013/0295631 A1* 11/2013 Zhao .................... C12N 9/1205
435/254.22

FOREIGN PATENT DOCUMENTS

| JP | 2016505256 A | 2/2016 |
| WO | 2015138855 A1 | 9/2015 |
| WO | 2017005807 A1 | 1/2017 |

OTHER PUBLICATIONS

Jensen, E.D., Ferreira, R., Jakoičiūnas, T. et al. Transcriptional reprogramming in yeast using dCas9 and combinatorial gRNA strategies. Microb Cell Fact 16, 46 (2017). (Year: 2017).*
Bao et al, "Homology-Integrated CRISPR-Cas (HI-CRISPR) System for One-Step Multigene Disruption in *Saccharomyces cerevisiae*", ACS Synthetic Biology, vol. 4, pp. 585-594, (2015).
Deaner et al, "Enabling Graded and Large-Scale Multiplex of Desired Genes Using a Dual-Moded Cas 9 Activator in *Saccharomyces verevisiae*", ACS Synth Biol, vol. 6, pp. 1931-1943, (2017).
DiCarlo et al, "Genome engineering in *Saccharomyces cerevisial* using CRISPR-Cas systems", Nucleic Acid Research, vol. 41, No. 7, pp. 4336-4343, (2013).
Douglass et al, "Population genomics shows no distinction between pathogenic Candida krusei and environmental Pichia kudriavzevii: one species, four names", PLOS Pathogens, pp. 1-27 Jul. 19, 2018.
Eller et al, "Facile Accelerated Specific Therapeutic (FAST) Platform to Counter Multidrug-Resistant Bacteria", bioRxiv, pp. 1-32, Nov. 21, 2019.
Gao et al, "Self-processing of ribozyme-flanked RNAs into Guide RNAs in vitro and in vivo for CRISPR-mediated genome editing", Journal of Integrative Plant Biology, vol. 56, No. 4, pp. 343-349, Apr. 2014.
Innings et al., "Multiplex Real-Time PCR Targeting the RNase P RNA Gene for Detection and Identification of *Candida* Species in Blood", Journal of Clinical Microbiology, vol. 45, No. 3, pp. 874-880, Mar. 2007.
Liu et al, "Characterization of glyceraldehyde-3-phosphate dehydrogenase gene R+GPD1 and development of genetic transformation method by dominant selection in oleaginous yeast Rhodosporidium torulodies", Applied Genetics and Molecular Biotechnology, vol. 97, No. 2, pp. 719-729, Jan. 2013.
Marck et al, "The RNApolymerase III-dependent family of genes in hemiascomycetes: comparative RNomics decoding strategies, transcription and evolutionary implications", Nucleic Acids Research, vol. 34, No. 6, pp. 1816-1835, (2006).
Otoupal et al, "Multiplexed CRISPR-Cas9 based genome editing of Rhodosporidium toruloides", bioRxiv, 42 pages, Feb. 10, 2019.
Poster presentation, "Development of a genetic toolbox for metabolic engineering of Issatchenkia orientalis", 2019 Genomic Sciences Program Annual Principal Investigator Meeting, Tysons, VA, Feb. 24-27, 2019; Public Presentation DOE Conference on Feb. 25, 2019.
Raab et al, "Metabolic engineering of *Saccharomyces cerevisial* for the biotechnological production of succinic acid", Metabolic Engineering, vol. 12, pp. 518-525, (2010).
Schwartz et al, "CRISPR-Cas9-Mediated Genome Editing and Transcriptional Central in Yarrowia lipolytica", Synthetic Biology: Methods and Protocols, vol. 1772, pp. 327-345, (2018).
Schwartz et al, "Synthetic RNA Polymerase III Promotes Faciliate High-Efficiency CRISPR-Cas9-Mediated Genome Editing in Yarrowia lipolytica", ACS Synthetic Biology, vol. 5, pp. 356-359, (2016).
Tran et al, "Development of a CRISPR/Cas9-Based Tool for Gene Deletion in Issatchenkia orientalis", mSphere, vol. 4, No. 3, pp. 1-11, May/Jun. 2019.

(Continued)

*Primary Examiner* — Neil P Hammell
*Assistant Examiner* — Khaleda B Hasan
(74) *Attorney, Agent, or Firm* — Lathrop GPM LLP; Lisa Hillman

(57) ABSTRACT

The present disclosure provides polynucleotides and vectors for the genomic engineering and editing of non-conventional yeasts such as *Issatchenkia orientalis*. The polynucleotides and vectors can be used as tools that are efficient to alter the expression of one or more gene products in the yeast, and specifically to induce the production of organic acids or other bioproducts of interest in the yeast.

20 Claims, 29 Drawing Sheets

Specification includes a Sequence Listing.

(56) References Cited

OTHER PUBLICATIONS

Weninger et al, "Combinatorial optimization of CRISPR/Cas 9 expression enables precision genome engineering in the methylotrophic yeast Pichia pastoris", Journal of Biotechnology, vol. 235, pp. 139-149, (2016).
Xiao et al, "Exploiting Issatchenkia orientalis SD108 for succinic acid production", Microbial Cell Factories, vol. 13, No. 121, (2014).
Zheng et al, "5S rRNA Promoter for Guide RNA Expression Enabled Highly Efficient CRISPR/Cas9 Genome Editing in Aspergillus niger", ACS Synthetic Biology, 7 pages, Apr. 24, 2018.

* cited by examiner

A
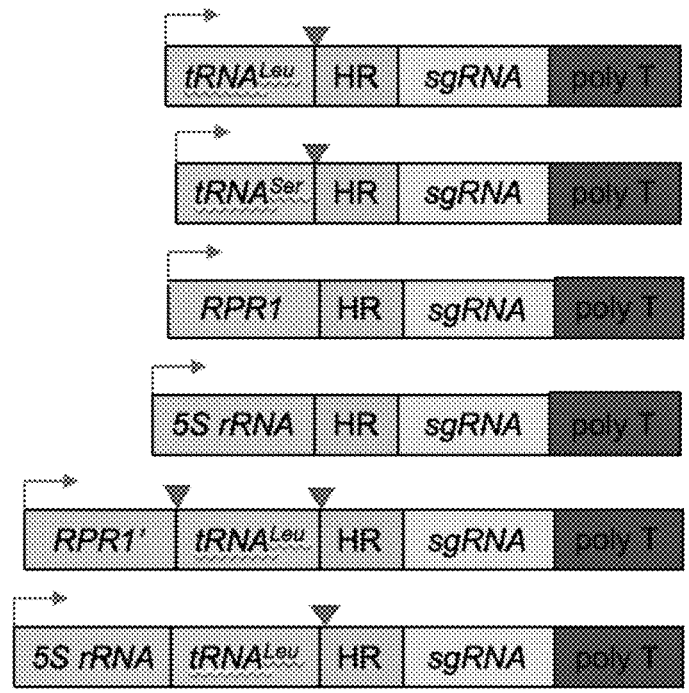
B
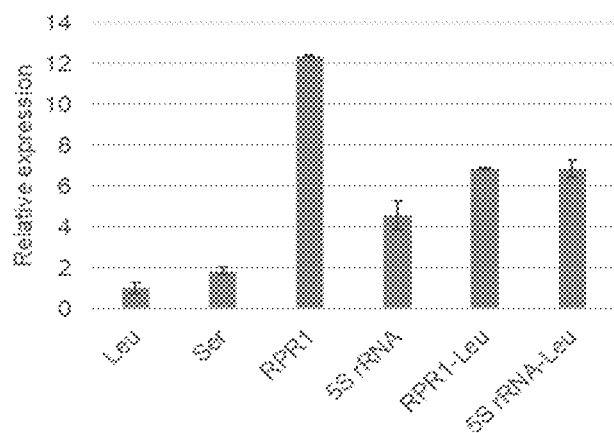
FIG. 3

```
;GTAAAGAGGCATCCTCCGCAATGGCAAAGGATTATCATGTCA
:CATTTCTCCGTAGGAGGCGTTACCGTTTCCTAATAGTACAGT
         40              45
 Gly Lys Glu Ala Ser Ser Ala Met Ala Lys Asp Tyr His Val
```

SDH1 1b → guide 1

8 bp deletion

```
;GTAAAGAGGCATCCTCCGCAATGGCAAAGGATTATCATGTCA
;GTAAAGAGGCATCCTCCGCAATGGCAAAGGATTATCATGTCA
;GTAAAGAGGC        CAATGGCAAAGGATTATCATGTCA
;GTAAAGAGGC        CAATGGCAAAGGATTATCATGTCA
;GTAAAGAGGC        CAATGGCAAAGGATTATCATGTCA
;GTAAAGAGGCATCCTCCGCAATGGCAAAGGATTATCATGTCA
;GTAAAGAGGCATCCTCCGCAATGGCAAAGGATTATCATGTCA
;GTAAAGAGGC        CAATGGCAAAGGATTATCATGTCA
;GTAAAGAGGC        CAATGGCAAAGGATTATCATGTCA
```

FIG. 6A

```
CCGGCAGCTGAAGGTGAATCCAGTGGAGGCTGTTGTACGACAGGTGAGA
GGCCGTCGACTTCCACTTAGGTCACCTCCGACAACATGCTGTCCACTCT
         20              25              30
 Arg Gln Leu Lys Val Asn Pro Val Glu Ala Val Val Arg Gln Val Arg
```

SDH2 1b → guide 2

8 bp deletion

```
CCGGCAGCTGAAGGTGAATCCAGTGGAGGCTGTTGTACGACAGGTGAGA
CCGGCAGCTGAAGGTGAATCCAG        GTTGTACGACAGGTGAGA
CCGGCAGCTGAAGGTGAATCCAG        GTTGTACGACAGGTGAGA
CCGGCAGCTGAAGGTGAATCCAG        GTTGTACGACAGGTGAGA
```

FIG. 6B

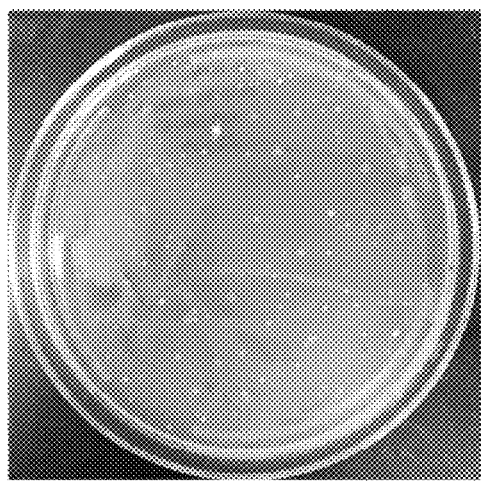
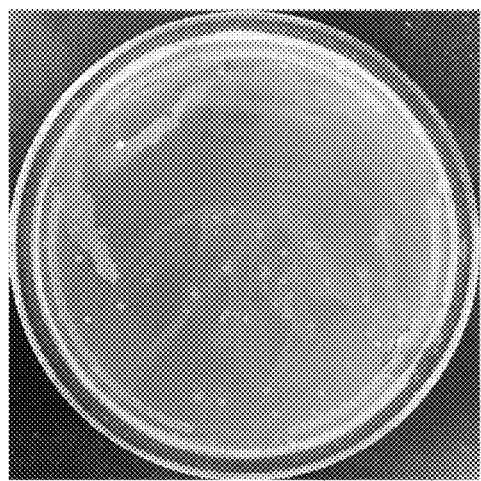
FIG. 13

G
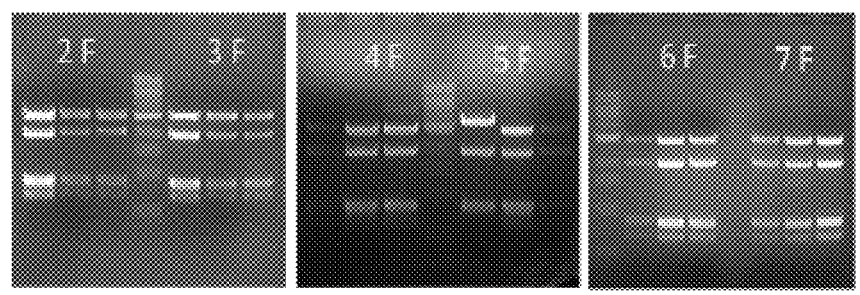
FIG. 19 Con't

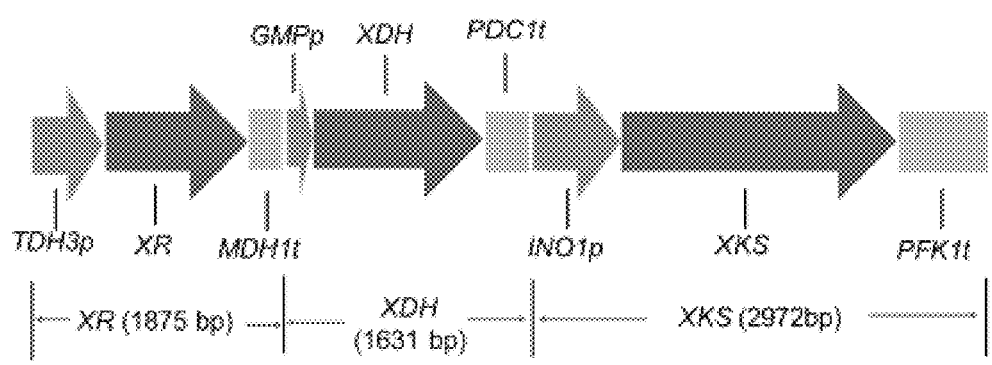
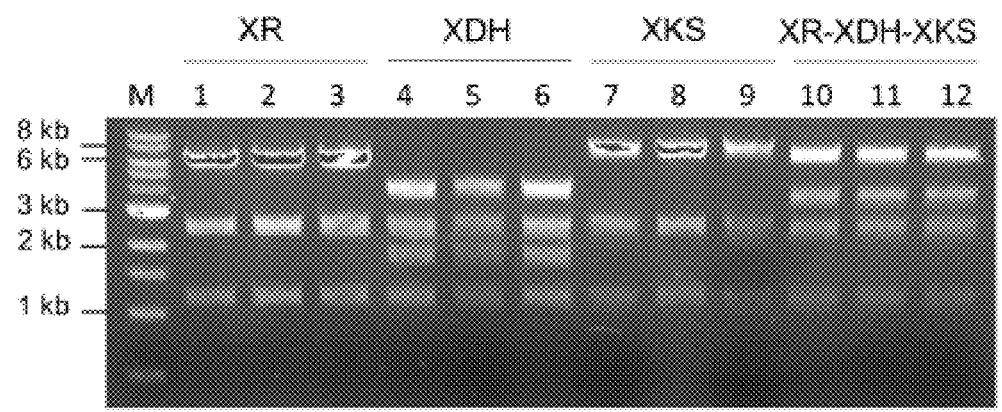
FIG. 20

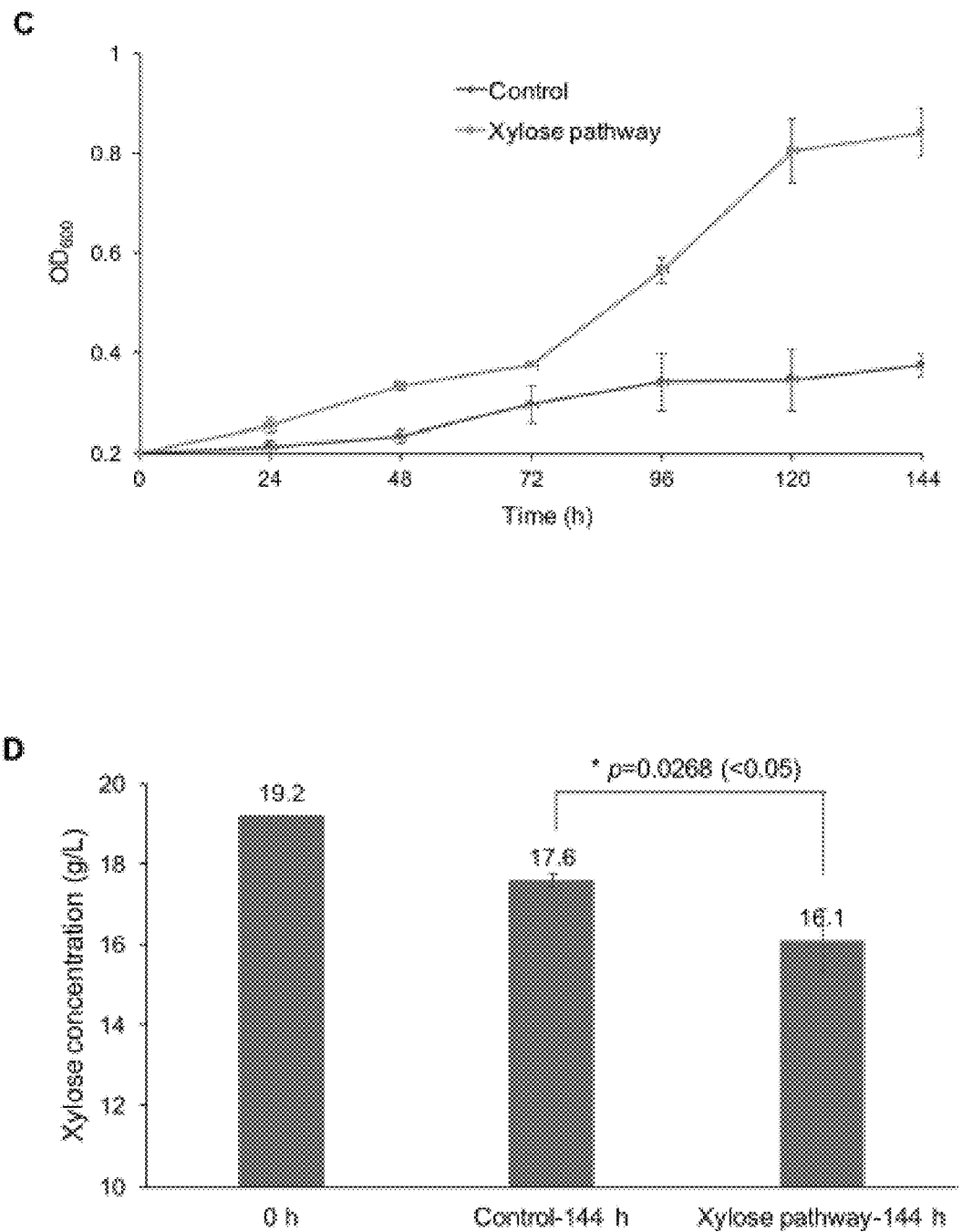
FIG. 20 Con't

SEQUENCE LISTING

```
<160> NUMBER OF SEQ ID NOS: 171

<210> SEQ ID NO 1
<211> LENGTH: 59
<212> TYPE: DNA
<213> ORGANISM: Artificial Sequence
<220> FEATURE:
<223> OTHER INFORMATION: GFP cassette-F

<400> SEQUENCE: 1
taacctaagg acttaaatat ttgtacaaac atgttccatt gatttaacct gatccaaag      59

<210> SEQ ID NO 2
<211> LENGTH: 60
<212> TYPE: DNA
<213> ORGANISM: Artificial Sequence
<220> FEATURE:
<223> OTHER INFORMATION: GFP cassette-R

<400> SEQUENCE: 2
ggaacaaaag ctggagctcc accgcggtgg cggccgcttg gctaaagaat aagatgaacg     60

<210> SEQ ID NO 3
<211> LENGTH: 59
<212> TYPE: DNA
<213> ORGANISM: Artificial Sequence
<220> FEATURE:
<223> OTHER INFORMATION: IoURA3 cassette-F
```

<400> SEQUENCE: 3
gtaatacgac tcactatagg gcgaattggt accgggcccg ttgacattgt ctagcggca        59

<210> SEQ ID NO 4
<211> LENGTH: 60
<212> TYPE: DNA
<213> ORGANISM: Artificial Sequence
<220> FEATURE:
<223> OTHER INFORMATION: IoURA3 cassette-R

<400> SEQUENCE: 4
taaaaaatag acatacccct tttggatcag gttaaatcaa tggaacatgt ttgtacaaat        60

<210> SEQ ID NO 5
<211> LENGTH: 20
<212> TYPE: DNA
<213> ORGANISM: Artificial Sequence
<220> FEATURE:
<223> OTHER INFORMATION: ADE2-spacer

<400> SEQUENCE: 5
gagacagcat tgcaaaatgt                                                   20

<210> SEQ ID NO 6
<211> LENGTH: 20
<212> TYPE: DNA
<213> ORGANISM: Artificial Sequence
<220> FEATURE:
<223> OTHER INFORMATION: LEU2-spacer

<400> SEQUENCE: 6
tatctacttt ggggagagag                                                   20

<210> SEQ ID NO 7
<211> LENGTH: 20
<212> TYPE: DNA
<213> ORGANISM: Artificial Sequence
<220> FEATURE:
<223> OTHER INFORMATION: HIS3-spacer

<400> SEQUENCE: 7
cattagccaa acattcaggg                                                   20

<210> SEQ ID NO 8
<211> LENGTH: 20
<212> TYPE: DNA
<213> ORGANISM: Artificial Sequence
<220> FEATURE:
<223> OTHER INFORMATION: TRP1-tracer

<400> SEQUENCE: 8
ccaagctatg tcgagcaaag                                                   20

<210> SEQ ID NO 9
<211> LENGTH: 20
<212> TYPE: DNA
<213> ORGANISM: Artificial Sequence
<220> FEATURE:
<223> OTHER INFORMATION: SDH1-spacer

<400> SEQUENCE: 9
ataatccttt gccattgcgg                                                   20

<210> SEQ ID NO 10
<211> LENGTH: 20

```
<212> TYPE: DNA
<213> ORGANISM: Artificial Sequence
<220> FEATURE:
<223> OTHER INFORMATION: SDH2-spacer

<400> SEQUENCE: 10
gctgaaggtg aatccagtgg                                              20

<210> SEQ ID NO 11
<211> LENGTH: 811
<212> TYPE: DNA
<213> ORGANISM: Artificial Sequence
<220> FEATURE:
<223> OTHER INFORMATION: centromere-like sequence (CEN-L) CEN-0.8kb

<400> SEQUENCE: 11
tctagctatt ttgtttaggt tgggtaaaaa cctacggaaa gacaattgga gcttaggcta   60
tctattgata gatcaattat ttgttttaag aactatagaa ttaaaaacaa ggcagtagtt  120
gtagattttt aagattattt agagtagata gtaaaggctg tactgaatat caatgaggat  180
ttgcagaacc aacaagtggc ctgcatcaag ctatttaagt gattctattg gtattttact  240
agaaaaggaa ggctaatcat ttttccaatg acggttcata taatccaagt tttaaatggt  300
ttgcatcatc ataatagggg tatctaaaag gcataaatcg acgaaagtga taaaaattac  360
ttattaaacg acgtatttac atccacgttt ttgctggaag tactgaatct gcctactgct  420
agtttgggga agacaataat acacaaaata aagacgatga tgaagattcc agttttttt   480 aaagataaaa aatagatat atatgtataa ttgtatgaat agttttaata ataacttatg   540 ttgctattt gatagcaatt catttttacta ttgaaaaggt tacccaggca aataatatgt  600
ttagcacatc agattctgta ctaataataa tatagagtta tgttataacg tcaggcaata  660
cttatgtgta tagcgaaata gtaaatggca gattgtaaac cgtatgtttt cactactcag  720
actcatacga tatgtctaga agcccaacca atgaattaga ggactgtttg atatcaacat  780
ccagtcactt tgagtgtaat aaaactattt a                                 811

<210> SEQ ID NO 12
<211> LENGTH: 46159
<212> TYPE: DNA
<213> ORGANISM: Artificial Sequence
<220> FEATURE:
<223> OTHER INFORMATION: centromere-like sequence (CEN-L) CEN1-46159bp

<400> SEQUENCE: 12
cttttgaata attttctaaa ttcaagttaa gtttaagtaa tttgggatac tatgactaag   60
gatggtaaaa gaattagaaa aaagtaaaaa aggaaaatca agaatgtgct gattcggaga  120
aaagtggaat ttagggagag agagagcaag gaatttaaat acaatctagt ttctccgtga  180
aatagaaaac tcacctccta taagtggttt ccgtttgact aaaaatcaca caatgatgaa  240
atagccgaaa tagacaggtt ccccgtattt ttttccgcaaa aaaaagaag ctattttga   300 aattgttaca acaaagcata agggtgggtg gtaaagagcg gaaataaaa ctctgtttct  360 ctctgctttt tcaatttcag cttaatagac tttcaggtag tttaggttta caaacttgcg  420
agtggcatat gctagggaac acgttacttt gcactttaga cttctccctt ttattaaagg  480
gaggagaaga cgatattggt atgtaaaagt gggtaatatt tacatagctg aagaagctgc  540
tcttgagatc ttaattgtca agttagtttg agtaaagaca ggaacaactg gaactatcaa  600
tacagagaca gccatgatat tttgactgag tttccgctcc agatatagta aaagaatgtt  660
```

```
tccggtaata tgtcttgcta atatgatagg tgtgacctgc attgaaatac taatagttcc    720
ctatatttt  tccgttgtgt tacatttcc  cctgcgtggc gctcccaatc aatttctact    780
ctgcttgtgt tattctcaga tgatgtttcg gccattttg  tgtaattct  tcttgcagta    840
ttttatttc  cggtgggatg tttaatatat ctcattcttc tgaaaagaaa aaattttaat    900
agtaaacaat ccaatgagat aaggacagcc ttttatgcct atagagttaa caacaacaaa    960
caaacaaaca tcaatttttt tacaatctct ccatcctacc ttggataatt gtcacatacc    1020
acttctctgg taatgccaaa agaggaaaa  aaatatccta aaaataggt  tgaaaaatta    1080
aattgccgcg catggcaatg cagtgtgtgc tgccttttca atctgcaact agatagagta    1140
tcacttttta atgggacgac aaaacgaaca actgaataga tagtgtacat attgaactta    1200
ttttttttg  gattacttag tggtggttgt tgggtttact gccatttaac aaaacacaac    1260
atgtttaaac tttgagaggt agagtgacat cgttgagaga tggctccatc atttccatgt    1320
atgaccctat ttttgtttt  ttgtgtttct ttgtttcttg ttattttttt tatttacaca    1380
aaagcttaat aatctacaac ctttgacgat ttttgattct atctccgaat tcatggtttt    1440
gtttgttccc gcttttcct  gttccgcagt gtttctcttt tttccatgca caaaaatcta    1500
tccccacttt gggtatatca cagtatttct ttaattagga aaacccagtg tataacatca    1560
atctctgctt ttttgttcat actctggaac atattttggt ctacttatct ttttgatgca    1620
gtggaataca ctaaaatcag aagtatgaac cttgttgtca gatgggtttg aattttaaac    1680
ccctagaata gccagctgct agtactattg ctaactcggt atacattttt ttggtgttgc    1740
gggaaaatta tatgctactg tatggacaaa attatatcct tccatcatgg attaattcaa    1800
gataaagaaa aaatacaagc tataatactt cagcaatcgc cgagatcgga tattctacaa    1860
aagattgaca tattaccgcc taaacagcat gaccaaggct gtttgaactt attccgaaac    1920
aaattttcag ggctgacata gtcgtctagc tagttttgct gacagttaga caaacctgta    1980
aatatttaac ttggtaagga gacttgttgg aaggttaact caagcagtgg aaactaatga    2040
ttagcaccaa ggtatcattt taccatctct acgacagtag atctcagacc accttggaac    2100
acctttatcg gaagtccttg aatcgtcctt tttttcagtc cctttagttg aaactcaact    2160
aacaaagtta aaccagacat tctctaataa attgtcctaa aaaaacacga atgaaacttt    2220
gctaaaataa taatatatga tatcttcgaa tcacaatcat ccgtcggtaa tgaagagatc    2280
aatgaatgct gaaatattca atgttctcta gaaattgata attgctaagg aacagtgttg    2340
cttgttacct attatggcca aattaaacaa cttattcaaa gttcaacagt aacaaaactg    2400
cggttagatc agatagacag acgaaggtgc ttgatttaag tgatataata atgtccttaa    2460
aaaaaacaca tcggctttgt cgcttctatt gggtgtatga catttgtgat ctttactgtc    2520
tgatataaac gtgcaatgct cttcttttgc atccactgaa cgtaaaaaac atgtaagaaa    2580
aaaatacctg aacttttctt ttttcaactc tagtcttgtt ctcgttatat gcatagcttg    2640
atcttttct  ttgctttcag atgtgctgat gacaagaaaa caaacaagt  agcttcaata    2700
aacgatcctt agaccaaata ttttaagtaa tatcagagtc gccaatctct gtcttctttt    2760
aaatactgca gctacttctc tttagggata ttaaatagaa ttatctattt tattgcttat    2820
aatttcacca aataaattat tttgagctga atacaaaacg tgttttttcgt caagctgtta   2880
ataaaaatcc aactattcag ggtcctagga aacaaatatt cctctgctaa cctccggagt    2940
aaaaactaag cagtgtcttg taatggttag caaaagcaat aacgcactaa aacttaggtt    3000
tatatgtgac aacctaattg agactgatat gtctacattt ctttaagttc aaccatagtc    3060
```

```
tcaaaaagtg tattataata actacgccct ggatacccct attagaaatg ttttattttc    3120
ttttctgatt aaccttttct atgttcccta ttaaaattct tttagcggca gtccagtcta    3180
tagctttaat aatattcaat gtagaatcag ttcacgttaa tataactcct tagcaattat    3240
tgctctaaaa ataaaaagat tgggttggtt ttcatttaag aaattattag gtcatactag    3300
tttacgtaat aaactatttc agcaattccc tgttagctca gtcggtagag cgttcggctt    3360
ttaagatctt ccaagaagtc gaccgaaatg tccagggttc gagccctga tagggagatt     3420 ttttcttttg aagttttttt atgttatata tctaacttac ataacctgtt atcacaaaaa    3480
cctataataa taaatcgaat acaagctaag caaatgcaaa aatagttatt ttggacgtga    3540 ttttttttaaa acaaggacta gaatagttaa cctcaaaaag atattgccac gactaagata   3600
gattaattac ttctagtaag ttcatagcga acattcatct atttgtttac catgttacct    3660
attctgaacc ttggcatagc agcattgaat ggatgtctaa caatttgata ctttaaactt    3720
ccattttgcc ttgtatgcaa tgccaagtag tctagcatga acactaagt tagtaagtgc      3780 tcctttctct gtatcttgtt atgtgcacac atccatctca caatataacc cttttgtaac    3840
cattgaacta gttaggtcaa aatgttagcc aaggatacaa ttctttataa gtttctgaat    3900
gttgtagaaa gttgaaaccc aattaatgcc attaatgttt tgctttaaaa gcacttagtt    3960
gggagtcgca actcttgttt tgattaaatg catttcggag tgacatggta tttggtattt    4020
ttctatatta ttgtgtatac catgtccatt tgaacctaat ttggtgtagt gcaggcttcc    4080
ccttgttgat aacctatgtg ataggtattt taatatattc tagtttatag tcagcgttga    4140
aggcatattc tacactgttg ctatgactaa tgcattcgct tcctgtaaga aagctcgttg    4200
agatcatcta aattttcaaa aacgacataa taacatttaa atttacaaga acagcggtat    4260 tcgacttttaa ttaagtgttc ccaatattac ctgatcaatc agaatcttta cttaaataaa   4320
cagtctatgg ttggacatca tgcagtgtac cttgacacat aatcgtttgc cccacctatg    4380
aaatcaaaca tttgaattcg gctcttcact tgtatgatta atctcaacct aaaaggcttt    4440
attgctagta cacatcgagc tgcttctcga ctattgtcca tatgccatta agatggattt    4500
tctgaaagcc acaatagaca gacactcgat aatagtacct ccaatccaac attgctaact    4560
gcaacaaaag tattacgaaa catgatccac cagatagcta gtaaactttc ctccctggca    4620
ccaataattc acttttgttt tatcctgaag ctttcgacaa attgaagtat tcaaagttct    4680
cttttatagc caaattccta gttctttcca ttgttttcag atgtgttttt tattgccaac    4740
ctatagaaaa tatttttaat tattacagtt tttgtctaaa aaaaggcatg agtttgatat    4800
atctgcttca aaaagcgga tttccagacc aatactagcc ttcaccccct ttgtacttgc     4860
ttcagcaaac aaaaattaga gtgccatcaa gctaaaaggc taaaaattat tatttcaaaa   4920
ataaattact ttcttatact agtttctcaa aataaattcc attggcatgt ttgtggcagc    4980
gaggtatcac tttccaagtt ttttcagtt catatagtta actttgagtt ttatcgcaca    5040
gtcgtctgct ttgtgggtag cgttatgctc ttctaagtat atgtacagcc cacatcatca    5100
ttagaaaggg agcattgaaa tccatctgta tgttgttgca tttatcggcc cttcaatgcc    5160
gatacccaag tgaattgttt caaatcttct atatgatagt tctttgtaaa tgtagttgaa    5220
tcacatctct cggggaaccc ttcttttgta gttcttgttt tagccattcc ttttaatct     5280 tccaagtcac acacttatcg ccagccatat atagcataca gacaggaaac atcttgcaaa    5340
catcttctat taggagggc taattttttgg atgttttagg cacttattga ttcaaactta    5400
```

```
cttagagacg cctttcacca tcatactatc caagttgctt tagtacttgt tcgtattcgc   5460
aacgttttct gccatcttgt ttcatagacc actaattta tgactaaaac cattaatggc    5520
atccaatgag ctaaaaaaac atgccaaagt acaaactata gtttcaaacg aaaattagtt   5580
tgttttacgt ttctttaaaa taacgcaccc attggaaaag tcgtttgttt tcaattaaaa   5640
aaatcgacgg tgaattcaga gaaagccttt gagagcaaat tattttttgct cctgacctt   5700 ttacatgaac tctttctcac ggatttcatt taataactac tgttacacaa agtacagga    5760 ctactcgccg atttccaatc tttctagcct accaaacact aaaattcaac catggtcaaa   5820
tgcttccaag aaatctgatt tcttggaaaa tctggaacaa gaagaacgtc atgcaagatt   5880
agtttgtcag aagcaataac gtcacctctt tccctgtaaa caccagcctt attgactgag   5940
tgaataatta ttggagcata acttttgttg gataacagct ttgcatcatt aataatatga   6000
atcaaagcac ctgtgtcaat aacaaatcgg gtcttattat ccacaagttt tacctcacca   6060
tcttcagtag gcctaacttc cgatgcgacc ttttcatctc cttctgctaa cattccacca   6120
ggtacggttc attttcgact tctgacaagt tcacaatgcc agcaaagttg gccgaatctt   6180
ctttgcagaa tgtttcttag aacagttatt cagggcgtcc ttttcttctg cacttagggc   6240
aacaggtttt ttgtgatttt ccctttacc tctactggcc aggtcaacaa cggattttc    6300 tggactttcc aaaggctcca ccctgtactg tctgtatgca taatacatgt ctttgacgtt   6360
tgcagacatc aacttcttcc ttttagaggg aagataagtt tcaattgctt gcaaaaacgg   6420
agcagcaaca agtttggta taactgaaca aaacactgtg gccgctaata gttttgactc    6480
cgggacgtga tgggatgcca agctaagata gttttccaga tcattcaact tggatggatt   6540
gttaatcttg ttgttcaact ctctaaaaat ctcaatctta aaacaattca acgatgctat   6600
ctcatggttc agcttagaat aaagggctaa gccatattca tcttcaaacc tttcatagac   6660
attggattca aaatatgctt taatggcggc tgataaaacg ttaccaaaca tgtttggtgg   6720
gacactaata taagaaacat tggcctcact gtcagtaaaa aatagatcga agtcgaaaga   6780
tgggattatt gttagaagcg ttttagcaca tcacatctta aagacaggcc aatccagttt   6840
attcttactt ttagttcctt tcgggactgc aagcttagtg atgcatttct catatgtttc   6900
aaaagtgaca tcattactga tgacagcagt atcatcaata atttcaatgg tagttgacat   6960
ttcgttaatg attggtaggt aataaatatt ggaaacttgt gagaagtcct gcaccttcag   7020
tataaagtta attattagat gaaatctatt taaaaagcta cttgtagaaa gtttgaatgg   7080
aaaaagtttt acaattacgt atattttcc ccgactccca tttcatttg cattttcggt     7140 tatacgatcc tagcaaaaga tgacctgaag gaactgcacc atagagttta ccgttgctta   7200
ggtttaaggc aatactagct tatgacctgc agtaagctgt aacctctgaa aaacatgctc   7260
ctttagatgt atggatataa gccttcattg ctatttaata ataatcaaaa aaaaaaaaac   7320
agtgaatctg cttgctgggc attgcagaaa aaataaatgg tcattttagg ttggaaagcc   7380
tgaggagtgt gtgtatttga tgattgcata cgcggcaata ccactattaa taagcactga   7440
taaccatagc tatagcggtt gtggtagtgg ggtcagtcgc ataatgtttt acgtagttaa   7500
ctagtcttaa ctggaatctt tgattgccaa gtgaaattac actaaatcac actttgttca   7560
cttggtgagc atacaacccct actgtagtcc ccttaagcag tgaagaaaaa acaaaacagt   7620
ttataatgaa gctgggtata tataatacca gctggaacgc tgaatttcac tttataagtc   7680
acgaaatttg ggacttaatc atgcaggagc agcattcgtt agtaaaacaa actacgatct   7740
agttaaaata ctatgtaaat aggccacatc tgcaaaaaac ttataacgtg tttatcgcag   7800
```

-continued

```
gtagtttata aagccagcat tacagtactt ttaccaaata ccccttttta tgaagaaatt    7860
cacctacata tactcttata tggaataaaa attatttta cattgatgtc taccatgatg    7920
aatagtggct tacaaggaag acttttgtac aaggcttggt ttatcttatc gtttcgtaat    7980
tgagaaaatt agagaatacg cacttttaca gtagcggtcg atattattga ctggctgcaa    8040
cagtcttgga ccagttgatc taatttactt aatttctcat tattgcaggt tttgttatgg    8100
ttcttgacat aattatgtat catccttgaa tacaatcagt taatttgttc cctattattt    8160
cgaaagtata tagaaaagtt acatatcagt gatctatgat tttaagtacc attactaagt    8220
cattctagta gttgtcgaaa tgagaaaagt caaatttgat aaatcgtgtc actaatagtg    8280
aatgactcta gtaataggta caagactact tgaactacta aatgctattg aacgttcaca    8340
aattaatgca atgtggttcg aagttatcag tgagtgaaga agcaagcaag aagagaatca    8400
ctatggtgag aatcatcttc caacatttgt ttaagttgtt tgtagacttt tttaaattca    8460
tcaagtaatg atttagaaac tagtattgct tctgaaattg tatcctgttt acacttaaag    8520
attctacttt tgatatccat attaaagtta taggttgaaa tatcattaaa aaaatttatg    8580
tagaatagca tatggagaac acgctaagta aaaaaatact aaccggattg gactcatcgt    8640
gattggtgag ggtatttatt gtttgattgg ctaatgcttt aattacctct ttcaaccgat    8700
ttccaaatct ttttaatttc ttcatattga gattagatca tagtatcaaa atactgttaa    8760
cttgctagtg gcctatttta atttgaaatt gataaggaac aaacaagtag atcaccaatg    8820
taagagaaaa cattaaacag atgttcttgg agaactaagg cttaaagtac ataggagaga    8880
aacgtgcaat aatcagtctc taaaatacgt accagcaaca attacaaaat gtgacggact    8940
tggggtaacg tgtcaaaatt atttccttat ttgggatctt ttaacagctg aatcttttta    9000
aaaataatca ctaaccttaa caatagcaaa aacagtgtat gtaacaatga taattatgat    9060
acacgtatta gtaagtacgc cataggtgta taatcacacg agtagacaat gggtgtggtg    9120
gaacttagtt gtagtagaag cagtaaatag atctctctct tccgcctttt gctgctttca    9180
ctcccgatta ggagctttat tgtctatcta cttgcacttc cttttcggg acacattctg    9240
aaaaatccct ttcacattat gaaaatgttg ctggtggtgc gtattttaga acctgattat    9300
tgcttatttg tatcttatat attttataca ctatttctcc gaggcagcta tagaatgttc    9360
cctctttatg tagtaattgt ttaatctaaa aatagcattt tgagggattt aattatctcc    9420
tagaacttct gtctaacctt ctacaatctt tttcaacctt ccatataatt gcccgattag    9480
gaaatagga gatggtcctt tatctgatct cttatactac cccgtcgctt tagaaacttc    9540
atcccgaagt ttattatctt tatcaattgc tcttgcatta tcccataatg ttttctgtaa    9600
gtcttctggg atctctaaaa ataatgaaaa tgggatgctt gaactatgac aagggtcaca    9660
atctttctag tagacatcca atgtatcgtt tgtttcatcg ataccagcta taccgataat    9720
ctcggtcagt ctacttcttg cttcagctat cattcttggg ggtaccttgg gaaactgttt    9780
atccgcttgt aaggatcttc taagccatct gacattgatt actctatcct ttttattcgt    9840
tttcggtaaa tcaacttcgt aggcgttgtc tgatatcttc ttgacaacct tgtagggtcc    9900
gtagtatacc ggttgtattt tgtaatacaa tctatcacta ccgtatgcat ctttgtgcaa    9960
tagtatccaa tctccaactt caaatgtctc gtacactctc gacttattat gctgtatttc   10020
```

```
ctggcttctt tgcgcttcaa tcatgttttc tttcacattt tccatgatga ctttcatttc   10080
taatgcgaat tcttcagctt tattgctgta ccttctactt gaaacacgac tgctagaaat   10140
aaacattggc gagtctggta agtaaccata gcaaacttca aatggtgatg aacttatcga   10200
gacttgatgg gaactgttgt aggcaaattc ggccattgac aaccatttgt ctcaactgta   10260
gagatcgtta ctcgcataat tccttagtaa ttggtttaag attctatttt ttcttccact   10320
ctggccatct gtttgagggt gattagtggt tgagaagagt gatgatgtac caagaattct   10380
atgtcattat ctgaaaccat tcttttttgga atcccatgta atttaaaaca attttctacc   10440
atcaatttcg cacattgctc tgcggttgca gttttcctag tggggatgaa atgtgccatc   10500
ttcgtgaatc tatccaccac taccaaaatc atatcgtgtc cattttttgca tctggggaca   10560 cctttgacga aatccaaact gatgtctgtc catcttcctt caggaattgg aagaggggaa   10620
aataatcctc tttgaccagt tgtctcgggt ttggttttct ggcaaaccgt acatctttga   10680
caatatccct tcacgctttt tagcatattt gaccagtaaa acataggtg aagtctcatg   10740 tatgttttga ataccccgaa atgaccagca gagttaccgt catgagcgtt accaataatt   10800
tcctgaacca acttagactt aggggagact actattcttc gatcattttc tccttaacc   10860 accaagaaat ataataaatt atcctcaatt gaataatgtt tagtgtagtt atggattgac   10920
ttcgggatcg acaaattttc ttttaaaatg tcgtatatct ccttaatttc gttgtcttct   10980
tcgtatgact ggataatccg ttctatcact tcatggtttg gtgttaacac ctatttttat   11040
gtgttgatac taacttcatt ttcctcgtct gggtacctag acaaagcgtc tgctactgaa   11100
ttagtaggac ctcaagtatt gaatttttgaa atcgtaatca gctaatccta ggaatgattg   11160
agcatctttg gcattttttcg gaattggcca actcttgatt ttgtctatct tagcagggtc   11220
agtctggata cctctgcttg aaatgagatg tcctaagaaa cctaaggttt tgaagtaaaa   11280
tgagcatttc ttttcttcgc aatcagctta tttctcctga gcaattccaa tattttttcta   11340 atgtgactgt agtgttcttc gacagtcttt gagtaaatta taatatcatc caggtacacc   11400
tgaacaaatt ggttcaaata aggtgctaga atcctattca tcattcttttg aaaagtacta   11460 ggggcgttgg ttaaaccgta aggcatcaca acccactcgt agtgaccgta atctgtggaa   11520 aatgctatttt tttcaatatc atcttctgcg attctgacct gaaagtaacc tgacatcaaa   11580
tccaacttgg aaaatactga agctcctcca aaaaatgtga ttaatttgtc gattcgtggt   11640
attgggaact tgtctttttac cgtattgtta ttcagtaacc catagtcaac acacattttc   11700
atactaccat ctttcttctg gaacaagtaa caaaaaacta ttgaaagaac taggggcaga   11760
cttgataaag gctagtttca acagttcatc aacctgttta ttcagttctt gtttctctga   11820
atagcttgat ttgtactggc gtctgtatgt actcttggta ggttcaatga gtataattct   11880
gtgagtcaaa tccctttggg gaggtaaact ggtgggttgg tcattggtca ccacatctct   11940
aaatttttca tgaattttat ttctaattcc aacaacacca ccgtaaggtt cttctaaaac   12000
attattattt tcttttttctt caactgactg cacaaacact aataatggat aattatcaac   12060 attcttttaaa tttcttctga ctgcacgcat agatttaata gctataagtt cattttcttt   12120
tgtttcttct aagtcatttc cgttatttaa ttttatttct ttttgatatc tgggatttca   12180
ggagtttccg tttcctttttc gatattttcc cagtcaactt tatttccatg atctttaaca   12240
aatgggaaac ctaatatcat tttatggttg atatcctcta agactaagaa cctaatattc   12300
tcattttgcc attcgtctct tagcttgaac tacagttttg ttttttctac tgaaggtaga   12360
```

```
cttgtagcaa tattgtgatc aactaccttt atggcctcta attagtttat tttctttggc    12420
ccgtttttta ccaccataac cagcactata taatctaata aaattttagc tccatttaaa    12480
accttccaag ttccgaccaa ggcataatct gtactttatg tcgagaaaga taattaaaac    12540
agtaaccaat aaaaccacag ccctctttat cagtttcaaa gatgccattc aggcctagtt    12600
agctgattta tcaaattcag gatttagcta tttctaaatt ttgatagtaa agtttatatt    12660
tgttttttgtt taaaagcgat cccgcatgtc tatttagctc agtgtacaac tgatattcct    12720
gtaactgtac caggtgattt tgatttccat tgtccttcat atgttctttt atataggctc    12780
tttcaaaaac ggttcaactg ataacatcac gatggatatc taaagtgaa ttaatagatc      12840
aaagcaagag aggatttcca aggaataggg caattctagt ataggaagac tgtggattgt    12900
cgagacaaac aaaagttgag ttgtgaacct tttgttatg agaagttcaa ttcgcactcc      12960
ttttctttac aagcttggga attcagatag agataatacc tacatctact gaatattaag    13020
tgaaccaaaa atcactgtaa cagcactcag tcaactaaag tcgactgttt aagctcctct    13080
ttagaaagcc ccactcgtct ctaaattagt ttctatgcta taagcatcag agagctcctc    13140
taagaatgta agaaaagtga aaagcttctt ttggtctgat agttttttaa ttaaacagtt    13200
cagtaacaga aaaactcgtt ttgagctttt ccttgttaat ccacgactttt tggatataca    13260
ttatatgctg taggtccttt gtaataacaa tagctatttt ggcatcgagt tgtacaagtt    13320
gacatttcgt tttatgttgc tattatttaa taatattaag tgtttcttat caaatgtata    13380
taacctttgt cggatgaata acgaaccaag ttacaaacct agcaattgga ctctttccgc    13440
tagcctttgc tggttgactt gagaaggtag ttttttcatga taagttgcac cctggccatc    13500
tctatgaaaa tcaatatttc aataatctta tatacactta taatgaacgc gcattactca    13560
gacaaagaaa caaggacttc ttggaattcc aagttgtggt tgttcaattg aatctttatg    13620
tttgacttct tctttatccg ctttatagaa aacttcctgg gacaacaagg ttcgaacaag    13680
aacatgaaca agaacatgaa cttttgctca attaaaccca tttgctctaa ttcattaatg    13740
aagtgaaaaa ataggattgg aaaggttttt cgctagagaa atcgcttttc tcagcagtct    13800
taagtatctg gcaatcactg tggttccctt tggtttcaaa gtgtacaatc gttacctcat    13860
aaaagttttc agtatgaatg aaatgatgtt tactagggaa cataaaccat tgggatcttt    13920
ctagacttaa actgccttttt aaaagctggg ccttcagaaa cgattcatca tagggagttt    13980
tggagcttcc ttggatgtgc tccttatgta aactattcct tagttctcaa aaaaaaaagc    14040
aaaaagaact gtagtgattt aacatcatct gtaggaatct ttagctacat ctcttctcag    14100
ttttgttcaa tatgactttg ttttggagat tagcctgttt ctaaaagtaa acgtagttat    14160
gtttcaaggt gctttagaca gcttagggag tggattttct ggagatatgg cttgcgcatg    14220
tcatgtgccg agtagtcacc acgggtcacc tcctggaaaa gtataaacac gatctcaaac    14280
tcgattggtt ctgaaaggtt ttcatatgat aagctaaaaa atggttttcg cgttaaagct    14340
agaattgtct gatttccttc atcgatgtga agtgatccag tctgaccacg cataaaatcc    14400
ggaatggaaa tcacaccaaa agatgaggaa atatccaatt atgcttaaat tgtcaactca    14460
aacacaagat gtcgcagcaa acatttgacg ggcttgtagg ctttaaaacc aagaattctg    14520
aaataaaaac agtactaatt agaactttat catgaagaca catgtatcat ttaatgctcg    14580
acaccaggtg atgacaaaca gcacctctct ggtgaaaggg atacaacagt tctgccttat    14640
ctatctgaaa ataaaggtgg agtttgtatt aggaaagaaa aaacatcgag tttatgttga    14700
ttcctgatat tgtgaatgga gttgtacaat ttgattaaaa gccaggtttg agtagcatcc    14760
```

```
aactaatctc tggtgtggct atcaaaccaa tgtgttttg gaattgatgc tgcattcaac   14820
gtgtcaacat gccaagattt tacggcaaaa aactatcaac cctgaaaaag atcttggttg   14880
tgtgggtgtt gacatattga caaggattgg gtgagaaaga aataatatta agtgtaaacc   14940
gcagcaaaca gttttgtctc tccatcatac actacatatt tgataatgtt ttacttgcca   15000
atgatgagga tatatttgac agtatctatt atatcttgta tgaggcgaga tggaaaagaa   15060
aagactatta atctaagctt tgacagtatg ttacctatat cgttagggggc tgatatcgaa   15120 ccagtcttta atgtaaaaac cttactttaa attacttaaa ttcaagagat ggaagagatg   15180
gaagaaacca ctggaaaggc tgagcttgat cagaccaatt aaaaaagacg atatttatc    15240 tcagcaact gacactatac tatatagaac acgggattat agatgtgctt aaaaacgaag    15300
taaaagatat tgggtacgag cagttgttga gaccaaagac ggccaccagc atccatccat   15360
tgaaaagtca aaacactcaa aagaaaagag ttactggtat tagaagcaga gatttatttg   15420
aaattatatt gttggagcca aagtctatag ttccagatca atggaaattg gacagtgtgt   15480
ttattgggta tagaaagaaa tgtcttattt acgtctataa tgttgggttg ttccctgcca    15540
taatttggtt gctatcgtta atattagtca ttgttaagca gcattgctta aatatacttt   15600
ttctataact atatggcggt ttatagtaca acattctaag gattcttgaa ctttggaaat   15660
cacctctgga gcttttaaga tgcatcagca tgtctcattc atctgcaata tatcatgtga   15720
ccatgcttta tgctcaggga gagtagggta tttaggattt gatgaaccgt atagaactat   15780
aaaattctgc aactattctc atgttatatg ctgttatata agctctacaa gtacagataa    15840
cgcgtttgct tgaattttgt tcgtgcagga gtgtttgtta tttgattaag atgagaagag   15900
aatctattat gttatccta aagttagcct aaatctcgtt gcccgaatgt ttaccgtgta   15960
aaagctactt ttttttaccac ttggagcatc attttagggt tgttctgtaa gcagcttaag   16020
gttatgtaag gtcaagtttt tcttgccatt aggggactta gaattgttga gagttaaaga   16080
agaaacgtag tgttatgttt atgttgagaa attcaacatt gacctgaaaa agaccctagt   16140
acattgactt acataaacta aactagatca taatcgacaa cgttagctgg gaagttagct   16200
agatttcaac aaaaaactta gtataaacaa taagtaaacc ttataaatta ttgtttttttt   16260 gctctcagag caaatggtaa gttgcacgcc cttatacata cgcaaaatac attaaactct   16320
tatagaaaaa aaaaacttgt gctcttaaag gtcggcctaa caatcttgca aatagctatt   16380
tgggccaata acacaacaat gctctgataa ttcagaagag ttctggttgt ttgcagagga   16440
ctagcctctt aattatcaaa agcattttgc ctgttattgt ggaacaatca ttagcaatgt   16500
aatacataaa tccttttgtt gcattctact aaattaagct gttattcact cacatgactc    16560
tacccttagc agctgcttga attccatgtg ttggattttc ttagtatacg tttctactaa    16620
cttcagcaac gtctaaccgt ttacccttat gctttgcatc aaatgacgga gtctctgcag    16680
ccttttctgg attcagcttt ggactatgtg attgctgtcc cttatgttcc agtttttttc    16740 tttttcattta tttgttcgtt acctacccgt ccttgagcat tttcatcaaa agaaatccgt    16800
gtgtgactat tcctcttata gtacatgatt taaatatatg agaccccgt taaaacagca    16860 ctgtctaaag gatgcttaaa taatagattc taatcaccaa cttgtttgta ctctcagttc     16920
aatggtccct ctatcagggc tgactcacca tgcttaataa acataacgct aatttcaaca   16980
ttatcccaca cattggagtt ttttttttcca tcaaaaaaat aatatataaa tagctttctt    17040
agattagtgt attctttttc gcctaatatt tgtgatgagc taaaagatag atcgataagg    17100
```

```
tctagcaaga aaagagtcat ttagttctca aaggtaactg ttttttttttt tcatgtcaca    17160 atgaccaata tttaaagtcg ctgatcttga aattgcaaaa aaaaaaagaa acactattca    17220
actaacacat acaacctttt tgtacataaa aacaagtagc tttttcaaac agctacttaa    17280
aattcagcta catcgtgaaa ctattggctt ttcagctagt ttggtccgac tggaaacgta    17340
cgtcctttat aatttttttgt tggactttttc tactggagaa tctgaatttc gagaccaagt    17400
atttaattat atgtccaaaa agaacgtaat aatctggaag tacgtcttta ctactcaaat    17460
tttcaaactt aattttactg tgtgtattgg atgaatcttc cataaataca gtactttgta    17520
aaactagaac tctctaagat cctgcatttt cccagtttaa aatatgtacg ggttgaaaac    17580
agaagagtaa tagccgtcta acaaactttt gatatcccta aagaaaacat ttctacgaca    17640
atattatttg taatattgga tagcttccat ttccgatctt ttgccgcacg aaactcaaat    17700
caaaaacata caattttttgt aatgcaataa tgtaatcttg ataatttcta aaaaaaacac    17760
ccaaaaggtt tcattgatcc attctgtagg aataaatcag aaaaaaacat gtgcttcttt    17820
ctaaacttta tcaaaatatt tgtcaagcta tagttttttat agacactctt ctttttttctt    17880 tctctccaca gtctaatcta ccaaacattt tcttagagag ttataataaa tgtcaaaact    17940
ctatacagac aattatgtat gactgttatg ccttttcctg aacttattta aacagtatgt    18000
ttcagaaaac gttttgcggc aaagtcgaat tcgtggttcg cttagtttat atttcatgtg    18060
gaagtcatgt aagcctcttg ttataggata gtaaacgccg gctgttttaa acaggaaggc    18120
tatagcttaa ggaatatcgt gcatccataa aatcatttct gtaagggctc atatataaga    18180
agttgacgtc aacgaaaaat caatcaatag gtgcaaatgg aacattacga agtgatctat    18240
cgaccagcaa gaaagtttg caccttatga gtatccggca atttctcgga ttttcatgtt    18300
tagatctcgt tgcaaatttt cactaaagag tgctatgtcg aaacagtgct gagggtaatt    18360
tttacaatta cctagagggt aagattaggt actaagatgt gatgtcactt tcagaaatag    18420
tgctcactta aagttgtgta actggcgatg gtttcattcg aagcaaacta tagtacatgt    18480
gcatttaaac cagaaagagt acgattcttt ttaactttttg agcatctttc atgattgatc    18540
cggcatagtt tcgttatcag attcaacact gtagatagtt aacaataggc caatttcagg    18600
atcagtattc atttctgatt gtttgacagc tatattaaga cctatgttct gagttaagca    18660
cagaaataac aattaaaatt tatatcagca ttagttatgg aagacaccct cagtcatcat    18720
ggcaccaaaa caaagattaa taagaaacca gttcaactcc aactgaatct attgatatcg    18780
atctatataa tttgtggatt cttttttaagt tatccaactg ctggactaaa tatgggcatc    18840
acgtcaggaa ttgtgcctct tgaacaccag tttttataga atttacagct actataaata    18900
tctacattgt ggcataacgc tattccttaa ccactgttct ccaatgtcaa ctcatctagt    18960
attttttata taaaatatca tttcttattt tgttcgcgct gtttgcaaag aaatttgttt    19020
tactatcata aaattgatta atttgtctcc caagacctttt tacatgtata tcattactat    19080
taatgtgctt attcgatagt tatccgcata tattctgagt atcatcatac ttcgctggaa    19140
gttttccaat atataattta tttttttaggt tctatcgttt tatttacata tatatcaatg    19200
ttgtttattt attgttgata ttgaataact tataaatcca ttaaaaagga tattgcataa    19260
ttctcactat ttggttctca atgaacagaa cttataaata tacttgaagt tattgtttta    19320
gttttctgta tacagtaaca ttcctaaatt catttagtaa attgaaatta tgccataaat    19380
aagtttatcg actcagagac agcttttataa agatattcct aatcctctta ctaataaaac    19440
aaaagttgca ttcactatttt ttctgggaga gtctgattca ttttttgtttt tgctcaggaa    19500
```

-continued

```
atttaatcgt gttataatat aaaagaagaa ttttcctcaa gagtactctt agacatattt    19560
atggagaatg agtttgtttg cctgaatggt aaagtagcta agaatctata cttttttcag    19620
ggttttttt atattgactt aatgattgga ataataaatc agatttgtaa aaaaattgac     19680
ggaattagtt tgagtggctt cccatgtaaa tatgctctct atcagatata ttaaacatga    19740
aaatttatta tacctcattg tactctcgac attagttaaa tctccaagtt cttcctggcg    19800
caatatattt atataatcat aatggagcta atgaaaagaa tcttgctcaa gcttgctatc    19860
tatttttga ctactggatt tagcgaaata taaggttatt gctttacaga ggcctttaca     19920
agatggatac tcatgaatat taagagaagc tagtttgcg tactttatta atggtagaat     19980
ctcttaataa caagtattct ttagtgatga gctaaataaa aattatacgt caaataaatg    20040
ctacacaaat ttagttcttg agagaatagg aaatgtagag ctcgagaaaa tcgcatgaaa    20100
agatgaaaaa tgttacggtt gtttattaat cccatttatt tttgggtaac tgtttcttat    20160
tttcctaata ttactagaaa aatataatcc agaaagatgc ttttgagttg gttccagcca    20220
tggcatcaaa tatcgaagga ttttctaatt agctctattt gactaaagca aaacgagaaa    20280
atactcatcg tgtttgtgat agatgaaaca cctattttgc ttctattgta tttaaggaaa    20340
ttagaaggtc cacttcaaca tctagttggg ccacaacctt tctgaataat gcttctttac    20400
ctggtactat aattagcaac cttatacgga atctgttaat gcgcacgtgc ccgaaacaaa    20460
atgtgtcaat acattacctt cacttataca tttatatttt gtgcatgata tttggttata    20520
tcttctagta tctctttaaa tagttttgtt acacccaagg tgactgaata ttcgtaccaa    20580
acagtcctct aattcattgc ttgggcttct agacatgtcg tatgagtctg agtagtgaaa    20640
acatacgatt tacaacccgc cctttactat ttcgctatac acataggtat tgcctgacat    20700
tatagcatat gtcgaagtaa atattatgga attttgtat taataatttt tatttcaaag     20760
taatgtgatt ttctaagagt ttggtcaaca acgggatcaa acaagtagta aatatccaaa    20820
gtgctacttt tcattaaatt tttttttcc attattgaca aatcttttc tttgcacaaa      20880
cagttccatt tttaaagcat caggagcaag aactctttag ccgctgcttt tcaagaggct    20940
gcaggaattt gttagtgtcc ttgttcaaat gaagaatact aacttcaaac gaggagacct    21000
agttcaaaga attactatta ttgaaattgt tcaatataca tagcttttgc cctttatatc    21060
gtactgtaca tttgcaaagt tttcaaacta ggaagcagac cgtctcttga ctctgtttac    21120
aaaacccgaa gctatctttt ttaattttcc ctttatgcgt aatacaaaac ctggaaaaat    21180
aacgagaagt ttttgcaata ttcgaaactt tgcaaattaa cccggtctgc aatatttttt    21240
gagcagcttt tcactgttag ctttactctc ttcattttg taaacataat gatgtcttta     21300
atgactagaa ggggaacttg ttattatcgt agcgccactt atctctacta tatttcagta    21360
gtgaaacttt agccagacaa aattgtccta aacctttggg atttgttaaa atccccttttg   21420
aatttcgttt aactataagt aattatccga agtctacatt tactatcatc catttttata   21480
ttgccaaata cttgatagaa actatagata gctatgaagt cttcaacaaa tcgatttttt    21540
cctcatagct ttcttaataa cttgctgtta tatattgtaa tcccaaaata tgaaattgtt    21600
gattatagcg cccagcttca aagccttgac aaaaatactg gaaatgatgc gtaaaccatt    21660
gagctttgtt ttgagaatct tcttttttgtt ctttagaata aaggaaata actgtttata    21720
ttattcttaa cagaaggaaa aagaaagagt tgtcaacgcg tacatatttg tataataaaa    21780
gctccttttc aataaacgtc taaggcggaa ctgatagtat attcatgctt gaataatta    21840
```

```
ctttcgggct atttccgtcc ataaagcgtc tctagaggcc agcatttaac ttcttataaa   21900
atcaaaaatg gattactctt acgtgattta atcaccagct catggaggtc tttttttttca  21960
attgggtgct gtttagtaaa aaagttaagt tatatttcca ggcgacttta agaaggcttc   22020
gcctaccaaa cactaaccaa aacaaataac agagacatag accagcggta ttctctcttt   22080
tgccttatgc gtgaattact taaccttgcc tcgatgtaag ctctatcatt ttgaacatgt   22140
ttttttatgt tttacacag  acccaatttg ataaactata actatatgta cactttataa   22200
gccattgatt ttagtgtaaa cgagatcgaa aaagaaacag atgctcctcg gtaatttcac   22260
agaagtcaat atctgttttt ttttttgtaca acaatcaagg aaaaagtggt tcaccggttt   22320
caaatgccaa atgctagaat ttgagcgccg agtttcatat tatatgaagt taggtaattc   22380
taaaaagtct ttttgcaaaa ttaagtataa gtttccaaag tacttcgaaa ataacattca   22440
gcggcgtgca gagacattag gtaaaagtag tcgtttctgg ccaatggtat atatatttg    22500
atggtttgaa atattttcct cggttgttca attagaagag ttgaattggg gtgtaaaaca   22560
gtataacata cctactgatg ttatcataaa cataatttcc aactcagtaa tatttgtttt   22620
tctaagaaat agtgtatgtt ccacttacaa actcgactta acaattata ctgtcgctta    22680
acaaaaccag tagtctttga acttttttgca aggataaagt gttttttttgg gaatatattt  22740
agacttgagt ttcaatgctc tgaaaaaggc tatcactttc ctatcaaggc agagaacaac   22800
tacatataga gaaacaacat aagttaatga gcatatatca gcatctttga tttaaacagc   22860
tctagtattg gaagcaaaaa taaaaaatat tactgttttg tagcctatat aatgcttgcc   22920
tacaaaatgt tttctgtcat aattgtaaaa agttgtttcg aatgggcaag ctaagtccca   22980
tgcctttttta tttacatcag gaatatcttt tccgcttctc tagagaacga aaagtcgtga  23040
gcgtcatagg tgcagcagaa aaataaaaag tcagtagatt gagtagattt ttgtttactt   23100
tcccttgagt acttgcgccc actcaatgag agttaaagca actgatcatg ctgattctga   23160
ttgttaagag agataaattta aacattggtg aatcgaaatg cgaacatcat tatgagccaa   23220
atgaagccaa acagacttga tcaggcaacc tgtcaaaatt aaggagttag tatttactaa   23280
tgcatatggt tgtgtttata tttcttagca ttcaaaaagt gcacccgtcc ttggatatct   23340
agcttagtag acacatgatg ttccctacaa gtatcagatt attgccttgc ttaatttagt   23400
ttttatgttg tattatataa gttctttaca aaactccatt ttaaatactt ccacatagat   23460
ttccaaagta gagttaatac ttgtcaatat ttcctagtaa taacaatatc tatacctctc   23520
tcatcagatt cgagaaaata ggaacgttct atgtattata atcatgatta ctttgttgat   23580
atcaagcttg ttcgtgttct tggatcgatt tggcattgtg cattaggctt tgacgtagtg   23640
acaaagctgc ttggttgaat attctttcag gcacctttct tgctagagtt tgatcacagt   23700
ctttccacaa gacatcataa gtcttttcct tgcctgattc ttctgaccat ccaccgatac   23760
cagtcatttc gttgattctt gccaacatct cacgctctgt tctaggcggt tcctggtaaa   23820
tattggggtt ttctttatag tatttaatcc actgtacatt tgattcacga tccttcaaat   23880
taataaccag taaatcgact tcataagcat tgtcgtttat tttcttgact agtctgtatg   23940
gcccatacta tactggttga attttttatgt acctttatatt cacaccaaag gcatcttgat 24000
gcactaacac taaatcacca actttatatt caaaatatct tcttttttcta ttatggtgtt  24060
ttccttgttg cccttgcgct ttacaatatt atccagtgtt tgctgtaaaa tcaatttcac   24120
acgtctcaca aattcttctg cgttaggtga atatttgtta tcctccaaat cccagctatt   24180
tacttttttt aatcatgttc gattcatacc cgtaggcgat ttcaaaagga cttgctttaa   24240
```

```
tggaatcttg gtacgttgaa ttgtaactaa gttcacacat agatagatgt tcatcccaga    24300
ataattgatc gtttgaagaa tatttccgaa gtaactgatt aacaatcttg ttgactcttt    24360
cggtttgacc atcagtttct ggatgatcag tagtcaagaa tagtagagaa ctaccattga    24420
gataatgtaa tgtctgccaa aacttattca taaaccgaat atctttgtca ctaaacaaac    24480
gagcacatgc agcagcatta agtcttttgt gcgctggtat aaaatgtgcc atttttgaaa    24540
agcgatcgac aacaaccatg atcatatcgt aacctgttct cgatctaggt aagcctgtaa    24600
tgaaatccat cgtaatgtcg gtccagcgac ctgttgtgat tggtaaaggg gaaaacaacc    24660
cttgtcttct tctggtgtta gtgttgtgct gttgacagat atggcaggtt tctacccatt    24720
tttgatttgt ctcaacatag atgaccaata aaaactatct ttaagattca ataagttttt    24780
ccatgcacca aagtgacaag catctttgga atcgtgtgca tttttgaata ttctatacgg    24840
tagtttcttg tagtttggaa taactactct aaagaaatct tgagactcta atgtcttata    24900
ataacgtacc tcatcttgat aacagaaatg tttgatatga tttttatct caactggaac     24960 ttttgttttc tctctcaaag ttctgaatat caaggcataa ttagtatttt ttttataacc    25020
cgtaataatt tctttttta actcttgatt ggcttcgata gtacctagtg tcaaggaatg     25080
tctctgtgtt tcatcctcct cttttacgt caattccagc aacgccaatt cgattttggc     25140
tagcgttaac ctgttttagt ggttgtatgg gtatctagat aacgcatcag cagcggaatt    25200
gttttttccc tgtaagtaac gaatatcaaa atcaaactgt ggtaaaaagt ccatccatct    25260
agccactcta gtggagtcta tgagattttg gtttttaag taaattaaac tcttgtgatc      25320
cgtcataaca atgaaatgtc ttcccatgag ataatatctc catgttctta atgcttcaac    25380
aacagccata aattcacggt catatattcc ataattcagt tgacttccaa ctagcttctt    25440
tgaaccgtaa gcaatcacac ctcgtcattt acctgtttcg tccaactgtt ctagagtata    25500
acctaacgat actccacacg catcggtatg tagaacaaat ttacaattgc ctgaccaact    25560
tgggtgcacc aaggtgggac ttgatatcaa agcgttcttt agttgattga aggcttcgtc    25620
ttgttcactt gtccatttac tttgttttgt catgaactta tgaattggat tggcaatttt    25680
ggaatgccct ttaataaacc ttctatagta cgaagttaaa ccaataaaac tttgtgcttc    25740
tttgatcgtg tttggcgttg gccaactctt tacctttta attttctcga gagcggtttg     25800
aatacaaatt ggtgtaataa catgtcctaa aaacctaaat tcttgataaa agaatcggta    25860
tttcgacttc ttcgtgatta gtttatgttt tcttagtgtc gacaaaactt ctttcacgtg    25920
cttaccgtga gtttcaacat cttcggagta tataaaaatg tcgtctaaat acacttggac    25980
aaatccattt atttttttag acaagacatt attcatcatc tgtggaaaag tcgcagatgc    26040
acttgttagt ccagccggca ttaccatcca ttcataatgg ccaaagtaga aaagccgtc     26100 ttctcgacat cttcatccgc aattctcact tggtagtaac caggcatcaa ctctaactta    26160
gaatagactt ttgccttacc aaatcttgaa atcaattgat caatatctgg aagtggaaac    26220
ttgttcttaa cagtattatt gtttagaatc ctataatcaa cacacatacg catagtacca    26280
tctttctttc taacaaatag cactggactg ttaaaggatt tggaactagt tttgatgaaa    26340
ccttgtttga ttaaaacttc aacttgtttt gttagttcct gtttctcaga gaagcttatt    26400
gggatttgta ttcatgggtt agttaatatt atcagggttt tcgacttcgt caacatcaat    26460
cgagtagata aaagtgagat aggattcatt tctcctaact aacttattaa cgtacttttc    26520
ttgatattga gtgaaacgct cgatagaggt ggattgatat ttaaaccagt tgatttaatg    26580
```

-continued

```
gcatcaacac tcattaaaaa aaaaaatttg aaattaattt attgacactt agtcaataga    26640
gttcccaata tgaatatctg gtggtcactg accaacatgt aaagcgactt aatatcactt    26700
atattaatag tttcattgac gtcttttcca aatggaatag ctataaaacc aataacaata    26760
ggatttttga taattgacgc tattcgagga ttaccaaatt aacactttt ttgccctgca    26820
tgattcacaa gcattttaac atcatttcct ttgttatgac tattatgtga agaatagtag    26880
aaaactgaat tatttatgct attaggattt gctggtggct tagtaaaact aaaaaaaact    26940
tgaatttctt gccaacttaa aattattata agcagctttt taggtccatc aggagccatg    27000
aatttactat ttttgtctcg ttcctatttt tttaaagttg ttggaccttg gtctgcgagg    27060
gatgccattc aaaatacaga tataatcagg cttgtagact atcttatctc tgtatctctc    27120
atggaagcgc actaaaattt cggaaacgga aatagcacct agggtctgtt gtaacaattc    27180
cgtattcctc attccttgtt caattgtact aaaatattga gcaatagtag gtttctcttc    27240
agcaacatcg aaaatagtag atataggtac cctaagttct tcctgcgagc tcttcgttgg    27300
ttgatctgac tttcttctac acataaattt gatgatttcc gtttcgtggc ttgttttttcg    27360
caatagaaac aaatgttttt ttaatttagc tttagaattg tgtcagcatt ctttcagtaa    27420
atctttatca gttaatttag tgggggacct ctcagaacct tttttttttt tcagggtgat    27480
aacagcgcat ataaccttct tatcatatga taacctacaa tattcataat atattctaat    27540
ttgtgataac cattccattg ccgcggctct tccttttaac gaaagcagtt tgctaacatt    27600
cagcaaaagt tatttttta cttataaaca tgtcgagcat gcctttttct cttggctgtt     27660
tgtgcacact gcagccttag ttcattttat catatattta tgtcttcctg gtcgttgtgt    27720
tctcaatata tccctctaca atcaccatat tagtttggat gttaggaagt tgaattgtac    27780
taacttgtta tctttatcta ataagaagtc gaacattgca ggtactacgt acttgttggt    27840
taatctttaa attttttttc tttcttttag ttcattgttt ctagatctaa atagaaatca    27900
ttccattgct gtttgcatgt tcttttcagt ttacttactt ccatctatta ttcttattgg    27960
cccattccat cttctcctat tagaatgatt ctgccaacta gactatgcaa aaagtacatg    28020
tagcctagta gtggtaaaca cgtatgactt tcactagga ccagttcatt cttttgctct     28080
tcttcgtttc ttagttatag cctccatggt tgaccgcaga atcatataac ttcaagctat    28140
gaaggtaacg cggcgttcta tacaatacat ttttatataa cccactgata gttaaatacc    28200
tgcctacagc agaaccattt atgatataaa ttttggatca gtgtttaaag atgctttgaa    28260
tgatctaaaa cttatttctg ccaatctaaa tgaaaaatcc gccatattat agttgagtga    28320
cagcctagtc cttaaatcgc gtctttaagt ttcttcacat tttttgcctt cacaaatata    28380
agcacatcat ttcaccgtat gttttttgtt caaaatactg agtcgtgctg cagggaattc    28440
atctacaatc ctaacaatct aagtttgtta actcctatat actattccat tcgttaattt    28500
tatttattt tttctaaaac atattagatg gtgcgtaaac gatgtttatc ttagtaaatg     28560
gctaatcaaa agtatcttat ttgcattgaa tagaaaaaag tttaggaaat tatttaaact    28620
tcgttcatag acaagctata tgttcttatt tatgtagaga agttataagc taattatttt    28680
tttcagccat tataagttta agcatataac tgtgttgaaa gccactaaat aagtgataaa    28740
aaaaatcaaa agacctacta gtatacagag ttaattctac atttgctacc ctaattataa    28800
aaagaaacta tcgaggtatt tctgtatttc ttctgaacaa ttgggggtttt aagtctacct    28860
acttctaaac cttgatcata gatacaatag gtgcacaaca catacacggt gtgtggtata    28920
ttatgagcag ccaattcacc attttgaaaa gctaaaactc tgtaccataa ctttcagtgg    28980
```

```
gatccgtatt atcaaaacta tatttaataa tcctatgtgc taactaaagc ctggaagctg   29040
tatatatata gtttagtttt aattcataaa gttttttcat tggactgccg gaatgtcatg   29100
ggcctttaaa acattcactg cttaactggt gtagattctt tgttacactg tgcattgtta   29160
ctcgtctttc gtgtgaattt cccatctcta ttctaatacc tgtattttc tgtttagatt    29220 ttggacattg agttacacta ctcgcttata tttgttgtag ctagtttgaa ctgaatcctg   29280
gaagtttatt atcttttgt gttctcacac cacttgccaa gagacttgag cctgaaaaaa   29340
aagaatgagt tgaaaaaat gtaggtttta cacaatttta atcattttc ttaagtatga     29400 atatcagctg tcttgtaaga tgttttccat caataagctg aactcacttt atagagcact   29460
gaatttcatt tttgtataac aattggttat ttcctttcag tctggcactc gcttttattc   29520 atttttcctaa taaatagcta attctgtttc gatcaggact tctaactgta gtgtgtacga  29580
catctaattc tagaaagggt attctcactt cctagttaag atgtgtatca tattctttta   29640
taaaactaaa agcacctagc ctattgagtt tataatactg aaagtctact gaactagtca   29700
tctttgtaca tttctttaga cttagatcca atcttgttgc tttagtttat tttctatata   29760
gttatttgaa ttaatcacaa gtatctaaca aaaggtccat acttaccgat ttgtgtagta   29820 ggattttttct tctatttctt tgtaggtagt agtgtttcta ggggaaaccct ttcaaattgg  29880 cccttctgag tctattctag tttgaaaaaa gcaaagttct cactaaataa cacatattaa   29940
taatagtctt tgctacggaa ctaattattt cttgatctaa actattttg ctcctgaata    30000 gaaggaccta gttaattttt atattagggc agaagaaatc aaagaaagaa gttgaataaa   30060
gaataggtat atttgtacta aagtttgcta aaagcgattt aggtggagct tctttttatt   30120
taaaaacccc aataatctta ataacaataa aggtcttcct gtaaactttt gaaaatgta    30180 ccggagtatt taagttaagt ccaaaccacg agaataggtc aaaagctgct acttagttta   30240
tatttcattg ccttttcagt atctcgagac ttctccgctg tcaataataa acagttgtct   30300
agctattttg tttaggttgg gtaaaaacct acggaaagac aataggagct tagactatct   30360
attgatagat caattatttg tttaagaac tatagaatta aaaacaaggc agtagttgta    30420
gattttaaag attatttaga gtagatagta aaggctgtac tgaatatcaa tgaggatttg   30480
cagaaccaac aagtggcctg catcaagcta tttaagtgat tctattggta ttttactaga   30540
aaaggaaagc taatcatttt tccaatgacg gttcatataa tccaagttt aaatggtttg    30600 catcatcata atagggggtat ctaaaaggca taaatcgacg aaagtgataa aaattactta   30660
ttaaacgacg tatttacatc cacgtttttg ctggaagtac tgaatctgcc tactgctagt   30720
ttggggaaga caataataca caaaataaag acgatgatga agattccagt ttttttcaaa   30780
gataaaaaaa tagatatata tgtataattg tatgaatagt tttaataata acttatgttg   30840
ctattttgat agcaattcat tttactattg aaaaggttac ccaggcaaat aatatgttta   30900
gcacatcaga ttctgtacta ataataatat agagttatgt tataacgtca ggcaatactt   30960
atgtgtatag cgaaatagta aatggcagat tgtaaaccgt atgttttac tactcagact    31020 catacgatat gtctagaagc ccaaccaatg aattagagga ctgtttgata tcaacatcca   31080
gtcactttga gtgtaataaa actatttata tagtttgctt cgaatgaaac catcgccagt   31140
tacacaactt taagtgagca ctatttctga aagtgacatc acatcttagt acctaatctt   31200
accctctagg taattgtaaa aattaccctc agcactgttt cgacatagca ctctttagtg   31260
aaaatttgca acgagatcta aacatgaaaa tccgagaaat tgccggatat tcataaggtg   31320
```

-continued

```
caaactttc  ttgctggtcg  atagatcact  tcgtaatgtt  ccatttgcac  ctattgattg   31380 attttcgtt  gacgtcaact  tcttatatat  gagcccttat  agaaatgatt  ttatggatgc   31440
acgattttcc  ttaagctata  gccttcctgt  ttaaaacagc  cggcgtttac  tatcctataa   31500
caagaggctt  acatgactcc  acatgaaata  taaactaagc  gaaccacgaa  ttcgactttg   31560
ccgcaaaacg  ttttctgaaa  catactgttt  aaataagttc  aggaaaaggc  ataacagtca   31620
tacataattg  tctgtataga  gttttgacat  ttattataac  tctctaagaa  aatgtttggt   31680
agattagact  gtggagagaa  agaaaaaaga  agagtgtcta  tgaaaactat  agcttgacaa   31740
atattttgat  aaagtttaga  agaagcaca  tgttttttc  tgatttattc  ctacagaatg   31800
gatcaatgaa  acctttggg  tgtttttt  agaaattatc  aagattaaat  tattgcatta   31860
caaaaattgt  atgtttttga  tttgagtttc  gtgcggcaaa  agatcggaaa  tggaagctat   31920
ccaatattac  aaataatatt  gtcgtagaaa  tgttttcttt  agggatatca  aaagtttgtt   31980
agacggctat  tactcttctg  ttttcaaccc  gtacatattt  tcaactggga  aaatgcagga   32040
tcttagagag  ttctagtttt  acaaagtact  gtatttatgg  aagattcatc  caatacacac   32100
agtaaaatta  agtttgaaaa  tttgagtagt  aaagacgtac  ttccagatta  ttacgttctt   32160
tttggacata  taattaaata  cttggtctcg  aaattcagat  tctccagtag  aaaagtccaa   32220
caaaaaatta  taaaggacgt  acgtttccag  tcggaccaaa  ctagctgaaa  agccaatagt   32280
ttcacgatgt  agctgaattt  taagtagctg  tttgaaaaag  ctacttgttt  ttatgtacaa   32340
aaaggttgta  tgtgttagtt  gaatagtgtt  tctttttt  tttgcaattt  caagatcagc   32400
gactttaaat  attggtcatt  gtgacatgaa  aaaaaaaac  agttaccttt  gagaactaaa   32460
tgactctttt  cttgctagac  cttatcgatc  tatctttag  ctcatcacaa  atattaggcg   32520
aaaaagaata  cactaatcta  agaaagctat  ttatatatta  ttttttgat  ggaaaaaaaa   32580 actccaatgt  gtgggataat  gttgaaatta  gcgttatgtt  tattaagcat  ggtgagtcag   32640
ccctgataga  gggaccattg  aactgagagt  acaaacaagt  tggtgattag  aatctattat   32700
ttaagcatcc  tttagacagt  gctgttttaa  cggggtctc  atatatttaa  atcatgtact   32760
ataagaggaa  tagtcacaca  cggatttctt  ttgatgaaaa  tgctcaagga  cgggtaggta   32820
acgaacaaat  aaatgaaaag  aaaaaaactg  gaacataagg  gacagcaatc  acatagtcca   32880
aagctgaatc  cagaaaaggc  tgcagagact  ccgtcatttg  atgcaaagca  taagggtaaa   32940
cggttagacg  ttgctgaagt  tagtagaaac  gtatactaag  aaaatccaac  acatggaatt   33000
caagcagctg  ctaagggtag  agtcatgtga  gtgaataaca  gcttaattta  gtagaatgca   33060
acaaaaggat  ttatgtatta  cattgctaat  gattgttcca  caataacagg  caaaatgctt   33120
ttgataatta  agaggctagt  cctctgcaaa  caaccagaac  tcttctgaat  tatcagagca   33180
ttgttgtgtt  attggcccaa  atagctattt  gcaagattgt  taggccgacc  tttaagagca   33240 aaagttttt  ttttctata  agagtttaat  gtatttgcg  tatgtataag  ggcgtgcaac   33300
ttaccatttg  ctctgagagc  aaaaaaacaa  taatttataa  ggtttactta  ttgtttatac   33360 taagttttt  gttgaaatct  agctaacttc  ccagctaacg  ttgtcgatta  tgatctagtt   33420
tagtttatgt  aagtcaatgt  actagggtct  ttttcaggtc  aatgttgaat  ttctcaacat   33480
aaacataaca  ctacgtttct  tctttaactc  tcaacaattc  taagtcccct  aatggcaaga   33540
aaaacttgac  cttacataac  cttaagctgc  ttacagaaca  accctaaaat  gatgctccaa   33600
gtggtaaaaa  aagtagcttt  tacacggtaa  acattcgggc  aacagatttt  aggctaactt   33660
taggataaac  ataatagatt  ctcttctcat  cttaaccaaa  taacaaacac  tcctgcacga   33720
```

```
acaaaattca agcaaacgcg ttatctgtac ttgtagagct tatataacag catataacat   33780
gagaatagtt gcagaatttt atagttctat acggttcatc aaatcctaaa taccctactc   33840
tccctgagca taaagcatgg tcacatgata tattgcagat gaatgagaca tgctgatgca   33900
tcttaaaagc tccagaggtg atttccaaag ttcaagaatc cttagaatgt tgtactataa   33960
accgccatat agttatagaa aaagtatatt taagcaatgc tgcttaacaa tgactaatat   34020
taaccatagc aaccaaatta tggcagggaa caacccaaca ttatagacgt aaataacaca   34080
tttctttcta tacccaataa acacactgtc caatttccat tgatctggaa ctatagactt   34140
tggctccaac aatataattt caaataaatc tctgcttcta ataccagtaa ctcttttctt   34200
ttgagtgttt tgacttttca atggatggat gctggtggcc gtctttggtc tcaacaactg   34260
ctcgtaccca atatctttta cttcgttttt aagcacatct ataatcccgt gttctatata   34320
gtatagtgtc agttgtctga gataaatatc cgtcttttt aattggtctg atcaagctca   34380
gcctttccag tggtttcttc catctcttcc atctcttgaa tttaagtaat ttaaagtaag   34440
gttttttacat taaagactgg ttcgatatca gcccctaacg ataggtaa catactgtca    34500
aagcttagat taatagtctt ttcttttcca tctcgcctca tacaagatat aatagatact   34560
gtcaaatata tcctcatcat tggcaagtaa aacattatca aatatgtagt gtatgatgga   34620
gagacaaaac tgtttgctgc ggtttacact taatattatt tctttctcac ccaatccttg   34680
tcaatatgtc aacacccaca caaccaagat cttttcagg gttgatagtt ttttgccgta    34740
aaatcgtggc atgttgacac gttgaatgca gcatcaattc caaaaacaca ttggtttgat   34800
agccacacca gagattagtt ggatgctact caaacctggc ttttaatcaa attgtacaac   34860
tccattcaca atatcaggaa tcaacataaa ctcgatgttt tttctttcct aatcaaact    34920
ccacctttat tttcagatag ataaggcaga actgttgtat ccctttcacc agagaggtgc   34980
tgtttgtcat cacctggtgt cgagcattaa atgatacatg tgtcttcatg ataaagttct   35040
aattagtact gttttatttt cagaattctt ggttttaaag cctacaagcc cgtcaaatgt   35100
ttgctgcgac atcttgtgtt tgagttgaca atttaagcat aattggatat ttcctcatct   35160
tttggtgtga tttccattcc ggattttatg cgtggtcaga ctggatcact tcacatcgat   35220
gaaggaaatc agacaattct agctttaacg cgaaaaccat tttttagctt atcatatgaa   35280
aacctttcag aaccaatcga gtttgagatc gtgtttatac ttttccagga ggtgacccgt   35340
ggtgactact cggcacatga catgcgcaag ccatatctcc agaaaatcca ctccctaagc   35400
tgtctaaagc accttgaaac ataactacgt ttacttttag aaacaggcta atctccaaaa   35460
caaagtcata ttgaacaaaa ctgagaagag atgtagctaa agattcctac agatgatgtt   35520
aaatcactac agttcttttt gcttttttt tttgagaact aaggaatagt ttacataagg    35580
agcacatcca aggaagctcc aaaactccct atgatgaatc gtttctgaag gcccagcttt   35640
taaaaggcag tttaagtcta gaaagatccc aatggtttat gttccctagt aaacatcatt   35700
tcattcatac tgaaaacttt tatgaggtaa cgattgtaca ctttgaaacc aaagggaacc   35760
acagtgattg ccagatactt aagactgctg agaaaagcga tttctctagc gaaaaacctt   35820
tccaatccta ttttttcact tcattaatga attagagcaa atgggtttaa ttgagcaaaa   35880
gttcatgttc ttgttcatgt tcttgttcga accttgttgt cctaggaagt tttctataaa   35940
gcggataaag aagaagtcaa acataaagat tcaattgaac aaccacaact tggaattcca   36000
agaagtcctt gtttctttgt ctgagtaatg cgcgttcatt ataagtgtat ataagattat   36060
```

```
tgaaatattg attttcatag agatggccag ggtgcaactt atcatgaaaa actaccttct    36120
caagtcaacc agcaaaggct agcggaaaga gtccaattgc taggtttgta acttggttcg    36180
ttattcatcc gacaaaggtt atatacattt gataagaaac acttaatatt attaaataat    36240
agcaacataa aacgaaatgt caacttgtac aactcgatgc caaaatagct attgttatta    36300
caaaggacct acagcatata atgtatatcc aaaagtcgtg gattaacaag gaaaagctca    36360
aaacgagttt ttctgttact gaactgttta attaaaaaac tatcagacca aaagaagctt    36420
ttcacttttc ttacattctt agaggagctc tctgatgctt atagcataga aactaattta    36480
gagacgagtg gggctttcta aagaggagct taaacagtcg actttagttg actgagtgct    36540
gttacagtga ttttggttc acttaatatt cagtagatgt aggtattatc tctatctgaa    36600
ttcccaagct tgtaaagaaa aggagtgcga attgaacttc tcataaacaa aaggttcaca    36660
actcaacttt tgtttgtctc gacaatccac agtcttccta tactagaatt gccctattcc    36720
ttggaaatcc tctcttgctt tgatctatta attccactt agatatccat cgtgatgtta    36780
tcagttgaac cgtttttgaa agagcctata taaaagaaca tatgaaggac aatggaaatc    36840
aaaatcacct ggtacagtta caggaatatc agttgtacac tgagctaaat agacatgcgg    36900
gatcgctttt aaacaaaaac aaatataaac tttactatca aaatttagaa atagctaaat    36960
cctgaatttg ataaatcagc taactaggcc tgaatggcat ctttgaaact gataaagagg    37020
gctgtggttt tattggttac tgttttaatt atctttctcg acataaagta cagattatgc    37080
cttggtcgga acttggaagg ttttaaatgg agctaaaatt ttattagatt atatagtgct    37140
ggttatggtg gtaaaaaacg ggccaaagaa aataaactaa ttagaggcca taaggtagt    37200
tgatcacaat attgctacaa gtctaccttc agtagaaaaa acaaaactgt agttcaagct    37260
aagaaacgaa tggcaaaatg agaatattag gttcttagtc ttagaggata tcaaccataa    37320
aatgatatta ggtttcccat ttgttaaaga tcatggaaat aaagttgact gggaaaatat    37380
cgaaaaggaa acgaaactc ctgaaatccc agatatcaaa aagaaataaa attaaataac    37440
ggaaatgact tagaagaaac aaaagaaaat gaacttatag ctattaaatc tatgcgtgca    37500
gtcagaagaa atttaaagaa tgttgataat tatccattat tagtgttttgt gcagtcagtt    37560
gaagaaaaag aaaataataa tgtttttagaa gaaccttacg gtggtgttgt tggaattaga    37620
aataaaattc atgaaaaatt tagagatgtg gtgaccaatg accaacccac cagtttacct    37680
ccccaagggg atttgactca cagaattata ctcattgaac ctaccaagag tacatacaga    37740
cgccagtaca aatcaagcta ttcagagaaa caagaactga ataacaggt tgatgaactg    37800
ttgaaactag cctttatcaa gtctgcccct agttcttca atagtttttt gttacttgtt    37860
ccagaagaaa gatggtagta tgaaatgtg tgttgactat gggttactga ataacaatac    37920
ggtaaaagac aagttcccaa taccacgaat cgacaaatta atcacatttt ttggaggagc    37980
ttcagtattt tccaagttgg atttgatgtc aggttacttt caggtcagaa tcgcagaaga    38040
tgatattgaa aaaatagcat ttccacaga ttacggtcac tacgagtggg ttgtgatgcc    38100
ttacggttta accaacgccc ctagtacttt tcaaagaatg atgaatagga ttctagcacc    38160
ttatttgaac caatttgttc aggtgtacct ggatgatatt ataatttact caaagactgt    38220
cgaagaacac tacagttaca ttagaaaaat attggaattg ctcaggagaa ataagctgat    38280
tgcgaagaaa agaaatgctc atttacttc aaaaccttag gtttcttagg acatctcatt    38340
tcaagcagag gtatccagac tgaccctgct aagatagaca aaatcaagag ttggccaatt    38400
ccgaaaaatg ccaaagatgc tcaatcattc ctaggattag ctgattacga tttcaaaatt    38460
```

| | |
|---|---|
| caatacttga ggtcctacta attcagtagc agacgctttg tctaggtacc cagacgagga | 38520 |
| aaatgaagtt agtatcaaca caataaaata ggtgttaaca ccaaaccatg aagtgataga | 38580 |
| acggattatc cagtcatacg aagaagacaa cgaaattaag gagatatacg acattttaaa | 38640 |
| agaaaatttg tcgatcccga agtcaatcca taactacact aaacattatt caattgagga | 38700 |
| taatttatta tatttcttgg tggttaaagg agaaaatgat cgaagaatag tagtctcccc | 38760 |
| taagtctaag ttggttcagg aaattattgg taacgctcat gacggtaact ctgctggtca | 38820 |
| tttcgggtat ttcaaaacat acatgagact tcaccctatg ttttactggt caaatatgct | 38880 |
| aaaaagcgtg aagggatatt gtcaaagatg tacggtttgc cagaaaacca aacccgagac | 38940 |
| aactggtcaa agaggattat tttcccctct tccgattcct gaaggaagat ggacagacat | 39000 |
| cagtttggat ttcgtcacag gtgtccccag atgcaaaaat ggacacgata tgattttggt | 39060 |
| agtggtggat agattcacga agatggcaca tttcatcccc actaggaaaa ctgcaaccgc | 39120 |
| agagcaatgt gcgaaattga tggtagaaaa ttgttttaaa ttacatggga ttccaaaaag | 39180 |
| aatggtttca gataatgaca tagaattctt ggtacatcat cactcttctc aaccactaat | 39240 |
| caccctcaaa cagatggcca gagtggaaga aaaaatagaa tcttaaacca attactaagg | 39300 |
| aattatgcga gtaacgatct ctacagttga dacaaatggt tgtcaatggc cgaatttgcc | 39360 |
| tacaacagtt cccatcaagt ctcgataagt tcatcaccat ttgaagtttg ctatggttac | 39420 |
| ttaccagact cgccaatgtt tatttctagc agtcgtgttt caagtagaag gtacagcaat | 39480 |
| aaagctgaag aattcgcatt agaaatgaaa gtcatcatgg aaaatgtgaa agaaaacatg | 39540 |
| attgaagcgc aaagaagcca ggaaatacag cataataagt cgagagtgta cgagacattt | 39600 |
| gaagttggag attggatact attgcacaaa gatgcatacg gtagtgatag attgtattac | 39660 |
| aaaatacaac cggtatacta cggaccctac aaggttgtca agaagatatc agacaacgcc | 39720 |
| tacgaagttg atttaccgaa aacgaataaa aaggatagag taatcaatgt cagatggctt | 39780 |
| agaagatcct tacaagcgga taaacagttt cccaaggtac ccccaagaat gatagctgaa | 39840 |
| gcaagaagta gactgaccga gattatcggt atagctggta tcgatgaaac aaacgataca | 39900 |
| ttggatgtct actagaaaga ttgtgaccct tgtcatagtt caagcatccc attttcatta | 39960 |
| tttttagaga tcccagaaga cttacagaaa acattatggg ataatgcaag agcaattgat | 40020 |
| aaagataata aacttcggga tgaagtttct aaagcgacgg ggtagtataa gagatcagat | 40080 |
| aaaggaccat ctccctattt cctaatcggg caattatatg gaaggttgaa aaagattgta | 40140 |
| gaaggttaga cagaagttct aggagataat taaatccctc aaaatgctat ttttagatta | 40200 |
| aacaattact acataaagag ggaacattct atagctgcct cggagaaata gtgtataaaa | 40260 |
| tatataagat acaaataagc aataatcagg ttctaaaata cgcaccacca gcaacatttt | 40320 |
| cataatgtga aagggatttt tcagaatgtg tcccgaaaaa ggaagtgcaa gtagatagac | 40380 |
| aataaagctc ctaatcggga gtgaaagcag caaaaggcgg aagagagaga tctatttact | 40440 |
| gcttctacta caactaagtt ccaccacacc cattgtctac tcgtgtgatt atacacctat | 40500 |
| ggcgtactta ctaatacgtg tatcataatt atcattgtta catacactgt ttttgctatt | 40560 |
| gttaaggtta gtgattattt ttaaaaagat tcagctgtta aagatcccca aataaggaaa | 40620 |
| taattttgac acgttacccc aagtccctca aaaaactttt tagccctagc tggccaagtg | 40680 |
| gtttgcgcag ggggataagt tggattagta ggtggtcgg attagaacaa ggcattttct | 40740 |
| tgacattttt ttttattatt ctggcgataa aatagagcag aggcgtaaca taaaaaaaaa | 40800 |

```
ccattagatg gtttcataaa ggggatagtg ggtatgtatt aagtttctc cctatcatgc    40860
tataacttca gcaaatttat tttgggctta ataataacac tgaccataga aatctatggt    40920
ttccagaata cagaaagctt tttggtctac atgttaatat actaaatatt aaagagcgta    40980
tcgataaaat ttcacaatca aggagacaaa ctgcaaaaat gccaaaccaa aatttcagta    41040
taattagaag atacgtttaa tattactgta atcctaaacc tattatctca gatattcatc    41100
tatttacatg ttaaaacaca gacgatggag tttgacttat atggttaggc gtatgtcctt    41160
acatccacac gaacgtctct tctaagatca gcctctgagg atcacacttt tacttcgaaa    41220
catcactctg tagttgccaa gctgataata ctaacgagaa gtatattgtc aattttttgta   41280
aggagaggtc tacaaccaaa gtgtcttact aattttttgat ttgcatttgt catacagtca   41340
aaagtttaga tagttttagt agaacttttc agcagttcag tacacacttc aaaggactca    41400
aaggcgtttt ttttggtgta ctgaacccaa ctaaggatta attttttacta tttgtacgaa    41460
tcaagaggct aatcgatgta cccattattc cattgctaat atgcggttag tcatcatttt    41520
ttgatagttg gtcaatgcca gacagaaacg aaaagttctc tgatctcctg atctcctgtc    41580
ttgttctttg ctttcagttt taggatcgac ggtggcacat tggttcaaaa taaaaatgct    41640
aatcttgtca tacaggagaa atactccagg gaattaattt aatatacatg aaattatgta    41700
taaccacaat ctaataacaa aatgagaaat acctcttgct attgagtttt tttttttattt    41760
tttatttta gtttatactt ctatctttg cataaaaaag aaacgaaact tttatgaagc     41820
tttcaataag caaggttcat tgagtattgt atcaatttgg aatataacag agcgttaatg    41880
aattttaagc tcgaagcata cgtgagttat ttgcagatag cttagtgtta aataaaattt    41940
gatggctgta atggaagtaa atctaagcta actctcgttt aagttcctaa tatgcatctc    42000
ctttttttg atgtaatatg ttacataaag ataagaccgg tcattttagg atattttaa      42060
atgaaaagta aggtataatc catatttatt gggatggttt gatctgcact gtatgtttat    42120
tcctggtgac aaattgagcg gtcaatgtct gtgtcgtttt acaagctttt agttggtgcc    42180
tctatttgac attactttt caatgttttc acataacaaa ggattctcca acctgattcc    42240
ttcattttct tgtttcaat tttatttttt gtgaccactg ctgttaaaag aaggtgttcc     42300
ttatgtccag gcagagtggt agacgacaaa cactgaatat tttattacag ttattgcagg    42360
accttcaaag ttggtacgta tttttgctca tatgctgaat ctacttggac atcaccggag    42420
atcaattttt tgccggtcta tcttaaaatt ccattaaaga aagcttttcc ttttttgaag    42480
gcttttctga caaaaaatgg ttgcttaaat cagccgacta ccaattctaa aacgttatgc    42540
aagcaattgc caccaaggaa agtctatcaa tattctatga tcagtaatat tgtgttattt    42600
atcaaaggga tacaggtaat caaaactttt agccaggttt ttatcaagaa tattgcttga    42660
atcgaaaagg ctcctaactt ttgtcatact catagacatg caatatgcgg tctcaagtac    42720
ctctgtgtct aggtacaatt ttctgtgcag acatcagagc ttttgtttgc tctgtttgaa    42780
agaaaaaaaa gataggaaaa atccctcaat ttcctaacat tcaggttagc atttggatat    42840
ctatgatgtt acccaacta tttatatttg tgagaataag ctgtttcaag gaaacaagtg     42900
aaatattatg gaagacaccg taaaaataaa tgcaaaaata ggtgtatttg caggtaccga    42960
aactgagtag tcaaaacaac atcgttgagt gattcaccaa cgaggatatt aaatagaaca    43020
tataacgctg gactgaaaat gtctttttgg aggtttttt catatgctac cgctcttacc     43080
acttgatatg ttgctataac attgaatcat tgcctaacca acatttattg agttgcaaa     43140
tggcagccac aagtcacgtg atttggttat gtgcttaggt agctgtattt tttgagactt    43200
```

```
ctcaaagagg ccgtgcggtt atctacggtt caaagaacat agagtataga cactttgagc   43260
ctgttgcttt tatagaattg gagcatatgg ctcattagca attaagttaa tcaacgagtg   43320
aatgtgtact aagtatggtt ttctgaaata cttacatagt acatcgtcat acagaaagta   43380
caatgcttat gttgtgacga gcatgatgca ttttagacag gtacatttag acaaaggcc   43440 atacagttaa cttagaaatg agagtcacgg ttctttaaga gttattttac ttccttaggg   43500
gaagctgtgc attgaactca caaagaggtt ggtaacacga ttattactag cggtattata   43560
tggccaggtt tcttgtactg ttgaaaatag gaaaagctgt atagattctt ttgagacaca   43620
ttaaagttcc aacaaactcc acagaggaat atttactgca gccagatttt tttcgtaata   43680
ttcttttaac ctttctattt aacctacatt gactagggca tattttacag ttacatctag   43740
catttgttcc agtaaaatac attcaagact gtgtttcttt atgtaagctc ataccagtgc   43800
agtttatacg tgagaattta accaagagag ctagtttcta aagtggtaca ttgaagaagc   43860
tggctagtgt agatgtatgg ccatggcgca tgcgccacat tgtcatgtga cattttggca   43920
gcatgcgcag gtactctttt tggcagagca ttcgataata tattgactaa gatgccaact   43980
aagataaagg cagacaggct ttaaaactca agattcgtag ggtggaacac acagtagaaa   44040
tttatgacaa cacgaatggg gggttaagct cctgcttcag ttctacgtgg aacatcccca   44100
ctgtctacca gcgaatagtt gtagaataca tagacttgtc tcgtgatgta agataaggtc   44160
taaggactca atgattggca tcgaaggaga aaccttagca ggagcacaac actcgataac   44220
ggccatgctg agtggttagc tatagctaac ccatggttac atttgtacgg ggtttattat   44280
tagttttccg acctgtgctt caaaatgaag aagcctcaaa gattacctgg tatgggtact   44340
tttctaaatt ctcttcaatt ctagtggtga gattaggaac atcaagctat gagtgagatt   44400
aggaacatca agctgtgagt gagattagac catcggccat ataggtaaga cgtctataca   44460
agtcagccaa ctatgggtgt gagcagttct tctatgcgaa tcgtgctatt tgtccgcctt   44520
atatccgtga agtttcccca ctctataaac atgtggacgc ggaaaaaata ttttccgttt   44580
tcagtggcgt gaagattccc agattttttca ttctgcttca agaatcttgc attttgccgt   44640
tttggcaatt agtccttcaa ggttctgtag gatcaccaca gcgaacgtcg ttctagctga   44700
cattctaacc gagaatattc ttatgcgctg aaacagagaa agggtgttat gtcgaacaaa   44760
tggtattgga aataatgtgt ttggcttgat cccttccccc attgggtcgg caattgaag   44820 cacacggtgt aactttccga gttgctgtat agcttagcca ctcatatctc tggcagcatc   44880
tagcgggttt tgcactaact ggaacagcat gtacgtcgaa acgtcaagag ggtgctgggt   44940
tttcaagaga gggggggcgg gggctttggc tggaaaacaa tagaaacaac cctacaagac   45000
tctgtaggtg aggccacaag tgaaacaaat gaccatatct ggaaagctta aaacgtttgc   45060
tttttctttg gactctagga cacttaacaa tctatcccgc attatttcaa gacctggaca   45120
aatgatggga gtacatagtt atgcttctag agttttgtag catgtcaaca ccaaactagt   45180
gcgcggcaga gttccacccg ggtacggaac ttcctttcca attttccggg gtagaccaat   45240
aaaacagtaa ctgcatttag gctgatcacc accgggacat agcatacgcc aacacgcaga   45300
cacacacaga ccaccttgtt actgtatatt accttggtct gtgtcgaaga tgcgctgttg   45360
ccactgaacg ttgtgtttct ctccaccacg agaacagagg cggcataaac aacaaaaaaa   45420
aaaccggggt aaaaggaacc acggctaaca tgtagctggc aataaaaatt accctgcgga   45480
aaaaaatgga aattttttag tggggccaga aaactgccga aaactgaccg aattgggaga   45540
```

| | | | | | |
|---|---|---|---|---|---|
| aattatcccc | caccaaaata | tgttctgagc | ggaaaccccc | gtgttttat | tattttccag | 45600 |
| taggaacgcc | gtgtctcccc | acaagtttga | cagcatgctg | tttctaattg | aacctgtgtt | 45660 |
| tactaatggc | tgcagcaaga | taatgatgta | tgtccaacaa | gagatgtgcc | tttaatggat | 45720 |
| ggctgcttga | tgtccatgag | ggcaatttgt | ttccctgggt | tcccccgtc | aggaggttta | 45780 |
| ccacaagggc | aagactccag | aacttgacca | attgcaggta | caatgcaatt | tttttttccg | 45840 |
| ctctcgccgt | tcagacatgc | tcccattttt | gctgactcgg | actaagtatg | tgtgaggccg | 45900 |
| cattttcctg | ttttttccaac | attgggtgat | tttgtgtagt | cgaacacaag | ggttttttcca | 45960 |
| ttgcatatat | taatcccata | gctggaaaga | cgggtattta | aactccctag | tttccaccct | 46020 |
| ggatatctct | caacacacct | aagttcaatc | tttttttttt | ccaaatttcc | tcttcaacca | 46080 |
| caaacaaata | tacactcaca | tattctaata | ctatttgttt | aaaaacaaaa | gaaagtacaa | 46140 |
| aaaaaaattc | acacaaaag | | | | | 46159 |

<210> SEQ ID NO 13
<211> LENGTH: 40807
<212> TYPE: DNA
<213> ORGANISM: Artificial Sequence
<220> FEATURE:
<223> OTHER INFORMATION: centromere-like sequence (CEN-L) CEN2-40807bp

<400> SEQUENCE: 13

| | | | | | |
|---|---|---|---|---|---|
| gtgtaattat | tttataaatt | ttatttatga | tatacatagt | taaccttact | ttagcaagtt | 60 |
| ttaaatccaa | cctattattt | tttgttttac | aacttgattt | gaaatgaaat | ttatcaaagt | 120 |
| cagaacctag | aaaattgtaa | gccgaattgg | ctttgagtgc | cctatcaaca | gataagacga | 180 |
| acatactcat | caatcaatag | accatatatt | tgtatttcga | aggcatatat | gactcactcg | 240 |
| tatgtctctt | gctattaatt | atcgatctat | ttcatctagc | aaaatcaaaa | aaaaagaag | 300 |
| cgcagagaaa | tgaatcaaat | ttagatattc | aaatttggaa | gcgttagcac | cggggcacta | 360 |
| aaacgagaac | aaactctaga | cgccgtgtta | tatagcagca | tatctcgttt | tcaaacagaa | 420 |
| cagtagcata | aaatcgtcat | tttgcattaa | aaagcatacg | ggtcagtaga | aataaaatag | 480 |
| gagatgttat | catctaggga | ataataattg | gatatatata | atgagcaaaa | tgtttactgg | 540 |
| aaacagaata | catgggatgt | tatttcttcg | aaacactacg | tggctgctat | gacatatcaa | 600 |
| gctcgattat | aagatattaa | tgactgaaac | atcaataacg | cattgtgagg | gtgaaaacca | 660 |
| cacaaggaat | aaggaacgat | tgaaggaac | agtaccgttt | gaagtaccgg | aagtcagtaa | 720 |
| tatcttcata | cagtattttt | cctgatctat | aactaagacg | tgctatttcc | ttttttttact | 780 |
| tcatggacca | aagtggtcct | agaaaagggg | gaaaaggctc | aattttcatt | ttaatattgg | 840 |
| tacgaaaaaa | gtttcagttt | ggtatatgct | tgagagagtt | taaaatttag | ccttcaatac | 900 |
| ccagtgctgc | actgaatttt | ccgtcagttt | acatttaccc | gccatgtttc | ttttccacaa | 960 |
| ttttaaagtt | tatgataatt | tctcagactc | agatccacac | gtccatggga | ttgcatgcac | 1020 |
| tgccggacgc | aattttttgtc | agattagtca | tgcttatctg | caaacagacc | tgaagtttca | 1080 |
| ctatggatac | tttagaccaa | taacgagatt | tgaatcactg | ccaaaaatcc | tccaatcagc | 1140 |
| ttattattac | tagataagat | atggtatgtt | aaagactaac | aaaagtcaat | aacacataac | 1200 |
| tgtttgctat | gtacttttta | atagtttaaa | ccactaaatt | gaaagggaa | agacgaatgt | 1260 |
| cttgcaagtt | ctgttttctc | cattctcatt | ataatagc | tgcatagtta | aatctttcaa | 1320 |
| gtcaagaatt | gaatatgggc | actatatata | tgatattgtc | tttctttaga | agtaaaagcc | 1380 |
| caaaaaacca | caaaaatcga | atacagagtt | atgtcggaaa | ttggctaact | ctccgatgta | 1440 |

```
aatgattgaa aacatcttca tgaaagctga ggaatgggaa ggacagtatc cgccacgcaa    1500
aaaaaattaa gctaatgcca gcacccatgc tgggagtcga acccagaatc ttttgattag    1560
aagtcaaacg cgttaaccat tacgctacac gggcattgct tgttttgtaa agggcttgga    1620
gtaacctgtc gaaattattt cctaatttgg gatgtttcga cggttgaatc tttttaagaa    1680
taatcactaa tcttatcaat atctatagta ttgtatgaag gaatgataat tgtgatatac    1740
gtattagtaa gtaggcaata ggtgtattag ctcacgagta gataatgggc gtggtagaag    1800
ttagtcgtag tagaagtagt aatagatttt tctcttcctc cttctgctgc tttcactccc    1860
gattaggagc tatatcaatt atatcaattc tatataatag gatattatcc gtcttatata    1920
cttcacgccc gcaacctgga atcaccctca gttgctactc ttttttcgta tagcagactc    1980
ctgtacgagc ttattacgtt ttaggtcttt atttttttta atatgccagt cctgtcaacc    2040
cgttgataaa taatttaact tcctactccg gatacttgac ccttgttaac ctccctattc    2100
taaaatcgaa acattaacat cagtatgtta tcgtctatct actggcactt ccttttttt    2160 tggatcacac cctgaaaagc cctctcacat atcgaaaaag gctaagagta ccgagttgtg    2220
gctatttcta acttacaaat gtcttaatga acttaagctt ggcaaaacct tgtacgactg    2280
gccaataatt atatcgatat caaaaatatc caattcaatg atagcctgtg taaactagct    2340
gagcatgttg caggtgctta atacgtgtat aaatgcacat gtagataatg gatatatggt    2400
gttgacaggc gttacattta cttagagat ccctattgca attaccgatt gaactattat    2460
caaaagatct tatactaaat aacaaataaa aacaaactaa gtcaaaggaa ctaactcgct    2520
atttaaaaga acatcaggtt tgtatcaatc tagattgata tacgtaggct gacgtttcaa    2580
agaacaaggg aagaaaacat aactaaatga gctaaaaaat agctcggctc tagttctgat    2640
ttacgcgtac gtatgctgga ctagctgtat cgagactgta aggatatcct tagtttgatg    2700
tttagtgctt taattatata tctaaacaat ttttatttg ggtgtctgtt tcttattttc    2760
ctaatattac tagaaaaata tattcaagga aggatgtttt tgagttggtt ccagccaagg    2820
catcaaatat cgaaggattt tctaattagc tctgtttgac taaagcaaaa cgagaaaata    2880
ctcatcgtgt ttgtaatagg taaagcatct atttgcttc tattgtattt aaggaaatta    2940
gaaggtccac ttcaacatct agttgggtca caacctttct gtataatact tcttcaccag    3000
gtactataat tatcaacctt atacggaatt tgttaatgcg tacgtgtccg aagcaaaatc    3060
tttcagtaca ttactttcac ttatacattt tgtatatttt gtgcatgatc tttgattata    3120
tcttctacta tctcttttaaa tagttttgtt gcactcaagg tgactggatg ttgataccaa    3180
acagtcctct aattcattgc ttgggcttct agacatgtcg tatgagtctg agtagtaaaa    3240
acatacggtt tacaatctgc catttactat ttcgctatac acataggtat tgcctgacgt    3300
tataacataa ctctatatta ttattagtac agaatctgat gtgctaaaca tattatttgc    3360
ctgggtaacc ttttcaatag taaaatgaat tgctatcaaa atagcaacat aagttattat    3420
taaaactatt catacaatta tacatatata tctattttt tatctttaaa aaaaactgga    3480
atcttcatca tcgtctttat tttgtgtatt attgtcttcc ccaaactagc agtaggcaga    3540
tccagtactt ccagcaaaaa cgtggatgta aatacgtcgt ttaataagta atttttatca    3600
ctttcgtcga tttatgcctt ttagataccc ctattatgat gatgcaaacc atttaaaact    3660
tggattatat gaaccgtcat tggaaaaatg attagcattc cttttctagt aaaataccaa    3720
tagaatcact taaatagctt gatgcaggcc acttgttggt tctgcaaatc ctcattgata    3780
```

```
ttcagtacag cctttactat ctactctaaa taatctttaa aatctacaac tactgccttg    3840
tttttaattc tatagttctt aaaacaaata attgatctat caatagatag cctaagcccc    3900
tattgtcttt ccgtaggttt ttacccaacc taaacaaaat agctagacaa ctgtttatta    3960
ttgacagcgg agaagtctcg agatactgaa aaggcaatga aacataaact aagtagcagc    4020
ttttaaccta ttctcgtggt ttggacttaa cttaaatact ctggtacatt tttcaaaagt    4080
ttacaggaag acctttattg ttattaagtt tatgggaggt tttttaaataa aaagaagctc    4140 cacctaaatc gcttttagca aactttagta caaatatacc tattctttat tcaacttctt    4200
tctttgattt catctgtctt aatataaaaa attaactagg tccttctatt caggagcaaa    4260
aatagtttag atcaagaaat aattagttcc gtagcaaaga ctattattaa tatgtgttat    4320
ttagtgagaa ctttgctttt ttcaaactag aatagactca gaagggccaa tttgaaaggt    4380 taccccctaga aacactacta cctacaaaga aatagaagaa aaatcctaat acacaaatcg    4440
gtaagtatgg acctttttgtt agatacttgt gattaactcg aataactata tagaaaataa    4500
actaaagcaa caagattgga tctaagtcta aagaaatgta caaagatgac tagttcagta    4560
gactttcagt attataaact caataggcta ggtgctttta gttttataaa agaatatgat    4620
acacatctta actaggaagt gagaatacccc tttctagaat tagatgtcgt acacactaca    4680
gttagaagtc ctgatcgaaa cagaattagc tatttattag gaaaatgaat aaaagcgagt    4740
gccagactga gaggaaataa ccaaatgtta tacaaaaatg aaattcagtg ctctataaag    4800
tgagttcagc ttattgatgg aaaacatcct acaagaccgc tgatattcat acttaagaaa    4860
aatgattaaa attgtgtaaa acttacattt ttttcaact cattctttt tttcaggctc    4920 aagtcccttg gcaagtggtg tgagaacaca aaagataat aaacttccag gattcagttc    4980
aaactagcta caacaaacat aagcgagtag tgtaactcaa tgtccaaaat ctaaacagaa    5040
aaatacaggt attagaatag agatgggaaa ttcacacgaa agacgagtag caatgcacag    5100
tgtaacaaag aatctacacc agttaagcag tgaatgtttt aaaggcccat gacattccgg    5160
cagtccaatg aaaaaacttt atgaattaaa actaaattat atatatatag cttccaggct    5220
ttagttagca cataggatta ttaaaatatag ttttgataat acggatccca ctgaaagtta    5280
tggtacagag ttttagcttt tcaaaatggt gaattggctg ctcataatat accacacacc    5340
gtgtttgtgt tgtgcaccta ttgtatctat gatcaaggtt tagaagtagg tagacttaaa    5400 acccccaattg ttcagaagaa atacaaaat acatcgatag tttctttta taattagggt    5460 agcaagtgta gaattaactc tgtatactag taggtctttt gattttttta tcacttattt    5520
agtggctttc aacacagtta tatgcttaaa cttataatgg ctgaaaaaaa taattagctt    5580
atagcttctc tacataaata agaacatata gcttgtctat gaacgaagtt taaatagttt    5640
cctaaaattt tttctattca atgcaaataa gatattttg attagccatt tcctaagata    5700
aacatcgttt acgcaccgtc taatatgttt tagaaaaaat aaaataaaat taacgaatgg    5760
aatagtatat aggagttaac aaacttagat tgttaggatt gtagatgaat tccctgcagc    5820
acgactcagt attttgaaca aaaaacatac ggtgaaatga tgtgcttata tttgtgaagg    5880
caaaaaatgt gaagaaactt agagatgcga tttaaggact aggctgtcac tcaactataa    5940
tatggcggat ttttcattta gattggcaga aataagtttt agatcattca aagcatcttt    6000
aaacactgat ccaaaattta tatcataaac ggttctgctg taggcaggta tttaactatc    6060
agtgggttat ataaaaatgt attatatagaa acgccgcgtt accttcatag cttgaagtta    6120
tatgattctg cggttaacca tggaggctat aactaagaaa cgaagaaaag caaaagaatg    6180
```

```
aactggtcct agtgaaaagt catacgtgtt taccactact aggctacatg tacttttttgc   6240
atagtctagt tggcagaatc attctaatag gagaagatgg aatgggtcaa taagaataat   6300
agatggaagt aagtaaactg aaaagaacat gcaaacagca atggaatgat ttctatttag   6360
atctagaaac aatgaactaa aagaaagaaa aaaaatttaa agattaacca acaagtacgt   6420
agtacctgca atgttcgact tcttattaga taaagataac aagttagtac aattcaactt   6480
cctaacatcc aaactaatat ggtgattgta gagggatata ttgagaacac aacgaccagg   6540
aagacataaa tatatgataa aatgaactaa ggctgcagtg tgcacaaaca gccaagagaa   6600
ataggcatgc tcgacatgtt tataagtaaa aaaataactt ttgctgaatg ttagcaaact   6660
gctttcgtta aaaggaagag ccgcggcaat gcaatggtta tcacaaatta gaatatatta   6720
tgaatattgt agggtatcat atgataagaa ggttatatgc gctgttatca ccctgaaaaa   6780
aaaaatggtt ctgagaggtc ccccactaaa ttaactgata aagatttact gaaagaatgc   6840
tgacacaatt ctaaagctaa attaaaaaaa catttgtttc tattgcgaaa acaagccac    6900
gaaacggaaa tcatcaaatt tatgtgtaga agaaagtcag atcaaccaac gaagagctcg   6960
caggaagaac ttagggtacc tatacctact attttcgatg ttgctgaaga gaaacctact   7020
attgctcaat attttagtac aattgaacaa ggaatgagga atacggaatt gttacaacag   7080
accctaggtg ctatttccgt ttccgaaatt ttagtgcgct tccatgagag atacagagat   7140
aagatagtct acaagcctga ttatatctgt attttgaatg gcatccctcg cagaccaagg   7200
tccaacaact ttaaaaaaat aggaacgaga cgaaaatagt aaattcatgg ctcctgatgg   7260
acctaaaaaa ctgcttataa taattttaag ttggtaagaa attcaagttt tttttagttt   7320
tactaagcca ccagcaaatc ctaatagcat aaataattca gttttctact attcttcaca   7380
taatattcat aacaaaggaa atgatgttaa aatgcttgtg aatcatgcag ggcaaaaaaa   7440
gtgttaattt ggtaatcctc gaatagcgtc aattatcaaa aatcctattg ttattggttt   7500
tatagctatt ccatttggaa aagacgtcaa tgaaactatt aatataagtg atattaagtc   7560
gctttacatg ttggtcagtg accaccagat attcatattg ggaactctat tgactaagtg   7620
tcaataaatt aatttcaaaa aatttaatga gtgttgatgc cgttaaatca actggtttaa   7680
atatcaatcc acctccatcg agcgtttcac tcaatatcaa gaaaagtacg ttaataagtt   7740
agttaggaga atgaatcct  atctcacttt tatctactcg attgatgttg acgaagtcga   7800
aaaccctgat aatattaact aacccatgaa tacaaatccc aataagcttc tctgagaaac   7860
aggaactaac aaaacaagtt gaagttttaa tcaaacaagg tttcatcaaa actagttcca   7920
aatcctttaa cagtccagtg ctatttgtta gaaagaaaga tggtactatg cgtatgtgtg   7980
ttgattatag gattctaaac aataaatactg ctaggaacaa gtttccactt ccagatattg   8040
atcaattgat ttcaagattt ggtaaggcaa aagtctattc taagttagag ttgatgcctg   8100
gttactacca agtgagaatt gcggatgaag atgtcgagaa gacggctttt tctactctgg   8160
ccattatgaa tggatggtaa tgccggctgg actaacaagt gcatctgcga cttttccaca   8220
gatgatgaat aatgtcttgt ctaaaaaaat aaatggattt gtccaagtgt atttagacga   8280
cattttata  tactccgaag atgttgaaac tcacggtaag cacgtgaaag aagttttgtc   8340
gacactaaga aaacataaac taattacgaa gaagtcgaaa tgcagattct tttatcaaga   8400
atttaggttt ttaggacaag ttgttacacc aatttgtatt caaaccgctc tcgagaaaat   8460
aaaaaaggta aagagttggc caacaccaaa gactgtcgaa gaagcacaaa ggtttattgg   8520
```

```
tttaacttcg tattatagaa ggtatatcaa agggcattcc aaaattgcta atccaattca   8580
taagttcatg acaaaacaaa ttaaatggac aagtgaacaa gacgaagcct tcaacaaact   8640
aaagaaagct ttgatatcaa gtcccatctt ggtgcaccca agctggtcag gcaattgtaa   8700
atttgttcta cataccgatg cgtgtggagt atcgttaggt tatactctag aacagttgga   8760
cgaaacaggt aaatgacgag gtgtgattgc ttacggttca aagaagctag ttggaagtca   8820
actgaattat ggaatatatg accgtgaatt tatggctgtt gttgaagcat taagaacatg   8880
gagatattat ctcatgggaa gacatttcat tgttatgacg gatcacaaga gtttaattta   8940
cttaaaaaac caaaatctca tagactccac tagagtggct agatggatgg acttttttacc  9000
acagtttgat tttgatattc gttacttaca gggaaaaaac aattccgctg ctgatgcgtt   9060
atctagatac ccatacaacc actaaaacag gttaacgcta gccaaaatcg aattggcgtt   9120
gctggaattg acgtaaaaag aggaggatga acacagaga cattccttga cactaagtac    9180
tatcgaagcc aatcaagagt taaaaaaaaa aattattacg ggttataaaa aaatactaa    9240
ttatgccttg atattcagaa ctttgagaga gaaaacaaaa gttccagttg ataaaaaaa    9300
tcatatcaaa catttctgtt atcaagatga ggtacgttat tataagacat tagagtctca   9360
agatttcttt aaagtagtta ttccaaacta caagaaacta ccgtatagaa tattcaaaaa   9420
tgcacacgat tccaaagatg cttgtcactt tggtgcatgg aaaacttatt tgaatcttaa   9480
agatagtttt tattggtcat ctatgttgag acaaatcaaa aatgggtaga aacctgccat   9540
atctgtcaac agcacaacac taacaccaga agaagacaag ggttgttttc ccctttacca   9600
atcccaacag gctacactat cattatggtt attgtcgatc gcttctcaaa aatgacacat   9660
cttataccca cgcacaaaag acttaatgct actgcatgtg ctcgtttgtt tagtgacaaa   9720
gatattcggt ttatgaataa gttctggcag acattacatt atctcaatgg tagttctcta   9780
ttattttcaa ctactaatca tccagaaact gatggtcaaa ctgaaagatt caacaagatt   9840
gttaatcagt tacttcggaa atattctgca aacgttcaat tatcctggaa tgagcatctg   9900
tctatgtgtg aacttagtta caattcaacg taccaagatt ccattaaagc aagtcctttt   9960
gaaatcgcct acgggtatga atcgaacatg attaaaaaaa gtaaatagct gggatttgga  10020
ggataacaaa tattcaccta acgcagaaga atttgtgaga cgtgtgaaat tgattttaga  10080
gcaaacactg gataatattg taaagcgcaa gggcaacaag gaaaacacca taatagaaaa  10140
agaagatatt ttgaatataa agttggtgat tttagtgtta gtgcatcaag atgcctttgg  10200
tgtgaatata aggtacacaa aaattcaacc agtatgatat gggccataca gactagtcga  10260
gaaaataaac ggcaatgctt ataaagtcga tttaccggtt attaatttga aggattgtga  10320
atcaaatgta cagtggatta aatactataa agaaaacccc aatatttacc acgaatcgcc  10380
tagaacagag cgtgagatgt tggcaagaat taacgaactg agtggtatcg gtggatggtc  10440
agaagaacca ggcaaagaaa agacttatga tgtcttctgg aaagactgtg atcaaactct  10500
agcaagaaag gtgcctgaaa gaatattcaa ccaagcagct ttgtcactac gtcaaagcct  10560
aatgcacaat gccaaatcga tccaagaaca cgaacaagct tgatatcaac aaagtaatca  10620
tgattataat acatagaacg ttcctatttt ctcgaatctg atgagagagg tatagatatt  10680
gttattacta ggaaatattg acaagtatta actctacttt ggaaatctat gtggaagtat  10740
ttaaaatgga gttttgtaaa gaacttatat aatacaacat aaaaactaaa ttaagcaagg  10800
caataatctg atacttgtag ggaacatcat gtgtctacta agctagatat ccaaggacgg  10860
gtgcactttt tgaatgctaa gaaatataaa cacaaccata tgcattagta aatactaact  10920
```

| | |
|---|---|
| ccttaattt gacaggttgc ctgatcaagt ctgtttggct tcatttggct cataatgatg | 10980 |
| ttcgcatttc gattcaccaa tgtttaaatt atctctctta acaatcagaa tcagcatgat | 11040 |
| cagttgcttt aactctcatt gagtgggcgc aagtactcaa gggaaagtaa acaaaaatct | 11100 |
| actcaatcta ctgactttt atttttctgc tgcacctatg acgctcacga cttttcgttc | 11160 |
| tctagagaag cggaaaagat atacctgatg taaataaaaa ggcatgggac ttagcttgcc | 11220 |
| cattcgaaac aactttttac aattatgaca ggaaacattt tgtaggcaag cattatatag | 11280 |
| gctacaaaac agtaatattt tttatttttg ctttcaatac tagagctgtt taaatcaaag | 11340 |
| atgctgatat atgctcatta acttatgttg tttctctata tgtagttgtt ctctgccttg | 11400 |
| ataggaaagt gatagccttt ttcagagcat tgaaactcaa gtctaaatat attcccaaaa | 11460 |
| aacactttat ccttgcaaaa agttcaaaga ctactggttt tgttaagcga cagtataatt | 11520 |
| gtttaagtcg agtttgcaag tggaacatac actatttctt agaaaacaa atattactga | 11580 |
| gttgaaaatt atgtttatga taacatcagt aggtatgtta tactgttttc caccccaatt | 11640 |
| caactcttct aattgaataa ccgaggaaaa tatttcaaac catcaaaata tatataccat | 11700 |
| tggccagaaa cgactacttt tacctaatgt ctctgcacgc cgctgaatgt tatttttcgaa | 11760 |
| gtactttgga aacttatact taattttgca aaaggacttt ttagaattac ctaacttcat | 11820 |
| ataatatgaa actcggcgct caaattctag catttggcat ttgaaaccgg taaaccactt | 11880 |
| tttccttgat tgttgtacaa aaaaaaaaca gatattggct tctgtgaaat taccgaggag | 11940 |
| catctgtttc tttttcgatc tcgtttacac taaaatcaat ggcttataaa gtgtacatat | 12000 |
| agttatagtt tatcaaattg ggtctgtgta aaaacataaa aaaacatgtt caaaatgata | 12060 |
| gagcttacat cgaggcaagg ttaagtaatt cacgcataag gcaaaagaga gaataccgct | 12120 |
| ggtctatgtc tctgttattt gttttggtta gtgtttggta ggcgaagcct tcttaaagtc | 12180 |
| gcctggaaat ataacttaac ttttttacta aacagcaccc aattgaaaaa aaagacctcc | 12240 |
| atgagctggt gattaaatca cgtaagagta atccattttt gattttataa gaagttaaat | 12300 |
| gctggcctct agagacgctt tatgacggaa aatagcccga aagtaattat ttcaagcatg | 12360 |
| aatatactat cagttccgcc ttagacgttt attgaaaagg agcttttatt atacaaatat | 12420 |
| gtacgcgttg acaactcttt cttttttcctt ctgttaagaa taatataaac agttatttcc | 12480 |
| ttttattcta aagaacaaaa agaagattct caaaacaaag ctcaatggtt tacgcatcat | 12540 |
| ttccagtatt tttgtcaagg ctttgaagct gggcgctata atcaacaatt tcatattttg | 12600 |
| ggattacaat atataacagc aagttattaa gaaagctatg aggaaaaaat cgattgttg | 12660 |
| aagacttcat agctatctat agtttctatc aagtatttgg caatataaaa atggatgata | 12720 |
| gtaaatgtag acttcggata attacttata gttaaacgaa attcaaaggg gatttttaaca | 12780 |
| aatcccaaag gtttaggaca attttgtctg gcctaaagtt tcactactga aatacagtag | 12840 |
| agataagtgg cgctacgata ataacaagtt ccccttctag tcattaaaga catcattatg | 12900 |
| tttacaaaaa tgaagagagt aaagctaaca gtgaaaagct gctcaaaaaa tattgcagac | 12960 |
| cgggttaatt tgcaaagttt cgaatattgc aaaaacttct cgttattttt ccaggttttg | 13020 |
| tattacgcat aaagggaaaa ttaaaaaaga tagcttcggg ttttgtaaac agagtcaaga | 13080 |
| gacggtctgc ttcctagttt gaaaactttg caaatgtaca gtacgatata aagggcaaaa | 13140 |
| gctatgtata ttgaacaatt tcaataatag taattctttg aactaggtct cctcgtttga | 13200 |
| agttagtatt cttcatttga acaaggacac taacaaattc ctgcagcctc ttgaaaagca | 13260 |

```
gcggctaaag agttcttgct cctgatgctt taaaaatgga gctgtctttg taaagaaaaa  13320
gatttgtcaa taatgaaaaa aaaatactta atgaaaagta gcactttgga tatttactac  13380
ttgtttgatc ccgttgttgg ccaaactctt agaaaattac attactttga aataaatatt  13440
attaatacaa aaaatttcat aatatttact tcgacatatg ctataatgtc gggcaatacc  13500
tatgtgtata gcgaaatagt aaagggcggg ttgtaaatcg tatgttttca ctactcagac  13560
tcatacgaca tgtctagaag cccaagcaat gaattagaag actgtttggt accaatattc  13620
agtcaccttg ggtgtaacaa aactatttaa agagatacta gaagatataa ccaaatatca  13680
tgcacaaaat ataaatgtat aagtgaaagt aatgtattga cacattttgt ttcgggcacg  13740
tgcgcattaa cagattccgt ataaggttga taattatagt acctggtgaa gaagcattat  13800
tcagaaaggt tgtagcccaa ctagatgttg aagtggacct tctaatttcc ttaaatacaa  13860
tagaagcaaa ataggtgttt cacctatcac aaacacgatg agtattttct tgttttgctt  13920
tagtcaaata gagctaatta gaaaatcctt cgatatttga tgccttggct ggaaccaact  13980
caaaaacatc tttctggatt atattttct agtaatatta ggaaaataag aaacagttac  14040
ccagaaatag atgggattaa taaacaaccg taacatttt tatcttttca tgcgattttc  14100
tcgagcttta cattttctat tctctcaaga gccaagtttg tgtagcattt gcttggccta  14160
taatttttat ttagctcaac gctaaagaat acttgttatt gaaaatacc accagtaata  14220
aagtacgcaa atatagcttc tctaaatatt catgagtatc caccttgtaa aggcctctgt  14280
agaaaaataa ccttatattt ggctaataat tctcacctta aaacagtttc aaaatcatat  14340
aaatggggtt cgtagaaagg tgaacaaaat aacccaatat atcaataact catgatccaa  14400
tttgttcatc agctagataa ttatctagct gatgaatact acttttccct agactcgtta  14460
agatttttca aaatatattg cgccagggaa actatacgtt gtactgttaa cattaaaatt  14520
aaagtatgga ataaaaaagt ttgttagttc aatatatgat tgatagatct gtttgcaaag  14580
taaaaacggt tcgatatat aactaaagca ttaaacatca aactaaaaac atctttatca  14640
gtctcaaaga ggccccggag gccgaacggg gaaaccaatg tctaaaccat atagttgtgt  14700
tgacaattct ttcttcaaag gttatttcac atatttacat ctagcatagt acatattttt  14760
aattccctat aataaccagt atatatcctt ttttaaacta ttttcatatg ttgtgttata  14820
cctttttgata atagttcaat ttatagttct tattccagaa ttccagagtt gaattaacag  14880
agtgctgcaa actgtatttt taaactttat ttattccaaa ggcacaacag tacaaactca  14940
taattccgtt tttgaggaaa gcttttcatt gttttatcct tagcaaaata gtctttttta  15000
tcattgttgt ttatgctaca ttataggagt catacgtggg attatttagt cgaagcttaa  15060
gctgatttga caaacacctt aaagttacca tgagagctcc tttagtatat agttcttttg  15120
tggtcatcta taatatatgc caaatagaat cggtttaccc tgaaatgatc tttaaataat  15180
aatagtctat agagctattt tagtctcact tatatacagt tttatcttca caaaagtttg  15240
aacaccttct tgtagcacat ttttgaacag cttaccaatt agttgcagca tctatctgtg  15300
ttactctgaa aaaatcaact actaaaaatt tggatttcag cagtgaaggt ttatctagtt  15360
gtcaagcatt atttcaaag aggttcaatc tcacgtaagt ctatttctaa ctactattct  15420
ataaaaggaa gcttaagcaa taaacaaagt gaaattattc tcactgtaga tatgtcgcat  15480
tttacccgct ccaggaactc ccaaatagtc taaaagaatt ctaaaactca accttgaaag  15540
acagctatta actaaaattt cacaattta aattctaaaa aataatgcgt ttgaggccaa  15600
caggaatcga acctgcaacc cttcgatctg gagtcgaaag ctctaccatt gagccatagc  15660
```

```
cccaacacct tgggataaga gtgttgctac tgatgcgtac tttagaatct gattattgct   15720
tatttttatc ttatatattt ttatatgtta attctctgaa acatatatg gaatgtcctc    15780 tgtttaaata gtaattcttt aatttaaaaa tagcattttg agggatttaa ttatcttcta   15840
gaacttctgt ttaaccttct acaaccttct tcaaccttct atatgattac ccgatgagga   15900
aatagagaga tagtcctttg tctgatctct tacattaccc cgccgcttta gaaacttcgt   15960
accgaagttt attgtcctta tcaattgctt ttgcattatc ccataaagtt ctctgtaaat   16020
cttctgggat ctctaaaaat aatgaaaatg ggatgcttga actatgacaa gggtcacaat   16080 cttttccagta gacatccaat gtatcgtttg tttcgtcgat accagctata ccgataatct   16140
cggtcagtct acttcttgct tcagctattg ttcttggggt accttgggaa actgtttatc   16200
cgcttgtaag aatcttctaa gccatctgac attgattact ctatcctttt tattcgtttt   16260
cggtaaatca acttcgtagg cgttgtctga tatcttcttg acaaccttgt agggtccgta   16320
gtataccggt tgtattttgt aatacaatct atcactacca tatgcatctt tgtgtaatag   16380
tatccaatct ccaacttcaa atgtttcgta cactctcgac ttattatgct gtgtttcctg   16440
gcttctttgc gcttcaatca tgttttcttt cacattttcc atgatgattt tcatttctaa   16500
tgcgaattct tcagctttat tgctgtacct tctacttgaa acacgactgc tagaaataaa   16560
cattggcgag tctggtaagt aaccatagca aacttcaaat ggtgatgaac cgatcgagac   16620
ttgatgggaa ctattgtagg caaattcggc cattgacaac catttgtccc aactgcagag   16680
atcgttactc gcataatttc ttagtaattg gtttaagatt ctgttcgttc tttctgtttg   16740
ggggtgatta gtggttgaga agagcgatga tgtaccaaga attctatgtc attatctgaa   16800
accattcttt ttggaatccc atgtaattta aaacaattat ctaccatcaa ttttgcacat   16860
tgctctgcgg ttgcagtttt cctagtgggg atgaaatgtg ccatcttcgt gaatctatcc   16920
accactccca aaatcatatc gtgtccattt ttgcatctgg ggacacctgt gaggaaatcc   16980
aaactatgtc tgtccatctt ccttcaggaa tcggaagagg ggaaaataat cctctttgac   17040
cagttgtctc gggtttagtt ttctggcaaa ccgtacatct ttgacaatat ctcttcacgc   17100
tttttagcat atttggccag taaaacatag ggtgaagtct catgtatgtt ttgaaatacc   17160
caaaatgacc agcagagtta ccgtcatgag cgttaccaat aatttcctga accaacttag   17220
acttagggga gactacaatt cttcgatcat ttcctccttt aaccactgag aaatatagta   17280
aattatcctc aattgaataa tgtttgatgt ggttatggat tgacttcggg accggcaaat   17340
tctctttaaa atgtcgtata tctccttaat ttcgttgtct tcatcgtacg acttattgat   17400
ccgttctagc agttcctgat ttggtgttaa caccgattct attgtgttga taccaacttc   17460
tttctcctcg taggggtacc tagacaaagc gtctgctact gaattagtag gacctttcac   17520
gtactgaatg gtgaaatcgt aatcagctaa ataatccaac catctgacca ctctatggct   17580
atctattgca ttctgtcgct ttaaatagac caacgatctg tgatctgttt tcaatacaaa   17640
gtgccgattt aataaatagt aacgccagtt ctttaatgct tcgacaacag cgagaaattc   17700
acggtcatat attgaataat ttaattctga acctattaat ttcctggagc cataggctat   17760
tacaccacat aattctccat ctggatcgag ctgttctaac acgtacccta atgcagtacc   17820
acaagcacct gtgtgtacca cagatgtata accatcttcc caaataggat gtactaaaat   17880
tggggtatta atcaactttc ctttcagctc ttcgaatggt ttatcttgag gttccttcca   17940
aacacatttc ttatttgcga attccattat aggagatgca atcttagaat gatctttgat   18000
```

```
aaatcttcga taataaccag ctaatcccag gaatgattga gcatctttgg cgttttttcgg   18060 aattggccaa ctcttgattt tgtctatctt agcagggcca gtccggatac ctctgcttga   18120
aatgagatgt cctaagaaac ctaaggtttt gaagtaaaat gaacatttct ttttcttcgc   18180
aatcagctta tttctcctga gcaattccaa tattttccca gtgttactgt agtgttcttc   18240
gacagtcttt gagtaaatta taatatcatc caggtacacc tgaacaaatt ggttcaaata   18300
aggtgctaga atcctattca tcattctttg aaaagtacta ggggcgttgg ttaaaccgta   18360
aggcatcaca acccactcgt agtgaccgta atctgtggaa aatgctgttt tttcaatatc   18420
atcttctgcg attctgacct gaaagtaacc tgacatcaaa tccaacttgg aaaatactga   18480
agctcctcca aaaaatgtga ttaatttgtc gattcgtggt attgggaact tgtcttttac   18540
cgtattgtta ttcagtaacc catagtcaac acacattttc atactaccat ctttcttctg   18600
gaacaagtaa caaaaaacta tgaaagaac taggggcaga cttgataaag gctagtttca   18660
acagttcatc aacctgttta ttcagttctt gtttctctga atagcttgat ttgtactggc   18720
gtctgtaagt actcttggta ggttcaatga gtataagtct gtgagtcaaa tccctttggg   18780
gaggtaaact ggtgggttgg tcattggtca ccacatctct aaatttttca tgaattttct   18840
ttctaattcc aacaacacca ccgtaaggtt cttctaaaac attattattt tcttttttctt   18900 caactgactg cacgcataga tttaatagct ataagttcat tttctttttgt ttcttctaag   18960 tcatttccgt tatttaattt tatttctttt tgatatctgg gatttcagga gtttccgttt   19020 cctttctcgat attttcccag tcaactttat ttccatgatc tttaacaaat gggaaaccta   19080
atatcatttt atggttgata tcctctaaga ctaagaacct aatattctca ttttgccatt   19140
cgtctcttag cttgaactac agttttgttt tttctactga aggtagactt gtagcaatat   19200
tgtgatcaac tacctttatg gcctctaatt agtttatttt ctttggcccg ttttttacca   19260
ccataaccag cactatataa tctaataaaa ttttagctcc atttaaaacc ttccaagttc   19320
cgaccaaggc ataatctgta ctttatgtcg agaaagataa ttaaaacagt aaccaataaa   19380
accacagccc tctttatcag tttcaaagat gccattcagg cctagttagc tgatttatca   19440
aattcaggat ttagctattt ctaaattttg atagtaaagt ttatatttgt ttttgtttaa   19500
aagcgatccc gcatgtctat ttagctcagt gtacaactga tattcctgta actgtaccag   19560
gtgattttga tttccattgt ccttcatatg ttcttttata taggctcttt caaaaacggt   19620
tcaactgata acatcacgat ggatatctaa agtggaatta atagatcaaa gcaagagagg   19680
atttccaagg aatagggcaa ttctagtata ggaagactgt ggattgtcga gacaaacaaa   19740
agttgagttg tgaacctttt gtttatgaga agttcaattc gcactccttt tctttaaaag   19800
cttgggaatt cagatagaga taatacctac atctactgaa tattaagtga accaaaaatc   19860
actgtaacag cactcagtca actaaagtcg actgtttaag ctcctcttta gaaagcccca   19920
ctcgtctcta aattagtttc tatgctataa gcatcagaga gctcctctaa gaatgtaaga   19980
aaagtgaaaa gcttctttttg gtctgatagt ttttttaatta aacagttcag taacagaaaa   20040
actcgttttg agcttttcct tgttaatcca cgacttttgg atatacatta tatgctgtag   20100
gtcctttgta ataacaatag ctattttggc atcgagttgt acaagttgac atttcgtttt   20160
atgttgctat tatttaataa tattaagtgt ttcttatcaa atgtatataa cctttgtcgg   20220
atgaataacg aaccaagtta caaacctagc aattggactc tttccgctag cctttgctgg   20280
ttgacttgag aaggtagttt ttcatgataa gttgcaccct ggccatctct atgaaaatca   20340
atatttcaat aatcttatat acacttataa tgaacgcgca ttactcagac aaagaaacaa   20400
```

```
ggacttcttg gaattccaag ttgtggttgt tcaattgaat ctttatgttt gacttcttct    20460
ttatccgctt tatagaaaac ttcctgggac aacaaggttc gaacaagaac aagaacaaga    20520
acatgaactt ttgctcaatt aaacccattt gctctaattc attaatgaag tgaaaaaata    20580
ggattggaaa ggttttctcgc tagagaaatc gcttttctca gcagtcttaa gtatctggca    20640
atcactgtgg ttccctttgg tttcaaagtg tacaatcgtt acctcataaa gtttttcagt    20700
atgaatgaaa tgatgtttac tagggaacat aaaccattgg gatctttcta gacttaaact    20760
gccttttaaa agctgggcct tcagaaacga ttcatcatag ggagttttgg agcttccttg    20820
gatgtgctcc ttatgtaaac tattccttag ttctcaaaaa aaaagcaaaa agaactgtag    20880
tgatttaaca tcatctgtag gaatctttag ctacatctct tctcagtttt gttcaatatg    20940
actttgtttt ggagattagc ctgtttctaa aagtaaacgt agttatgttt caaggtgctt    21000
tagacagctt agggagtgga ttttctggag atatggcttg cgcatgtcat gtgccgagta    21060
gtcaccacgg gtcacctcct ggaaaagtat aaacacgatc tcaaactcga ttggttctga    21120
aaggttttca tatgataagc taaaaatgg ttttcgcgtt aaagctagaa ttgtctgatt    21180
tccttcatcg atgtgaagtg atccagtctg accacgcata aaatccggaa tggaaatcac    21240
accaaaagat gaggaaatat ccaattatgc ttaaattgtc aactcaaaca caagatgtcg    21300
cagcaaacat ttgacgggct tgtaggcttt aaaaccaaga attctgaaat aaaaacagta    21360
ctaattggaa cttatcatg aagacacatg tatcatttaa tgctcgacac caggtgatga    21420
caaacagcac ctctctggtg aaagggatac aacagttctg ccttatctat ctgaaaataa    21480
aggtggagtt tgtattagga aagaaaaac atcgagttta tgttgattcc tgatattgtg    21540
aatggagttg tacaatttga ttaaaagcca ggtttgagta gcatccaact aatctctggt    21600
gtggctatca aaccaatgtg ttttttggaat tgatgctgca ttcaacgtgt caacatgcca    21660
agattttacg gcaaaaaact atcaaccctg aaaaagatct tggttgtgtg ggtgttgaca    21720
tattgacaag gattgggtga aaagaaata atattaagtg taaaccgcag caaacagttt    21780
tgtctctcca tcatacacta catatttgat aatgtttttac ttgccaatga tgaggatata    21840
tttgacagta tctattatat cttgtatgag gcgagatgga aaagaaaaga ctattaatct    21900
aagcttttac agtatgttac ctatatcgtt aggggctgat atcgaaccag tctttaatgt    21960
aaaaaccttta ctttaaatta cttaaattca agagatggaa gagatggaag aaaccactgg    22020
aaaggctgag cttgatcaga ccaattaaca aagacggata tttatctcag acaactgaca    22080
ctatactata tagaacacgg gattatagat gtgcttaaaa acgaagtaaa agatattggg    22140
tacgagcagt tgttgagacc aaagacggcc accagcatcc atccattgaa aagtcaaaac    22200
actcaaaaga aaagagttac tggtattaga agcagagatt tattgaaat tatattgttg    22260
gagccaaagt ctatagttcc agatcaatgg aaattggaca gtgtgtttat tgggtataga    22320
aagaaatgtg ttatttacgt ctataatgtt gggttgttcc ctgccataat ttggttgcta    22380
tcgttaatat tagtcattgt taagcagcat tgcttgaata tacttttttct ataactatat    22440
ggcggtttat agtacaacat tctaaggatt cttgaacttt ggaaatcacc cctggagctt    22500
ttaagatgca tcagcatgtc tcattcatct gtaatatatc atgtgaccat gctttatgct    22560
cagggagagt agggtattta ggatttgatg aaccgtatag aactataaaa ttctgcaact    22620
attctcatgt tatatgctgt tatataagct ctacaagtac agataacgcg tttgcttgaa    22680
ttttgttcgt gcaggagtgt tgttatttg gttaagatga gaagagaatc tattatgttt    22740
```

```
atcctaaagt tagcctaaat ctcgttgccc gaatgtttac cgtgtaaaag ctacttttt    22800
taccacttgg agcatcattt tagggttgtt ctgtaagcag cttaaggtta tgtaaggtca    22860
agttttctt gccattaggg gacttagaat tgttgagagt taaagaagaa acgtagtgtt    22920
atgtttatgt tgagaaattc aacattgacc tgaaaaagac tctagtacat tgacttacat    22980
aaactaaact agatcataat cgacaacgtt agctgggaag ttggctagat ttcaacaaaa    23040
aacttagtat aaacaataaa taaaccttat aaattattgt ttttttgctc tcagagcaaa    23100
tggtaagttg cacacccctta tacatacgca aaatacatta aactcttata gaaaaaaaa    23160
acttgtgctc ttaaaggtcg gcctaacaat cttgcaaata gctatttggg ccaataacac    23220
aacaatgctc tgataattca gaagagttct ggttgtttgc agaggactag cctcttaatt    23280
atcaaaagca ttttgcctgt tattgtggaa caatcattag caatgtaata cataaatcct    23340
tttgttgcat tctactaaat taagctgtta ttcactcaca tgactctacc cttagcagct    23400
gcttgaattc catgtgttgg attttcttag tatacgtttc tactaacttc agcaacgtct    23460
aaccgtttac ccttatgctt tgcatcaaat gacggagtct ctgcagcctt ttctggattc    23520
agctttggac tatgtgattg ctgtcccctta tgttccagtt tttttctttt catttatttg    23580
ttcgttacct acccgtcctt gagcattttc atcaaaagaa atccgtgtgt gactattcct    23640
cttatagtac atgatttaaa tatatgagac ccccgttaaa acagcactgt ctaaaggatg    23700
cttaaataat agattctaat caccaacttg tttgtactct cagttcaatg gtccctctat    23760
cagggctgac tcaccatgct taataaacat aacgctaatt tcaacattat cccacacatt    23820
ggagttttt tttccatcaa aaaaataata tataaatagc tttcttagat tagtgtattc    23880
ttttcgcct aatatttgtg atatgagcta aagatagat cgataaggtc tagcaagaaa    23940
agagtcattt agttctcaaa ggtaactgtt ttttttcat gtcacaatga ccaatattta    24000
aagtcgctga tcttgaaatt gcaaaaaaa aagaaacact attcaactaa cacatacaac    24060
cttttgtac ataaaacaa gtagcttttt caaacagcta cttaaaattc agctacatcg    24120
tgaaactatt cacttttcag ctagtttggt ccgactggaa acgtacgtcc tttataattt    24180
tttgttggac ttttctactg gagaatctga atttcgagac caagtattta attatatgtc    24240
caaaagaac gtaataatct ggaagtacgt ctttactact caaattttca aacttaattt    24300
tactgtgtgt attggatgaa tcttccataa atacagtact tggtaaaact agaaccctct    24360
aagatcctgc attttcccag tttaaaatat gtatgggttg aaaacagaag agtaatagcc    24420
gtctaacaaa cttttgatat ccctaaagaa aacatttcta cgacaatatt atttgtaata    24480
ttggatagct tccatttcca atcttttgcc gcacgaaact caaattaaaa acatacaata    24540
tttgtaatgc aataatgtaa tcttgataat ttctaaaaaa aaaacaccca aaaggtttca    24600
ttgatccatt ctgtaggaat aaatcagaaa aaaacagtgt gcttctttct aaactttatc    24660
aaaatgtttg tcaagctata gttttttatag acactcttct ttttctttc tctccacagt    24720
ctaatttacc aaacatttt ttatagagtt ataataaatg tcaaaactct atacagacaa    24780
ttatgtatga ctgttatgcc ttttcctgaa cttatttaaa cagtacgttt cagaaaacgt    24840
tttgcggcaa agtcgaattc gtggttcgct tagtttatat ttcatgtggg agtcatgtaa    24900
gcctctcgtt ataggatagt agacgccggc tgttttaaac aggaaggcta tagcttaagg    24960
aaaatcgtgc atccataaaa tcatttctgt aagggctcat atataagaag ttgacgtcaa    25020
cgaaaaatca atcaataggt gcaaatggaa cattacgaag tgatctatcg accagcaaga    25080
aaagtttgca ccttatgagt atctggcaat ttctcggatt ttcatgttta gatcacgttg    25140
```

```
caaattttca ctaaatagtg ctatgtggaa acagtgctga gggtaatttt tacaattacc   25200
tagagagtaa gattaggtac taagatgtga tgtcactttc agaaatagtg ctcacttaaa   25260
gttgtgtaac tggcgatggt ttcattcgaa gcaaactata gtacaggtgc gtttaaacca   25320
aaaagagtac gattcttttt aaattttgag catctttcat gattgagtta gcatagtttc   25380
gttatcagat tcaacactgt agatagttaa caataggcca atttcaggat cagtatttat   25440
ttctgattgt ttgacagcta tatttagacc tatgttctga gttaagcaca gaaataacga   25500
ttaaaattta tatcagcatt agttatggaa gacaccctca gtcatcatgg caccaaaaca   25560
aagattaata agaaaccagt tcaactccaa ctgaatctat tgatatcgat ctatataatt   25620
tgtggattct ttttaagtta tccaactgct ggactaaata tgggcatcac gtcaggaatt   25680
gtgcctcttg aacaccagtt tttatagaat ttacagctac tataaatatc tacattgtgg   25740
cataacgcta ttccttaacc actgttctcc aatgtcaact catctagtat tttttatata   25800
aaatatcatt tcttattttg ttcgcgctgt ttgcaaagaa atttgtttta ctatcataaa   25860
attgattaat ttgtctccca agacctttta catgtatatc attactatta atgtgcttat   25920
tcgatagtta tccgcatata ttctgaatat catcatactt cgctggaagt tttccattat   25980
ataaattatt ttttaggttc tatcgtttta tttacatata tatcaatgtt gtttatttat   26040
tgttgatatt gaataacttt taagtccatt aaaaaggata ttgcataatt ctcactattt   26100
ggttctcaat gaacagaatt tgtaaatata cttgaagtta ttttttcagt tttctgtata   26160
tagtgacatt cctaaactca tttagtaaat tgaaattagg ccataactag atttatcgac   26220
tcagagacag ctttataaag atattcctaa tcctcttact aataaaacaa aaattgcatt   26280 cactttttt ctgggagagt ctgattcatt tttgtttttg ctcaggaaat ttaatcgtgt   26340
tataatataa aagaagaatt tttctcaaga gtactcttag acatatttat ggagaatgag   26400
tttgtttgcc tgaatggtaa agtagctaag aatcttact ttttttcaggg ttttttttat   26460 cttgacttaa tgattggaat aataaattag atttgtaaaa aaattgacgg aattagtttg   26520
agtggcttcc catgtaaata tgctctctat cagatatatt aaacatgaaa atttattata   26580
cctcattgta ctctcgacat tagttaaatc tccaagttct tcctggcgca atatatttat   26640
ataatcataa tggagctaat gaaaagaatc ttgctcaagc ttgctatcta ttttttgact   26700
actggattta gcgaaatata aggttattgc tttacagagg cctttacaag atggatactc   26760
atgaatattt agagaagcta tatttgcgta ctttattact ggtggtattt ttcaataaca   26820
agtattcttt agcgttgagc taaataaaaa ttataggcca agcaaatgct acacaaactt   26880
ggctcttgag agaatagaaa atgtaaagct cgagaaaatc gcatgaaaag ataaaaaatg   26940
ttacggttgt ttattaatcc catctatttc tgggtaactg tttcttattt tcctaatatt   27000
actagaaaaa tataatccag aaagatgttt ttgagttggt tccagccaag gcatcaaata   27060
tcgaaggatt ttctaattag ctctatttga ctaaagcaaa acaagaaaat actcatcgtg   27120
tttgtgatag gtgaaacacc tattttgctt ctattgtatt taaggaaatt agaaggtcca   27180
cttcaacatc tagttgggct acaacctttc tgaataatgc ttcttcacca ggtactataa   27240
ttatcaacct tatacggaat ctgttaatgc gcacgtgccc gaaacaaaat gtgtcaatac   27300
attactttca cttatacatt tatattttgt gcatgatatt tggttatatc ttctagtatc   27360
tctttaaata gttttgttac acccaaggtg actgaatatt ggtaccaaac agtcttctaa   27420
ttcattgctt gggcttctag acatgtcgta tgagtctgag tagtgaaaac atacgattta   27480
```

```
caacccgccc tttactattt cgctatacac ataggtattg cccgacatta tagcatatgt  27540
cgaagtaaat attatgaaat tttttgtatt aataatattt atttcaaagt aatgtaattt  27600
tctaagagtt tggccaacaa cgggatcaaa caagtagtaa atatccaaag tgctactttt  27660
cattaagtat tttttttcca ttattgacaa atcttttttct ttacaaagac agctccattt  27720
ttaaagcatc aggagcaaga actctttagc cgctgctttt caagaggctg caggaatttg  27780
ttagtgtcct tgttcaaatg aagaatacta acttcaaccg aggagaccta gttcaaagaa  27840
ttactattat tgaaattgtt caatatacat agcttttgcc ctttatatcg tactgtacat  27900
ttgcaaagtt ttcaaactag gaagcagacc gtctcttgac tctgtttaca aaacccgaag  27960
ctatctttt taattttccc tttatgcgta atacaaaacc tggaaaaata acgagaagtt  28020
tttgcaatat tcgaaacttt gcaaattaac ccggtctgca atattttttg agcagctttt  28080
cactgttagc tttactctct tcattttttgt aaacataatg atgtctttaa tgactagaag  28140
gggaacttgt tattatcgta gcgccactta tctctactgt atttcagtag tgaaacttta  28200
ggccagacaa aattgtccta aacctttggg atttgttaaa atcccctttg aatttcgttt  28260
aactataagt aattatccga agtctacatt tactatcatc catttttata ttgccaaata  28320
cttgatagaa actatagata gctatgaagt cttcaacaaa tcgattttttt cctcatagct  28380
ttcttaataa cttgctgtta tatattgtaa tcccaaaata tgaaattgtt gattatagcg  28440
cccagcttca aagccttgac aaaaatactg gaaatgatgc gtaaaccatt gagctttgtt  28500
ttgagaatct tctttttgtt ctttagaata aaaggaaata actgtttata ttattcttaa  28560
cagaaggaaa aagaaagagt tgtcaacgcg tacatatttg tataataaaa gctccttttc  28620
aataaacgtc taaggcggaa ctgatagtat attcatgctt gaaataatta ctttcgggct  28680
atttccgtcc ataaagcgtc tctagaggcc agcatttaac ttcttataaa atcaaaaatg  28740
gattactctt acgtgattta atcaccagct catggaggtc ttttttttttca attgggtgct  28800
gtttagtaaa aaagttaagt tatatttcca ggcgacttta agaaggcttc gcctaccaaa  28860
cactaaccaa aacaaataac agagacatag accagcggta ttctctcttt tgccttatgc  28920
gtgaattact taaccttgcc tcgatgtaag ctctatcatt ttgaacatgt tttttttatgt  28980
ttttacacag acccaatttg ataaactata actatatgta cactttataa gccattgatt  29040
ttagtgtaaa cgagatcgaa aaagaaacag atgctcctcg gtaatttcac agaagccaat  29100
atctgttttt tttttgtaca acaatcaagg aaaaagtggt tcaccggttt caaatgccaa  29160
atgctagaat ttgagcgccg agtttcatat tatatgaagt taggtaattc taaaaagtcc  29220
ttttgcaaaa ttaagtataa gtttccaaag tacttcgaaa ataacattca gcggcgtgca  29280
gagacattag gtaaaagtag tcgtttctgg ccaatggtat atatatttg atggtttgaa  29340
atattttcct cggttgttca attagaagag ttgaattggg gtgtaaaaca gtataacata  29400
cctactgatg ttatcataaa cataatttcc aactcagtaa tatttgtttt tctaagaaat  29460
agtgtatgtt ccacttgcaa actcgactta acaattata ctgtcgctta acaaaaccag  29520
tagtctttga acttttgca aggataaagt gttttttggg aatatattta gacttgagtt  29580
tcaatgctct gaaaaaggct atcactttcc tatcaaggca gagaacaact acatatagag  29640
aaacaacata agttaatgag catatatcag catctttgat ttaaacagct ctagtattga  29700
aagcaaaaat aaaaaatatt actgttttgt agcctatata atgcttgcct acaaaatgtt  29760
tcctgtcata attgtaaaaa gttgtttcga atgggcaagc taagtcccat gcctttttat  29820
ttacatcagg tatatctttt ccgcttctct agagaacgaa aagtcgtgag cgtcataggt  29880
```

```
gcagcagaaa aataaaaagt cagtagattg agtagatttt tgtttacttt cccttgagta    29940
cttgcgccca ctcaatgaga gttaaagcaa ctgatcatgc tgattctgat tgttaagaga    30000
gataatttaa acattggtga atcgaaatgc gaacatcatt atgagccaaa tgaagccaaa    30060
cagacttgat caggcaacct gtcaaaatta aggagttagt atttactaat gcatatggtt    30120
gtgtttatat ttcttagcat tcaaaaagtg cacccgtcct tggatatcta gcttagtaga    30180
cacatgatgt tccctacaag tatcagatta ttgccttgct taatttagtt tttatgttgt    30240
attatataag ttctttacaa aactccattt taaatacttc cacatagatt tccaaagtag    30300
agttaatact tgtcaatatt tcctagtaat aacaatatct atacctctct catcagattc    30360
gagaaaatag gaacgttcta tgtattataa tcatgattac tttgttgata tcaagcttgt    30420
tcgtgttctt ggatcgattt ggcattgtgc attaggcttt gacgtagtga caaagctgct    30480
tggttgaata ttctttcagg cacctttctt gctagagttt gatcacagtc tttccacaag    30540
acatcataag tcttttcctt gcctgattct tctgaccatc caccgatacc agtcatttcg    30600
ttgattcttg ccaacatctc acgctctgtt ctaggcggtt cctggtaaat attggggttt    30660
tctttatagt atttaatcca ctgtacattt gattcacgat ccttcaaatt aataaccagt    30720
aaatcgactt cataagcatt gtcgtttatt ttcttgacta gtctgtatgg cccatactat    30780
actggtgaa ttttgtgta ccttatattc acaccaaagg catcttgatg cactaacact    30840
aaatcaccaa ctttatattc aaaatatctt ctttttctat tatggtgttt tccttgttgc    30900
ccttgcgctt tacaatatta tccagtgttt gctctaaaat caatttcaca cgtctcacaa    30960
attcttctgc gttaggtgaa tatttgttat cctccaaatc ccagctattt actttttta    31020
atcatgttcg attcataccc gtaggcgatt tcaaaaggac ttgctttaat ggaatcttgg    31080
tacgttgaat tgtaactaag ttcacacata gatagatgtt catcccagaa taattgatcg    31140
tttgaagaat atttccgaag taactgatta acaatcttgt tgactctttc ggtttgacca    31200
tcagtttctg gatgattagt agttgaaaat aatagagaac taccattgag ataatgtaat    31260
gtctgccaga acttattcat aaaccgaata tctttgtcac taaacaaacg agcacatgca    31320
gtagcattaa gtcttttgtg cgtgggtata agatgtgtca ttttgagaa gcgatcgaca    31380
ataaccataa tgatagtgta gcctgttggg attggtaaag gggaaaacaa cccttgtctt    31440
cttctggtgt tagtgttgtg ctgttgacag atatggcagg tttctaccca tttttgattt    31500
gtctcaacat agatgaccaa taaaaactat ctttaagatt caaataagtt ttccatgcac    31560
caaagtgaca agcatctttg gaatcgtgtg catttttgaa tattctatac ggtagtttct    31620
tgtagtttgg aataactact ttaaagaaat cttgagactc taatgtctta taataacgta    31680
cctcatcttg ataacagaaa tgtttgatat gatttttat ctcaactgga acttttgttt    31740
tctctctcaa agttctgaat atcaaggcat aattagtatt ttttttataa cccgtaataa    31800
ttttttttt taactcttga ttggcttcga tagtacttag tgtcaaggaa tgtctctgtg    31860
tttcatcctc ctcttttac gtcaattcca gcaacgccaa ttcgattttg gctagcgtta    31920
acctgtttta gtggttgtat gggtatctag ataacgcatc agcagcggaa ttgttttttc    31980
cctgtaagta acgaatatca aaatcaaact gtggtaaaaa gtccatccat ctagccactc    32040
tagtggagtc tatgagattt tggttttta agtaaattaa actcttgtga tccgtcataa    32100
caatgaaatg tcttcccatg agataatatc tccatgttct taatgcttca acaacagcca    32160
taaattcacg gtcatatatt ccataattca gttgacttcc aactagcttc tttgaaccgt    32220
```

```
aagcaatcac acctcgtcat ttacctgttt cgtccaactg ttctagagta taacctaacg   32280
atactccaca cgcatcggta tgtagaacaa atttacaatt gcctgaccag cttgggtgca   32340
ccaagatggg acttgatatc aaagctttct ttagtttgtt gaaggcttcg tcttgttcac   32400
ttgtccattt aatttgtttt gtcatgaact tatgaattgg attagcaatt ttggaatgcc   32460
ctttgatata ccttctataa tacgaagtta aaccaataaa cctttgtgct tcttcgacag   32520
tctttggtgt tggccaactc tttaccttt ttattttctc gagagcggtt tgaatacaaa   32580
ttggtgtaac aacttgtcct aaaaacctaa attcttgata aaagaatctg catttcgact   32640
tcttcgtaat tagtttatgt tttcttagtg tcgacaaaac ttctttcacg tgcttaccgt   32700
gagtttcaac atcttcggag tatataaaaa tgtcgtctaa atacacttgg acaaatccat   32760
ttattttttt agacaagaca ttattcatca tctgtggaaa agtcgcagat gcacttgtta   32820
gtccagccgg cattaccatc cattcataat ggccagagta gaaaaagccg tcttctcgac   32880
atcttcatcc gcaattctca cttggtagta accaggcatc aactctaact tagaatagac   32940
ttttgcctta ccaaatcttg aaatcaattg atcaatatct ggaagtggaa acttgttcct   33000
agcagtatta ttgtttagaa tcctataatc aacacacata cgcatagtac catctttctt   33060
tctaacaaat agcactggac tgttaaagga tttggaacta gttttgatga aaccttgttt   33120
gattaaaact tcaacttgtt ttgttagttc ctgtttctca gagaagctta ttgggatttg   33180
tattcatggg ttagttaata ttatcagggt tttcgacttc gtcaacatca atcgagtaga   33240
taaaagtgag ataggattca tttctcctaa ctaacttatt aacgtacttt tcttgatatt   33300
gagtgaaacg ctcgatggag gtggattgat atttaaacca gttgatttaa cggcatcaac   33360
actcattaaa tttttgaaa ttaatttatt gacacttagt caatagagtt cccaatatga   33420
atatctggtg gtcactgacc aacatgtaaa gcgacttaat atcacttata ttaatagttt   33480
cattgacgtc ttttccaaat ggaatagcta taaaaccaat aacaatagga ttttgataa    33540 ttgacgctat tcgaggatta ccaaattaac actttttttg ccctgcatga ttcacaagca   33600
ttttaacatc atttcctttg ttatgaatat tatgtgaaga atagtagaaa actgaattat   33660
ttatgctatt aggatttgct ggtggcttag taaaactaaa aaaaacttga atttcttacc   33720
aacttaaaat tattataagc agttttttag gtccatcagg agccatgaat ttactatttt   33780
cgtctcgttc ctattttttt aaagttgttg gaccttggtc tgcgagggat gccattcaaa   33840
atacagatat aatcaggctt gtagactatc ttatctctgt atctctcatg gaagcgcact   33900
aaaatttcgg aaacggaaat agcacctagg gtctgttgta acaattccgt attcctcatt   33960
ccttgttcaa ttgtactaaa atattgagca atagtaggtt tctcttcagc aacatcgaaa   34020
atagtaggta taggtaccct aagttcttcc tgcgagctct tcgttggttg atctgacttt   34080
cttctacaca taaatttgat gatttccgtt tcgtggcttg tttttcgcaa tagaaacaaa   34140
tgttttttta atttagcttt agaattgtgt cagcattctt tcagtaaatc tttatcagtt   34200
aatttagtgg gggacctctc agaaccattt tttttcaggg tgataacagc gcatataacc   34260
ttcttatcat atgataccct acaatattca taatatattc taatttgtga taaccattgc   34320
attgccgcgg ctcttccttt taacgaaagc agtttgctaa cattcagcaa aagttatttt   34380
tttacttata aacatgtcga gcatgccttt ttctcttggc tgtttgtgca cactgcagcc   34440
ttagttcatt ttatcatata tttatgtctt cctggtcgtt gtgttctcaa tatatccctc   34500
tacaatcacc atattagttt ggatgttagg aagttgaatt gtactaactt gttatcttta   34560
tctaataaga agtcgaacat tgcaggtact acgtacttgt tggttaatct ttaaattttt   34620
```

```
tttctttctt ttagttcatt gtttctagat ctaaatagaa atcattccat tgctgtttgc   34680
atgttctttt cagtttactt acttccatct attattctta ttgacccatt ccatcttctc   34740
ctattagaat gattctgcca actagactat gcaaaaagta catgtagcct agtagtggta   34800
aacacgtatg acttttcact aggaccagtt cattcttttg cttttcttcg tttcttagtt   34860
atagcctcca tggttaaccg cagaatcata taacttcaag ctatgaaggt aacgcggcgt   34920
tctatataat acatttttat ataacccact gatagttaaa tacctgccta cagcagaacc   34980
gtttatgata taaattttgg atcagtgttt aaagatgctt tgaatgatct aaaacttatt   35040
tctgccaatc taaatgaaaa atccgccata ttatagttga gtgacagcct agtccttaaa   35100
tcgcatctct aagtttcttc acattttttg ccttcacaaa tataagcaca tcatttcacc   35160
gtatgttttt tgttcaaaat actgagtcgt gctgcaggga attcatctac aatcctaaca   35220
atctaagttt gttaactcct atatactatt ccattcgtta attttatttt attttttcta   35280
aaacatatta gacggtgcgt aaacgatgtt tatcttagga aatggctaat caaaaatatc   35340
ttatttgcat tgaatagaaa aaattttagg aaactattta aacttcgttc atagacaagc   35400
tatatgttct tatttatgta gagaagctat aagctaatta ttttttttcag ccattataag   35460 tttaagcata taactgtgtt gaaagccact aaataagtga taaaaaaatc aaaagaccta   35520
ctagtataca gagttaattc tacacttgct accctaatta taaaaagaaa ctatcgatgt   35580 attttttgtat ttcttctgaa caattggggt tttaagtcta cctacttcta aaccttgatc   35640
atagatacaa taggtgcaca acacaaacac ggtgtgtggt atattatgag cagccaattc   35700
accattttga aaagctaaaa ctctgtacca taactttcag tgggatccgt attatcaaaa   35760
ctatatttaa taatcctatg tgctaactaa agcctggaag ctatatatat ataatttagt   35820
tttaattcat aaagttttt cattggactg ccggaatgtc atgggccttt aaaacattca   35880
ctgcttaact ggtgtagatt ctttgttaca ctgtgcattg ctactcgtct ttcgtgtgaa   35940
tttcccatct ctattctaat acctgtattt ttctgtttag attttggaca ttgagttaca   36000
ctactcgctt atgtttgttg tagctagttt gaactgaatc ctggaagttt attatctttt   36060
tgtgttctca caccacttgc caagggactt gagcctgaaa aaaaagaatg agttgaaaaa   36120
aaatgtaagt tttacacaat tttaatcatt tttcttaagt atgaatatca gcggtcttgt   36180
aggatgtttt ccatcaataa gctgaactca ctttatagag cactgaattt catttttgta   36240
taacatttgg ttatttcctc tcagtctggc actcgctttt attcattttc ctaataaata   36300
gctaattctg tttcgatcag gacttctaac tgtagtgtgt acgacatcta attctagaaa   36360
gggtattctc acttcctagt taagatgtgt atcatattct tttataaaac taaaagcacc   36420
tagcctattg agtttataat actgaaagtc tactgaacta gtcatctttg tacatttctt   36480
tagacttaga tccaatcttg ttgctttagt ttattttcta tatagttatt cgagttaatc   36540
acaagtatct aacaaaaggt ccatacttac cgatttgtgt attaggattt ttcttctatt   36600
tctttgtagg tagtagtgtt tctaggggta acctttcaaa ttggcccttc tgagtctatt   36660
ctagtttgaa aaaagcaaag ttctcactaa ataacacata ttaataatag tctttgctac   36720
ggaactaatt atttcttgat ctaaactatt tttgctcctg aatagaagga cctagttaat   36780
tttttatatt aagacagatg aaatcaaaga aagaagttga ataaagaata ggtatatttg   36840
tactaaagtt tgctaaaagc gatttaggtg gagcttcttt ttatttaaaa acctcccata   36900
aacttaataa caataaaggt cttcctgtaa acttttgaaa aatgtaccag agtatttaag   36960
```

```
ttaagtccaa accacgagaa taggttaaaa gctgctactt agtttatgtt tcattgcctt    37020
ttcagtatct cgagacttct ccgctgtcaa taataaacag ttgtctagct attttgttta    37080
ggttgggtaa aaacctacgg aaagacaata ggagcttagg ctatctattg atagatcaat    37140
tatttgtttt aagaactata gaattaaaaa caaggcagta gttgtagatt ttaaagatta    37200
tttagagtag atagatagta aaggctgtac tgaatatcaa tgaggatttg cagaaccaac    37260
aagtggcctg catcaagcta tttaagtgat tctattggta ttttactaga aaaggaaggc    37320
taatcatttt tccaatgacg gttcatataa tccaagtttt aaatggtttg catcatcata    37380
ataggggtat ctaaaaggca taaatcgacg aaagtgataa aaattactta ttaaacgacg    37440
tatttacatc cacgtttttg ctggaagtac tgaatctgcc tactgctagt ttggggaaga    37500
caataataca caaaataaag acgatgatga agattccagt tttttttaaa gataaaaaaa    37560
tagatatata tgtataattg tatgaatagt tttaataata acttatgttg ctattttgat    37620
agcaattcat tttactattg aaaaggttac ccaggcaaat aatatgttta gcacatcaga    37680
ttctgtacta ataataatat agagttatgt tataacgtca ggcaatactt atgtgtatag    37740
cgaaatagta aatggcagat tgtaaaccgt atgttttttac tactcagact catacgacat    37800
gtctagaagc ccaagcaatg aattagagga ctgtttggta tcaacatcca gtcaccttgg    37860
gtgtaataaa acttatttaa agagatagta gaagatataa tcaaagatca tgcacaaaat    37920
ataaatgtat aagtgaaagt aatgtattga cacattttgc ttcgggcacg tgcgcattaa    37980
cagattttgt ataaggttga taattatagt acctggtgaa gaagcattat tcagaaaggt    38040
tgtagcccaa ctgatgttg aagtggacct tctaatttcc ttaaatacaa tagaagcaaa    38100
atagatgctt tacctattac aaacacgatg agtattttct cgttttgctt tagtcaaaca    38160
gagctaatta gaaaatcctt cgatatttga tgccttggct ggaaccaact caaaaacatc    38220
tttctggatt atattttttct agtaatatta ggaaaataag aaacagacac ccaaaataaa    38280
aattgtttag atatataatt aaagcactaa acatcaaact aaggatatcc ttacagtctc    38340
gatacagcta gtccagcata cgtacgcgta atcagaact agaaccgagc tattttttag    38400
ctcatttagt tatgttttct tcccttgttc tttgaaacgt cagcctacgt atatcaatct    38460
agattgatac aaacctgatg ttcttttaaa tagcgagtta gttccttttga cttagtttgt    38520 ttttatttgt tatttagtat aagatctttt gataatagtt caatcggtaa ttgcaatagg    38580
gatctctaaa gtaaatgtaa cgcctgtcaa caccatatat ccattatcta catgtgcatt    38640
tatacacgta ttaagcacct gcaacatgct cagctagttt acacaggcta tcattgaatt    38700
ggatattttt gatatcgata tagttattgg ccagtcgtac aaggttttgc caagcttaag    38760
ttcattaaga catttgtaag ttagaaatag ccacaactcg gtactcttag cctttttcga    38820
tatgtgagag ggcttttcag ggtgtgatcc aaaaaaaaag gaagtgccag tagatagacg    38880
ataacatact gatgttaatg tttcgatttt agaatgggga ggttaacaag gatcaagtat    38940
ccggagtagg aagttaaatt atttatcaac gggttgacag gactggcata ttaaaaaaaa    39000
taaagaccta aaacgtaata agctcgtaca ggagtctgct atacgaaaaa agagtagcaa    39060
ctgagggtga ttccaggttg cgggcgtgaa gtatataaga cggataatat cctattatat    39120
agaattgata taattgatat agctcctaat cgggagtgaa agcagcagaa ggaggaagag    39180
aaaaatctat tactacttct actacgacta acttctacca cgcccattat ctactcgtga    39240
gctaatacac ctattgccta cttactaata cgtatatcac aattatcatt ccttcataca    39300
atactataga tattgataag attagtgatt attcttaaaa agattcaacc gtcaaaacat    39360
```

```
cccaaattag gaaataattt cgacacccttt ctcctggacc ctaatatttc atcagtttcc   39420
gatatagtgt aacggctatc acggtccgct ttcaccgggc agacccgggt tcgactcccg   39480
gtatcggaac attttatgcc tggttagctc aatcggtaga gcgtttgact cttaagattt   39540
cttcttataa agaagtgcaa tcaaaaggct gcgggttcga gccccgcatc gggcttaatt   39600
ttttatgttt ttgcttggtt gttactcaca gtatagaaca gctctaggtt catttattat   39660
tttatcctcc tttttatta attactcttt tatcaagaaa agttcagtta agaagcactt   39720
tatagaagaa cttgcttaag ggtgcaagga agaaatgct gtcaatgagt gatctgccag    39780
atgaagatat tctaagtttg tatatgtctt ataataatgc caaggaaaag gaaggggaga   39840
ttttggaact cattcgaaat cgagtcagat taaggagtag cattgaccat cttgtgaagg   39900
tgttacgggc agatggtaat gttagacgaa gtgttatgaa gatatttgaa aaacctctat   39960
ggagaagact gaacgatagt aaaattagaa aaaagataa gaagataggc gacaagattt     40020
ccaatgaaat cacacgctta gatcgaaaat atgcaaaact aagtctgaag tatgacttat   40080
tgaaggctga acattcagtt ttggagaatg aactggcaaa gctacagacg aattatgaag   40140
ggcttttccag cgacacatac acaccacagg gtggtaaagt aattggtaga agattcaat   40200
tcaaaaagtt gagcagaaag aggtaagtct gttattcaat gtttatagta tgtatatgta   40260
cacaatataa aagaagaaaa tccttttgta ttcacttaag ctgttttgaa gcatagtatt   40320
gcatagtttt caatgtacag atagatgaaa ccttttggtt catgagaaat gcttgaacaa   40380
aatgatttgc ctactataac atgccaagga gaacccaact cctcgtccaa cttggttttt   40440
atcgcagtgg ctaattgact tggctgtgtt ttatgttcat tatacaggga tgataaaata   40500
tcgacaatgt gtgttttgt ctcgtcgtct aaatctgtgg atttgacatt gatgttttcc    40560
gatgacataa tcttggctga gggaagttga ggtctgaagg tttacaatt aaaggtgatt    40620
gtgtttggta tgatattcaa tgtgctcgat ttcatttcat ctcctgccac gtcttataga   40680
aattgaggaa aaaaagaag tcacgtgccg aagaagaat ttacagtgaa acacagtaga     40740
tcgttaagaa attcttagat atatacatat atacagtgtt aaaggacaga atgtaagtaa   40800
caacgct                                                              40807
```

<210> SEQ ID NO 14
<211> LENGTH: 38649
<212> TYPE: DNA
<213> ORGANISM: Artificial Sequence
<220> FEATURE:
<223> OTHER INFORMATION: centromere-like sequence (CEN-L) ECN3-38649bp

<400> SEQUENCE: 14

```
ttaaaggtaa gactagcttt gcccaaaaaa aaaaattatt actgtttgac tgtcgtgtct     60
actctggatg cccttagtgt gccttgtttt gaggttcaca ttcaaagtca tgaggtctcc   120
taaatattat gcgattttgt ttattgcccc ttgtggttta ttgttccctt tttccacaca   180
taaaaaaacc cgcatttaaa aaaatttaaa aaaacgtcag ctacaggatt cgaacctgtg   240
cggccaaagg ccaaaagatt tcaagtcttt ctccttaacc actcggacaa actgactctt   300
ttttctttga aagtgttgct ggtggtacgt actttagaat ctgttattg cttgtttata    360
tcttatatat ttttatacgt taattctctg agaacatata tagaatgtcc tctgtttaaa   420
tagtaattct ttaatttaaa aatagttttt ttgagggatt taattatctt ccagaacttt   480
tgtttaacct tctataatct tcttcaacct tctatatgat tacccgatta agaaatagag   540
```

```
agatagtcct ttgtctgatc ttttacattc tctgtaaagg acttggtgta gggtgtcgaa    600
attatttcct aatttggaat gttttgatgg ttgaatcttt tcaagaatag ttaataatct    660
tatcaatatc tatagtattg tatgaaggaa tgataattgt gatatacgta ttagtaagta    720
cgcaatatgt gtataatcgc acgagtagac aatgggcgtg gtggaagtta gtcgtagtag    780
aagtagtaat agatttctct cttcctcctt ctgctgcttt cactcccgat taggagctat    840
atcagctata tcaattctat ataacaggat attgtctgtc ttatatactt cacgcccgca    900
acctggaatc accctcagtt gctgctcttt tttggaacac aacctaaaaa aaattccttt    960 catacccttga ttaggacgat gagtaacgtc tcgaaattat tttgaaaatt aggaaccagc   1020
tacttcttta ttctgtaaat aaatttacct tcttaatctt atcaatagga gcctctctac   1080
gtgaatccaa aacagtacac aactaatatt aatataaata acagcttatt ccctttttac   1140
ctagcttttt tcctaagagt tattttctgt aagttatttc aacaatagtt cactcaataa   1200
ctttaacatg aatattcaaa gaaaactat acgtgtcaa cactatctca ctcactacac    1260
acccaatatt tctataaata tcaaattact cttttcttgct taacttgttt tttgttagct   1320
tatatgttat tttgtaaaag ttcttttagc gatagttttt gaatgaattg ctatagagga   1380
gcctgtttaa aagaatttat aataaggagt tggaaaagtt aaatgttatg tatgcgtgat   1440
attccgatga aagctcagtt taacggacga attttgggag agttaactat acccttaaaa   1500
tttctaatct tagtattgat aaatccttct aagtaatcag ctataaaatt caagaagatt   1560
ttctttccat atctggtaaa gactttatat acctactaaa catgaaacca acaagttatt   1620
atcggagtat caaccaaccg attagtacca aatggttaac ctgctttta agaagtaagt    1680 tatttgattt gggatttgat actgtatatc aaggactcaa aattttccat gagaaactat   1740
gttactagac tgctgtttgt tctgggttat cggttttcc attcaaattt tcattggcaa    1800
aaagaaacat cttagtctt ccttagaacc ttccaaaaca ttacttttca ctttaaatgt     1860
cagcaataca atctttaaat acataactac tgcttgttct ttgtaataga attggtaact   1920
tgaggttcgg ttgcacaaat gtaattgcgg tgttatagct actaacaagt gataaaaaac   1980 gttttttgt aataagtatg caacatttgc cagatcacag agacatagtt acagacttcg    2040
caattgaggc tttctcggag attttttgct ggagaatata gatataattt gttcctgagc   2100
agttagacat tggccgtctt tctggagggt ttttcaaaaa cttcatagat acttaaaatg   2160
aaattccacc acttaaacga agaaagggag acttcttgaa attctaaatt tttgttgata   2220
aatggtaggc tctttatgtt tggcttttgc tttaatagtt ttctaaaaaa gctctagaac   2280
aggtaggtgc gatcaggaac atgagcttta ctcaattata accacgtact ccaattactt   2340
aaggaagtga taatgtaaga tccaagagtt cctcactaaa gagattgttt ttaattgtca   2400
aaattctaga aagcacgaag aattcctttg cttacattgt gtatgtgcgt taccttaaaa   2460
atgttttcga tgtggttgaa ccaatgcatt tggcattgac cgactgggac gcagaaaaca   2520
aatttggcat cttaccacac gtctggtatc aactaagaac tcagactgaa aaaatgtcac   2580
actctaggga tttatttaac ttttatggag gggttcctca cgtttattat attctgtagc   2640
ttttgaattt gcaaaaccaa agtgattat aagaatattt agcaaacttt tactacttat    2700
ttgctccgtt ttgctcaata cttccattta aaaaggatta gtttcttctt aaaggtaaat   2760
gcagttttac gccctgaaac gctaggaaat ttagctggag agtatcttac aaaaatacga   2820
ttgatgttag tcatgtagta gagaactcat aaaaagctag cttttttgaag aaatttagct   2880 tggttttgg tatatattgt tattcaaaag gttccattcg taatgcatga tattcgttgt    2940
```

```
taggtcaaaa tttgcattat ctttacttgt ttcatcaacg caatcttcga gtttatcata   3000
tgcaaagtca tagatgcgaa ctacactaaa agataaagag acatcccgct atgctaaaat   3060
tgttaaatcc aaaggaatat atttcaacaa gcagcgttac gcttgtggac gttaaaacta   3120
agcgccttga agtaaaaata gttttaatcc gatttttatc actaatacat tccgatcgtt   3180
tagagattca cacaaaaaat ggcagaccaa tagcactttt cttattcgta gaatatgtca   3240
gattttttga acaatttgga aggtaaaaaa acaaaggtgg tatttatagt gggaagaaag   3300
agacaacgag ttcgtattag gtgcagatat tgcgtgcagt ttcattcagt ttgaacaaaa   3360
gcctggtttg gtcgttaaat ttaaacaacc gcttgcagaa ccatcaaacc aacatgtctt   3420
tggagtggat gttatatcca gtggcacaag actctgagat tttaatctaa taacagtcgt   3480
acatatcaat gaaaaaaagc gaaaactcac gcttggttcg ttctgctttc ttccggaaag   3540
tgaatcagct ggtaactaga gccttttttat tatggaatta tgtgaacttt tgaaggagtg   3600
tttacccaag atgagtcttt tccaaattca cgccatattg ttacagacaa ttttaaagcg   3660
tcacaaaaca ctattataag tcattttgag accgataggg ttgctgcaaa gtatatataa   3720
cataaaccat tacacgcttc atgtgccaaa aaggtttagc ttgaaaaact ttagaggtat   3780
aaaatatatg ttgggaaaac catgtcggat tctgcctttg ggcatatttt acctattact   3840
tttttctcgg taatgtacta aatatttggg aggcaataca gaagagtctc ttagattggt   3900
aaaaaaatag ctaattctga tgacttgcca ttgccggggc agccaaaatt agagaacgct   3960
taccaagttt ttcatagatg ctcacaaata aaggagactg ccatcatcta ttggagcatc   4020
tgcgaatgaa ttggaaaaaa agattcgatc agagatggag agaatcttta tttccgtatg   4080
aaaacgttta gtacggcctt ttcatcttga cagcacccaa tagtgaaatt atacgcaatt   4140
cttttgaagat acaatacaag ataaaagaaa tcctctaatg ttcttttcaa gtttcttcat   4200
tcaagttttt taaaaaaaca gtaataaatt tgttctggga ataccatctt cagcggttga   4260
ttccagtttt tgtgtgttca tgaaagtagc atagccctct acgttttgta atgaactaaa   4320
cggctcttag aaacttgata ctagtattga aacagaagta tgatagtgtt taaacagaga   4380
catctccctg attcggttgg tgattctacg tacgttgttg gtgcattata aaaaaattgt   4440
tttttgagaa gagaagagaa acacgctgt tgaaaagcaa actaatcaat aaccatgaat   4500
atgaaaatat caacaggaga aaggttgaac tctttgccct caatgagcat ttttgtatga   4560
ggcgagatgg aaaagaaacg aatatttata caaactttgg tagcacgtca cctctatcat   4620
ctagggttgt tgaatatat attttctgta gtggtgtggt ggtttacagt attactttt    4680
caagatccat agattttgga aatcacttct tgaaattttt taaaatgctg ttaaatacct   4740
cctttgtttg ctgcataggc ctgccagtgt ttatttaaaa tgagtaaaat attcaagttt   4800
cgtgtagtta tgagtagttt tgatgtaagt gccagaatac cttttcatta aagtctcttt   4860
catgactaat cacagaatcc tttcatggtt gttttctaat aaacataaac atgtccacaa   4920
ccaattttc ttatctttac aaaggacttg aacttatcga atctggtag agggatttaa   4980
tgttattgag cagctcaata ttttattatt aacctgaaaa aaaccctatc atagcaacta   5040
gaaaaactta aacgaagtcc tgattagcaa tattaactgg gaggttaact gaactttagc   5100
aagcgactta gtataaagaa catatgagcc tcacaaatta ttcgttttat taaaaggtag   5160
aatctgttta cttaatatta atcatgccaa cccacagcta acccttatag tagtagaata   5220
acttttgcct ataacgatct atgtagaaat attgtgaata tcatgttgaa atagacaatg   5280
```

```
tataacattg gcaaaataaa tcacaccttg gaaatcaata aatattcaaa gcaaaagcat   5340
ttgttatttg aactagtaaa ttagtaaaac gctcggataa ttcagaacag ttctagccct   5400
ttgcaaatca gctaacaatt ttttacgcaa tagaaaaatg gtgcatactt tgggtgtagg   5460
atatctttag aaaggtaata cataaagcat tttagctcgt tctattaaat tgctttgtgg   5520
tttacccaat taagtttatt gttacagctg tatgtgagtt gtagttcttc ccctacgtgt   5580
gggatatttg tttaattagt tgtgttgatc tatcctttt tgccttttga gaaagttttg    5640
ctgatatagc ggcaacgttt tttcaaatag atatcagttg ccttcaaatg acaaaatatc   5700
tgcagccctt gcagaatgcc gttctgtact aagtaattga tgccccttac ggccaaatat   5760
tgttctttta tttctttact ggtaacagcc atctttgcag gttatcacca gaggaattct   5820
gcttgtgtaa ttgtttctct tatagtgctc gcttcaaata gatcaaaacc acgtcctcca   5880
gcattaacat tttctaaaga acacctacac aaccgcttct catcagcaac ttattcatac   5940
tttgactttg agattttagc gataacaaga gccctgtagt gctgaataat tgtaatgtta   6000
gagctaacaa taattgaaat attgtgtacc acttatttca tcaaagaaaa aataagatat   6060
agataaccct cttgtctctg tatattctta ttcaagtaaa aacttttgat atggagtcaa   6120
aggtgaatcg acaaggttta acaggtgaag agtcaaatcg cagaaccatt gttccttgcg   6180
cgaaatgcaa gaaaaagggg tttttagagg ccacacacct ttttttaata tcataagaat   6240
cagtatcttt agcgtctatc agattaaaag agtaatcatt gttcaataaa cagttacagt   6300
attattctat ataaaaacaa ctagctttt ctctgttttt aaaagttaac tacatcatga    6360
acccatccaa attgtattca tgcagtgttg acactggtcc aaatagaagc cctatgcaat   6420
tttctgatcg actgatccac cagagaatca agagcaaatt ctgtcccaca tctgcatgaa   6480
aacgaagtaa ttagaaagta cacatttact actcaagttt tcagactttc ttatagtatg   6540
catattagat gcacctgaga aaagtacatg tagcatggtg gcaaacacta ggcgagtgtt   6600
gcttctttgt ataataattc atcccctgga ataatcgtca ggttaatgga aaattgagct   6660
gtgtgccata aatagtcgac gagcaagtga agaaattttc cattctacat ttacagtgtt   6720
acgtccattc ttttgtatat attttgtact acaactaatt ttgtaccaaa agtacaggac   6780
ttccaaaata ttttacacaa gctatttcaa acaagacagc taaagtttaa gaaaagttat   6840
tcggttatgt aagatcttat acacatgaat ttgacttcaa tacaagctac taaaccaatc   6900
aatgggagct aacacaacac cttgaaaatg atctgccaat aaacaagaaa agattaatgc   6960
taagcttaat taagaaagaa ttgtttcttt ccaaaatata gacatatgtc aagctttatt   7020
acctttgaaa ttctcatcgt atatagcttt tgttttcat catgccatac atttccaaaa    7080
gatttctggt aagtaataac accgtctctt gagcttattt tccaagtacg aagttacttt   7140
ttgctttcac ctaactaaaa ataccaaact agagcagtaa caagaaggtt ctacaaaact   7200
tggatccaaa taaattttt ctatgttttc tcaaactttg caaacaaact ccgtctgcaa    7260
tatagctttt actcagcctc tttagtgata gctctagtgt cttcattttt gaaatcataa   7320
tattttggac aagtggaaaa gaaaaaaaaa tattacagcg tcagttactc ttccctctgt   7380
tccattagaa caggtttaga agaacagcat agattacttc agtttttttt cagcttataa   7440
gtaattatca atgtttatat ttgctattat ttacgcgtat gttagttaaa gatctacaaa   7500
cactttcgat agctatgaat tcttcaacaa gtctgttttt cttagttgct ttcttagttg   7560
catcctgcta tatgttgcat tcccttagta tgaaactata ttttatactg ccagacttca   7620
acccgacggc aaaagtattg gagatgagaa ttaaaccttg aactctgttt tcttgacgcc   7680
```

```
cccttgtttt ctttaaaaca aagagaaata acttgttttg tattatttgt agcaggtgta  7740
attcatacat atctgagata gagttgaaaa tatacttatg cgtgaaatga ttgctttat   7800
tcacttttaa tgtaagaagc attttttgag agcacccttt aaatgttagt aggatcagca  7860
ataagttact tttacgtggt tctttcgcca gcctatgaga atcattctct ttttttcagt  7920
agggtaccgt tgaataaaat tgtgtaacct ttaagcgatt ttaagaagtc tttgttcatt  7980
aatcacaaag cagagacatt tatgtctccc ttctacatgt gggtcaccta acactcctgt  8040
tgaaaagaa ttataatgtt gagaaatctt aaatttaagt acgatgattt ttaacctgca   8100
aaaaccactg atgtttgttg gcacgtattg actctacttt ggatatccat actaaattta  8160
tagattgaac tgcttataaa agaatgtata ttaaattaca tataaaaaca aactaagcaa  8220
aagaaataaa catcagaata aagaaattgt tagggcctga ttacggcaaa tcggcacact  8280
ggaccggctt ggtcttagtg agatcaatat agaaatctgc cgattggtct atgttttaat  8340
tacctatttc agaaattcta gtgtaaaggg atcgcaaagg aaacagatat ttccctgtgg  8400
tatgatagaa ttgattttct gtttctttta caaagcgcat aaggaaaaat ggcaatggtt  8460
tcacatgttg aatattaaaa tggtaatgct gaatttttat attctgaaga gtcacgtaaa  8520
tttaagcagt gcttttgcaa aattaagttt gagtccgcaa agtagttgga gaacaacatt  8580
tagtagcggg taagaacata acataagtag tcatttctgc cgaatggctt ataaacgtta  8640
atggtctatg ataccatcct cggttatttg gttggaaaag tcgaattgtg gtaaaaaaaa  8700
caatactcgc tggtgttatc ataaacctaa ctttcaactc agtagtactt agttttgcat  8760
aaaactgcat gtcttccact cgcaaaccaa atttgaaaaa attggcgtgt cgccagacaa  8820
aacttatagt cctagatttt tttgcaataa aaaggaagtt tcaagaaaaa tatttatgtg  8880
tgaatttcaa tgctataacg aagggtaaca ttttcaattt ttttattatc tatcacaatt  8940
tcttccaata ctcaaagagc ttacaagcgc ctaactatgt tgactcatct tgttgacgtg  9000
gacaattaaa gccttcacca ataggcggta taaacaccca ggttaggccc aatgaggctt  9060
aacagattga attgggcgta ctgtttgact taggaagtta ctattcccta actcatatag  9120
ttatgtttac atttcttatc cttcaatggt aaacggagct gtgtgtttct agcttagtgc  9180
atacctaata ctcattgaga tattatgtta aattgcattt tctaatgtga gtccatgtat  9240
tatccaataa aactttttaat atggctattc aaagtacaaa taaaacatgt caatatagag  9300
taactatatt gtttcgttag caataacaat accagttatt ccctataata atctacacac  9360
ttctctaaga acgcgggcta gcactttggg tagcactttc agaaacttct aacccactta  9420
gggaattttt ttaagcatat aaaattgacc actttatttt tcgcagagtt ttcgtaaatc  9480
tatttcgcaa gaattatcaa atagctcttt gacaaaccaa gaagtaccgc agtatactag  9540
ttaaaccttta taataaaatt tatcactgcc ataaacatcc ttgtgtaata atatgcgact  9600
acaaacttcc aacgttccgt aaactctaaa tccactttat tattttttctg cacttcttta  9660
tgcttctaac atgcatactt tgttcacatt ttttaaaaaa gtgtgcatat ccaatgaaga  9720
ctcttcaacc ttattgctat ctcttggacc taaaaaaaca ttagagagtc tagtagatga  9780
taatctcttt tgtccaattt caacaacaca gacaacacga catgtacccc cataaactcg  9840
acgttaggca atggtaaaca tcatgttgtt gttacttta tgtaacagtt cacctcctaa   9900
gaaactgtaa attaatggaa aaataaattg tgaattgggg atagttgagc aagagaaaat  9960
tttttgtttc catcttttta atggtatgtc tattctttgt atagcgtcca ttaccaaaat  10020
```

```
ctaggtgttt tctaaaacca tgctattcca atatgtggag cctaataaat acaaaacaat   10080 aagggcaaa gcaatactat atggaaatct ctcacggcta tatggaagaa acaaaaaaaa   10140
acaagacgaa ttttaacttt caggggacaa ttggggataa actgccaaga atgttataat   10200
aagaagacac attgatcaac aaaacacgca aatcagaaat taaccgatac tcatacagca   10260
ataaacactg ttttaaaaga atagaaaaca ctggaaaaca ttagctcgag gaagacaaga   10320
aaataggctc agtagagttt gggagccttt atccagtttc catgtattgt atattgaaaa   10380
taaagatgcg atcatacatc caagtagcga tttcacattc taaaattaag agaaggtaga   10440
ggacagaatc tattgactac aaatagatga gatatttagc attatatatg atgtcaaatt   10500
cttttcaaat tgcatgtttg ggattttttg tatggctgcc tccaggctaa aactcaaaag   10560
aacaatattg aaagaacagc gtgtagctct cttgcaggct attttgggcg atatttata    10620 tcatgggtta tatattgcac attggcatct taaagactcg taagcgaaat agagaaacca   10680
tttgtagtga gttttttgtca ttacagtggg actatatcgc catttattaa gaatttgttg   10740
agagatagag gcagcagact aaggtactac gaggtgaact gaataaaaat caagtgatgg   10800
ctagacaaaa tatgccggcc ttttttctaa atatattggt gttcagtaat ttattatttg   10860
aaagcaaaca aaagttcatc acaagttatc caaaattagg aatttccttg tagagattgc   10920
ctctaggaag tgcaaatgta gcctagagca ggctcgatca cttcagctac tcaatgaaag   10980
gctggtaact gctcctgtct tagcactaac aataatcgaa gaatgataca actttaaaac   11040
catcgcaatt gatatgtgga acattaaggc aattaaaacc aagtatcaag ttgttggctg   11100
tacggcaata cggatcaaaa agattattat atgccaaatt ttgatcttca tcaagaaaag   11160
aatttcaaac gatcgtaaag ctctaaataa attaagaagc ttacctcttc taaaaactat   11220
ttcttgattt agactgatca ccattcgttc gcatatctgg aaaatcagaa acagttccga   11280
gaaggtgtat tagccagatg gctatttttt atcgtccaat acgggtcgac attcagtgta   11340
ttaaaaggca ccctgacaag acactagata ccttatttcg atgactgatg attttgaagc   11400
tgaatgaaat tgccctcttg aagaaaacat gacagtcatt caagggcatg gaaacagagg   11460
tttcaactga ggtatgtgaa tgacaaagcc ttttgaatcc tgaaatacgt tgcgtgaaaa   11520
agacggttca ccgaataaat gagaattaaa cttaaagttc ctatctccct gagaaaattt   11580 tatttttatct ggtaatcgga tgtaacgagt attctcgcat atttgaacct agcaaagata   11640
ttgggggaaa agacacaatt tgtcaacgcc attatgacat cacaagacgt tattttaata   11700
cctttaaaat ctaaaaatta ctatcaagaa gtttcgtttg aaattgtatg attgagaacc   11760
aaaaaatatg tagatatatg tgcgctgtgt gcatagatcc aaaccaacca atattgccat   11820 acttgggggtt ttttggatga ttgtttcaga tagaggggta acatctacca gtacattcta   11880
caaaattttc aacaaaaaag ggatcatcag tcctgctata tactaccatt cattcagaaa   11940
tgaaagacca gccgaaaatg ataagagcta caacgctcta ttttacttga gaaaactatt   12000
ttatcaagaa cacgctagat tggaatatca tcggtttgca aaagaattca gtcattattt   12060
aacttatttt gaaggtattg gcgcattcct gtttaatata gatttcttca gtatccagaa   12120
cagcaccaat tttgtcgttg actattatat attatatcat taaaatcaac gataagaaca   12180
aaaaaggagc cagatatttg acaaaaatcc accgctagac acaaggttaa ctaaaaggca   12240
caaacgggat ataagaagac ggatgtaccg gcacaactag gacgtgcatt atcaagtgat   12300
agccaacatt tttgtataaa taatacgtta gtttaccttt ctctgctaac ttataacaat   12360
ctactcctgt agtacctcgg gccatgcacg tcagtgatag aacttgactc attcccattt   12420
```

```
gaggttggtt tacatacata caaaaaaaag tattatgcta cacaatcaat ggttaaaaaa   12480
gtgcaatagt aacaacgatt ggtatcaaac aatgttaaaa ttacgcgcaa ccattggaat   12540
tgctgaattt gggtaatagt ctcagacgtt gcaagattat ggaaaaggca cacctctgcc   12600
ctgttccctc actctagcgt atacgcaatt taattaattt ccaacttcgt tacaatcatc   12660
attgatggca taaaccaact gatttaagcc tgaaagaacc aaagaatatt cttttccaag   12720
gtgtgataat gctacagatt gttcttct tgtccagata gatgggtcac tttcttttcc     12780
ttcgacgata caactgttga aaaaattaaa atacgctcgt gtagcttgcc agcaataaac   12840
ttttagaatt tttgacagcc acatttgctc tcctactgca gtcaaatata tctttggaaa   12900
accaaatatt actacctaaa tcaccagcga tctatcatat cattacttt tctttatgtg    12960 agaatcccga attggcgttt attgtatttc aatatttta aggtctgatt acttttttag    13020
gggatcagta aggaacctct tttggactat tcaggttaaa acacaacatt tacttgcatc   13080 tttccttag tttcgatttt caactacttc gggcgtctta aatagttcgc agtttcgaag    13140
ttgtttatac tcttataggt aatgagaaca tacacattaa ctcattgtgt taaaaataac   13200
cccctggcaa gtagggtaag tgaaagtaga cccaaatgat ttttcttct ctagataagt    13260 gctgctcgtc caaaacttaa aaggaaaata taataaacgc gaaactttg acaagctcat    13320 gcaattagtg gaaatgaga gctatccatg agaataacct tcaaatgatg ctcagtgagg    13380
aatagcaaag gcccttaag gaaaaaaaac ccttttgaat ccagacatct ctgtaacata    13440
tgaaatacaa agatccgggt tgacatttac atttacttca agatcacaga aacagtttgt   13500
ttttaagtta cgtttaactt cttttcaatg atcaaaatag aatataaaaa aagctcttaa   13560
ggctgtcaag ctagattaag agtattggag cggtataaga ggccattata gcaatagcac   13620
aaagtagttt taatgtacag attaaagtaa cagccaaaaa aagatcctt tagctcaatg    13680 agaatacatc ttgtataatc attttttgaa aacttcatta gaatttcaaa tcatgggata   13740
ttttaagagc tcgccaaaaa gaatttactg gcatgtatca gttctacctt ggatagctat   13800
taaaagtttt attggataat acatgaactc acattagaaa atgcaattta acataatatc   13860
tcaatgagta ttaggtatgc actaagctag aaacacacag ctccgtttac cattgaatga   13920
taagaaatgt aactatatga gtcagggaat agtaacttcc taagtcaaac agtacgccca   13980
attcaatgtg ttaagcctca ttgggcctaa cctgggttta taccgcctat tggtgaacgc   14040
tttaattgtc tacgtcaaca aaactgatat aggtagtttc acgttgcaga accctctggg   14100
gaggaaagcc tgcattttcc agcccatatt ttttatgtcc acttttcctg tctgtattcc   14160
ttaagatctt tcctgtctcc tattgttaat cgttgaagat gcatatggga aaaatcatga   14220
tgctataact tagcatattt caggcaggta tattgaagtt aattttatta ctacaaataa   14280
agattttcac ataaataagc tcgaaatatt ctcaccgact tatgtcactc ggcattagat   14340
gtgatatttt gattactttg aatgtgcaca tggatttcta aatggcaaac ttgttgatat   14400
atgtaatcaa acattggcc aatcgggcaa caaacacgct tatcaggccc aatgaggcta    14460
atcggacaga attccgcgaa atagcagaat caagatcttg ctatttccca atcttgatag   14520 ttattttac attgcgtagc ttaacgatac aaacctacct acgcgtacct aacttgttac    14580
agacttagta tattcctata ggtatgagtt tatttccttt tgcttaattt gttttgatat   14640
gtagtttaat attgaaacct gtaaacagcg gtttatcaga ataacaccca taaatattta   14700
acctcctaat aaactagtcc tcagttttg tttttccctc actttcaagg gggctgtcgt    14760
```

```
ggcgtaatca ggtctggaaa caatagcttc acttaataca taatatatgt tctataaaaa   14820
agaagcaaaa acaaatgctc tcactcagag tcgaactgag gatcgctaca ttactagtgt   14880
agcgccttac caacttggcc ataagagctt tgttgtggct gtaaaatcgc acaagtagac   14940
aatcggcata gtggaagtta gttctagtaa aagtagtaac agatgtctct cttcctccat   15000
ctgctccttt tactcccgat taggaactat atcagctata tcaattctat ataacaggat   15060
atcgtctgcc ttatatactt cacgcccgca acctggaatc accctcagtt gctactcttt   15120
ttcgtatagc agatttctgt acgagcttat tacgttttag gtctttattt tttttatgca   15180
gttttttttt tttttttttt tttttattta ctttattatg ttttgtcttt atttttttg    15240
gatcacacct tgaaaagccc tctcacatat cgaaaaaggc caagagtacc gagttgtggc   15300
tatttctaac ttacaaatgt ctcaatgaac ttaagcttgg caaaaaacct tgtacgactg   15360
gtcaataatt atatcgatat caaaatatcc aattcaatga tagccagtgt aaactagctg   15420
agcatgttgc aggtgcttaa tacgtgtata aatgcacatg tatacaatgg gtatatggtg   15480
ttgacaggtg ttacatttac tttagagatc cctattgcaa ttactgattg aactattatc   15540
aaaagatctt atactaaata acaaataaaa acaaactaag tcaaaggaac taactcgcta   15600
tttaaaagaa catcaggttt gtatcaatct agattgatac acgtaggctg acgtttcaaa   15660
gaacaaggga agaaaacata actaaatgag ctaaaacata gctcggctct agttctgatt   15720
tacgcgtacg tatgctggac tagctgtatt gagactgata aggatatcct tagtttgatg   15780
tttagtgctt taattatata tctaaacaat ttttattttg ggtgtctgtt tcttattttc   15840
ctaatattac tagaaaaata tattccagga agatgttttt gagttggttc cagccaaggc   15900
atcaaatatc gaaggatttt ctaattagct ctgtttgact aaagcaaaac gagaaaatac   15960
tcatcgtgtt tgtaataggt aaagcatcta ttttgcttct attgtattta aggaaattag   16020
aaggtccact tcaacatcta gttgggtcac aacctttctg tataatactt cttcaccagg   16080
tactataatt atcaacctta tacaaaatct gttaatgcgc acgtgcccga agcaaaatgt   16140
gtcaatacat tactttcact tatacattta tattttgtgc atgatctttg attatatctt   16200
ctactatctc tttaaataag ttttattaca cccaaggtga ctggatgttg ataccaaaca   16260
gtcctctaat tcattgcttg ggcttctaga catgtcgtat gagtctgagt agtaaaaaca   16320
tacggtttac aatctgccat ttactatttc gctatacaca taggtattgc ctgacgttat   16380
aacataactc tatattatta ttagtacaga atctgatgtg ctaaacatat tatttgcctg   16440
ggtaacattt tcaatagtaa aatgaattgc tatcaaaata gcaacataag ttattattaa   16500
aactattcat acaattatac atatatatct atttttttat ctttaaaaaa aaactggaat   16560
cttcatcatc gtctttattt tgtgtattat tgtcttcccc aaactagcag taggcatatt   16620
cagtacttcc agcaaaaaaa cgtggatgta aatacgtcgt ttaataagta attttatca    16680
ctttcgtcga tttatgcctt ttagataccc ctattatgat gatgcaaacc atttaaaact   16740
tggattatat gaaccgtcat tggaaaaatg attagtcttc cttttctagt aaaataccaa   16800
tagaataact taaatagctt gatgcaggcc acttgttggt tccgcaaatc cacatttata   16860
ttcagtacag cctttactat ctatctactc taaataatct ttaaaatcta caactactgc   16920
cttgttttta attctatagt tcttaaaaca aataattgat ctatcaatag atagcctaag   16980
ctcctattgt ctttccgtag gttttttatcc aacctaaaca aaataactag acaactgttt  17040
attattgaca gcggagaagt ctcgagatac tgaaaaggca atgaaacata aactaagtag   17100
cagcttttga cctattctcg tggtttggac ttaacttaaa tactccggta cattttttcaa  17160
```

```
aagtttacag gaagaccttt attgttatta agattattgg ggttttttaaa taaatagaag  17220
ctccacctaa atcgctttta gcaaacttta gtacaaatat acctattctt tattcaactt  17280
ctttctttga tttcttctgc cctaatataa aaataacta ggtccttcta ttcaggaaca   17340
aaaatagttt agatcaagaa ataattagtt ccatagcaaa gactattatt aatatgtgtt  17400
atttagcgag aaattttctt tttcaaacta gaatagactc agaagggcca atttgaaagg  17460
ttaccoctag aaacactacc acctacaaag aaatagaaga aaaatcctaa tacacaaatc  17520
ggtaagtatg gaccttttgt tagctacttg tgattaattc aaataactat atagaaaata  17580
aactaaagca acaagattgg atctaagtct aagaagtgt acaagatga ctagttcagt    17640
agactttcag tattataaac tcaataggct aggtgctttt agttttataa agaatatga   17700
tacacatctt aactaggaag tgagaatacc ctttctagaa ttagatgtcg tacacactac  17760
agttagaagt cctgatcgaa acagaattag ctatttatta ggaaaatgaa taaaagcgag  17820
tgccagacta gaggaaata accaaatgtt atacaaaaat gaaattcagt gctctataaa   17880
gtgagttcag cttattgatg gaaaacatcc tacaagaccg ctgatattca tacttaagaa  17940
aaatgattaa aattgtgtaa aacttacatt tttttttcaac tcattctttt ttttcaggct 18000
caagtctctt ggcaagtggt gtgagaacac aaaaagataa taaacttcca ggattcagtt  18060
caaattagct acaacaaata taagcgagta gtgtaactca acgtccaaaa tctaaacaga  18120
aaaatacagg tgttagaata gagatgggaa attcacacga aagacgagta acaatgcaca  18180
atgtaacaaa gaatctacac cagttaagca gtgaatgttt taaaggccca tgacattccg  18240
gcagtccaat gaaaaaactt tatgaattaa aactaaatta tatatatata gcttccaggc  18300
tttagttagc acataagatt attaaatata gttttgataa tacggatccc actgaacgtt  18360
atggtacaga gttttagctt ttcaaaatgg tgaattggct gctcataata taccccacac  18420
cgtgtttgtg ttgtgcacct attgtatcta tgatcaaggt tcagaagttg gtagacttaa  18480
aaccccaatt attcagaaga aatacagaga tacatcgata gtttctgtct aaaattaggg  18540
tagcaaatgt agaattaact ctgtatacta gtaggtcttt tgattttttt atcacttatt  18600
aagtttcttt gaacatcgtt atatgcttga acttataatg gctgataaaa ataattagct  18660
tataacttct ctacataaat aagaatatat agcttgtcta tgaacgaagt ttaaataatt  18720
tcctaaactt ttttctattc aatgcaaata agatactttt gattagccat ttactaagat  18780
aaacatcgtt tacgcaccat ctaatatgtt ttagaaaaaa taaaataaaa ttaacgaatg  18840
gaatagtata ttggagttaa caaacttaga ttgttaggat ggtagatgaa ttccctgcag  18900
catgactcag tattttgaac aaaaaacata cggtgaaatg atgtgcttat atttgtgaag  18960
gcaaaaaatg tgaagaaact taaagacgcg atttaaggac taggctgtca ctcaactata  19020
atatggcgga ttttcatttt agattggcag aaataagttt tagatcattc aaagcatctt  19080
taaacactga tccaaaattt atatcataaa tggttctgct gtaggcaggt atttaactat  19140
cagtgggtta tataaaaatg tattatatag aacgccgcgt taccttcata gcttgaagtt  19200
atatgattct gcggtcaacc atggaggcta taactaagaa acgaagaaga gcaaaagaat  19260
gaactggtcc cagtgaaaag tcatacgtgt ttaccactac taggctacat gtactttttg  19320
catagtctag ttggcagaat cattctaata ggagaagatg gaatgggtca ataagaataa  19380
tagatggaag taagtaaact gaaaagacca tgcaaacagc aatggaatga tttctattta  19440
gatctagaaa caatgaacta aagaaagaa aaaaatttaa agattaacca acaagtacgt   19500
```

```
agtacctgca atgttcgact tcttattaga taaagataac aagttagtac aattcaactt    19560
cctaacatcc aaactaatat ggtgattgta gagggatata ttaagaacac aacgaccagg    19620
aagacataaa tatatgataa aatgaactaa ggctgcagtg tgtacaaaca cagccaagag    19680
aaaaaggcat gctcgacatg tttataagta aaaaaataac ttttgctgaa tgttagcaaa    19740
ctgctttcgt taaaggaag agccgcggca atggaatggt tatcacaaat tagaatatat     19800
tatgaatatt gtagggtatc atatgataag aaggttatat gcgctgttat caccctgaaa    19860
aaaaaaggt tctgagaggt cccccactaa ttaactgata aagatttact gaagaaccca     19920
cggcctaatt ctaaagctaa actgagaaaa acaagtcacg aaacagaaat catcaaattt    19980
gtgtgtaaaa gaaagtcaga tcaaccaaca aagagctctc aggaagaact tagggtacct    20040
atacgtacta ttttcgatgt tgctgaagag aaacctacta ttgctcgata ttttaataca    20100
attgaacaaa gaatgagaaa cacagaattg ttacaacgga gcctaggtgc tatttcatga    20160
gagatacaga gataaaatag cctaccaatc tggctatatc agtactttga atggcatccc    20220
ttgaatagca aggtccaaca acttaaatca actggtataa accacaactc agagttatca    20280
atcagctact ttcaatatca agaaggtgt gttaacaagt tggttaagag aaatgaatct     20340
tatctcgctt ttatctactc gattgtggat aaatatgtgg agaaaacggc tttttctact    20400
gattttgacc attacgaatg gatgataatg ccggttggac taacaaatgc acctgcgact    20460
tttcaacaga tgatggataa tgtcttgcct gaaagaatag atcgatttgt ccaagtgtat    20520
ttagacgaca ttttatata ctccgaagat gttgaaactc acggtaagca cgtgaaagaa     20580
gttttgtcga cactaagaaa acataaacta attacgaaaa agtcgaaatg cagattcttt    20640
tatcaagaat ttaggttttt aggaccagtt gttacaccaa tttgtattca aaccgctcta    20700
gagaaaataa aaaaggtaaa gagttggcca acaccaaaga ctgtcaaaga agcacaaagt    20760
tttattggtt taacttcgta ctatagaagg tttattaaag ggcattccaa aattgctaat    20820
ccaattcata agttcataac aaaacaaagt aaatggacaa gtgaacaaga cgaagccttc    20880
aatcaactaa agaacgcttt gatatcaagt cccaccttgg tgcacccaag ttgatcaggc    20940
aattgtaaat ttgttctaca taccgatgcg tgtggagtat cattaggtta tactctagaa    21000
cagttggacg aaacaggtaa atgacgaggt gtaattgctt acggttcaaa gaagctagtt    21060
ggaagtcaac taaattatgg aatatatgat cgtgaattta tggctattgt tgaagcatta    21120
agaacatgga gatattatct catgggaaga catttcattg ttatgacgga tcacaagagt    21180
ttaatttact taaaaaacca aaatctcata gactccacta aagtggctag atggatggac    21240
tttttaccac agtttgattt tgatattcgt tacttacagg gaaaaaacaa ttccgctgct    21300
gatgcgttat ctagataccc atataaccac gaaaacaact taacgctagc caaaatcaaa    21360
ttggcgttgc tggaattgac gtaaaaagag gaggatgaaa cacagagaca ttccttgaca    21420
ctaggtatta tcgaagccca tcaagattta aaaaagaaa ttattacggg ttataaaaaa      21480
gatactaatt atgccttgat attcagaact ttgagagaga aaacaaaagt tccagttgag    21540
ataaaaaatc atatcaaaca tttctgttat caagatgatg tactttatta taagacatta    21600
gagtctcaag atttctttag agtagttatt ccaaactaca agaaactact gtatagaata    21660
ttcaaaaatg cacacgattc caaagatgct cgtcactttg gtgcatggaa aacttatttg    21720
aatctcaaag atagttttta ttggtcatct atgttggcac aaattagaaa atgggtagaa    21780
acctgtcgta tctgtcaaca gcacaacacc aacactagag gaagacaagg gttgttttcc    21840
cctttaccaa tcccaacagg tcgctggacc gacattacga tggatttcat tacaggctta    21900
```

-continued

```
cctagatcgg gaacaggtta cgatatgatc atggttgttg ttgatcgctt ttcaaaaatg    21960
gcacatttta taccaacgca caaaagactt aatgctgcag catgtgctcg tttgtttagt    22020
gacaaagata ttcggtttat gaataagttc tggcaaacat tacattatct caatggtagt    22080
tctctattat tttaactact gatcatccag aaactgatgg tcaaaccgaa agagtcaact    22140
agatcgttaa tcagttactt cggaaatatt cttcaaacga tcaattatcc tggaatgagc    22200
atctatctat gtgtgaactt agttacaatt caacgtacca agattccatt aaagcaagtc    22260
cttttgaaat cgcctacgag tatgaaccga acatgattag aaaagtaaat agctgggatt    22320
tggaggataa caaatattca cctaacgcag aagaatttgt gagacgtgtg aaattgattt    22380
tacagcacac tggataatat tgtaaagcac aatggcgaca aggaaaacac cataatagaa    22440
aaagaagata ctttgaatat aaagttggtg acttagtgtt agtgcatcaa gatgcctttg    22500
gtgtgaatat aaggtacaca aaaattcaac cagtatgata tgggccatac agactagtcg    22560
agaaaataaa cggcaatgct tataaagtcg atttaccggt tattaatttg aaggatcgtg    22620
aatcaaatgt acagtggatt gaatactata agaaaaccc caatatttac caggaaccgc    22680
ctagaacaga gcgtgagatg ttggcaagaa ttaacgaact gagtggtatc ggtggatggt    22740
cagaagaacc aggcaaagaa aagacttatg atgtcttctg gaaagactgt gatcaaactc    22800
tagcaagaaa ggtacctgaa cgaatattca atcaagcaga tttgtcacta cgtcaaagcc    22860
taatgtacaa tgccaaattg atccaagaac acgaacaggt ttgatatcaa taaagtaatc    22920
atgattataa tatatagaac gttcctattt gtctctcagc tgaagaaaaa aaaatacaga    22980
tattgctcct accaaaacac aaaacatatt gttttttgat tgaaataagt tagccactct    23040
cgatttaaag aaatacaaat tgagctcata aaaaaattat tgttactgcc aggatccacc    23100
tacatttatt attctaatct ggtttaatgt tttgcagctt cattggttca ggcccccatc    23160
cggaattatt ccaggttgcg ggcgtgaagt atataaggca gacgatatcc tgttatatag    23220
aattgatata gctgatatag ttcctaatcg ggagtaaaag gagcagatgg aggaagagag    23280
acatctgtta ctacttttac tagaactaac ttccactatg ccgattgtct acttgtgcga    23340
ttttacagcc acaacaaagc tcttatggcc aagttggtaa ggcgctacac tagtaatgta    23400
gcgatcctca gttcgactct gagtgagagc atttgttttt gcttcttttt tatagaacat    23460
atattatgta ttaagtgaag ctattgtttc cagacctgat tacgccacga cagccccttg    23520
aaagtgagga aaaacaaaa actgaggact agtttattag gaggttaaat atttatgggt    23580
gttattctga taaccgctg tttacaggtt tcaatattaa actacatatc aaaacaaatt    23640
aagcaaaagg aaataaactc atacctatag gaatatacta agtctgtaac aagttaggta    23700
cgcgtaggta ggtttgtatc gttaagctac gcaatgtaaa aataactatc aagattggga    23760
aatagcaaga tcttgattct gctatttcgc ggaattctgt ccgattagcc tcattgggcc    23820
tgataagcgt gtttgttgcc cgattggcca atgttttgat tacatatatc aacaagtttg    23880
ccatttagaa atccatgtgc acattcaaag taatcaaaat atcacatcta atgccgagtg    23940
acataagtcg gtgagaatat ttcgagctta tttatgtgaa aatctttatt tgtagtaata    24000
aaattaactt caatatacct gcctgaaata tgctaagtta tagcatcatg attttttccca   24060 tatgcatctt caacgattaa caataggaga caggaaagat cttaaggaat acagacagga    24120
aaagtgggca taaaaatat gggctggaaa atgcaggctt tcctccccag aggggttctgc    24180 aacgtgaaac tacctatatc agttttgttg acgtagacaa ttaaagcgtt caccaatagg    24240
```

```
cggtataaac ccaggttagg cccaatgagg cttaacacat tgaactgggc gtactgtttg    24300
acttaggaag ttactatttc ctgactcata tagttacatt tcttatcatt caatggtaaa    24360
cggagctgtg tgtttctagc ttagtgcata cctaatactc attgagatat tatgttaaat    24420
tgcattttct aatgtgagtt catgtattat ccaataaaac ttttaatagc tatccaaggt    24480
agaactgata catgtcagta aattcttttt ggcgagctct taaaatatcc catgatttga    24540
aattctaatg aagttttcaa aaatgatta tacaagatgt attctcattg agctaaaggg    24600 atctttttt ggctgttact ttaatctgta cattaaaact actttgtgct attgctataa    24660
tggcctctta taccgctcca atactcttaa tctagcttga cagccttaag agcttttttt    24720
atattctatt ttgatcattg aaaagaagtt aaacgtaact taaaaacaaa ctgtttctgt    24780
gatcttgaag taaatgtaaa tgtcaacccg gatctttgta tttcatatgt tacagagatg    24840
tctggattca aaagggtttt ttttccttaa agggcctttg ctattcctca ctgagcatca    24900
tttgaaggtt attctcatgg atagctctca ttttccacta attgcatgag cttgtcaaaa    24960
gtttcgcgtt tattatattt tccttttaag ttttggacga gcagcactta tctagagaaa    25020
gaaaaattat ttgggtctac tttcacttac cctacttgcc aggggttat ttttaacaca    25080 atgagttaat gtgtatgttc tcattaccta taagagtaaa acaacttcga aactgcgaac    25140
tatttaagac gcccgaagta gttgaaaatc gaaactaaag gaaagatgca agtaaatgtt    25200
gtgttttaac ttgaatagtc caaaagaggt tccttactga tcccctaaaa aagtaatcag    25260
accttaaaaa tattgaaata caataaacgc caattcggga ttctcacata agaaaaaaag    25320
taatgatatg atagatcgct ggtgatttag gtagtaatat ttggttttcc aaagatatat    25380
ttgactgcag taggagagca aatgtggctg tcaaaaattc taaaagttat tgctggcaag    25440
ctacacgagc gtatttaat tttttcaaca gttgtatcgt cgaaggaaaa gaaagtgacc    25500
catctatctg gacaagaagg aaacaatctg tagcattatc acaccttgga aaagaatatt    25560
ctttggttct ttcaggctta aatcacttgg tttatgccat caatgatgat tgtaacgaag    25620
ttggaaatta attaaattgc gtatacgcta gagtgaggga acagggcaga ggtgtgcctt    25680
ttccataatc ttgcaacgtc tgagactatt acccaaattc agcaattcca atggttgcgc    25740
gtaattttaa cattgtttga taccaatcgt tgttactatt gcactttttt aaccattgat    25800
tgtgtagcat aatacttttt tttgtatgta tgtaaaccaa cctcaaatgg gaatgagtca    25860
agttctatca ctgacatgca tggcccgagg taccacagga gtagattgtt ataagttagc    25920
agagaaaggt aaactaacgt attatttata caaaaatgtt ggctatcact tgataacgca    25980
cgtcctagtt gtgccggtac acccgtcttc ttatatcccg tttgtgcctt ttagttaacc    26040
ttgtgtctag cggtggattt ttgtcaaata tctggctcct tttttgttct tatcgttgat    26100
tttaatgata taatatataa tagtcaacga caaaattggt gctgttctgg atactgaaga    26160
aatctatatt aaacaggaat gcgccaatac cttcaaaata agttaaataa tgactgaatt    26220
cttttgcaaa ccgatgatat tccaatctag cgtgttcttg ataaaatagt tttctcaagt    26280
aaaatagagc gttgtagctc ttatcatttt cggctggtct tcatttctg aatgaatggt    26340 agtatatagc aggactgatg atccctttt tgttgaaaat tttgtagaat gtactggtag    26400
atgttacccc tctatctgaa acaatcatcc aaaaaacccc aagtatggca atattggttg    26460
gtttggatct atgcacacag cgcacatata tctatatatt ttttggttct caatcataca    26520
atttcaaacg aaacttcttg atagtgattt ttagatttta aaggtattaa aataacgtct    26580
tgtgatgtca taatggcgtt gacaaattgt gtcttttccc ccaatatctt tgctaggttc    26640
```

```
aaatatgcga gaatactcgt tacatccgat taccagataa aataaaattt tctcagggag   26700
atagaaactt taagtttaat tctcatttat tcggtgaacc gtcttttcca cgcaaagtat   26760
ttcaggattc aaaaggcttt gtcattcaca tacctcagtt gaaacatctg tttccatgcc   26820
cttgaatgac tgtcatgttt tcttcaagag ggcaatttca ttcagcttca aaatcatcag   26880
gcatcgaaat aaggtatcta gtgtcttgtc agggtgcctt ttaatacact gaatgtcgac   26940
ccgtattgga cgataaaaaa tagccatctg gctaatacac cttctcggaa ctgtttctga   27000
tttttccagat atgcgaacaa atggtgatca gtctaaatca ggaaatagtt tttagaagag   27060
gtaagcttct taatttattt agagctttac gatcgtttga aattcttttc ttgatgaaga   27120
tcaaaatttg gcatataata atcttttttga tccgtattgc cgtacagcca caacttgat   27180
acttggtttt aattgcctta atgttccaca tatcaattgc gatggtttta aagttgtatc   27240
attcttcgat tattgttagt gctaagacag gagcagttac cagcctttca ttaagtagct   27300
gaagtgatcg agcctgctct aggctacatt tgcacttcct agaggcaatc tctacaagga   27360
aattcctaat tttggataac ttgtgatgaa cttttgtttg ctttcaaata ataaattact   27420
gaacaccaat atatttagaa aaaaggccgg catattttgt ctagctatca cttgattttt   27480
attcagttca cctcgtagta ccttagtctg ctgcctctat ctctcaacaa attcttaata   27540
aatggcgata tagtcccact gtaatgacaa aaactcacta caaatggttt ctctattttg   27600
cttacgagtc tttaagatgc caatgtgcaa tatataaccc ttgatataaa tatccgccca   27660
aaatagcctg caagagagct acacgctgtt ctttcaatat tgttcttttg agttttagcc   27720
tggaggcagc catacaaaaa atcccaaaca tgcaatttga aaagaatttg acatcatata   27780
taatgctaaa tatctcatct atttgtagtc aatagattct gtcctctacc ttctcttaat   27840
tttagaatgt gaaatcgcta cttggatgta tgatcgcatc tttattttca atatacaata   27900
catgaaaact ggataaaggc tcccaaactc tactgagcct attttcttgt cttcctcgag   27960
ctaatgtttt ccagtgtttt ctattctttt aaaacagtgt ttattgctgt atgagtatcg   28020
gttaatttct gatttgcgtg ttttgttgat caatgtgtct tcttattata acattcttgg   28080
cagtttatcc ccaattgtcc cctgaaagtt aaaattcgtc ttgtttttttt tgtttcttcc   28140
atatagccgt gagagatttc catatagtat tgctttgccc cttattgttt tgtatttatt   28200
aggctccaca tattggaata gcatggtttt agaaaacacc tagattttgg taatggacgc   28260
tatacaaaga atagacatac cattaaaaag atggaaacaa aaaattttct cttgctcaac   28320
tatccccaat tcacaattta ttttccatt aatttacagt ttcttaggag gtgaactgtt   28380
acataaaagt aacaacaaca tgatgtttac cattgcctaa cgtcgagttt atgggggtac   28440
atgtcgtgtt gtctgtgttg ttgaaattgg acaaagaga ttatcatcta ctagactctc   28500
taatgttttt ttaggtccaa gagatagcaa taaggttgaa gagtcttcat tggatatgca   28560
cactttttta aaaaatgtga acaaagtatg catgttagaa gcataaagaa gtgcagaaaa   28620
ataataaagt ggatttagag tttacggaat gttggaagtt tgtagtcgca tattattaca   28680
caaggatgtt tatggcagtg ataaatttta ttataaggtt taactagtat actgcggtac   28740
ttcttggttt gtcaaagagc tatttgataa ttcttgcgaa atagatttac gaaaactctg   28800
cgaaaaataa agtggtcaat tttatatgct taaaaaaatt ccctaagtgg gttagaagtt   28860
tctgaaagtg ctacccaaag tgctagcccg cgttcttaga gaagtgtgta gattattata   28920
gggaataact ggtattgtta ttgctaacga aacaatatag ttactctata ttgacatgtt   28980
```

```
ttatttgtac tttgaatagc catattaaaa gtttattgg ataatacatg gactcacatt    29040
agaaaatgca atttaacata atatctcaat gagtattagg tatgcactaa gctagaaaca    29100
cacagctccg tttaccattg aatgataaga aatgtaacta tatgagtcag gaaatagtaa    29160
cttcctaagt caaacagtac gcccaattca atctgttaag cctcattggg cctaacctgg    29220
gtgtttatac cgcctattgg tgaatgcttt aattgtccac gtcaacaaga tgagtcaaca    29280
tagttaggcg cttgtaagct cttgagtat tggaagaaat tgtgatagat aataaaaaaa    29340
ttgaaaatgt taccttcgt tatagcattg aaattcacac ataaatattt ttcttgaaac    29400
ttctttttta ttgcaaaaaa atctaggact ataagttttg tctggcgaca cgccaatttt    29460
ttcaaatttg gtttgcgagt ggaagacatg cagttttatg caaaactaag tactactgag    29520
ttgaaagtta ggtttatgat aacaccagcg agtattgttt tttttaccac aattcgactt    29580
ttccaaccaa ataaccgagg atggtatcat agaccattaa cgtttagaag ccatttggca    29640
gaaatgacta cttatgttat gttcttaccc gctactaaat gttgttctcc aactactttg    29700
cggactcaaa cttaatcttg caaaagcact gcttaaattt acgtgactct tcagaatata    29760
aaaattcagc attaccattt taatattcaa catgtgaaac cattgccatt tttccttatg    29820
cgttttgtaa aagaaacaga aaatcaattc tatcatacca cagggaaata tctgtttcct    29880
ttgcgatccc tttacactag aatttctgaa ataggtaatt aaaacataga ccaatcggca    29940
gatttctata ttgatctcac caagaccaag ccggtccagt gtgccgattt gccgtaatca    30000
ggccctaaca atttctttat tctgatgttt attctttg cttagtttgt ttttatatgt    30060
aatttaatat acattctttt ataagcagtt caatctataa atttagtatg gatatccaaa    30120
gtagagtcaa tacgtgccaa caaacatcag tggttttgc aggtttaaat tatcgtactt    30180
aaatttaaga tttctcaaca ttataattct tttcaacag gagtgttagg tgacccacat    30240
gtagaaggga gacataaatg tctctgcttt gtgattaatg aacaaagact tcttaaaatc    30300
gcttaaaggt tacacaattt tattcaacgg taccctactg aaaaaaagag aatgattctc    30360
ataggctggc gaaagaacca cgtaaaagca acttattgct gatcctacta acatttaaag    30420
ggtgctctca aaaaatgctt cttacattaa aagtgaataa aagcaatcat ttcacgcata    30480
agtatatttt caactctatc tcagatatgt atgaattaca cctgctacaa ataatacaaa    30540
acaagttatt tctctttgtt ttaaagaaaa caaggggggcg tcaagaaaac agagttcaag    30600
gtttaattct catctccaat acttttgccg ttgggttgaa gtctggcagt ataaaatata    30660
gtttcatact aagggaatgc aacatatagc aggatgcaac taagaaagca actaagaaaa    30720
acagacttgt tgaagaattc atagctatcg aaagtgtttg tagatcttta actaacatac    30780
gcgtaaataa tagcaaatat aaacattgat aattacttat aagctgaaaa aaaactgaag    30840
taatctatgc tgttcttcta aacctgttct aatggaacag agggaagagt aactgacgct    30900
gtaatatttt ttttttcttt tccacttgtc caaaatatta tgattcaaa aatgaagaca    30960
ctagagctat cactaaagag gctgagtaaa agctatattg cagacggagt ttgtttgcaa    31020
agtttgagaa aacaaaaaaa atttatttgg atccaagttt tgtagaacct tcttgttact    31080
gctctagttt ggtattttta gttaggtgaa agcaaaagt aacttcgtac ttggaaaata    31140
agctcaagag acggtgttat tacttaccag aaatcttttg gaaatgtata gcatgatgaa    31200
aaacaaaagc tatattcgat gagaatttca aaggtaataa agcttgacat atgtctatat    31260
tttggaaaga aacaattctt tcttaattaa gcttagcatt aatctttct tgttaattgg    31320
cagatcattt tcaaggtgtt gtgttagctc ccattgattg gtttagtagc ttgtattgaa    31380
```

```
gtcaaattca tgtgtataag atcttacata accgaataac ttttcttaaa ctttagctgt    31440
catgtttgaa atagcttgtg taaaatattt tggaagtcct gtactttggg tacaaaatta    31500
gttgtagtac gaaatatata caaaagaatg gacgtaacac tgtaaatgta gaatggaaaa    31560
tttcttcact tgctcgtcga ctattttatgg cacacagctc aattttccat taacctgacg    31620
attattccag gggatgaatt attatacaaa gaagcaacac tcgcctagtg tttgccacca    31680
tgctacatgt acttttctca ggtgcatcta atatgcatac tataagaaag tctgaaaact    31740
tgagtagtaa atgtgtactt tctaattact tcgttttcat gcagatgtgg gacagaattt    31800
gctcttgatt ctctggttga tcagtcgatc agaaaattgc atagggcttc tatttggacc    31860
agtgtcaaca ctgcatgaat acaatctgga tgggttcatg atgtagttaa cttttaaaaa    31920
cagagaaaaa gctagttgtt tttatataga ataatactgt aactgtttat tgaacaatga    31980
ttactctttt aatctgatag acgctaaaga tactgattct tatgatatta aaaaaaggtg    32040
tgtgacctct aaaaaccctt ttttcttgca tttcgcgcaa ggaacaatgg ttctgcgatt    32100
tgactcttca cctgttaaac cttgtcgatt caccttgtac tccatatcaa agttttttac    32160
ttgaataagg atatacagag acaagaaggt tatctatatc ttattttttc tttgatgaaa    32220
taagtggtac acaatatttc aattattgtt agctctaaca ttacaattat tcagcactac    32280
agggctcttg ttatcgctaa aatctcaaag tcaaagtatg aataagttgc tgatgagaag    32340
cggttgtgta ggtgttcttt agaaaatgtt aatgctggag gacgtggttt tgatctatt    32400 gaagcgcgca ctataagaga aacaattaca caagcagaat tcctctggtg ataacctgca    32460
aagatagctg ttaccagtaa agaaataaaa gaacaatatt tggccgtaag gggcatcaat    32520
tacttagtac agagcggcat tctgcaaggg ctgcagatat tttgtcattt gaaggcaact    32580
gatatctatt tgaaaaaacg ttgccgctat atcagcaaaa cttcctcaaa aggcaaaaaa    32640
ggatagatca acacaactaa tcaaacaaat atcccacacg tagggaaga actacaactc    32700 acatacagct gtaacaataa acttaattgg gtaaaccaca aagcaattta atagaacgag    32760
ctaaaatgtt ttatgtatta cctttctaaa gatatcctac acccaaagta tgcaccattt    32820
ttctattgct taaaaaattg ttagctgatt tgcaaagggc tagaactgtt ctgaattatc    32880
cgagcgtttt actaatttac tagttcaaat aacaaatgct tttgctttga atatttattg    32940
atttccaagg tgtgatttat tttgccaatg ttatacattg tctatttcaa catgatattc    33000
acaatatttc tacatagatc gttataggca aaagttattc tactactata agggttagct    33060
gtgggttggc atgattaata ttaagtaaac agattctacc tttttaataaa acgaataatt    33120 tgtgaggctc atatgttctt tatactaagt cgcttgctaa agttcagtta acctcccagt    33180
taatattgct aatcaggact tcgtttaagt ttttctagtt gctatgatag ggttttttc     33240 aggttaataa taaaatattg agctgctcaa taacattaaa tccctctacc agatttcgat    33300
aagttcaagt cctttgtaaa gataagaaaa attggttgtg gacatgttta tgtttattag    33360
aaaacaacca tgaaaggatt ctgtgattag tcatgaaaga gactttaatg aaaaggtatt    33420
ctggcactta catcaaaact actcataact acacgaaact tgaatatttt actcatttta    33480
aataaacact ggcaggccta tgcagcaaac aaaggaggta tttaacagca ttttaaaaaa    33540
tttcaagaag tgatttccaa aatctatgga tcttgaaaaa gtaatactgt aaaccaccac    33600
accactacag aaaatatata ttcaaacaac cctagatgat agaggtgacg tgctaccaaa    33660
gtttgtataa atattcgttt cttttccatc tcgcctcata caaaaatgct cattgagggc    33720
```

```
aaagagttca accttctctcc tgttgatatt ttcatattca tggttattga ttagtttgct    33780
tttcaacagc gtgttttctc ttctcttctc aaaaaacaat ttttttataa tgcaccaaca    33840
acgtacgtag aatcaccaac cgaatcaggg agatgtctgt gtttaaacac tatcatacat    33900
ctgtttcaat actagtatca agtttctaag agccgtttag ttcattacaa aacgtagagg    33960
gctatgctac ttttatgaac acacaaaaac tggaatcaac cgctgaagat ggtattccca    34020
gaacaaattt attactgttt ttttaaaaaa cttgaatgaa gaaacttgaa aagaacatta    34080
gaggatttct tttatcttgt attgtatctt caaagaattg cgtataattt cactattggg    34140
tgctgtcaag atgaaaaggc cgtactaaac gttttcatac ggaaataaag attctctcca    34200
tctctgatcg aatctttttt tccaattcat tcgcagatgc tccaatagat gatggcagtc    34260
tcctttattt gtgagcatct atgaaaaact tgataagcgt tctctaattt tggctgcccc    34320
ggcaatagca agtcatcaga attagctatt tttttaccaa tctaagagac tcttctgtat    34380
tgcctcccaa atatttagta cattaccgag aaaaaagtaa taggtaaaat atgcccaaag    34440
gcagaatccg acatggtttt cccaacatat attttatacc tctaaagttt ttcaagctaa    34500
acctttttgg cacatgaagc gtgtaatggt ttatgttata tataatttgc agcaacccta    34560
tcggtctcaa aatgacttat aatagtgttt tgtgacgctt taaaattgcc tgtaacaata    34620
tggcgtgaat ttggaaaaga ctcatcttgg gtaaacactc cttcaaaggt tcacataatt    34680
ccataataaa aaggctctag ttaccaactg attcactttc cggaagaaag cagaacgaac    34740
caagcgtgag ttttcgcgtt ttttcattga tatgtacgac tgttattaga ttaaaatctc    34800
agagtcttgt gccactggat ataacatcca ctccaaagac atgttggttt gatggttctg    34860
caagcggttg tttaaattta acgaccaaac caggcttttg ttcaaactga atgaaactgc    34920
acgcaatatc tacgtctaat acgaactcgt tgtctctttc ttcccactat aaataccacc    34980
tttgttttt taccttccaa attgttcaaa aaatctgaca tattctacga ataagaaaag    35040
tgctattggt ctgccatttt ttgtgtgaat ctctaaacga tcggaatgta ttagtgataa    35100
aaatcggatt aaaactattt ttacttcaag gcgcttagtt ttaacgtcca caagcgtaac    35160
gctgcttgtt gaaatatatt cctttggatt taacaatttt agcatagcgg gatgtctctt    35220
tatctttag tgtagttcgc atctatgact ttgcatatga taaactcgaa gattgcgttg    35280
atgaaacaag taaagataat gcaaattttg acctaacaac gaatatcatg cattacgaat    35340
ggaacctttt gaataacaat atataccaaa aaccaagcta aatttcttca aaaagctagc    35400
ttttttatgag ttctctacta catgactaac atcaatcgta tttttgtaag atactctcca    35460
gctaaatttc gtagcatttc ggggcgtaaa actgcattta cctttaagaa gaaactaatc    35520
cttttttaaat ggaagtattg agcaaaacgg cgcaaataag tagtaaaagt ttgctaaata    35580
ttcttataaa tcactttggt tttgcaaatt caaaagctac agaatataat aaacgtgagg    35640
aacccctcca taaagtcaa ataaatccct agagtgtgtc atttttttcag tctgagttct    35700
tagttgatac cagacgtgtg gtaagatgcc aaatttgttt tctgcgtccc agtcggtcaa    35760
tgccaaatgc attgtttcaa ccacatcgaa aacatttta aggtaacgca catacacaat    35820
gtaagcaaag gaatccttcg tgctttctag aattttgaca attaaaaaca atctctttag    35880
tgaggaactc ttggatctta cattatcact tccttaagtg attggaatac gtggttataa    35940
ttgagtaaag ctcatgttcc tgatcgcacc tacctgttct agagcttttt tagaaaacta    36000
ttaaagcaaa agccaaacat aaagagccta ccatttatca acaaaaattt agaatttcaa    36060
gaagtctccc tttcttcgtt taagtggtgg aatttcattt taagtatcta tgaagtttt    36120
```

```
gaaaaaccct ccagaaagac ggccaatgtc taactgctca ggaacaaatt atatctatgt    36180
tctccagcaa aaaatctccg agaaagcctc aattgcgaag tctgtaacta tgtctctgtg    36240
atctggcaaa tgttgcatac ttatgacaaa aaacgtttt ttatcacttg ttagtagcta     36300
taacaccgca attacatttg tgcaaccgaa cctcaagtta ccaattctat tacaaagaac    36360
aagcagtagt tatgtattta aagattgtat tgctgacatt taaagtgaaa agtaatgttt    36420
tggaaggttc taaggaaaga ctaagatgtt tcttttttgcc actgaaaatt tgaatgaaaa   36480
aaccgataac ccagaacaaa cagcagtcta gtaacatagt ttctcatgga aaattttgag    36540
tccttgatat acagtatcaa atcccaaatc aaataactta cttcttaaaa agcaggttaa    36600
tcatttggta ctaatcggtt ggttgatact ccgataataa cttgttggtt tcatgtttag    36660
taggtatata tagtctttat ttgaattcaa aaagctcgac tgtagtagat cactataata    36720
cagcatggaa actaactggg gttgtaaaaa atttattccg aggcttgcaa aggaaacaga    36780
accaattgaa ctacttcatt ggcttggttc ccagagtgac gcaagcttca catgtttaat    36840
tgttttcctg gtgaaaaggg catattaagt atggttgaaa atgagaccct gtatcatatc    36900
tgaaaatgcc aaaaatcaga caaagtttat ttctcagcat ttgtttatct cgacaatatc    36960
gaaatttccc caactaaatc tgccagtttt cttggttatt ttatctgagg ggaaagtttg    37020
attttgctct ctggccctaa cggcccgcca atatataaat ttcatggtac ggcaggaaga    37080
gcagaagatt gaaacatatg agattgaaac gtttgctttt ttattttgcc agaaattgtg    37140
gttttcaact ggttaaagtt tttataatta caagtgacaa atgttttaat taactatgtc    37200
agcaatagtt agttatcaca accccaaacc aacaattta acaaatagtt caactttcat     37260
tgtttccttt aaaaatcctt tgcctttatc ataaatcgag ttgagcaaac tattatactt    37320
aatttgaata ccgccacata atttgtagcc ctccagcaga atttatgcag gtcaacatgg    37380
cactaacatt cttatgttga gataggtaat taaaacatta acctatttat gggcattta     37440
tcgatctcac tagggccagt ccgatcttgt gagacaattt tccttaatca aagtcccgct    37500
attttccaat cctgataagt atcactatat aatgtagctc aaaagtctgt gtcgagattt    37560
tagaagacta gttccctcaa aaggcaattc tccaaatcta atcacaccaa aaaattaaat    37620
aatacatttt tccaaaaaaa acaaatgctc tcactcagag tcgaactgag gatcgctaca    37680
ttactagtgt agcgccttac caacttggcc ataagagctt tgttgatcct ctaattgacc    37740
atgagtaaac tgttctaatt attgctaaac tgaatatagt cacatctaca gtttaatatt    37800
ttagtataga aatgtttttt tcatacttta cagatgagta agcaaatctg gttaatgcaa    37860
cgtaattatc gtttagataa gtaactttaa cactggccaa tcaaaccact ggcatcatta    37920
tcactctcaa tgaggatata caaattaatt tagattttt atcggaagtt tgaagcttag     37980
ttatcttgtg ttaatatgtt gttatttgcg agagtgagaa tgatatttgt aattcggctg    38040
gttaatgctt caatcagcct tttgaataaa taaaaaataa aactgattcg tatagatata    38100
tccaaggaac ataatttgc gtgaaattag aggaaaatag gccaaatatg tagcaatcaa     38160
gcaaaggtta ttgacacgac gcttaaaatc ttgagggaga tcaggcaaag gactatctcc    38220
ctacttcata atcaggtaat catataaaag gttgaagaag attatagaag gttaaacaga    38280
agttctagaa gataattata tccttcaaaa tgctattttt aaattaaaga attactattt    38340
aaacagagga cattccatat atgttctcag agaattaacg tataaaaata tataagatat    38400
aaacaagcaa taatcagatt ctaaagtact catcaccagc aacaatttca atttttaagaa   38460
```

```
aaggtcccttggcccagttggttaaggcgtggtgctaataacgccaagatcagcagttcg    38520 atcctgctagggaccaatctttcatttgggcgtgtggcgtagttggtagcgcgttcgcct    38580 tgcaaccgaaaggtcatcggttcgactccggtctcgtccatttcttttta aaattttta    38640 aacgaaaat    38649
```

<210> SEQ ID NO 15
<211> LENGTH: 42742
<212> TYPE: DNA
<213> ORGANISM: Artificial Sequence
<220> FEATURE:
<223> OTHER INFORMATION: centromere-like sequence (CEN-L) CEN4-42742bp

<400> SEQUENCE: 15

```
cttttgaataattttttttt gataaaattaagttaaattagggtgatttgagaatgtgtg      60 aatgtgtgtgataaagaataaaacaaaagctaaaaaaaggaaaattagcataccaaca     120 atacggagaaaagtgatattaggaggggggagcacggaatttaaatacaatttagtttct    180 ccgtaaatggggaaaatccgcctctggaaatggtttccgttttactgaaatcacccaat     240 gttggaaaggccgaaatagccaggttccccatattttttcgaaaaaaaaacggaagcca     300 ttttcaaaattgttacgaaaaagtaatgggacggggggtggggagcggaaagggacact    360 ttgttttatttatttttttttttttcatctacaacggcaatatttatcaagtatcttgg     420 gtttacctgtttgtgtttaccacacgttaagaggagtattttactttgtcatcaagttctc     480 ccgtctgagcattcggcgaggtggatgactgtgtgcctaaatgcccgacatcggtgtatg     540 aatgaggagatcgtccatacaactggacaagccgtcacgaggtcccgactatcacgttg     600 ggtcaggtaaacccaagtcgactagagccgtcagtagagagagtggcttcacttttttc    660 tccccactatgtaccatacaaatgtggagagagggaaacacggcattttagaaaacgggg     720 tttccgctccgaatatggaaaaaactgttttccggcggcagctcttgccattatgataggt     780 gagacctacatggaaatacggatatttcccccatattttttccgctgtgttttcgttttttcc     840 cttttcccttttcccttttcccagcgcgccgcccccaagccatttccactcagcccggg     900 ttattatcaagtggagaattttctacactttttctgtgtgttttgctcttatgtttttttccg     960 tctcttgtgggatgtttaatgcacctcactcctctaaaaataaaaggaaaatttttagt    1020 ttgaacaacatgggcggattatatcaaccccccgacgctctcagagttgacaaggacaaac    1080 atacaccagttatttctactgttttctccattctaccccggataattgacagatgggattt    1140 ccccgataatcttcacaaagagcagatgaaggaaaaaatagcatgaaaaattaaaattgc    1200 cgcgcctgtgtgcgaaatgcgtgccgccagctcactctgcaattgggtgaaatgccact    1260 cttgaatgaggcacaaaaaacagagaaatgaatgggcaatgtacatgttcaatttaattg    1320 tccggtttggttaacaggtggggatcgggctgtaccgtcctttacaaaacatataacatg    1380 tttaatctttgagaggcatagagagaatttatttgaggaacggtcccttcatttccaga    1440 tatgaccttatttttgtattttttgttccctgtcaatttgtttatttacatgcaggctta    1500 gtaatgtacaacattctacgattattgatgctatcccacattgatagccttggttggcc    1560 ccgcttttccccgttctgctgtgtacctctttttttcatcttccacagaaatctatcccc    1620 actttgggtatatcacagtatatctttttattaggaaaaccagtgtataatatcaatctc    1680 tgcttttttgttcataccccctaaacataattggtctactatcttttgtgatgcagtaga    1740 atatactaaatcaaagtatgaaccttgttgtcagatgggttcgaatttttaaaccccta    1800 aaatccccagctgctagtacctattgctaactcggtatacatgttttttgcgttacggaaaa    1860
```

-continued

```
attatatgct actgtatgga caaaattata tccttccatc atggattaat tcaagataaa    1920
ggaaaaatac aagctataat acctcagcaa tcgccgagat cggatattct acaaaagatt    1980
ggcatattac cgcctaaaca gcgtgaccaa ggctgtttga acttattccg aaacaaattt    2040
ccagggctga catagtcgtc tagctagttt tgctgacagt tagacaaacc cgtaaatatt    2100
tagctgggta aggagacatg ttggaaggtt aactcaagca gtggaaacta atgattagca    2160
gcaaggtatc attttaccat ctctacgaca gtagatctca gaccaccttg aaacaccttt    2220
atcggaagtc cttgaatcgt ccttttttc agtcccttta gttgaagttc aactaacaaa    2280
gttaaaccag acattcttta ataaattgtc ctaaaaaac acgaatgaaa ctttgctaaa    2340
ataataatat atgatatctt cgaatcacaa tcatccgtcg gtaatgaaga gatcaattaa    2400
tgctgaaata ttcaatgttc tttagaaatt gataattgct aaggaacagt gttgcttgtt    2460
accaattatg gccaaattaa acagcttatt caaagttcaa cagcaacaaa actgcggtta    2520
gatcagatag acagacgaag gtgcttgatt caagtgatat aataatgtcc ttaaaaaaaa    2580
cacatcagct ttgtcgcttc tattgggtgt atgacatttg tgatccttac tatctgatat    2640
aaacgtgcaa tgatcttctt ttgcatccac tgaacgtaaa aaacatgtaa gaaaaaaata    2700
cctgaacttt tcttttttca actctactct tgttctcgtt atatgcatag cttgatcttt    2760
ttctttgctt tcagatgtgc tgatgacaag aaaacaaaac ctgtagcatc aataaacgaa    2820
ccttagacca aactacgcaa gatgacattt gaacaacaac tcataggaat accagcatgt    2880
acgcattcgg ctaaatttat ttcctttag tatcacaagt tagtaacctg ctagttcctt    2940
accagtatga gaaccacgta aatttcgaga caaatttgaa gcaccaattt tgtgagtatc    3000
acaatagtgg ctaatcgtag ttctttgttg gatgctgtaa ttactaattt tcatcctaac    3060
aaacaataag agtagttttt ttgtcgccta ttcactaaat agcatttttt gaactaaatc    3120
catatatttt atcaagcagt taacaaaaag gcaggcattg agaattttag aaaatcaata    3180
ttactgtggt aacccccaca acaaaatcaa ctaacttata gtaatagtaa gtggaaaata    3240
ttttagatgg ttagtcctac taatgccgcc tcacgctcga agattaagaa accggccag    3300
cttgtatttg aataagaaaa tatatcagct tatgcatatt caaataacat cgacacctaa    3360
aaattcgaat aggctcaaca atctcaatgg ttgaagaag ttaccataca tattcattta    3420
gccttcgact tgtcaggtta tttatttatt atgggatatt ttcatacctg tggccattga    3480
aacagtagca aaacaatat cgcggtgaaa caccaactcc caaatcaaaa ccaaatggaa    3540
atatataact aacttgtact aggttttatt aaaatgattc ccaatctcaa aagtgccact    3600
tagaaaatta ttgcctgaag ggtccaaatg aaccatggaa aataagtttc gatctcggcc    3660
aactacataa aaataaattc ccttttcaat aagcaccaga taaatctcaa tactatgaaa    3720
accaagagta tatatatgta aattctgcaa tttcaaaaaa aaattaaaat gatcgaaccc    3780
aggatcgaac tggggacgtt atgcgtgtta agcatatgcc ataaccaact agaccatccg    3840
accacttatg agctagaaat gttgctggtg ggacctactt tagaatctga ttattgctta    3900
tttatatctt atatatttt atacgttaat tctctgagaa cataaatgga atgtcctctg    3960
tttagatagc aattctttaa tttacaaata gcattttgaa gaatttaatt atcttctaga    4020
acttctgttt aaccttctat aatcttcttc aaccttctat attattaccc gattaggaaa    4080
tagagaggta gtcctttgtc tgatctctta cattaccccg ccgctttaga aacttcgtcc    4140
cggagtttat tatcattatc aattgctttt gcattatccc ataaagtttt ctgtaaatct    4200
```

```
tctaggatct ctaaaaataa tgaatatggg atgcttgaac tatgacaagg gtcacaatct    4260
ttccagtaga catccaatgt atcgtttgtt tcgtcgatac tagctatacc gataatctcg    4320
gtcagtctac ttcttgcttc agctatcatt cttgggggta ccttggaaaa ctgtttatcc    4380
gcttgtaagg atcttctaag ccatctgaca ttgattactc tatccttttt attcgttttc    4440
ggtaaatcaa cttcgtaggc gttgtctgat atcttcttga caaccttgta gggtccgtag    4500
tataccggtt gtattttgta atacaatcta tcactaccat atgcatcttt gtgtaatagt    4560
atccaatctc caacttcaaa tgtttcgtac actctcgact tattatgctg tgtttcctga    4620
cttctttgcg cttcaatcat gttttctttc acattttcca tgatgacttt catttttaat    4680
gcgaattctt cagctttgtt gctgaccttc tacttgaaac acgactgcta gaaataaaca    4740
ttggcgagtc tggtaagtaa ccatagcaaa cttcaaatgg tgatgaactt atcgagactt    4800
gatgggaact gttgtaggca aattcggcca ttgacaacca tttgtctcaa ctgtagagat    4860
cgttactcgc ataattcctt agtaattggt ttaagattct gttcgttctt tctgtttgac    4920
catctgtttg agggtgatta gtggttgaga agagtgatga tgtaccaaga attctatgtc    4980
attatctgaa accattcttt ttggaatccc atgtaattta aaacaatttt ctaccatcaa    5040
tttcgcacat tgctctgcgg ttgcagtttt cctagtgggg atgaaatgtg ccatcttcgt    5100
gaatctatcc accactccca aaatcatatc gtgtccattt ttgcatctgg ggacacctgt    5160
gatgaaatcc aaactatgtc tgtccatctt ccttcaggaa tcggaagagg ggaaaataat    5220
cctctttgac cagttgtctc gggtttggtt ttctggcaaa cagtacatct ttgacaatat    5280
ctcttcacgc ttttagcat atttggccag taaaacatag ggtgaagtct cacgtatgtt    5340
ttgaaatacc cgaaatgact agcggagtta ccaccatgtg cgttaccaat gatttcctga    5400
accaacttag acttaggggA cactactatt cttcgataat ttcctccttt aaccaccaag    5460
aaatataata aattatcatc aattgaataa tgtttgacgt ggttatggat tgacttcggg    5520
atcggcatat tttctttaa aatctcgtat atctccttaa tttcgttgtc ttcatcgtac    5580
gactggataa tctgttctag gagttcctga tttggtgtta acacctattc tattgtgttg    5640
atactaactt cattttcctc gtctgggtac ctagacaaag cgtctgctac tgaattagta    5700
ggacctcaag tattgaattg tgaattcgta atcagctaat cctaggaatg attgagcaca    5760
tttggcgttt ttcggaattg gccaactctg gattttgtct atcttagcag ggtcagtctg    5820 gataccctctg cttgaaatga gatgtcctaa gaaacctaag gttttgaagt aaaatgagca    5880 tttcttttc ttagtaatca gcttatttct cctgagcaat tccagtattt ttctaatgtg    5940
attgtagtgt tcttcaatag tcttggagta aattataata tcatccaggt acacctgaac    6000
aaattggttc aaataaggtg ctagaatcct attcatcatt cttttggaaag tactaggggc    6060 gttggttaaa ccgaaaggca tcacaaccca ctcgtagtga ccgtaatctg tggaaaaggc    6120
tgttttttcc atatcatttt ctgcgatgct gacctgaaag taccctgaca tcaaatccaa    6180
cttggaaaat actgaagctc ctccaaaaca tgtgattaat tcgtcgattc gtggtattgg    6240
gaacttgtct tttaccgtat tgttatttaa taacctataa tcaacacaca ttctcatact    6300
accatctttc ttcttgacaa gtaacaaagg actattgaaa gaactagggg cagacttgat    6360
aaaggctagt ttcaacagtt catcaacctg tttattcagt tcttgtttct ctgaatagct    6420
tgatttgtac tggcgtctgt aagtactctt gctaggttca atgcatataa gtctgtgagt    6480
caaatccctt tgaggaggta aatcggtagg ttggtcattg gtcaccacat ctctaaattc    6540
ttcatgaatt ttatttctaa ttccatcaac accattgtaa ggttcttcta aaacattatt    6600
```

```
attttcttttt acttcaactg actgcacaaa cagtaataat ggataattat caacattctt    6660
taaatttctt  ctaactgcac gcatggagtt gatacctata agttcatttt cttttgtttc    6720
ttttgagccg  ttttcgtcgc ttgactctat ttgttcttcg atatctagga tttcaggagt    6780
ttccgttttcc ttttcgatat tttcccagtc aactttgttt ccatgatctt taacaaatgg   6840
gaaacctaat  atcattttat ggttgatatt ctctaagact aagaatctaa tattctcatt    6900
ttgccattcg  tctcttagct taaattgtaa ttctaaggtt aattctcctt aacgctgat     6960
cgttttctta  ttagcggcga caacatcttc aaattcggta ggctctaaat aattttctaa    7020
ttgatgtgat  ttaacaaatt cgtaatccaa aaagtttctt gacgcaccgc tgtcaactaa    7080
agcaacacat  tccttaaata attcgttttt aactttcaaa agcggaagtt ctttcctatc    7140
catgtaaacg  ttcaaaacac ttaaattttc tatatccttg ttatttagta tatacttgtc    7200
aaacttagta  gagtgttgaa tctcgttctt taattgcaga tttgcatttt ctattgtagg    7260
tgtgtttata  gcaatatggg aaccaaccac cttttggttc ctaactaatt taaattttct    7320
ctgtcttgtt  ttctaccagt gtaaccacca ttatagtttc tgttgtaatt cttgtttctt    7380
ttataactgt  caaaattccg accacgataa ttttttatttt taatggagtc tatttccatt   7440
ggttcacctc  tccatctatc ttgatgcgag aatctaaagt ctctagctct gggtgctgag    7500
tccttctcaa  agtctcttgc taaaaatttg gcttcagcaa gcgagtttgg tctatgttgg    7560
aatacgcgtc  ctctaatttc tgcacgtaat ccttgcacaa acctatctct ggtggcccat    7620
tcgttttcat  actcacctgg gagtaaggtc cggtacccct caaattcctg gataaattgt    7680
tccacggaat  ttttaccttg gtgacagcca ttgtattttg ctgccacttg tctcaactca    7740
aattcgtctg  ttggacagaa ttcgagtgta aactcttcga caaattgatg ccataaaggt    7800
aattcggagt  ttccataccct gttagtgaac caggcgagag cggatccatc gaggttgagc   7860
attgcggttg  ctaccttaaa taattctgtg acatcctttc ccatactttc ttgtagttta    7920
aaggccatgt  caagtttgaa cagaaattgt tgggctaaac gaacagagtt cttttcgtta    7980
cccttgaata  ccatgtttaa gttaacttgc gacgggttag aacctgcatg catcgcgtta    8040
acttctgaat  tcatgttgtt taatttcttt gttgaacttt tctaactagc cggtgctacc    8100
aattgaaagt  gttgctggtg ttgcgtactc tagaatctga ttcttgctta tttatatctt    8160
atatattttt  atacgttaat tctctgagaa catatatgga atatcctctg tttaaatagt    8220
aaatctttaa  tttaaaaata gcattttgag ggatataatt atcttctaga acttctgttt    8280
aaccttctac  aatcttcttc aaccttctat atgattaccc gatgaggaaa tagagagata    8340
gtcctttgtc  tgatctctta cattttttgaa agttttgcta gtggtgcgta ctctagaatc    8400
tgattcttgc  ttatttatat cttatatatt tttatacgtt aattctctga gaacatatat    8460
ggaatatcct  ctgtttaaat agtaaatctt taatttaaaa atagcatttt gagggatata    8520
attatcttct  agaacttctg tttaaccttc tacaatcttc ttcaaccttc tatatgatta    8580
cccaattagg  aaatagagag gtagtccttt gtctgatctc ttacagtttt taataggact    8640
tggaataagg  tgtcaaaatc atttcctagt tctggatgtt tctacggtta aatctttttat   8700
caaaaaagta  atcatagcct tatccatagt tacagtattg tttataacaa tgataattgt    8760
gatacacgtg  ttagtaagta cgcaataggt gtataaccgc acgagtagac aataagcgtg    8820
gtggaagtta  gtcgtagtag aagtagtaat ctatttctct cttttttctt ctgccgcttc    8880
cactcccgat  taggacctat atcagctata tcaattctat ataacggaat atcgtctgtc    8940
```

```
tttgtactt cacgcccgca acctggaatc accctcggtt gctactcttt ttcgtatagc   9000
agactcctgt acgagcttat tacgttttag gtctattttg ttttactatg ccagttctgt   9060
cataacccgt tgatgaatga taattaattt atgccaatga cagtgtctcc gacggcttct   9120
ccatgcctat gccctacatg atcaacggga ctaactctct ttgcttccta ctccggatac   9180
ttgacccttg ttaacttccc ttattctaaa atcgaaacct taacatcagt atgttatcgt   9240
ctacctactg gcacttcctt ttttggaaca catcctgaaa aatccctttc actaccccgg   9300
ctcttgggaa acatcgcccc gatgttcctc aaaacggtgc aacaaaataa ctggataatc   9360
ccggatgggg gcactgaacc aatgaagctg caaaacatta aaccagatta gaataataaa   9420
tgtaggtgga tcctggcagt aacaataatt tttttatgag ttcaatttgt atttctttaa   9480
atcgagagtg gctaacttat ttcaatcaaa aaacaatatg ttctatgttt tggtaggagc   9540
aatatctgta ttttttttct tcagctgagg gacaaatagg aacgttctat gtattataat   9600
tatgattact ttgttgatat caaacttgtt cgtgttcttg aattaattcg gctttgtaca   9660
ttggactttg acgtagtgac aaagctgctt ggttgaaatat tctttcaggc accttttcttg   9720
ctagagtttg atcacagtct ttccagaaga catcataagt cttttctttg cctggttctt   9780
ctgatcatcc accgatacca ctcagttcgt taattcttgc caacatctca cgctctgttc   9840
taggcggttc ctggtaaata ttggggtttt ctttatagta tttaatccac tgtacatttg   9900
attcacgatc cttcaaatta ataactggta aatcgacttt ataagcattg ccgtttattt   9960
tctcgactag tctgtatggc ccatatcata ctggttgaat ttttgtgtac cttatattca  10020
caccaaaggc atcttgatgc actaacacta agtcaccaac tttatattca aagtatcttc  10080
ttttttctatt atggtgtttt ccttgtcgcc cttatgcttt acaatattat ccagtgtgct  10140
gtaaaatcaa tttcacacgt ctcacaaatt cttctgcgtt aggtgaatat ttgttatcct  10200
ccaaatccca gctatttact tttctaatca tgctcggttc atactcgtag gcgatttcaa  10260
aaggacttgc tttaatggaa tcttggtacg ttgaattgta actaagttca cacatagaca  10320
gatgctcatt ccaggataat tgaacgtttg cagaatattt ccgaagtaac tgattaacaa  10380
tcttgttgaa tctttcagtt tgaccatcag ttttctggatg attagtagtt gaaaataata  10440
gagaactacc attgagataa tgtaatgtct gccaaaactt attcataaac cgaatatctt  10500
tgtcactaaa caaacgagca catgcagcag cattaagtct tttgtgcgct ggtataaaat  10560
gtgccatttt tgaaaagcga tcgacaacaa ccataatgat agtgtagcct gttctcgatc  10620
taggtaaacc tgtaatgaaa tccatcgtaa tgtcggtcca gcgacctgtt gggattggta  10680
aaggggaaaa caaccccttgt cttcctctag tgttggtgtt gtgctgttga cagatacgac  10740
aggtttctac ccattttcta atttgtgcca acatagatgg ccaataaaaa ctatctttaa  10800
gattcaaata agttttccat gcaccaaagt gaccagcatc tttggcatcg tgtgcatttt  10860
tgaatattct atacggtagt ttcttgtagt ttggaataac tactctaaag aaatcttgag  10920
actctaatgt cttataataa agtacctcat cttgataaca ggaatgtttg atatgatttt  10980
taatttcaac tggaactttt gttttatctc tcacagttct aaatatcaag gcataattat  11040
tatcttttt ataacccgta ataatttccc ttttgattt ttgattagct tcgatagtac  11100
ctagtgtcaa cgaatgtttc tgtgttttat tctcctcttc ttgagtcaat tctagcaacg  11160
ccagttcgat tttggctagc gttaagttgt tttcgtggtt gtatgggtat ctagataatg  11220
catcagcagc ggaattgttt tttccctgta agtaacgaat atcaaaatca aactgtggta  11280
aaaagtccat ccatctagcc actctagtgg agtctatgag attttggttt tttaagtaaa  11340
```

```
ttaaactctt gtgatccgtc ataacaatga catgtcttcc catgagataa tatcttcatg    11400
ttcttaatgc ttcaacaaca gccaaaaatt cacgatcata tattccatga ttcagttgac    11460
ttccaactag cttctttgaa ccgtaagcaa tcacacctcg tcatttacct gtttcgtcca    11520
actgttctag agtataacct aacgatactc cacacgcatc ggtatgtaga acaaatttac    11580
aattgcctga ccaacttggg tgcaccaagg tgggacttga tatcaaagcg ttctttagtt    11640
ggttgaaggc ttcgtcttgt tcacttgtcc atttaatttg ttttgtcatg aacttatgaa    11700
ttggattggc aattttggaa tgccctttaa taaaccttct atagtacgaa gttaaaccaa    11760
taaaactttg tgcttctttg atcgtgtttg gcgttggcca actctttacc ttttttattt    11820
tctctagagc ggtttgaata caaattggtg taacaacttg tcctaaaaac ttaaattctt    11880
gataaaaaaa tctgcatttc gacttcttcg taattagttt atgttttctt agtgtcaaca    11940
aaacttcttt cacgtgctta ccgtgagttt caacatcttc ggagtatata aaaatgtcgt    12000
ctaaatagac ttggacaaat cgatctattc tttcaggcaa gacagtatcc atcatctgtt    12060
gaaaagtcgc aggtgcgctt gttagtccag ccggcattac catccattca taatggccaa    12120
aatcagtaga aaatgccgtt ttctccacgt cttcatcagc aattctcact tggtagtaac    12180
caggcgtcaa ctctaactta gaatagactt ttgccttacc aaatcttgaa atcaattgat    12240
caatatctgg aagtggaaac ttgttcctag cagtattatt gtttagaatc ctataatcaa    12300
cacacatacg catagtacca tctttcttct taacaaatag cactggactg ttaaaaggtt    12360
tggaactagt tttgatgaaa ccttgtttga ttaaaacttc aacttgtttt gttagttcca    12420
gtttctcaga gaagcttaat tggtattgtt tttttcaaag agaactcatt agggtaatac    12480
aaggcaacat atgcccgcat cttttctttg gcggtagttc agttgatgga tctcaagtaa    12540
acttttcaag tgtttccttt ttcaatcctc ttgcatgatt tgcgtctagg ggtcgatatt    12600
taaatcagct ttggctttat cgatatcagg acttactaaa tacccctaaag ttagatcact    12660 aaattgcctc ttgataaatg ggtttcccaa catgaatagc gcatgctcag tatcaaacat    12720
ttaaaatgac ctaacctcac ttatactgat agtttctttg actacctcaa aagggacaat    12780
tacgtctgcg atagcaacac cagagtttcc gataatcttt actgttattg atccatcgag    12840
cttggccttt tgctaaacac atgaacttcc tcaacagttt tattaataac tgtaaaagtg    12900
gttctggagc aaccaaaatg tcatctgcat atttgatata aacgacacca caaattaatt    12960 ttggttttc ttttttggga tggtcataat gtgagtgtgg gatggcatcc actcattttt    13020
cggacattta tacttactat gaaagttcct tttcgtattt cgcatcatta tcatgccctt    13080
taacatcctc ttataaatac tatttgaata aaggaacatg aaattatcca tgatacatta    13140
ggttgccgat ggctgaaaag gcatgaaata aattgagttc tttggcggac tttgttctat    13200
aagggaaacc atttaaatca ttgtataagt gcccatgtag cttcttgcat gtctatatct    13260
ccaatagact cgccccaaca tggttaaaac acacatcaag cttttatgtt agactgcaac    13320
aatctcaccc ccattaactg ctcaatatcg gtaaggccat caaggaatag tggtcaactc    13380
ttaatgtcag aaatagcgac gtatatagac acttaaagt tttctttata gcctctcatc    13440
gattgacctg gtttcaatcg acacaattac ttgacaatat tcaccacaga gtctctgtct    13500
ttgtcgacag gaacaaagcg tttcagaatc tatcttcaaa tttagaccaa ctaaaatcca    13560
gtatttgcta gttcatatgc atttgagaag tgtgtaattt acgttcgtta tttttcaaac    13620
ctgcaacagc ccttataact tttctgacat ctggtagccc atatgtagca aattctcttc    13680
```

-continued

```
caatgtctgc tgaccattct atgcctctag cccttatatc cagtaatgga aatccggggc   13740
ctttctagtc tggaattaat cagagaagtt gggtggtttt gtataatttt attctgcatt   13800
gaacatagtt gagttttgtt ctcgttttat cgatttagct ttgataaatc agctagttgt   13860
tcttatccca ttgcaatcat ataaggcaat aagataaact gttttaccat tgtccaaaat   13920
gcaaatattc aatatagttt agtttctaaa agcagccaat aaatacatgt caagcaaata   13980
caatactgcc ttgatgtgcc ctaattctac ttcagataac catgttacac gttatagatt   14040
gaacgtttaa aagagttact tcaaaatacc acataaaaag aacccaagga aagaaaata    14100
atctacaacc tttattgata tcatgtgata cagcaggtat gtcgacacac attatgcact   14160
gatggcaact agctaatgac aactagtaat atgttttgtg tttagttaga gatgatatca   14220
ttatttattg tggcgccaaa ccgacaattg ataagagagg taactccgct cttactgtag   14280
cttttaatac gcatattatt tagaaatccc ttagtaatca agtgtcgaac taaatatgga   14340
tatcgtacca tcaatagctg attgatcgga cctagtcatc catattgctc tccaagagtt   14400
atatattagt gtataaatta actactgtgg ctgaaaatta caactttcaa atacacaacc   14460
aacgttgcag gtttgttgtg ataaaaagtg taacttgatg tggggttgca ctgtatagtt   14520
ttgatgttat actgccatta attgggatat aaaatgttta ccaccaccaa catgtgtcat   14580
ctgataaacc acagacacag caacaaatct ggcacttgaa ggtttgttgt aaagcttttg   14640
ttgctaaaat tggagaggta ttttttccctg ataaggagaa ttcagaccgt cttttttggaa  14700
gtatcttgaa aaccttgtgg atacttattt cgaacgccca ccacttggac ggagaaagga   14760
taatgacttc ttgcgatttt acaattttgc tgataaatta aaggcctttc atggtagctt   14820
ttgtgggaac ggctctacgg aaaagttctt gagacatcca ggtttgacaa aaagataaag   14880
tctactaaaa tctatttaca ggccccaatt gattaaaaag gtgaaaatat aggttttaca   14940
aagctcttct gtaaatgtat tgtttcggat tacaatacat ttttagcaag cacggaaatt   15000
cccttttgtt acaatataca ggagtgttcg ttaaggaaag gttttgacgt ggatggaatg   15060
atgcacctgt aacatatcgg tggaaacaca agaaaccata tgggcctttt accagactaa   15120
gagcatcttt taaatattca gtttatagac atggtgcatc tttcagagtg acagaacatc   15180
tttgggggag ttactcacgt atattattct atagatttta ggatttcaag gatccactgt   15240
gagctaatag gattggtagt gggcttgtgc tacaaatttg ctcagttttg ctcgatgtcg   15300
ccaaccttaa aaacattaat gtgttttttaa ggattaacgc agttccgtgc tccgttatga   15360
tggaaaggtt aaagggaaag taacctatag ttttggtttg tatcagccat gttctagctc   15420
ggaagtcaac gaacaagctg tttggaaaaa tctagcattg tttttgattt cttcatcaat   15480
gtgattatta ggcccgaatc gtttacggcc gtagttatta agacatatta tactagaaag   15540
ataaaaggat atcccattat gcatatattg ttaactcgaa cggaagagat caaatcaacc   15600
atttgagtgt ttacaaagac aatggcaaaa caacagcact cctcttaaga acacgatgtg   15660
gcaccttcgc ttaacctttt ggaaagtaaa ggtagtgttt gtagtaaaaa aagaagggaa   15720
gaagatattg agattgtgtt atatccggat attgtgaaca aagtcacaca gtccgcccaa   15780
attcatggtt taattgtaga gcttatccag tcagtatgtt tctggaattg atgctgtatt   15840
caatgtgaca acatgccaat atttcaaatc tatgacagat gtatatatga atgacataaa   15900
cgaaaaaatc cattgttgag tatggttatt tctgcaaaat aaatcagcag gtaattatgg   15960
tatttgtatt acgaaattaa gtgaactgct caagaaatct ttctaagatg agcttttgcc   16020
acaatagcgt tacatttttt agatggtttt gaaacttcac acaaaagtct tgcaagacaa   16080
```

```
ttttgaccta atagagttgc tgctgtaaag tttctacggc acaaaactat caaccttgaa    16140
aaaaatctcg attgtgttgg tgttgacaca ttgacaaggt ttaggtgaga aagaaatatt    16200
atgaagtgta aaccgcagca aacagttttg tctctccatc atacacccca tatttgataa    16260
tgttttactt gtcaatgatc ggaatatatt tgacagtatc tattgtgtgt ggaacaaaaa    16320
agggaaaact agatatgcgc cttttgacat ctacgaaaag aaaagtccac cgtgaaaagc    16380
tttggaaata taaaacataa attgggtgaa ccatctccaa agctgtttct ttattattcg    16440
tttagaagtg ttagaagtct ggtacttttg gcataaaacc agttaggaaa tatataggaa    16500
agaatggacg taacattaaa aatgtatcag gaaaaatttt ttacttgctc gtggattatt    16560
tatgactcac agcttagttt tccatttccc cgataatact cccagagggt gaattgctat    16620
aaaaaagtaa cattcgcata gtatttgcca ctgtgctaca tgcactttc  tcattatatt    16680
acttttttta cattactagt tttatatgaa gtgtacagga ctacttgcat tatctaaaag    16740
caggtattat taaagcatgt tcttatctgg gttttgttac cagattcaag tcgttataac    16800
aactcatgaa gcttacactg atatatttat tagtgaacaa tggaaagata caaccatata    16860
acgatatcga gaaattcaag ttgttattag ttgatttata caaaccacta gaaaaaagtg    16920
tcatttccaa ttaataactg catcgcgaca gaaaacttag ttaaagacta tatcaatcat    16980
atagaaagat aatgaaaaaa aattcaaaaa aattcctcca cacaaagcaa cggaacttgt    17040
agctggtaaa acaataaagc tgctgttata cggtgccatt gaatgtgtaa acacaagtgg    17100
gtatttattt taaaatgata gtagtgtcca gaaggtcatc atagatatca ttgaaaaggt    17160
caggacaact ccgactttct gtaaactgtc aataagtttc tagaccttca cttttttaaat    17220
ggggataaga gaaaatgcat atagacaaac aaacaaatac cttgtgagaa gaaaacagct    17280
atagtatacc tactagaagt gcttgattgt aaggccgaat atacatatcc atccgaaata    17340
gcatttggat cattaataat catttatttta gacaataaag gatctaataa aatccgccat    17400
aaatgtgtca gaggctagta tctaagaatt agtatgtaaa tatctgacag acttatcaag    17460
tggaactcac tgcaagactt taacttattc aacgaaattg gggacttaat caaatttgga    17520
acgatattgt atactcccca ttaattactc ttggctggat tgtatatgga tcggtggaag    17580
accggatttt atataatggc attatgagct atagttcctt ggaaaaaaac gagtttaagg    17640
atgaaaataa agatattata gtcaatttcg ttgtagtaat taataaaaaa ggtcaaagtg    17700
tccaaggatg tgttcaagga gtgttcaacc agatataaca gtctcacgca gaacccaatc    17760
aggaaaatac gctttgaaat ggaaagcatc gcaaacaaaa aagcctgatt ttcttgtgaa    17820
tgatttcaca aaaagtccaa acatatcttg cttaataact agcttttgtc aaaaaaaact    17880
gatcttctaa ggtagaaatc catcaattat ggatgaaaca cggaactcat tgttgaaaa     17940
acgcactaga aacaagcaac tgtaattaac gtttatgtga aatcttagat acacaagtgc    18000
ctaacggctg agaaggccac agttatgttt tccgatagtt gaaagtgct  attcataagc    18060
tgtcaaaaca aaatcatgag acacatctaa caaatacaat tatacaaatt cagaagttat    18120
ataatacaat ccatctaaga cctcgttact acattgtggt aatggattaa ttgatggagc    18180
tatatggcaa aatcaaaaag ttagaactaa caaaggaagg ggatagacaa acaatgtaac    18240
tgactattgt aaataatgat agtaacagtt cacagtctaa aaatcagagg gaaaaacttt    18300
gtaagaagaa gaaataagt atattactat tattatctca agcttttata tgtcaaaaac    18360
gaatgcgatg ttttgaggag gaatatttat agacctggca agcatctgat tcgtaaaatt    18420
```

-continued

```
atttcgcaag accaaactga atgtactgta caatgaatca ttattaagat gtccgaaatg    18480
agttagctga aactaaggaa ttaccagatg actcagtgga caaacaaggt attgaagaaa    18540
taataccggt gtcggaatat gacgaaccaa aaaatgatc aacccaattt aaaccattta    18600
cggcacacgg cttaagacag aggcaaacaa aaaaggcagc atttaaccaa gagagcataa    18660
tggccgatgc cgagactaat gacattcctt tttttcaaa gacaaataac aaataaaatt    18720
ttctgggaaa gtcaaatctg tataaacaca atgcacctgg tactatttta tctatttatc    18780
aattgcctgt atctcaagtc tcgagaagag acgaaaacca acattggggt tactttatgg    18840
aaagacatta taggagtcta tgcgcgcata ataactgaga accaaaatca ccaaagtcta    18900
atataaaaat ttcgcaaaag gaaagtaaaa acgatgtaag cgccgactaa gaaatacacc    18960
attcccaaag gtcaaaaaca acactggtaa caaaatattt gcacaataga gaaagttgtt    19020
gcatgtgtcg aatattttt atggattaac aataatggtt aagatagtgt atgatgagat    19080
gatcaaagaa aaaacaagt ttcccacaga ctcaacgata tttttgatt tgaaattagg    19140 aaaccatata ctataatcca attaccgaaa ttttcatgag taagctacta tccttgttaa    19200
gtgttattag accagacatt aaatacgctg caagatattt tgcaaactgt actttcacgt    19260
ctgaaaatgt attaagataa tgcatgcaag tactcagata tttcattgca acaaaacatt    19320
aaagttttgt ttgacaatga aaacaaatat gaagagttaa tttcattctc taactcgggc    19380
aactctacta gtaattcgaa atctataccg atcaaaagag cgtgcttatg tttgttaaag    19440
gacttataat gtgaagatca gcaaaaaaaa ctaattagta gtcacacaac tttatcatta    19500
taaatcagta tttagctgaa gaagactgtg aaattaaaaa aaaacgaaac agcagttaat    19560
ttagctaaag tacacaaaat acatatcact gtcaatactc agaattttc aagaaatgga    19620 tacctgaact atggataata attcacaacg tcatgatcaa ggagtagtgt gtaaagagta    19680
ataatagaag cacgaactca tattgtaagg aaacatctta atggtaaaaa aatggaggc    19740 tgaaaccttg tcatttttata tggagactat tcatactaca tgaggaaaac caggtactta    19800
tatatctagg cccctatat atagagaaag aatggtgaag acataatatt tactgcgagt    19860
gatgtgaggc tggttgatag tgaaatcatt aaggaaaata ccaggaagta ttttaaataa    19920
ctcgattgaa gaacttgcct gtagttctct ccttggagtc aataaaagta ctgcccaagg    19980
gaacatcagc aagaagatat ctagtaaggt atttgtgtac gattacgtga gagaccgaag    20040
aatccataca agtttgaagt atggcttcct aaattttcta tctgggtcta tttctaatta    20100
taggtgagtt ggttttgctc aagtggcaca tgtatgagtg tccttgtaat tatgaattca    20160
cttattactt ttattcttct ccgctttgaa tcagttatat aataaagcct agttttacct    20220
ctttaaaaat gcaaagtaac caaaaaaag gtgctagcta tatcacatgt tattttcacc    20280
gttttctttg gtatacccac agttttagat aatttatttt aagcaaaaat aaatgaatag    20340
tttaattgat atcacacttt gttagaagta aaagttagaa cagaggtatt ttaactcatg    20400
atactcgatg aagttcatta tagaaccgca tttgtaagct tcgagatttg gttcaaatta    20460
taaaaaaaat cgaaagaaat acctcattac ccaaatctgg aacagcatgc attgataggg    20520
ccggaaattt atttattaag ttacatgtta gaaaaaagtg aacagtcaga acttagttca    20580
atacgcggta aatatgttaa ataaatttta cttggtttgc atttttcac ttttcagtat    20640 ctcaataact atcccttatt atcaatgaaa atctatctag ttattttgtt aagttggat    20700 aaaaatctac ggaaagacat tactacttga aggtatctat tgatagatca attatttgtt    20760
ttaagaacta tagaattaaa aacaaggcag taatggtaga ttttaaagat tatttagagt    20820
```

```
agatagatag taaaggctgt actgaatata aatgtggatt tgcagaacca ataagtgacc   20880
tgtaatcaag ctacttaagt aattctaatg gtattttacc acaggaaagc taatcctttt   20940
cccaatgacg gttcatatga tccaagtttt aaatgttttg tatcatcata tcataatagg   21000
ggtatttgaa aggcatagat cgacgaaagt gataaaaatt acttattaaa cgacgtattt   21060
acatccacgt ttttgctgga agtactgaat ctgcctactg ctagtttggg gaagacaata   21120
atacacaaaa taaagacaat gatgaagatt ccagttbbtt ttaaagataa aaaaatagat   21180
atatatgtat aattgtatga atagttttaa taataactta tgttgctatt ttgatagcaa   21240
ttcattttac tattgaaaag gttacccagg caaataatat gtttagcaca tcagattctg   21300
tactaatagt aatatagagt tatgctataa cgtcaggcaa tacttatgtg tatagcgaaa   21360
tagtaaatgg cagattgtaa accgtatgtt ttcactactc agactcatac gacatgtcta   21420
gaagcccaag caatgaatta gaggactgtt tggtatcaac atccagtcac cttgggtgta   21480
ataaaactta tttaaagaga tagtagaaga tataatcaaa gatcatgcac aaaatataaa   21540
tgtataagtg aaggtaatgt attgacacat tttgcttcgg gcacgtgcgc attaacagat   21600
tttgtataag gttgctaatt atagtacctg gtgaagaagc attattcaga aaggttgtgg   21660
cccaactaga tgttgaagtg gaccttctac tttccttaaa tacaatagaa gcaaaataga   21720
tgctttacct atcacaaaca cgatgagtat tttctcgttt tgcttagtc aaatagagct    21780 aattagaaaa tccttcgata tttgatgcct tggctggaac caactcaaaa acatcttctt   21840
ggaatatatt tttctagtaa tatcgggaaa ataagaaaca gttacccaga aataaatggg   21900
attaataaac aaccgtaaca tttttbatct tttcatgcga tttactcgag ctctacattt   21960
tctattacct caagaactaa attbgtgtag catttatttg acgtataatt tttatttagc   22020
tcatcactaa agaatacttg ttattaagag attctaccat taataaagta cgcaaatcta   22080
gcttttctga agtcttgtta acttttaatc tcataaatgc ataaataaca tatcagatgt   22140
atcgtattta aataaatata atgcacatga tttaggaaaa aaaaaaacca tttgtcctca   22200
aacaaaagag tagatcagac ataaaaaatt gaagagattt cattctttbt aagatatctg   22260
tttttggttc aataattgac taatctatca agtaaattaa gtaagagtgt ttatataatc   22320
ctcttataaa ctgttgctgt gatgtcagtc tgactaattc tatcatctgt gattaatatc   22380
tgcttagcat cactgaatta atttatatta ttagttgtta tcatctattg ttcatcagac   22440
attbgttttt ttaatgtaag ctaatacact tatgatgtga gtaagtgacg tgcaacagtt   22500
acgtccaaga tattgctatg aatataaagc ccttttcagt tcaatatttt tttacacatt   22560
atcaaaacta tttgatcaac agattgacag ccaattccga agatgaagtt ttaatattaa   22620
acttttgaaa gcaaaaatcc cacaactaag agtgttctt gccaataat agttcaagcg     22680 tagcccatgg caaaaacatt ggaattaaaa aatctccgag accgggaatt gaacccgggt   22740
ctcccgcgtg acaagcggaa attctagcca ctaaactatc tcggacaact gcgcaagccc   22800
ggaatcgaac caggggctca acgatggcaa cgttgaattt taccactaaa ccacttgcgc   22860
ttgttgagtt ctgaaagtgt tgctggtggt gggtacttta gaatctgatt attgcttatt   22920
tatatcttat atattttat acgttaattc tctgagaaca tatagggaat atcctctgtt    22980
tagatagcaa ttttbaattt acaaatagca ttttgaggaa tttaattatc ttctagaact   23040
tctgtttaac cttctataat cttcttcaac cttctatatt attacccgat taggaaatag   23100
agagatagtc ctttgtctga tcttttacat taccccgccg ctttagaaac ttcgtcccgg   23160
```

```
agtttattat cattatcaat tgcttttgca ttatcccata aagttttctg taaatcttct   23220
gggatctcta aaaataatga atatgggatg cttgaactat gacaagggtc acaatctttc   23280
cagtagacat ccaatgtatc gtttgtttcg tcgataccag ctataccgat aatctcggtc   23340
agtctacttc ttgcttcagc tattgttctt ggggtacctt gggaaactgt ttatccgttt   23400
gtaagaatct tctaagccat ctgacattga ttactctatc cttttattc gttttcggta    23460 aatcaacttc gtaagcgttg tctgatatct ttttgacaac cttgtagggt ccgtagtata   23520
ccggttgtat tttgtaatac aatctatcac taccatatac atctttgtgt aataatatcc   23580
aatctccagc ttcaaatgtt tcgtacactc tcgacttatt atgctgtgtt tcctgacttc   23640
tttgcgcttc aatcatgttt tcttcacat tttccatgat gactttcatt tttaatgcga   23700
attcttcagc tttattgctg taccttctac ttgaaacacg actgctagaa ataaacattg   23760
gcgagtctgg taagtaacca tagcaaactt caaatggtga tgaacctatc gagacttgat   23820
gggaactatt gtaggcaaat tcggccattg acaaccattt gtcccaactg tagagatcgt   23880
tactatcata atgtctctgt tattggttta agattctgtt cgttctttcc gtttgaccat   23940
ctgtttgagg gtgattagtg gttgagaaga gtgatgatgt accaagaatt ctatgccatt   24000
atctgaaacc attcttttg gaatccaatg taatttaaaa caattgtcta ctatcaattt    24060
tgcacattgc tctgcggttg cagttttcct agtgggatg aaatgtgcca tcttcgtgaa    24120
tctatccacc actaccaaaa tcatatcgtg tccattttg catctgggaa cacctgtgac    24180
gaaatccaaa ctgatgtctg tccatcttcc ttcaggaatt ggaagagggg aaaataatcc   24240
tctttgacca gttgtctcgg gtttggtttt ctggcaaacc gtacatcttt gacaatatct   24300
cttcacgctt tttagcataa ttggccagta aacataggg tgaagtctca tgtatgtttt    24360
gaaataccca aaatgaccag cagagttacc gtcatgagcg ttaccaataa tttcctgagc   24420
caacttagac ttaggggaga ctacaattct tcgatcattt cctcctttaa ccactgagaa   24480
atatagtaaa ttatcctcaa ttgaataatg tttgatgtgg ttatggattg acttcgggat   24540
cggcaaattc tcttttaaaa tgtcgtatat ctccttagtt tcgttgtctt catcgtacga   24600
cttaatgatc cgttctagaa gttcctgatt tggtgttaac accgattcta ttgtgttgat   24660
accaacttca ttttcctcgt aggggtacct agacaaagcg tctgctactg aattagtagg   24720
acctcaagta ttgaattgtg aattcgtaat cagctaatcc taggaatgat tgagcatctt   24780
tggcgttttt cggaattggc cagctcttga ttttgtctat cttagcaggg tcagtctgga   24840
tacctctgct tgaaatgaga tgtcctaaga aacctaaggt tttgaagtaa aatgagcatt   24900 tcttttctt cgcaatcagc ttatttctcc tgagcaattc caatattttt ctaatgtgac    24960
tgtagtgttc ttcaacagtc tttgagtaaa ttataatatc atccaggtac acctgaacaa   25020
attggttcaa ataaggtgct agaatcctat tcatcattct ttggaaagta ctaggggcgt   25080
tggttaaacc gaaaggcatc acaacccact caaagtgacc gtaatctgtg aaaatgctg    25140 tttttcaat atcatcttct gcgattctga cttgaaagta acctgacatc aaatccaact    25200
tggaaaatac tgaagctcct ccaaaacatg tgattaattt gtcgattcgt ggtattggga   25260
acttgtcttt taccgtattg ttatttaata acctataatc aacacacatt ctcatactac   25320
catctttctt cttggcaagt aacaaaggac tattgaaaga actaggtgca aacttgataa   25380
aggctagttt caacagttca tcaacctgtt tattcagctc ttgtttctct gaatagcttg   25440
atttgtactg gcgtctgtat gtactcttgg taggttcaat gagtataatt ctgtgagtca   25500
aatccctttg gggaggtaaa ctggtaggtt ggtcattggt caccacatct ctaaattctt   25560
```

```
catgaatttt ctttctaatt ccatcaacac catcgtaagg ttcttctaaa acattattat   25620
tttcttttac ttcaactgac tgcacaaaca gtaataatgg ataattatca acattcttta   25680
aatttcttct aactgcacgc atggagttga tacctataag ttcattttttt ttgtctcttc   25740 aatttttttca ttatcattaa ttgttttgca agtactctct aagttaatat atatcccgta   25800
accttaattc ttcttcaaaa agtagagctt ctagcgccac taattctttt ttatttctct   25860
ttcgatcatc cttagcccta taatctttaa taaagaggag actgaaaatt attttatgat   25920
tggtattctt caaaagcaaa catttgttgt ctttattgcg cccattatat tttaaaacaa   25980
gttgcggtct taaaatcaat ttagctctat gtgtaattgc tttcttatta gcggatataa   26040
caacttcaaa tctagtagac tttgaaaaac tctctcatgg atgtaaccta acaaatacat   26100
aatccttaat gtttcttggc gcgctgtcat caactaaagc aacagaatac ctaaacagtc   26160
tctctttcaa aatctcttct attgcgagac agagttttct taataaaatc aaaatccttaa   26220 gttttgcttc tctatctgaa ttctgggggc gaaaccacct ttaagcgttt agcaaaatga   26280
aaccataaaa gtagtcttaa attgaaaata ctttatttgt tagtatacca agtaaggacc   26340
gattcaacaa ggactaatac ctccatctcc aaactaggaa aagtacgtga cttgcttct   26400 aatccatttc tgtgtgtagc ttaaaattgg taaccaatct attaacaaat gttatgacaa   26460
gcgcctatat ttttttgtta catttgaaaa acatttttaa gtctagtagg aataagttgg   26520
aacctgcgtt catcgctttc acttcgaaaa tctctttatt ggtctcttgg accctaaaac   26580
ctccgatact agcagttgta agtgttattg gcagaatttc gactagacat tacttatagc   26640
gttttttgtt ttatgtcatt tatttattga ttatactgct tatacacttt atatattata   26700
atttattcaa tataattaat tcaaactaca tatgtgaatt ttgaataccct tagactgaag   26760 ttcaaaatca aagactgatg tgagcttgca acccgaaaaa gcaaactttc actgattgat   26820
catccatggg ctgcaactga aaggcacgta gatttgtttt tctctaagga cagtacatgc   26880
taggtttgtg ggaaatgagg aaagctttgt gtacgccaac ttacacgcag gaggagaaat   26940
ttggaaaata ccctatatag tttataaaca ataagttctt tgttccatct agcaaaacct   27000
agaccagtcg agataataca catatacata agtcattttc catgatgtta tttcatcaga   27060
ggtaattatt acattctaaa attaatgcca acgacatagt gatttaaaag tgagaggttt   27120
tttcaggcgt tgaactttaa gtttgagtat ttttcaaaa ctttttttg aaaaaaccct   27180 tctagggata gtgcagtttt aagtcgggtt tacaagaagc atttaaacta gttgatgaat   27240
atttgaatat tactgtcagt gtttctgcac gatgctaaat gttattctca aagtactttg   27300
gaagctcata cttaattttg caaaaggact ttttagaatt atctaacttc atataatatg   27360
aaactcagcg ctcaaattct accattcggc atttgaaacc ggtgaaccac tttttccttg   27420
attgttgtac aaaaaaaaca gatattgact tctgcgaaat taccgaggag catctgtttc   27480
tttttcgatc tcgtttacac taaaatcaat ggcttataaa gtgtacatat agttatagtt   27540
tattaaattg ggtctgtgta aaaacataaa aaaacatgtt caaaatgata gagcttacat   27600
cgaagcaagg ttaagtgatt tacgcataag gcaaaagaga gaataccgct ggtctatgtc   27660
tctgttattt gttttggtta gtgtttggta gaggaaacct tcttaaagtc gcctggaaat   27720
ataacttaac ttttttacta aacagcaccc aattgaaaaa aaaagacctc catgagctgg   27780
tgattaaatc acgtaagagt aatccatttt tgattttata agaagttaaa tgctggcctc   27840
tagagacgct ttatggacgg aaatagcccg aaaataatta tttcaagcat gaatatacta   27900
```

```
tcagttccgc cttagacgtt tattgaaaag gagcttttat tatacaaata tgtacgcgtt    27960
gacaactctt tcttttttcct tctgttaaga ataatataaa cggttatttc cttttattct    28020
aaagaacaaa aggaagctcc tcaaaacaaa gctgaaggtt tacgcatcat ttcgagtata    28080
tttgtcaggg ctttgaagcc gggcgctata atcaacaatt tcatattttg ggattacaat    28140
atataacagc aatttattaa gaaagctatg aggaaaaaat cgatttgttg aagacttcat    28200
agctatctat agtttctatc aagtatttgg caatataaaa atggatgata gtaaatgtag    28260
acttcggata attacttata gttaaacgaa attcaagggg attttaaca aatcccaaag    28320 ctttaggaca atttttggctg gcctaaagtt tcactactga atacagtag agataagtgg    28380 cgctacgata ataacaagtt cccccttctag tcattcaaaa cattatgttt acaaaaatga    28440
agagagtaaa gctaacagtg aaaagctgct caaaaaatat tgcagaccgg gttaatttgc    28500
aaagtttcga atattgcaaa aacttctcgt tattttttcca ggttttgtat tacgcataaa    28560
aggaaaatta aaaagatag cttcgggttt tgtaaacaga gtcaagagac ggtctgcttc    28620
ctagtttgaa aactttgcaa atgtacagta cgatataaag ggcaaaagct atgtatattg    28680
aacaatttca ataatagtaa ttctttgaac taggtctcct cgtttgaaat tagtgtactt    28740
catttaacca agaacagtaa caaatttctg cagcctcctg aaaagcagcg gctaaagagt    28800
tcttgctcct gatgctttaa aaatggaact gtttgtgcaa agaaaaagat ttgtcaataa    28860
tggaaaaaaa aaatttaatg aaaagtagca ctttggatat ttactacttg tttgatcccg    28920
ttgttggcca aactcttaga aaatcacatt actttgaaat aaaaattatt aatacaaaag    28980
attccataat atttacttcg acatatgcta taatgtcagg caatacctat gtgtatagcg    29040
aaatagtaaa gggcgggttg taaatcgtat gttttcacta ctcagactca tacgacatgt    29100
ctagaagccc aagcaatgaa ttagaggact gtttgatacg aatattcagt caccttgggt    29160
gtaacaaaac tatttaaaga gatactagaa gatataacca aatatcatgc acaaaatata    29220
aatgtataag tgaaggtaat gtattgacac attttgtttc gggcacgtgc gcattaacag    29280
attccgtata aggttgataa ttatagtacc tggtgaagaa gcattattca gaaaggttgt    29340
agcccaacta gatgttgaag tggaccttct aatttcctta aatacaatag aagcaaaata    29400
ggtgtttcac ctatcacaaa cacgatgagt attttcttgt tttgctttag tcaaatagag    29460
ctaattagaa aatccttcga tatttgatgc cttggctgga accaactcaa aaacatcttt    29520
ctggattata ttttttctagt aatattagga aaataagaaa cagttaccca gaaatagatg    29580
ggattaataa acaaccgtaa cattttttat cttttcatgc gattttctcg agctttacat    29640
tttctattct ctcaagagcc aagtttgtgt agcatttgct tggcctataa ttttttattta    29700 gctcaacgct aaagaatact tgttattgaa aaataccacc agtaataaag tacgcaaata    29760
tagcttctct aaatattcat gagtatccat cttgtaaagg cctctgtaaa gcaataaccct    29820 tatatttcgc taaatccagt agtcaaaaaa tagatagcaa gcttgagcaa gattcttttc    29880
attagcttca ttatgattat ataaatatat tgcgccagga agaacttgga gatttaacta    29940
atgtcgagag tacaatgagg tataataaat tttcatgttt aatatatctg atagcgagca    30000
tatttacatg ggaagccact caaactaatt ccgtcaattt ttttacaaat ctaatttatt    30060
attccaatca ttaagtcaag ataaaaaaaa ccctgaaaaa agtatagatt cttagctact    30120
ttaccattca ggcaaacaaa ctcattctcc ataaatatgt ctaagagtac tcttgagaaa    30180
aattcttctt ttatattata acacgattaa atttcctgag caaaaacaaa aatgaatcag    30240
actctcccag aaaaatagtg aatgcaattt ttgttttatt agtaagagga ttaagaatat    30300
```

```
ccttataaag ctatctctga gtcgataaat ctatctatgg cctaatttca atttactaaa   30360
tgagtttagg aatgtcacta tatacagaaa actgaaaaaa taacttcaag tatatttaca   30420
aattctgttc attgagaacc aaatagtgag aattatgcaa tatccttttt aatggattta   30480
taagttattc aatatcaaca ataaataaac aacattgata tatatgtaaa taaaacggta   30540
gaacctaaaa aataatttat ataatggaaa acttccagcg aagtatgatg atattcagaa   30600
tatatgcgga taactgtcga ataagcacat taatagtaat gatatacatg taaaaggtct   30660
tgggagacaa attaatcaat tttatgatag taaaacaaat ttctttgcaa acagcgcgaa   30720
caaaataaga aatgatattt tatataaaaa atactagatg agttgacatt ggagaacagt   30780
ggttaaggaa tagcgttatg ccacaatgta gatatttata gtagctgtaa attctataaa   30840
aactggtgtt caagaggcac aattcctgac gtgatgccca tatttagtcc agcagctgga   30900
taacttaaaa agaatccaca aattatatag atcgatatca atagattcag ttggagttga   30960
actggtttct tattaatctt tgttttggtg ccatgatgac tgagggtgtc ttccataact   31020
aatgctgata taaattttaa tcgttatttc tgtccttaac tcagaacata ggtctaaata   31080
tagctgtcaa acaatcagaa ataaatactg atcctgaaat tggcctattg ttaactatct   31140
acagtgttga atctgataac gaaactatgc cggatcaatc atgaaagatg ttcaagcgtt   31200
aaaaagaatc gtactctttt tggtttaaac gcacctgtac tatagtttgc tttgaataaa   31260
accatcgcca gttacccaac tttaagtgag cactatttct gaaagtgaca tcacatctta   31320
gtacctaatc ttactctcta ggtaattgta aaaattaccc tcagcactgt ttcgacatag   31380
cactctttag tgaaaatttg caacgtgatc taaacatgaa aatccgagaa attgccggat   31440
actcataagg tgcaaacttt tcttgctggt cgatagatca cttcgtaatg ttccatttgc   31500
acctattgat tgattttttcg ttgacgtcaa cttcttatat atgagccctt acagaaatga   31560
ttttatggat gcacgatatt cctgtttaaa acagccggcg tttactatcc tataacaaga   31620
ggcttacatg actcccacat gaaatataaa ctaagcgaac cacgaattcg actttgccgc   31680
aaaacgtttt ctgaaacata ctgtttaaat aagttcagga aaaggcataa cagtcataca   31740
taattgtctg tatagagttt tgacatttat tataactctc taagaaaatg tttggtagat   31800
tagactgtgg agagaaagaa aaaagaagag tgtctataaa aactatagct tgacaaatat   31860
tttgataaag tttagaaaga agcacatgtt tttttctgat ttattcctac agaatggatc   31920
aatgaaacct tttgggtgtt ttttttagaa attatcaaga ttaaattatt gcattacaaa   31980
aattgtatgt ttttgatttg agtttcgtgc ggcaaaagat tggaaatgga agctatccaa   32040
tattacaaat aatattgtcg tagaaatgtt ttctttaggg atatcaaaag tttgttagac   32100
ggctattact cttctgtttt caacccgtac atatttaaa ctgggaaaat gcaggatctt   32160
agagagttct agttttacaa agtactgtgt ctatggaaga ttcatccaat acacacagta   32220
aaattaagtt tgaaaatttg agtagtaaag acgtacttcc agattattac gttcttctta   32280
gacatataat taaatacttg gtctcgaaat tcagattctc cagtagaaaa gtccaacaaa   32340
aaattataaa ggacgtacgt ttccagtcgg accaaactag ctgaaaagcc aatagtttca   32400
cgatgtagct aaatttttaag tagctgtttg aaaaagctac ttgtttttat gtacaaaaag   32460
gttgtatgtg ttagttgaat agtgtttctt ttttttttg caatttcaag atcagcgact   32520
ttaaatattg gtcattgtga catgaaaaaa aaacagttac ctttgagaac taaatgactc   32580
ttttcttgct agaccttatc gatctatctt ttagctcatc acaaatatta ggcgaaaaag   32640
```

```
aatacactaa tctaagaaag ctatttatat attattttt  tgatggaaaa aaaaactcca  32700
atgtgtggga taatgttgaa attagcgtta tgtttattag gcatggtgag tcagccctga  32760
tagagggacc attgaactga gagtacaaac aagttggtga ttagaaccta ttatttaagc  32820
atcctttaga cagtgctgtt ttaacggggg tctcatatat ttaaatcatg tactataaga  32880
ggaatagtca cacacggatt tcttttgatg aaaatgctca aggacggcta ggtaacaaac  32940
aaataaatga aaagaaaaaa actggaacat aagggacagc aatcacatag tccaaagctg  33000
aatccagaaa aggctgcaga gactccgtca tttgatgcaa agcataaggg taaacggtta  33060
gacgttgctg aagttagtag aaacgtatac taagaaaatc caacacatgg aattcaagca  33120
gctgctaagg gtagagtcat gtgagtgaat aacagcttaa ttcagtagaa tgcaacaaaa  33180
ggatttatgt attacattgc taatgattgt tccacaataa caggcagcat gcttttgata  33240
attaagaggc tagtcctctg cggataacta gagctcttct gaattatcag agtattgttg  33300
tgttattggt ccatatagct tttgcaagat tgttaggccg acctttaaga gcacaagttt  33360
ttttttttcta taagagttta atgtattttg catatgtata agggcgtgca acttaccatt  33420
tgctctgaga gcaaaaaaac aataatttat aaggtttatt ttttgtttat actaagtttt  33480
ttgttaaaat ctagccaact tcccagctaa cattgtcgat tatgatctag tttagtttat  33540
gtaagtcaat gtactagggt cttttttcagg tcaatgttga atttctcaac ataaacataa  33600
cactacgttt cttctttaac tctcaacaat tctaagtccc ctaatggcaa gaaaaacttg  33660
accatacata atcttaagct gcttacagaa caaccctaca atgatgctcc aagtggtaaa  33720
aaagtaactt ctaaacggta aacattcggg caatgagatt taggctaact ttaggattaa  33780
cataatagat tctcttctca tcttaaccaa cttataaaca cttctgcacg aataaaattc  33840
acgcaaacgc gttatctgta cttgtagagc ttatataaca gcatataaca tgagaatagt  33900
tgcagaattt tatagttcta tacggttcat caaatcctat ataccctact ctccctgagc  33960
ataaagcatg gacacatgat atattgcaga cgaatgacac atgctgatgc atcttaaaat  34020
gctccaggag tgatttccaa agttcaagaa tccttagaat gttgtactat aaaccgccat  34080
atagttatag aaaaagtata ttcaagcaat gctgcttaac aatgactaat ataaacacag  34140
tccaatttcc attgatttgg aactatagtt tttggttcca acaatataat ttcaaataaa  34200
tctctgcttc caataccagt aactcttttc tcttgagtgt tttgacttttt caatggatgg  34260
atgttggtgg ccgcctttga tctcaacaaa tgctcatacc caataccttt tacttcgttt  34320
ttgagcacat ctataatccc gtgttctgta tagtatagtg tcagtcgtct gagataaata  34380
tccgtctttt ttaattggtc tgatcaatct cagcatttcc agtggtttct tccatttctt  34440
ccatctcttg aatttaagta atttaaagta aggttttttac attaaaaact ggttcgatat  34500
cagcccttaa cgatataggt aacatactat caaagcttag attaattgta ctttctttt  34560
catctcgcct tatacaagac ataatcgata ctgtcaaata tatccgatt  attgacaagt  34620
aaaacattat caaatatggg gtgtatgatg gagagacaaa actgtttgct gcggtttaca  34680
cttcataata tttctttctc acctaaacct tgtcaatgtg tcaacaccaa cacaatcgag  34740
atttttttca aggttgatag ttttgtgccg tagaaacttt acagcagcaa ctctattagg  34800
tcaaaattgt cttgcaagac ttttgtgtga agtttcaaaa ccatctaaaa aatgtaacgc  34860
tattgtggca aaagctcatc ttagaaagat tcttgagca  gttcacttaa tttcgtaata  34920
caaataccat aattacctgc tgattttattt tgcagaaata accatactca acaatggatt  34980
ttttcgttta tgtcattcat atatacatct gtcatagatt tgaaatattg gcatgttgtc  35040
```

```
acattgaata cagcatcaat tccagaaaca tactgactgg ataagctcta caattaaacc   35100
atgaatttgg gcggactgtg tgactttgtt cacaatatcc ggatataaca caatctcaat   35160
atcttcttcc cttcttttt tactacaaac actacctttta cttttccaaaa ggttaagcga   35220
aggtgccaca tcgtgttctt aagaggagtg ctgttgtttt gccattgtct ttgtaaacac   35280
tcaaatggtt gatttgatct cttccgttcg agttaacaat atatgcataa tgggatatcc   35340
ttttatcttt ctagtataat atgtcttaat aactacggcc gtaaacgatt cgggcctaat   35400
aatcacattg atgaagaaat caaaaacaat gctagatttt ccaaacagc ttgttcgttg    35460
acttccgagc tagaacatgg ctgatacaaa ccaaaactat aggttacttt ccctttaacc   35520
tttccatcat aacggagcac ggaactgcgt taatccttaa aaacacatta atgttttaa    35580
ggttggcgac atcgagcaaa actgagcaaa tttgtagcac aagcccacta ccaatcctat   35640
tagctcacag tggatccttg aaatcctaaa atctatagaa taatatacgt gagtaactcc   35700
cccaaagatg ttctgtcact ctgaaagatg caccgtgtct ataaactgaa tatttaaaag   35760
atgctcttag tctggtaaaa ggcccatatg gtttcttgtg tttccaccga tatgttacag   35820
gtgcatcatt ccatccacgt caaaacctttt ccttaacgaa cactcctgta tattgtaaca   35880
aagggaatt tccgtgcttg ctaaaaatgt attgtaatcc gaaacaatac atttacagaa    35940
gagctttgta aaacctatat tttcaccttt ttaatcaatt ggggcctgta aatagatttt   36000
agtagacttt atcttttttgt caaacctgga tgtctcaaga acttttccgt agagccgttc   36060
ccacaaaagc taccatgaaa ggcctttaat ttatcagcaa aattgtaaaa tcgcaagaag   36120
tcattatcct ttctccgtcc aagtggtggg cgttcgaaat aagtatccac aaggttttca   36180
agatacttcc aaaaagacgg tctgaattct ccttatcagg gaaaaatacc tctccaattt   36240
tagcaacaaa agctttacaa caaaccttca agtgccagat ttgttgctgt gtctgtggtt   36300
tatcagatga cacatgttgg tggtggtaaa cattttatat cccaattaat ggcagtataa   36360
catcaaaact atacagtgca accccacatc aagttacact ttttatcaca acaaacctgc   36420
aacgttggtt gtgtatttga agttgtaat tttcagccac agtagttaat ttatacacta    36480
atatataact cttggagagc aatatggatg actaggtccg atcaatcagc tattgatggt   36540
acgatatcca tatttagttc gacacttgat tactaaggga tttctaaata atatgcgtat   36600
taaaagctac agtaagagcg gagttacctc tcttatcaat tgtcggtttg gcgccacaat   36660
aaataatgat atcatctcta actaaacaca aaacatatta ctagttgtca ttagctagtt   36720
gccatcagtg cataatgtgt gtcgacatac ctgctgtatc acatgatatc aataaaggtt   36780
gtagattatt ttcttttcct tgggttcttt ttatgtggta ttttgaagta gctcttttaa   36840
acgttcaatc tataacgtgt aacatggtta tctgaagtag aattagggca catcaaggca   36900
gtattgtatt tgcttgacat gtatttattg gctgctttta gaaactaaac tatattgaat   36960
atttgcattt tggacaatgg taaaacagtt tatcttattg ccttatatga ttgcaatggg   37020
ataagaacaa ctagctgatt tatcaaagct aaatcgataa aacgagaaca aaactcaact   37080
atgttcaatg cagaataaaa ttatacaaaa ccacccaact tctctgatta attccagact   37140
agaaaggccc cggatttcca ttactggata taagggctag aggcatagaa tggtcagcag   37200
acattggaag agaatttgct acatatgggc taccagatgt cagaaaagtt ataagggctg   37260
ttgcaggttt gaaaaataac gaacgtaaat tacacacttc tcaaatgcat atgaactagc   37320
aaatactgga ttttagttgg tctaaatttg aagatagatt ctgaaacgct ttgttcctgt   37380
```

```
cgacaaagac agagactctg tggtgaatat tgtcaagtaa ttgtgtcgat tgaaaccagg    37440
tcaatcgatg agaggctata aagaaaactt taaagtgtct atatacgtcg ctatttctga    37500
cattaagagt tgaccactat tccttgatgg ccttaccgat attgagcagt taatgggggt    37560
gagattgttg cagtctaaca taaaagcttg atgtgtgttt taaccatgtt ggggcgagtc    37620
tattggagat atagacatgc aagaagctac atgggcactt atacaatgat ttaaatggtt    37680
tcccttatag aacaaagtcc gccaaagaac tcaatttatt tcatgccttt tcagccatcg    37740
gcaacctaat gtatcatgga taatttcatg ttcctttatt caaatagtat ttataagagg    37800
atgttaaagg gcatgataat gatgcgaaat acgaaaagga actttcatag taagtataaa    37860
tgtccgaaaa atgagtggat gccatcccac actcacatta tgaccatccc aaaaaagaaa    37920
aaccaaaatt aatttgtggt gtcgtttata tcaaatatgc agatgacatt ttggttgctc    37980
cagaaccact tttacagtta ttaataaaac tgttgaggaa gttcatgtgt ttagcaaaag    38040
gccaagctcg atggatcaat aacagtaaag attatcggaa actctggtgt tgctatcgca    38100
gacgtaattg tccctttga ggtagtcaaa gaaactatca gtataagtga ggttaggtca    38160
ttttaaatgt ttgatactga gcatgcgcta ttcatgttgg gaaacccatt tatcaagagg    38220
caatttagtg atctaacttt aggtatttta gtaagtcctg atatcgataa agccaaagct    38280
gatttaaata tcgaccccta gacgcaaatc atgcaagagg attgaaaaag gaaacacttg    38340
aaaagtttac ttgagatcca tcaactgaac taccgccaaa gaaaagatgc gggcatatgt    38400
tgccttgtat taccctaatg agttctcttt gaaaaaaaca ataccaatta agcttctctg    38460
agaaactgga actaacaaaa caagttgaag ttttaatcaa acaaggtttc atcaaaacta    38520
gttccaaacc ttttaacagt ccagtgctat ttgttaagaa gaaagatggt actatgcgta    38580
tgtgtgttga ttataggatt ctaaacaata atactgctag gaacaagttt ccacttccag    38640
atattgatca attgatttca agatttggta aggcaaaagt ctattctaag ttagagttga    38700
cgcctggtta ctaccaagtg agaattgctg atgaagacgt ggagaaaacg gcattttcta    38760
ctgattttgg ccattatgaa tggatggtaa tgccggctgg actaacaagc gcacctgcga    38820
cttttcaaca gatgatggat actgtcttgc ctgaaagaat agatcgattt gtccaagtct    38880
atttagacga cattttttata tactccgaag atgttgaaac tcacggtaag cacgtgaaag    38940
aagtttgtt gacactaaga aaacataaac taattacgaa gaagtcgaaa tgcagatttt    39000
tttatcaaga atttaagttt ttaggacaag ttgttacacc aatttgtatt caaaccgctc    39060
tagagaaaat aaaaaggta aagagttggc caacgccaaa cacgatcaaa gaagcacaaa    39120
gttttattgg tttaacttcg tactatagaa ggtttattaa agggcattcc aaaattgcca    39180
atccaattca taagttcatg acaaaacaaa ttaaatggac aagtgaacaa gacgaagcct    39240
tcaaccaact aaagaacgct ttgatatcaa gtcccaccct ggtgcaccca agttggtcag    39300
gcaattgtaa atttgttcta cataccgatg cgtgtggagt atcgttaggt tatactctag    39360
aacagttgga cgaacaggt aaatgacgag gtgtgattgc ttacgttca aagaagctag    39420
ttggaagtca actgaatcat ggaatatatg atcgtgaatt tttggctgtt gttgaagcat    39480
taagaacatg aagatattat ctcatgggaa gacatgtcat tgttatgacg gatcacaaga    39540
gtttaattta cttaaaaaac caaaatctca tagactccac tagagtggct agatggatgg    39600
acttttacc acagtttgat tttgatattc gttacttaca gggaaaaaac aattccgctg    39660
ctgatgcgtt atctagatac ccatacaacc acgaaaacaa cttaacgcta gccaaaatcg    39720
aactggcgtt gctagaattg actcaagaag aggagaataa aacacagaaa cattcgttga    39780
```

```
cactaggtac tatcgaagct aatcaaaaat caaaaaggga aattattacg ggttataaaa   39840
aagataataa ttatgccttg atatttagaa ctgtgagaga taaaacaaaa gttccagttg   39900
aaattaaaaa tcatatcaaa catttctgtt atcaagatga ggtactttat tataagacat   39960
tagagtctca agatttcttt agagtagtta ttccaaacta caagaaacta ccgtatagaa   40020
tattcaaaaa tgcacacgat gccaaagatg ctggtcactt tggtgcatgg aaaacttatt   40080
tgaatcttaa agatagtttt tattggccat ctatgttggc acaaattaga aaatgggtag   40140
aaacctgtcg tatctgtcaa cagcacaaca ccaacactag aggaagacaa gggttgtttt   40200 ccccttacc aatcccaaca ggtcgctgga ccgacattac gatggatttc attacaggtt   40260
tacctagatc gagaacaggc tacactatca ttatggttgt tgtcgatcgc ttttcaaaaa   40320
tggcacattt tataccagcg cacaaaagac ttaatgctgc tgcatgtgct cgtttgttta   40380
gtgacaaaga tattcggttt atgaataagt tctggcagac attacattat ctcaatggta   40440
gttctctatt attttcaact actaatcatc cagaaactga tggtcaaact gaaagattca   40500
acaagattgt taatcagtta cttcggaaat attctgcaaa cgttcaatta tcctggaatg   40560
agcatctgtc tatgtgtgaa cttagttaca attcaacgta ccaagattcc attaaagcaa   40620
gtccttttga aatcgcctac gagtatgaac cgagcatgat tagaaaagta aatagctggg   40680
atttggagga taacaaatat tcacctaacg cagaagaatt tgtgagacgt gtgaaattga   40740
ttttacagca cactggataa tattgtaaag cataagggcg acaaggaaaa caccataata   40800 gaaaagaag atactttgaa tataaagttg gtgacttagt gttagtgcat caagatgcct   40860
ttggtgtgaa tataaggtac acaaaaattc aaccagtatg atatgggcca tacagactag   40920
tcgagaaaat aaacggcaat gcttataaag tcgatttacc agttattaat ttgaaggatc   40980
gtgaatcaaa tgtacagtgg attaaatact ataaagaaaa ccccaatatt taccaggaac   41040
cgcctagaac agagcgtgag atgttggcaa gaattaacga actgagtggt atcggtggat   41100
gatcagaaga accaggcaaa gaaaagactt atgatgtctt ctggaaagac tgtgatcaaa   41160
ctctagcaag aaaggtgcct gaaagaatat tcaaccaagc agctttgtca ctacgtcaaa   41220
gtccaatgta caaagccgaa ttaattcaag aacacgaaca agtttgatat caacaaagta   41280
atcataatta taatacatag aacgttccta tttgtccctc agctgaagaa aaaaaataca   41340
gatattgctc ctaccaaaac atagaacata ttgtttttg attgaaataa gttagccact   41400
ctcgatttaa agaaatacaa attgaactca taaaaaaatt attgttactg ccaggatcca   41460
cctacattta ttattctaat ctggtttaat gtttgtcagc ttcattggtt cagtgccccc   41520
atccgggatt atccagttat tttgttgcac cgttttgagg aacatcgggg cgatgtttcc   41580
caagagccgg ggtagtgaaa gggatttttc aggatgtgtt ccaaaaaagg aagtgccagt   41640
aggtagacga taacatactg atgttaaggt ttcgatttta gaataaggga agttaacaag   41700
ggtcaagtat ccggagtagg aagcaaagag agttagtccc gttgatcatg tagggcatag   41760
gcatggagaa gccgtcggag acactgtcat tggcataaat taattatcat tcatcaacgg   41820
gttatgacag aactggcata gtaaaacaaa atagacctaa aacgtaataa gctcgtacag   41880
gagtctgcta tacgaaaaag agtagcaacc gagggtgatt ccaggttgcg ggcgtgaagt   41940
acaaaagaca gacgatattc cgttatatag aattgatata gctgatatag gtcctaatcg   42000
ggagtggaag cggcagaaga aaaagagag aaatagatta ctacttctac tacgactaac   42060
ttccaccacg cttattgtct actcgtgcgg ttatacacct attgcgtact tactaacacg   42120
```

| | | | | |
|---|---|---|---|---|
| tgtatcacaa | ttatcattgt | tataaacaat | actgtaacta | tggataaggc tatgattact 42180 |
| tttttgataa | aagatttaac | cgtagaaaca | tccagaacta | ggaaatgatt ttgacacctt 42240 |
| attccaagtc | ctattaaaaa | ctgtaagaga | tcagacaaag | gactacctct ctatttccta 42300 |
| attgggtaat | catatagaag | gttgaagaag | attgtagaag | gttaaacaga agttctagaa 42360 |
| gataattata | tccctcaaaa | tgctattttt | aaattaaaga | tttactattt aaacagagga 42420 |
| tattccatat | atgttctcag | agaattaacg | tataaaaata | tataagatat aaataagcaa 42480 |
| taatcagatt | ctagagtacg | caccactagc | aaaactttca | aaatataagc aatgcccgtg 42540 |
| tagcgtaatg | gttaacgcgt | tgacttcta | atcaaaagat | tctgggttcg actcccagca 42600 |
| tgggtgcagg | catgtgctta | atattttta | tttttatta | attttcaac cagcaaaacc 42660 |
| aagttttttt | aactgaataa | aagaatgttt | ggccacttct | ctatgtgtca tttgtctttt 42720 |
| tgatgggtta | tttctatcaa | ag | | 42742 |

<210> SEQ ID NO 16
<211> LENGTH: 38285
<212> TYPE: DNA
<213> ORGANISM: Artificial Sequence
<220> FEATURE:
<223> OTHER INFORMATION: centromere-like sequence (CEN-L) CEN5-38285bp

<400> SEQUENCE: 16

| | | | | |
|---|---|---|---|---|
| ctcacagcaa | acacaaaaat | atcacaagat | cgctatgtat | gtagtcgata ggttgtcatg 60 |
| attactattc | atctaaacac | ctagacatgt | agagcctatt | agagtaagct cactaatttt 120 |
| gactttgaat | cctccaaaga | gttacaaacc | aaaaataatt | tgggaaaaa ttactccggc 180 |
| ctaattcttt | gtcggtatat | caaggaagga | aaactccaat | ggtttaaaag actaggataa 240 |
| aactaataag | ggacattata | aaatctaaaa | acttaaaact | tgtccccatt ttgattatca 300 |
| ggttatttt | gacataaaaa | tcttctctaa | tgtttcgtct | cgtccaaaat tgaatgcttt 360 |
| gaatagagtg | aacaggaata | attattaaca | cagaaagcct | aactgtacac aaggaaaaca 420 |
| ctataagtag | aattacgtat | gtcaacctat | aaaaagggt | ccaaagttga caactcaata 480 |
| tctaaatctt | gcacgattaa | gaggttggtt | tttataccct | ttttagggta accagaatgc 540 |
| catctacttc | aagcagaaaa | gaaatgtaa | aaacacccgt | ttttaatggc taatctgata 600 |
| ctcttcagaa | aagatttatg | aagaaccagc | cgtaaaagtc | tcaaaattta ttcggatagt 660 |
| aattccattc | aatacaaata | aattgaaaaa | atcaagccc | gatgcggggc tcgaacccgc 720 |
| agccttttga | ttgcacttct | ttataagaag | aaatcttaag | agtcaaacgc tctaccgatt 780 |
| gagctaacca | ggcataaaat | gttccgatac | cgggagtcga | acccgggtct gcccggtgaa 840 |
| agcggaccgt | gatagccgtt | acactatatc | ggaaactgat | gaaatattag ggtccaggag 900 |
| aaaggtgtcg | aaattatttc | ctaatttggg | atgttttgac | ggttgaatct ttttaagaat 960 |
| aatcactaat | cttatcaata | tctatagtat | tgtatgaagg | aatgataatt gtgatatacg 1020 |
| tattagtaag | taggcaatag | gtgtattagc | tcacgagtag | ataatgggcg tggtagaagt 1080 |
| tagtcgtagt | agaagtagta | atagattttt | ctcttcctcc | ttctgctgct ttcactcccg 1140 |
| attaggagct | atatcaatta | tatcaattct | atataatagg | atattatccg tcttatatac 1200 |
| ttcacgcccg | caacctggaa | tcaccctcag | ttgctactct | ttttcgtgta gcagactcct 1260 |
| gtacgagctt | attacgtttt | aggtctattt | tgttttacta | tgccagttct gtcataaccc 1320 |
| gttgatgaat | gataattaat | ttatgccaat | gacagtgtct | ccgacggctt ctctatgcct 1380 |
| attcttacat | gatcaacggg | gctaactctc | tttgcttcct | actccggata cttgacccctt 1440 |

```
gttaacttcc cttattctaa aatcgaaacc ttaacatcag tatgttatcg tctatctact    1500
ggcacttcct tttttggaac acatcctgaa aaatcccttt cactacccg gctcttggga    1560 aacatcgccc cgatgttcct caaaacggtg caacaaaata actggataat cccggatggg    1620
ggcactgaac caatgaagct gcaaaacatt aaaccagatt agaataataa atgtaggtgg    1680
atcctggcag taacaataat tttttttatga gctcaatttg tatttcttta aatcgagagt    1740
ggctaactta tttcaatcaa aaaacaatat gttctatgtt ttggtaggag caatatctgt    1800 atttttttc ttcagctgag ggacaaatag gaacgttcta tgtattataa ttatgattac    1860
tttgttgata tcaaacttgt tcgtgttctt gaattaattc ggctttgtac attggacttt    1920
gacgtagtga caaagctgct tggttgaata ttctttcagg cacctttctt gctagagttt    1980
gatcacagtc tttccagaag acatcataag tcttttcttt gcctggttct tctgaccatc    2040
caccgatacc actcagttcg ttaattcttg ccaacatctc acgctctgtt ctaggcggtt    2100
cctggtaaat attggggttt tctttatagt atttaatcca ctgtacattt gattcacgat    2160
ccttcaaatt aataaccggt aaatcgactt tataagcatt gccgtttatt ttctcgacta    2220
gtctgtatgg cccatatcat actggttgaa ttttgtgta ccttatattc acaccaaagg    2280
catcttgatg cactaacact aagtcaccaa ctttatattc aaagtatctt cttttctat    2340 tatggtgttt tccttgtcgc ccttgtgctt tacaatatta tccagtgtgc tgtaaaatca    2400
atttcacacg tctcacaaat tcttctgcgt taggtgaata tctgttatcc tccaaatccc    2460
agctatttac ttttctaatc atgttcgatt catacccgta ggcgatttca aaaggacttg    2520
ctttaatgga atcttggtac gttgaattgt aactaagttt acacatagat agatgttcat    2580
cccagaataa ttgatcgttt gaagaatatt tccgaagtaa ctgattaacg atctagttga    2640
ctctttcggt ttgaccatca gtttctggat gattagtagt cgaaaatagt agagaactac    2700
cattgagata atgtaatgtt tgccagaact tattcataaa ccgaatatct ttgtcactaa    2760
ctattctttg tgggacaccg tgtaacttga taacattgtc actaaacaaa cgagcacatg    2820
ctgcagcatt aagtcttttg tgcgctggta taaaatgtgc catttttgaa aagcgatcaa    2880
caacaaccat gatcatatcg taacctgttc ccgatctagg taaacctgta atgaaatcca    2940
tcgtaatgtc ggtccagcga cctgttggga ttggtaaagg ggaaaaccac ccttgtcttc    3000
ctcagtgttg gtgttgtgtt gttgacagat atggcaggtt tctacccatt tttgatttgt    3060
ctcaacatag atgaccatta aaaactatct ttaagattca aataagtttt ccatgcacca    3120
aagtgacaag catctttgga atcgtgtgca ttttgaatat tctatacggt agtttcttgt    3180
agtttggaat aactactcta aagaaatctt gagactctaa tgtcttataa taacgtacct    3240
catcttgata acagaaatgt ttgatttgat tttttatctc aactggaact tttgtttat    3300 ctctcaaagt tctgaatatc aaggcataat tagtatcttt tttataaccc gtaataattt    3360 cttttttaa atcttgatgg gcttcgataa tacctagtgt caaagaatgt atctgtgttt    3420
catgctcctc tttttacgtc aattccagca acgccaattc gattttggtt agcgttaagt    3480
tgttttcgtg gttatatggg tatctagata acgcatcagc ggcagaattg ttctttccct    3540
gtaagtaaca aatatcaaaa tcaaattgtg gtaaaaagtc catccatcta gccactctag    3600
tggagtctat aagatttggt tttttaagt aaattaaact tttgtgatcc gtcataacaa    3660
tgacatgtct tccatgagaa taatatcttc atgttcttaa tgcttcaaca acagccaaaa    3720
attcacgatc atatattcca tgattcagtt gacttccaac tagcttcttt gaaccgtaag    3780
```

```
aaatcacatc tcgtcattta cctgtctcgt ccaacttttc tagagtataa cctaatgata    3840
ctccacacgc atcggtattt agaacaaatt tacaattgcc tgaccagctt gggtgcacca    3900
agatgggact tgatatcaaa gctttcttta gtttgttgaa ggcttcgtct tgttcacttg    3960
tccatttaat ttgttttgtc atgaacttat gaattggatt ggcaattttg gaatgccctt    4020
taataaacct tctatagtac gaagttaaac caataaaact ttgtgcttct ttgatcttgt    4080
ttagcgttgg ccaactcttt acctttttaa ttttctcgag agcggtttga atacaaattg    4140
gtgtaacaac atgtcctaag aacctaaatt cttgataaaa gaatctgcat ttcgacttct    4200
tcgtaattag tttatgtttt cttagtgtcg acaaaacttc tttcacgtgc ttaccgtgag    4260
tttcaacatc ttcggagtat ataaaaatgt cgtctaaata cacttggaca aatccattta    4320
ttttttaga caagacatta ttcatcatct gtggaaaagt cgcagatgca cttgttagtc      4380
cagccggcat taccatccat tcgtaatggc caaaatcagt agaaaatgcc gttttctcca    4440
cgtcttcatc agcaattctc acttggtagt aaccaggcgt caactctaac ttagaataga    4500
cttttgtctt accaaatctt gaaatcaatt gatcaatatc tggaagtgga aacttgttct    4560
taacagcatt attgtttaaa atcctataat caacacacat acgcatagta ccatcttttct    4620
ttttaacaaa tagcactgga ctgttaaaag gtttggaact agttttgatg aaaccttgtt    4680
tgattaaaac ttcaacttgt tttgttagtt ccagtttctc agagaagctt aatgggtatt    4740
gttttttcca aagagaactc attagggtaa gacaaggcaa catatgcccg catcttttct    4800
ttggcggtag ttcagttggt ggatctcaag taaacttttc aagtgtttcc tttttcaatc    4860
ctcttgcatg atttgcgtct aggggccgat atttaaatca gctttggctt tatcgatatc    4920
gggacttact aaataccttca agttagatc actaaattgc tcttgataa atgggtttcc    4980
caacatgaat accacatgct cagtatcaaa catttaaaat gacctaacct cacttatact    5040
gatagtttct ttgactacct caaatgggac aattacgtct gcgatagcaa caccagagtt    5100
tccgataatc tttactgtta ttgatccatc gagcttggcc ttttgctaaa cacatgaact    5160
tcctcaacag ttttattaat aactgtaaaa gtggttctgg agcaaccaaa atgtcatctg    5220
catatttgat ataaacgaca ccacaaatta attttggttt ttcttttttg ggatggtcat    5280
aatgtgagtg tgggatggca tccactcatt ttttggacat ttatacttac tatgaaagtt    5340
cctttttcgta tttcgcatca ttatcatgcc ctttaacatc ctcttataaa tactatttga    5400
ataaaggaac atgaaattat ccatgataca ttaggttacc gatggctgaa aaggcatgaa    5460
ataaattgag ttctttggcg gactttgttc tataagggaa accatttaaa tgattgtata    5520
agtgcccatg taacttcttg catgtgtata tctccaatag actcgcctca acatggttaa    5580
aacacacatc aagcttttat gttagactgc aacaatctca cccccattaa ctgctcaata    5640
tcggtaaggc catcaaggaa tagtggtcaa ctcttaatgt cagaaatagc gacgtacata    5700
gacactttaa agttttcttt atagcctctc atcgattgac ctggtttcaa tcgacacaat    5760
tacttgacaa tattcaccac agagtctctg tctttgtcga caggaacaaa gcgtttcaga    5820
atctatcttc aaatttagac cgactaaaat ccagtatttg ctagttcata tgcatttgag    5880
aagtgtgtaa tttacgttcg ttattttcg aacctgcaac agcccttata atttttctga     5940
catctggtag cccatatgta gcaaattctc ttccaatgtt tgctgaccat tctatgcctc    6000
tagcccttat atccagtaat ggaaatccgg ggcctttcta gtctgaaatt aatcagagaa    6060
gttgggtggt tttgtataat tttattctgc attgaacata gttgagtttt gttctcgttt    6120
tatcgattta gctttgataa atccgctagt tattcttctc ccattgcaat catataagac    6180
```

```
aataagataa actgttttac cattggccaa aatgcaaata ttcaatatag tttagtttct    6240
aaaagcagcc aataaataca tgtcaagcaa atacaatact gccttgacgt gccctaattc    6300
tacttcagat aaccatgtta cacgttatag attgaacgtt taaaagagtt acttcaaaat    6360
accacataaa aagaacccaa ggaaaagaaa ataatctaca acctttattg atatcatgtg    6420
atacagcagg tatgtcgact cacattatgc actgatggca actagctaat gacaactagt    6480
aatatgtttt gcgtttagtt agagatgata tcattattta ttgtggcgcc aaaccgacaa    6540
ttgataagag aggtaactcc gctcttactg tagcttttaa tacgcatatt atttagaaat    6600
cccttagtaa tcaagtgtcg aactaaatat ggatatcgta ccatcaatag ctgattgatc    6660
ggacctagtc atccatattg ctctccaaga gttatatttt agtgtataaa ttaactactg    6720
tagctgaaaa ttcaactttt caaatacaca accaacgttg ccggtttgtt gtgataaaat    6780
gtgtaacttg atgtgaggtt gcactgtata gttttgatgt tatactgcca ttaattggga    6840
tataaaatgt ttaccaccac caacatgtgt catctgataa accacagaca cagcaacaga    6900
tctggcactt gaaggtttgt tgtaaagctt ttgttgctaa aattggagag gtattttttcc    6960 ctgataagga gaattcagac cgtctttttg gaagtatctt gaaaaccttg tggatactca    7020
tttcgaacgc ccaccacttg gacggagaaa ggatgatgac ttcttgcgat tttacatttt    7080
tgctgataaa ttaaaggcct ttcatggtag cttttgtggg aacggctcta cggaaaagtt    7140
cttgagacat ccaggtttga caaaaagata aagtctacta aaatctattt acaggcccca    7200
attgattaaa aaggtgaaaa tataggtttt acaaagctct tctgtaaatg tattgtttcg    7260
gattacaata cattttttagc aagcacggaa attcccttttt gttacaatat acaggagtgt    7320
tcgttaagga aaggttttga cgtggatgga atgatgcacc tgtaacatat cggtggaaac    7380
acaagaaacc atatgggcct tttaccagac taagagcatc ttttaaatat tcagtttata    7440
gacacggtgc atctttcaga gtgacagaac atctttgggg gagttactca cgtatattat    7500
tctatagatt ttaggatttc aaggatccac tgtgagctaa taggattggt agtgggcttg    7560
tgctacaaat ttgctcagtt ttgctcgatg tcgccaacct taaaaacatt aatgtgtttt    7620
taaggattaa cgcagttccg tgctccgtta tgatggaaag gttaaagaga aagtaaccta    7680
tagttttggt ttgtatcagc catgttctag ctcggaagtc aacgaacaag ctgtttggaa    7740
aaatccagca ttgttttttga tttcttcatc aatgtgatta ttaggcccga atcgtttacg    7800
gccgtagtta ttaagacata ttatactaga aagataaaag gatatcccat tatgcatata    7860
ttgttaactc gaacggaaga gatcacatca accatttgag tgtttacaaa gacaatggca    7920
aaacaacagc actcctctta agaacacgat gtggcacctt cgcttaacct tttggaaagt    7980
aaaggtagcg tttgtagtaa aaaagaagg gaagaagata ttgagattgt gttatatccg    8040
gaaattgtga acaaagtcac acagtccgcc caaattcatg gtttaattgt agagcttatc    8100
cagtcagtat gtttctggag ttgatgctgt attcaatgtg acaacatgcc aatatttcaa    8160
atctatgaca gatgtatata tgaatgacat aaacgaaaaa atccattgtt gagtatggtt    8220
atttctgcaa aataaatcag caggtaatta tggtatttgt attacgaaat taagtgaact    8280
gctcaagaga tctttctaag atgagctttt gccacaatag cgttacattt tttagatggt    8340
tttgaaactt cacacaaaag tcttgcaaga caattttgac ctaatagagt tgctgctgta    8400
aagtgtctac ggcacaaaac tatcaacctt gaaaaaaatc tcgattgtgt tggtgttgac    8460
acattgacaa ggtttaggtg agaaagaaat attatgaagt gtaaaccgca gcaaacagtt    8520
```

```
ttgtctctcc atcatacacc ccatatttga taatgtttta cttgtcaatg atcgggatat    8580
atttgacagt atctattata tcttgtatgt ggcgagatgg aaaagaaaag actattaatc    8640
taagctttga cagtatgtta cctatatcgt taagggctga tatcgaacca gttttaatg     8700
taaaaacctt actttaaatt acttaaattc aagagatgga agaggtcgaa gaaaccactg    8760
gaaatgttga gattgatcag accaattaaa aaagacggat atttatctca gacaactgac    8820
actatactat atagaacacg ggattataga tgtgcttaaa aacgaagtaa aagatattgg    8880
gtacgagcag ttgttgagac aaagacggc caccagcatc catccattga aaagtcaaaa     8940
cactcaaaag aaaagagtta ctggtattag aagcagagat ttatttgaaa ttatattgtt    9000
ggagccaaag tctatagttc cagatcaatg gaaattggac agtgtgttta ttgggtatag    9060
aaagaaatgt gttatttacg tctataatgt tgggttgttc cctgccataa tttggttgct    9120
atcgttaata ttagtcattg ttaagcagca ttgcttgaat atactttttc tataactata    9180
tggcggttta tagtacaaca ttctaaggat tcttgaactt tggaaatcac ctctggagct    9240
tttaagatgc atcagcatgt ctcattcatc tgcaatatat catgtgacca tgctttatgc    9300
tcagggagag tagggtattt aggatttgat gaaccgtata gagctataaa attctgcaac    9360
tattctcatg ttatatgctg ttatataagc tctacaagta cagataacgc gtttgcttga    9420
attttgttcg tgcaggagtg tttgttattt ggttaagata agaagagaac ctattatgtt    9480
tatcctaaag ttagcctaaa tcttgttgcc cgaatgttta ccgtgtaaaa gctacttttt    9540
ttaccacttg gagcatcatt ttagggttgt tctgtaagca gcttaaggtt atgtaaggtc    9600
aagttttttct tgccattagg ggacttagaa ttgttgagag ttaaagaaga aacttagtgt   9660
tatgtttatg ttgagaaatt caacattgac ctgaaaaaga ccctagtaca ttgacttaca    9720
taaactaaac tagatcataa tcgacaacgt tagctggaaa gttagctaga tttcaacaaa    9780
aaaacttagt ataaacaata agtaaacctt ataaattatt gttttttgc tctcagagca     9840
aatggtaagt tgcacgccct tatacatacg caaaatacat taaactctta tagaaaaaaa    9900
aacttgtgct cttaaaggtc ggcctaacaa tcttgcaaat agctatttgg gccaataaca    9960
caacaatgct ctgataattc agaagagttc tggttgtttg cagaggacta gcctcttaat   10020
tatcaaaagc attttgcctg ttattgtgga acaatcatta gcaatgtaat acataaatcc   10080
ttttgttgca ttctactaaa ttaagcggtt attcactcac atgactaccc ttagcagctg   10140
cttgaattcc atgtgttgga ttttcttagt atacgtttct actaacttca gcaacgtcta   10200
accgtttacc cttatgcttt gcatcaaatg acggagtctc tgcagccttt tctggattca   10260
gctttggact atgtgattgc tgtcccttat gttccagttt ttttctttc atttatttgt    10320
tcgttaccta cccgtccttg agcatttttca tcaaaagaaa tccgtgtgtg actattcctc   10380
ttatagtaca tgatttaaat atatgagacc cccgttaaaa cagcactgtc taaaggatgc   10440
ttaaataata ggttctaatc accaacttgt ttgtactctc agttcaatgg tccctctatc   10500
agggctgact caccatgctt aataaacata acgctaattt caacattatc ccacacattg   10560
gagttttttt ttccatcaaa aaataatat ataaatagct ttcttagatt agtgtattct    10620
ttttcgccta atatttgtga tgagctaaaa gatagatcga taaggtctag caagaaaaga   10680
gtcatttagt tctcaaaggt aactgttttt ttttcatgtc acaatgacca atatttaaag   10740
tcgctgatct tgaaattgca aaaaaaaag aaacactatt caactaacac atacaacctt    10800
tttgtacata aaaacaagta gcttttcaa acagctactt aaaatttagc tacatcgtga    10860
aactattggc ttttcagcta gtttggtccg actggaaacg tacgtccttt ataatttttt   10920
```

```
gttggacttt tctactggtg aatctgaatt tcgagaccaa gtatttaatt atatgtataa    10980
gaagaacgta ataatctgga agtacgtctt tactactcaa attttcaaac ttaattttac    11040
tgtgtgtatt ggatgaatct tccataaata cagtacttgg taaaactaga accctctaag    11100
atcctgcatt ttcccagttt aaaatatgta cgggttgaaa acagaagagt aatagccgtc    11160
taacaaactt ttgatatccc taaagaaaac atttctacga caatattatt tgtaatattg    11220
gatagcttcc atttccgatc ttttgccgca cgaaactcaa atcaaaaaca tacaattttt    11280
gtaatgcaat aatgtaatct tgataatttc taaaaaaaac acccaaaagg tttcattgat    11340
ccattctgta ggaataaatc agaaaaaaac atgtgcttct ttctaaactt tatcaaaata    11400
tttgtcaagc tatagttttt atagacactc ttcttttttc tttctctcca cagtctaatc    11460
taccaaacat tttcttagag agttataata aatgtcaaaa ctctatacag acaattatgt    11520
atgactgtta tgccttttcc tgaacttatt taaacagtat gtttcagaaa acgttttgcg    11580
gcaaagtcga attcgtggtt cgcttagttt atatttcatg tgggagtcat gtaagcctct    11640
tgttatagga tagtaaacgc cggctgtttt aaacaggaat atcgtgcatc cataaaatca    11700
tttctgtaag ggctcatata taagaagttg acgtcaacga aaaatcaatc aataggtgca    11760
aatggaacat tacgaagtga tctatcgacc agcaagaaaa gtttgcacct tatgcgtatc    11820
cggcaatttc tcggattttc atgtttagat cacgttgcaa attttcacta aagagtgcta    11880
tgtcgaaaca gtgctgaggg taattttttac aattacctag agggtaagat tagatactaa    11940
gatgtgatgt cactttcaga aatagtgctc acttaaagtt gggtaactgg cgatggtttt    12000
attcgaagca aactatagta caggtgcgtt taaaccaaaa agagtacgat tcttttttaac    12060 gcttgaacat ctttcatgat tgatccggca tagtttcgtt atcagattca acactgtaga    12120
tagttaacaa taggccaatt tcaggatcag tatttatttc tgattgtttg acagctatat    12180
ttagacctat gttctgagtt aagcacagaa ataacgatta aaatttatat cagcattagt    12240
tatggaagac accctcagtc atcatggcac caaaacaaag attaataaga aaccagttca    12300
actccaactg aatctattga tatcgatcta tataatttgt ggattctttt taagttatcc    12360
agctgctgga ctaaatatgg gcatcacgtc aggaattgtg cctcttgaac accagttttt    12420
atagaattta cagctactat aaatatctac attgtggcat aacgctattc cttaaccact    12480
gttctccaat gtcaactcat ctagtatttt ttatataaaa tatcatttct tattttgttc    12540
gcgctgtttg caaagaaatt tgttttacta tcataaaatt gattaatttg tctcccaaga    12600
ccttttacat gtatatcatt actattaatg tgcttattcg atagttatcc gcatatattc    12660
tgaatatcat catacttcgc tggaagttttt ccattatata aattattttt taggttctat    12720
cgttttattt acatatatat caatgttgtt tatttattgt tgatattgaa taacttataa    12780
atccattaaa aaggatattg cataattctc actatttggt tctcaatgaa cagaacttat    12840
aaatatactt gaagttattg ttttagtttt ctgtatacag taacattcct aaattcattt    12900
ggtaaattga aattatgcca taaataagtt tatcgactca gagacagctt tataaagata    12960
ttcctaatcc tcttactaat aaaacaaaag ttgcattcac tattttctg ggagagtctg    13020 attcattttt gttttttgctc aggaaattta atcgtgttat aatataaaag aagaattttt    13080
ctcaagagta ctcttagaca tatttatgga gaatgagttt gtttgcctga atggtaaagt    13140
agctaagaat ctatactttt ttcagggttt tttttatctt gacttaatga ttggaataat    13200
aaattagatt tgtaaaaaaa ttgacggaat tagtttgagt ggcttcccat gtaaatatgc    13260
```

```
tctctatcag atatattaaa catgaaaatt tattatacct cattgtactc tcgacattag  13320
ttaaatctcc aagttcttcc tggcgcaata tatttatata atcataatgg agctaatgaa  13380
aagaatcttg ctcaagcttg ctatctattt tttgactact ggatttagcg aaatataagg  13440
ttattgcttt acagaggcct ttacaagatg gatactcatg aatattaaga gaagctagat  13500
ttgcgtactt tattaatggt agaatctctt aataacaagt attctttagt gatgagctaa  13560
ataaaaatta tacgtcaaat aaatgctaca caaatttagt tcttgaggta atagaaaatg  13620
tagagctcga gtaaatcgca tgaaaagatg aaaaatgtta cggttgttta ttaatcccat  13680
ttatttctgg gtaactgttt cttattttcc taatattact agaaaaatat aatccagaaa  13740 gatgttttg agtttgttcc agccatggca tcaaatatca aaggattttc taattagttc  13800
tattagacta aagcaaagcg agaaaatact catcgtgttt gtgataggtg aaacacctat  13860
tttgcttcta ttgtatttaa ggaaattaga aggtccactt caacatctag ttgggctaca  13920 accttctga ataatgcttc ttcaccaggt actataatta tcaaccttat acggaatctg  13980
ttaatgcgca cgtgcccgaa acaaaatgtg tcaatacatt actttcactt atacatttat  14040
attttgtgca tgatatttgg ttatatcttc tagtatctct ttaaatagtt ttgttacacc  14100
caaggtgact gaatattggt accaaacagt cttctaattc attgcttggg cttctagaca  14160
tgtcgtatga gtctgagtag tgaaaacata cgatttacaa cccgcccttt actatttcgc  14220
tatacacata ggtattgcct gacattatag catatgtcga agtaaatatt atggaatctt  14280
ttgtattaat aatatttatt tcaaagtaat gtaattttct aagagtttgg ccaacaacgg  14340
gatcaaacaa gtagtaaata tccgaagtgc tactttcat taaattttt ttttccatta  14400 ttgacaaatc ttttctttg cacaaacagt tccattttta aagcatcagg agcaagaact  14460
ctttagccgc tgcttttcag gaggctgcag aaatttgtta ctgttcttgg ttaaatgaag  14520
tacactaatt tcaaacgagg agacctagtt caaagaatta ctattattga aactgttcaa  14580
tgtacatagc ttttgcccctt tatatcgtac tgtacatttg caaagttttc aaactaggaa  14640
gcagaccgtc tcttgactct gtttacaaaa cccgaagcta tcttttttaa ttttccttt  14700 atgcgtaata caaaacctgg aaaaataacg agaagttttt acaatattcg aaactttgca  14760
aattaacccg gtctgcaata ttttttgagc agcttttcac tgttagcttt actctcttca  14820
tttttgtaaa cataatgttt tgaatgacta gaaggggaac ttgttattat cgtagcgcca  14880
cttatctcta ctgtatttca gtagtgaaac tttaggccag ccaaaattgt cctaaagctt  14940
tgggatttgt taaatccccc tttgaatttc gtttaactat aagtaattat ccgaagtcta  15000
catttactat catccatttt tatattgcca aatacttgat agaaactata gatagctatg  15060
aagttttcaa caaatcgatt ttttcctcat agctttctta ataaattgct gttatatatt  15120
gtaatcccaa aatatgaaat tgttgattat agcgcccggc ttcaaagccc tgacaaatat  15180
actcgaaatg atgcgtaaac cttcagcttt gttttgagga gcttccttt gttctttaga  15240 ataaaaggaa ataaccgttt atattattct taacggaagg aaaaagaaag agttgtcaac  15300
gcgtacatat ttgtataata aaagctacgt ttcaataaac gtctaaggcg gaactgatag  15360
tatatttatg cttgaaataa ttattttcgg gctatttccg tccataaagc gtctctagag  15420
gccagcattt aacttcttat aaaatcaaaa attggattac tcttacgtga tttaatcacc  15480
agctcatgga ggtctttttt tttcaattgg gtgctgtttta gtaaaaaaag ttaagttata  15540
tttccaggcg actttaagaa ggcttcgcct accaaacact aactaaaaca aataacagag  15600
acatagacca gcagtattct ctcttttgcc ttatgcgtga atcacttaac cttgcctcga  15660
```

```
tgtaagctct atccttttga acatgttttt ttatgttttt acacagaccc aatttaataa   15720
actataacta tatgtacact ttataagcca ttgattttag tgtaaacgag atcgaaaaag   15780
aaacagatgc tcctcggtaa tttcacagaa gtcaatatct gttttttttg tacaacaatc   15840
aaggaaaaag tggttcaccg gtttcaaatt atatgaagtt aggtaattct aaaaagtcct   15900
tttgcaaaat taagtatgag cttccaaagt actttgagaa taacatttag catcgtgcag   15960
aaacactgac agtaatattc aaatattcat caactagttt aaatgcttct tgtaaacccg   16020
acttaaaact gcactatccc tagaagggtt ttttcaaaaa aagtttttga aaaaatactc   16080
aaacttaaag ttcaacgcct gaaaaaacct ctcacttttta aatcactatg tcgttggcat   16140
taattttaga atgtaataat tacctctgat gaaataacat catggaaaat gacttatgta   16200
tatgtgtatt atctcgactg gtctaggttt tgctagatgg aacaaagaac ttattgttta   16260
taaactaaat agggtatttt ccaaatttct cctcctgcgt gtaagttggc gtacacaaag   16320
ctttcctcat ttcccacaaa ccccacatgt actgtcctta gagaaaaaca aatctacgtg   16380
cctttcagtt gcagcccatg gatgatcagt aagtaaaagt ttgcttttttc gggttgcaag   16440 ctcacatcag tctttgattt tgaacttcag tctaaggtat tcaaaattca catatgtatt   16500
ttgaattaat tatattaaat aaattataat atataaagtg cataagcagt ataatcaata   16560
aataaatgac ataaaacaaa aaagctataa gtaatgtcta gtcgaaattc tgccagtaac   16620
acttacaact gctagtatcg gaggttttag ggtccaagag accaataaag agattttcga   16680
agtgaaagcg atgaacgcag gctccaactt attgctacta ggcttaaaaa tgttttttcaa   16740 atgtaacaaa gaaatatagg cgcttgtcat aacatttgtt aatagattgg ataccaatttt   16800 taagctacag aaatggatta gaaagcaagt cacgtacttt tcctagtttg gagatggagg   16860
tattagtcct tgttgaatcg gtccttactt ggtatactaa caaataaagt attttcaatg   16920
taagactact tttatggttt cattttgcta aacgcttaaa ggtggtttcg cccccagaat   16980
tcagatagag aagcaaaact aaggattttg attttattaa gaaaactctg tctcgcaata   17040
gaagagattt tgaaagagag actgtttagg tattctgttg ctttagttga tgacagcgcg   17100
ccaagaaaca ttaaggatta tgtatttgtt aggttacatc catgagagag ttttttcaaag   17160 tctactagat ttgaagttgt tatatccgct aataagaaag caattacaca tagagctaaa   17220
ttgattttaa gaccgcaact tgttttaaaa tataatgggc gcaataaaga caacaaatgt   17280
ttgcttttga agaataccaa tcataaaata attttcagtc tcctctttat taaagattat   17340
agggctaagg atgatcgaaa gagaaataaa aaagaattag tggcgctaga agctctactt   17400
tttgaagaag aattaaggtt acgggatata tattaactta gagagtactt gcaaacaat   17460 taatgataat gaaaaaattg aagagacaaa aaaaatgaac ttataggtat caactccatg   17520
cgtgcagtta gaagaaattt aaagaatgtt gataattatc cattattact gtttgtgcag   17580
tcagttgaag taaagaaaaa taataatgtt ttagaagaac cttacgatgg tgttgatgga   17640
attagaaata aaattcatga agaatttaga gatgtggtga ccaatgacca acctaccagt   17700
ttacctcccc aaagggattt gactcacaga attatactca ttgaacctac caagagtaca   17760
tacagacgcc agtacaaatc aagctattca gagaaacaag aactgaataa acaggttgat   17820
gaactgttga aactagcctt tatcaagtct gcccctagtt ctttcaatag ttttttgtta   17880
cttgttccag aagaaagatg gtagtatgaa aatgtgtgtt gactatgggt tactgaataa   17940
caatacggta aaagacaagt tctcaatacc acgaatcgac aaattaatca catgttttgg   18000
```

```
aggagcttca gtattttcca agttggattt gatgtcaggt tactttcaag tcagaatcgc   18060
agaagatgat attgaaaaaa cagcattttc cacagattac ggtcactttg agtgggttgt   18120
gatgcctttc ggtttaacca acgcccctag tactttccaa agaatgatga ataggattct   18180 agcacccttat ttgaaccaat ttgttcaggt gtacctggat gatattataa tttactcaaa   18240
gactgttgaa gaacactaca gtcacattag aaaaatattg gaattgctca ggagaaataa   18300
gctgattgcg aagaaaaaga aatgctcatt ttacttcaaa accttaggtt tcttaggaca   18360
tctcatttca agcagaggta tccagactga ccctgctaag atagacaaaa tcaagagctg   18420
gccaattccg aaaaacgcca agatgctca atcattccta ggattagctg attacgaatt   18480
cacaattcaa tacttgaggt cctactaatt cagtagcaga cgctttgtct aggtacccct   18540
acgaggaaaa tgaagttggt atcaacacaa tagaatcggt gttaacacca aatcaggaac   18600
ttctagaacg gatcattaag tcgtacgatg aagacaacga aactaaggag atatacgaca   18660
ttttaaaaga gaatttgccg atcccgaagt caatccataa ccacatcaaa cattattcaa   18720
ttgaggataa tttactatat ttctcagtgg ttaaaggagg aaatgatcga agaattgtag   18780
tctcccctaa gtctaagttg gctcaggaaa ttattggtaa cgctcatgac ggtaactctg   18840
ctggtcattt tgggtatttc aaaacataca tgagacttca ccctatgttc tactggccaa   18900
ttatgctaaa aagcgtgaag agatattgtc aaagatgtac ggtttgccag aaaaccaaac   18960
ccgagacaac tggtcaaaga ggattatttt cccctcttcc aattcctgaa ggaagatgga   19020
cagacatcag tttggatttc gtcacaggtg ttcccagatg caaaaatgga cacgatatga   19080
ttttggtagt ggtggataga ttcacgaaga tggcacattt catccccact aggaaaactg   19140
caaccgcaga gcaatgtgca aaattgatag tagacaattg ttttaaatta cattggattc   19200
caaaaagaat ggtttcagat aatggcatag aattcttggt acatcatcac tcttctcaac   19260
cactaatcac cctcaaacag atggtcaaac ggaaagaacg aacagaatct aaaccaata   19320 acagagacat tatgatagta acgatctcta cagtttgggac aaatggttgt caatggccga   19380
atttgcctac aatagttccc atcaagtctc gataggttca tcaccatttg aagtttgcta   19440
tggttactta ccagactcgc caatgtttat ttctagcagt cgtgtttcaa gtagaaggta   19500
cagcaataaa gctgaagaat tcgcattaaa aatgaaagtc atcatggaaa atgtgaaaga   19560
aaacatgatt gaagcgcaaa gaagtcagga aacacagcat aataagtcga gagtgtacga   19620
aacatttgaa gctggagatt ggatattatt acacaaagat gtatatggta gtgatagatt   19680
gtattacaaa atacaaccgg tatactacgg accctacaag gttgtcaaaa agatatcaga   19740
caacgcttac gaagttgatt taccgaaaac gaataaaaag gatagagtaa tcaatgtcag   19800
atggcttaga agattcttac aaacggataa acagtttccc aaggtacccc aagaacaata   19860
gctgaagcaa gaagtagact gaccgagatt atcggtatag ctggtatcga cgaaacaaac   19920
gatacattgg atgtctactg gaaagattgt gaccccttgtc atagttcaag catcccctat   19980
tcattatttt tagagatccc agaagattta cagaaaactt tatgggataa tgcaaaagca   20040
attgataatg ataataaact ccgggacgaa gtttctaaag cggcggggta atgtaaaaga   20100
tcagacaaag gactatctct ctatttccta atcgggtaat catatagaaa gttaaaaga   20160 agttctagaa gataattaaa tccctcaaaa tgctattttt aaattaaaga attactattt   20220
aaatagagga cattccatat atgttctcag agaattaaca tataaatat ataagatata   20280 acaatcaata atcagattct aaagtacgta ccaccagaaa cacttttaag tcaaagtttg   20340
actggatggc caagttggtt aaggcgtgcg actgttaatc gcaagatcgt gagttcaacc   20400
```

```
ctcactctgg tcgttttttt aacggttgcc ttcgtgattt agttgataca agtaactaac    20460
catgtggaaa ggtattagtc acacttcgaa tattttaca aaatgtaagg aatacatgta    20520
ggcttcaata tatttctctt agagtcacgt tcgaactctt caccatttac cgcaccatta    20580
atattttcgt ggattctact tgtatcagtt ttgctgacct taacctattc atgtttatct    20640
ttgaacctat tcaagtacct tacggaattt ctcctgatgg cgcctttacc agtctttcca    20700
aagtcactca ttgtagatat aatgtcttta ctatttttcg ttgtctattt atagtatttc    20760
tctagatata tgtggttgta ttgttctgct tcaatgagta atctttgtac aaggtgaaaa    20820
gtctttaaca tttcttttac ctttttctca cgagtcaaga ttttccata caatatgatg    20880
tcatggatat attttatttt cgcataggat tgaaccccta tggaaaaatc ttatataaaa    20940
agggatcaaa aacgaactga aaaaaaggaa atgacctctt tctgataaga aatatcagat    21000
gtctatttag ctggacatat aggtggactc acttttgaag aatgagaaag gtagacttaa    21060
ctatatgaac tagaaaatag ttaaatcctt gttctaaaat cttggctaag tcggctagat    21120
cgaccccatc aggattgtta aggatgtttg tagtttgatt ggttatggtt ttactcagct    21180
gttctaccag acgtatattt tgcagggttt ggggccagag tttcttttttt attttctttg    21240
agctacaaac cattactcta attaccatat tcttcgtttt gttcaaagct gatttcgctt    21300
tagtgtggaa tcatgtgtat tgtgtgtata agattttgtt tgaatagcat ctaatagaga    21360
aagttacatg tagcatagta gtacaaagga tagtatgaac gtccgtaagt tcaataatag    21420
gcaatataaa tgctatgcca taattacttt ttatgtagca attcattccc tgttagaatc    21480
gcaactataa tgagaaagtg aattgtgagt tggggtgagt cgataaccaa gtaaagattc    21540
tctcatccta atcctttgaa gttactccta ttcctttata taaatctcga ttttttttccc    21600
catcaagaca agtatggaaa ctttatgtaa ttaaagaaca ttaatttatg aaatcaactt    21660
atacaagagg aataagattt ttttctttac taattaattt taatttttttt gtggttttgc    21720
aaagagattg atcagttgtt atatggcttt gcttttagag aataaacctt aattttattt    21780
tgtgctcttt tggtttccct gttttcattt tcacaagtga cagtaaagtg atatagccac    21840
cagatataaa ggtagcgcgg cgttctatat aatacatttt tatataaccc actgatagtt    21900
aaatacctgc ctacagcaga accatttatg atataaattt tggatcagtg tttaaagatg    21960
ctttgaatga tctaaaactt atttctgcca atctaaatga aaaatccgcc atattatagt    22020
tgagtgacag cctagtcctt aaatcgcgtc tttaagtttc ttcacatttt ttgccttcac    22080
aaaataagc acatcatttc accgtatgtt ttttgttcaa aatactgagt cgtgctgcag    22140
ggaattcatc tacaatccta acaatctaag tttgttaact cctatatact attccattcg    22200
ttaattttat tttatttttt ctaaaacata ttagacggtg cgtaaacgat gtttatctta    22260
ggaaatggct aatcaaaagt atcttatttg cattaaatag aaaaaagttt aggaaattat    22320
ttaaacttcg ttcatagaca agctatatgt tcttatttat gtagagaagt tataagctaa    22380
ttatttttttt cagccattat aagtttaagc atataactgt gttgaaagcc actaaataag    22440
tgataaaaaa atcaaaagac ctactagtat acagagttaa ttctacactt gctaccctaa    22500
ttataaaaag aaactatcga tgtatttctg tatttcttct gaacaattgg ggttttaagt    22560
ctaccaactt ctgaaccttg atcatagata caataggtgc acaacacata cacggtgtgt    22620
ggtatattat gagcagccaa ttcaccattt tgaaaagcta aaactctgta ccataacttt    22680
cagtgggatc cgtattatca aaactatatt taataatcct atgtgctaac taaagcctgg    22740
```

```
aagctatata tatataattt agttttaatt cataaagttt tttcattgga ctgccggaat   22800
gtcatgggcc tttaaaacat tcactgctta actggtgtag attctttgtt acactgtgca   22860
ttgctactcg tctttcgtgt gaatttccca tctctattct aatacctgta tttttctgtt   22920
tagattttgg acattgagtt acactactcg cttatgtttg ttgtagctag tttgaactga   22980
atcctggaag tttattatct ttttgtgttc tcacaccact tgccaaggga cttgagcctg   23040
aaaaaaagaa tgagttgaaa aaaatgtagg ttttacacaa ttttaatcat ttttcttaag   23100
tatgaatatc agctgtcttg taagatgttt tccatcaata agctgaactc actttataga   23160
gcactgaatt tcattttgt ataacaattg gttattcct ttcagtctgg cactcgcttt    23220
tattcatttt cctaataaat agctaattct gtttcgatca ggacttctaa ctgtagtgtg   23280
tacgacatct aattctagaa agggtattct cacttcctag ttaagatgtg tatcatattc   23340
ttttataaaa ctaaaagcac ctagcctatt gagtttataa tactgaaagt ctactgaact   23400
agtcatcttt gtacacttct ttagacttag atccaatctt gttgctttag tttattttct   23460
atatagttat ttgaattaat cacaagtagc taacaaaagg tccatactta ccgatttgtg   23520
tattaggatt tttcttctat ttctttgtag gtagtagtgt ttctaggggt aacctttcaa   23580 attggcctt ctgagtctat tctagtttga aagaaaatt tctcgctaaa taacacatat     23640
taataatagt ctttgctatg gaactaatta tttcttgatc taaactattt ttgctcctga   23700
atagaaggac ctagttattt tttatattag ggcagaagaa atcaaagaaa gaagttgaat   23760
aaagaatagg tatatttgta ctaaagtttg ctaaaagcga tttaggtgga gcttctattt   23820
atttaaaaac cccaataatc ttaataacaa taaaggtctt cctgtaaact tttgaaaaat   23880
gtaccggagt atttaagtta agtccaaacc acgagaatag gtcaaaagct gctacttagt   23940
ttatgtttca ttgccttttc agtatctcga gacttctccg ctgttaataa taaacagttg   24000
tctagttatt ttgtttaggt tggataaaaa cctacggaaa gacaatagga gcttaggcta   24060
tctattgata gatcaattat ttgttttaag aactatagaa ttaaaaacaa ggcagtagtt   24120
gtagatttta aagattattt agagtagata gtaaaggctg tactgaatat caatgaggat   24180
ttgcggaacc aacaagtggc ctgcatcaag ctatttaagt gattctattg gtatttact    24240 agaaaaggaa agctaatcat ttttccaatg acggttcata taatccaagt tttaaatggt   24300
ttgcatcatc ataataggg tatctaaaag gcataaatcg acgaaagtga taaaaattac    24360
ttattaaacg acgtatttac atccacgttt tgttggaag tactgaatct gcctactgct    24420
agtttgggga agacaataat acacaaaata aagacgataa tgaagattcc agttttttt   24480 aaagataaaa aaatagatat atatgtataa ttgtatgaat agttttaata taacttatg    24540 ttgctatttt gatagcaatt cattttacta ttgaaaagat tacctaggca aataatatgt   24600
ttagcacatc agattttgca ctaataataa tatagactta tgttataacg tctggcaata   24660
cctatgtgta tagcgaaata gtaaagggcg ggttgtaaat cgtatgtttt cactactcag   24720
actcatacga catgtctaga agcccaagca atgaattaga agactgtttg gtaccaatat   24780
tcagtcacct tgggtgtaac aaaactattt aaagagatac tagaagatat aaccaaatat   24840
catgcacaaa atataaatgt ataagtgaaa gtaatgtatt gacacatttt gtttcgggca   24900
cgtgcgcatt aacagattcc gtataaggtt gataattata gtacctggtg aagaagcatt   24960
attcagaaag gttgtagccc aactagatgt tgaagtggac cttctaattt ccttaaatac   25020
aatagaagca aaataggtgt ttcacctatc acaaacacga tgagtatttt ctcgctttgc   25080
tttagtctaa tagaactaat tagaaaatcc tttgatattt gatgccatgg ctggaacaaa   25140
```

```
ctcaaaaaca tctttctgga ttatattttt ctagtaatat taggaaaata agaaacagtt  25200
acccagaaat aaatgggatt aataaacaac cgtaacattt ttcatctttt catgcgattt  25260
actcgagctc tacattttct attacctcaa gaactaaatt tgtgtagcat ttatttgacg  25320
tataattttt atttagctca tcactaaaga atacttgtta ttaagagatt ctaccattaa  25380
taaagtacgc aaatctagct tctcttaata ttcatgagta tccatcttgt aaaggcctct  25440
gtaaagcaat aaccttatat ttcgctaaat ccagtagtca aaaatagat agcaagcttg   25500 agcaagattc ttttcattag ctccattatg attatataaa tatattgcgc caggaagaac  25560
ttggagattt aactaatgtc gagagtacaa tgaggtataa taaattttca tgtttaatat  25620
atctgataga gagcatattt acatgggaag ccactcaaac taattccgtc aattttttta  25680
caaatctaat ttattattcc aatcattaag tcaagataaa aaaaccctg aaaaagtat    25740 agattcttag ctactttacc attcaggcaa acaaactcat tctccataaa tatgtctaag  25800
agtactcttg agaaaaattc ttcttttata ttataacacg attaaatttc ctgagcaaaa  25860
acaaaaatga atcagactct cccagaaaaa tagtgaatgc aacttttgtt ttattagtaa  25920
gaggattagg aatatcttta taaagctgtc tctgagtcga taaacttatt tatggcataa  25980
tttcaattta ccaaatgaat ttaggaatgt tactgtatac agaaaactaa aacaataact  26040
tcaagtatat ttataagttc tgttcattga gaaccaaata gtgagaatta tgcaatatcc  26100
tttttaatgg atttataagt tattcaatat caacaataaa taaacaacat tgatatatat  26160
gtaaataaaa cgatagaacc taaaaaataa tttatataat ggaaaacttc cagcgaagta  26220
tgatgatatt cagaatatat gcggataact atcgaataag cacattaata gtaatgatat  26280
acatgtaaaa ggtcttggga gacaaattaa tcaattttat gatagtaaaa caaatttctt  26340
tgcaaacagc gcgaacaaaa taagaaatga tattttatat aaaaaatact agatgagttg  26400
acattggaga acagtggtta aggaatagcg ttatgccaca atgtagatat ttatagtagc  26460
tgtaaattct ataaaaactg gtgttcaaga ggcacaattc ctgacgtgat gcccatattt  26520
agtccagcag ctggataact taaaaagaat ccacaaatta tatagatcga tatcaataga  26580
ttcagttgga gttgaactgg tttcttatta atctttgttt tggtgccatg atgactgagg  26640
gtgtcttcca taactaatgc tgatataaat tttaatcgtt atttctgtgc ttaactcaga  26700
acataggtct aaatatagct gtcaaacaat cagaaataaa tactgatcct gaaattggcc  26760
tattgttaac tatctacagt gttgaatctg ataacgaaac tatgccggat caatcatgaa  26820
agatgttcaa gcgttaaaaa gaatcgtact ctttttggtt taaacgcacc tgtactatag  26880
tttgcttcga ataaaaccat cgccagttac ccaactttaa gtgagcacta tttctgaaag  26940
tgacatcaca tcttagtatc taatcttacc ctctaggtaa ttgtaaaaat taccctcagc  27000
actgtttcga catagcactc tttagtgaaa atttgcaacg tgatctaaac atgaaaatcc  27060
gagaaattgc cggatacgca taaggtgcaa acttttcttg ctggtcgata gatcacttcg  27120
taatgttcca tttgcaccta ttgattgatt tttcgttgac gtcaacttct tatatatgag  27180
cccttacaga aatgatttta tggatgcacg atattcctgt ttaaaacagc ggcgtttac   27240 tatcctataa caagaggctt acatgactcc cacatgaaat ataaactaag cgaaccacga  27300
attcgacttt gccgcaaaac gttttctgaa acatactgtt taaataagtt caggaaaagg  27360
cataacagtc atacataatt gtctgtatag agttttgaca tttattataa ctctctaaga  27420
aaatgtttgg tagattagac tgtggagaga aagaaaaaag aagagtgtct ataaaaacta  27480
```

```
tagcttgaca aatattttga taaagtttag aaagaagcac atgttttttt ctgatttatt   27540
cctacagaat ggatcaatga aaccttttgg gtgttttttt tagaaattat caagattaca   27600
ttattgcatt acaaaaattg tatgttttg atttgagttt cgtgcggcaa aagatcggaa    27660
atggaagcta tccaatatta caaataatat tgtcgtagaa atgttttctt tagggatatc   27720
aaaagtttgt tagacggcta ttactcttct gttttcaacc cgtacatatt ttaaactggg   27780
aaaatgcagg atcttagagg gttctagttt taccaagtac tgtatttatg gaagattcat   27840
ccaatacaca cagtaaaatt aagtttgaaa atttgagtag taaagacgta cttccagatt   27900
attacgttct tcttatacat ataattaaat acttggtctc gaaattcaga ttcaccagta   27960
gaaaagtcca acaaaaaatt ataaaggacg tacgtttcca gtcggaccaa actagctgaa   28020
aagccaatag tttcacgatg tagctaaatt ttaagtagct gtttgaaaaa gctacttgtt   28080
tttatgtaca aaaaggttgt atgtgttagt tgaatagtgt ttcttttttt tttgcaattt   28140
caagatcagc gactttaaat attggtcatt gtgacatgaa aaaaaaacag ttaccctttga  28200
gaactaaatg actcttttct tgctagacct tatcgatcta tcttttagct catcacaaat   28260
attaggcgaa aaagaataca ctaatctaag aaagctattt atatattatt tttttgatgg   28320
aaaaaaaaac tccaatgtgt gggataatgt tgaaattagc gttatgttta ttaagcatgg   28380
tgagtcagcc ctgatagagg gaccattgaa ctgagagtac aaacaagttg gtgattagaa   28440
cctattattt aagcatcctt tagacagtgc tgttttaacg ggggtctcat atatttaaat   28500
catgtactat aagaggaata gtcacacacg gatttctttt gatgaaaatg ctcaaggacg   28560
ggtaggtaac gaacaaataa atgaaaagaa aaaaactgga acataaggga cagcaatcac   28620
atagtccaaa gctgaatcca gaaaaggctg cagagactcc gtcatttgat gcaaagcata   28680
agggtaaacg gttagacgtt gctgaagtta gtagaaacgt atactaagaa aatccaacac   28740
atggaattca agcagctgct aagggtagtc atgtgagtga ataaccgctt aatttagtag   28800
aatgcaacaa aaggatttat gtattacatt gctaatgatt gttccacaat aacaggcaaa   28860
atgctttga taattaagag gctagtcctc tgcaaacaac cagaactctt ctgaattatc    28920
agagcattgt tgtgttattg gcccaaatag ctatttgcaa gattgttagg ccgaccttta   28980
agagcacaag ttttttttc tataagagtt taatgtattt tgcgtatgta aagggcgtg     29040
caacttacca tttgctctga gagcaaaaaa acaataattt ataaggttta cttattgttt   29100
atactaagtt ttttgttga aatctagcta actttccagc taacgttgtc gattatgatc    29160
tagtttagtt tatgtaagtc aatgtactag ggtcttttc aggtcaatgt tgaatttctc    29220
aacataaaca taacactaag tttcttcttt aactctcaac aattctaagt cccctaatgg   29280
caagaaaaac ttgaccttac ataaccttaa gctgcttaca gaacaaccct aaaatgatgc   29340
tccaagtggt aaaaaagta gctttacac ggtaaacatt cgggcaacaa gatttaggct     29400
aactttagga taaacataat aggttctctt cttatcttaa ccaaataaca aacactcctg   29460
cacgaacaaa attcaagcaa acgcgttatc tgtacttgta gagcttatat aacagcatat   29520
aacatgagaa tagttgcaga attttatagc tctatacggt tcatcaaatc ctaaataccc   29580
tactctccct gagcataaag catggtcaca tgatatattg cagatgaatg agacatgctg   29640
atgcatctta aaagctccag aggtgatttc caaagttcaa gaatccttag aatgttgtac   29700
tataaaccgc catatagtta tagaaaaagt atattcaagc aatgctgctt aacaatgact   29760
aatattaacg atagcaacca aattatggca gggaacaacc caacattata gacgtaaata   29820
acacatttct ttctataccc aataaacaca ctgtccaatt tccattgatc tggaactata   29880
```

```
gactttggct ccaacaatat aatttcaaat aaatctctgc ttctaatacc agtaactctt    29940
ttcttttgag tgttttgact tttcaatgga tggatgctgg tggccgtctt tggtctcaac    30000
aactgctcgt acccaatatc ttttacttcg tttttaagca catctataat cccgtgttct    30060
atatagtata gtgtcagttg tctgagataa atatccgtct tttttaattg gtctgatcaa    30120
tctcaacatt tccagtggtt tcttcgacct cttccatctc ttgaatttaa gtaatttaaa    30180
gtaaggtttt tacattaaaa actggttcga tatcagccct taacgatata ggtaacatac    30240
tgtcaaagct tagattaata gtcttttctt ttccatctcg ccacatacaa gatataatag    30300
atactgtcaa atatatcccg atcattgaca agtaaaacat tatcaaatat ggggtgtatg    30360
atggagagac aaaactgttt gctgcggttt acacttcata atatttcttt ctcacctaaa    30420
ccttgtcaat gtgtcaacac caacacaatc gagattttt tcaaggttga tagttttgtg    30480
ccgtagacac tttacagcag caactctatt aggtcaaaat tgtcttgcaa gacttttgtg    30540
tgaagtttca aaaccatcta aaaaatgtaa cgctattgtg gcaaaagctc atcttagaaa    30600
gatctcttga gcagttcact taatttcgta atacaaatac cataattacc tgctgattta    30660
ttttgcagaa ataaccatac tcaacaatgg attttttcgt ttatgtcatt catatataca    30720
tctgtcatag atttgaaata ttggcatgtt gtcacattga atacagcatc aactccagaa    30780
acatactgac tggataagct ctacaattaa accatgaatt tgggcggact gtgtgacttt    30840
gttcacaatt tccggatata acacaatctc aatatcttct tcccttcttt ttttactaca    30900
aacgctacct ttactttcca aaaggttaag cgaaggtgcc acatcgtgtt cttaaggaga    30960
gtgctgttgt tttgccattg tctttgtaaa cactcaaatg gttgatgtga tctcttccgt    31020
tcgagttaac aatatatgca taatgggata tccttttatc tttctagtat aatatgtctt    31080
aataactacg gccgtaaacg attcgggcct aataatcaca ttgatgaaga aatcaaaaac    31140
aatgctggat ttttccaaac agcttgttcg ttgacttccg agctagaaca tggctgatac    31200
aaaccaaaac tataggttac tttctctttta accttccat cataacggag cacggaactg    31260
cgttaatcct taaaaacaca ttaatgtttt taaggttggc gacatcgagc aaaactgagc    31320
aaatttgtag cacaagccca ctaccaatcc tattagctca cagtggatcc ttgaaatcct    31380
aaaatctata gaataatata cgtgagtaac tcccccaaag atgttctgtc actctgaaag    31440
atgcaccgtg tctataaact gaatatttaa aagatgctct tagtctggta aaaggcccat    31500
atggtttctt gtgtttccac cgatatgtta caggtgcatc attccatcca cgtcaaaacc    31560
tttccttaac gaacactcct gtatattgta acaaaaggga atttccgtgc ttgctaaaaa    31620
tgtattgtaa tccgaaacaa tacatttaca gaagagcttt gtaaaaccta tattttcacc    31680
tttttaatca attggggcct gtaaatagat tttagtagac tttatctttt tgtcaaacct    31740
ggatgtctca agaacttttc cgtagagccg ttcccacaaa agctaccatg aaaggccttt    31800
aatttatcag caaaaatgta aaatcgcaag aagtcatcat cctttctccg tccaagtggt    31860
gggcgttcga aatgagtatc cacaaggttt tcaagatact tccaaaaaga cggtctgaat    31920
tctccttatc agggaaaaat acctctccaa ttttagcaac aaaagcttta caacaaacct    31980
tcaagtgcca gatctgttgc tgtgtctgtg gtttatcaga tgcacatgt tggtggtggt    32040 aaacatttta tatcccaatt aatggcagta taacatcaaa actatacagt gcaacctcac    32100
atcaagttac acattttatc acaacaaacc ggcaacgttg gttgtgtatt tgaaagttgt    32160 aatttttcagc tacagtagtt aatttataca ctaaaatata actcttggag agcaatatgg    32220
```

```
atgactaggt ccgatcaatc agctattgat ggtacgatat ccatatttag ttcgacactt    32280
gattactaag ggatttctaa ataatatgcg tattaaaagc tacagtaaga gcggagttac    32340
ctctcttatc aattgtcggt ttggcgccac aataaataat gatatcatct ctaactaaac    32400
gcaaaacata ttactagttg tcattagcta gttgccatca gtgcataatg tgagtcgaca    32460
tacctgctgt atcacatgat atcaataaag gttgtagatt attttctttt ccttgggttc    32520
tttttatgtg gtattttgaa gtaactcttt taaacgttca atctataacg tgtaacatgg    32580
ttatctgaag tagaattagg gcacgtcaag gcagtattgt atttgcttga catgtattta    32640
ttggctgctt ttagaaacta aactatattg aatatttgca ttttggccaa tggtaaaaca    32700
gtttatctta ttgtcttata tgattgcaat gggagaagaa taactagcgg atttatcaaa    32760
gctaaatcga taaacgaga acaaaactca actatgttca atgcagaata aaattataca    32820
aaaccaccca acttctctga ttaatttcag actagaaagg ccccggattt ccattactgg    32880
atataagggc tagaggcata gaatggtcag caaacattgg aagagaattt gctacatatg    32940
ggctaccaga tgtcagaaaa attataaggg ctgttgcagg ttcgaaaaat aacgaacgta    33000
aattacacac ttctcaaatg catatgaact agcaaatact ggattttagt cggtctaaat    33060
ttgaagatag attctgaaac gctttgttcc tgtcgacaaa gacagagact ctgtggtgaa    33120
tattgtcaag taattgtgtc gattgaaacc aggtcaatcg atgagaggct ataagaaaa    33180
ctttaaagtg tctatgtacg tcgctatttc tgacattaag agttgaccac tattccttga    33240
tggccttacc gatattgagc agttaatggg ggtgagattg ttgcagtcta acataaaagc    33300
ttgatgtgtg ttttaaccat gttgaggcga gtctattgga gatatacaca tgcaagaagt    33360
tacatgggca cttatacaat catttaaatg gtttcccctta tagaacaaag tccgccaaag    33420
aactcaattt atttcatgcc ttttcagcca tcggtaacct aatgtatcat ggataatttc    33480
atgttccttt attcaaatag tatttataag aggatgttaa agggcatgat aatgatgcga    33540
aatacgaaaa ggaactttca tagtaagtat aaatgtccaa aaaatgagtg gatgccatcc    33600
cacactcaca ttatgaccat cccaaaaaag aaaaaccaaa attaatttgt ggtgtcgttt    33660
atatcaaata tgcagatgac attttggttg ctccagaacc acttttacag ttattaataa    33720
aactgttgag gaagttcatg tgtttagcaa aaggccaagc tcgatggatc aataacagta    33780
aagattatcg gaaactctgg tgttgctatc gcagacgtaa ttgtcccatt tgaggtagtc    33840
aaagaaacta tcagtataag tgaggttagg tcatttttaaa tgtttgatac tgagcatgtg    33900
gtattcatgt tgggaaaccc atttatcaag aggcaattta gtgatctaac tttaaggtat    33960
ttagtaagtc ccgatatcga taaagccaaa gctgatttaa atatcggccc ctagacgcaa    34020
atcatgcaag aggattgaaa aaggaaacac ttgaaaagtt tacttgagat ccaccaactg    34080
aactaccgcc aaagaaaaga tgcgggcata tgttgccttg tcttacccta atgagttctc    34140
tttgaaaaaa acaatacca ttaagcttct ctgagaaact ggaactaaca aaacaagttg    34200
aagtttttaat caaacaaggt ttcatcaaaa ctagttccaa acctttttaac agtccagtgc    34260
tatttgttaa aaagaaagat ggtactatgc gtatgtgtgt tgattatagg attttaaaca    34320
ataatgctgt taagaacaag tttccacttc cagatattga tcaattgatt tcaagatttg    34380
gtaagacaaa agtctattct aagttagagt tgatgcctgg ttactaccaa gtgagaattg    34440
cggatgaaga tgtcgaaaag acggcttttt ttactctggc cattatgaat ggatggtaat    34500
gccggctgga ctaacaagtg catctgcgac ttttccacag atgatgaata atgtcttgtc    34560
taaaaaaata aatggatttg tccaagtgta tttagacgac atttttatat actccgaaga    34620
```

```
tgttgaaact cacggtaagc acgtgaaaga agttttgtcg acactaagaa aacataaact   34680
aattacgaag aagtcgaaat gcagattctt ttatcaagaa tttaggttct taggacatgt   34740
tgttacacca atttgtattc aaaccgctct cgagaaaatt aaaaaggtaa agagttggcc   34800
aacgctaaac aagatcaaag aagcacaaag ttttattggt ttaacttcgt tttatagaag   34860
gtttatcaaa gggcattcca aaattgctaa tccaattcat aagttcatga caaaacaaag   34920
taaatggaca agtgaacaag acgaagcctt caacaaacta agaaagctt tgatatcaag    34980 tcccatcttg gtgcacccaa gctggtcagg caattgtaaa tttgttctaa ataccgatgc   35040
gtgtggagta tcattaggtt atactctaga aagttggac gagacaggta atgacgagg     35100 tgtgatttct tacggttcaa agaagctagt tggaagtcaa ctgaatcatg aatatatga    35160 tcgtgaattt ttggctgttg ttgaagcatt aagaacatga agatattatc tcatgggaag   35220
acatgtcatt gttatgacgg atcacaaaag tttaatttac ttaaaaaacc aaaatcttat   35280
agactccact agagtggcta gatggatgga cttttttacca caatttgatt ttgatatttg  35340
ttacttacag ggaaagaaca attctgccgc tgatgcgtta tctagatacc catataacca   35400
cgaaaacaac ttaacgctaa ccaaaatcga attggcgttg ctggaattga cgtaaaaaga   35460
ggagcatgaa acacagatac attctttgac actaggtatt atcgaagccc atcaagattt   35520
aaaaaaagaa attattacgg ttataaaaa agatactaat tatgccttga tattcagaac    35580
tttgagagat aaaacaaaag ttccagttga gataaaaaat caaatcaaac atttctgtta   35640
tcaagatgag gtacgttatt ataagacatt agagtctcaa gatttcttta gagtagttat   35700
tccaaactac aagaaactac cgtatagaat attcaaaatg cacacgattc caaagatgct   35760
tgtcactttg gtgcatggaa aacttatttg aatcttaaag atagttttta atggtcatct   35820
atgttgagac aaatcaaaaa tgggtagaaa cctgccatat ctgtcaacaa cacaacacca   35880
acactgagga agacaagggt ggttttcccc tttaccaatc ccaacaggtc gctggaccga   35940
cattacgatg gatttcatta caggtttacc tagatcggga acaggttacg atatgatcat   36000
ggttgttatt gatcgctttt caaaaatggc acatttata ccagcgcaca aaagacttaa    36060
tgctgcagca tgtgctcgtt tgtttagtga caatgttatc aagttacacg gtgtcccaca   36120
aagaatagtt agtgacaaag atattcggtt tatgaataag ttctggcaaa cattacatta   36180
tctcaatggt agttctctac tatttcgac tactaatcat ccagaaactg atggtcaaac    36240
cgaaagagtc aactagatcg ttaatcagtt acttcggaaa tattcttcaa acgatcaatt   36300
attctgggat gaacatctat ctatgtgtaa acttagttac aattcaacgt accaagattc   36360
cattaaagca agtccttttg aaatcgccta cgggtatgaa tcgaacatga ttagaaaagt   36420
aaatagctgg gatttggagg ataacagata ttcacctaac gcagaagaat ttgtgagacg   36480
tgtgaaattg atttttacagc acactggata atattgtaaa gcacaagggc gacaaggaaa   36540
acaccataat agaaaagaa gatactttga atataaagtt ggtgacttag tgttagtgca    36600
tcaagatgcc tttggtgtga atataaggta cacaaaaatt caaccagtat gatatgggcc   36660
atacagacta gtcgagaaaa taacggcaa tgcttataaa gtcgatttac cggttattaa    36720
tttgaaggat cgtgaatcaa atgtacagtg gattaaatac tataagaaa accccaatat    36780 ttaccaggaa ccgcctagaa cagagcgtga atgttggca cgaatcaatg aaatgactgg    36840
tatcggtgga tggtcagaag aatcaggcaa agaaaagact tatgatgtct tctgaaaga    36900 ctgtgatcaa actctagcaa gaaaggtgcc tgaaagaata ttcaaccaag cagatttgtc   36960
```

```
actacgtcaa agcctaatgc acaatgccaa atcgatccaa aaaaacgaac aagcttgata   37020
tcaacaaagt aatcatgatt ataatatata gaacgttcct atttgtctct cagctgaaga   37080
aaaaaaatac agatattgct cctaccaaaa cacaaaacat attgtttttt gattgaaata   37140
agttagccac tctcgattta aaaaaataca aattgagctc ataaaaaaat tattgttact   37200
gccaggatcc acctacattt attattctaa tctggtttaa tgtttgcagc ttcattggtt   37260
cagtgccccc atccgggatt atccagttat tttgttgcac cgttttgagg aacatcgggg   37320
cgatgtttcc caagagccgg ggtagtgaaa gggattttc aggatgtgtt ccaaaaaagg    37380
aagtgccagt agatagacga taacatactg atgttaaggt ttcgatttta gaataaggga   37440
agttaacaag ggtcaagtat ccggagtagg aagcaaagag agttagtccc gttgatcatg   37500
tagagaatag gcatagagaa gccgtcggag acactgtcat tggcataaat taattatcat   37560
tcatcaacgg gctatgacag gactggcaca gtaaaaaata aagacctaaa acgtaataag   37620
ctcgtacagg agtctgctat acgaaaaaga gtagcaactg agggtgattc caggttgcgg   37680
gcgtgagtat atcagacaga cgatattccg ttatatagaa ttgatatagc tgatataggt   37740
cctaatcggg agtggaagca gcagaaggag gaagagagaa atagattact acttctacta   37800
cgactaactt ccactacgcc cattgtctac tcgtgcgatt atacacctat tgcgtactta   37860
ctaatacgtg tatcacaatt atcattgtta taaacaatac tgtaactatg gataaggcta   37920
tgattgcttt tttgataaaa gatttaacca tagaaacatc cagaactagg aaatgatttt   37980
gacaccttac acctagttct ttgcacaaac ataacaagcg caagtggttt agtggtaaaa   38040
ttcaacgttg ccatcgttga gcccctggtt cgattccggg cttgcgcatc tatccgagat   38100
agtttagtgg ctagaatttc cgcttgtcac gcgggagacc cggggttcaat tcccggtctc   38160 ggagattttt tttgttttcc aatgcatttg ttgtgtccgt tgaggcactt acgatttcta   38220
aaaaagtttt actatatatt ctaatcgtct atcaaatata tttctaaaat tattaaatac   38280
acaat                                                              38285
```

<210> SEQ ID NO 17
<211> LENGTH: 600
<212> TYPE: DNA
<213> ORGANISM: Issatchenkia orientalis

<400> SEQUENCE: 17

```
caacggtgta atcagagaga aaattgctct tgcacagcaa cagcagcaac agcagcagca     60
gcaagcccaa caagagaaag ctggaaccca acaggacgca taactatact ccagccacaa    120
gtttctgtag cttctacttt ggtatatcat tagtaaacaa taacaataac tcaccaataa    180
ccattataac ggcaaatcat tttcacgtgc cggcgcattc gccgtgagcc cacgcatata    240
ctcggcaaaa acaccgaaac agcagcaact gggctgtccc aaaggggaaa tttctgccgt    300 ggacccccggg gccatatcgg caaactcgcc gagacgcttg tagtttattg gtcaattgga    360
caaagttgcc aatttttaggt gaaaggagga gtaaattatg gacagggtgg cctgttgtca    420
ttggaaagtc ggcaaataga gtcaattttag aatattttag aaggattgga gacaccaaag    480
aggtggccat tggaggtagc ataaaaggag gaccatttcc tgccaagtgg agaggtactg    540
taaagccatg tttttaactt tcatctcatc aaagcagagc aaactaaaaa aacgaatata    600
```

<210> SEQ ID NO 18
<211> LENGTH: 186
<212> TYPE: DNA
<213> ORGANISM: Issatchenkia orientalis

```
<400> SEQUENCE: 18
cgaaaaatgc accacacccg agaaaaaga ggccgatagt caccgcgttt tctgtggagt      60
gtggcccggg tggagtaatg gttataaaag gaacattttc ccacccaggg ggtcttcaat    120
tggtttctcc ttcttgggct ttcaagaat cacgtacaat tgtatatctt aaaacacaca    180
cacaaa                                                              186

<210> SEQ ID NO 19
<211> LENGTH: 600
<212> TYPE: DNA
<213> ORGANISM: Issatchenkia orientalis

<400> SEQUENCE: 19
tatggatatg gagatgaatt tgaatttaga tttgggtctt gatttggggt tggaattaaa      60
aggggataac aatgagggtt ttcctgttga tttaaacaat ggacgtggga ggtgattgat    120
ttaacctgat ccaaaagggg tatgtctatt ttttagagag tgttttttgtg tcaaattatg   180 gtagaatgtg taaagtagta taaactttcc tctcaaatga cgaggtttaa acaccccccc    240
gggtgagccg agccgagaat ggggcaattg ttcaatgtga aatagaagta tcgagtgaga    300
aacttgggtg ttggccagcc aaggggggggg gggggaagga aaatggcgcg aatgctcagg   360
tgagattgtt ttggaattgg gtgaagcgag gaaatgagcg acccgaggt tgtgacttta    420 gtggcggagg aggacggagg aaaagccaag agggaagtgt atataagggg agcaatttgc    480
caccaggata gaattggatg agttataatt ctactgtatt tattgtataa tttatttctc    540
cttttgtatc aaacacatta caaacacac aaaacacaca aacaaacaca attacaaaaa     600

<210> SEQ ID NO 20
<211> LENGTH: 600
<212> TYPE: DNA
<213> ORGANISM: Issatchenkia orientalis

<400> SEQUENCE: 20
aatacacgag agattatagc aatacacgag aaaccataag atactaaggt aaatcatggc      60
aaatcatatt aactattgac ctctgacaaa cagttatggc cctttaaaga aggtaaaacg    120
tgggaagcct tgggacagga aaaaaaaaaa aaaccttctc tctcaatgag ccaacttttc    180
attacatcat catcgtccac aatttaattg gacaatagga aaatgcaaaa caaataaagc    240
tgagtaaaga gcggcaaaaa tatgcaaaag agacaaagat ttgccaaaga ggcaaagatc    300
tgcagaaatg ggaaaaaaaa ctgcataaat tgcaaaacgc gcttctattt ttagtacatt    360
cgccagcggc cgtgctgttt atcttttgcc gcttacggaa ggcgcgcgcc gccggtggct    420
gttttctggt aaagtgactg ttccacgggg ggaagctata aaaagcgtga aatccctccc    480
acatttccta atcccagtgg taaacccaac ttcttttcta tagttttttt agctttattc    540
tttctcactt atcaactttt atcgttcata gtctctcgct tacaaactaa cacaataaaa     600

<210> SEQ ID NO 21
<211> LENGTH: 600
<212> TYPE: DNA
<213> ORGANISM: Issatchenkia orientalis

<400> SEQUENCE: 21
cagggaggat ccactcctaa cgtctctcca taatgtctct gttggcccat gtctctgtcg      60
ttgacaccgt aaccacacca accaacccgt ccattgtact gggatggtcg tccatagaca    120
```

```
cctctccaac ggggaacgcc tcattcgtaa accgccaagg ttaccgttcc tcctgactcg    180
ccccgttgtt gatgctgcgc acctgtggtt gcccaacatg gttgtatatc gtgtaaccac    240
accaacacat gtgcagcaca tgtgtttaaa agagtgtcat ggaggtggat catgatggaa    300
gtggacttta ccacttggga actgtctcca ctcccgggaa gaaagaccc ggcgtatcac     360 gcggttgcct caatggggca atttggaagg agaaatatag ggaaaatcac gtcgctctcg    420
gacggggaag agttccagac tatgagggggg ggggtggtat ataaagacag agatgtcca    480 cccccagaga gaggaagaag ttggaacttt agaagagaga gataactttc cccagtgtcc    540
atcaatacac aaccaaacac aaactctata tttacacata taacccctc caaccaaaca    600
```

```
<210> SEQ ID NO 22
<211> LENGTH: 600
<212> TYPE: DNA
<213> ORGANISM: Issatchenkia orientalis
<220> FEATURE:
<221> NAME/KEY: misc_feature
<222> LOCATION: (170)..(189)
<223> OTHER INFORMATION: n is a, c, g, or t

<400> SEQUENCE: 22
catattcgac gactccgggg agtctagtaa aggcgggttt tgtctttgcc agttgatgtt    60
gctgagagga cttgtttgtc cgtttcttcc gatttaatag tatagaatca acctactgtt   120
aattacacta cgttatacta acacaaacaa aaacaaaaca acgacaacan nnnnnnnnn    180 nnnnnnnnnt tcaggttgtg tcactccgac ggaccatagt tgggtaatcg tgcattctga   240
gagagtcgcg agaagtgagg acccgacct acgtaaacta cctcgacgg gggcgagtgg     300 aggagtgggg cgatggagga gtggggcgat ggagtgagtg gaggagtggg gggggggggg   360
gcggaaaaat aggtagcgaa aggacccgct atcaccccac ccggagaact cgttgccggg   420
aagtcatatt tcgacactcc gggagtcta taaaaggcgg gttttgtctt ttgccagttg   480
atgttgctga gaggacttgt ttgccgtttc ttccgattta atagtataga atcaaccact    540
gttaattaca cacgttatac taacacaaca aaaacaaaaa caacgacaac aacaacaaca    600
```

```
<210> SEQ ID NO 23
<211> LENGTH: 600
<212> TYPE: DNA
<213> ORGANISM: Issatchenkia orientalis

<400> SEQUENCE: 23
atgccatatt gtatgtgtat tgtattaagt gtgtattgtc ttaagtgtgt aagagacatt    60
tatttgtgtc aacaatagcg acgccactga aaacctcaaa tatcgtatt attaatcccc    120 ttcccccag cgcagatcgt cccgtcgatt tctattgttt gggcattatc agcgacgcga   180
cggcgacgcg acggcgataa tgggcgacgg tcacaagatg gaacgagaaa acagttttt    240 tcggatagga ctcatttcc aggtgagaat ggggtgacc cggggagaaa ccttccgcga    300
gtggagtgcg agtggagtgg gaaatgtggc cccccccccc cttgtgggcc atgaggttga   360
caaataccgt gtggcccggt gatggagtga gaaagagagg gaaatgataa tgggaaaaca   420
aggagaggcc cgtttcccgg gatttatata aagaggtgtc tctatcccag ttgaagtaga   480
gatttgttga tgtagttgtt ccttccaata aatttgttca atcagtacac agctaatact    540
attattacag ctactactaa tactactact actattacta ccacccccaa cacaaacaca    600
```

```
<210> SEQ ID NO 24
<211> LENGTH: 600
```

<212> TYPE: DNA
<213> ORGANISM: Issatchenkia orientalis

<400> SEQUENCE: 24

| | | | | | |
|---|---|---|---|---|---|
| tctacctgtt | tttttgttaa | tcctacacaa | gaagcccctc | ctatctttgt | ctttagttga | 60 |
| ataagcctct | taggagatgc | cattaaacca | atttcatgtc | gccaccagag | cctgcaatgg | 120 |
| cagacgtttg | cgccacgtca | taatgtggaa | ggggaaggag | gggaaggggg | tggcaaaccc | 180 |
| caggaactgt | aaataatagc | ctgattgtaa | accacgcgtg | tggcgcatgc | gcgcttttcc | 240 |
| ccttttgagc | cctccaacct | atccctgatg | accccctcgc | tgagccacat | tggttacgta | 300 |
| ttatgaaccg | gtccttttaa | agaataacga | ctgggaaggt | ggcaagtatg | ggaggcaaat | 360 |
| caaactccaa | atataaatag | ccaccaatat | cctgcttgtt | tttgggataa | ttggaatcaa | 420 |
| acaatgtttg | tagaaaccaa | ctaacaagag | catagaacct | ctgcatacaa | caatcaagca | 480 |
| caaacggaca | ttataaatcg | ttaaacacaa | atcgttaaaa | gcaaatctta | caatacaaat | 540 |
| cgttaaaagc | aaatcttaca | atacaaatcg | ttaaaaacaa | atcgtacaat | acaaacaaac | 600 |

<210> SEQ ID NO 25
<211> LENGTH: 186
<212> TYPE: DNA
<213> ORGANISM: Issatchenkia orientalis

<400> SEQUENCE: 25

| | | | | | |
|---|---|---|---|---|---|
| cgaaaaatgc | accacacccg | gagaaaaaga | ggccgatagt | caccgcgttt | tctgtggagt | 60 |
| gtggcccggg | tggagtaatg | gttataaaag | gaacattttc | ccacccaggg | ggtcttcaat | 120 |
| tggtttctcc | ttcttgggct | ttcaaagaat | cacgtacaat | tgtatatctt | aaaacacaca | 180 |
| cacaaa | | | | | | 186 |

<210> SEQ ID NO 26
<211> LENGTH: 600
<212> TYPE: DNA
<213> ORGANISM: Issatchenkia orientalis

<400> SEQUENCE: 26

| | | | | | |
|---|---|---|---|---|---|
| cctctatcgt | atcgtatcgt | agcgtatcgt | accgtaccgt | atcacagtat | agtctaatat | 60 |
| tccgtatctt | attgtatcct | atcctattcg | atcctattgt | atttctgtgc | accatttaa | 120 |
| tttctattgc | tataatgtcc | ttattagttg | ccactgtgag | gtgaccaatg | gacgagggcg | 180 |
| agccgttcag | aagccgcgaa | gggtgttctt | cccatgaatt | tcttaaggag | ggcggctcag | 240 |
| ctccgagagt | gaggcgagac | gtctcggtta | gcgtatcccc | cttcctcggc | ttttacaaat | 300 |
| gatgcgctct | taatagtgtg | tcgttatcct | tttggcattg | acggggagg | gaaattgatt | 360 |
| gagcgcatcc | atattttggc | ggactgctga | ggacaatggg | ggttttccg | ggtggcgtgg | 420 |
| gctacaaatg | atacgatggt | tttttctctt | tcggagaagg | cgtataaaaa | ggacacggag | 480 |
| aacccattta | ttctaataac | agttgagctt | ctttaattat | ttgttaatat | aatattctat | 540 |
| tattatatat | tttcttccca | ataaaacaaa | ataaaacaaa | acacagcaaa | acacaaaaat | 600 |

<210> SEQ ID NO 27
<211> LENGTH: 482
<212> TYPE: DNA
<213> ORGANISM: Issatchenkia orientalis

<400> SEQUENCE: 27

| | | | | | |
|---|---|---|---|---|---|
| ctctcttctt | tccctccaca | gtagaaacca | aatcaaacac | cgttttgtcg | ttaacaccgt | 60 |

```
gttgtcgtta acaccgtgct gctcttccct atctgtctac acacaccgt acaccagaac    120 tttctttaca cacacccac tagtcctct tccccccccc ccaccggaga ctttccgaat     180
tgggagcgtc tgctgaccgc cgggtctttt gtgttccgga atcctcatca tttggattgt    240
tgcccaaagt ggagtgagcc cggagtatct taccatacag tgagaggcac attaagtgta    300
caataggtat atatagatat aactatatat agggggggacc ttgctactag tgcagtatag    360
aaagtccagt agatactttc ccccaatttg ggcttatttt tttcttcagg ctgtataaca    420
tccaacacac acacacacac acatacacac acacacctac tcatatatat ataactctta    480
ca                                                                   482

<210> SEQ ID NO 28
<211> LENGTH: 600
<212> TYPE: DNA
<213> ORGANISM: Issatchenkia orientalis

<400> SEQUENCE: 28
tagagcagaa attctacaat acgttagata tactctcatg ggcccttgta tgctacaatc     60
gacagatcta caatgaatcg ggagaagtga ttctggataa tcgccgttta cgtgaaaatc    120
agggtgcaag ttttattatg cacatagtgg agataataca gcaaattgtc caagaccttta    180 ttttgcttgt tttgactttg ttcccaccat tttcggattc tgtgaaacgt gtacgtgtac    240
gtgccgctgc tgttgtagat tctaatgcca atgccaatcc gaatgccaat ggcaatggtg    300
atgttgataa caatggcaat ggcaatggca atggcaatgg tgatgcagct gtgctggcgc    360
caatggttga caaccagtaa agtctaggtt ttggtgggat tgataagctt catacggttt    420
actaatctcc agcgagaagc gagaccgtct cgtgtgctcg aagattctat accgcgagta    480
taaaaggaga gtagttgtcg ccaccgttgg cctttatat ggtggaggtt atcttttgtt     540
tgtatagcag ttagatcaag caagagttta tccagttact caattaccca ataatctaca    600

<210> SEQ ID NO 29
<211> LENGTH: 600
<212> TYPE: DNA
<213> ORGANISM: Issatchenkia orientalis

<400> SEQUENCE: 29
gtgctttgag catctgcact atggtgacct ccatcaaatg aaagtaaaaaa cgttcctttc     60 ccatacttgt tgtcgttgac gtctgggaat gtcacccaaa ataagtgtgt tgaatgttgt    120
cacttgaata aacacatgct actgactatt ggcactttat tattgcagtg ttgactttca    180
ctacgcgacg ttcatgaaaa accacggagc tgttggtagc tagaacaact ttttatcgat    240
tcgacacgtt actactctat tttgccacac attttctgtg ggcggtatct ttagtgggga    300
caaaatgtgt tactctagtt ctccgcgtgc tcaaaagaaa acataattgt gggaaaatac    360
ccactggtgg ctgttttgga ggcggaaata gaaccacagc atacgcaatt gctattaggc    420
ataaaaaaca ttttggagta ggctggacac aagaaaactg tttatgaatg tgcgttttag    480
gatactcgaa aaccagccat ctgtatagtc atatttactg tttggaaggc tggtatgaag    540
aggtcatgat aattcaacga ctcttaacag gggtgatgtg ttggaatttg tataagggga    600

<210> SEQ ID NO 30
<211> LENGTH: 600
<212> TYPE: DNA
<213> ORGANISM: Issatchenkia orientalis

<400> SEQUENCE: 30
```

```
agccctgggt ttttttttcg accttctaag cagtagaata atttcttggt gtagttcttg    60
acaaattact cattgcattg ctttctattg cattttcat gttgagagtc ctgcaacggc    120
agtttatatg aaaaaaaga aaaaaaaga aaaaacgaa aaaagaaag aacaaggtag    180 cacggtagca cggtagcatg gtagcacaac aatggtgaga aatctttgtt ttttaagagt    240
tttcagccgt ttgcaatcgc caattggaag agacaagcgg tagcacgcat gttgcccagt    300
gaaattccag cttggcccca gaaacgcgga tctcccccc ccggtcgttc cgagtgtttt    360
caagaaaccc gagtgggccc atatttttta cacacttcct tccctttcca cccgttgcaa    420
agcccgcgca aaggccgtcg tatatgataa gtatttaaaa ggcacctcgt atccaaacga    480
tggagggcat ggttaggagg ttctccttg aaggatttcc tgtcagttca aatagtgtta    540
caagtacaag tacaagtaca agtcataga agtgaaatat agccgaatac aaaaacaaga    600
```

<210> SEQ ID NO 31
<211> LENGTH: 600
<212> TYPE: DNA
<213> ORGANISM: Issatchenkia orientalis

<400> SEQUENCE: 31

```
actgtgatcc ttgatgcttt actgtgatct ctgatactct ctgatactct ttgatactct    60
tttccatgca tgtttcgctt tgccctcagc tactgcttca cctcccctcc cctctccccc    120
ttctttctcc cgtttctgcg ttcaacttct ttatagaccc actaaccccc aacactgtat    180
ttaacacatc cccattgacc ttcattgacc ctcccccacc agcgtatttc tcttttctct    240
ccccattctc tctgctcttc tcggctcgtt gtcgctcgcg gtcatttttt ttcgcccttc    300
ttttcccgca tttcccgtag ctggtgtagt ccgaaactgt gctgatcttc ttcctcatat    360
gggaccatct gggtagagct cctctattta ttatccgacc ctattccacc ttccttgctt    420
ggttgacaat ttaagatgaa gttcctccca tttcttttgt actccttttc tcctctcttg    480
tacttttgtc tactttttctt gtttcttccc tctgtaagcc atccaaagaa cagaacccat    540
ctttctcgtg ctgcttaaac taaaccgaac ccacacgcaa tcttaaaaga accataaaac    600
```

<210> SEQ ID NO 32
<211> LENGTH: 600
<212> TYPE: DNA
<213> ORGANISM: Issatchenkia orientalis

<400> SEQUENCE: 32

```
caacggtgta atcagagaga aaattgctct tgcacagcaa cagcagcaac agcagcagca    60
gcaagcccaa caagagaaag ctggaaccca acaggacgca taactatact ccagccacaa    120
gtttctgtag cttctacttt ggtatatcat tagtaaacaa taacaataac tcaccaataa    180
ccattataac ggcaaatcat tttcacgtgc cggcgcattc gccgtgagcc cacgcatata    240
ctcggcaaaa acaccgaaac agcagcaact gggctgtccc aaaggggaaa tttctgccgt    300
ggaccccggg gccatatcgg caaactcgcc gagacgcttg tagtttattg gtcaattgga    360
caaagttgcc aattttaggt gaaaggagga gtaaattatg gacagggtgg cctgttgtca    420
ttggaaagtc ggcaaataga gtcaatttag aatattttag aaggattgga gacaccaaag    480
aggtggccat tggaggtagc ataaaaggag gaccattcc tgccaagtgg agaggtactg    540
taaagccatg ttttaacttt tcatctcatc aaagcagagc aaactaaaaaa aacgaatata    600
```

<210> SEQ ID NO 33

<211> LENGTH: 600
<212> TYPE: DNA
<213> ORGANISM: Issatchenkia orientalis

<400> SEQUENCE: 33

```
tatgtgtata actggacgaa ccataaaagg gcaaatgctg tttggaaaca gcctgcaaag    60
caaaaatttt acacttataa atgctcactc ttgattaaaa aaactagata ataaagcgtt   120
ttgtttacat attaatttat ttttcttatt cttcccacta aagctagcac atgtgagtaa   180
aaaataaatt ttaaaagta ttttcacaga atgagaatac ttttgatat ttaacaccaa    240
aagttacata gcactgattt ccgatatagt gtaacggcta tcacggtccg ctttcaccgg   300
gcagacccgg gttcgactcc cggtatcgga atattttttt acttttcctc ttgattgttg   360
tcacgtgtta tacactaggg ctagtagtaa ccctaattac tgtcttcgga acttgcgcgt   420
tttttttgttc tccttggtct ggcatcaatc ccctctctgt agctgaatat ttttccatgt  480
atttttagata agtgtaaatt attaagacga taaattttc tgtttacttt cacttctttc   540
ctttcatttg gcactcaaaa gttaggtaag aagaagcat tttttgcaga cgatcctaag   600
```

<210> SEQ ID NO 34
<211> LENGTH: 600
<212> TYPE: DNA
<213> ORGANISM: Issatchenkia orientalis

<400> SEQUENCE: 34

```
cataattcca tttactgaag cacgagtttt tcatcttgaa gactctcgta gacagacctg    60
accaacgttc cgtcagctgg aatccctagt aaggtatcct tatctgtagc tgtcttcagt   120
aacaaatcga agtgcttaca cattgaacga atcgaaaga ctcgggcaat taggagatgc    180
cgaaacccac accaccaggc agtgtggaca tgactggatg aatactacaa caaaccaacc   240
acaagttcag atgaccactg aaaaatccaa agacatgtaa caccagggta agcatcaatt   300
aaagttggtc tctctcaccc cacctctgca attcagtaac gttatccgga acctcaaagg   360
aaaaatcgag tgataatttt tcctttgttt cctccgcgtc ggataaaagc ttctccggac   420
tattagagag aaatcagtat ataagggaca tgttttcttc attggaagca gacgagttgc   480
tgttgggtgg gttctctttc tacattagac aagcaaatac tataagcaac aaatacatca   540
gtgtttttaat aaacaagaaa acagacggcg aaagtccatt caaaacaaat aaaccaaaca   600
```

<210> SEQ ID NO 35
<211> LENGTH: 331
<212> TYPE: DNA
<213> ORGANISM: Issatchenkia orientalis

<400> SEQUENCE: 35

```
aagtttgtcg agtttagaaa aaaacccttc aaaaatgaca aatttgccac tgccttcgga    60
gtttatgcgc caacgggaat aggaatttga ccttttttt ttacaccctc aatctatttt   120
attttatttt tcattttat ttggttattt accaactcca tccaatggtg gacgagaacg    180
tcagaggatt gacgtatttg ccaaccaaag cggttttgcc tctctacatt tcatttggtt   240
ctggcgctgt tgagcaacaa ctaagtcacac acaaagtcat acacgtactt gagtatacac   300
tcctcataca tacacgtaca cataaataac t                                  331
```

<210> SEQ ID NO 36
<211> LENGTH: 600
<212> TYPE: DNA
<213> ORGANISM: Issatchenkia orientalis

```
<400> SEQUENCE: 36
ctgtagtgga ggtgaggttg caattctgga agggaacag tccatggttc ccaaaatgct      60
agtattaatc atattttca tttgggtcga cactggttta gaaatccatt taccgaaacc     120
cttaaccaaa gaacgtatgt acaacatgag acagacaaca aaaatagatg atattcattt    180
acttagggga ggaaactggt gattaaggga gacgacgatt atttcaagtt taactcttga    240
aataatccca aggtaataat taacttgact aaagtgttat taagaagtta caatagccaa    300
ataattgttt caaacgaata atggtgctag ggtgatttca tatcaagtgt ttagttttat    360
tttacttgcc gtaaatattg tggctatttg caaaaaggg acaattagta atcaattcag     420
cagaaaaaat aattgaagag tttttttttt aataaccact ttttaccaac ctgtctccat    480
taggatataa gaaggaagtc ttctccatag tttttgatta ttaatctatt ttgcctttcc    540
attacttaac tggttactaa caacatcaac tattcttta tctctataga ttaatacaag     600

<210> SEQ ID NO 37
<211> LENGTH: 600
<212> TYPE: DNA
<213> ORGANISM: Issatchenkia orientalis

<400> SEQUENCE: 37
tttgaaacat catgaaaact gtttcaccct ctgtgaagca taaacactag aaagccaatg     60
aagagctcta caagcctcat atgggttcaa tgggtctgca atgaccgcat acgggcttgg    120
acaattacct tctattgaat ttctgagaag agatacatct gaccagcaat gtaagcagac    180
aatcccaatt ctgtaaacaa cctctttgtc cataattccc catcagaaga gtgaaaaatg    240
ccctcaaaat gcatgcgcca cacccacctc tcaactgcac tgcgccacat ctgagggtcc    300
tttcaggggt cgactacccc ggacacctcg cagaggagcg acgtcacgta cttttaaaat    360
ggcagagacg cgcagtttct tgaagaaagg ataaaaatga atggtgcgg aaatgcgaaa     420 atgatgaaaa attttcttgg tggcgaggaa attgagtgca ataattggca cgaggttgtt    480
gccacccgag tgtgagtata tatcctagtt tctgcacttt tcttcttctt ttctttacgt    540
tttcttttca actttttttt acttttttcct tcaacagaca atctaacttt atatatcaca    600

<210> SEQ ID NO 38
<211> LENGTH: 582
<212> TYPE: DNA
<213> ORGANISM: Issatchenkia orientalis

<400> SEQUENCE: 38
tgtctatcca aaaataccac aaggcaatac ccaagaacaa cagatactcc aataatcaag     60
gaaatagtat actttccagt tataaactac tgataagaat tcacaatttc caggaaatta    120
atcgacacca gccattgaga tagcgactct tgccaatttt gaatatcaaa acaatagacc    180
attatggagg gggggggctc tatacgtcct attccattct cataccttc gcattataaa     240 agaaattcaa ttgatgtgta tagacttact aaaccataaa cagaaacaag catttgatag    300
agaacttgtt tggagttggg gcaatttgga agaacacctt caaacctgat cttcaatagc    360
cactttgttc agatatccga tagatcacgc tatagaatgg gaaatcagtc attgttacat    420
ttctcgctct tataaataga caaggttgtt catcaaatct ggaaatgctg tctacaccaa    480
cagacagcaa gacctatacc tatttattag ttgatctcta cacaaacaac tcaacgaggt    540
ttagcaacat ccaaggagag agagaaaaaa aatagtacca ag                       582
```

<210> SEQ ID NO 39
<211> LENGTH: 600
<212> TYPE: DNA
<213> ORGANISM: Issatchenkia orientalis

<400> SEQUENCE: 39

```
ggccgagtcc tcttgcacgg agtgtgtccg aaaagggcag ctctgcagtg ggggagagga      60
ggtcgcacgt ctatgcggtg ttggcatggc ctgtgcgtgt acctgtcccc tccctgggca     120
tcccccactg cgcgccttct ccattgggcg ctgcgggcac tccgcgccgt taatacagga     180
ggggggggga aagcttaaga ttagagcggg tacagtcagt gggtgtattg accccatttc     240
tgtcagtata accccccgt tgagccgccg gtttggttgt ttatggataa aattttttt       300 tccccgcatg gagaagattg aggggagaa ggaatgggaa aaaggccaga gccatctcca      360
cagcggaatc cgaccgttaa tggggtgaaa caccccacc aggtagagca ggaagaatgg      420
ggaaacaagg tggagagatg gtcattgttg ggaatagtgg gaaatgagg gggaagagaa      480 tgactataaa atgggaaggg ggtccaagtt atccaagcag tccagttaga aagggaaaa     540 taaagctata gatagaaacc aaccaaacaa ccaaacaatt aaacaaacaa ttaaacgaac    600
```

<210> SEQ ID NO 40
<211> LENGTH: 600
<212> TYPE: DNA
<213> ORGANISM: Issatchenkia orientalis

<400> SEQUENCE: 40

```
ggttgtgctt gatgcaagaa tccgtgcgta tgaaaagaat aacaaaaact tgctggataa      60
aatgaataat agaagactca acaacagtga acttgagaat cagttcaaga gaatcattgc    120
gctctgcatc aatactgatc ctgaaaatat tgatgataaa ctactttcaa gtttgcttat    180
gtctgtagaa aacgatcctg atccagaaat cgggcaaatc agaaaagtcc ttaaaatagt    240
gggtgatcta gatggggaac ctaaacaaga tcaacacatc tcaaaccctg catctgtttc    300
tgcttcctcc catacaccac tagcctctgc atccgtcgcc acaggttctt cttcggcatc    360
caaatccgct tctatagcta agtaacccct gatgttctat ttttgtatac ttgaaaataa    420
caaccgtgtc tgaatttacc ggagcgggct atgcacataa atttgattag gtacaatgag    480
ggcgaatatc ttcgcaaagg ttcttatcac gcagccactc tcatttttcc ccgctatcaa    540
tacattcttt tcttgtccta ttcctctgtc cccgtgatcc tacaacacaa ctaaacaaaa    600
```

<210> SEQ ID NO 41
<211> LENGTH: 364
<212> TYPE: DNA
<213> ORGANISM: Issatchenkia orientalis

<400> SEQUENCE: 41

```
acacctttaa aagagttgca tcatccaagt gttgtaagat gcttgtccag ctactgtagt      60
taatcagctc aagtttcaga acagtttcag agcctatctt catgacatca ctcatctgtg    120
cttaacctta caaacatcgg caatcggaga ttgatcatga gcacattatt tgagctgttg    180
ctttattagg catcatattc ccgataaatc caatcgggct tgaatgatg actatactat     240 cgagccatac cttcttaaat caactatata taactggtaa tacttctgtc tgatagctat    300
caatatctga gtggggtttt taacttcctt ttcccttcca catccgcaat caagaacaga    360
taaa                                                                 364
```

```
<210> SEQ ID NO 42
<211> LENGTH: 240
<212> TYPE: DNA
<213> ORGANISM: Issatchenkia orientalis

<400> SEQUENCE: 42
gcactagatg gtccattttg taacgcatgt gtaaaccgat agaggacaac ttttcgaccg      60
ataagagaga cgtttaaaaa aaaaatgaga ctggggaatt ctgaagggtg gggtgtctaa    120
gtttaaattc taggtgtaaa ctgaacagtg taaagtcttc tactataatt gtatagcttt    180
cagctcgaag gtgaagacag tgtggtgtgc tctgtacttt gttgatggga atcgggtata    240

<210> SEQ ID NO 43
<211> LENGTH: 600
<212> TYPE: DNA
<213> ORGANISM: Issatchenkia orientalis

<400> SEQUENCE: 43
tatgtgtata actggacgaa ccataaaagg gcaaatgctg tttggaaaca gcctgcaaag     60
caaaaaattt acacttataa atgctcactc ttgattaaaa aaactagata ataaagcgtt    120
ttgtttacat attaatttat ttttcttatt cttcccacta aagctagcac atgtgagtaa    180
aaataaaatt ttaaaaagta ttttcacaga atgagaatac ttttttgatat ttaacaccaa    240 aagttacata gcactgattt ccgatatagt gtaacggcta tcacggtccg ctttcaccgg    300
gcagacccgg gttcgactcc cggtatcgga atatttttt acttttcctc ttgattgttg    360
tcacgtgtta tacactaggg ctagtagtaa ccctaattac tgtcttcgga acttgcgcgt    420
ttttttgttc tccttggtct ggcatcaatc ccctctctgt agctgaatat ttttccatgt    480
attttagata agtgtaaatt attaagacga taaattttc tgtttacttt cacttctttc    540
ctttcatttg gcactcaaaa gttaggtaag aaagaagcat ttttttgcaga cgatcctaag   600

<210> SEQ ID NO 44
<211> LENGTH: 600
<212> TYPE: DNA
<213> ORGANISM: Issatchenkia orientalis

<400> SEQUENCE: 44
caataaggat ttatgtccag gaggagaaaa aagaattagc aaacgtgtct gatttaccaa     60
ttatagcagg ggaaacaaca aataacgaag aataaagctt taataagaac ttataactat    120
gcaattaaga gaagcactgg gaaagaactg cccttttct aatttggaaa ggaaaataag    180
gggaggaaaa gcaagcgtgg aagcaccagt atttgatctc ttcatcgagc aagtaaccct    240
ttgcaagatt tgaggaaatg gagaactcaa gtgtttaatt aaggcgtcaa tttcttccga    300
aagaagcaat cctcctaat taggaaatga cgcgaaagac gtcttgcaaa ggaaggcgta    360
cggtggagga gttttggaag aggaaggtgt gcagtggggg atcgttcggc attattaatc    420
acatcatttc cacggaaaaa atcactcatc acggctcagc tgtaaccgaa agttgatttg    480
taagcaaggg accctagag aagactataa atagtcagga cacccctat ttcagggttc    540 ttgtactttt tagttagggt gaccattacg atacatagac aacaagatat acagcaagaa    600

<210> SEQ ID NO 45
<211> LENGTH: 600
<212> TYPE: DNA
<213> ORGANISM: Issatchenkia orientalis

<400> SEQUENCE: 45
```

```
ttgatagttc cagttgttcc tgtctttact caaactaact tgacaattaa gatctcaaga    60
gcagcttctt cagctatgta aatattaccc acttttacat accaatatcg tcttctcctc   120
cctttaataa aagggagaag tctaaagtgc aaagtaacgt gttccctagc atatgccact   180
cgcaagtttg taaacctaaa ctacctgaaa gtctattaag ctgaaattga aaaagcagaa   240
agaaacagag ttttattgtc cgctctttac cacccaccct tatgctttgt tgtaacaatt   300
tcaaaaatag cttcttttt tttgcgaaaa aaatacgggg aacctgtcta tttcggctat   360
ttcatcattg tgtgattttt agtcaaacgg aaaccactta taggaggtga gttttctatt   420
tcatggagaa actagattgt atttaaattc cttgctctct ctctccctaa attccacttt   480
tctccgaatc agcacattct tgatttcct ttttactttt ttcttattc ttttaccatc   540 cttagtcata gtatcccaaa ttacttaaac ttaacttgaa tttagaaaat tattcaaaag   600
```

<210> SEQ ID NO 46
<211> LENGTH: 600
<212> TYPE: DNA
<213> ORGANISM: Issatchenkia orientalis

<400> SEQUENCE: 46

```
aatatgttct gagcggaaac ccccgtgttt ttattatttt ccagtaggaa cgccgtgtct    60
ccccacaagt ttgacagcat gctgtttcta attgaacctg tgtttactaa tggctgcagc   120
aagataatga tgtatgtcca acaagagatg tgcctttaat ggatggttgc ttgatgtcca   180
tgagggcaat ttgtttccct gggttccccc gtcaggaggt ttaccacaag ggcaagactc   240
cagaacttga ccaattgcag gtacaatgca attttttttc cgctctcgcc gttcagacat   300
gctcccattt tgctgactc ggactaagta tgtgtgaggc cgcatttcc tgttttttcca   360 acattgggtg attttgtata gtcgaacaca agggttttc cattgcatat attaatccca   420
tagctggaaa gacgggtatt taaacctcct agtttccacc ctggatatct ctcaacagac   480
ctaagttcaa ccttttttt tccaaatttc ctcttcaacc acaaacaaat atacactcac   540
atattctaat actatttgtt taaaaacaaa agaaagtaca aaaaaaaatt cacacaaaag   600
```

<210> SEQ ID NO 47
<211> LENGTH: 504
<212> TYPE: DNA
<213> ORGANISM: Issatchenkia orientalis

<400> SEQUENCE: 47

```
tggttgcagt agaaaagctc tttcaagagg tataaactaa tgatctctca atagtgaaac    60
gccaccagaa aatgtgctca gctggtttga gttatgtcac ttgcggtgac caactactat   120
ttctctcact tggaacgagg cgcgtctgca aaacatgtcg tgtcgcagca ggctattagt   180
tgtagcacaa acacaactgc cgtctaagtc gcgccacaac agaggagaat gatgcaccga   240
gtacggattt ccccttacgg atgagtttac ttccggccaa tcgtgtgcga gaaaattgca   300
attttgtcgg cgcgggcttt ttttcgtatg tgtttggggg atttatagtt gtcagcggac   360
ccactttgga gaggaaccac ttgggagacc tgtttatcca attctttctt ctgaataacct   420 gtttgtctct ttccttgatt tcccctttct tcctattttc tttgatttc ctatagacta   480 acaatcaaat agaatattct aaca                                           504
```

<210> SEQ ID NO 48
<211> LENGTH: 600
<212> TYPE: DNA
<213> ORGANISM: Issatchenkia orientalis

```
<400> SEQUENCE: 48
atgtaggagc agtgcctgag agaggtgtca aggtaaacgt tatcggtagg agcatggctg     60
gagtggaaac gcgaggaacg ccttctggct agtccctccc tattttccct ctccccccc    120 cgcattaaga atcgagatat tagctcctca ggatgtatcg gaagaagcga ggcatacatt   180
tgtgtggagg ctcgggatcc gaatatggct attctgttca gtgaaaaggg ggggaggga    240 agatttgcct attcttgtta aacccgcac cagtggcggt gagtttccgt tctcccgttg     300
gaaaaaaaaa agaaaagtgg tgtgccggat taacttggtg gtccgggtaa acttgcgcgt   360
ttctttttcc aagactgtac tggagttttt ccatttgctt gcagatgcgg aaaaatggtg   420
tggacatgct tctccttctt gttgaaaaat gtatttaagt ccccacaaat cccccaactt   480
tctccacttt tttcacctttc tgtcttagct tctcttttga ttttaattttt tatcttcttt 540 cagcatccaa acactttaaa aaaatcactt ataatatata tagcatagca cattcaagag   600

<210> SEQ ID NO 49
<211> LENGTH: 225
<212> TYPE: DNA
<213> ORGANISM: Issatchenkia orientalis

<400> SEQUENCE: 49
gcgggacagg tacatacacc tgtagaggag gctaacggtg actttagatg tggaagttta    60
atgtctctat ggcgtctacg tgaatatttc caacgaggag cagtatacta taaaaggaca   120
agtgtttctc ccactgtttg taatgtgttg gtggtagttt tatcccccat atattttcta   180
caagacaaga caacccaata ccttatacat tcacaacata taaca                   225

<210> SEQ ID NO 50
<211> LENGTH: 460
<212> TYPE: DNA
<213> ORGANISM: Issatchenkia orientalis

<400> SEQUENCE: 50
ctagacaggg aggatgagac cacggaaaaa agagccgaca ggtctctgga tgccgctgaa    60
aatcatacct cgcatgaaca ctttagctac gaaaacggta atggcttaac aaaggactca   120
tcccttccct ctagatgggc ttgaaggcgt agtacattat ataagcctgt gtagacaaac   180
aaatacttct atgaggttac aacccgagtt ccgactactc aattaggaaa ctatttctgt   240
aacgttgatt catgtagctg tctgtcagcg cgcatgccta attgggaaaa acaccataat   300
tctcaatttt cattggccag ccctttaatg tgggtcgttt ttcatacaat ttcgcctttc   360
gcttagcatt aaaaaactaa acttctactc actggacgtg gtgtgtattt tgtttctgac   420
aaggtagagg tgtcgacaaa caagaaggta tgtataaagg                         460

<210> SEQ ID NO 51
<211> LENGTH: 600
<212> TYPE: DNA
<213> ORGANISM: Issatchenkia orientalis

<400> SEQUENCE: 51
tgataaactt tggtttcttt caaaacgtta ggcagttctt ttgctaaaac ctttccaagt    60
gatgttggaa ctatagaatt tattaatgta gccaaagata tcagtcgtaa agcccattgc   120
ctcataaaat ttgataaaata tatagacggt aatgacaaca gcaaagaacc tatacatgta   180
cgtttgacag ctcctggaaa atacatgtga tcaaatgaat ccagactgtc tatccccagg   240
```

```
tttataaagt catgaatggc ttgaacatta aatgattcct ctactttggt gtatggagca      300
accaataaca tatacgttat tgatgtaaac aatgtcagat ccaacaaatg ctgtagtgtg      360
cttgttgtca tcaatccttg gataacgaga tatagagaaa gattaaccat acgttgaaac      420
gaagaaggac gtaaagagaa gaacgtaagg agtacacgct atactcgtgc cctcacattt      480
ttctagtcca actaaatttt atattttgtt tgatctttttt cattgacctt ttagctagtc     540
ttgccttctc ctttgcttct tttttgtgag tataggagca caccaaaaga acagtaagtg      600
```

<210> SEQ ID NO 52
<211> LENGTH: 600
<212> TYPE: DNA
<213> ORGANISM: Issatchenkia orientalis

<400> SEQUENCE: 52

```
aagggtacgt atagttataa gagtggatat agtaatatgg ccttagtaat atggccttag       60
tagtgttggc catggtgtaa attatggtat taacattagt acaagtggtg gcgagaacaa      120
cagcaatagc aggggtatta cgacgtgggt tgacaaagca atgcctaaag cggaaagagg      180
caagtttgag aggaaaaaag agagtcctat taatttatac cattattaac aaaacgcctt      240
cgacggcatc gacgcgtcgc tgacgcatat tgtgcgcggg ccacgtgtca gcgacgcgtc      300
gacgacgggt ttaattccat ttaagattta atttattcaa gctataggag aacaaaagaa      360
gcttattaaa cacaagaaag gggagcgatt tccccccatt ttatgtcttc tccctctcga      420
ctccaatttc tgacaaatac agaaaatcta atctcactta tgcagcgtga ggttttaaat      480
atgtaatgga agatttgaag cgtcaagtgt ccacagtgag aatttcgggt ttccatataa      540
agtcgccacc ccccgcccat taattgtaga aattagctga acttaaccaa tgcagtatta      600
```

<210> SEQ ID NO 53
<211> LENGTH: 600
<212> TYPE: DNA
<213> ORGANISM: Issatchenkia orientalis

<400> SEQUENCE: 53

```
cgtcaaagga actcaacact gtcaacggta tcactaatgg gaagtttaat aatatctact       60
tttatttcct ttaaattttt tttgtttcat cttttaatta acaacagga cttttaataa      120 caaacactta cagcaactgc ttctacaaac aaatcattta cactactact acgttttggg      180
aaccaagaga attatcatat actccagaaa tgtctgctta aatcatttgt ttgatcaaga      240
attatattca taaatatta taaattaagt tatcgtttgt tcctacccac gatttttttc      300
taaacatttg ttcactatcg aattagaaaa atactcact ttaaaagtct atttttatc       360 aaccccttat taaaaaaagt ccttcaatat gtccccgtaa attaaatact attaagaaac      420
cgaccattat ggcgttccac ttttacccccc ctcctttaac ttattaattc aagaaaaaaa      480
aattaattgt cacatattaa agtctatctc tactatcact attatccacc ctttattaca      540
atctcattag aaattattac aacagtcact gcaactaata aattaaccaa attgtctgaa      600
```

<210> SEQ ID NO 54
<211> LENGTH: 500
<212> TYPE: DNA
<213> ORGANISM: Artificial Sequence
<220> FEATURE:
<223> OTHER INFORMATION: PFK1t terminator

<400> SEQUENCE: 54

```
tattcgagaa ggtttctact gacgtcttgg ataattcttc tttgaccttc tatattctat       60
```

```
cttaatttttt cccttgttat ttatttgttg tctctttctt cttttactgt ccttttcttt     120
ctttgctgtc cttttgtttc ttttttttc cttccctctc aaaaaaggaa actgggccta      180 ttttttttt tttctgacgt atgttaagat gcaatgttat aatgaaattt aaattattat      240
ttatgttaat gaaaaaaaaa acagcaaaaa cgtgtgacta tttctgcctg catgttatta    300
tgttattgta aagtaaaata gtaccttcga tgggaaatca aaccagtttt caatccgttt     360
tcaccgaaag agctcgaatt gtgcgtaatt ttgtggtctg tacggcgatt atttgcaaat    420
cgggaatggt gtgcgaaaac taacaaaatt aatgtatgct ctaaatatgt cccatcagct    480
ggaaggagaa caatagacgg                                                500

<210> SEQ ID NO 55
<211> LENGTH: 421
<212> TYPE: DNA
<213> ORGANISM: Artificial Sequence
<220> FEATURE:
<223> OTHER INFORMATION: MDH1t terminator

<400> SEQUENCE: 55
aggtgaaaca caacaacctc cttttttagc ttgaaagaga caaattctaa acaaaaaaac     60
cgaataaaaa cactgaacaa aactggaaaa aaaaaacatt agacaaagct gcgctgaatt    120
ggctctaata cattatgctc tatcttatat atagtacata tggacacgtt ttccatttca    180 cccttacat ataagtaaag agaggataac accataaaac ttacaccta ttcaatctta     240 cgattatttt atatttattt agctatttat tgataactta aatatctaac tacatattta    300
tctattcatt tatttcttga ttcatttatt gaagcattta caaaatcact tatacattct    360
tttggctcaa aaaggtaagc tactttagat gctcctctga acaactttat aaccctgtac    420
g                                                                    421

<210> SEQ ID NO 56
<211> LENGTH: 293
<212> TYPE: DNA
<213> ORGANISM: Artificial Sequence
<220> FEATURE:
<223> OTHER INFORMATION: PDC1t terminator

<400> SEQUENCE: 56
tgacatctga atgtaaaatg aacattaaaa tgaattacta aactttacgt ctactttaca     60
atctataaac tttgtttaat catataacga aatacactaa tacacaatcc tgtacgtatg    120
taatactttt atccatcaag gattgagaaa aaaagtaat gattccctgg gccattaaaa     180
cttagacccc caagcttgga taggtcactc tctatttcg tttctccctt ccctgataga     240
agggtgatat gtaattaaga ataatatata attttataat aaaagttta aac            293

<210> SEQ ID NO 57
<211> LENGTH: 300
<212> TYPE: DNA
<213> ORGANISM: Artificial Sequence
<220> FEATURE:
<223> OTHER INFORMATION: 853t terminator

<400> SEQUENCE: 57
atacttaaat gattagacga ataaactact ctatataacg ttttataatg ttaatgttca     60
tgctttgata gtctctcccg gagaatgtac tctgcgcttc atagttctct tgattttgct    120
ccgtataagg tgcacaggtt tagaccttt tttttttcag aggtacttgc atgaaaacct    180
```

```
agagtgaata tttcttgtag tggatctgtc acaatctaaa tccccctcgta gtactcctca    240 aacaacagca ggagctctcc gaaggattaa taatttgtcg tatccatttt ggtcatctac    300
```

<210> SEQ ID NO 58
<211> LENGTH: 225
<212> TYPE: DNA
<213> ORGANISM: Artificial Sequence
<220> FEATURE:
<223> OTHER INFORMATION: 3540t terminator

<400> SEQUENCE: 58

```
gcgggacagg tacatacacc tgtagaggag gctaacggtg actttagatg tggaagttta     60
atgtctctat ggcgtctacg tgaatatttc caacgaggag cagtatacta taaaaggaca    120
agtgtttctc ccactgtttg taatgtgttg gtggtagttt tatcccccat atattttcta    180
caagacaaga caacccaata ccttatacat tcacaacata taaca                    225
```

<210> SEQ ID NO 59
<211> LENGTH: 300
<212> TYPE: DNA
<213> ORGANISM: Artificial Sequence
<220> FEATURE:
<223> OTHER INFORMATION: 3376t terminator

<400> SEQUENCE: 59

```
ctacaacaag atgtttgttc aaggggagca acttgtccct cgttaaataa tttgtaagaa     60
aaaacttctt ccttttatct ctttcttttt ttctttttaa aaaactatct agtaaggaaa    120
tatacacaat ttactttgta cgctgtctct ctttctcttt ctctctctat gtctatctct    180
ccctatcgct ctgtatgtat gtacattacc gtcttcccca aatggctcaa cccgactgcg    240
agaagacttc aaaacactca attatggtct ttagattttc cagtacgttg ttgacagata    300
```

<210> SEQ ID NO 60
<211> LENGTH: 300
<212> TYPE: DNA
<213> ORGANISM: Artificial Sequence
<220> FEATURE:
<223> OTHER INFORMATION: 5025t terminator

<400> SEQUENCE: 60

```
gtggattagg ttactgctct ttcttttggt aatttataat ttaaacaagt ttatttaatt     60
tgaaactctt atttacttag attagatttt aaacttacat acttttaata actctgggat    120
atcctattta atataactaa tagctaaatt gttcttttttc agttgaatct tttggcgatt    180
ctctctctcc ctttcctgtt ctttaccatc tttaccgtaa agtattggaa taaagtaatg    240
tttgcaatta gggaggtcca taaaaatatc gacccgtcgc ttttcctttt attcttaccc    300
```

<210> SEQ ID NO 61
<211> LENGTH: 272
<212> TYPE: DNA
<213> ORGANISM: Artificial Sequence
<220> FEATURE:
<223> OTHER INFORMATION: 527t terminator

<400> SEQUENCE: 61

```
atgtctaacg tctagcatgt ggcgtctaac gtctagtctg ttatagttga atgattattt     60
acttgtatac tttagcttaa agtaatgatg aaatgttttt ttttgtcttg tccttttttgg    120 ccgtgacttt ccagtttcaa cggttttaga gtttccaatc aagatgttca tgaggtggtg    180
aacactgtgt tggtgactcc ggggtgtaaa agaaagttct tttggagggg aattgcttat    240
```
gtctgtgatt cccaatcact cattatacta ta                                        272

<210> SEQ ID NO 62
<211> LENGTH: 300
<212> TYPE: DNA
<213> ORGANISM: Artificial Sequence
<220> FEATURE:
<223> OTHER INFORMATION: 2204t (Tef1at) terminator

<400> SEQUENCE: 62
gtatagccat atagtttaat tcctttatac tttttataac tatttcttac actaattatt          60
attatcaatt atttattgta gaatttgact cttgcgtcga tcaccatgac agggctatct         120
taacaagggg taattttgt tgatggagtc aagtagcatt ccgacgggaa gtgtcgatgc          180
ctctgaacga aatcttccga ttagctctgc aaagaagtgg aaattgtcag cgcattatta        240
taattgcaag ttggagagat agcgattaag cttttgactt ctactcatat acaaactttt        300

<210> SEQ ID NO 63
<211> LENGTH: 150
<212> TYPE: DNA
<213> ORGANISM: Artificial Sequence
<220> FEATURE:
<223> OTHER INFORMATION: s2204t terminator

<400> SEQUENCE: 63
gtatagccat atagtttaat tcctttatac tttttataac tatttcttac actaattatt          60
attatcaatt atttattgta gaatttgact cttgcgtcga tcaccatgac agggctatct         120
taacaagggg taattttgt tgatggagtc                                            150

<210> SEQ ID NO 64
<211> LENGTH: 182
<212> TYPE: DNA
<213> ORGANISM: Artificial Sequence
<220> FEATURE:
<223> OTHER INFORMATION: 1414t terminator

<400> SEQUENCE: 64
aataaatgaa actttactaa actaatgacc aatctatata tcctttatga atttaatttt          60
atgtaatgac tagaacaata ttatttttt gtgtacgaat gattaactag aatttgcaat         120
agatacgact tcaaaattga acaatacgat ttatcgctta gctatgcttt tattgagaaa        180
tc                                                                         182

<210> SEQ ID NO 65
<211> LENGTH: 300
<212> TYPE: DNA
<213> ORGANISM: Artificial Sequence
<220> FEATURE:
<223> OTHER INFORMATION: 4288t terminator

<400> SEQUENCE: 65
atcactttct gtcaattgtc ttaattattt taatatggta tttttatttg aaatactaaa          60
gcacattttc ctttccacat ttaatttctt aatgaacttt atttctttat gatttctaga         120
tctatacttc tatttgtcaa ctaactagat taattttaac acttacatt cttttttaaa          180 actatgaatc ataacatgct tgatagctct tatttgtttt ttttacaga tcaaaaaaca         240 cctttttgtag aagtaattgg tctggtttgt atgtgacatt aatactattt tctttggaag        300

<210> SEQ ID NO 66

```
<211> LENGTH: 136
<212> TYPE: DNA
<213> ORGANISM: Artificial Sequence
<220> FEATURE:
<223> OTHER INFORMATION: 3767t terminator

<400> SEQUENCE: 66
attctgaggc gaactataga atgaataacg aatggtatac tgtggctatc ttccaccttc      60
cctctatttt ttttttggaa aaacatctaa agaatcccat ttttatactg tgtagttaat     120
tgaattctta agtttc                                                     136

<210> SEQ ID NO 67
<211> LENGTH: 143
<212> TYPE: DNA
<213> ORGANISM: Artificial Sequence
<220> FEATURE:
<223> OTHER INFORMATION: 5125t terminator

<400> SEQUENCE: 67
taattcaaag tgtccctcat tcttcttaat gtctaacgtc tatacttttg tactgtacaa      60
tgaaaaataa atgattatcc atccgtccat tatttactg tttttttata tatagatcta     120
tatgttacac tgcacagaaa cat                                             143

<210> SEQ ID NO 68
<211> LENGTH: 80
<212> TYPE: DNA
<213> ORGANISM: Artificial Sequence
<220> FEATURE:
<223> OTHER INFORMATION: 73t terminator

<400> SEQUENCE: 68
atgtcctatt cctattttc tttctataca tgcttcagat acttctccgt ttatcatatt      60
tatactagcg cttttcattc                                                  80

<210> SEQ ID NO 69
<211> LENGTH: 300
<212> TYPE: DNA
<213> ORGANISM: Artificial Sequence
<220> FEATURE:
<223> OTHER INFORMATION: 4282t terminator

<400> SEQUENCE: 69
aggtatagtc tcatctactg acaattacct gtgtatagta acatttaata tttaacgatt      60
aatactttat gaacagtgcc agaactatac taattaacga ttttctgatg agaattacaa     120
ggtatgactc atttggtgtt atattttata atggagtaag cagtacattt tcctccggta     180
aacggctgtc cttatttaat catacgctta aatatgaggg cataatatgg tgtctaatcc     240
catttctaga aatagtatgc tttccaatta ggctggactt tgttatcgaa ctgcggtcat     300

<210> SEQ ID NO 70
<211> LENGTH: 300
<212> TYPE: DNA
<213> ORGANISM: Artificial Sequence
<220> FEATURE:
<223> OTHER INFORMATION: 697t terminator

<400> SEQUENCE: 70
aggtatagtc tcatctactg acaattacct gtgtatagta acatttaata tttaacgatt      60
aatactttat gaacagtgcc agaactatac taattaacga ttttctgatg agaattacaa     120
ggtatgactc atttggtgtt atattttata atggagtaag cagtacattt tcctccggta     180
```

```
aacggctgtc cttatttaat catacgctta aatatgaggg cataatatgg tgtctaatcc    240
catttctaga aatagtatgc tttccaatta ggctggactt tgttatcgaa ctgcggtcat    300
```

<210> SEQ ID NO 71
<211> LENGTH: 300
<212> TYPE: DNA
<213> ORGANISM: Artificial Sequence
<220> FEATURE:
<223> OTHER INFORMATION: 4194t terminator

<400> SEQUENCE: 71

```
tttgaatcaa ctttccccct aaggtttaat acatgcccat gatttttaac gactttatt     60 ataaataacg actttatagc tttatgatta ctaaattatt actactacga caatattcag   120
ggtatgcata ataacattaa ttttaaaaca tgaggcattc cttgaattta tgcctttaca   180
agtatcaaca atagcttaaa aaagcttttt tcgcatcatg ccgagcctcc taaaattaga   240
taccgcgctg cccttaggga aaaaaaaacc ccaaaactcc tcttgttggg agggccgtca   300
```

<210> SEQ ID NO 72
<211> LENGTH: 300
<212> TYPE: DNA
<213> ORGANISM: Artificial Sequence
<220> FEATURE:
<223> OTHER INFORMATION: Random sequence terminator

<400> SEQUENCE: 72

```
aactgtttca ccctctgtga agcataaaca ctagaaagcc aatgaagagc tctacaagcc    60
tcatatgggt tcaatgggtc tgcaatgacc gcatacgggc ttggacaatt accttctatt   120
gaatttctga gaagagatac atctgaccag caatgtaagc agacaatccc aattctgtaa   180
acaacctctt tgtccataat tccccatcag aagagtgaaa aatgccctca aaatgcatgc   240
gccacaccca cctctcaact gcactgcgcc acatctgagg gtcctttcag gggtcgacta   300
```

<210> SEQ ID NO 73
<211> LENGTH: 374
<212> TYPE: DNA
<213> ORGANISM: Saccharomyces cerevisiae

<400> SEQUENCE: 73

```
gatcgccaac aaatactacc ttttatcttg ctcttcctgc tctcaggtat taatgccgaa    60
ttgtttcatc ttgtctgtgt agaagaccac acacgaaaat cctgtgattt tacattttac   120
ttatcgttaa tcgaatgtat atctatttaa tctgcttttc ttgtctaata aatatatatg   180
taaagtacgc tttttgttga aattttttaa acctttgttt attttttttt cttcattccg   240
taactcttct accttcttta tttactttct aaaatccaaa tacaaaacat aaaaataaat   300
aaacacagag taaattccca aattattcca tcattaaaag atacgaggcg cgtgtaagtt   360
acaggcaagc gatc                                                    374
```

<210> SEQ ID NO 74
<211> LENGTH: 811
<212> TYPE: DNA
<213> ORGANISM: Artificial Sequence
<220> FEATURE:
<223> OTHER INFORMATION: centromere-like sequence (CEN-L)
      CEN-0.8kb-2(CEN-L)

<400> SEQUENCE: 74

```
tctagctatt ttgtttaggt tgggtaaaaa cctacggaaa gacaattgga gcttaggcta    60
```

```
tctattgata gatcaattat ttgttttaag aactatagaa ttaaaaacaa ggcagtagtt    120
gtagatttta aagattattt agagtagata gtaaaggctg tactgaatat caatgaggat    180
ttgcagaacc aacaagtggc ctgcatcaag ctatttaagt gattctattg gtattttact    240
agaaaaggaa ggctaatcat ttttccaatg acggttcata taatccaagt tttaaatggt    300
ttgcatcatc ataatagggg tatctaaaag gcataaatcg acgaaagtga taaaaattac    360
ttattaaacg acgtatttac atccacgttt ttgctggaag tactgaatct gcctactgct    420
agtttgggga agacaataat acacaaaata aagacgatga tgaagattcc agttttttt    480 aaagataaaa aaatagatat atatgtataa ttgtatgaat agttttaata ataacttatg    540
ttgctatttt gatagcaatt cattttacta ttgaaaaggt tacccaggca ataatatgt    600 ttagcacatc agattctgta ctaataataa tatagagtta tgttataacg tcaggcaata    660
cttatgtgta tagcgaaata gtaaatggca gattgtaaac cgtatgtttt cactactcag    720
actcatacga tatgtctaga agcccaacca atgaattaga ggactgtttg atatcaacat    780
ccagtcactt tgagtgtaat aaaactatt a                                   811

<210> SEQ ID NO 75
<211> LENGTH: 156
<212> TYPE: DNA
<213> ORGANISM: Artificial Sequence
<220> FEATURE:
<223> OTHER INFORMATION: ade2-gblock

<400> SEQUENCE: 75
ctttggtctc ctgcagaatt cgcagttgca gactctgtta gcgttgaaag caccgagaca    60
gcattgcaaa atgaaatttg gtttcccatt tatgctgaag tccaaaactg aagcatatga    120
tgagacagca ttgcaaaatg tgtttggaga cctttc                             156

<210> SEQ ID NO 76
<211> LENGTH: 996
<212> TYPE: DNA
<213> ORGANISM: Artificial Sequence
<220> FEATURE:
<223> OTHER INFORMATION: IdhD

<400> SEQUENCE: 76
atgaagattt ttgcttacgg cattcgtgat gatgaaaagc catcacttga agaatggaaa    60
gcggctaacc cagagattga agtggactac acacaagagc tattgacacc tgaaacagtt    120
aagttggctg agggatcaga ttcagctgtt gtttaccaac aactggacta tacacgtgaa    180
acattgacag ctttagctaa cgttggtgtt actaacttgt cattgcgtaa cgttggtaca    240
gataacattg attttgatgc agcacgtgaa tttaacttta acatttcaaa tgttcctgtt    300
tattcaccaa atgctattgc agaacactca atgattcaat tatctcgttt gctacgtcgc    360
acgaaagcat tggatgccaa aattgctaag cacgacttgc gctgggcacc aacaattgga    420
cgtgaaatgc gtatgcaaac agttggtgtt attggtacag ccatattgg ccgtgttgct    480 attaacattt tgaaaggctt tggggcaaag gttattgctt atgataagta cccaaatgct    540
gaattgcaag cagaaggttt gtacgttgac acattgacg aattatatgc acaagctgat    600
gcaatttcat tgtatgttcc tggtgtgcct gaaaaccatc atctaatcaa tgcagaggct    660
attgctaaga tgaaggatgg cgtggttatc atgaatgctg cgcgtggtaa tttgatggac    720
attgatgcta ttattgatgg tttgaattct ggtaagattt cagacttcgg tatggacgtt    780
```

| | |
|---|---|
| tatgaaaatg aagttggctt gttcaatgaa gattggtctg gtaaagaatt cccagatgct | 840 |
| aagattgctg acttgatttc acgcgaaaat gtattggtta cgccacatac ggctttctat | 900 |
| acaactaaag ctgttctaga aatggttcac caatcatttg atgcagcagt tgctttcgcc | 960 |
| aaaggtgaga agccagctat tgctgttgaa tattaa | 996 |

```
<210> SEQ ID NO 77
<211> LENGTH: 969
<212> TYPE: DNA
<213> ORGANISM: Artificial Sequence
<220> FEATURE:
<223> OTHER INFORMATION: XR

<400> SEQUENCE: 77
```

| | |
|---|---|
| atggttcctg ctatcaagct caactccggc ttcgacatgc cccaggtcgg cttcggcctc | 60 |
| tggaaggtcg acggctccat cgcttccgat gtcgtctaca cgctatcaa ggcaggctac | 120 |
| cgcctcttcg atggtgcctg cgactacggc aacgaggttg agtgcggcca gggtgtagcc | 180 |
| cgcgccatca aggagggcat cgtcaagcgc gaggagctct tcatcgtctc caagctctgg | 240 |
| aacaccttcc acgacggcga ccgcgtcgag cccatcgtcc gcaagcagct tgccgactgg | 300 |
| ggtctcgagt acttcgatct ctacctgatc cacttccccg tcgccctcga gtacgtcgac | 360 |
| ccctcggtcc gctaccctcc cggctggcac tttgatggca agagcgagat ccgcccctca | 420 |
| aaggccacca tccaagagac ctggacggcc atggagtcgc tcgtcgagaa gggtctctcc | 480 |
| aagagcattg gcgtctccaa cttccaggcc cagctcctgt acgacctcct gcgctacgcc | 540 |
| aaggtccgcc ccgccactct ccagatcgag caccaccct acctcgtcca gcagaacctc | 600 |
| ctcaaccttg ccaaggctga gggcatcgcc gtgaccgcct actcctcctt cggccctgct | 660 |
| tctttccgcg agttcaacat ggagcacgcc cagaagctcc agcctctcct cgaggacccc | 720 |
| accatcaagg ctattggtga caagtacaac aaggatcctg cccaggtcct cctccgttgg | 780 |
| gccacccagc gcgggcctggc catcatcccc aagtctagcc gcgaggccac catgaagtcc | 840 |
| aacctcaact ctcttgattt cgatctctcc gaggaggaca tcaagaccat ctctggtttc | 900 |
| gaccgcggca tccgcttcaa ccagcccacc aactacttct ccgctgagaa cctctggatt | 960 |
| ttcggttag | 969 |

```
<210> SEQ ID NO 78
<211> LENGTH: 1152
<212> TYPE: DNA
<213> ORGANISM: Artificial Sequence
<220> FEATURE:
<223> OTHER INFORMATION: XDH

<400> SEQUENCE: 78
```

| | |
|---|---|
| atggctaccg acggcaagtc taacctctcc ttcgtcctta acaagcccct cgacgtctgc | 60 |
| ttccaggaca agcccgtccc caagatcaac tccccccatg acgtactcgt cgccgtcaac | 120 |
| tacaccggca tctgcggctc cgatgtccac tactggctcc atggcgctat cggccacttt | 180 |
| gttgtgaagg accccatggt tctcggccac gagtccgccg gtactattgt tgccgtcggc | 240 |
| gatgccgtca agactctttc cgtcggcgac cgtgtcgccc tcgagcccgg ctaccctgc | 300 |
| cgccgctgcg tccactgcct ttccggccac tacaacctct gccccgaaat gcggttcgcc | 360 |
| gccacccctc cttacgacgg caccctgacc ggcttctgga ccgccccgc cgacttctgc | 420 |
| tacaagctcc ccgagaccgt ctcgctccag gagggtgccc tgatcgagcc cctcgctgtc | 480 |
| gccgtccaca tcaccaagca ggccaagatc cagcccggtc agaccgtggt cgttatgggc | 540 |

```
gccggcccg   tcggcctcct   ctgcgccgcc   gttgccaagg   cctacggcgc   ctccaaggtt      600
gtctcggtcg  acattgtccc   ctccaagctc   gagttcgcca   agtcgttcgc   cgccacccac      660
acctacctct  cgcagcgcgt   gtcgcccgag   gagaacgcgc   gcaacattat   cgcggccgcc      720
gaccttggcg  agggtgccga   tgccgtcatt   gacgccagcg   gcgctgagcc   ctccatccag      780
gcggcactcc  acgtcgtccg   tcagggcggc   cactacgtcc   agggcggtat   gggcaaggac      840
aacatcatct  tccccattat   ggcgctctgc   atcaaggagg   tcacggctag   cggctcgttc      900
cgctacggca  gcggtgacta   caggctggct   attcagcttg   ttgagcaggg   caaggttgat      960
gtcaagaagc  tcgtcaacgg   cgttgttccc   ttcaagaatg   ccgaggaggc   tttcaagaag     1020
gttaaggagg  gtgaggttat   caagatcctc   attgctggcc   ctaacgagga   tgtcgagggt     1080
agtcttgata  ctactgttga   tgagaagaag   ctgaatgagg   ccaaggcttg   cggtggttct     1140
ggctgctgct  aa                                                                 1152
```

<210> SEQ ID NO 79
<211> LENGTH: 1872
<212> TYPE: DNA
<213> ORGANISM: Artificial Sequence
<220> FEATURE:
<223> OTHER INFORMATION: XKS

<400> SEQUENCE: 79

```
atgaccacta  ccccatttga   tgctccagat   aagctcttcc   tcgggttcga   tctttcgact       60
cagcagttga  agatcatcgt   caccgatgaa   aacctcgctg   ctctcaaaac   ctacaatgtc      120
gagttcgata  gcatcaacag   ctctgtccag   aagggtgtca   ttgctatcaa   cgacgaaatc      180 agcaaggtg   ccattatttc   ccccgtttac   atgtggttgg   atgcccttga   ccatgttttt      240
gaagacatga  agaaggacgg   attccccttc   aacaaggttg   ttggtatttc   cggttcttgt      300
caacagcacg  gttcggtata   ctggtctaga   acggccgaga   aggtcttgtc   cgaattggac      360
gctgaatctt  cgttatcgag   ccagatgaga   tctgctttca   ccttcaagca   cgctccaaac      420
tggcaggatc  actctaccgg   taaagagctt   gaagagttcg   aaagagtgat   tggtgctgat      480
gccttggctg  atatctctgg   ttccagagcc   cattacagat   tcacgggct    ccagattaga      540 aagttgtcta  ccagattcaa   gcccgaaaag   tacaacagaa   ctgctcgtat   ctctttagtt      600
tcgtcatttg  ttgccagtgt   gttgcttggt   agaatcacct   ccattgaaga   agccgatgct      660
tgtggaatga  acttgtacga   tatcgaaaag   cgcgagttca   cgaagagct    cttggccatc      720 gctgctggtg  tccaccctga   gttggatggt   gtagaacaag   acggtgaaat   ttacagagct      780
ggtatcaatg  agttgaagag   aaagttgggt   cctgtcaaac   ctataacata   cgaaagcgaa      840
ggtgacattg  cctcttactt   tgtcaccaga   tacggcttca   accccgactg   taaaatctac      900
tcgttcaccg  agacaatttt   ggccacgatt   atctcgttgc   ctttggctcc   aaatgatgct      960
ttgatctcat  tgggtacttc   tactacagtt   ttaattatca   ccaagaacta   cgctccttct     1020
tctcaatacc  atttgtttaa   acatccaacc   atgcctgacc   actacatggg   catgatctgc     1080
tactgtaacg  gttccttggc   cagagaaaag   gttagagacg   aagtcaacga   aaagttcaat     1140
gtagaagaca  agaagtcgtg   ggacaagttc   aatgaaatct   tggacaaatc   cacagacttc     1200
aacaacaagt  tgggtattta   cttcccactt   ggcgaaattg   tccctaatgc   cgctgctcag     1260
atcaagagat  cggtgttgaa   cagcaagaac   gaaattgtag   acgttgagtt   gggcgacaag     1320
aactggcaac  ctgaagatga   tgtttcttca   attgtagaat   cacagacttt   gtcttgtaga     1380
```

|  |  |
|---|---|
| ttgagaactg gtccaatgtt gagcaagagt ggagattctt ctgcttccag ctctgcctca | 1440 |
| cctcaaccag aaggtgatgg tacagatttg cacaaggtct accaagactt ggttaaaaag | 1500 |
| tttggtgact tgttcactga tggaaagaag caaacctttg agtctttgac cgccagacct | 1560 |
| aaccgttgtt actacgtcgg tggtgcttcc aacaacggca gcattatccs caagatgggt | 1620 |
| tccatcttgg ctcccgtcaa cggaaactac aaggttgaca ttcctaacgc ctgtgcattg | 1680 |
| ggtggtgctt acaaggccag ttggagttac gagtgtgaag ccaagaagga atggatcgga | 1740 |
| tacgatcagt atatcaacag attgtttgaa gtaagtgacg agatgaatct gttcgaagtc | 1800 |
| aaggataaat ggctcgaata tgccaacggg gttggaatgt tggccaagat ggaaagtgaa | 1860 |
| ttgaaacact aa | 1872 |

<210> SEQ ID NO 80
<211> LENGTH: 717
<212> TYPE: DNA
<213> ORGANISM: Artificial Sequence
<220> FEATURE:
<223> OTHER INFORMATION: gfp

<400> SEQUENCE: 80

|  |  |
|---|---|
| atgagtaaag gagaagaact tttcactgga gttgtcccaa ttcttgttga attagatggt | 60 |
| gatgttaatg ggcacaaatt ttctgtcagt ggagagggtg aaggtgatgc aacatacgga | 120 |
| aaacttaccc ttaaatttat ttgcactact ggaaaactac ctgttccatg ccaacactt | 180 |
| gtcactactt tctcttatgg tgttcaatgc ttttcaagat acccagatca tatgaaacgg | 240 |
| catgactttt tcaagagtgc catgcccgaa ggttatgtac aggaaagaac tatattttc | 300 |
| aaagatgacg ggaactacaa gacacgtgct gaagtcaagt ttgaaggtga taccctgtt | 360 |
| aatagaatcg agttaaaagg tattgatttt aagaagatg gaaacattct tggacacaaa | 420 |
| ttggaataca actataactc acacaatgta tacatcatgg cagacaaaca aaagaatgga | 480 |
| atcaaagtta acttcaaaat tagacacaac attgaagatg gaagcgttca actagcagac | 540 |
| cattatcaac aaaatactcc aattggcgat ggccctgtcc tttaccaga caaccattac | 600 |
| ctgtccacac aatctgcct tcgaaagat cccaacgaaa agagagacca catggtcctt | 660 |
| cttgagtttg taacagctgc tgggattaca catggcatgg atgaactata caaatag | 717 |

<210> SEQ ID NO 81
<211> LENGTH: 711
<212> TYPE: DNA
<213> ORGANISM: Artificial Sequence
<220> FEATURE:
<223> OTHER INFORMATION: mCherry

<400> SEQUENCE: 81

|  |  |
|---|---|
| atggtgagca agggcgagga ggataacatg gccatcatca aggagttcat gcgcttcaag | 60 |
| gtgcacatgg agggctccgt gaacggccac gagttcgaga tcgagggcga gggcgagggc | 120 |
| cgcccctacg agggcaccca gaccgccaag ctgaaggtga ccaagggtgg ccccctgccc | 180 |
| ttcgcctggg acatcctgtc cctcagttc atgtacggct ccaaggccta cgtgaagcac | 240 |
| cccgccgaca tccccgacta cttgaagctg tccttcccg agggcttcaa gtgggagcgc | 300 |
| gtgatgaact tcgaggacgg cggcgtggtg accgtgaccc aggactcctc cctgcaggac | 360 |
| ggcgagttca tctacaaggt gaagctgcgc ggcaccaact ccccctcaga cggccccgta | 420 |
| atgcagaaga aaaccatggg ctgggaggcc tcctccgagc ggatgtaccc cgaggacggc | 480 |
| gccctgaagg gcgagatcaa gcagaggctg aagctgaagg acggcggcca ctacgacgct | 540 |

```
gaggtcaaga ccacctacaa ggccaagaag cccgtgcagc tgcccggcgc ctacaacgtc    600
aacatcaagt tggacatcac ctcccacaac gaggactaca ccatcgtgga acagtacgaa    660
cgcgccgagg ccgccactc caccggcggc atggacgagc tgtacaagta a              711
```

<210> SEQ ID NO 82
<211> LENGTH: 60
<212> TYPE: DNA
<213> ORGANISM: Artificial Sequence
<220> FEATURE:
<223> OTHER INFORMATION: CEN-0.8kb-F primer

<400> SEQUENCE: 82

```
taactgcggt caagatattt cttgaatcag gcgcctctag ctattttgtt taggttgggt    60
```

<210> SEQ ID NO 83
<211> LENGTH: 60
<212> TYPE: DNA
<213> ORGANISM: Artificial Sequence
<220> FEATURE:
<223> OTHER INFORMATION: CEN-0.8kb-R primer

<400> SEQUENCE: 83

```
attctgatat tatccaaaga tgttgagggc cctaaatagt tttattacac tcaaagtgac    60
```

<210> SEQ ID NO 84
<211> LENGTH: 22
<212> TYPE: DNA
<213> ORGANISM: Artificial Sequence
<220> FEATURE:
<223> OTHER INFORMATION: ade2-seq-F primer

<400> SEQUENCE: 84

```
tgaacacatt gatggttcat tc                                             22
```

<210> SEQ ID NO 85
<211> LENGTH: 25
<212> TYPE: DNA
<213> ORGANISM: Artificial Sequence
<220> FEATURE:
<223> OTHER INFORMATION: ade2-seq-R primer

<400> SEQUENCE: 85

```
tcttttacaa catagttacc tctac                                          25
```

<210> SEQ ID NO 86
<211> LENGTH: 21
<212> TYPE: DNA
<213> ORGANISM: Artificial Sequence
<220> FEATURE:
<223> OTHER INFORMATION: GFP-qPCR-F primer

<400> SEQUENCE: 86

```
gatggtgatg ttaatgggca c                                              21
```

<210> SEQ ID NO 87
<211> LENGTH: 22
<212> TYPE: DNA
<213> ORGANISM: Artificial Sequence
<220> FEATURE:
<223> OTHER INFORMATION: GFP-qPCR-R primer

<400> SEQUENCE: 87

```
gggtaagttt tccgtatgtt gc                                             22
```

```
<210> SEQ ID NO 88
<211> LENGTH: 21
<212> TYPE: DNA
<213> ORGANISM: Artificial Sequence
<220> FEATURE:
<223> OTHER INFORMATION: TRP1-qPCR-F primer

<400> SEQUENCE: 88
tccccgttat ttcaaggttc g                                          21

<210> SEQ ID NO 89
<211> LENGTH: 20
<212> TYPE: DNA
<213> ORGANISM: Artificial Sequence
<220> FEATURE:
<223> OTHER INFORMATION: TRP1-qPCR-R primer

<400> SEQUENCE: 89
cttgtcccca aacgaacttg                                            20

<210> SEQ ID NO 90
<211> LENGTH: 60
<212> TYPE: DNA
<213> ORGANISM: Artificial Sequence
<220> FEATURE:
<223> OTHER INFORMATION: Assembly-ScARS-F primer

<400> SEQUENCE: 90
gcgcacattt ccccgaaaag tgccacctgg gtccctcgag gatcgccaac aaatactacc   60

<210> SEQ ID NO 91
<211> LENGTH: 60
<212> TYPE: DNA
<213> ORGANISM: Artificial Sequence
<220> FEATURE:
<223> OTHER INFORMATION: Assembly-ScARS-R primer

<400> SEQUENCE: 91
atgagacaat gattgccgct agacaatgtc aacctgcagg atcgcttgcc tgtaacttac   60

<210> SEQ ID NO 92
<211> LENGTH: 50
<212> TYPE: DNA
<213> ORGANISM: Artificial Sequence
<220> FEATURE:
<223> OTHER INFORMATION: 1387F-F primer

<400> SEQUENCE: 92
aaggacttaa atatttgtac aaacatgttc catctagagc cacctgggtc              50

<210> SEQ ID NO 93
<211> LENGTH: 59
<212> TYPE: DNA
<213> ORGANISM: Artificial Sequence
<220> FEATURE:
<223> OTHER INFORMATION: 1387F-R primer

<400> SEQUENCE: 93
atcgctgaga taggtgcctc actgattaag cattggtaac tgtcagacca agtttactc     59

<210> SEQ ID NO 94
<211> LENGTH: 57
<212> TYPE: DNA
<213> ORGANISM: Artificial Sequence
<220> FEATURE:
<223> OTHER INFORMATION: 1032F-F primer
```

-continued

<400> SEQUENCE: 94
atctaaagta tatatgagta aacttggtct gacagttacc aatgcttaat cagtgag    57

<210> SEQ ID NO 95
<211> LENGTH: 50
<212> TYPE: DNA
<213> ORGANISM: Artificial Sequence
<220> FEATURE:
<223> OTHER INFORMATION: 1032F-R Primer

<400> SEQUENCE: 95
aacacccgct gacgcgccct gacgggcttg tcgcggaacc cctatttgtt    50

<210> SEQ ID NO 96
<211> LENGTH: 55
<212> TYPE: DNA
<213> ORGANISM: Artificial Sequence
<220> FEATURE:
<223> OTHER INFORMATION: 1337F-F primer

<400> SEQUENCE: 96
gaatgtattt agaaaaataa acaaataggg gttccgcgac aagcccgtca gggcg    55

<210> SEQ ID NO 97
<211> LENGTH: 52
<212> TYPE: DNA
<213> ORGANISM: Artificial Sequence
<220> FEATURE:
<223> OTHER INFORMATION: 1337F-R primer

<400> SEQUENCE: 97
cgctagacaa tgtcaacctt ccctgtttac gcgtctcgag cctgatgcgg ta    52

<210> SEQ ID NO 98
<211> LENGTH: 48
<212> TYPE: DNA
<213> ORGANISM: Artificial Sequence
<220> FEATURE:
<223> OTHER INFORMATION: 1742F-F primer

<400> SEQUENCE: 98
taaggagaaa ataccgcatc aggctcgaga cgcgtaaaca gggaaggt    48

<210> SEQ ID NO 99
<211> LENGTH: 56
<212> TYPE: DNA
<213> ORGANISM: Artificial Sequence
<220> FEATURE:
<223> OTHER INFORMATION: 1742F-R primer

<400> SEQUENCE: 99
ggtttctcgt gtattgctat aatctctcgt gtattcgtct gtagagtaaa gaaact    56

<210> SEQ ID NO 100
<211> LENGTH: 57
<212> TYPE: DNA
<213> ORGANISM: Artificial Sequence
<220> FEATURE:
<223> OTHER INFORMATION: 667F-F primer

<400> SEQUENCE: 100
taagatgaac gagaagtttc tttactctac agacgaatac acgagagatt atagcaa    57

<210> SEQ ID NO 101

```
<210> SEQ ID NO 101
<211> LENGTH: 55
<212> TYPE: DNA
<213> ORGANISM: Artificial Sequence
<220> FEATURE:
<223> OTHER INFORMATION: 667F-R primer

<400> SEQUENCE: 101
actccagtga aaagttcttc tcctttactc attttattg tgttagtttg taagc        55

<210> SEQ ID NO 102
<211> LENGTH: 58
<212> TYPE: DNA
<213> ORGANISM: Artificial Sequence
<220> FEATURE:
<223> OTHER INFORMATION: 790F-F primer

<400> SEQUENCE: 102
ttcatagtct ctcgcttaca aactaacaca ataaaaatga gtaaaggaga agaacttt    58

<210> SEQ ID NO 103
<211> LENGTH: 59
<212> TYPE: DNA
<213> ORGANISM: Artificial Sequence
<220> FEATURE:
<223> OTHER INFORMATION: 790F-R primer

<400> SEQUENCE: 103
aattgtacta gatatttagt aaaagcatta gttagatcta tttgtatagt tcatccatg   59

<210> SEQ ID NO 104
<211> LENGTH: 58
<212> TYPE: DNA
<213> ORGANISM: Artificial Sequence
<220> FEATURE:
<223> OTHER INFORMATION: 951F-F primer

<400> SEQUENCE: 104
gattacacat ggcatggatg aactatacaa atagatctaa ctaatgcttt tactaaat    58

<210> SEQ ID NO 105
<211> LENGTH: 60
<212> TYPE: DNA
<213> ORGANISM: Artificial Sequence
<220> FEATURE:
<223> OTHER INFORMATION: 951F-R primer

<400> SEQUENCE: 105
tatagcacgt gatgaaaagg acccaggtgg ctctagatgg aacatgtttg tacaaatatt  60

<210> SEQ ID NO 106
<211> LENGTH: 58
<212> TYPE: DNA
<213> ORGANISM: Artificial Sequence
<220> FEATURE:
<223> OTHER INFORMATION: XR-cassette-F primer

<400> SEQUENCE: 106
tctaacctaa ggacttaaat atttgtacaa acatgttcca ttgatttaac ctgatcca    58

<210> SEQ ID NO 107
<211> LENGTH: 60
<212> TYPE: DNA
<213> ORGANISM: Artificial Sequence
<220> FEATURE:
<223> OTHER INFORMATION: XR-cassette-R primer

<400> SEQUENCE: 107
```
tgactatcgg cctctttttc tccgggtgtg gtgcattttt cgcgtacagg gttataaagt    60

<210> SEQ ID NO 108
<211> LENGTH: 58
<212> TYPE: DNA
<213> ORGANISM: Artificial Sequence
<220> FEATURE:
<223> OTHER INFORMATION: XDH-cassette-F primer

<400> SEQUENCE: 108
actttagatg ctcctctgaa caactttata accctgtacg cgaaaaatgc accacacc    58

<210> SEQ ID NO 109
<211> LENGTH: 59
<212> TYPE: DNA
<213> ORGANISM: Artificial Sequence
<220> FEATURE:
<223> OTHER INFORMATION: XDH-cassette-R primer

<400> SEQUENCE: 109
ttgctgtgca agagcaattt tctctctgat tacaccgttg gttcatctta ttctttagc    59

<210> SEQ ID NO 110
<211> LENGTH: 59
<212> TYPE: DNA
<213> ORGANISM: Artificial Sequence
<220> FEATURE:
<223> OTHER INFORMATION: XKS-cassette-F primer

<400> SEQUENCE: 110
ataataaaaa gtttaaactt ggctaaagaa taagatgaac caacggtgta atcagagag    59

<210> SEQ ID NO 111
<211> LENGTH: 60
<212> TYPE: DNA
<213> ORGANISM: Artificial Sequence
<220> FEATURE:
<223> OTHER INFORMATION: XKS-cassette-R primer

<400> SEQUENCE: 111
cctcactaaa gggaacaaaa gctggagctc caccgcggtg gcccgtctat tgttctcctt    60

<210> SEQ ID NO 112
<211> LENGTH: 60
<212> TYPE: DNA
<213> ORGANISM: Artificial Sequence
<220> FEATURE:
<223> OTHER INFORMATION: URA3-cassette-F primer

<400> SEQUENCE: 112
caacatccag tcactttgag tgtaataaaa ctatttaggg ccgttgacat tgtctagcgg    60

<210> SEQ ID NO 113
<211> LENGTH: 58
<212> TYPE: DNA
<213> ORGANISM: Artificial Sequence
<220> FEATURE:
<223> OTHER INFORMATION: URA3-cassette-R primer

<400> SEQUENCE: 113 taaaaatag acatacccct tttggatcag gttaaatcaa tggaacatgt ttgtacaa    58

<210> SEQ ID NO 114
<211> LENGTH: 22
<212> TYPE: DNA

```
<213> ORGANISM: Artificial Sequence
<220> FEATURE:
<223> OTHER INFORMATION: qPCR-XR-F primer

<400> SEQUENCE: 114
aggctattgg tgacaagtac aa                                          22

<210> SEQ ID NO 115
<211> LENGTH: 22
<212> TYPE: DNA
<213> ORGANISM: Artificial Sequence
<220> FEATURE:
<223> OTHER INFORMATION: qPCR-XR-R primer

<400> SEQUENCE: 115
cctcggagag atcgaaatca ag                                          22

<210> SEQ ID NO 116
<211> LENGTH: 21
<212> TYPE: DNA
<213> ORGANISM: Artificial Sequence
<220> FEATURE:
<223> OTHER INFORMATION: qPCR-XDH-F primer

<400> SEQUENCE: 116
gtgactacag gctggctatt c                                           21

<210> SEQ ID NO 117
<211> LENGTH: 21
<212> TYPE: DNA
<213> ORGANISM: Artificial Sequence
<220> FEATURE:
<223> OTHER INFORMATION: qPCR-XDH-R primer

<400> SEQUENCE: 117
ccctgctcaa caagctgaat a                                           21

<210> SEQ ID NO 118
<211> LENGTH: 22
<212> TYPE: DNA
<213> ORGANISM: Artificial Sequence
<220> FEATURE:
<223> OTHER INFORMATION: qPCR-XKS-F primer

<400> SEQUENCE: 118
gattcacagg gctccagatt ag                                          22

<210> SEQ ID NO 119
<211> LENGTH: 21
<212> TYPE: DNA
<213> ORGANISM: Artificial Sequence
<220> FEATURE:
<223> OTHER INFORMATION: qPCR-XKS-R primer

<400> SEQUENCE: 119
caacacactg gcaacaaatg a                                           21

<210> SEQ ID NO 120
<211> LENGTH: 50
<212> TYPE: DNA
<213> ORGANISM: Artificial Sequence
<220> FEATURE:
<223> OTHER INFORMATION: Eno2t_CEN/ARS_Fwd promoter assembly

<400> SEQUENCE: 120
aaggacttaa atatttgtac aaacatgttc catctagagc cacctgggtc            50
```

<210> SEQ ID NO 121
<211> LENGTH: 60
<212> TYPE: DNA
<213> ORGANISM: Artificial Sequence
<220> FEATURE:
<223> OTHER INFORMATION: Eno2t_CEN/ars_Rev Promoter assembly

<400> SEQUENCE: 121
tatagcacgt gatgaaaagg acccaggtgg ctctagatgg aacatgtttg tacaaatatt    60

<210> SEQ ID NO 122
<211> LENGTH: 60
<212> TYPE: DNA
<213> ORGANISM: Artificial Sequence
<220> FEATURE:
<223> OTHER INFORMATION: FBAp_GFP_Fwd promoter assembly

<400> SEQUENCE: 122
ctactactac tattactacc accccaaca caaacacaat gagtaaagga gaagaacttt    60

<210> SEQ ID NO 123
<211> LENGTH: 57
<212> TYPE: DNA
<213> ORGANISM: Artificial Sequence
<220> FEATURE:
<223> OTHER INFORMATION: FBAp_GFP_Rev promoter assembly

<400> SEQUENCE: 123
ggacaactcc agtgaaaagt tcttctcctt tactcattgt gtttgtgttg ggggtgg    57

<210> SEQ ID NO 124
<211> LENGTH: 55
<212> TYPE: DNA
<213> ORGANISM: Artificial Sequence
<220> FEATURE:
<223> OTHER INFORMATION: scUra_Fwd promoter assembly

<400> SEQUENCE: 124
gaatgtattt agaaaaataa acaaataggg gttccgcgac aagcccgtca gggcg    55

<210> SEQ ID NO 125
<211> LENGTH: 52
<212> TYPE: DNA
<213> ORGANISM: Artificial Sequence
<220> FEATURE:
<223> OTHER INFORMATION: scURA_Ura3p_Rev promoter assembly

<400> SEQUENCE: 125
cgctagacaa tgtcaacctt ccctgtttac gcgtctcgag cctgatgcgg ta    52

<210> SEQ ID NO 126
<211> LENGTH: 62
<212> TYPE: DNA
<213> ORGANISM: Artificial Sequence
<220> FEATURE:
<223> OTHER INFORMATION: TEF1t_FBAp_Fwd promoter assembly

<400> SEQUENCE: 126
aagaataaga tgaacgagaa gtttctttac tctacagacg atgccatatt gtatgtgtat    60
tg    62

<210> SEQ ID NO 127
<211> LENGTH: 56
<212> TYPE: DNA

<213> ORGANISM: Artificial Sequence
<220> FEATURE:
<223> OTHER INFORMATION: Tef1t_FBAp_Rev promoter assembly

<400> SEQUENCE: 127
tacacactta atacaataca catacaatat ggcatcgtct gtagagtaaa gaaact    56

<210> SEQ ID NO 128
<211> LENGTH: 48
<212> TYPE: DNA
<213> ORGANISM: Artificial Sequence
<220> FEATURE:
<223> OTHER INFORMATION: Ura_Ura3p_Fwd promoter assembly

<400> SEQUENCE: 128
taaggagaaa ataccgcatc aggctcgaga cgcgtaaaca gggaaggt    48

<210> SEQ ID NO 129
<211> LENGTH: 50
<212> TYPE: DNA
<213> ORGANISM: Artificial Sequence
<220> FEATURE:
<223> OTHER INFORMATION: CEN/ARS/Amp _Rev promoter assembly

<400> SEQUENCE: 129
aacacccgct gacgcgccct gacgggcttg tcgcggaacc cctatttgtt    50

<210> SEQ ID NO 130
<211> LENGTH: 700
<212> TYPE: PRT
<213> ORGANISM: Artificial Sequence
<220> FEATURE:
<223> OTHER INFORMATION: Dicer polypeptide

<400> SEQUENCE: 130

Met Lys Ile Pro Pro Ser Arg Ile Asp Cys Ile Gln Asp Phe Phe Phe
1               5                   10                  15

Phe Phe Gln Thr Phe Phe Leu Leu Asn Leu Leu Tyr Ile Ile Ile Glu
            20                  25                  30

Ala Asp Asn Ser Arg Ile Ser Ser Thr Met Ser Lys Arg Ala Leu Gly
        35                  40                  45

Glu Val Glu Ser Ser Val Val Glu Glu Lys Val Leu Lys Lys Lys Gln
    50                  55                  60

Lys Leu Asp Lys Gln Asp Lys Glu Lys Asp Lys Lys Ser Lys Arg Ser
65                  70                  75                  80

Lys Arg Asp Lys Ser Glu Asp Ser Lys Asn Leu Lys Glu Lys Arg Lys
                85                  90                  95

Asp Lys Tyr Gly Val Asn Ser Lys Asn Ala Asp Gly Gln Asn Leu Glu
            100                 105                 110

Lys Ile Glu Pro Ala Ile Ile Lys Gln Ile Ala Ile Ser Asp Leu Met
        115                 120                 125

Ser Val Glu His Ser Val Cys Val Ile Gln Glu Asn Leu Lys Lys Leu
    130                 135                 140

Met Gln Leu Ala Pro Asn Leu Arg Asp Leu Glu Gln Tyr Thr Asn Phe
145                 150                 155                 160

Leu Ile Ala Gln Ser Thr Lys Ser Gly Met Gly Thr Asn Gly Asp Ile
                165                 170                 175

Thr Ala Lys Ile Leu Leu Leu Ser Lys Ser His Lys Ile Gln Leu Ala
            180                 185                 190

Ser Gln Leu Lys Thr Leu Ser Glu Asn Gly Gln Leu Pro Ile Val Lys

```
                195                 200                 205
Gln Ile Ile Asp Phe Asp Asn Asp Thr Val Leu Glu Asn Val Ser Asp
210                 215                 220
Val Gln Leu Lys Leu Lys Glu Lys Asn Arg Glu Leu His Arg Gly Gly
225                 230                 235                 240
Thr Ser Ser Glu Ala Phe Asn Ser Leu Leu Pro Pro Leu Pro Thr Ile
                245                 250                 255
Asp Asp Ser Val Leu Glu Ala Lys Val Phe Val His Lys Ser Ala Thr
            260                 265                 270
Asn Asn Glu Leu Leu Ser Ser Lys Gln Asp Thr Val Gln Ser Asn Asn
        275                 280                 285
Glu Arg Leu Glu Phe Leu Gly Asp Ala Val Leu Glu Thr Val Ile Ser
    290                 295                 300
Asp Val Ile Glu Tyr Arg Tyr Arg Gly Phe Asp Glu Gly Gln Leu Ser
305                 310                 315                 320
Ser Leu Arg Ser Thr Leu Val Lys Asn Glu Thr Ile Glu Leu Leu Ser
                325                 330                 335
Arg Ala Tyr Lys Phe Pro Glu Arg Gln Met Glu Leu Leu Asp Ser His
            340                 345                 350
Met Val Lys Thr Glu Leu Thr Glu Phe Lys Val Gly Lys Asn Lys Arg
        355                 360                 365
Ile Ala Asp Leu Phe Glu Ala Tyr Ile Gly Ala Leu Phe Ile Asp Lys
    370                 375                 380
Gly Arg Asn Gly Pro Ala Tyr Asp Phe Ile Lys Asp Trp Leu Ser Lys
385                 390                 395                 400
Val Tyr Ser Pro Ile Leu Lys Glu Phe Asp Gly Phe Asp His Leu Lys
                405                 410                 415
Tyr Leu His Val Ser Ser Lys Leu Arg Asn Gln Leu Leu Ser Glu Thr
            420                 425                 430
Pro Glu Thr Val Ala Cys Lys Ala Asp Gln Asn Lys Ser Lys His Ile
        435                 440                 445
Gln Phe Asp Thr Leu Asp Ser Glu Glu Asp Lys Val Ser Glu Val Glu
    450                 455                 460
Ser Thr Ser Ser Ala Thr Val Leu Glu Lys Glu Leu Lys Phe Pro Ile
465                 470                 475                 480
Thr Phe Thr Ser Ser Glu Pro Val Asn Lys Leu Ala Lys Gly Glu Leu
                485                 490                 495
Tyr Ala Leu Ile Gly Ser Ala Lys Leu His Pro Ile Tyr Lys Asn Glu
            500                 505                 510
Lys Ser Gln Asn Asp Ser Lys His Tyr Leu Thr Thr Cys Ser Ile Ala
        515                 520                 525
Glu Asp Ile Leu Gly Tyr Gly Glu Gly Arg Asn Leu Lys Asp Ser Ser
    530                 535                 540
Ala Arg Ala Ala Gln Ala Ala Leu Leu Asn Lys Pro Met Ile Glu Lys
545                 550                 555                 560
Tyr His Leu Leu Arg Met Met Thr Pro Arg Ser Glu Thr Arg Ala Ser
                565                 570                 575
Gln Lys Leu Glu Phe Val Glu Lys Pro Glu Val Ala Ser Ser Thr Thr
            580                 585                 590
Leu Lys Gln Tyr Thr Pro Lys Phe Leu Lys Thr Val Gln Tyr Ile Gly
        595                 600                 605
Lys Asp Glu Ile Pro Thr Pro Asn Ser Ser Ser Lys Asn Lys Leu Val
    610                 615                 620
```

```
Asp Leu Leu Ala Lys Lys Gly Val Val Pro Arg Tyr His Val Glu Glu
625                 630                 635                 640

Asp Lys Glu Asn Lys Ser Ile Leu Pro Met Phe Arg Thr Thr Leu Lys
            645                 650                 655

Val Asn Asp Ile Asp Val Ala Tyr Cys Ile Asp Ala Ser Lys Lys Lys
        660                 665                 670

Gly Leu Asn Lys Val Ser Gln Trp Leu Leu Gln Lys Ile Glu Glu Val
    675                 680                 685

Gly Glu Lys Thr Ile Tyr His Asp Leu Lys Leu Glu
690                 695                 700

<210> SEQ ID NO 131
<211> LENGTH: 55
<212> TYPE: DNA
<213> ORGANISM: Artificial Sequence
<220> FEATURE:
<223> OTHER INFORMATION: 4194t_mcherry_Fwd terminator assembly

<400> SEQUENCE: 131
aaaaacccca aaactcctct tgttgggagg gccgtcaatg gtgagcaagg gcgag        55

<210> SEQ ID NO 132
<211> LENGTH: 55
<212> TYPE: DNA
<213> ORGANISM: Artificial Sequence
<220> FEATURE:
<223> OTHER INFORMATION: 4194t_mcherry_rev terminator assembly

<400> SEQUENCE: 132
tgatggccat gttatcctcc tcgcccttgc tcaccattga cggccctccc aacaa        55

<210> SEQ ID NO 133
<211> LENGTH: 55
<212> TYPE: DNA
<213> ORGANISM: Artificial Sequence
<220> FEATURE:
<223> OTHER INFORMATION: Ura_Ura3p_Fwd terminator assembly

<400> SEQUENCE: 133
ttagaaaaat aaacaaatag gggttccgcg ctcgagacgc gtaaacaggg aaggt        55

<210> SEQ ID NO 134
<211> LENGTH: 55
<212> TYPE: DNA
<213> ORGANISM: Artificial Sequence
<220> FEATURE:
<223> OTHER INFORMATION: Amp_Ura3p_IO_Rev terminator assembly

<400> SEQUENCE: 134
aatgtcaacc ttccctgttt acgcgtctcg agcgcggaac ccctatttgt ttatt        55

<210> SEQ ID NO 135
<211> LENGTH: 55
<212> TYPE: DNA
<213> ORGANISM: Artificial Sequence
<220> FEATURE:
<223> OTHER INFORMATION: GFP_4194t_Fwd terminator assembly

<400> SEQUENCE: 135
attacacatg gcatggatga actatacaaa tagtttgaat caacttttcc cctaa        55

<210> SEQ ID NO 136
<211> LENGTH: 55
```

```
<212> TYPE: DNA
<213> ORGANISM: Artificial Sequence
<220> FEATURE:
<223> OTHER INFORMATION: GFP_4194_Rev terminator assembly

<400> SEQUENCE: 136
tgtattaaac cttaggggaa aagttgattc aaactatttg tatagttcat ccatg      55

<210> SEQ ID NO 137
<211> LENGTH: 55
<212> TYPE: DNA
<213> ORGANISM: Artificial Sequence
<220> FEATURE:
<223> OTHER INFORMATION: mcherry_pgk1t_Fwd terminator assembly

<400> SEQUENCE: 137
ccaccggcgg catggacgag ctgtacaagt aaatcaaaca tagatcaacg taatg      55

<210> SEQ ID NO 138
<211> LENGTH: 55
<212> TYPE: DNA
<213> ORGANISM: Artificial Sequence
<220> FEATURE:
<223> OTHER INFORMATION: mcherry_pgk1t_Rev terminator assembly

<400> SEQUENCE: 138
ttatattaaa ttcattacgt tgatctatgt ttgatttact tgtacagctc gtcca      55

<210> SEQ ID NO 139
<211> LENGTH: 57
<212> TYPE: DNA
<213> ORGANISM: Artificial Sequence
<220> FEATURE:
<223> OTHER INFORMATION: PDC1t_TDH3p_Fwd terminator assembly

<400> SEQUENCE: 139
gaataatata taattttata ataaaaagtt taaactatgg atatggagat gaatttg    57

<210> SEQ ID NO 140
<211> LENGTH: 59
<212> TYPE: DNA
<213> ORGANISM: Artificial Sequence
<220> FEATURE:
<223> OTHER INFORMATION: PDC1t_TDH3p_Rev terminator assembly

<400> SEQUENCE: 140
tctaaattca aattcatctc catatccata gtttaaactt tttattataa aattatata  59

<210> SEQ ID NO 141
<211> LENGTH: 50
<212> TYPE: DNA
<213> ORGANISM: Artificial Sequence
<220> FEATURE:
<223> OTHER INFORMATION: PGKt_ARS_Fwd terminator assembly

<400> SEQUENCE: 141
ttattattat tattattatt attattatca tatctagagc cacctgggtc           50

<210> SEQ ID NO 142
<211> LENGTH: 60
<212> TYPE: DNA
<213> ORGANISM: Artificial Sequence
<220> FEATURE:
<223> OTHER INFORMATION: PGK1t_CEN/ARS_Rev terminator assembly

<400> SEQUENCE: 142
```
acgtgatgaa aaggacccag gtggctctag atatgataat aataataata ataataataa    60

<210> SEQ ID NO 143
<211> LENGTH: 81
<212> TYPE: DNA
<213> ORGANISM: Artificial Sequence
<220> FEATURE:
<223> OTHER INFORMATION: ADE2 disruption sequence

<400> SEQUENCE: 143
tgttagcgtt gaaagcaccg agacagcatt gcaaaatgtt ggtttgaaat ttggtttccc    60
atttatgctg aagtccaaaa c    81

<210> SEQ ID NO 144
<211> LENGTH: 38
<212> TYPE: DNA
<213> ORGANISM: Artificial Sequence
<220> FEATURE:
<223> OTHER INFORMATION: ADE2 disruption DNA sequence

<400> SEQUENCE: 144
tgttagcgtt gaaagcaccg agacagcatt gcaaaatg    38

<210> SEQ ID NO 145
<211> LENGTH: 35
<212> TYPE: DNA
<213> ORGANISM: Artificial Sequence
<220> FEATURE:
<223> OTHER INFORMATION: ADE2 disruption DNA sequence

<400> SEQUENCE: 145
aaatttggtt tcccatttat gctgaagtcc aaaac    35

<210> SEQ ID NO 146
<211> LENGTH: 42
<212> TYPE: DNA
<213> ORGANISM: Artificial Sequence
<220> FEATURE:
<223> OTHER INFORMATION: DNA sequencing for SDH1 disruption

<400> SEQUENCE: 146
gtaaagaggc atcctccgca atggcaaagg attatcatgt ca    42

<210> SEQ ID NO 147
<211> LENGTH: 10
<212> TYPE: DNA
<213> ORGANISM: Artificial Sequence
<220> FEATURE:
<223> OTHER INFORMATION: DNA sequencing for SDH1 disruption

<400> SEQUENCE: 147
gtaaagaggc    10

<210> SEQ ID NO 148
<211> LENGTH: 24
<212> TYPE: DNA
<213> ORGANISM: Artificial Sequence
<220> FEATURE:
<223> OTHER INFORMATION: DNA sequencing for SDH1 disruption

<400> SEQUENCE: 148
caatggcaaa ggattatcat gtca    24

<210> SEQ ID NO 149
<211> LENGTH: 49

```
<212> TYPE: DNA
<213> ORGANISM: Artificial Sequence
<220> FEATURE:
<223> OTHER INFORMATION: DNA sequencing for SDH2 disruption

<400> SEQUENCE: 149
ccggcagctg aaggtgaatc cagtggaggc tgttgtacga caggtgaga          49

<210> SEQ ID NO 150
<211> LENGTH: 23
<212> TYPE: DNA
<213> ORGANISM: Artificial Sequence
<220> FEATURE:
<223> OTHER INFORMATION: DNA sequencing for SDH2 disruption

<400> SEQUENCE: 150
ccggcagctg aaggtgaatc cag                                      23

<210> SEQ ID NO 151
<211> LENGTH: 18
<212> TYPE: DNA
<213> ORGANISM: Artificial Sequence
<220> FEATURE:
<223> OTHER INFORMATION: DNA sequencing for SDH2 disruption

<400> SEQUENCE: 151
gttgtacgac aggtgaga                                            18

<210> SEQ ID NO 152
<211> LENGTH: 17
<212> TYPE: DNA
<213> ORGANISM: Artificial Sequence
<220> FEATURE:
<223> OTHER INFORMATION: alignment of the centromere sequences predicted
      by in silico GC3 analysis

<400> SEQUENCE: 152
tctagctatt ttgttta                                             17

<210> SEQ ID NO 153
<211> LENGTH: 17
<212> TYPE: DNA
<213> ORGANISM: Artificial Sequence
<220> FEATURE:
<223> OTHER INFORMATION: alignment of the centromere sequences predicted
      by in silico GC3 analysis

<400> SEQUENCE: 153
tgtaataaaa ctattta                                             17

<210> SEQ ID NO 154
<211> LENGTH: 815
<212> TYPE: DNA
<213> ORGANISM: Artificial Sequence
<220> FEATURE:
<223> OTHER INFORMATION: centromere-like sequence (CEN-L) CEN0.8-1

<400> SEQUENCE: 154
tctagctatt ttgtttaggt tgggtaaaaa cctacggaaa gacaatagga gcttaggcta    60
tctattgata gatcaattat ttgttttaag aactatagaa ttaaaaacaa ggcagtagtt   120
gtagatttta aagattattt agagtagata gatagtaaag gctgtactga atataaatgt   180
ggatttgcgg aaccaacaag tggcctccat caagctattt aagttattct attggtattt   240
tactagaaaa ggaaggctaa tcattttttcc aatgacggtt catataatcc aagttttaaa   300
```

```
tggtttgcat catcataata ggggtatcta aaaggcataa atcgacgaaa gtgataaaaa    360
ttacttatta aacgacgtat ttacatccac gttttttgctg gaagtactga atctgcctac   420
tgctagtttg gggaagacaa taatacacaa aataaagacg atgatgaaga ttccagtttt   480
ttttaaagat aaaaaaatag atatatatgt ataattgtat gaatagtttt aataataact   540
tatgttgcta ttttgatagc aattcatttt actattgaaa aggttacccca ggcaaataat   600 atgtttagca catcagattc tgtactaata ataatataga catatgctat aacgtcaggc   660
aatacttatg tgtatagcga aatagtaaag ggctcgtcgt aaatcgtatg ttttcacgac   720
ttagactcat aagacatgtc tagaagccca accaatgaat tagaggactg tttgatatca   780
acatccagtc actttgagtg taataaaact attta                              815

<210> SEQ ID NO 155
<211> LENGTH: 811
<212> TYPE: DNA
<213> ORGANISM: Artificial Sequence
<220> FEATURE:
<223> OTHER INFORMATION: centromere-like sequence (CEN-L) CEN0.8-2

<400> SEQUENCE: 155
tctagctatt ttgtttaggt tgggtaaaaa cctacggaaa gacaattgga gcttaggcta    60
tctattgata gatcaattat ttgttttaag aactatagaa ttaaaaacaa ggcagtagtt   120
gtagatttta aagattattt agagtagata gtaaaggctg tactgaatat caatgaggat   180
ttgcagaacc aacaagtggc ctgcatcaag ctatttaagt gattctattg gtattttact   240
agaaaaggaa ggctaatcat ttttccaatg acggttcata taatccaagt tttaaatggt   300
ttgcatcatc ataatagggg tatctaaaag gcataaatcg acgaaagtga taaaaattac   360
ttattaaacg acgtatttac atccacgttt tgctggaag tactgaatct gcctactgct   420
agtttgggga agacaataat acacaaaata agacgatga tgaagattcc agttttttt   480 aaagataaaa aatagatat atatgtataa ttgtatgaat agttttaata ataacttatg   540
ttgctatttt gatagcaatt cattttacta ttgaaaaggt tacccaggca aataatatgt   600
ttagcacatc agattctgta ctaataataa tatagagtta tgttataacg tcaggcaata   660
cttatgtgta tagcgaaata gtaaatggca gattgtaaac cgtatgtttt cactactcag   720
actcatacga tatgtctaga agcccaacca atgaattaga ggactgtttg atatcaacat   780
ccagtcactt tgagtgtaat aaaactatttt a                                  811

<210> SEQ ID NO 156
<211> LENGTH: 816
<212> TYPE: DNA
<213> ORGANISM: Artificial Sequence
<220> FEATURE:
<223> OTHER INFORMATION: centromere-like sequence (CEN-L) CEN0.8-3

<400> SEQUENCE: 156
tctagctatt ttgtttaggt tgggtaaaaa cctacggaaa gacaatagga gcttaggcta    60
tctattgata gatcaattat ttgttttaag aactatagaa ttaaaaacaa ggcagtagtt   120
gtagatttta aagattattt agagtagata gatagtaaag gctgtactga atataaatgt   180
ggatttgcgg aaccaacaag tggcctccat caagctattt aagttattct attggtatttt   240 tactagaaaa gaaaggctaa tcattttttcc aatgaaggtt catataatcc aagttttaaa   300
tggtttgcat catcataata ggggtatctg aaaggcataa atcaacgaaa gtgatagaaa   360
ttacttatta aacaacgtat ttcatccac gttttttgct ggaagtactg aatctgccta   420
```

```
ctgctagttt ggggaagaca ataatacaca aaataaagac gatgatgaag attccagttt    480
tttttaaaga taaaaaaata gatatatatg tataattgta tgaatagttt taataataac    540
ttatgttgct attttgatag caattcattt tactattgaa aaggttaccg gggcaaataa    600
tatgtttagc acatcagatt ctgtactaat aataatatag acatatgcta taacgtcagg    660
caatacttat gtgtatagcg aaatagtaaa gggctcgtcg taaatcgtat gttttcacga    720
cttagactca taagacatgt ctagaagccc aaccaatgaa ttagaggact gtttgatatc    780
aacatccagt cactttgagt gtaataaaac tattta                              816
```

<210> SEQ ID NO 157
<211> LENGTH: 812
<212> TYPE: DNA
<213> ORGANISM: Artificial Sequence
<220> FEATURE:
<223> OTHER INFORMATION: centromere-like sequence (CEN-L) CEN0.8-4

<400> SEQUENCE: 157

```
tctagctatt ttgtttaggt tgggtaaaaa cctacggaaa gacaatagga gcttaggcta     60
tctattgata gatcaattat ttgttttaag aactatagaa ttaaaaacaa ggcagtagtt    120
gtagatttta aagattattt agagtagaca gtaaaggcag tactgaatat caatgaggat    180
ttgcagaacc aacaagtggc ctgcatcaag ctatttaagt gattctattg gtattttact    240
agaaaaggaa ggctaatcat ttttccaatg acggttcata taatccaagt tttaaatgtt    300
ttgtatcatc ataataggqg tatctgaaag gcataaatca acgaaagtga tagaaattac    360
ttattaaaca acgtatttac atccacgttt tttgctggaa gtactgaatc tgcctactgc    420
tagtttgggg aagataataa tacacaaaat aaagacgatg atgaagattc cagttttttt    480
taaagataaa aaaatagata tatatgtata attgtatgaa tagttttaat aataacttat    540
gttgctattt tgatagcaat tcatttttact attgaaaagg ttaccggggc aaataatatg    600
tttagcacat cagattctgt actaataata atatagagtt atgttataac gtcaggcaat    660
acttatgtgt atagcgaaat agtaaatggc agatcgtaaa ccgtatgttt tcactactca    720
gactcatacg acatgtctag aagcccaacc aatgaattag aggactgttt gatatcaaca    780
tccagtcact ttgagtgtaa taaaactatt ta                                  812
```

<210> SEQ ID NO 158
<211> LENGTH: 812
<212> TYPE: DNA
<213> ORGANISM: Artificial Sequence
<220> FEATURE:
<223> OTHER INFORMATION: centromere-like sequence (CEN-L)

<400> SEQUENCE: 158

```
tctagctatt ttgtctaggt tgggtaaaaa cctacggaaa gacaatagga gcttaggcta     60
tctattgata gatcaattat ttgttttaag aactatagaa ttaaaaacaa ggcagtagtt    120
gtagatttta aagattattt agagtagaca gtaaaggcag tactgaatat caatgaggat    180
ttgcagaacc aacaagtggc ctgcatcaag ctatttaagt gattctattg gtattttact    240
agaaaaggaa ggctaatcat ttttccaatg acggttcata taatccaagt tttaaatgtt    300
ttgtatcatc ataataggqg tatctgaaag gcataaatca acgaaagtga tagaaattac    360
ttattaaaca acgtatttac atccacgttt tttgctggaa gtactgaatc tgcctactgc    420
tagtttgggg aagataataa tacacaaaat aaagacgatg atgaagattc cagttttttt    480
```

| | | |
|---|---|---|
| taaagataaa aaaatagata tatatgtata attgtacgaa tagttttaat aataacttat | 540 | |
| gttgctattt tgatagcaat tcattttact attgaaaagg ttaccggggc aaataatatg | 600 | |
| tttagcacat cagattctgt actaataata atatagacat atgctataac gtcaggcaat | 660 | |
| acttatgtgt atagcgaaat agtaaagggc tcgtcgtaaa tcgtatgttt tcacgactta | 720 | |
| gactcataag acatgtctag aagcccaacc aatgaattag aggactgttt gatatcaaca | 780 | |
| tccagtcact ttgagtgtaa taaaactatt ta | 812 | |

<210> SEQ ID NO 159
<211> LENGTH: 811
<212> TYPE: DNA
<213> ORGANISM: Artificial Sequence
<220> FEATURE:
<223> OTHER INFORMATION: centromere-like sequence (CEN-L) CEN0.8-6

<400> SEQUENCE: 159

| | | |
|---|---|---|
| tctagctatt ttgtttaggt tgggtaaaaa cctacggaaa gacaatagga gcttaggcta | 60 | |
| tctattgata gatcaattat ttgttttaag aactatagaa ttaaaaacaa ggcagtagtt | 120 | |
| gtagatttta aagattattt agagtagaca gtaaaggcag tactgaatat caatgaggat | 180 | |
| ttgcagaacc aacaagtggc ctgcatcaag ctatttaagt gattctattg gtattttact | 240 | |
| agaaaaggaa ggctaatcat ttttccaatg acggttcata taatccaagt tttaaatggt | 300 | |
| ttgcatcatc ataatagggg tatctaaaag gcataaatcg acgaaagtga taaaaattac | 360 | |
| ttattaaacg acgtatttac atccacgttt ttgctggaag tactgaatct gcctactgct | 420 | |
| agtttgggga agacaataat acacaaaata aagacgatga tgaagattcc agttttttt | 480 | |
| aaagataaaa aaatagatat atatgtataa ttgtatgaat agttttaata ataacttatg | 540 | |
| ttgctatttt gatagcaatt cattttacta ttgaaaaggt taccggggca aataatatgt | 600 | |
| ttagcacatc agattctgta ctaataataa tatagagtta tgttataacg tcaggcaata | 660 | |
| cttatgtgta tagcgaaata gtaaatggca gatcgtaaac cgtatgtttt cactactcag | 720 | |
| actcatacga catgtctaga agcccaacca atgaattaga ggactgtttg gtatcaacat | 780 | |
| ccagtcactt tgagtgtaat aaaactattt a | 811 | |

<210> SEQ ID NO 160
<211> LENGTH: 812
<212> TYPE: DNA
<213> ORGANISM: Artificial Sequence
<220> FEATURE:
<223> OTHER INFORMATION: centromere-like sequence (CEN-L) CEN0.8-8

<400> SEQUENCE: 160

| | | |
|---|---|---|
| tctagctatt ttgtttaggt tgggtaaaaa cctacggaaa gacaattgga gcttaggcta | 60 | |
| tctattgata gatcaattat ttgttttaag aactatagaa ttaaaaacaa ggcagtagtt | 120 | |
| gtagatttta aagattattt agagtagata gtaaaggctg tactgaatat caatgaggat | 180 | |
| ttgcagaacc aacaagtggc ctgcatcaag ctatttaagt gattctattg gtattttact | 240 | |
| agaaaaggaa ggctaatcat ttttccaatg acggttcata taatccaagt tttaaatgtt | 300 | |
| ttgtatcatc ataatagggg tatctgaaag gcataaatca acgaaagtga tagaaattac | 360 | |
| ttattaaaca acgtatttac atccacgttt tttgctggaa gtactgaatc tgcctactgc | 420 | |
| tagtttgggg aagataataa tacacaaaat aaagacgatg atgaagattc cagttttttt | 480 | |
| taaagataaa aaaatagata tatatgtata attgtacgaa tagttttaat aataacttat | 540 | |
| gttgctattt tgatagcaat tcattttact attgaaaagg ttaccggggc aaataatatg | 600 | |

-continued

```
tttagcacat cagattctgt actaataata atatagacat atgctataac gtcaggcaat    660
acttatgtgt atagcgaaat agtaaagggc tcgtcgtaaa tcgtatgttt tcacgactta    720
gactcataag acatgtctag aagcccaacc aatgaattag aggactgttt gatatcaaca    780
tccagtcact ttgagtgtaa taaaactatt ta    812
```

<210> SEQ ID NO 161
<211> LENGTH: 811
<212> TYPE: DNA
<213> ORGANISM: Artificial Sequence
<220> FEATURE:
<223> OTHER INFORMATION: centromere-like sequence (CEN-L) CEN0.8-9

<400> SEQUENCE: 161

```
tctagctatt tgtttaggt tgggtaaaaa cctacggaaa gacaataggg gcttaggcta     60
tctattgata gatcaattat ttgttttaag aactatagaa ttaaaaacaa ggcagtagtt    120
gtagatttta aagattattt agagtagata gtaaaggctg tactgaatat caatgaggat    180
ttgcagaacc aacaagtggc ctgcatcaag ctatttaagt gattctattg gtattttact    240
agaaaaggaa ggctaatcat ttttccaatg acggttcata taatccaagt tttaaatggt    300
ttgcatcatc ataatagggg tatctaaaag gcataaatcg acgaaagtga taaaaattac    360
ttattaaacg acgtatttac atccacgttt tgctggaag tactgaatct gcctactgct     420
agtttgggga agacaataat acacaaaata aagacgatga tgaagattcc agttttttt     480 aaagataaaa aatagatat atatgtataa ttgtacgaat agttttaata ataacttatg     540
ttgctatttt gatagcaatt cattttacta ttgaaaaggt taccggggca ataatatgt     600 ttagcacatc agattctgta ctaataataa tatagacata tgctataacg tcaggcaata    660
cttatgtgta tagcgaaata gtaaagggct cgtcgtaaat cgtatgtttt cacgacttag    720
actcataaga catgtctaga agcccaacca atgaattaga ggactgtttg atatcaacat    780
ccagtcactt tgagtgtaat aaaactattt a    811
```

<210> SEQ ID NO 162
<211> LENGTH: 812
<212> TYPE: DNA
<213> ORGANISM: Artificial Sequence
<220> FEATURE:
<223> OTHER INFORMATION: centromere-like sequence (CEN-L) CEN0.8-10

<400> SEQUENCE: 162

```
tctagctatt tgtttaggt tgggtaaaaa cctacggaaa gacaattgga gcttaggcta     60
tctattgata gatcaattat ttgttttaag aactatagaa ttaaaaacaa ggcagtagtt    120
gtagatttta aagattattt agagtagata gtaaaggcag tactgaatat caatgaggat    180
ttgcagaacc aacaagtggc ctgcatcaag ctatttaagt gattctattg gtattttact    240
agaaaaggaa ggctaatcat ttttccaatg acggttcata taatccaagt tttaaatgtt    300
ttgtatcatc ataatagggg tatctgaaag gcataaatca acgaaagtga tagaaattac    360
ttattaaaca acgtatttac atccacgttt tttgctggaa gtactgaatc tgcctactgc    420
tagtttgggg aagataataa tacacaaaat aaagacgatg atgaagattc cagttttttt    480
taaagataaa aaatagata tatatgtata attgtacgaa tagttttaat aataacttat     540
gttgctattt tgatagcaat tcattttact attgaaaagg ttaccggggc aaataatatg    600
tttagcacat cagattctgt actaataata atatagacat atgctataac gtcaggcaat    660
```
acttatgtgt atagcgaaat agtaaagggc tcgtcgtaaa tcgtatgttt tcacgactta    720
gactcataag acatgtctag aagcccaacc aatgaattag aggactgttt gatatcaaca    780
tccagtcact ttgagtgtaa taaaactatt ta    812

<210> SEQ ID NO 163
<211> LENGTH: 812
<212> TYPE: DNA
<213> ORGANISM: Artificial Sequence
<220> FEATURE:
<223> OTHER INFORMATION: centromere-like sequence (CEN-L) Consensus
      sequence

<400> SEQUENCE: 163
tctagctatt tgtttaggt tgggtaaaaa cctacggaaa gacaatagga gcttaggcta    60
tctattgata gatcaattat tgttttaag aactatagaa ttaaaaacaa ggcagtagtt    120
gtagatttta aagattattt agagtagata gtaaaggctg tactgaatat caatgaggat    180
ttgcagaacc aacaagtggc ctgcatcaag ctatttaagt gattctattg gtattttact    240
agaaaaggaa ggctaatcat ttttccaatg acggttcata taatccaagt tttaaatggt    300
ttgcatcatc ataatagggg tatctgaaag gcataaatca acgaaagtga tagaaattac    360
ttattaaaca acgtatttac atccacgttt tttgctggaa gtactgaatc tgcctactgc    420
tagtttgggg aagacaataa tacacaaaat aaagacgatg atgaagattc cagtttttt    480 taaagataaa aaatagata tatatgtata attgtatgaa tagtttttaat aataacttat    540 gttgctattt tgatagcaat tcattttact attgaaaagg ttaccggggc aaataatatg    600
tttagcacat cagattctgt actaataata atatagacat atgctataac gtcaggcaat    660
acttatgtgt atagcgaaat agtaaagggc tcgtcgtaaa tcgtatgttt tcacgactta    720
gactcataag acatgtctag aagcccaacc aatgaattag aggactgttt gatatcaaca    780
tccagtcact ttgagtgtaa taaaactatt ta    812

<210> SEQ ID NO 164
<211> LENGTH: 108
<212> TYPE: DNA
<213> ORGANISM: Artificial Sequence
<220> FEATURE:
<223> OTHER INFORMATION: ade2 knockout

<400> SEQUENCE: 164
gcagttgcag actctgttag cgttgaaagc accgagacag cattgcaaaa tgttggtttg    60
aaatttggtt tcccatttat gctgaagtcc aaaactgaag catatgat    108

<210> SEQ ID NO 165
<211> LENGTH: 2907
<212> TYPE: DNA
<213> ORGANISM: Artificial Sequence
<220> FEATURE:
<223> OTHER INFORMATION: Argonaute polypeptide can be g45 Ago

<400> SEQUENCE: 165
atgtcaggag gaagcaacag aggccgtgga ggaatcagag gtgggacacg aggcggtaga    60
ggaggcagag gcggcagggg cggcaaagga agcagaggag gcagaggtgg ggttggtggt    120
ggtgacgcac aggtggtgaa acccgaatat caattcaaac cggagtttga atcacaaatg    180
actgcaccgg atccaacctt cagaattaaa gagttgttgg cccaggaaga gaaaccagaa    240
aaacctggcg atccgtacca actcgtcaaa agacctgggt ttgtaccgt tggtataaag    300

-continued

```
accaaagtcg gtacgaatta cctcaagttc aatgtctcgc acatgaaatt ctggtactat    360
aacgtcacat tccagccgga gattgcagca aagaaaaaaa tcaagaagga tctattggaa    420
atccttctga aaaagtctcc attcagcgga ttgaagggga attatttca taatggctca    480
gacgcaatat attcgtcggc accattgccg atcaaaaggg aggacggaaa agtcagattt    540
gatttccagc aagatgatta caaaggtgtt gtctcctcga ctgtgatggc tgccttaaga    600
ggttcggaga agaagaagac cgaaggtgat cctccagttt attgtaccgt tgaatacatt    660
tataaattgg atatggatga tttgaataac tgggtccaaa ttaaagataa gaaaaacatc    720
gaagctgctg cttacatttc tgccctcaat gttttattgg ttaccaaat tgccaaaaag     780
gccaatgtct tcactgcagg caggtctaag ttcttctttg tcgagcatcc tgaaaaatgc    840
cagtctttcc aaagaggttt atatctagcc agcggttatt atgcttctgt tttaccaact    900
tttgataatg tcatgcttaa cgtgaggccc gttgctggtg cgtttatcaa atcccataat    960
aaggatggta ctccaatgtc tgttgcagat ttagttgcag attatttgg agaaaccgat    1020
ctgaagaagg ttccgaactc tgaaatagtc aaccaaaggt ttttcttcaa aggtatcaaa   1080
attttgagga cttatttggg ccataagtcc aaaccaaagg gtattttttga tataagtagg  1140
tcagatactg ctaacaatta taaattcgac tgtgatggta agcaaacatc agttgctgaa   1200
tactttgcag aaacgtacaa cttgaagctg aagtatcccg atgcgccttt agttcatttg   1260
ggtggcagca attacctacc aatggaagcg tgtatcattg tcccaggtca agagttcaag   1320
ggggaaatct ccgatgtaag gggtattctg agtttcacta cccacagacc tcatgttata   1380
gctggcctag ttcaacaaga gggtatcaag aatttatcaa ctgcaattga tagtgaagaa   1440
tctgctagaa ttggtaaaaa gttggttgtt gtcccttcga gagttttacc agctcctgtt   1500
ctggagtata agaatgcaaa aattgcttat agtgaaaaac cggcagatgg taagtcggaa   1560
aaagccaagg gatcttggga tctaattaac aagcaattct ataatcctgt taaaggtgtc   1620
aagaagttga cggtcttagt tttggaaaat tctaggagac ccctccgtgc gtacgaaaag   1680
gatgacattg aagatgcttg taatgaattt gttaattcag ctgcaaagac aggcgtgaaa   1740
ttcgataaga actatctctt tgaaccagtt tcctatgaca atgtcatgta cctctcgaag   1800
gaaatcatca agtcatgaa accttttacaa tcaaaaactg actacgtttt aacaattttg    1860
aatcagaaag attcacagat ttattcggcg gttaaaactg cactggataa ggatttgggt   1920
atcttgaatc aatgtactct agcaaataag tttgcaaaga gaaaatttgg caagtttgat   1980
ctacaaatgt acgcactgat gagcatgaaa acttgtatta agcttggagg taccaaccat   2040
gtcctatcta agaacgatgt tggtatgctt gtggtagatg gcttgccgac attacttttt   2100
ggtgccgatg tgactcaccc aaccaacaac tccaacggta catctatagc agccgttgtc   2160
ggctctgttg acggacattt caattctttc cctggctcca tctcagttca agaacaaaaa   2220
gtcgaaacta ttgctgaaat gtccaaaatg tgtgttgaaa gaatcatgga atactacaaa   2280
tctgtgggta aattaccaac aagagtattg tttatatagag atggtgtttc attgggccag   2340
ttcaatatta tcttggacga ggaagttaca gcagtcaaga attctttcaa ggttatctcc   2400
aacaacctcg gtattaaatt cgatcctaaa ttaacatttg ttactattct aaagaatcat   2460
agtactagat ttttcccact agaaaagaat gcagctaatt ctcaaggaaa acaagttgca   2520
gtcacagcac aagataatat tattcctggt tctattgttg aaaaaggtgt gacgtcgaga   2580
agtttatacg atttctttct acagtcacaa caggccctac aaggaactgc tattccaggg   2640
cattattatg tgttgtatga cgagaataac tggactccag atgaattaca gaaaattacc   2700
```

-continued

```
tacaatttgt gtagtatatt tggtagggca accaaatcag ttagagttgt tcctcctgca    2760
tattatgcag acttattgtg tgaaagagct acatgttttg taaagaatgt gaaagttctg    2820
aagaaccaat cgccagtgga agctgcaaag aaggctatag gtgatggtat ccacaagaat    2880
gtcaagggta gaatgatcta tatttaa                                        2907
```

<210> SEQ ID NO 166
<211> LENGTH: 968
<212> TYPE: PRT
<213> ORGANISM: Artificial Sequence
<220> FEATURE:
<223> OTHER INFORMATION: Argonaute polypeptides

<400> SEQUENCE: 166

```
Met Ser Gly Gly Ser Asn Arg Gly Arg Gly Gly Ile Arg Gly Gly Thr
1               5                   10                  15

Arg Gly Gly Arg Gly Gly Arg Gly Gly Arg Gly Gly Lys Gly Ser Arg
            20                  25                  30

Gly Gly Arg Gly Gly Val Gly Gly Gly Asp Ala Gln Val Val Lys Pro
        35                  40                  45

Glu Tyr Gln Phe Lys Pro Glu Phe Glu Ser Gln Met Thr Ala Pro Asp
    50                  55                  60

Pro Thr Phe Arg Ile Lys Glu Leu Leu Ala Gln Glu Lys Thr Arg
65                  70                  75                  80

Lys Pro Gly Asp Pro Tyr Gln Leu Val Lys Arg Pro Gly Phe Gly Thr
                85                  90                  95

Val Gly Ile Lys Thr Lys Val Gly Thr Asn Tyr Leu Lys Phe Asn Val
            100                 105                 110

Ser His Met Lys Phe Trp Tyr Tyr Asn Val Thr Phe Gln Pro Glu Ile
        115                 120                 125

Ala Ala Lys Lys Ile Lys Lys Asp Leu Leu Glu Ile Leu Leu Lys
    130                 135                 140

Lys Ser Pro Phe Ser Gly Leu Lys Gly Lys Leu Phe His Asn Gly Ser
145                 150                 155                 160

Asp Ala Ile Tyr Ser Ser Ala Pro Leu Pro Ile Lys Arg Glu Asp Gly
                165                 170                 175

Lys Val Arg Phe Asp Phe Gln Gln Asp Asp Tyr Lys Gly Val Val Ser
            180                 185                 190

Ser Thr Val Met Ala Ala Leu Arg Gly Ser Glu Lys Lys Thr Glu
        195                 200                 205

Gly Asp Pro Pro Val Tyr Cys Thr Val Glu Tyr Ile Tyr Lys Leu Asp
    210                 215                 220

Met Asp Asp Leu Asn Asn Trp Val Gln Ile Lys Asp Lys Lys Asn Ile
225                 230                 235                 240

Glu Ala Ala Ala Tyr Ile Ser Ala Leu Asn Val Leu Leu Gly Tyr Gln
                245                 250                 255

Ile Ala Lys Lys Ala Asn Val Phe Thr Ala Gly Arg Ser Lys Phe Phe
            260                 265                 270

Phe Val Glu His Pro Glu Lys Cys Gln Ser Phe Gln Arg Gly Leu Tyr
        275                 280                 285

Leu Ala Ser Gly Tyr Tyr Ala Ser Val Leu Pro Thr Phe Asp Asn Val
    290                 295                 300

Met Leu Asn Val Arg Pro Val Ala Gly Ala Phe Ile Lys Ser His Asn
305                 310                 315                 320
```

-continued

```
Lys Asp Gly Thr Pro Met Ser Val Ala Asp Leu Val Ala Asp Tyr Phe
            325                 330                 335

Gly Glu Thr Asp Leu Lys Lys Val Pro Asn Ser Glu Ile Val Asn Gln
        340                 345                 350

Arg Phe Phe Lys Gly Ile Lys Ile Leu Arg Thr Tyr Leu Gly His
        355                 360                 365

Lys Ser Lys Pro Lys Gly Ile Phe Asp Ile Ser Arg Ser Asp Thr Ala
        370                 375                 380

Asn Asn Tyr Lys Phe Asp Cys Asp Gly Lys Gln Thr Ser Val Ala Glu
385                 390                 395                 400

Tyr Phe Ala Glu Thr Tyr Asn Leu Lys Leu Lys Tyr Pro Asp Ala Pro
                405                 410                 415

Leu Val His Leu Gly Gly Ser Asn Tyr Leu Pro Met Glu Ala Cys Ile
                420                 425                 430

Ile Val Pro Gly Gln Glu Phe Lys Gly Glu Ile Ser Asp Val Arg Gly
            435                 440                 445

Ile Leu Ser Phe Thr Thr His Arg Pro His Val Ile Ala Gly Leu Val
        450                 455                 460

Gln Gln Glu Gly Ile Lys Asn Leu Ser Thr Ala Ile Asp Ser Glu Glu
465                 470                 475                 480

Ser Ala Arg Ile Gly Lys Lys Leu Val Val Pro Ser Arg Val Leu
                485                 490                 495

Pro Ala Pro Val Leu Glu Tyr Lys Asn Ala Lys Ile Ala Tyr Ser Glu
            500                 505                 510

Lys Pro Ala Asp Gly Lys Ser Glu Lys Ala Lys Gly Ser Trp Asp Leu
        515                 520                 525

Ile Asn Lys Gln Phe Tyr Asn Pro Val Lys Gly Val Lys Lys Leu Thr
        530                 535                 540

Val Leu Val Leu Glu Asn Ser Arg Arg Pro Leu Arg Ala Tyr Glu Lys
545                 550                 555                 560

Asp Asp Ile Glu Asp Ala Cys Asn Glu Phe Val Asn Ser Ala Ala Lys
                565                 570                 575

Thr Gly Val Lys Phe Asp Lys Asn Tyr Leu Phe Glu Pro Val Ser Tyr
                580                 585                 590

Asp Asn Val Met Tyr Leu Ser Lys Glu Ile Ile Lys Val Met Lys Pro
        595                 600                 605

Leu Gln Ser Lys Thr Asp Tyr Val Leu Thr Ile Leu Asn Gln Lys Asp
        610                 615                 620

Ser Gln Ile Tyr Ser Ala Val Lys Thr Ala Leu Asp Lys Asp Leu Gly
625                 630                 635                 640

Ile Leu Asn Gln Cys Thr Leu Ala Asn Lys Phe Ala Lys Arg Lys Phe
                645                 650                 655

Gly Lys Phe Asp Leu Gln Met Tyr Ala Leu Met Ser Met Lys Thr Cys
                660                 665                 670

Ile Lys Leu Gly Gly Thr Asn His Val Leu Ser Lys Asn Asp Val Gly
            675                 680                 685

Met Leu Val Val Asp Gly Leu Pro Thr Leu Leu Gly Ala Asp Val
        690                 695                 700

Thr His Pro Thr Asn Asn Ser Asn Gly Thr Ser Ile Ala Ala Val Val
705                 710                 715                 720

Gly Ser Val Asp Gly His Phe Asn Ser Phe Pro Gly Ser Ile Ser Val
                725                 730                 735

Gln Glu Gln Lys Val Glu Thr Ile Ala Glu Met Ser Lys Met Cys Val
```

```
                         740                 745                 750
Glu Arg Ile Met Glu Tyr Tyr Lys Ser Val Gly Lys Leu Pro Thr Arg
            755                 760                 765

Val Leu Phe Tyr Arg Asp Gly Val Ser Leu Gly Gln Phe Asn Ile Ile
        770                 775                 780

Leu Asp Glu Glu Val Thr Ala Val Lys Asn Ser Phe Lys Val Ile Ser
785                 790                 795                 800

Asn Asn Leu Gly Ile Lys Phe Asp Pro Lys Leu Thr Phe Val Thr Ile
                805                 810                 815

Leu Lys Asn His Ser Thr Arg Phe Phe Pro Leu Glu Lys Asn Ala Ala
            820                 825                 830

Asn Ser Gln Gly Lys Gln Val Ala Val Thr Ala Gln Asp Asn Ile Ile
        835                 840                 845

Pro Gly Ser Ile Val Glu Lys Gly Val Thr Ser Arg Ser Leu Tyr Asp
    850                 855                 860

Phe Phe Leu Gln Ser Gln Gln Ala Leu Gln Gly Thr Ala Ile Pro Gly
865                 870                 875                 880

His Tyr Tyr Val Leu Tyr Asp Glu Asn Asn Trp Thr Pro Asp Glu Leu
                885                 890                 895

Gln Lys Ile Thr Tyr Asn Leu Cys Ser Ile Phe Gly Arg Ala Thr Lys
            900                 905                 910

Ser Val Arg Val Pro Pro Ala Tyr Tyr Ala Asp Leu Leu Cys Glu
        915                 920                 925

Arg Ala Thr Cys Phe Val Lys Asn Val Lys Val Leu Lys Asn Gln Ser
    930                 935                 940

Pro Val Glu Ala Ala Lys Lys Ala Ile Gly Asp Gly Ile His Lys Asn
945                 950                 955                 960

Val Lys Gly Arg Met Ile Tyr Ile
                965

<210> SEQ ID NO 167
<211> LENGTH: 2331
<212> TYPE: DNA
<213> ORGANISM: Artificial Sequence
<220> FEATURE:
<223> OTHER INFORMATION: dicer 1 polypeptide

<400> SEQUENCE: 167
atgcaaagca gcaattgcac agatgtgttg agtgagctta aagatgcggt tcaaatgtt       60 cgaacgggac taagaaaagt actggatatt gctccaaatc ggaccttata tcaaatatta     120
cttgattcaa ctaaaaaccc ccttcttcag agtattttga gtattccaga tgaatctcat     180
ttgactcaaa tgatatttat cttttgcaatt gaattaaagg aaatgtatga tactggaagg     240
ctggaaatct tggaatatct cataaaagga gatattgaac agattaaaac gtgtaacgga     300
aataccaaac aggaaacttt cgaaaataat agcccaaacg atagttcatc taagtttcat     360
gaagacaata tccctaatta taggaaaaaa cttgaaacat gtgatggtac tgaaatattt     420
attgaggaag ttggtaaaga caaagtaagg aattcaaata gttttgagag tacgccagat     480
aacatttctt catcgaattg taggaaagat gaaacccgct cagcggttga tcaacgagat     540
gcagagaccg aaaaagaggt gaattccaat gcgaaagaac cggactctta catcagtgaa     600
ttatttacat cggacgtaat gagaagtgag atgtacgtgc agaggaact  agtttataaa     660 cgagatagaa agtggggcct tttgaaacaa gaagaattgc cacaagctcc tagtattgaa     720
gatccggaac ttctgagaaa ggttttcagt catcagtcaa tagtcaatta tttgaatatt     780
```

```
tcgcctgagt tcaaggtcca attacataac gagagattgg aattcttagg tgatgcatta    840
ttacaattcg tcacgtcaat gattatctat gaaaggtttc ccaattttag tgaaggtcaa    900
ttatcgatac tacggagcac tatcgtgtct aactccagtt tacttaaatg gtcacaaatg    960
tatggctttg ataaacaact acgtaagaat cttatcgatt cttccatctt agcaggtaat   1020
aataaattat atgccgatat ttttgaggct taccttggcg gtattgctga acagtatatg   1080
atggaaacca gcgaagggga aaccaatgtg aacgacttta tgaaaggatg gtttgaagtc   1140
aaatcatgga ttgaagagtt atccgaaaat catatacgtg ggtttgatcc aagtattgtt   1200
ttcaagatgc agtattccaa atctagcaag caagatctga ggttattact tggccagaat   1260
aacaaccccg attatatcag agtaaacctg agcaataaga gaatcttgtc ttgtataaag   1320
gtgaataata aagtgtacgg atatggtatt ggtactagca caaagaagc cgatgcaagg   1380
gcagccgttg atgcaatatc caccccagaa attaggaaga tttgtccaga agatatatgg   1440
gatagatttg aaagcaacgt aggtctaaat gagaaaggag gattgaaatt gagacaatac   1500
cctacgaagg tgacctcaca tgagctgcaa atcctgaaga aggaaatcgc cattaagttt   1560
aagaatggcg atatcaagct gcttgcctct gagaataatc caaacagttt attaataacc   1620
aatcaagata gaatggaggt ggctgaaaaa agggacagta tactctcaat agataataca   1680
gagggtgaat cagacaccag tcaaattgag gagagtaaag aagtatttga acattctcgt   1740
aatcgaccta ctccttgcgga tgactgtatg gagcagaaga gagggtgaa agagaaggta   1800
agtgccagac agaaaaagga aaagcaaaga aaaccacaaa tagagatggt gaaggagcaa   1860
gagatgaaga atttcaagga gagcacacag tactattcga aggaatacac tttaggtcga   1920
ggtggtgttt ttgggtctga aagtgccaag gttcgtaagg gtaaacagaa gaagcgtcgt   1980
gggatttgta gaaatgcggc ctttgaagtg gtggataatg acaataatga tggacgttct   2040
gacacgttca tcattgaatg tcatgaggtc tacgagagtt gcgatgagat agacgtggag   2100
agtaagaacc ggatatatgc tgcctatgat agacgggggt ccaatcccaa cttccggatt   2160
tatagaacga caaacgatga gtacctaagc gagctatggt ttggtagttt acagatagtc   2220
tcctatggtc ttgacaaaaa caagaaaaaa gcttctcaaa aggcagcaat gctagcatgt   2280
aaacgtgagg actattatgg tttagatgat agcaatgaaa atgatccata a             2331
```

<210> SEQ ID NO 168  
<211> LENGTH: 776  
<212> TYPE: PRT  
<213> ORGANISM: Artificial Sequence  
<220> FEATURE:  
<223> OTHER INFORMATION: dicer 1 polypeptide

<400> SEQUENCE: 168

```
Met Gln Ser Ser Asn Cys Thr Asp Val Leu Ser Glu Leu Lys Asp Ala
1               5                   10                  15

Val Gln Asn Val Arg Thr Gly Leu Arg Lys Val Leu Asp Ile Ala Pro
            20                  25                  30

Asn Arg Thr Leu Tyr Gln Ile Leu Leu Asp Ser Thr Lys Asn Pro Leu
        35                  40                  45

Leu Gln Ser Ile Leu Ser Ile Pro Asp Glu Ser His Leu Thr Gln Asn
    50                  55                  60

Asp Ile Ile Phe Ala Ile Glu Leu Lys Glu Met Tyr Asp Thr Gly Arg
65                  70                  75                  80

Leu Glu Ile Leu Glu Tyr Leu Ile Lys Gly Asp Ile Glu Gln Ile Lys
```

```
                        85                  90                  95
Thr Cys Asn Gly Asn Thr Lys Gln Glu Thr Phe Glu Asn Asn Ser Pro
                    100                 105                 110

Asn Asp Ser Ser Ser Lys Phe His Glu Asp Asn Ile Pro Asn Tyr Lys
                    115                 120                 125

Glu Lys Leu Glu Thr Cys Asp Gly Thr Glu Ile Phe Ile Glu Glu Val
130                 135                 140

Gly Lys Asp Lys Val Arg Asn Ser Asn Ser Phe Glu Ser Thr Pro Asp
145                 150                 155                 160

Asn Ile Ser Ser Asn Cys Arg Lys Asp Glu Thr Arg Ser Ala Val
                165                 170                 175

Asp Gln Arg Asp Ala Glu Thr Glu Lys Glu Val Asn Ser Asn Ala Lys
                180                 185                 190

Glu Pro Asp Ser Tyr Ile Ser Glu Leu Phe Thr Ser Asp Val Met Arg
                195                 200                 205

Ser Glu Met Tyr Val Pro Glu Glu Leu Val Tyr Lys Arg Asp Arg Lys
                210                 215                 220

Trp Gly Leu Leu Lys Gln Glu Glu Leu Pro Gln Ala Pro Ser Ile Glu
225                 230                 235                 240

Asp Pro Glu Leu Leu Arg Lys Val Phe Ser His Gln Ser Ile Val Asn
                245                 250                 255

Tyr Leu Asn Ile Ser Pro Glu Phe Lys Val Gln Leu His Asn Glu Arg
                260                 265                 270

Leu Glu Phe Leu Gly Asp Ala Leu Leu Gln Phe Val Thr Ser Met Ile
                275                 280                 285

Ile Tyr Glu Arg Phe Pro Asn Phe Ser Glu Gly Gln Leu Ser Ile Leu
                290                 295                 300

Arg Ser Thr Ile Val Ser Asn Ser Ser Leu Leu Lys Trp Ser Gln Met
305                 310                 315                 320

Tyr Gly Phe Asp Lys Gln Leu Arg Lys Asn Leu Ile Asp Ser Ser Ile
                325                 330                 335

Leu Ala Gly Asn Asn Lys Leu Tyr Ala Asp Ile Phe Glu Ala Tyr Leu
                340                 345                 350

Gly Gly Ile Ala Glu Gln Tyr Met Met Glu Thr Ser Glu Gly Glu Thr
                355                 360                 365

Asn Val Asn Asp Phe Met Lys Gly Trp Phe Glu Val Lys Ser Trp Ile
                370                 375                 380

Glu Glu Leu Ser Glu Asn His Ile Arg Gly Phe Asp Pro Ser Ile Val
385                 390                 395                 400

Phe Lys Met Gln Tyr Ser Lys Ser Lys Gln Asp Leu Arg Leu Leu
                405                 410                 415

Leu Gly Gln Asn Asn Pro Asp Tyr Ile Arg Val Asn Leu Ser Asn
                420                 425                 430

Lys Arg Ile Leu Ser Cys Ile Lys Val Asn Lys Val Tyr Gly Tyr
                435                 440                 445

Gly Ile Gly Thr Ser Asn Lys Glu Ala Asp Ala Arg Ala Val Asp
                450                 455                 460

Ala Ile Ser Asn Pro Glu Ile Arg Lys Ile Cys Pro Glu Asp Ile Trp
465                 470                 475                 480

Asp Arg Phe Glu Ser Asn Val Gly Leu Asn Glu Lys Gly Gly Leu Lys
                485                 490                 495

Leu Arg Gln Tyr Pro Thr Lys Val Thr Ser His Glu Leu Gln Ile Leu
                500                 505                 510
```

Lys Lys Glu Ile Ala Ile Lys Phe Lys Asn Gly Asp Ile Lys Leu Leu
            515                 520                 525

Ala Ser Glu Asn Asn Pro Asn Ser Leu Leu Ile Thr Asn Gln Asp Arg
        530                 535                 540

Met Glu Val Ala Glu Lys Arg Asp Ser Ile Leu Ser Ile Asp Asn Thr
545                 550                 555                 560

Glu Gly Glu Ser Asp Thr Ser Gln Ile Glu Glu Ser Lys Glu Val Phe
                565                 570                 575

Glu His Ser Arg Asn Arg Pro Thr Leu Ala Asp Asp Cys Met Glu Gln
            580                 585                 590

Lys Lys Arg Val Lys Glu Lys Val Ser Ala Arg Gln Lys Lys Glu Lys
        595                 600                 605

Gln Arg Lys Pro Gln Ile Glu Met Val Lys Gln Glu Met Lys Asn
        610                 615                 620

Phe Lys Glu Ser Thr Gln Tyr Tyr Ser Lys Glu Tyr Thr Leu Gly Arg
625                 630                 635                 640

Gly Gly Val Phe Gly Ser Glu Ser Ala Lys Val Arg Lys Gly Lys Gln
                645                 650                 655

Lys Lys Arg Arg Gly Ile Cys Arg Asn Ala Ala Phe Glu Val Val Asp
            660                 665                 670

Asn Asp Asn Asn Asp Gly Arg Ser Asp Thr Phe Ile Ile Glu Cys His
        675                 680                 685

Glu Val Tyr Glu Ser Cys Asp Glu Ile Asp Val Glu Ser Lys Asn Arg
        690                 695                 700

Ile Tyr Ala Ala Tyr Asp Arg Arg Gly Ser Asn Pro Asn Phe Arg Ile
705                 710                 715                 720

Tyr Arg Thr Thr Asn Asp Glu Tyr Leu Ser Glu Leu Trp Phe Gly Ser
                725                 730                 735

Leu Gln Ile Val Ser Tyr Gly Leu Asp Lys Asn Lys Lys Ala Ser
                740                 745                 750

Gln Lys Ala Ala Met Leu Ala Cys Lys Arg Glu Asp Tyr Tyr Gly Leu
        755                 760                 765

Asp Asp Ser Asn Glu Asn Asp Pro
    770                 775

<210> SEQ ID NO 169
<211> LENGTH: 1980
<212> TYPE: DNA
<213> ORGANISM: Artificial Sequence
<220> FEATURE:
<223> OTHER INFORMATION: Dicer 2 polypeptide

<400> SEQUENCE: 169

| | |
|---|---|
| atgagcaaaa gagctttagg cgaggtagaa tcttcagtgg ttgaggaaaa agttttaaag | 60 |
| aagaagcaaa aacttgataa acaagacaaa gaaaaagaca aaaagtccaa gcgatctaaa | 120 |
| agagacaaat ctgaagactc taaaaatctc aaggaaaaga ggaaggacaa atacggtgtc | 180 |
| aactccaaaa atgcagatgg ccaaaattta gagaaaatcg aacctgctat tatcaagcag | 240 |
| attgcaattt ctgatttgat gtcagttgag cattcagttt gtgtcattca agagaatttg | 300 |
| aaaaagctca tgcagttagc accaaactta agagacctag aacaatatac gaactttctt | 360 |
| attgcacaat caacaaagtc aggtatgggt accatggtg atattactgc caaatattg | 420 |
| ttgttatcaa aatctcataa aattcagttg gcatctcagt tgaaaacatt atcagagaat | 480 |
| ggtcagttgc cgattgttaa acaaataata gactttgaca cgacacagt tctggaaaat | 540 |

-continued

```
gtaagtgacg tgcagctaaa gttaaaggag aagaacaggg agctacatcg tggtggaact    600
tcctcagaag ctttcaactc gctacttcca ccactaccta caattgacga ttctgtgcta    660
gaagccaaag tgtttgttca taatctgct actaacaatg agttattatc ttcgaaacaa    720
gataccgtgc agtctaacaa cgaaaggcta gaattcctag gtgatgctgt cttggagacc    780
gtcatctcgg atgtcattga atatagatat agaggatttg atgaagggca actatcatct    840
ctaagatcta cattggttaa aaatgagaca attgaattac tttcgagagc ctataaattt    900
ccagaacgtc aaatggaatt gctagattct catatggtga agactgaact tacagaattc    960
aaagtaggca aaataagag aatcgctgat ttatttgaag cgtatattgg tgctctattt    1020
atagacaagg gaagaaatgg accggcttac gactttatta aggactggct gtcaaaagtt    1080
tattctccca ttttaaagga gtttgatggt tttgaccatt tgaagtatct ccatgttagt    1140
tccaaattgc gtaaccaact attaagcgaa accccagaaa ccgttgcatg caaagcagat    1200
cagaataaat caaacatat tcagttcgac accttagact ccgaggaaga taaggtgtct    1260
gaggtggaga gtacatcttc agcaaccgta ctagagaaag aactgaaatt tccaatcact    1320
tttacgtcct cggaacctgt gaacaaactt gctaagggag aactatatgc acttatagga    1380
agtgctaaac tacatccaat ttacaagaat gaaaaatctc aaaacgatag taaacactat    1440
ttgacaacat gctccattgc ggaggatatt ctagggtacg gtgaaggtag aaaccttaag    1500
gattctagtg cacgtgcggc tcaagctgcg ttactgaata aaccgatgat tgaaaagtat    1560
catttactga gaatgatgac tccacgttcg gaaacacgag caagtcaaaa actagagttt    1620
gtggagaaac cagaagttgc tagtagcacc acgcttaagc agtacacacc taagtttttg    1680
aagactgttc aatatatcgg taaagatgaa attcccactc ctaacagctc ttcaaagaac    1740
aagcttgtcg atttattggc taagaaaggg gttgttccta ggtaccacgt cgaagaagac    1800
aaggaaaata agagtatttt gccgatgttc agaaccactt tgaaagtcaa cgatatcgat    1860
gttgcatatt gtattgatgc cagtaaaaag aagggattaa acaaggtatc tcaatggtta    1920
ctacagaaaa ttgaagaagt aggtgaaaaa actatttacc atgatctaaa gctggaataa   1980
```

<210> SEQ ID NO 170
<211> LENGTH: 659
<212> TYPE: PRT
<213> ORGANISM: Artificial Sequence
<220> FEATURE:
<223> OTHER INFORMATION: Dicer 2 polypeptide

<400> SEQUENCE: 170

```
Met Ser Lys Arg Ala Leu Gly Glu Val Glu Ser Ser Val Val Glu Glu
1               5                   10                  15

Lys Val Leu Lys Lys Gln Lys Leu Asp Lys Gln Asp Lys Glu Lys
            20                  25                  30

Asp Lys Lys Ser Lys Arg Ser Lys Arg Asp Lys Ser Glu Asp Ser Lys
        35                  40                  45

Asn Leu Lys Glu Lys Arg Lys Asp Lys Tyr Gly Val Asn Ser Lys Asn
    50                  55                  60

Ala Asp Gly Gln Asn Leu Glu Lys Ile Glu Pro Ala Ile Ile Lys Gln
65                  70                  75                  80

Ile Ala Ile Ser Asp Leu Met Ser Val Glu His Ser Val Cys Val Ile
                85                  90                  95

Gln Glu Asn Leu Lys Lys Leu Met Gln Leu Ala Pro Asn Leu Arg Asp
            100                 105                 110
```

-continued

```
Leu Glu Gln Tyr Thr Asn Phe Leu Ile Ala Gln Ser Thr Lys Ser Gly
            115                 120                 125

Met Gly Thr Asn Gly Asp Ile Thr Ala Lys Ile Leu Leu Ser Lys
130                 135                 140

Ser His Lys Ile Gln Leu Ala Ser Gln Leu Lys Thr Leu Ser Glu Asn
145                 150                 155                 160

Gly Gln Leu Pro Ile Val Lys Gln Ile Asp Phe Asp Asn Asp Thr
                165                 170                 175

Val Leu Glu Asn Val Ser Asp Val Gln Leu Lys Leu Lys Glu Lys Asn
                180                 185                 190

Arg Glu Leu His Arg Gly Gly Thr Ser Ser Glu Ala Phe Asn Ser Leu
            195                 200                 205

Leu Pro Pro Leu Pro Thr Ile Asp Asp Ser Val Leu Glu Ala Lys Val
210                 215                 220

Phe Val His Lys Ser Ala Thr Asn Asn Glu Leu Leu Ser Ser Lys Gln
225                 230                 235                 240

Asp Thr Val Gln Ser Asn Asn Glu Arg Leu Glu Phe Leu Gly Asp Ala
                245                 250                 255

Val Leu Glu Thr Val Ile Ser Asp Val Ile Glu Tyr Arg Tyr Arg Gly
            260                 265                 270

Phe Asp Glu Gly Gln Leu Ser Ser Leu Arg Ser Thr Leu Val Lys Asn
            275                 280                 285

Glu Thr Ile Glu Leu Leu Ser Arg Ala Tyr Lys Phe Pro Glu Arg Gln
        290                 295                 300

Met Glu Leu Leu Asp Ser His Met Val Lys Thr Glu Leu Thr Glu Phe
305                 310                 315                 320

Lys Val Gly Lys Asn Lys Arg Ile Ala Asp Leu Phe Glu Ala Tyr Ile
                325                 330                 335

Gly Ala Leu Phe Ile Asp Lys Gly Arg Asn Gly Pro Ala Tyr Asp Phe
            340                 345                 350

Ile Lys Asp Trp Leu Ser Lys Val Tyr Ser Pro Ile Leu Lys Glu Phe
        355                 360                 365

Asp Gly Phe Asp His Leu Lys Tyr Leu His Val Ser Ser Lys Leu Arg
    370                 375                 380

Asn Gln Leu Leu Ser Glu Thr Pro Glu Thr Val Ala Cys Lys Ala Asp
385                 390                 395                 400

Gln Asn Lys Ser Lys His Ile Gln Phe Asp Thr Leu Asp Ser Glu Glu
                405                 410                 415

Asp Lys Val Ser Glu Val Ser Thr Ser Ser Ala Thr Val Leu Glu
            420                 425                 430

Lys Glu Leu Lys Phe Pro Ile Thr Phe Thr Ser Ser Glu Pro Val Asn
        435                 440                 445

Lys Leu Ala Lys Gly Glu Leu Tyr Ala Leu Ile Gly Ser Ala Lys Leu
    450                 455                 460

His Pro Ile Tyr Lys Asn Glu Lys Ser Gln Asn Asp Ser Lys His Tyr
465                 470                 475                 480

Leu Thr Thr Cys Ser Ile Ala Glu Asp Ile Leu Gly Tyr Gly Glu Gly
                485                 490                 495

Arg Asn Leu Lys Asp Ser Ser Ala Arg Ala Ala Gln Ala Ala Leu Leu
            500                 505                 510

Asn Lys Pro Met Ile Glu Lys Tyr His Leu Leu Arg Met Met Thr Pro
        515                 520                 525
```

```
Arg Ser Glu Thr Arg Ala Ser Gln Lys Leu Glu Phe Val Glu Lys Pro
    530                 535                 540

Glu Val Ala Ser Ser Thr Thr Leu Lys Gln Tyr Thr Pro Lys Phe Leu
545                 550                 555                 560

Lys Thr Val Gln Tyr Ile Gly Lys Asp Glu Ile Pro Thr Pro Asn Ser
                565                 570                 575

Ser Ser Lys Asn Lys Leu Val Asp Leu Leu Ala Lys Lys Gly Val Val
            580                 585                 590

Pro Arg Tyr His Val Glu Glu Asp Lys Glu Asn Lys Ser Ile Leu Pro
        595                 600                 605

Met Phe Arg Thr Thr Leu Lys Val Asn Asp Ile Asp Val Ala Tyr Cys
    610                 615                 620

Ile Asp Ala Ser Lys Lys Lys Gly Leu Asn Lys Val Ser Gln Trp Leu
625                 630                 635                 640

Leu Gln Lys Ile Glu Glu Val Gly Leu Lys Thr Ile Tyr His Asp Leu
                645                 650                 655

Lys Leu Glu

<210> SEQ ID NO 171
<211> LENGTH: 2103
<212> TYPE: DNA
<213> ORGANISM: Artificial Sequence
<220> FEATURE:
<223> OTHER INFORMATION: Dicer 3 polypeptide

<400> SEQUENCE: 171
atgaaaattc caccttcacg gatcgactgt atacaggatt ttttttttt ttttcaaacg      60 ttttcttgc ttaatctttt gtatattatt atagaggcag ataattctcg aatatcgtca    120
acaatgagca aaagagcttt aggcgaggta gaatcttcag tggttgagga aaaagtttta    180
aagaagaagc aaaaacttga taaacaagac aaagaaaaag acaaaaagtc caagcgatct    240
aaaagagaca atctgaaga ctctaaaaat ctcaaggaaa agaggaagga caaatacggt    300
gtcaactcca aaatgcaga tggccaaaat ttagagaaaa tcgaacctgc tattatcaag    360
cagattgcaa tttctgattt gatgtcagtt gagcattcag tttgtgtcat tcaagagaat    420
ttgaaaaagc tcatgcagtt agcaccaaac ttaagagacc tagaacaata tacgaacttt    480
cttattgcac aatcaacaaa gtcaggtatg ggtaccaatg gtgatattac tgccaaaata    540 tgttgttat caaatctca taaaattcag ttggcatctc agttgaaaac attatcagag    600
aatggtcagt gccgattgt taaacaaata atagactttg acaacgacac agttctggaa    660
aatgtaagtg acgtgcagct aaagttaaag gagaagaaca gggagctaca tcgtggtgga    720
acttcctcag aagctttcaa ctcgctactt ccaccactac ctacaattga cgattctgtg    780
ctagaagcca aagtgtttgt tcataaatct gctactaaca atgagttatt atcttcgaaa    840
caagataccg tgcagtctaa caacgaaagg ctagaattcc taggtgatgc tgtcttggag    900
accgtcatct cggatgtcat tgaatataga tatagaggat ttgatgaagg caactatca    960 tctctaagat ctacattggt taaaaatgag acaattgaat tactttcgag agcctataaa   1020
tttccagaac gtcaaatgga attgctagat tctcatatgg tgaagactga acttacagaa   1080
ttcaaagtag gcaaaaataa gagaatcgct gatttatttg aagcgtatat tggtgctcta   1140
tttatagaca aggaagaaa tggaccggct tacgactta ttaaggactg gctgtcaaaa   1200
gtttattctc ccatttaaa ggagtttgat ggttttgacc atttgaagta tctccatgtt   1260
agttccaaat tgcgtaacca actattaagc gaaaccccag aaaccgttgc atgcaaagca   1320
```

```
gatcagaata aatcaaaaca tattcagttc gacaccttag actccgagga agataaggtg    1380
tctgaggtgg agagtacatc ttcagcaacc gtactagaga aagaactgaa atttccaatc    1440
acttttacgt cctcggaacc tgtgaacaaa cttgctaagg gagaactata tgcacttata    1500
ggaagtgcta aactacatcc aatttacaag aatgaaaaat ctcaaaacga tagtaaacac    1560
tatttgacaa catgctccat tgcggaggat attctagggt acggtgaagg tagaaacctt    1620
aaggattcta gtgcacgtgc ggctcaagct gcgttactga ataaaccgat gattgaaaag    1680
tatcatttac tgagaatgat gactccacgt tcggaaacac gagcaagtca aaaactagag    1740
tttgtggaga aaccagaagt tgctagtagc accacgctta agcagtacac acctaagttt    1800
ttgaagactg ttcaatatat cggtaaagat gaaattccca ctcctaacag ctcttcaaag    1860
aacaagcttg tcgatttatt ggctaagaaa ggggttgttc ctaggtacca cgtcgaagaa    1920
gacaaggaaa ataagagtat tttgccgatg ttcagaacca ctttgaaagt caacgatatc    1980
gatgttgcat attgtattga tgccagtaaa aagaagggat taaacaaggt atctcaatgg    2040
ttactacaga aaattgaaga agtaggtgaa aaaactattt accatgatct aaagctggaa    2100
taa                                                                 2103
```

GENETIC TOOLBOX FOR METABOLIC ENGINEERING OF NON-CONVENTIONAL YEAST

PRIORITY

This application claims the benefit of U.S. Ser. No. 62/979,798, filed Feb. 21, 2020, which is incorporated by reference herein in its entirety.

STATEMENT REGARDING FEDERALLY SPONSORED RESEARCH OR DEVELOPMENT

This invention was made with government support under DE-SC0018260 and DE-SC0018420 awarded by the U.S. Department of Energy. The government has certain rights in the invention.

INCORPORATION BY REFERENCE OF SEQUENCE LISTING

The instant application contains a Sequence Listing which has been submitted in ASCII format via EFS-Web and is hereby incorporated by reference in its entirety. Said ASCII copy, created on Jun. 18, 2021, is named "428262-000075 seq id_ST25" and is 389,692 bytes in size.

BACKGROUND OF THE INVENTION

*Saccharomyces cerevisiae* has been regarded as a preferred workhorse in synthetic biology and metabolic engineering due to its well-characterized physiology and to the availability of powerful genetic modification tools. However, *S. cerevisiae* is far from being the only yeast available, and many non-conventional yeasts have emerged as attractive production hosts due to their highly unusual metabolic, biosynthetic, physiological, and fermentative capacities. Owing to its extraordinary tolerance to multiple stresses including extremely low pH conditions, *Issatchenkia orientalis* (also named *Pichia kudriavzevii* or *Candida krusei*) is a promising platform microorganism for the manufacture of organic acids. It can be used in ethanol fermentation at pH 2 and engineered to produce D-xylonate, succinic acid, itaconic acid, muconic acid and D-lactic acid.

However, the tools for genetic engineering of non-conventional yeasts such as *I. orientalis* remain very limited, which significantly prohibits extensive metabolic engineering efforts and sophisticated genetic manipulations. For example, stable episomal plasmid, efficient genome editing tools, and strong constitutive promoters and terminators are foundational technologies that are not available for efficient engineering.

Episomal plasmids for *Saccharomyces cerevisiae* include centromere-based low-copy number plasmids and 2µ-based high-copy number plasmids. However, there is no stable episomal plasmid or core functional element, such as an autonomously replicating sequence (ARS) for non-conventional yeasts like *I. orientalis*. In *S. cerevisiae* it has been demonstrated that CEN-ARS endowed plasmids display much higher stability than ARS by itself. Therefore, it would be desirable to isolate a functional CEN sequence capable of efficiently induce direct precise plasmid segregation in non-conventional yeasts like *I. orientalis*.

Similar to CENs, promoters and terminators are also important for metabolic engineering endeavors. They are the two essential distinct elements of expression systems and can be rationally designed to achieve the desired regulation or tunable gene expression levels. A toolset of well characterized constitutive promoters remains necessary to explore the full potential of metabolic engineering in non-conventional yeast such as *I. orientalis*. Particularly, since promoters are constitutive and tunable in nature, and pathway optimization for chemical production is highly tunable, it would be desirable to identify promoters with a broad range of transcriptional strengths. Similarly, terminators play an important role in controlling the level of gene expression by stabilizing the mRNA level. Studies involving the characterization of terminators from *S. cerevisiae* and other yeasts like *S. stipitis* have demonstrated that the terminator sequence affects the half-life of the transcript which later influences the level of protein expression. Therefore, it would also be highly desirable to discover and characterize terminators.

Furthermore, while many precise genome engineering tools are available for *S. cerevisiae*, such as CRISPR/Cas (Clustered Regularly Interspaced Short Palindromic Repeats and CRISPR-associated proteins)-based tools; no such tools exist for a non-conventional yeast like *I. orientalis*. Notably, there are no available promoters for sgRNA expression in a non-conventional yeast like *I. orientalis*.

Additionally, in metabolic pathway engineering, complete biosynthetic pathways are often required to be heterologously expressed to obtain products of interest at high yields. The conventional sequential-cloning methods, including restriction enzyme based T4-ligation, Gibson assembly, and Golden Gate assembly, not only involve multiple inefficient steps, but also rely on unique restriction sites that become limited for assembly of large-size plasmids harboring multiple genes in one-step fashion. 'DNA assembler' is an in vivo assembly method that enables rapid construction of large biochemical pathways in a one-step fashion based on the homologous recombination (HR) mechanism in *S. cerevisiae*. It would be desirable to extend such DNA assembler method to non-conventional yeast like *I. orientalis* for fast and reliable pathway construction.

The lack of versatile and efficient tools for the genomic engineering of non-conventional yeast drastically limits their utilization. Strategies are needed in the art that allow for the efficient strain engineering of non-conventional yeast, including the isolation and characterization of autonomously replicating sequence (ARS), centromere (CEN) sequences, constitutive promoters and terminators having various strengths, the development of optimized CRISPR/Cas9 system and in vivo DNA assembly. Such comprehensive tools for the metabolic engineering of non-conventional yeast are highly desirable notably for the production of biofuels and chemicals.

SUMMARY OF THE INVENTION

Provided herein are polynucleotides, vectors, and systems for the genomic engineering and editing of non-conventional yeast such as *Issatchenkia orientalis*.

The polynucleotides, vectors, and systems described herein can be used as tools to alter the expression of one or more gene products in non-conventional yeast.

An embodiment provides a polynucleotide comprising a centromere-like sequence (CEN-L) having a sequence of SEQ ID NO:11, SEQ ID NO:74, or SEQ ID NO: 154-163 or a sequence having about 80, 85, 90, 95, 96, 97, 98, 99% or more sequence identity to SEQ ID NO:74, SEQ ID NO: 11-16, or SEQ ID NO: 154-163. The polynucleotide can further comprise a *Saccharomyces cerevisiae* autonomously replicating sequence (ScARS). The ScARS can have the sequence of SEQ ID NO:73.

Another embodiment provides an expression cassette comprising: (i) a guide RNA (gRNA) targeting a polynucleotide of interest and a catalytically-active RNA-guided DNA endonuclease protein, wherein the gRNA is operably linked to a RNA polymerase (RNAP) III promoter; (ii) a polynucleotide encoding a catalytically active RNA-guided DNA endonuclease protein, wherein the polynucleotide is operably linked to a promoter sequence and to a terminator sequence; (iii) a *Saccharomyces cerevisiae* autonomously replicating sequence (ScARS); and (iv) a centromere-like sequence (CEN-L) having a sequence of SEQ ID NO: 11, SEQ ID NO:74, or SEQ ID NO: 154-163 or a sequence having about 80, 85, 90, 95, 96, 97, 98, 99% or more sequence identity to SEQ ID NO:74, SEQ ID NO: 11-16, or SEQ ID NO:154-163. The catalytically active RNA-guided DNA endonuclease protein can be a CRISPR associated protein 9 (Cas9), an improved Cas9 (iCas9), or Cas12a. The Cas9 can be from *Streptococcus pyogenes* (SpCas9), *Neisseria meningitides* (NmCas9), *Streptococcus thermophilus* (St1Cas9), or *Staphylococcus aureus* (SaCas9). The iCas9 can be a Cas9 protein fused to a nuclear localization sequence (NLS) to guide the Cas9 protein to a target site, and the NLS can be a SV40 NLS. The expression cassette can be incorporated in a vector. The vector can be a plasmid or a viral vector. The RNAP III promoter can be a RPR1 promoter, a 5S rRNA promoter, a tRNA$^{Leu}$ promoter, a tRNA$^{Ser}$ promoter, a 5S rRNA-tRNA$^{Leu}$ promoter, or a RPR1-tRNA$^{Leu}$ promoter.

Yet another embodiment provides an expression cassette comprising: (i) one or more polynucleotide sequences encoding one or more proteins of interest, wherein the one or more polynucleotide sequences are each operably linked to a promoter sequence and to a terminator sequence; (ii) a *Saccharomyces cerevisiae* autonomously replicating sequence (ScARS); and (iii) a centromere-like sequence (CEN-L) having a sequence of SEQ ID NO:11, SEQ ID NO:74, or SEQ ID NO:154-163 or a sequence having about 80, 85, 90, 95, 96, 97, 98, 99% or more sequence identity to SEQ ID NO:74, SEQ ID NO:11-16, or SEQ ID NO: 154-163. The promoter can be a constitutive promoter, such g247, g5025, g853, g917, g3376, g2204, g3504, g3824, g43, g3767, g172, g973, or g4288, for example. The terminator can be g4288t, g697t, g1414t, g4282t, g2204t, g3767t, g5025t, g3824t, g527t, g4194t, g853t, g5125t, g3376t, or g3540t. The expression cassette can be incorporated in a vector.

An embodiment provides a recombinant yeast comprising one of the vectors described herein. The yeast can be *Issatchenkia orientalis*.

Another embodiment provides a method of altering the expression of one or more gene products in a yeast comprising introducing the vector described herein into a yeast, wherein the expression of at least one gene product is increased, the expression of at least one gene product is decreased, at least one polynucleotide or fragment thereof is deleted as compared to a yeast that has not been transformed.

An additional embodiment provides a system for targeted genome engineering comprising one or more vectors, each vector comprising: (i) a guide RNA (gRNA) that binds a target polynucleotide and a catalytically-active RNA-guided DNA endonuclease protein; (ii) a polynucleotide encoding a catalytically active RNA-guided DNA endonuclease protein that binds to a gRNA, generates a double-stranded nucleic acid break, and induces deletion of a target polynucleotide; (iii) a RNA polymerase III promoter that does not induce capping at 5' end of a polynucleotide or polyadenylation at 3' end of the polynucleotide; (iv) a *Saccharomyces cerevisiae* autonomously replicating sequence (ScARS); (v) a centromere-like sequence (CEN-L) having a sequence of SEQ ID NO:11, SEQ ID NO:74, or SEQ ID NO: 154-163 or a sequence having about 80, 85, 90, 95, 96, 97, 98, 99% or more sequence identity to SEQ ID NO:74, SEQ ID NO: 11-16, or SEQ ID NO: 154-163; or (vi) a polynucleotide encoding a protein of interest, operably linked to a promoter sequence and to a terminator sequence.

Another embodiment provides a method of genetically altering a non-conventional yeast comprising delivering to the non-conventional yeast: (i) a polynucleotide having 90% or more sequence identity to the sequence of SEQ ID NO: 165, (ii) a polynucleotide having 90% or more sequence identity to the sequence of SEQ ID NO: 167, 169, 171, or combinations thereof, and (iii) one or more nucleic acids molecules encoding full length antisense RNAs or full length sense cDNAs having 90% or more sequence identity to one or more endogenous nucleic acid molecules of the non-conventional yeast, wherein the non-conventional yeast is genetically altered. The one or more nucleic acids molecules encoding full length antisense RNAs or full length sense cDNAs can be present in a plasmid RNAi library. The non-conventional yeast can be *Issatchenkia orientalis*. The polynucleotide having 90% or more sequence identity to the sequence of SEQ ID NO: 165 and the polynucleotide having 90% or more sequence identity to the sequence of SEQ ID NO: 167, 169, 171 can be present on one or more plasmids.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The features, objects and advantages other than those set forth above will become more readily apparent when consideration is given to the detailed description below. Such detailed description makes reference to the following drawings, wherein:

FIG. 3 panel A discloses constructs of various promoters for sgRNA expression. Triangles indicate tRNA cleavage site FIG. 3 panel B discloses the evaluation of various promoters for sgRNA expression by measuring alg9 expression by qPCR. Error bars represent standard deviation of biological triplicates.

FIG. 6B discloses DNA sequencing analysis for SDH2 disruption. CCGGCAGCTGAAGGTGAATCCAGTG-GAGGCTGTTGTACGACAGGTGAGA is SEQ ID NO: 149; CCGGCAGCTGAAGGTGAATCCAG is SEQ ID NO:150; GTTGTACGACAGGTGAGA is SEQ ID NO:151.

FIG. 7A discloses succinic acid productivity. FIG. 7B discloses Succinic acid concentration. FIG. 7C discloses acetate concentration. FIG. 7D discloses glycerol concentration. FIG. 7E discloses sugar consumption. FIG. 7F discloses cell growth.

FIG. 8A discloses succinic acid productivity. FIG. 8B discloses Succinic acid concentration. FIG. 8C discloses acetate concentration. FIG. 8D discloses glycerol concentration. FIG. 8E discloses sugar consumption. FIG. 8F discloses cell growth.

FIG. 13 panel A discloses the ~80% (117/147) ade2 knockout efficiency by CRISPR-Cas9 using ScARS plasmid. Panel B discloses the ~94% (117/124) ade2 knockout efficiency by CRISPR-Cas9 using ScARS/CEN-L plasmid.

FIG. 20 Panel A discloses the schematic representation of the assembled xylose utilization pathway. Each gene and its promoter/terminator were individually assembled first in *I. orientalis*. Panel B discloses the restriction digestion analysis of randomly picked colonies from assembled individual XR/XDH/XKS helper plasmids and combined XR-XDH-XKS plasmid by HindIII and EcoRI, M represents 1 kb DNA ladder. Panel C discloses the functional analysis of the xylose utilization pathway by monitoring cell growth in SC-URA medium supplemented with 2% xylose. Cells carrying the ScARS/CEN-L were used as the negative control. Panel D discloses residual xylose concentrations in liquid culture of the engineered strain containing the xylose utilization pathway and control strain. Error bars represent standard deviations for biological triplicates. The asterisk indicates statistical difference (p<0.05) using a two-tailed Student t test.

Figure 1A:
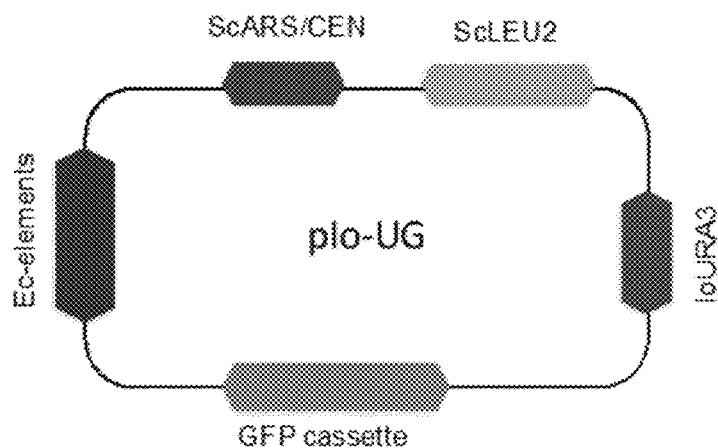
FIG. 1A discloses the design and construction map of an episomal plasmid plo-UG containing *I. orientalis* URA3 selection marker, GFP expression cassette, and *S. cerevisiae* functional parts ScARS/CEN and LEU2 selection marker.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the embodiments above and the claims below. Reference should therefore be made to the embodiments above and claims below for interpreting the scope of the invention.

DETAILED DESCRIPTION

Overview

Non-conventional yeasts provide a platform for production of, for example, organic acids thanks to their unusual ability to grow in extreme conditions such as highly acidic conditions. Non-conventional yeasts are any yeasts that are not *Saccharomyces* sp. or *Schizosaccharomyces* sp. Non-conventional yeasts can be, for example, *Issatchenkia* sp. such as *Issatchenkia orientalis*, *Brettanomyces* sp. such as *Brettanomyces naardenensis*, *Candida* sp. such as *Candida shehatae*, *Candida tenuis*, *Candida antarctica*, *Candida lusitaniae*, *Candida stellate*, *Candida ethanolic*, *Yarrowia* sp. such as *Yarrowia lipolytica* (formerly *Candida lipolytica*), *Pachysolen* sp. such as *Pachysolen tannophilus*, *Debaryomyces* sp. such as *Debaryomyces hansenii* (*Candida famata*), *Debaryomyces* (*Schwanniomyces*) *castelli*, *Debaryomyces* (*Schwanniomyces*) *occidentalis*, *Pichia* sp. such as *Pichia segobiensis*, *Pichia pastoris*, *Pichia kudriavzevii*, *Pichia fermentans*, *Scheffersomyces* sp. such as *Scheffersomyces stipitis* (formerly *Pichia stipitis*), *Hansenula* sp. such as *Hansenula polymorpha*, *Kluyveromyces* sp. such as *Kluyveromyces lactis*, *Kluyveromyces marxianus*, *Torulaspora* such as *Torulaspora delbrueckii*, *Saccharomycopsis* sp. such as *Saccharomycopsis fibuligera*, *Cryptococcus* sp., *Clavispora* such as *Clavispora lusitaniae*, *Aureobasidium* sp. such as *Aureobasidium pullulans*, *Zygosaccharomyces* sp., such as *Zygosaccharomyces rouxii*, *Zygosaccharomyces bailii*, *Hortaea* sp. such as *Hortaea werneckii*, *Ogataea* sp. such as *Ogataea polymorpha*, *Dekkera* sp. such as *Dekkera bruxellensis*, *Metschnikowia* sp. such as *Metschnikowia pulcherrima*, *Wickerhamomyces* sp. such as *Wickerhamomyces anomalus*, *Endomycopsis* sp. such as *Endomycopsis capsularis*, *Torulopsis* sp., *Rhodotorula* sp., *Williopsis* sp., and Hanseniaspora sp. The lack of efficient and consistent synthetic biology tools has hindered efforts to engineer these organisms. Provided herein are autonomously replicating sequences (ScARS), CEN sequences such as an 0.8 kb centromere-like (CEN-L) sequence; a set of constitutive promoters and terminators; and a rapid and efficient in vivo DNA assembly method for non-conventional yeast like *I. orientalis*, which exhibited ~100% fidelity. The polynucleotides and vectors can be used for the efficient genome editing of non-conventional yeast using CRISPR/Cas9 systems for multiplex gene deletion, or for the targeted induction of gene expression; thereby providing editing tools for rapid strain development and metabolic engineering of non-conventional yeast for production of biofuels and chemicals.

Polynucleotides

Polynucleotides contain less than an entire microbial genome and can be single- or double-stranded nucleic acids. A polynucleotide can be RNA, DNA, cDNA, genomic DNA, chemically synthesized RNA or DNA or combinations thereof. A polynucleotide can comprise, for example, a gene, open reading frame, non-coding region, or regulatory element.

A gene is any polynucleotide molecule that encodes a polypeptide, protein, or fragments thereof, optionally including one or more regulatory elements preceding (5' non-coding sequences) and following (3' non-coding sequences) the coding sequence. In one embodiment, a gene does not include regulatory elements preceding and following the coding sequence. A native or wild-type gene refers to a gene as found in nature, optionally with its own regulatory elements preceding and following the coding sequence. A chimeric or recombinant gene refers to any gene that is not a native or wild-type gene, optionally comprising regulatory elements preceding and following the coding sequence, wherein the coding sequences and/or the regulatory elements, in whole or in part, are not found together in nature. Thus, a chimeric gene or recombinant gene comprise regulatory elements and coding sequences that are derived from different sources, or regulatory elements and coding sequences that are derived from the same source but arranged differently than is found in nature. A gene can encompass full-length gene sequences (e.g., as found in nature and/or a gene sequence encoding a full-length polypeptide or protein) and can also encompass partial gene sequences (e.g., a fragment of the gene sequence found in nature and/or a gene sequence encoding a protein or fragment of a polypeptide or protein). A gene can include modified gene sequences (e.g., modified as compared to the sequence found in nature). Thus, a gene is not limited to the natural or full-length gene sequence found in nature.

Polynucleotides can be purified free of other components, such as proteins, lipids and other polynucleotides. For example, the polynucleotide can be 50%, 75%, 90%, 95%, 96%, 97%, 98%, 99%, or 100% purified. A polynucleotide existing among hundreds to millions of other polynucleotide molecules within, for example, cDNA or genomic libraries, or gel slices containing a genomic DNA restriction digest are not to be considered a purified polynucleotide. Polynucleotides can encode the polypeptides described herein (e.g., SDH1, SDH2).

Polynucleotides can comprise additional heterologous nucleotides that do not naturally occur contiguously with the polynucleotides. As used herein the term "heterologous" refers to a combination of elements that are not naturally occurring or that are obtained from different sources.

Polynucleotides can be isolated. An isolated polynucleotide is a naturally-occurring polynucleotide that is not immediately contiguous with one or both of the 5' and 3' flanking genomic sequences that it is naturally associated with. An isolated polynucleotide can be, for example, a recombinant DNA molecule of any length, provided that the nucleic acid sequences naturally found immediately flanking the recombinant DNA molecule in a naturally-occurring genome is removed or absent. Isolated polynucleotides also include non-naturally occurring nucleic acid molecules. Polynucleotides can encode full-length polypeptides, polypeptide fragments, and variant or fusion polypeptides.

Degenerate polynucleotide sequences encoding polypeptides described herein, as well as homologous nucleotide sequences that are at least about 80, or about 85, 90, 91, 92, 93, 94, 95, 96, 97, 98, or 99% identical to polynucleotides described herein and the complements thereof are also polynucleotides. Degenerate nucleotide sequences are polynucleotides that encode a polypeptide described herein or fragments thereof, but differ in nucleic acid sequence from the wild-type polynucleotide sequence, due to the degeneracy of the genetic code. Complementary DNA (cDNA) molecules, species homologs, and variants of polynucleotides that encode biologically functional polypeptides also are polynucleotides.

Polynucleotides can be obtained from nucleic acid sequences present in, for example, a yeast or bacteria. Polynucleotides can also be synthesized in the laboratory, for example, using an automatic synthesizer. An amplification method such as PCR can be used to amplify polynucleotides from either genomic DNA or cDNA encoding the polypeptides.

Polynucleotides can comprise non-coding sequences or coding sequences for naturally occurring polypeptides or can encode altered sequences that do not occur in nature.

Unless otherwise indicated, the term polynucleotide or gene includes reference to the specified sequence as well as the complementary sequence thereof.

The expression products of genes or polynucleotides are often proteins, or polypeptides, but in non-protein coding genes such as rRNA genes or tRNA genes, the product is a functional RNA. The process of gene expression is used by all known life forms, i.e., eukaryotes (including multicellular organisms), prokaryotes (bacteria and archaea), and viruses, to generate the macromolecular machinery for life. Several steps in the gene expression process can be modulated, including the transcription, up-regulation, RNA splicing, translation, and post-translational modification of a protein.

A polynucleotide can be a cDNA sequence or a genomic sequence. A "genomic sequence" is a sequence that is present or that can be found in the genome of an organism or a sequence that has been isolated from the genome of an organism. A cDNA polynucleotide can include one or more of the introns of a genomic sequence from which the cDNA sequence is derived. As another example, a cDNA sequence can include all of the introns of the genomic sequence from which the cDNA sequence is derived. Complete or partial intron sequences can be included in a cDNA sequence.

Polynucleotides as set forth in SEQ ID NO: 1 through SEQ ID NO: 142 a functional fragment thereof; or having at least 95% identity to SEQ ID NO:1-SEQ ID NO:142, are provided herein. In some embodiments, the isolated polynucleotides have at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.9%, and any number or range in between, identity to SEQ ID NO: 1 through SEQ ID NO: 142 or a functional fragment thereof.

The terms "sequence identity" or "percent identity" are used interchangeably herein. To determine the percent identity of two polypeptide molecules or two polynucleotide sequences, the sequences are aligned for optimal comparison purposes (e.g., gaps can be introduced in the sequence of a first polypeptide or polynucleotide for optimal alignment with a second polypeptide or polynucleotide sequence). The amino acids or nucleotides at corresponding amino acid or nucleotide positions are then compared. When a position in the first sequence is occupied by the same amino acid or nucleotide as the corresponding position in the second sequence, then the molecules are identical at that position. The percent identity between the two sequences is a function of the number of identical positions shared by the sequences (i.e., % identity=number of identical positions/total number of positions (i.e., overlapping positions)×100). In some embodiments the length of a reference sequence aligned for comparison purposes is at least 80% of the length of the comparison sequence, and in some embodiments is at least 90% or 100%. In an embodiment, the two sequences are the same length.

Ranges of desired degrees of sequence identity are approximately 80% to 100% and integer values in between. Percent identities between a disclosed sequence and a claimed sequence can be at least 80%, at least 83%, at least 85%, at least 90%, at least 95%, at least 98%, at least 99%, at least 99.5%, or at least 99.9%. In general, an exact match indicates 100% identity over the length of the reference sequence.

Polypeptides and polynucleotides that are sufficiently similar to polypeptides and polynucleotides described herein can be used herein. Polypeptides and polynucleotides that are about 90, 91, 92, 93, 94 95, 96, 97, 98, 99 99.5% or more identical to polypeptides and polynucleotides described herein can also be used herein. For example, a polynucleotide can have 80% 85%, 90%, 91%, 92%, 93%, 94%, 95%, 96%, 97%, 98%, 99% or more identity to any of the SEQ ID NOs described herein.

Expression Cassettes

A recombinant construct is a polynucleotide having heterologous polynucleotide elements. Heterologous polynucleotide elements are polynucleotides that do not occur together in nature. Any sequence of any origin can be a heterologous polynucleotide element in the polynucleotides provided herein. Exemplary heterologous polynucleotide elements include, for example, expression cassettes, cDNA sequences, genomic sequences, open reading frames (ORFs), regulatory elements, and others. Recombinant constructs include expression cassettes or expression constructs, which refer to an assembly that is capable of directing the expression of a polynucleotide or gene of interest. An expression cassette generally includes regulatory elements such as a promoter that is operably linked to (so as to direct transcription of) a polynucleotide and often includes a polyadenylation sequence or other regulatory elements as well.

An "expression cassette" refers to a fragment of DNA comprising a coding sequence of a selected gene or gene fragment or other polynucleotide (e.g. a gRNA or a polynucleotide encoding a polypeptide) and optionally, regulatory elements preceding (5' non-coding sequences) and following (3' non-coding sequences) the coding sequence that are required for expression of the selected gene product, fragment thereof, or other polynucleotide. The expression cassette is usually included within a vector, to facilitate cloning and transformation. Different expression cassettes can be transformed into different organisms including bacteria, yeast, plants and mammalian cells, as long as the correct regulatory elements are used for each host.

A recombinant construct or expression cassette can be contained within a vector. In addition to the components of the recombinant construct, the vector can include, one or more selectable markers, a signal which allows the vector to exist as single-stranded DNA (e.g., a M13 origin of replication), at least one multiple cloning site, and an origin of replication (e.g., a SV40 or adenovirus origin of replication).

Generally, a polynucleotide or gene that is introduced into an organism is part of a recombinant construct. A polynucleotide can comprise a gene of interest, e.g., a coding sequence for a protein, or can be a sequence that is capable of regulating expression of a gene, such as a regulatory element. A recombinant construct can include, for example, regulatory elements operably linked 5' or 3' to a polynucleotide encoding one or more polypeptides of interest. For example, a promoter can be operably linked with a polynucleotide encoding one or more polypeptides of interest or a polynucleotide of interest (e.g., RNA) when it is capable of affecting the expression of the polynucleotide (i.e., the polynucleotide is under the transcriptional control of the promoter). Polynucleotides can be operably linked to regulatory elements in sense or antisense orientation. The expression cassettes or recombinant constructs can additionally contain a 5' leader polynucleotide. A leader polynucleotide can contain a promoter as well as an upstream region of a gene. The regulatory elements (i.e., promoters, enhancers, transcriptional regulatory regions, translational regulatory regions, translational termination regions, etc.) and/or the polynucleotide encoding a signal anchor can be native/endogenous to the host cell or to each other. Alternatively, the regulatory elements can be heterologous to the host cell or to each other. The expression cassette or recombinant construct can additionally contain one or more selectable marker genes.

A polynucleotide can be operably linked when it is positioned adjacent to or close to one or more regulatory elements, which direct transcription and/or translation of the polynucleotide.

A nucleic acid expression cassette can be a circular or linear nucleic acid molecule. In some cases, a nucleic acid expression cassette is delivered to cells (e.g., a plurality of different cells or cell types including target cells or cell types and/or non-target cell types) in a vector (e.g., an expression vector).

A fragment of a polynucleotide, polypeptide, or protein is meant to refer to a sequence that is less than a "full-length" sequence. A functional fragment includes "fragments," "variants," "analogues," or "chemical derivatives" of a molecule. A functional fragment comprises at least a biologically active fragment, which is a fragment that retains a biological activity (either functional or structural) that is substantially similar to a biological activity of the full-length polynucleotide, polypeptide, or protein. A biological activity of a polynucleotide can be its ability to influence expression in a manner known to be attributed to the full-length sequence. For example, a functional fragment of a regulatory element such as a promoter, for example, will retain the ability to influence transcription as compared to the full-length regulatory element. As used herein, the term "functional variant" refers to a sequence that is substantially similar in structure and biological activity to either the entire molecule, or to a fragment thereof. For example, a "functional variant" can have one or more sequence alterations or one or more sequence differences compared to the molecule or a fragment thereof while having similar biological activity.

A vector or expression cassette can comprise one or more polynucleotides of interest, encoding for one or more products of interest, or any combination thereof.

A polynucleotide can transcribed from a nucleic acid template into product of interest, such as a sgRNA, tRNA or mRNA for example; and a transcribed mRNA can subsequently be translated into peptides, polypeptides, or proteins of interest. Transcripts and encoded polypeptides can be collectively referred to as "gene product." A polypeptide is a linear polymer of amino acids that are linked by peptide bonds.

In an embodiment a polynucleotide of interest can be a guide RNA (gRNA) targeting a nucleic acid of interest and a catalytically-active RNA-guided DNA endonuclease protein or catalytically-inactive RNA-guided DNA endonuclease protein, a polynucleotide encoding a catalytically active RNA-guided DNA endonuclease protein or catalytically-inactive RNA-guided DNA endonuclease protein, or a polynucleotide sequence encoding one or more proteins of interest.

As used herein, "single guide RNA," "guide RNA (gRNA)," "guide sequence" and "sgRNA" can be used interchangeably herein and refer to a single RNA species capable of directing RNA-guided DNA endonuclease mediated double-stranded cleavage of a target DNA. Single-stranded gRNA sequences are transcribed from double-stranded DNA sequences inside the cell. A guide RNA is a specific RNA sequence that recognizes a target DNA region of interest and directs an RNA-guided DNA endonuclease there for editing. A gRNA has at least two regions. First, a CRISPR RNA (crRNA) or spacer sequence, which is a nucleotide sequence complementary to the target nucleic acid, and second a tracer RNA, which serves as a binding scaffold for the RNA-guided DNA endonuclease. The target sequence that is complementary to the guide sequence is known as the protospacer. The crRNA and tracer RNA can exist as one molecule or as two separate molecules, as they are in nature. gRNA and sgRNA as used herein refer to a single molecule comprising at least a crRNA region and a tracer RNA region or two separate molecules wherein the first comprises the crRNA region and the second comprises a tracer RNA region. The crRNA region of the gRNA is a customizable component that enables specificity in every CRISPR reaction. A guide RNA used in the systems and methods can also comprise an endoribonuclease recognition site for multiplex processing of gRNAs. If an endoribonuclease recognition site is introduced between neighboring gRNA sequences, more than one gRNA can be transcribed in a single expression cassette. Direct repeats can also serve as endoribonuclease recognition sites for multiplex processing. A guide RNA used in the systems and methods described herein are short, single-stranded polynucleotide molecules about 20 nucleotides to about 300 nucleotides in length. The spacer sequence (targeting sequence) that hybridizes to a complementary region of the target DNA of interest can be about 14, 15, 16, 17, 18, 19, 20, 25, 30, 35 or more nucleotides in length. A sgRNA capable of directing RNA-guided DNA endonuclease mediated substitution of, insertion at, or deletion of target sequence can be about 10, 11, 12, 13, 14, 15, 16, 17, 18, 19, 20, 30, 40, 50 or more nucleotides in length. A sgRNA capable of directing RNA-guided DNA endonuclease mediated substitution of, insertion at, or deletion of target sequence can be about 50, 40, 30, 20, 19, 18, 17, 16, 15, 14, 13, 12, 11 or less nucleotides in length. The sgRNA used to direct insertion, substitution, or deletion can include HR sequences for homology-directed repair. sgRNAs can be synthetically generated or by making the sgRNA in vivo or in vitro, starting from a DNA template. A sgRNA can target a regulatory element (e.g., a promoter, enhancer, or other regulatory element) in the target genome. A sgRNA can also target a protein coding sequence in the target genome.

A "catalytically active RNA-guided DNA endonuclease protein," or "DNA endonuclease" refers to an endonuclease protein directed to a specific DNA target by a gRNA, where it causes a double-strand break. There are many versions of RNA-guided DNA endonucleases isolated from different organisms. Each RNA-guided DNA endonuclease binds to its target sequence in the presence of a protospacer adjacent motif (PAM), on the non-targeted DNA strand. Therefore, the locations in a genome that can be targeted by different RNA-guided DNA endonuclease can be dictated by locations of PAM sequences. An RNA-guided DNA endonuclease cuts 3-4 nucleotides upstream of the PAM sequence. Recognition of the PAM sequence by an RNA-guided DNA endonuclease protein is thought to destabilize the adjacent DNA sequence, allowing interrogation of the sequence by the sgRNA, and allowing the sgRNA-DNA pairing when a matching sequence is present. RNA-guided DNA endonucleases can be isolated from different bacterial species recognizing different PAM sequences. For example, the SpCas9 nuclease cuts upstream of the PAM sequence 5'-NGG-3' (where "N" can be any nucleotide base), while the PAM sequence 5'-NNGRR(N)-3' is required for SaCas9 (from *Staphylococcus aureus*) to target a DNA region for editing. While the PAM sequence itself is necessary for cleavage, it is not included in the single guide RNA sequence.

Non-limiting examples of RNA-guided DNA endonuclease proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof. In some embodiments, the RNA-guided DNA endonuclease directs cleavage of both strands of target DNA within about 1, 2, 3, 4, 5, 6, 7, 8, 9, 10, 15, 20, 25, 50, 100, 200, 500, or more base pairs from the first or last nucleotide of a target sequence. In an embodiment, the catalytically active RNA-guided DNA endonuclease protein can be a CRISPR associated protein 9 (Cas9), an improved Cas9 (iCas9), or Cas12a. The Cas9 can be from *Streptococcus pyogenes* (SpCas9), *Neisseria meningitides* (NmCas9), *Streptococcus thermophilus* (St1Cas9), or *Staphylococcus aureus* (SaCas9). The iCas9 can be a Cas9 protein fused to a nuclear localization sequence (NLS) to guide the Cas9 protein to a target site, and the NLS can be a SV40 NLS.

A "polynucleotide sequence encoding one or more proteins of interest" refers to any polynucleotide sequence that encodes a protein sought to be expressed in a cell by a vector.

Regulatory Elements

A vector or expression cassette can comprise one or more polynucleotides that are linked in a manner such that the product is not found in a cell in nature. In particular, the two or more polynucleotides can be operatively linked, such as a polynucleotide encoding a product of interest, one or more protein tags, functional domains, regulatory elements and the like. Regulatory elements controlling transcription can be generally derived from mammalian, microbial, yeast, viral, or insect genes. An ARS can usually confer the ability to replicate in a host, and a selection gene to facilitate recognition of transformants can additionally be incorporated. Those of skill in the art can select a suitable regulatory region to be included in a vector. For example, a vector or expression cassette can comprise a promoter operably linked to the polynucleotide of interest; a terminator, operably linked to the polynucleotide of interest; an autonomously replicating sequence; and a centromere-like sequence.

As used herein, a "promoter" refers to a polynucleotide sequence capable of facilitating transcription of genes in operable linkage with the promoter. Several types of promoters are well known in the art and suitable for use with the present expression cassettes. The promoter can be constitutive or inducible. "Constitutive promoter" allows for unregulated expression in cells, while "inducible promoter" refers to a promoter that is capable of directly or indirectly activating transcription of one or more polynucleotide in response to an inducer. Cas9 expression can be achieved by using a constitutive RNA Polymerase (RNAP) II promoter. On the other hand, sgRNA expression typically requires an RNAP III promoter because of the mRNA processing associated with RNAP II, which induces as 5'-end capping and 3'-end polyadenylation.

In an embodiment the gRNA can be operably linked to a RNA polymerase (RNAP) III promoter. The RNAP III promoter can be a RPR1 promoter, a 5S rRNA promoter, a tRNA$^{Leu}$ promoter, a tRNA$^{Ser}$ promoter, a 5S rRNA-tRNA$^{Leu}$ promoter, or a RPR1-tRNA$^{Leu}$ promoter. In another embodiment the polynucleotide of interest (i.e., other than a gRNA) can be operably linked to a promoter sequence. The promoter can be a constitutive promoter, such g247, g5025, g853, g917, g3376, g2204, g3504, g3824, g43, g3767, g172, g973, or g4288, for example.

In an embodiment, a promoter can have the sequence of SEQ ID NO:19, SEQ ID NO: 20, SEQ ID NO: 23, SEQ ID NO:25, SEQ ID NO:26, SEQ ID NO:32, SEQ ID NO:37, SEQ ID NO:46, SEQ ID NO:48, or SEQ ID NO:49.

As used herein "terminator" refers to a polynucleotide sequences that can be recognized by protein factors associated with the RNA polymerase II, and which trigger the termination process. Therefore, terminators are important players in the regulation of polynucleotide expression in a cell, in combination with promoters.

In an embodiment the polynucleotide of interest can be operably linked to a terminator sequence. The terminator can be g4288t, g697t, g1414t, g4282t, g2204t, g3767t, g5025t, g3824t, g527t, g4194t, g853t, g5125t, g3376t, or g3540t.

In an embodiment, a terminator can have the sequence of SEQ ID NO:19, SEQ ID NO:20, SEQ ID NO: 23, SEQ ID NO:25, SEQ ID NO:26, SEQ ID NO:32, SEQ ID NO:37, SEQ ID NO:46, or SEQ ID NO:49.

In an embodiment, a strong promoter can be associated with a strong terminator for the proper control of the expression of a polynucleotide of interest, operably linked to both the promoter and the terminator. In an embodiment, a strong promoter can have the sequence of SEQ ID NO: 19, SEQ ID NO:20, SEQ ID NO:23, SEQ ID NO:25, SEQ ID NO:26, SEQ ID NO:32, SEQ ID NO:37, SEQ ID NO:46, SEQ ID NO:48, or SEQ ID NO:49, and a strong terminator can have the sequence of SEQ ID NO: 19, SEQ ID NO:20, SEQ ID NO:23, SEQ ID NO:25, SEQ ID NO:26, SEQ ID NO:32, SEQ ID NO:37, SEQ ID NO:46, or SEQ ID NO:49. Any combination of a strong promoter with a strong terminator can be used.

An "autonomously replicating sequence," or "ARS" is a DNA replication starting point present in the yeast genome; it is similar to the origin of replication in bacteria, and directs the replication of the genomic DNA and episomal plasmid.

In an embodiment, the vector described herein can comprise a *Saccharomyces cerevisiae* autonomously replicating sequence (ScARS). A SCARS can be, for example, SEQ ID NO:73. Other ScARS include for example ARS305, ARS306, ARS307, ARS309, and ARS310. Additionally, Wang & Gao (Front. Microbiol. Sep. 13, 2019: doi.org/10.3389/fmicb.2019.02122) describe 520 ScARSs, any of which can be used herein.

As used herein, a "centromere sequence," or "CEN" refers to the specialized DNA sequence of each chromosome that promotes the formation of a kinetochore, the large multiprotein complex that links the sister chromatids to the spindle microtubules to ensure faithful chromosome segregation during cell division. For the majority of yeast species (e.g., *S. cerevisiae* and *Kluyveromyces lactis*), point CENs contain ~125 bp of DNA and three protein binding motifs (CDEI, CDEII and CDEIII), while regional CENs possess a large array of binding sites for centromeric proteins, forming multiple CenH3 (CEN-specific histone 3) nucleosomes attached to microtubules within a specific region of the chromosome. CENs are large polynucleotides, that cannot easily be integrated into an expression cassette. Therefore, and as described herein, a "centromere-like sequence," or "CEN-L" can be used. A CEN-L refers to a non-naturally occurring polynucleotide encoding a conserved fragment of a CEN sequence, for integration into expression cassette or vector. A CEN-L can be about 50, 40, 30, 20, 10, 5, 4, 3, 2, 1% or less the size of a naturally-occurring CEN polynucleotide.

Another embodiment provides a polynucleotide comprising a centromere-like sequence (CEN-L) having a sequence of SEQ ID NO: 11, SEQ ID NO:74, or SEQ ID NO: 154-163 or a sequence having about 80, 85, 90, 95, 96, 97, 98, 99% or more sequence identity to SEQ ID NO:74, SEQ ID NO: 11-16, or SEQ ID NO: 154-163.

Additional regulatory elements that may be useful in vectors, include, but are not limited to, polyadenylation sequences, translation control sequences (e.g., an internal ribosome entry segment, IRES), enhancers, or introns. Such elements may not be necessary, although they may increase expression by affecting transcription, stability of the mRNA, translational efficiency, or the like. Such elements can be included in a polynucleotide construct as desired to obtain optimal expression of the polynucleotides in the cell(s).

An embodiment provides a polynucleotide comprising a centromere-like sequence (CEN-L) having a sequence of SEQ ID NO: 11, SEQ ID NO:74, or SEQ ID NO: 154-163 or a sequence having about 80, 85, 90, 95, 96, 97, 98, 99% or more sequence identity to SEQ ID NO:74, SEQ ID NO: 11-16, or SEQ ID NO: 154-163. Another embodiment provides a polynucleotide comprising a CEN-L and a *Saccharomyces cerevisiae* autonomously replicating sequence (ScARS). The polynucleotides can be incorporated in a vector.

An embodiment provides a vector comprising: a gRNA operably linked to a RNAP III promoter; a polynucleotide encoding a catalytically active RNA-guided DNA endonuclease protein, operably linked to a promoter sequence and to a terminator sequence; a ScARS; and CEN-L having the sequence of SEQ ID NO:74, SEQ ID NO: 11-16, SEQ ID NO:163 or a sequence having about 80, 85, 90, 95, 96, 97, 98, 99% or more sequence identity to SEQ ID NO:74, SEQ ID NO: 11-16, or SEQ ID NO: 154-163.

Another embodiment provides a vector comprising: one or more polynucleotide sequences encoding one or more proteins of interest, each operably linked to a promoter sequence and to a terminator sequence; a ScARS; and a CEN-L having the sequence of SEQ ID NO:74, SEQ ID NO: 11-16, or SEQ ID NO: 154-163 or a sequence having about 80, 85, 90, 95, 96, 97, 98, 99% or more sequence identity to SEQ ID NO:74, SEQ ID NO: 11-16, or SEQ ID NO: 154-163.

In an embodiment, an expression cassette can comprise a guide RNA (gRNA) targeting a polynucleotide of interest and a catalytically-active RNA-guided DNA endonuclease protein. The gRNA can be operably linked to a RNA polymerase (RNAP) III promoter. A target polynucleotide can be any polynucleotide that one wants to target in a genome using a CRISPR/Cas9 system as described herein. Methods are known in the art to design gRNA that targets a polynucleotide of interest, and one of skill in the art can use general knowledge in the art to design such gRNA for virtually every polynucleotide. An expression cassette can further comprise a polynucleotide encoding a catalytically active RNA-guided DNA endonuclease protein, wherein the polynucleotide is operably linked to a promoter sequence and to a terminator sequence. Any suitable promoter sequence and terminator sequence can be used. For example, a promoter sequence such as that shown in SEQ ID NO:17-53 can be used; and a terminator sequence such that shown in SEQ ID NO:54-72 can be used. An expression cassette can further comprise a *Saccharomyces cerevisiae* autonomously replicating sequence (ScARS); for example, a ScARS as shown in SEQ ID NO:73 can be used. An expression cassette can further comprise a centromere sequence. For example a centromere sequence having the sequence of SEQ ID NO:11-16, or SEQ ID NO:74, or SEQ ID NO: 154-163 can be used. In another example a centromere sequence or a sequence can have about 80, 85, 90, 95, 96, 97, 98, 99% or more sequence identity to SEQ ID NO:74, SEQ ID NO: 11-16, or SEQ ID NO: 154-163. An expression cassette can further comprise one or more polynucleotide sequences encoding one or more proteins of interest. The one or more polynucleotide sequences can each be operably linked to a promoter sequence and to a terminator sequence. A polynucleotide of interest can be any polynucleotide that one wants to introduce in a genome using an expression cassette as described herein. Non-limiting examples of polynucleotide of interest can include polynucleotide as shown in SEQ ID NO:75-79.

In an embodiment, an expression cassette can comprise a gRNA targeting a polynucleotide of interest and a catalytically-active RNA-guided DNA endonuclease protein, operably linked to a RNAP III promoter; a target polynucleotide; a polynucleotide encoding a catalytically active RNA-guided DNA endonuclease protein, operably linked to a promoter sequence (e.g., SEQ ID NO: 17-53) and to a terminator sequence (e.g., SEQ ID NO: 54-72); a ScARS (e.g., SEQ ID NO:73); and a centromere sequence (e.g., SEQ ID NO:11-16, SEQ ID NO:74 or SEQ ID NO:154-163_or a sequence having about 80, 85, 90, 95, 96, 97, 98, 99% or more sequence identity to SEQ ID NO:74, SEQ ID NO:11-16, or SEQ ID NO: 154-163.

In an embodiment, an expression cassette can comprise a polynucleotide of interest (e.g., SEQ ID NO:75-79) operably linked to a promoter sequence (e.g., SEQ ID NO:17-53) and to a terminator sequence (e.g., SEQ ID NO: 54-72); a SCARS (e.g., SEQ ID NO:73); and a centromere sequence (e.g., SEQ ID NO: 11-16, SEQ ID NO:74, or SEQ ID NO: 154-163, or a sequence having about 80, 85, 90, 95, 96, 97, 98, 99% or more sequence identity to SEQ ID NO:74, SEQ ID NO: 11-16, or SEQ ID NO: 154-163).

Vectors

A vector or expression vector is a replicon, such as a plasmid, a phage, or a cosmid, to which a nucleic acid or a polynucleotide of interest can be incorporated so that said nucleic acid can be replicated and therefore transferred to target cells. A vector can also be modified to comprise various types of regulatory elements for the modulation of the expression of the polynucleotide of interest. Many suitable vectors and features thereof are known in the art. Examples of expression vectors include plasmids, yeast artificial chromosomes, yeast integrative plasmids, yeast replicative plasmids, shuttle vectors, episomal plasmids, and viral vectors. In an embodiment, the viral vector is a lentivirus vector, an adenovirus vector, or an adeno-associated vector (AAV). In one embodiment, the vector can a plasmid or a viral vector. Vectors can be introduced and propagated in a prokaryote or a eukaryote. In some embodiments, a prokaryote is used to amplify copies of a vector to be introduced into a eukaryotic cell or as an intermediate vector in the production of a vector to be introduced into a eukaryotic cell (e.g. amplifying a plasmid as part of a viral vector packaging system). In some embodiments, a prokaryote is used to amplify copies of a vector.

In an embodiment, the expression cassettes described herein are comprised into a vector. The vector can be a plasmid or a viral vector.

Recombinant Microorganisms

A recombinant, transgenic, or genetically engineered microorganism is a microorganism, e.g., bacteria, fungus, or yeast that has been genetically modified from its native state. Thus, a "recombinant yeast" or "recombinant yeast cell" refers to a yeast cell that has been genetically modified from the native state. A recombinant yeast cell can have, for example, nucleotide insertions, nucleotide deletions, nucleotide rearrangements, gene disruptions, recombinant polynucleotides, heterologous polynucleotides, deleted polynucleotides, nucleotide modifications, or combinations thereof introduced into its DNA. These genetic modifications can be present in the chromosome of the yeast or yeast cell, or on a plasmid in the yeast or yeast cell. Recombinant cells disclosed herein can comprise exogenous polynucleotides on plasmids. Alternatively, recombinant cells can comprise exogenous polynucleotides stably incorporated into their chromosome.

A heterologous or exogenous polypeptide or polynucleotide refers to any polynucleotide or polypeptide that does not naturally occur or that is not present in the starting target microorganism. A heterologous or exogenous polypeptide or polynucleotide can be a wild-type, synthetic, or mutated polypeptide or polynucleotide. A homologous or endogenous polypeptide or polynucleotide refers to any polynucleotide or polypeptide that naturally occurs or that is otherwise present in a starting target microorganism.

An embodiment provides a recombinant yeast comprising one or more vectors or expression cassettes described herein. A yeast can be *Issatchenkia orientalis*, a mutant thereof, or a variant thereof.

*Issatchenkia orientalis* (also named *Pichia kudriavzevii* or *Candida krusei*) is a non-conventional yeast. Non-conventional yeasts can have properties such as growing in extreme conditions, or having unusual metabolic, biosynthetic, physiological, or fermentative capacities. For example, *Issatchenkia orientalis* can grow in extremely low pH conditions, such as pH 2. Other non-conventional yeasts include, for example, *Zygosaccharomyces rouxii* (tolerance to osmotic stresses), *Kluyveromyces marxianus* (tolerant to high temperatures), *Ogataea* (*Hansenula*) *polymorpha* (tolerant to high temperatures), *Zygosaccharomyces bailii* (acetic acid tolerance) and *Dekkera bruxellensis* (tolerant to ethanol). Other non-conventional yeasts include, for example, those in the Pichiaceae family, including, for example, *Brettanomyces* sp., *Dekkera* sp., *Enteroramus* sp., *Hansenula* sp., *Komagataella* sp., *Kregervanrija* sp., *Martiniozyma* sp., *Phaffomyces* sp., *Pichia* sp., and *Saturnispora* sp.

Methods of Use

Embodiments provide methods of altering the expression of one or more gene products in a yeast comprising introducing a vector or expression cassette described herein into a yeast, wherein the expression of one or more gene products is increased, the expression of one or more gene products is decreased, the expression of one or more gene products is deleted, combinations thereof as compared to the expression of the gene product in a yeast that has not been transformed.

As used herein, "decreasing gene expression," or "deleting gene expression" can both refer to the use of a vector as described herein comprising at least a gRNA operably linked to a RNAP III promoter and a polynucleotide encoding a catalytically active RNA-guided DNA endonuclease protein, operably linked to a promoter sequence and to a terminator sequence to use the CRISPR/Cas tool for genome engineering of the yeast sought to be transformed by such vector.

The Clustered Regularly Interspersed Short Palindromic Repeats/CRISPR-associated (CRISPR/Cas) system, CRISPR/Cas system, is a powerful tool for rapid genome engineering in which a single guide RNA (sgRNA) containing a spacer sequence complementary to the targeted DNA sequence guides Cas9, a DNA endonuclease enzyme, to a genomic target. Upon binding, Cas9 creates a double-strand DNA break. DNA repair mechanisms, non-homologous end joining (NHEJ) or homologous recombination (HR), can be exploited to introduce gene insertions and deletions. CRISPR/Cas9 has been implemented in various species, such as *Escherichia coli, S. cerevisiae*, and mammalian cells. The vectors and expression cassettes described herein have been specifically designed to generate the first CRISPR/Cas9-based system efficient in non-conventional yeasts like *I. orientalis* for targeted and markerless gene disruption.

The elements of CRISPR systems include, for example, direct repeats, homologous recombination editing templates, guide sequences, tracrRNA sequences, target sequences, priming sites, regulatory elements, and RNA-guided DNA endonucleases. Given a target sequence one of skill in the art can design functional CRISPR elements specific for a particular target sequence. The methods described herein are not limited to the use of specific CRISPR elements, but rather are intended to provide unique arrangements, compilations, and uses of CRISPR elements in non-conventional yeasts like *I. orientalis*.

One non-limiting example can include the gene disruption of one or more genes, for example, a subunit of a succinate dehydrogenase enzyme (SDH), by transforming a vector comprising a gRNA targeting SDH1 and/or SDH2. The resultant recombinant yeast can have impaired succinic acid metabolism, leading to the accumulation of such organic acid. Succinic acid has a pKa of 4.61, which places it below the optimal growth pH for most organisms, but where non-conventional yeasts like *I. orientalis* can still thrive. Therefore, in an embodiment, vectors and expression cassettes as described herein can provide a tool for the production of chemicals, including organic acids such as succinic acid. Non-limiting examples of chemicals that can be derived from succinic acid include 1,4-butanediol, 1,4-diaminobutane, succinamide, succinonitrile, N-Methyl-2-pyrrolidinone, 2-pyrrolidinone, N-Vinyl-2-pyrrolidinone, γ-Butyro-lactone (GBL), and tetradrofuran (THF). Examples of organic acids can include itaconic acid, muconic acid, or lactic acid.

As used herein, "increasing gene expression" refers to the use of an expression cassette or vector as described herein comprising at least one or more polynucleotide sequences encoding one or more proteins of interest, each operably linked to a promoter sequence and to a terminator sequence, to induce the expression of said one or more proteins of interest in the yeast sought to be transformed by such vector or expression cassette.

The one or more proteins of interest can be part of a functional pathway, and by increasing the expression of one or more protein pertaining to a same functional pathway, the vector as described herein can be used to alter the metabolism of the yeast. For example by inducing the expression of xylose reductase, xylitol dehydrogenase, and xylulokinase, the xylose utilization pathway can be rendered functional in the yeast, which can be able to grow and ferment in conditions where xylose is the main carbon source.

In an embodiment, a method of decreasing the expression of one or more gene products in a yeast, or of deleting at least one polynucleotide or fragment thereof from a yeast genome is provided. The methods can comprise contacting the yeast with a vector comprising an expression cassette. The expression cassette can comprise, for example, a guide RNA (gRNA) targeting a polynucleotide of interest and a catalytically-active RNA-guided DNA endonuclease protein. The gRNA can be operably linked to a RNA polymerase (RNAP) III promoter. An expression cassette can further comprise a polynucleotide encoding a catalytically active RNA-guided DNA endonuclease protein, wherein the polynucleotide is operably linked to a promoter sequence and to a terminator sequence. Any suitable promoter sequence and terminator sequence can be used. For example, a promoter sequence such as that shown in SEQ ID NO: 17-53 can be used; and a terminator sequence such that shown in SEQ ID NO:54-72 can be used. An expression cassette can further comprise a *Saccharomyces cerevisiae* autonomously replicating sequence (ScARS); for example, a ScARS as shown in SEQ ID NO:73 can be used. An expression cassette can further comprise a centromere sequence. For example a centromere sequence having the sequence of SEQ ID NO: 11-16, SEQ ID NO:74, or SEQ ID NO: 154-163_or a sequence having about 80, 85, 90, 95, 96, 97, 98, 99% or more sequence identity to SEQ ID NO:74, SEQ ID NO:11-16, or SEQ ID NO: 154-163 can be used.

In an embodiment, an expression cassette can comprise a gRNA targeting a polynucleotide of interest and a catalytically-active RNA-guided DNA endonuclease protein, operably linked to a RNAP III promoter; a target polynucleotide; a polynucleotide encoding a catalytically active RNA-guided DNA endonuclease protein, operably linked to a promoter sequence (e.g., SEQ ID NO:17-53) and to a terminator sequence (e.g., SEQ ID NO: 54-72); a ScARS (e.g., SEQ ID NO:73); and a centromere sequence (e.g., SEQ ID NO:11-16, SEQ ID NO:74, or SEQ ID NO: 154-163 or a sequence having about 80, 85, 90, 95, 96, 97, 98, 99% or more sequence identity to SEQ ID NO:74, SEQ ID NO: 11-16, or SEQ ID NO: 154-163).

In an embodiment, a method of increasing the expression of one or more gene products in a yeast is provided. The method can comprise contacting the yeast with a vector comprising an expression cassette. The expression cassette can comprise one or more polynucleotide sequences encoding one or more proteins of interest. The one or more polynucleotide sequences can each be operably linked to a promoter sequence and to a terminator sequence. A polynucleotide of interest can be any polynucleotide that one wants to introduce in a genome using an expression cassette as described herein. Non-limiting examples of polynucleotide of interest can include polynucleotide as shown in SEQ ID NO:75-79. Any suitable promoter sequence and terminator sequence can be used. For example, a promoter sequence such as that shown in SEQ ID NO: 17-53 can be used; and a terminator sequence such that shown in SEQ ID NO:54-72 can be used. An expression cassette can further comprise a *Saccharomyces cerevisiae* autonomously replicating sequence (ScARS); for example, a ScARS as shown in SEQ ID NO:73 can be used. An expression cassette can further comprise a centromere sequence. For example a centromere sequence having the sequence of SEQ ID NO: 11-16, or SEQ ID NO:74 or SEQ ID NO: 154-163 or a sequence having about 80, 85, 90, 95, 96, 97, 98, 99% or more sequence identity to SEQ ID NO:74, SEQ ID NO: 11-16, or SEQ ID NO: 154-163 can be used.

In an embodiment, an expression cassette can comprise a polynucleotide of interest (e.g., SEQ ID NO:75-79) operably linked to a promoter sequence (e.g., SEQ ID NO:17-53) and to a terminator sequence (e.g., SEQ ID NO: 54-72); a SCARS (e.g., SEQ ID NO:73); and a centromere sequence (e.g., SEQ ID NO:11-16, SEQ ID NO:74, or SEQ ID NO: 154-163 or a sequence having about 80, 85, 90, 95, 96, 97, 98, 99% or more sequence identity to SEQ ID NO:74, SEQ ID NO: 11-16, or SEQ ID NO: 154-163).

System are provided for targeted genome engineering comprising one or more vectors or expression cassettes.

Each vector or expression cassette can comprise: (i) a guide RNA (gRNA) that binds a target polynucleotide and a catalytically-active RNA-guided DNA endonuclease protein; (ii) a polynucleotide encoding a catalytically active RNA-guided DNA endonuclease protein that binds to a gRNA, generates a double-stranded nucleic acid break, and induces deletion of a target polynucleotide; (iii) a RNA polymerase III promoter that induces capping a 5' end of a polynucleotide, and polyadenylation a 3' end of the polynucleotide; (iv) a Saccharomyces cerevisiae autonomously replicating sequence (ScARS); (v) a centromere-like sequence (CEN-L) having the sequence of SEQ ID NO:11-Systems 16 or 74; or (vi) a polynucleotide of interest operably linked to a promoter sequence and to a terminator sequence.

In an embodiment, a system comprising one or more plasmids is provided. In another embodiment, a system comprising one or more viral vectors is provided.

In an embodiment, the system can comprise one or more plasmids or viral vectors for decreasing the expression of one or more gene product in a yeast, or to delete one or more polynucleotides or fragment thereof from a yeast genome. The plasmids or viral vectors can comprise an expression cassette. The expression cassette can comprise a guide RNA (gRNA) targeting a polynucleotide of interest and a catalytically-active RNA-guided DNA endonuclease protein. The gRNA can be operably linked to a RNA polymerase (RNAP) III promoter. An expression cassette can further comprise a polynucleotide encoding a catalytically active RNA-guided DNA endonuclease protein, wherein the polynucleotide is operably linked to a promoter sequence and to a terminator sequence. Any suitable promoter sequence and terminator sequence can be used. For example, a promoter sequence such as that shown in SEQ ID NO: 17-53 can be used; and a terminator sequence such that shown in SEQ ID NO:54-72 can be used. An expression cassette can further comprise a Saccharomyces cerevisiae autonomously replicating sequence (ScARS); for example, a ScARS as shown in SEQ ID NO:73 can be used. An expression cassette can further comprise a centromere sequence. For example a centromere sequence having the sequence of SEQ ID NO: 11-16, SEQ ID NO:74, or SEQ ID NO: 154-163_or a sequence having about 80, 85, 90, 95, 96, 97, 98, 99% or more sequence identity to SEQ ID NO:74, SEQ ID NO:11-16, or SEQ ID NO: 154-163 can be used.

In an embodiment, the system can comprise one or more plasmids or viral vectors for increasing the expression of one or more gene products in a yeast. The plasmids or viral vectors can comprise an expression cassette. The expression cassette can comprise one or more polynucleotide sequences encoding one or more proteins of interest. The one or more polynucleotide sequences can each be operably linked to a promoter sequence and to a terminator sequence. A polynucleotide of interest can be any polynucleotide that one wants to introduce in a genome using an expression cassette as described herein. Non-limiting examples of polynucleotide of interest can include polynucleotide as shown in SEQ ID NO:75-79. Any suitable promoter sequence and terminator sequence can be used. For example, a promoter sequence such as that shown in SEQ ID NO:17-53 can be used; and a terminator sequence such that shown in SEQ ID NO:54-72 can be used. An expression cassette can further comprise a Saccharomyces cerevisiae autonomously replicating sequence (ScARS); for example, a ScARS as shown in SEQ ID NO:73 can be used. An expression cassette can further comprise a centromere sequence. For example a centromere sequence having the sequence of SEQ ID NO:11-16, SEQ ID NO:74, or SEQ ID NO: 154-163 or a sequence having about 80, 85, 90, 95, 96, 97, 98, 99% or more sequence identity to SEQ ID NO:74, SEQ ID NO: 11-16, or SEQ ID NO: 154-163 can be used.

CRISPR-AID System

The systems described herein can be used to form a combinatorial metabolic engineering strategy based on a tri-functional CRISPR system that combines orthogonal proteins for transcriptional activation, transcriptional interference, and gene deletion (CRISPR-AID) in non-conventional yeast.

CRISPR-AID, a tri-functional CRISPR system combining transcriptional activation (CRISPRa), transcriptional interference (CRISPRi), and gene deletion (CRISPRd), for combinatorial metabolic engineering of non-conventional yeast is provided herein. The systems enable the exploration of the gain- and loss-of-function combinations that work synergistically to improve the desired phenotypes. CRISPR-AID not only includes three modes of genome engineering (gene activation, gene interference, and gene deletion), but also has different mechanisms of genome modulation than, for example, RNAi and offers several advantages. For example, down-regulation using CRISPRi or RNAi is required for the modulation of essential genes, while CRISPRd enables more stable and in many cases significant phenotypes when targeting non-essential genes; CRISPRa is less biased for overexpression of large genes during large scale combinatorial optimization; CRISPRi blocks transcription in the nucleus while RNAi affects mRNA stability and translation, and CRISPRi is generally found to have higher repression efficiency in many situations. Using CRISPR-AID, different modes of genomic modifications (i.e. activation, interference, and deletion) can be introduced via gRNAs on a plasmid or other delivery method. Combinatorial metabolic engineering can be achieved by testing all the possible gRNA combinations. All the combinations of the metabolic engineering targets of the metabolic and regulatory network related to a desired phenotype can be explored.

An embodiment provides a system for targeted genome engineering of a non-conventional yeast, the system comprising one or more vectors comprising: (i) a first single guide RNA (sgRNA) that is capable of binding a target nucleic acid and binding a first nuclease-deficient RNA-guided DNA endonuclease protein; (ii) a second sgRNA that is capable of binding a target nucleic acid and binding a second nuclease-deficient RNA-guided DNA endonuclease protein; (iii) a third sgRNA that is capable of binding a target nucleic acid and binding a catalytically-active RNA-guided DNA endonuclease protein; (iv) a polynucleotide encoding a first nuclease-deficient RNA-guided DNA endonuclease protein that binds to the first sgRNA and causes transcriptional activation; (v) a polynucleotide encoding a second nuclease-deficient RNA-guided DNA endonuclease protein that binds to the second sgRNA and causes transcriptional interference; (vi) a polynucleotide encoding a catalytically active RNA-guided DNA endonuclease protein that binds to the third sgRNA and causes a double-stranded nucleic acid break and causes gene deletion; (v) a Saccharomyces cerevisiae autonomously replicating sequence (ScARS) as described herein; (vi) a centromere-like sequence (CEN-L) as described herein having, e.g., the sequence of SEQ ID NO: 11, SEQ ID NO:74, SEQ ID NO: 154-163 or SEQ ID NO: 154-163 or a sequence having about 80, 85, 90, 95, 96, 97, 98, 99% or more sequence identity to SEQ ID NO:74, SEQ ID NO: 11-16, or SEQ ID NO: 154-163 or any combination thereof. In the system components (i), (ii), (iii), (iv), (v), and (vi) can located on the same or different 1, 2, 3, 4, 5, or 6 vectors of the system. One, two, three, four, five, or more of components (i), (ii), (iii), (iv), (v), and (vi) can located on 1, 2, 3, 4, 5, or 6 vectors.

The *Saccharomyces cerevisiae* autonomously replicating sequence (ScARS) and centromere-like sequence (CEN-L) are present and used as described above.

In an embodiment, the first single guide RNA (sgRNA) is operably linked to a RNA polymerase (RNAP) III promoter as described herein. In an embodiment, the polynucleotide encoding a catalytically active RNA-guided DNA endonuclease protein that binds to the third sgRNA is operably linked to a promoter sequence and to a terminator sequence The system for targeted genome engineering can comprise more than one first single guide RNA (sgRNA) (e.g., 2, 3, 4, 5, 10, or more) that are capable of binding a target nucleic acid sequence and binding a first nuclease-deficient RNA-guided DNA endonuclease protein; more than one second sgRNA (e.g., 2, 3, 4, 5, 10, or more) that are capable of binding a target nucleic acid sequence and binding a second nuclease-deficient RNA-guided DNA endonuclease protein; more than one third sgRNA (e.g., 2, 3, 4, 5, 10, or more) that is capable of binding a target nucleic acid and binding a catalytically-active RNA-guided DNA endonuclease protein; a polynucleotide encoding a first nuclease-deficient RNA-guided DNA endonuclease protein that binds to the first group of sgRNA and causes transcriptional activation; a polynucleotide encoding a second nuclease-deficient RNA-guided DNA endonuclease protein that binds to the second group of sgRNA and causes transcriptional interference; and a polynucleotide encoding a catalytically active RNA-guided DNA endonuclease protein that binds to the third group of sgRNA and causes a double-stranded nucleic acid break and causes gene deletion.

The single guide RNA (sgRNA) capable of directing nuclease-deficient RNA-guided DNA endonuclease mediated transcriptional activation of target DNA, the sgRNA capable of causing transcriptional interference, and the sgRNA that capable of directing catalytically active RNA-guided DNA endonuclease mediated gene deletion or knock-out of target DNA can each target a different target nucleic acid.

As used herein, the term "targeted genome engineering" refers to a type of genetic engineering in which DNA is inserted, deleted, modified, modulated or replaced in the genome of a living organism or cell. Targeted genome engineering can involve integrating nucleic acids into or deleting nucleic acids from genomic DNA at a target site of interest in order to manipulate (e.g., increase, decrease, knockout, activate, interfere with) the expression of one or more genes. Targeted genome engineering can also involve recruiting RNA polymerase to or repressing RNA polymerase at a target site of interest in the genomic DNA in order to activate or repress expression of one or more genes.

In another embodiment, each of (i), (ii), (iii), (iv), (v), and (vi) can be combined together on one vector or present in various combinations. The one or more vectors can be plasmids or viral vectors. In other embodiments, the viral vector is a lentivirus vector, an adenovirus vector, or an adeno-associated vector (AAV). In some embodiments, a vector is a yeast expression vector. Examples of vectors for expression in yeast *Saccharomyces cerevisiae* include pYepSec1 (Baldari, et al., 1987. EMBO J. 6: 229-234), pMFa (Kuijan and Herskowitz, 1982. Cell 30: 933-943), pJRY88 (Schultz et al., 1987. Gene 54: 113-123), pYES2 (Invitrogen Corporation, San Diego, Calif.), and picZ (InVitrogen Corp, San Diego, Calif.)

Nuclease-deficient RNA-guided DNA endonucleases can cause transcriptional activation or transcriptional interference. There are many versions of RNA-guided DNA endonucleases isolated from different bacteria.

Each RNA-guided DNA endonuclease binds to its target sequence only in the presence of a protospacer adjacent motif (PAM), on the non-targeted DNA strand. Therefore, the locations in a genome that can be targeted by different RNA-guided DNA endonuclease can be dictated by locations of PAM sequences. A catalytically-active RNA-guided DNA endonuclease cuts 3-4 nucleotides upstream of the PAM sequence. Recognition of the PAM sequence by a RNA-guided DNA endonuclease protein is thought to destabilize the adjacent DNA sequence, allowing interrogation of the sequence by the sgRNA, and allowing the sgRNA-DNA pairing when a matching sequence is present. Exemplary protospacers and PAM motifs the can be used of the systems and methods described herein are listed in Table 15. The three independent RNA-guided DNA endonuclease proteins of the tri-functional systems described herein can have protospacer adjacent motif (PAM) sequences and gRNA scaffold sequences that are different from each other.

A nuclease-deficient RNA-guided DNA endonuclease protein can be operably linked to at least one activation domain to form a nuclease-deficient RNA-guided DNA endonuclease that causes transcriptional activation. As used here, the term "activation domain" refers to a transcription factor that increases transcription of the gene that it targets. Activation domains can be derived from a transcription factor protein. Activation domains can contain amino acid compositions rich in acidic amino acids, hydrophobic amino acids, prolines, glutamines, or hydroxylated amino acids. Alpha helix structural motifs can also be common in activation domains. Activation domains contain about 5 amino acids to about 200 amino acids (La Russa, M. F., et al., Mol. Cell. Biol. 35:3800-3809 (2015); Maeder, M. I., et al., Nat. Methods 10:977-979 (2013); Qi, I. S., et al., Cell 152:1173-1183 (2013); Gilbert, L. A., et al., Cell 159:647-661 (2014); Zalatan, J. G., et al., Cell 160:339-350 (2015); Chavez A., et al., Nat. Methods 12:326-8 (2015)).

Two DNA sequences are operably linked if the nature of the linkage does not interfere with the ability of the sequences to affect their normal functions relative to each other. For instance, a promoter region would be operably linked to a coding sequence of the protein if the promoter were capable of effecting transcription of that coding sequence.

A nuclease-deficient RNA-guided DNA endonuclease protein can be, for example dSpCas9, dLbCpf1, dSt1Cas9, or dSaCas9 and an activation domain can be, for example, plodSpCas9-V, plodSpCas9-VP plodSpCas9-VPR, plodSt1Cas9-V, plodSt1Cas9-VP, plodSt1Cas9-VPR, plodLbCpf1-V, plodLbCpf1-VR, or plodLbCpf1-VPR. A nuclease-deficient RNA-guided DNA endonuclease protein can be, for example, dLbCpf1 and a one activation domain can be, for example, plodSpCas9-VP.

A nuclease-deficient RNA-guided DNA endonuclease protein can be operably linked to at least one repression domain to form a nuclease-deficient RNA-guided DNA endonuclease protein that causes transcriptional interference. A repression domain is a transcription factor that decreases transcription of the gene that it targets. (La Russa, M. F., et al., Mol. Cell. Biol. 35:3800-3809 (2015); Maeder, M. I., et al., Nat. Methods 10:977-979 (2013); Qi, I. S., et al., Cell 152:1173-1183 (2013); Gilbert, L. A., et al., Cell 159:647-661 (2014); Zalatan, J. G., et al., Cell 160:339-350 (2015)). Like activation domains, repression domains can vary in length and amino acid sequence, and do not have significant sequence homology with one another. Repression domains can have amino acid compositions rich in alanines, prolines, and charged amino acids. Repression domains can contain about 5 amino acids to about 200 amino acids. A repression domain can be small (e.g., about 5 to 200 amino acids, about 5 to 150 amino acids, about 10 to 100 amino acids, about 20 to 80 amino acids, about 10 to 50 amino acids) while demonstrating strong transcriptional repression.

A nuclease-deficient RNA-guided DNA endonuclease protein can be operably linked multiple repression domains (e.g., 2, 3, 4, 5, 6, 7, 8, 9, 10 or more repression domains) to form a nuclease-deficient RNA-guided DNA endonuclease protein that causes transcriptional interference.

Examples of nuclease-deficient RNA-guided DNA endonuclease protein that cause transcriptional interference include dSpCas9, dLbCpf1, dSt1Cas9, or dSaCas9. Examples of repression domains include MXI1, RD1153, or combinations thereof.

A catalytically active RNA-guided DNA endonuclease protein is an RNA-guided DNA endonuclease protein that is directed by RNA base pairing and capable of cleaving a phosphodiester bond within a polynucleotide chain. Catalytically active RNA-guided DNA endonuclease proteins include, for example, Cas9 from *Streptococcus pyogenes* (SpCas9), Cpf1 from Lachnospiraceae bacterium ND2006 (LbCpf1), *Streptococcus thermophilus* (St1Cas9), and *Staphylococcus aureus* (SaCas9).

As used herein, the term "target DNA" refers to chromosomal DNA. Target DNA includes nucleic acids that can be activated, repressed, deleted, knocked-out, or interfered with. For example, target DNA can include protein coding sequences and promoter sequences. Target DNA can be about 18 nucleotides to about 25 nucleotides in length. Target DNA for CRISPRa can be, for example, about 250 base pairs upstream of the coding sequences or about 200 base pairs upstream of the transcription starting site (TSS). Target DNA for CRISPRa can be, for example, about 23 base pairs (e.g., 21, 22, 23, 24, or 25 base pairs) in length. Target DNA for CRISPRi can be, for example, about 100 base pairs to about 150 base pairs upstream of the coding sequences or 50 base pairs to about 100 base pairs upstream of the TSS. Target DNA for CRISPRa can be, for example, about 20 base pairs (e.g., 18, 19, 20, 21, or 22 base pairs) in length. Target DNA for CRISPRd can be, for example, about 21 base pairs (e.g., 19, 20, 21, 22 or 23 base pairs) in length. Most organisms have the same genomic DNA in every cell, but only certain genes are active in each cell to allow for cell function and differentiation within the body. The genome of an organism (encoded by the genomic DNA) is the (biological) information of heredity which is passed from one generation of organism to the next.

A system described herein can further comprise one or more additional sgRNA molecules that are capable of binding a target nucleic acid and a catalytically-active RNA-guided DNA endonuclease protein that causes a double-stranded nucleic acid break of one or more additional target nucleic acid molecules. In this aspect, the genome can be cut at several different sites (e.g., 1, 2, 3, 4, 5, 6, 7, 8, 9, or 10 sites) at or near the same time, and the homology directed repair donor included in the sgRNA expression plasmid can be inserted into those one or more sites (Bao, Z., et al., 2015, ACS Synth. Biol., 5:585-594).

The systems described herein can utilize orthogonal RNA-guided DNA endonuclease proteins. Orthogonal refers to ligand-protein pairs, whereby the RNA-guided DNA endonuclease protein is only functional when in the presence of its cognate gRNA pair. For example, a nuclease-deficient RNA-guided DNA endonuclease protein (e.g., dSpCas9, dLbCpf1, dSt1Cas9, or dSaCas9) is functional only when bound to a sgRNA ortholog. A catalytically active RNA-guided DNA endonuclease protein (e.g., Cas9) can be functional only when bound to a sgRNA ortholog.

A nuclease-deficient RNA-guided DNA endonuclease or catalytically active RNA-guided DNA endonuclease, can be expressed from an expression cassette. An expression cassette is a distinct component of vector DNA comprising a gene and regulatory elements to be expressed by a transformed or transfected cell, whereby the expression cassette directs the cell to make RNA and protein. Different expression cassettes can be transformed or transfected into different organisms including bacteria, yeast, plants, and mammalian cells as long as the correct regulatory element sequences are used.

Once a target DNA and RNA-guided DNA endonuclease have been selected, the next step is to design a specific guide RNA sequence. Several software tools exist for designing an optimal guide with minimum off-target effects and maximum on-target efficiency. Examples include Synthego Design Tool, Desktop Genetics, Benchling, and MIT CRISPR Designer.

A guide RNA used in the systems and methods can be short, single-stranded polynucleotide molecules about 20 nucleotides to about 300 nucleotides in length. The spacer sequence (targeting sequence) that hybridizes to a complementary region of the target DNA of interest can be about 20-30 nucleotides in length.

A sgRNA capable of directing nuclease-deficient RNA-guided DNA endonuclease mediated transcriptional activation of target DNA can be about 43 nucleotides (e.g., about 40, 41, 42, 43, 44, 45, or 46 nucleotides) in length. A sgRNA can guide a nuclease-deficient RNA-guided DNA endonuclease near the promoter or enhancer regions of a gene to activate transcription (e.g., about 250 bp upstream of the coding sequences or about 200 bp upstream of the TSS). The activation domain(s) of the nuclease-deficient RNA-guided DNA endonuclease recruits RNA polymerase to activate the expression of the target gene.

A sgRNA capable of directing nuclease-deficient RNA-guided DNA endonuclease mediated transcriptional interference of target DNA can be about 96 nucleotides (e.g., about 91, 92, 93, 94, 95, 96, 97, 98, 99, or 100 nucleotides) in length. A sgRNA can guide a nuclease-deficient RNA-guided DNA endonuclease near the promoter or enhancer regions of a gene to interfere with transcription (e.g., about 100-150 bp upstream of the coding sequence or 50-100 bp upstream of TSS). The repression domain(s) of the nuclease-deficient RNA-guided DNA endonuclease interferes with the binding of the RNA polymerase, which in turn represses transcription of the target gene.

A sgRNA capable of directing catalytically-active RNA-guided DNA endonuclease mediated gene deletion of target DNA can be can be about 248 nucleotides (e.g., 236, 237, 238, 239, 240, 241, 242, 243, 244, 245, 246, 247, 248, 249, 250, 251, 252, 253, 254, 255, 256, 257, 258, 259, or 260 nucleotides) in length. A sgRNA can guide a catalytically active RNA-guided DNA endonuclease to the coding sequence of a gene. The sgRNA used to direct gene deletion can include DNA donor sequences for homology-directed repair.

sgRNAs can be synthetically generated or by making the sgRNA in vivo or in in vitro, starting from a DNA template. One method of making sgRNAs comprises expressing the sgRNA sequence in cells from a transformed or transfected plasmid. The sgRNA sequence is cloned into a plasmid vector, which is then introduced into cells. The cells use their normal RNA polymerase enzyme to transcribe the genetic information in the newly introduced DNA to generate the sgRNA.

sgRNA can also be made by in vitro transcription (IVT). sgRNA is transcribed from a corresponding DNA sequence outside the cell. A DNA template is designed that contains the guide sequence and an additional RNA polymerase promoter site upstream of the sgRNA sequence. The sgRNA is then transcribed using commercially available kits with reagents and recombinant RNA polymerase.

sgRNAs can also be synthetically generated. Synthetically generated sgRNAs can be chemically modified to prevent degradation of the molecule within the cell.

A sgRNA can target a regulatory element (e.g., a promoter, enhancer, or other regulatory element) in the target genome. A sgRNA can also target a coding sequence in the target genome.

The sgRNAs of the systems and methods described herein can also be truncated (e.g., comprising 12-16 nucleotide targeting sequences). For example, Sg27 gRNAs is a truncated version of the full length Sg1. The sgRNA can be unmodified or modified. For example, modified sgRNAs can comprise one or more 2'-O-methyl and/or 2'-O-methyl phosphorothioate nucleotides.

A first single guide RNA (sgRNA) that is capable of binding a target nucleic acid sequence and binding a first nuclease-deficient RNA-guided DNA endonuclease protein; a second sgRNA that is capable of binding a target nucleic acid sequence and binding a second nuclease-deficient RNA-guided DNA endonuclease protein; a third sgRNA that is capable of binding a target nucleic acid sequence and binding a catalytically active RNA-guided DNA endonuclease protein; a polynucleotide encoding a first nuclease-deficient RNA-guided DNA endonuclease protein that binds to the first sgRNA and causes transcriptional activation; a polynucleotide encoding a second nuclease-deficient RNA-guided DNA endonuclease protein that binds to the second sgRNA and causes transcriptional interference; and a polynucleotide encoding a catalytically active RNA-guided DNA endonuclease protein that binds to the third sgRNA and causes a double-stranded nucleic acid break and causes gene deletion can be located on the same or different vectors of the system.

The three sgRNAs or three pools of sgRNAs that can be used in the CRISPR-AIDs systems and methods herein are orthogonal to each other, meaning that the first sgRNA or first pool of sgRNAs are only be recognized by the nuclease-deficient RNA-guided DNA endonuclease capable of causing transcriptional activation; the second sgRNA or second pool of sgRNAs can only be recognized by the nuclease-deficient RNA-guided DNA endonuclease capable of causing transcriptional interference; and, the third sgRNA or third pool of sgRNAs can only be recognized by the catalytically active RNA-guided DNA endonuclease capable of causing gene deletion.

sgRNAs are not particularly limited and can be any sgRNA.

sgRNA that is capable of binding a target nucleic acid sequence and binding a nuclease-deficient RNA-guided DNA endonuclease protein that causes transcriptional interference can be expressed in an expression cassette comprising a type II promoter or a type III promoter.

One or more expression cassettes or vectors that express sgRNA and/or RNA-guided DNA endonuclease proteins can further comprise a polynucleotide encoding for a marker protein in all systems described herein. The marker protein can be, for example, an antibiotic resistance protein or a florescence protein for easier monitoring of genome integration and expression, and to label or track particular cells.

A polynucleotide encoding a marker protein can be expressed on a separate vector from a vector that expresses sgRNA and/or RNA-guided DNA endonuclease proteins.

A marker protein is a protein encoded by a gene that when introduced into a cell (prokaryotic or eukaryotic) confers a trait suitable for artificial selection. Marker proteins are used in laboratory, molecular biology, and genetic engineering applications to indicate the success of a transformation, a transfection or other procedure meant to introduce foreign DNA into a cell. Marker proteins include, but are not limited to, proteins that confer resistance to antibiotics, herbicides, or other compounds, which would be lethal to cells, organelles or tissues not expressing the resistance gene or allele. Selection of transformants is accomplished by growing the cells or tissues under selective pressure, i.e., on media containing the antibiotic, herbicide or other compound. If the marker protein is a "lethal" marker, cells which express the marker protein will live, while cells lacking the marker protein will die. If the marker protein is "non-lethal," transformants (i.e., cells expressing the selectable marker) will be identifiable by some means from non-transformants, but both transformants and non-transformants will live in the presence of the selection pressure.

Selective pressure refers to the influence exerted by some factor (such as an antibiotic, heat, light, pressure, or a marker protein) on natural selection to promote one group of organisms or cells over another. In the case of antibiotic resistance, applying antibiotics cause a selective pressure by killing susceptible cells, allowing antibiotic-resistant cells to survive and multiply.

Selective pressure can be applied by contacting the cells with an antibiotic and selecting the cells that survive. The antibiotic can be, for example, kanamycin, puromycin, spectinomycin, streptomycin, ampicillin, carbenicillin, bleomycin, erythromycin, polymyxin B, tetracycline, or chloramphenicol.

In some embodiments, the systems and methods do not utilize synthetic CRISPR-repressible promoters (e.g., CRP-a) or synthetic CRISPR-activatable promoters (e.g., CAP). Synthetic CRISPR-repressible or CRISPR-activatable promoters are designed for CRISPRa and CRISPRi in mammalian cells (Kiani, S., et al., 2015, Nat. Methods, 12:1051-1054). A repressible promoter can express genes constitutively unless they are switched off by a repressor (e.g., protein or small molecule). An activatable promoter, or inducible promoter, can express genes only when an activator (e.g., protein or small molecule) is present.

Methods of Altering Gene Expression Via CRISPR-AID

An embodiment provides a method of altering the expression of gene products. The methods comprise introducing into a cell a system for targeted genome engineering as described herein; wherein the expression of at least one gene product (e.g., about 1, 2, 3, 4, 5, 10, or more) is increased, the expression of at least one gene product (e.g., about 1, 2, 3, 4, 5, 10, or more) is decreased, and the expression of at least one gene product (e.g., about 1, 2, 3, 4, 5, 10, or more) is deleted relative to a cell that has not been transformed or transfected with the system for targeted genome engineering.

The methods can further comprise selecting for successfully transformed or transfected cells by applying selective pressure (e.g., culturing cells in the presence of selective media).

One or more vectors of a system described herein can further comprise a polynucleotide encoding for a marker protein such as an antibiotic resistance protein or a florescence protein.

Transformation or transfection is the directed modification of the genome of a cell by introducing recombinant DNA from another cell of a different genotype, leading to its uptake and integration into the subject cell's genome. In bacteria, the recombinant DNA is not typically integrated into the bacterial chromosome, but instead replicates autonomously as a plasmid. A vector can be introduced into cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.). It will be appreciated by those skilled in the art that the design of the expression vector can depend on such factors as the choice of the host cell to be transformed, the level of expression desired, etc.

Methods for transforming or transfecting a cell with an expression vector may differ depending upon the species of the desired cell. For example, yeast cells may be transformed by lithium acetate treatment (which may further include carrier DNA and PEG treatment) (the LiAc/SS carrier and DNA/PEG method) or electroporation. Mammalian cells can be transfected via liposome-mediated transfection, using non-liposomal transfection agents (e.g., polymers and lipids), or by electroporation. These methods are included for illustrative purposes and are in no way intended to be limiting or comprehensive. Routine experimentation through means well known in the art may be used to determine whether a particular expression vector or transformation method is suited for a given host cell. Furthermore, reagents and vectors suitable for many different host microorganisms are commercially available and/or well known in the art.

Any gene product pathway, combination of pathways, operon, group of related genes, or groups of unrelated genes can be targeted using systems described herein.

The method can occur in vivo or in vitro. The cell can be a eukaryotic cell or a prokaryotic cell. Eukaryotic cells include mammalian cells (e.g., mouse, human, dog, monkey), insect cells (e.g., bee, fruit fly) plant cells, algae cells, and fungal cells (e.g., yeast). The cell can be a yeast cell such as *Issatchenkia orientalis*.

Any combination of genes can be targeted by the systems described herein.

RNA Interference

An embodiment provides a system for RNAi in non-conventional yeast. The system can comprise one or more nucleic acid molecules encoding one or more dicer polypeptides and one or more Argonaute ("Ago") polypeptides and/or one or more dicer polypeptides and one or more Argonaute polypeptides. The Argonaute polypeptide can be g45 Ago encoded by, for example, SEQ ID NO: 165.

```
ATGTCAGGAGGAAGCAACAGAGGCCGTGGAGGAATCAGAGGTGGGACACGAGGCGGTAGAGGAGGCAG

AGGCGGCAGGGGCGGCAAAGGAAGCAGAGGAGGCAGAGGTGGGGTTGGTGGTGGTGACGCACAGGTGGTGAAACCCGAAT

ATCAATTCAAACCGGAGTTTGAATCACAAATGACTGCACCGGATCCAACCTTCAGAATTAAAGAGTTGTTGGCCCAGGAA

GAGAAAACCAGAAAACCTGGCGATCCGTACCAACTCGTCAAAAGACCTGGGTTTGGTACCGTTGGTATAAAGACCAAAGT

CGGTACGAATTACCTCAAGTTCAATGTCTCGCACATGAAATTCTGGTACTATAACGTCACATTCCAGCCGGAGATTGCAG

CAAAGAAAAAAATCAAGAAGGATCTATTGGAAATCCTTCTGAAAAAGTCTCCATTCAGCGGATTGAAGGGGAAATTATTT

CATAATGGCTCAGACGCAATATATTCGTCGGCACCATTGCCGATCAAAAGGGAGGACGGAAAAGTCAGATTTGATTTCCA

GCAAGATGATTACAAAGGTGTTGTCTCCTCGACTGTGATGGCTGCCTTAAGAGGTTCGGAGAAGAAGAAGACCGAAGGTG

ATCCTCCAGTTTATTGTACCGTTGAATACATTTATAAATTGGATATGGATGATTTGAATAACTGGGTCCAAATTAAAGAT

AAGAAAAACATCGAAGCTGCTGCTTACATTTCTGCCCTCAATGTTTTATTGGGTTACCAAATTGCCAAAAAGGCCAATGT

CTTCACTGCAGGCAGGTCTAAGTTCTTCTTTGTCGAGCATCCTGAAAAATGCCAGTCTTTCCAAAGAGGTTTATATCTAG

CCAGCGGTTATTATGCTTCTGTTTTACCAACTTTTGATAATGTCATGCTTAACGTGAGGCCCGTTGCTGGTGCGTTTATC

AAATCCCATAATAAGGATGGTACTCCAATGTCTGTTGCAGATTTAGTTGCAGATTATTTTGGAGAAACCGATCTGAAGAA

GGTTCCGAACTCTGAAATAGTCAACCAAAGGTTTTTCTTCAAAGGTATCAAAATTTTGAGGACTTATTTGGGCCATAAGT

CCAAACCAAAGGGTATTTTGATATAAGTAGGTCAGATACTGCTAACAATTATAAATTCGACTGTGATGGTAAGCAAACA

TCAGTTGCTGAATACTTTGCAGAAACGTACAACTTGAAGCTGAAGTATCCCGATGCGCCTTTAGTTCATTTGGGTGGCAG

CAATTACCTACCAATGGAAGCGTGTATCATTGTCCCAGGTCAAGAGTTCAAGGGGGAAATCTCCGATGTAAGGGGTATTC

TGAGTTTCACTACCCACAGACCTCATGTTATAGCTGGCCTAGTTCAACAAGAGGGTATCAAGAATTTATCAACTGCAATT

GATAGTGAAGAATCTGCTAGAATTGGTAAAAAGTTGGTTGTTGTCCCTTCGAGAGTTTTACCAGCTCCTGTTCTGGAGTA

TAAGAATGCAAAAATTGCTTATAGTGAAAAACCGGCAGATGGTAAGTCGGAAAAAGCCAAGGGATCTTGGGATCTAATTA

ACAAGCAATTCTATAATCCTGTTAAAGGTGTCAAGAAGTTGACGGTCTTAGTTTTGGAAAATTCTAGGAGACCCCTCCGT

GCGTACGAAAAGGATGACATTGAAGATGCTTGTAATGAATTTGTTAATTCAGCTGCAAAGACAGGCGTGAAATTCGATAA

GAACTATCTCTTTGAACCAGTTTCCTATGACAATGTCATGTACCTCTCGAAGGAAATCATCAAAGTCATGAAACCTTTAC
```

```
AATCAAAAACTGACTACGTTTTAACAATTTTGAATCAGAAAGATTCACAGATTTATTCGGCGGTTAAAACTGCACTGGAT

AAGGATTTGGGTATCTTGAATCAATGTACTCTAGCAAATAAGTTTGCAAAGAGAAAATTTGGCAAGTTTGATCTACAAAT

GTACGCACTGATGAGCATGAAAACTTGTATTAAGCTTGGAGGTACCAACCATGTCCTATCTAAGAACGATGTTGGTATGC

TTGTGGTAGATGGCTTGCCGACATTACTTTTAGGTGCCGATGTGACTCACCCAACCAACAACTCCAACGGTACATCTATA

GCAGCCGTTGTCGGCTCTGTTGACGGACATTTCAATTCTTTCCCTGGCTCCATCTCAGTTCAAGAACAAAAAGTCGAAAC

TATTGCTGAAATGTCCAAAATGTGTGTTGAAAGAATCATGGAATACTACAAATCTGTGGGTAAATTACCAACAAGAGTAT

TGTTTTATAGAGATGGTGTTTCATTGGGCCAGTTCAATATTATCTTGGACGAGGAAGTTACAGCAGTCAAGAATTCTTTC

AAGGTTATCTCCAACAACCTCGGTATTAAATTCGATCCTAAATTAACATTTGTTACTATTCTAAAGAATCATAGTACTAG

ATTTTTCCCACTAGAAAAGAATGCAGCTAATTCTCAAGGAAAACAAGTTGCAGTCACAGCACAAGATAATATTATTCCTG

GTTCTATTGTTGAAAAAGGTGTGACGTCGAGAAGTTTATACGATTTCTTTCTACAGTCACAACAGGCCCTACAAGGAACT

GCTATTCCAGGGCATTATTATGTGTTGTATGACGAGAATAACTGGACTCCAGATGAATTACAGAAAATTACCTACAATTT

GTGTAGTATATTTGGTAGGGCAACCAAATCAGTTAGAGTTGTTCCTCCTGCATATTATGCAGACTTATTGTGTGAAAGAG

CTACATGTTTTGTAAAGAATGTGAAAGTTCTGAAGAACCAATCGCCAGTGGAAGCTGCAAAGAAGGCTATAGGTGATGGT

ATCCACAAGAATGTCAAGGGTAGAATGATCTATATTTAA
```

The polypeptide encoded by SEQ ID NO: 165 is SEQ ID NO:166:

```
MSGGSNRGRGGIRGGTRGGRGGRGGRGGKGSRGGRGGVGGGDAQVVKPEY
QFKPEFESQMTAPDPTFRIKELLAQEEKTRKPGDPYQLVKRPGFGTVGIK
TKVGTNYLKFNVSHMKFWYYNVTFQPEIAAKKKIKKDLLEILLKKSPFSG
LKGKLFHNGSDAIYSSAPLPIKREDGKVRFDFQQDDYKGVVSSTVMAALR
GSEKKKTEGDPPVYCTVEYIYKLDMDDLNNWVQIKDKKNIEAAAYISALN
VLLGYQIAKKANVFTAGRSKFFFVEHPEKCQSFQRGLYLASGYYASVLPT
FDNVMLNVRPVAGAFIKSHNKDGTPMSVADLVADYFGETDLKKVPNSEIV
NQRFFFKGIKILRTYLGHKSKPKGIFDISRSDTANNYKFDCDGKQTSVAE
YFAETYNLKLKYPDAPLVHLGGSNYLPMEACIIVPGQEFKGEISDVRGIL
SFTTHRPHVIAGLVQQEGIKNLSTAIDSEESARIGKKLVVVPSRVLPAPV
LEYKNAKIAYSEKPADGKSEKAKGSWDLINKQFYNPVKGVKKLTVLVLEN
SRRPLRAYEKDDIEDACNEFVNSAAKTGVKFDKNYLFEPVSYDNVMYLSK
EIIKVMKPLQSKTDYVLTILNQKDSQIYSAVKTALDKDLGILNQCTLANK
FAKRKFGKFDLQMYALMSMKTCIKLGGTNHVLSKNDVGMLVVDGLPTLLL
GADVTHPTNNSNGTSIAAVVGSVDGHFNSFPGSISVQEQKVETIAEMSKM
CVERIMEYYKSVGKLPTRVLFYRDGVSLGQFNIILDEEVTAVKNSFKVIS
NNLGIKFDPKLTFVTILKNHSTRFFPLEKNAANSQGKQVAVTAQDNIIPG
SIVEKGVTSRSLYDFFLQSQQALQGTAIPGHYYVLYDENNWTPDELQKIT
YNLCSIFGRATKSVRVVPPAYYADLLCERATCFVKNVKVLKNQSPVEAAK
KAIGDGIHKNVKGRMIYI
```

The dicer polypeptide can be dicer 1 encoded by, for example, SEQ ID NO:167:

```
ATGCAAAGCAGCAATTGCACAGATGTGTTGAGTGAGCTTAAAGATGCGGT
TCAAAATGTTCGAACGGGACTAAGAAAAGTACTGGATATTGCTCCAAATC
GGACCTTATATCAAATATTACTTGATTCAACTAAAAACCCCCTTCTTCAG
AGTATTTTGAGTATTCCAGATGAATCTCATTTGACTCAAAATGATATTAT
CTTTGCAATTGAATTAAAGGAAATGTATGATACTGGAAGGCTGGAAATCT
TGGAATATCTCATAAAAGGAGATATTGAACAGATTAAAACGTGTAACGGA
AATACCAAACAGGAAACTTTCGAAAATAATAGCCCAAACGATAGTTCATC
TAAGTTTCATGAAGACAATATCCCTAATTATAAGGAAAAACTTGAAACAT
GTGATGGTACTGAAATATTTATTGAGGAAGTTGGTAAAGACAAAGTAAGG
AATTCAAATAGTTTTGAGAGTACGCCAGATAACATTTCTTCATCGAATTG
TAGGAAAGATGAAACCCGCTCAGCGGTTGATCAACGAGATGCAGAGACCG
AAAAAGAGGTGAATTCCAATGCGAAAGAACCGGACTCTTACATCAGTGAA
TTATTTACATCGGACGTAATGAGAAGTGAGATGTACGTGCCAGAGGAACT
AGTTTATAAACGAGATAGAAAGTGGGGCCTTTTGAAACAAGAAGAATTGC
CACAAGCTCCTAGTATTGAAGATCCGGAACTTCTGAGAAAGGTTTTCAGT
CATCAGTCAATAGTCAATTATTTGAATATTTCGCCTGAGTTCAAGGTCCA
ATTACATAACGAGAGATTGGAATTCTTAGGTGATGCATTATTACAATTCG
TCACGTCAATGATTATCTATGAAAGGTTTCCCAATTTTAGTGAAGGTCAA
TTATCGATACTACGGAGCACTATCGTGTCTAACTCCAGTTTACTTAAATG
GTCACAAATGTATGGCTTTGATAAACAACTACGTAAGAATCTTATCGATT
CTTCCATCTTAGCAGGTAATAATAAATTATATGCCGATATTTTTGAGGCT
TACCTTGGCGGTATTGCTGAACAGTATATGATGGAAACCAGCGAAGGGGA
AACCAATGTGAACGACTTTATGAAAGGATGGTTTGAAGTCAAATCATGGA
TTGAAGAGTTATCCGAAAATCATATACGTGGGTTTGATCCAAGTATTGTT
TTCAAGATGCAGTATTCCAAATCTAGCAAGCAAGATCTGAGGTTATTACT
```

```
TGGCCAGAATAACAACCCCGATTATATCAGAGTAAACCTGAGCAATAAGA
GAATCTTGTCTTGTATAAAGGTGAATAATAAAGTGTACGGATATGGTATT
GGTACTAGCAACAAAGAAGCCGATGCAAGGGCAGCCGTTGATGCAATATC
CAACCCAGAAATTAGGAAGATTTGTCCAGAAGATATATGGGATAGATTTG
AAAGCAACGTAGGTCTAAATGAGAAAGGAGGATTGAAATTGAGACAATAC
CCTACGAAGGTGACCTCACATGAGCTGCAAATCCTGAAGAAGGAAATCGC
CATTAAGTTTAAGAATGGCGATATCAAGCTGCTTGCCTCTGAGAATAATC
CAAACAGTTTATTAATAACCAATCAAGATAGAATGGAGGTGGCTGAAAAA
AGGGACAGTATACTCTCAATAGATAATACAGAGGGTGAATCAGACACCAG
TCAAATTGAGGAGAGTAAAGAAGTATTTGAACATTCTCGTAATCGACCTA
CTCTTGCGGATGACTGTATGGAGCAGAAGAAGAGGGTGAAAGAGAAGGTA
AGTGCCAGACAGAAAAGGAAAAGCAAAGAAAACCACAAATAGAGATGGT
GAAGGAGCAAGAGATGAAGAATTTCAAGGAGAGCACACAGTACTATTCGA
AGGAATACACTTTAGGTCGAGGTGGTGTTTTTGGGTCTGAAAGTGCCAAG
GTTCGTAAGGGTAAACAGAAGAAGCGTCGTGGGATTTGTAGAAATGCGGC
CTTTGAAGTGGTGGATAATGACAATAATGATGGACGTTCTGACACGTTCA
TCATTGAATGTCATGAGGTCTACGAGAGTTGCGATGAGATAGACGTGGAG
AGTAAGAACCGGATATATGCTGCCTATGATAGACGGGGGTCCAATCCCAA
CTTCCGGATTTATAGAACGACAAACGATGAGTACCTAAGCGAGCTATGGT
TTGGTAGTTTACAGATAGTCTCCTATGGTCTTGACAAAAACAAGAAAAAA
GCTTCTCAAAAGGCAGCAATGCTAGCATGTAAACGTGAGGACTATTATGG
TTTAGATGATAGCAATGAAAATGATCCATAA
```

The polypeptide encoded by SEQ ID NO: 167 is SEQ ID NO: 168:

```
MQSSNCTDVLSELKDAVQNVRTGLRKVLDIAPNRTLYQILLDSTKNPLLQ
SILSIPDESHLTQNDIIFAIELKEMYDTGRLEILEYLIKGDIEQIKTCNG
NTKQETFENNSPNDSSSKEHEDNIPNYKEKLETCDGTEIFIEEVGKDKVR
NSNSFESTPDNISSSNCRKDETRSAVDQRDAETEKEVNSNAKEPDSYISE
LFTSDVMRSEMYVPEELVYKRDRKWGLLKQEELPQAPSIEDPELLRKVFS
HQSIVNYLNISPEFKVQLHNERLEFLGDALLQFVTSMIIYERFPNFSEGQ
LSILRSTIVSNSSLLKWSQMYGFDKQLRKNLIDSSILAGNNKLYADIFEA
YLGGIAEQYMMETSEGETNVNDFMKGWFEVKSWIEELSENHIRGFDPSIV
FKMQYSKSSKQDLRLLLGQNNNPDYIRVNLSNKRILSCIKVNNKVYGYGI
GTSNKEADARAAVDAISNPEIRKICPEDIWDRFESNVGLNEKGGLKLRQY
PTKVISHELQILKKEIAIKFKNGDIKLLASENNPNSLLITNQDRMEVAEK
RDSILSIDNTEGESDTSQIEESKEVFEHSRNRPTLADDCMEQKKRVKEKV
SARQKKEKQRKPQIEMVKEQEMKNFKESTQYYSKEYTLGRGGVFGSESAK
VRKGKQKKRRGICRNAAFEVVDNDNNDGRSDTFIIECHEVYESCDEIDVE
SKNRIYAAYDRRGSNPNFRIYRTINDEYLSELWFGSLQIVSYGLDKNKKK
ASQKAAMLACKREDYYGLDDSNENDP
```

The dicer polypeptide can be dicer 2 encoded by, for example, SEQ ID NO: 169:

```
ATGAGCAAAAGAGCTTTAGGCGAGGTAGAATCTTCAGTGGTTGAGGAAAA
AGTTTTAAAGAAGAAGCAAAAACTTGATAAACAAGACAAAGAAAAAGACA
AAAAGTCCAAGCGATCTAAAAGAGACAAATCTGAAGACTCTAAAAATCTC
AAGGAAAGAGGAAGGACAAATACGGTGTCAACTCCAAAAATGCAGATGG
CCAAAATTTAGAGAAAATCGAACCTGCTATTATCAAGCAGATTGCAATTT
CTGATTTGATGTCAGTTGAGCATTCAGTTTGTGTCATTCAAGAGAATTTG
AAAAAGCTCATGCAGTTAGCACCAAACTTAAGAGACCTAGAACAATATAC
GAACTTTCTTATTGCACAATCAACAAAGTCAGGTATGGGTACCAATGGTG
ATATTACTGCCAAAATATTGTTGTTATCAAAATCTCATAAAATTCAGTTG
GCATCTCAGTTGAAAACATTATCAGAGAATGGTCAGTTGCCGATTGTTAA
ACAAATAATAGACTTTGACAACGACACAGTTCTGGAAAATGTAAGTGACG
TGCAGCTAAAGTTAAAGGAGAAGAACAGGGAGCTACATCGTGGTGGAACT
TCCTCAGAAGCTTTCAACTCGCTACTTCCACCACTACCTACAATTGACGA
TTCTGTGCTAGAAGCCAAAGTGTTTGTTCATAAATCTGCTACTAACAATG
AGTTATTATCTTCGAAACAAGATACCGTGCAGTCTAACAACGAAAGGCTA
GAATTCCTAGGTGATGCTGTCTTGGAGACCGTCATCTCGGATGTCATTGA
ATATAGATATAGAGGATTTGATGAAGGGCAACTATCATCTCTAAGATCTA
CATTGGTTAAAAATGAGACAATTGAATTACTTTCGAGAGCCTATAAATTT
CCAGAACGTCAAATGGAATTGCTAGATTCTCATATGGTGAAGACTGAACT
TACAGAATTCAAAGTAGGCAAAAATAAGAGAATCGCTGATTTATTTGAAG
CGTATATTGGTGCTCTATTTATAGACAAGGGAAGAAATGGACCGGCTTAC
GACTTTATTAAGGACTGGCTGTCAAAAGTTTATTCTCCCATTTTAAAGGA
GTTTGATGGTTTTGACCATTTGAAGTATCTCCATGTTAGTTCCAAATTGC
GTAACCAACTATTAAGCGAAACCCCAGAAACCGTTGCATGCAAAGCAGAT
CAGAATAAATCAAAACATATTCAGTTCGACACCTTAGACTCCGAGGAAGA
TAAGGTGTCTGAGGTGGAGAGTACATCTTCAGCAACCGTACTAGAGAAAG
AACTGAAATTTCCAATCACTTTTACGTCCTCGGAACCTGTGAACAAACTT
GCTAAGGGAGAACTATATGCACTTATAGGAAGTGCTAAACTACATCCAAT
TTACAAGAATGAAAAATCTCAAAACGATAGTAAACACTATTTGACAACAT
GCTCCATTGCGGAGGATATTCTAGGGTACGGTGAAGGTAGAAACCTTAAG
GATTCTAGTGCACGTGCGGCTCAAGCTGCGTTACTGAATAAACCGATGAT
TGAAAAGTATCATTTACTGAGAATGATGACTCCACGTTCGGAAACACGAG
CAAGTCAAAAACTAGAGTTTGTGGAGAAACCAGAAGTTGCTAGTAGCACC
ACGCTTAAGCAGTACACACCTAAGTTTTTGAAGACTGTTCAATATATCGG
TAAAGATGAAATTCCCACTCCTAACAGCTCTTCAAAGAACAAGCTTGTCG
ATTTATTGGCTAAGAAAGGGGTTGTTCCTAGGTACCACGTCGAAGAAGAC
AAGGAAAATAAGAGTATTTTGCCGATGTTCAGAACCACTTTGAAAGTCAA
CGATATCGATGTTGCATATTGTATTGATGCCAGTAAAAAGAAGGGATTAA
ACAAGGTATCTCAATGGTTACTACAGAAAATTGAAGAAGTAGGTGAAAAA
ACTATTTACCATGATCTAAAGCTGGAATAA
```

The polypeptide encoded by SEQ ID NO: 169 is SEQ ID NO: 170:

```
MSKRALGEVESSVVEEKVLKKKQKLDKQDKEKDKKSKRSKRDKSEDSKNL
KEKRKDKYGVNSKNADGQNLEKIEPAIIKQIAISDLMSVEHSVCVIQENL
KKLMQLAPNLRDLEQYTNFLIAQSTKSGMGTNGDITAKILLLSKSHKIQL
ASQLKTLSENGQLPIVKQIIDFDNDTVLENVSDVQLKLKEKNRELHRGGT
SSEAFNSLLPPLPTIDDSVLEAKVFVHKSATNNELLSSKQDTVQSNNERL
EFLGDAVLETVISDVIEYRYRGFDEGQLSSLRSTLVKNETIELLSRAYKF
PERQMELLDSHMVKTELTEFKVGKNKRIADLFEAYIGALFIDKGRNGPAY
DFIKDWLSKVYSPILKEFDGFDHLKYLHVSSKLRNQLLSETPETVACKAD
QNKSKHIQFDTLDSEEDKVSEVESTSSATVLEKELKFPITFTSSEPVNKL
AKGELYALIGSAKLHPIYKNEKSQNDSKHYLTICSIAEDILGYGEGRNLK
DSSARAAQAALLNKPMIEKYHLLRMMTPRSETRASQKLEFVEKPEVASST
TLKQYTPKFLKTVQYIGKDEIPTPNSSSKNKLVDLLAKKGVVPRYHVEED
KENKSILPMFRTTLKVNDIDVAYCIDASKKKGLNKVSQWLLQKIEEVGEK
TIYHDLKLE
```

The dicer polypeptide can be dicer 3 encoded by, for example, SEQ ID NO: 171:

```
ATGAAAATTCCACCTTCACGGATCGACTGTATACAGGATTTTTTTTTTT
TTTTCAAACGTTTTCTTGCTTAATCTTTTGTATATTATTATAGAGGCAG
ATAATTCTCGAATATCGTCAACAATGAGCAAAAGAGCTTTAGGCGAGGTA
GAATCTTCAGTGGTTGAGGAAAAAGTTTTAAAGAAGAAGCAAAAACTTGA
TAAACAAGACAAAGAAAAGACAAAAAGTCCAAGCGATCTAAAAGAGACA
AATCTGAAGACTCTAAAAATCTCAAGGAAAAGAGGAAGGACAAATACGGT
GTCAACTCCAAAAATGCAGATGGCCAAAATTTAGAGAAAATCGAACCTGC
TATTATCAAGCAGATTGCAATTTCTGATTTGATGTCAGTTGAGCATTCAG
TTTGTGTCATTCAAGAGAATTTGAAAAAGCTCATGCAGTTAGCACCAAAC
TTAAGAGACCTAGAACAATATACGAACTTTCTTATTGCACAATCAACAAA
GTCAGGTATGGGTACCAATGGTGATATTACTGCCAAAATATTGTTGTTAT
CAAAATCTCATAAAATTCAGTTGGCATCTCAGTTGAAAACATTATCAGAG
AATGGTCAGTTGCCGATTGTTAAACAAATAATAGACTTTGACAACGACAC
AGTTCTGGAAAATGTAAGTGACGTGCAGCTAAAGTTAAAGGAGAAGAACA
GGGAGCTACATCGTGGTGGAACTTCCTCAGAAGCTTTCAACTCGCTACTT
CCACCACTACCTACAATTGACGATTCTGTGCTAGAAGCCAAAGTGTTTGT
TCATAAATCTGCTACTAACAATGAGTTATTATCTTCGAAACAAGATACCG
TGCAGTCTAACAACGAAAGGCTAGAATTCCTAGGTGATGCTGTCTTGGAG
ACCGTCATCTCGGATGTCATTGAATATAGATATAGAGGATTTGATGAAGG
GCAACTATCATCTCTAAGATCTACATTGGTTAAAAATGAGACAATTGAAT
TACTTTCGAGAGCCTATAAATTTCCAGAACGTCAAATGGAATTGCTAGAT
TCTCATATGGTGAAGACTGAACTTACAGAATTCAAAGTAGGCAAAAATAA
GAGAATCGCTGATTATTTGAAGCGTATATTGGTGCTCTATTTATAGACA
AGGGAAGAAATGGACCGGCTTACGACTTTATTAAGGACTGGCTGTCAAAA
GTTTATTCTCCCATTTTAAAGGAGTTTGATGGTTTTGACCATTTGAAGTA
TCTCCATGTTAGTTCCAAATTGCGTAACCAACTATTAAGCGAAACCCCAG
AAACCGTTGCATGCAAAGCAGATCAGAATAAATCAAAACATATTCAGTTC
GACACCTTAGACTCCGAGGAAGATAAGGTGTCTGAGGTGGAGAGTACATC
TTCAGCAACCGTACTAGAGAAAGAACTGAAATTTCCAATCACTTTTACGT
CCTCGGAACCTGTGAACAAACTTGCTAAGGGAGAACTATATGCACTTATA
GGAAGTGCTAAACTACATCCAATTTACAAGAATGAAAAATCTCAAAACGA
TAGTAAACACTATTTGACAACATGCTCCATTGCGGAGGATATTCTAGGGT
ACGGTGAAGGTAGAAACCTTAAGGATTCTAGTGCACGTGCGGCTCAAGCT
GCGTTACTGAATAAACCGATGATTGAAAAGTATCATTTACTGAGAATGAT
GACTCCACGTTCGGAAACACGAGCAAGTCAAAAACTAGAGTTTGTGGAGA
AACCAGAAGTTGCTAGTAGCACCACGCTTAAGCAGTACACACCTAAGTTT
TTGAAGACTGTTCAATATATCGGTAAAGATGAAATTCCCACTCCTAACAG
CTCTTCAAAGAACAAGCTTGTCGATTTATTGGCTAAGAAAGGGGTTGTTC
CTAGGTACCACGTCGAAGAAGACAAGGAAAATAAGAGTATTTTGCCGATG
TTCAGAACCACTTTGAAAGTCAACGATATCGATGTTGCATATTGTATTGA
TGCCAGTAAAAAGAAGGGATTAAACAAGGTATCTCAATGGTTACTACAGA
AAATTGAAGAAGTAGGTGAAAAAACTATTTACCATGATCTAAAGCTGGAA
TAA
```

The polypeptide encoded by SEQ ID NO: 171 is SEQ ID NO: 130:

```
MKIPPSRIDCIQDFFFFFQTFFLLNLLYIIIEADNSRISSTMSKRALGEV
ESSVVEEKVLKKKQKLDKQDKEKDKKSKRSKRDKSEDSKNLKEKRKDKYG
VNSKNADGQNLEKIEPAIIKQIAISDLMSVEHSVCVIQENLKKLMQLAPN
LRDLEQYTNFLIAQSTKSGMGTNGDITAKILLLSKSHKIQLASQLKTLSE
NGQLPIVKQIIDFDNDTVLENVSDVQLKLKEKNRELHRGGTSSEAFNSLL
PPLPTIDDSVLEAKVFVHKSATNNELLSSKQDTVQSNNERLEFLGDAVLE
TVISDVIEYRYRGFDEGQLSSLRSTLVKNETIELLSRAYKFPERQMELLD
SHMVKTELTEFKVGKNKRIADLFEAYIGALFIDKGRNGPAYDFIKDWLSK
VYSPILKEFDGFDHLKYLHVSSKLRNQLLSETPETVACKADQNKSKHIQF
DTLDSEEDKVSEVESTSSATVLEKELKFPITFTSSEPVNKLAKGELYALI
GSAKLHPIYKNEKSQNDSKHYLTICSIAEDILGYGEGRNLKDSSARAAQA
ALLNKPMIEKYHLLRMMTPRSETRASQKLEFVEKPEVASSTTLKQYTPKF
LKTVQYIGKDEIPTPNSSSKNKLVDLLAKKGVVPRYHVEEDKENKSILPM
FRTTLKVNDIDVAYCIDASKKKGLNKVSQWLLQKIEEVGEKTIYHDLKL
E.
```

A small interfering RNA (siRNA) is an RNA molecule derived from cleavage of longer double-stranded RNA (dsRNA) within a cell by an enzyme comprising an RNase III domain, to produce an RNA molecule composed of two at least substantially complementary strands having a length of between about 15 and 30 nucleotides. Each strand can comprise a 5' phosphate group and a 3' hydroxyl group. siRNA molecules can be generated extracellularly, e.g., in a cell extract, in a composition comprising an isolated dicer polypeptide, or using chemical synthesis.

A vector is a nucleic acid or a virus or portion thereof (e.g., a viral capsid) capable of mediating entry of, e.g., transferring, transporting, etc., a nucleic acid molecule into a cell. Where the vector is a nucleic acid, the nucleic acid molecule to be transferred is generally linked to, e.g., inserted into, the vector nucleic acid molecule. A nucleic acid vector can include sequences that direct autonomous replication (e.g., an origin of replication) in a cell and/or can include sequences sufficient to allow integration of part or all of the nucleic acid into host cell DNA. Useful nucleic acid vectors include, for example, plasmids, cosmids, artificial chromosomes, and naturally occurring or modified viral genomes or portions thereof or nucleic acids (DNA or RNA) that can be packaged into viral capsids. Vectors often include one or more selectable markers. Expression vectors typically include regulatory sequence(s), e.g., expression control sequences such as a promoter, sufficient to direct transcription of an operably linked nucleic acid. An expression vector can comprise sufficient cis-acting elements for expression; other elements for expression can be supplied by the host cell or in vitro expression system. Vectors often include one or more appropriately positioned sites for restriction enzymes, e.g., to facilitate introduction of the nucleic acid to be transported or expressed into the vector.

RNA interference (RNAi) and related RNA-silencing pathways produce short (21-30-nt) guide RNAs that are loaded onto an Argonaute protein, where they pair with target transcripts to direct silencing of specific mRNAs or genomic regions. RNaseIII endonuclease dicer successively cleaves double-stranded RNA (dsRNA) into siRNAs, which are loaded into the effector protein Argonaute to guide the silencing of target transcripts. Silencing is sequence-specific such that the duplex (base-paired) region of the RNA (dsRNA or siRNA) is targeted for inhibition. 100% sequence identity between a siRNA or dsRNA and the target gene is not required for silencing, provided that the correspondence is sufficient to enable the siRNA (or siRNAs derived by cleavage of the dsRNA) to direct silencing of the mRNA. A gene or mRNA whose expression is silenced by RNAi is the target gene or target mRNA, and the siRNA that mediates such silencing targets the gene or mRNA.

In some embodiments functional RNAi pathways are reconstituted using genetic engineering in non-conventional yeast. In an embodiment the non-conventional yeast lacks an endogenous functional RNAi pathway.

Dicer polypeptides (e.g., SEQ ID NO:168, 170, or 130 or a sequence having about 80, 85, 90, 95, 96, 97, 98, 99% or more sequence identity to SEQ ID NO:168, 170, or 130) are capable of cleaving a dsRNA to yield siRNAs under appropriate conditions, e.g., within a non-conventional yeast cell in which its expression is achieved by genetic engineering. That is, dicer nucleic acid sequences (e.g., SEQ ID NO:167, 169, or 171 or a sequence having about 80, 85, 90, 95, 96, 97, 98, 99% or more sequence identity to SEQ ID NO: 167, 169, or 171) are delivered to a non-conventional yeast cell via transformation or other suitable means.

Argonaute polypeptides (e.g. SEQ ID NO: 166 or a sequence having about 80, 85, 90, 95, 96, 97, 98, 99% or more sequence identity to SEQ ID NO: 166 are capable of binding at least the guide strand of an siRNA (also known as the "antisense strand"). Ago polypeptides have endonuclease activity directed against mRNA strands that are complementary to the guide strand of a bound siRNA under appropriate conditions. That is, Ago nucleic acid sequences (e.g., SEQ ID NO: 165 or a sequence having about 80, 85, 90, 95, 96, 97, 98, 99% or more sequence identity to SEQ ID NO:165) are delivered to a non-conventional yeast cell via transformation or other suitable means.

In an embodiment an siRNA is delivered to a cell of interest, e.g., a non-conventional yeast cell. Delivery encompasses making an siRNA available within a non-conventional yeast cell using any suitable method. For example, a nucleic acid or combinations thereof (e.g. an RNAi plasmid library) that can be transcribed to yield one or more siRNA precursors, e.g., dsRNA, is delivered into a cell. The cell is maintained under conditions in which the siRNA precursor is expressed and cleaved to yield siRNA. If the nucleic acid is under control of an inducible expression control element, such maintaining could comprise maintaining the cell under inducing conditions. In some embodiments, delivery refers to contacting a cell with an siRNA. In some embodiments, delivery refers to introducing an siRNA precursor, e.g., a dsRNA, into a cell, and maintaining the cell under conditions in which the siRNA precursor is cleaved to yield siRNA. In some embodiments, delivery is via an RNAi library, that is a set of two or more vectors (e.g., plasmids) that encode one or more antisense RNA molecules, e.g., full length antisense RNA molecules. In another embodiment, an RNAi library is a library that expresses or overexpresses full length sense CDNAs. The delivery of a library to a culture of non-conventional yeast will result in a population of non-conventional yeast cells with different characteristics due to RNAi. The different cells can then be analyzed for beneficial characteristics. Methods of making RNAi libraries are discussed in, e.g., Clark & Ding, Biomed Biotechnol. 2006; 2006: 45716.

In an embodiment dsRNA is endogenous to the non-conventional yeast cell or can be a non-endogenous dsRNA whose expression in the cell is achieved by genetic engineering of the cell (e.g., by delivery of an RNAi library of dsRNA to the cell). Any siRNA precursor, e.g., any dsRNA can be used, provided that it has sufficient homology to a targeted gene such that the resulting siRNAs direct silencing by RNAi. In an embodiment, the sequence of the siRNA precursor, e.g., dsRNA, is selected to correspond to a known sequence, such as a portion of an mRNA of a gene, or the entire mRNA of a gene whose silencing is desired.

An RNAi library of vectors (e.g., plasmids) can provide collections of nucleic acids that comprise templates for transcription of a multiplicity of dsRNA, the dsRNAs corresponding to at least 10 genes of a non-conventional yeast. In some embodiments the collection comprises nucleic acids that comprise templates for transcription of dsRNAs corresponding to at least 20, 50, 100, 500, 1000, 2000, 3000, 4000, 5000, 6000, or more genes. In some embodiments, each template is provided as part of a separate nucleic acid, e.g., a vector. In some embodiments two or more templates are provided as part of a single nucleic acid. In some embodiments the collection comprises dsRNAs corresponding to at least 10%, 20%, 50%, 75%, 90%, 95%, 98%, 99%, or 100% of the genes of a non-conventional yeast.

Non-conventional yeast cells can be genetically engineered to express one or more functional RNAi pathway polypeptides, e.g., yeast dicer and/or Argonaute polypeptides. In some embodiments, the cells are genetically engineered non-conventional yeast cells, optionally, wherein the cells lack a functional endogenous RNAi pathway, and wherein expression of the one or more functional non-conventional yeast RNAi pathway polypeptides, e.g., a dicer polypeptide and an Argonaute polypeptide, reconstitutes the RNAi pathway in the cells.

Vectors can comprise a dicer polypeptide, an Ago polypeptide, or both. In an embodiment a vector comprises nucleic acids encoding full length antisense RNAs or full length sense cDNAs. These full length antisense RNAs or full length sense cDNAs can have homology to one or more genes or mRNAs of a non-conventional yeast. In some embodiments the vector is a plasmid. Other vectors include artificial chromosomes and linear nucleic acid molecules that are distinct from linearized plasmids. In some embodiments the vector is an integrating vector. In some embodiments the vector comprises an expression control element operably linked to a nucleic acid to be transcribed (e.g., a nucleic acid that encodes a polypeptide of the invention or that provides a template for transcription of a dsRNA). Three well known plasmid systems used for recombinant expression and replication in yeast cells include integrative plasmids, low-copy-number ARS-CEN plasmids, and high-copy-number 2u plasmids. See, e.g., Christianson et al., "Multifunctional yeast high-copy-number shuttle vectors". Gene. 110:119-22 (1992); Sikorski, "Extrachromosomal cloning vectors of *Saccharomyces cerevisiae*", in Plasmid, A Practical Approach, Ed. K. G. Hardy, IRL Press, 1993; Parent & Bostian, Recombinant DNA technology: yeast vectors, p. 121-178. In Wheals et al. (eds.) The yeasts, vol. 6. Yeast genetics. Academic Press, Longon, UK (1995).

A nucleic acid encoding a functional RNAi pathway polypeptide or providing a template for transcription of a dsRNA can be introduced into a non-conventional yeast cell using any suitable method. Yeast cells can be transformed by chemical methods using, e.g., lithium acetate to achieve transformation efficiencies of approximately 104 colony-forming units (transformed cells)/μg of DNA. Other suitable means include, for example, electroporation. Yeast vectors (e.g., plasmids) can comprise a yeast origin of replication, an antibiotic resistance gene, a bacterial origin of replication (for propagation in bacterial cells), multiple cloning sites, a yeast nutritional marker gene to promote maintenance and/or genomic integration in yeast cells, or combinations thereof. A yeast nutritional gene (or auxotrophic marker) can be, e.g., TRP1 (phosphoribosylanthranilate isomerase); URA3 (orotidine-5'-phosphate decarboxylase); LEU2 (3-Isopropylmalate dehydrogenase); HIS3 (imidazoleglycerolphosphate dehydratase or IGP dehydratase); or LYS2 (α-aminoadipate-semialdehyde dehydrogenase). Yeast vectors (e.g., plasmids) can also comprise expression control sequences, e.g., promoter sequences, terminator sequences, or both.

Some embodiments provide a nucleic acid molecule, e.g., a vector, comprising (i) a first polynucleotide that encodes a dicer polypeptide (ii) a second polynucleotide that encodes an Argonaute polypeptide (iii) and, optionally, a third polynucleotide that comprises a template for transcription of a dsRNA. In an embodiment, the third polynucleotide that comprises a template for transcription of a dsRNA is present in a nucleic acid molecule (e.g., vector) separate from the dicer and Ago nucleic acid molecule. In an embodiment the first polynucleotide that encodes a dicer polypeptide and the second polynucleotide that encodes an Argonaute polypeptide are present on separate nucleic acid molecules (e.g., vectors).

In some embodiments, a library of yeast strains can be generated using a library of nucleic acids, e.g., vectors, each of which comprises a template for transcription of a dsRNA that corresponds to a different non-conventional yeast gene or target mRNA, wherein the template is operably linked to an expression control element. Optionally, such nucleic acids, e.g., vectors, also comprise polynucleotides that encode an RNAi pathway polypeptide, e.g., a dicer or Argonaute polypeptide.

Any gene of interest can be targeted for silencing in various embodiments. The target gene can be an endogenous gene or a non-endogenous gene. The target gene can encode a protein that has at least one known function or a protein whose function(s) are unknown. In some embodiments the protein is an enzyme. In some embodiments the target gene encodes a transcription factor. In some embodiments the target gene encodes a structural protein.

Provided herein are methods of genetically altering a non-conventional yeast comprising delivering to the non-conventional yeast:
(i) a polynucleotide having about 80, 85, 90, 95, 96, 97, 98, 99% or more sequence identity to the sequence of SEQ ID NO:165,
(ii) a polynucleotide having about 80, 85, 90, 95, 96, 97, 98, 99% or more sequence identity to the sequence of SEQ ID NO: 167, 169, 171 or combinations thereof, and
(iii) one or more nucleic acids molecules encoding full length antisense RNAs or full length sense cDNAs having about 80, 85, 90, 95, 96, 97, 98, 99% or more sequence identity to one or more endogenous nucleic acid molecules of the non-conventional yeast, wherein the non-conventional yeast is genetically altered. In an embodiment the no-conventional yeast is *I. orientalis*.

The compositions and methods are more particularly described below and the Examples set forth herein are intended as illustrative only, as numerous modifications and variations therein will be apparent to those skilled in the art. The terms used in the specification generally have their ordinary meanings in the art, within the context of the compositions and methods described herein, and in the specific context where each term is used. Some terms have been more specifically defined herein to provide additional guidance to the practitioner regarding the description of the compositions and methods.

As used herein, the term "and/or" includes any and all combinations of one or more of the associated listed items. As used in the description herein and throughout the claims that follow, the meaning of "a", "an", and "the" includes plural reference as well as the singular reference unless the context clearly dictates otherwise. The term "about" in association with a numerical value means that the value varies up or down by 5%. For example, for a value of about 100, means 95 to 105 (or any value between 95 and 105).

All patents, patent applications, and other scientific or technical writings referred to anywhere herein are incorporated by reference herein in their entirety. The embodiments illustratively described herein suitably can be practiced in the absence of any element or elements, limitation or limitations that are specifically or not specifically disclosed herein. Thus, for example, in each instance herein any of the terms "comprising," "consisting essentially of," and "consisting of" can be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the claims. Thus, it should be understood that although the present methods and compositions have been specifically disclosed by embodiments and optional features, modifications and variations of the concepts herein disclosed can be resorted to by those skilled in the art, and that such modifications and variations are considered to be within the scope of the compositions and methods as defined by the description and the appended claims.

Any single term, single element, single phrase, group of terms, group of phrases, or group of elements described herein can each be specifically excluded from the claims.

Whenever a range is given in the specification, for example, a temperature range, a time range, a composition, or concentration range, all intermediate ranges and subranges, as well as all individual values included in the ranges given are intended to be included in the disclosure. It will be understood that any subranges or individual values in a range or subrange that are included in the description herein can be excluded from the aspects herein. It will be understood that any elements or steps that are included in the description herein can be excluded from the claimed compositions or methods.

In addition, where features or aspects of the compositions and methods are described in terms of Markush groups or other grouping of alternatives, those skilled in the art will recognize that the compositions and methods are also thereby described in terms of any individual member or subgroup of members of the Markush group or other group.

The following are provided for exemplification purposes only and are not intended to limit the scope of the embodiments described in broad terms above.

EXAMPLES

Example 1. Evaluation of the Incorporation of an Autonomously Replicating Sequence from S. Cerevisiae on Plasmid Stability To design an expression vector for the efficient alteration of the genome of a non-conventional yeast like *I. orientalis*, it is highly desirable for the vector or plasmid to be stable. An autonomously replicating sequence from *S. cerevisiae* (ScARS) was evaluated for its ability to be functional in *I. orientalis*.

Figure 1B:
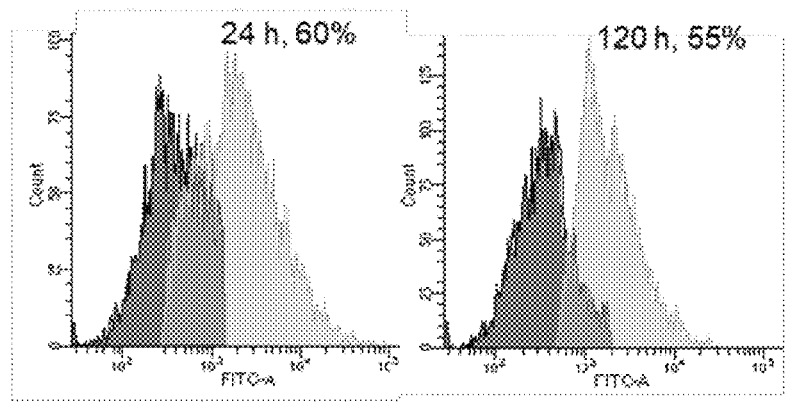
FIG. 1B discloses the GFP expression peaks at 24 h and 120 h measured by flow cytometry FIG. 2 panel a discloses DNA transformation of *I. orientalis* by heat shock with 500 ng of plo-UG. Panel b discloses DNA transformation of *E. coli* by electroporation with plasmid DNA extracted from 24 h and 120 h *I. orientalis* cultures. Panel c discloses GFP expression profiles by ScARS and ScARS/CEN plasmids in *I. orientalis* at 24 h.
Figure 2:
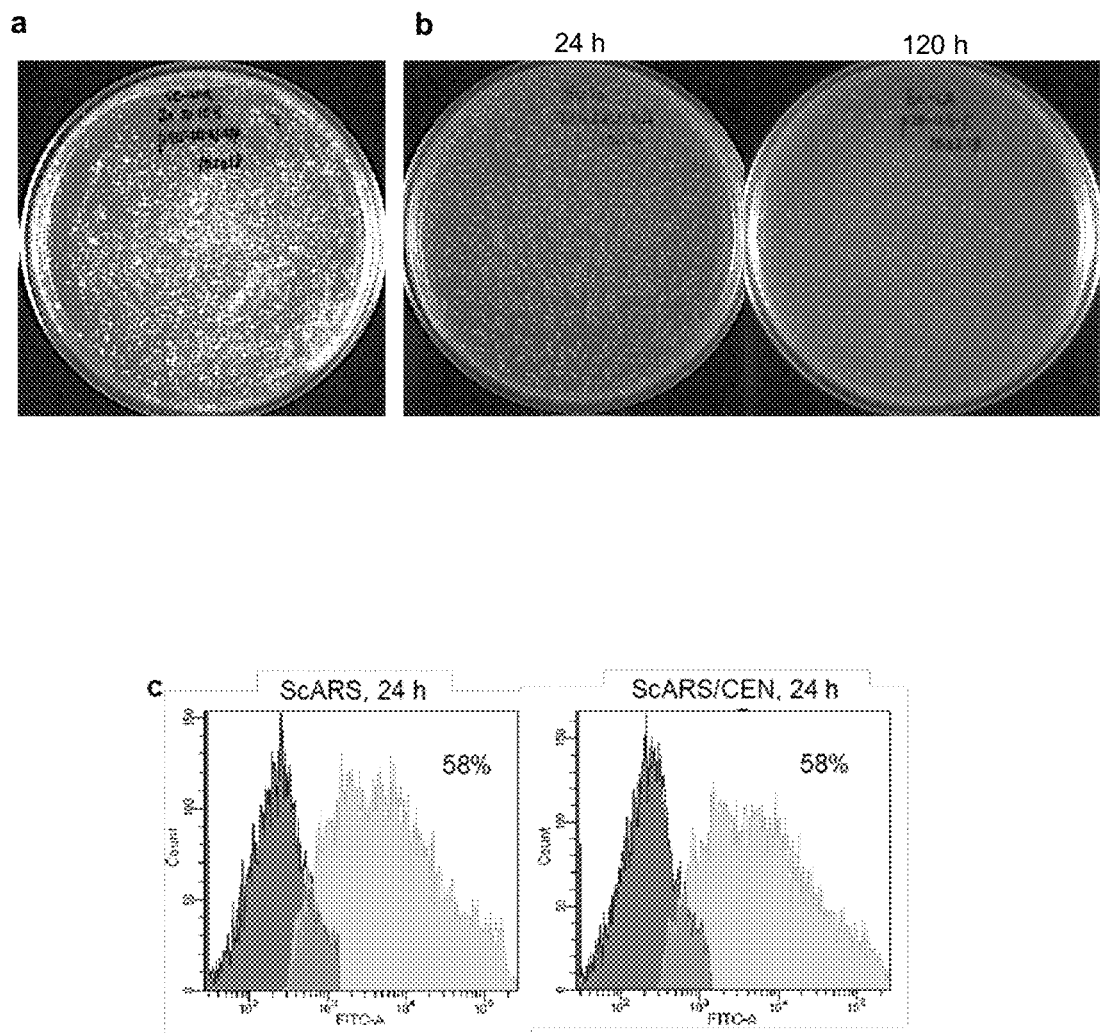

A plasmid (plo-UG), which was derived from pRS415, containing *I. orientalis* uracil auxotrophic selection marker (IoURA3), ScARS, and a green fluorescence protein (GFP) gene as a reporter was constructed (FIG. 1A). Approximately 1000 yeast colonies were obtained with 500 ng plo-UG by heat shock transformation (FIG. 2A), and around 55% of the cells cultured in liquid media could express the GFP at a symmetric peak for at least 5 days (FIG. 1B). Plasmids were then extracted from *I. orientalis* and transformed to *E. coli*, and the number of colonies for 120 h was equivalent to that at the 24 h (FIG. 2B), which confirmed that the ScARS works well in *I. orientalis*. Compared to the centromere-stabilizing plasmid, which showed >80% GFP expression efficiency in *S. cerevisiae*, the functionality test of centromere from *S. cerevisiae* (ScCEN) in *I. orientalis* shown that no improvement was obtained by integrating ScCEN to plo-UG (FIG. 2C).

Example 2. Evaluation of Various Promoters Efficiency to Induce sGRNA Transcription To design a CRISPR/Cas9-based tool efficient in a non-conventional yeast like *I. orientalis*, expression of functional Cas9 and sgRNA is required. Cas9 expression can be achieved by using a constitutive RNA Polymerase (RNAP) II promoter. On the other hand, sgRNA expression typically requires an RNAP III promoter because of the mRNA processing associated with RNAP II, such as 5'-end capping and 3'-end polyadenylation. Should an RNAP II promoter be used for sgRNA expression, the sgRNA needs to be flanked with ribozyme sequences like hammerhead and hepatitis delta virus ribozyme sequences. These ribozymes can execute cleavage on both ends of sgRNA and release the mature sgRNA without those post-transcriptional modifications.

In yeasts, genes transcribed by RNAP III promoter include all the tRNA genes, SNR6, SNR52, RPR1, SCR1, and 5S rRNA, tRNA by itself can act as promoter, and fusion of tRNA with other promoters, such as the hybrid promoter SCR1'-tRNA$^{Gly}$ in *Yarrowia lipolytica*, can excise sgRNA from the primary transcript by tRNA maturation processing. The efficacy of RNAP III promoters to express sgRNA in *I. orientalis* was evaluated. The partial sequence of RPR1 in *I. orientalis* ATCC 6258, and 5S rRNA in *I. orientalis* served as the starting point for sgRNA expression in a CRISPR/Cas9-based system.

As shown in FIG. 3A, a series of promoters was evaluated, including a leucine tRNA (URNA$^{Leu}$), a serine tRNA (tRNA$^{Ser}$), 5S rRNA, RPR1, and fusions of 5S rRNA and RPR1' with tRNA$^{Leu}$. RPR1 promoter contains 250 bp upstream of RPR1 partial sequence. RPR1' promoter contains 250 bp upstream of RPR1 and first 120 bp of RPR1. The promoter elements of RPR1 can be located upstream or internal to the mature product. However, the exact promoter elements of RPR1 from *I. orientalis* are unknown. Therefore, two different RPR1 promoters were tested. As illustrated in FIG. 3B, qPCR was employed to quantify the transcription levels of sgRNAs depending on the promoter used to direct its expression.

Example 3. Evaluation of the Efficacy of the Plasmid to Disrupt the Expression of One Gene A iCas9 system, which is short for improved Cas9 was used herein. The iCas9 system was shown to have higher disruption efficiency in *S. cerevisiae* than the wild-type Cas9. iCas9 was tagged with SV40 nuclear localization sequences at both N- and C-termini and driven by a strong constitutive promoter, TEF1ap.

Figure 4A:
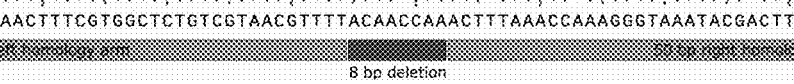
FIG. 4A discloses DNA sequencing of ADE2 disruption. TGTTAGCGTTGAAAGCACCGAGACAGCAT-TGCAAAATGTTGGTTTGAAATTTGGTTTCC CATT-TATGCTGAAGTCCAAAAC is ID SEQ NO:143; TGT-TAGCGTTGAAAGCACCGAGACAGCATTGCAAAATG is SEQ ID NO: 144; AAATTTGGTTTCCCATTTATGCT- GAAGTCCAAAAC is SEQ ID NO:145.
Figure 4B:
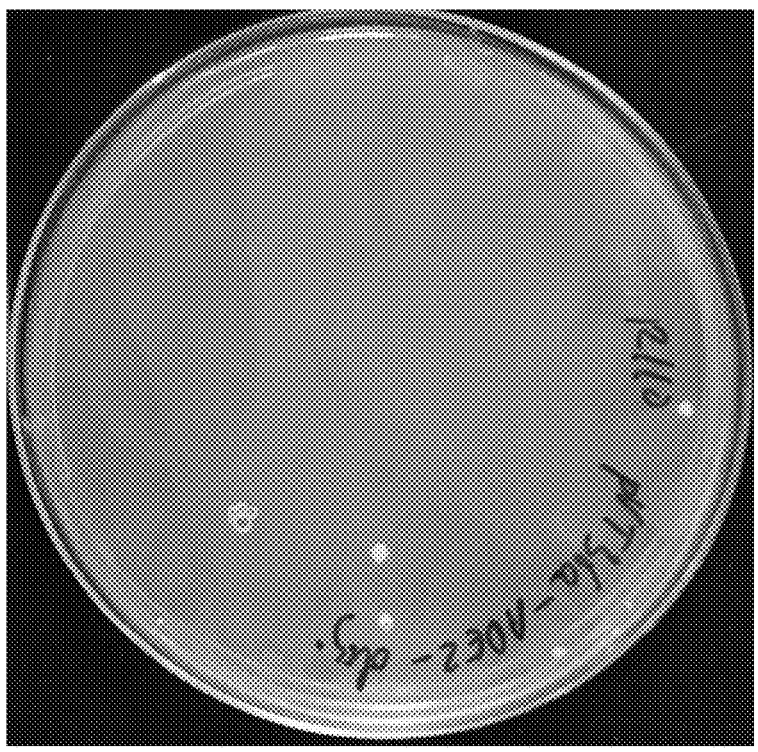
FIG. 4B discloses the transformation of plasmid without HR donor.

As a proof of concept, the ADE2 gene was targeted because ade2 mutant shows a conspicuous red phenotype. Whether HR or NHEJ was the dominant repairing mechanism in *I. orientalis* was not known; therefore, in addition to the NHEJ mechanism, the HR mechanism was evaluated by cloning an HR disruption donor into the plasmid. The HR donor contained an 8 bp deletion in the middle and two 50 bp homology arms flanked at both sides of the centered 8 bp deletion. The 8 bp deletion included the PAM sequence and the last 3 bp of spacer. If HR was the primary mode of DNA double-strand break repair, the defined 8 bp would be deleted from the genome. The highest ADE2 disruption efficiency of 97.0±1.2% of colonies was attained with RPR1'-tRNA$^{Leu}$ promoter (Table 1). RPR1 and 5S RNA-tRNA$^{Leu}$ promoters also produced high-efficiency ADE2 disruptions, 93.3±1.1% and 89.8±1.5%, respectively. tRNA$^{Leu}$, tRNA$^{Ser}$, and 5S rRNA promoters resulted in lower efficiencies. For all cases, growing the cells for a prolonged period of time in liquid SC-URA (SC-uracil) after transformation was not necessary to observe ADE2 disruption. DNA sequencing analysis showed deletion of 8 bp, and without HR donor, few transformants survived and retained the wild-type white color (FIG. 4A-B). Taken together, these data suggested HR is the main DNA repairing mechanism.

TABLE 1

ADE2 knockout efficiencies using different promoters for sgRNA expression. Error represents standard deviation of biological triplicates.

| Promoters for sgRNA expression | ADE2 disruption efficiency (%) |
|---|---|
| tRNA$^{Leu}$ | 84.4 ± 2.3 |
| tRNA$^{Ser}$ | 76.9 ± 1.6 |
| 5S rRNA | 66 ± 15 |
| RPR1 | 93.3 ± 1.1 |
| RPR1'-tRNA$^{Leu}$ | 97.0 ± 1.2 |
| 5S RNA-tRNA$^{Leu}$ | 89.8 ± 1.5 |

To determine whether sgRNA levels correlate with ADE2 disruption efficiencies, qPCR was employed to quantify the transcription levels of sgRNAs (FIG. 3B). Transcript levels produced from tRNA$^{Leu}$, tRNA$^{Ser}$, and 5S rRNA promoters were lower than those produced from other promoters, which might explain the lower ADE2 knockout efficiencies. RPR1 promoter produced approximately 2-fold more sgRNA in comparison to RPR1'-tRNA$^{Leu}$ promoter, but ADE2 disruption efficiency by RPR1 promoter was not as high as that by RPR1'-tRNA$^{Leu}$ promoter. Because it resulted in the highest ADE2 knockout efficiency, the RPR1'-tRNA$^{Leu}$ promoter was chosen as the promoter for sgRNA expression for subsequent knockouts.

Figure 5A:
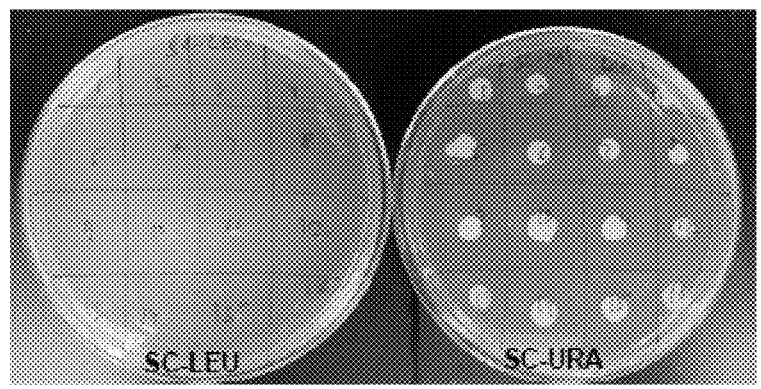
FIG. 5A shows the disruption of auxotrophic gene LEU2 on SC-LEU plate and SC-URA plate.
Figure 5B:
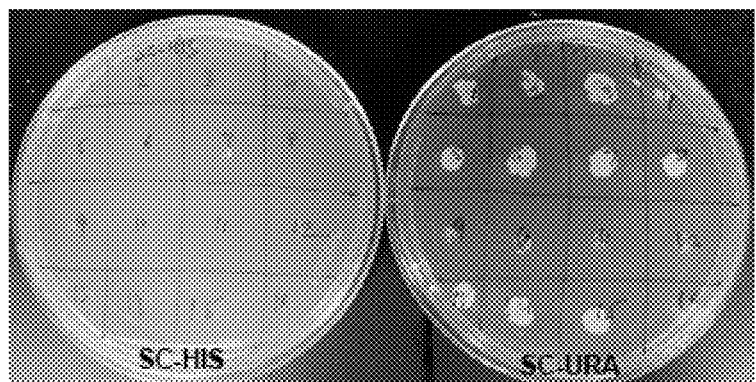
FIG. 5B shows the disruption of auxotrophic gene HIS3 on SC-HIS plate and SC-URA plate.
Figure 5C:
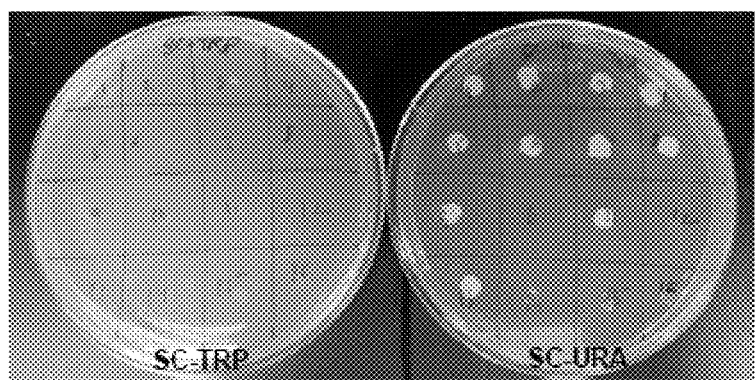
FIG. 5C shows the disruption of auxotrophic gene TRP1 on SC-TRP plate and SC-URA plate FIG. 6A discloses DNA sequencing analysis for SDH1 disruption. GTAAAGAGG-CATCCTCCGCAATGGCAAAGGATTATCATGTCA is SEQ ID NO:146; GTAAAGAGGC is SEQ ID NO:147; CAATGGCAAAGGATTATCATGTCA is SEQ ID NO:148.
Figure 7A:
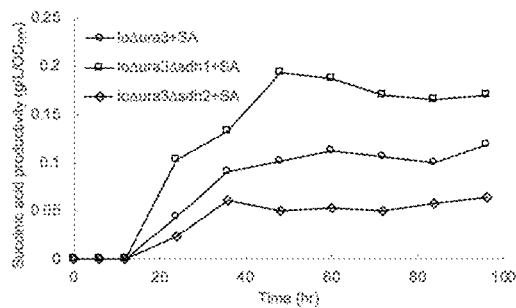
FIG. 7A-F discloses growth and metabolite profiles in batch cultures using shake flasks of strains loΔura3+SA, loΔura3Δsdh1+SA, and loΔura3Δsdh2+SA in SC-URA media containing 25.52 g/L calcium carbonate and 50 g/L glucose.
Figure 7B:
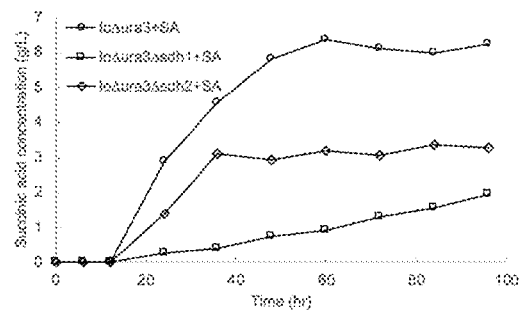
Figure 7C:
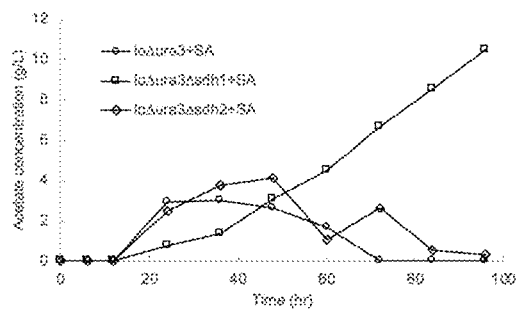
Figure 7D:
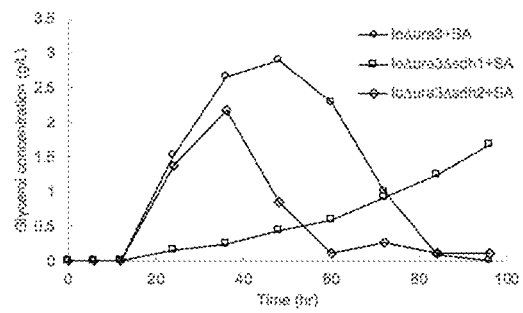
Figure 7E:
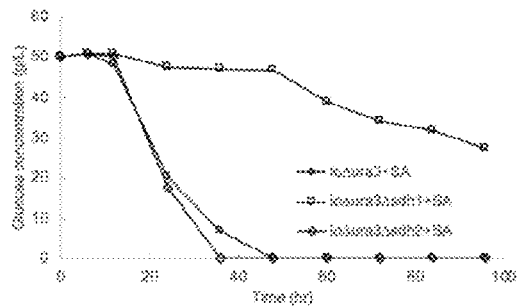
Figure 7F:
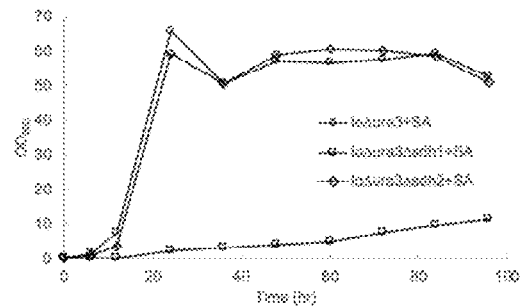
Figure 8A:
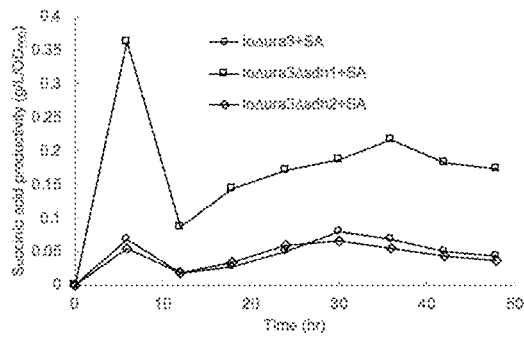
FIG. 8A-F discloses growth and metabolite profiles in batch cultures using shake flasks of strains loΔura3+SA, loΔura3Δsdh1+SA, and loΔura3Δsdh2+SA in YPAD media containing 50 g/L glucose.
Figure 8B:
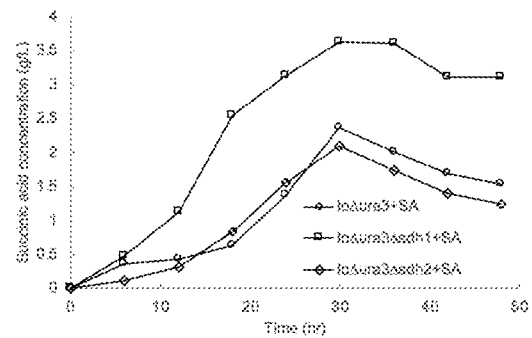
Figure 8C:
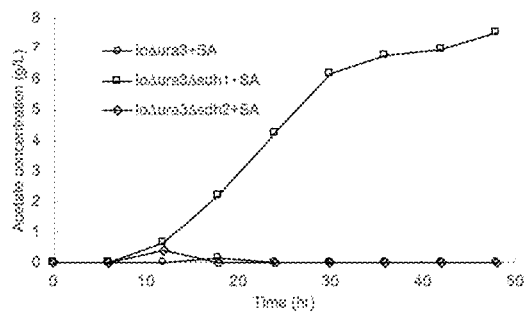
Figure 8D:
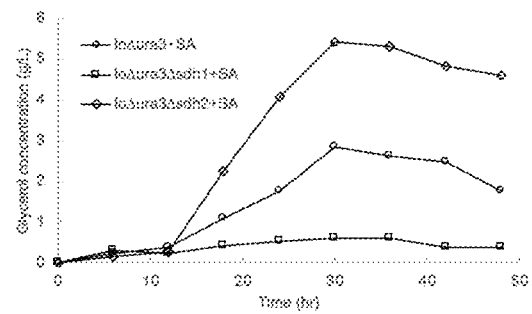
Figure 8E:
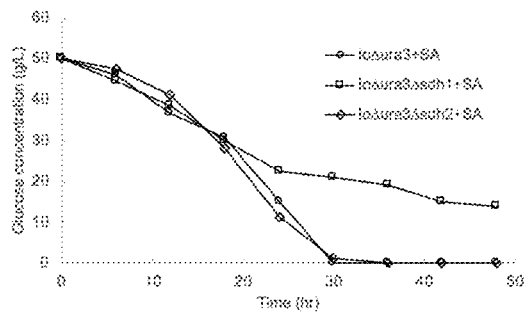
Figure 8F:
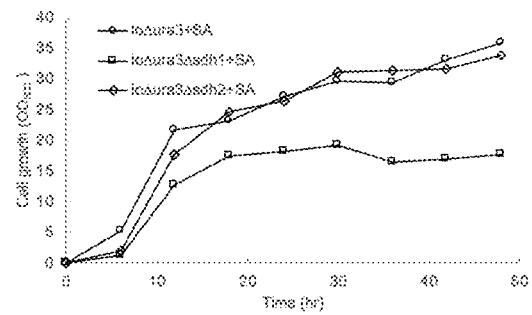

To further validate CRISPR function in *I. orientalis*, several additional genes were chosen for disruptions. LEU2, HIS3, and TRP1 are essential for yeast to produce their own leucine, histidine, and tryptophan, respectively. Successful disruptions of these genes also provides for mutants with leu2, his3, or trp1 auxotrophy. For each knockout, 16 randomly selected transformants were streaked on SC-URA plates and plates of SC minus the auxotrophic compound produced by the targeted gene. After 2 days of incubation, no colonies were observed on SC-LEU (SC-leucine), SC-HIS (SC-histidine), and SC-TRP (SC-tryptophan) plates (FIGS. 5A-C). This might indicate all these auxotrophic genes were disrupted with efficiency of 100%. Nevertheless, sequencing 6 randomly selected colonies on SC-URA plates from each knockout revealed that LEU2, HIS3, and TRP1 disruption efficiencies were 100% (6/6), 83.3% (5/6), and 66.7% (4/6), respectively (Table 2). To account for this discrepancy, it was reasoned that since *I. orientalis* is diploid, it might be possible that only one allele of each gene was knocked out.

TABLE 2

Single gene and double gene disruption efficiencies.

| Genes | Disruption efficiency (%) |
|---|---|
| LEU2 | 100 |
| HIS3 | 83.3 |
| TRP1 | 66.7 |
| ADE2 and TRP1 | 57.5 |
| ADE2 and HIS3 | 79.3 |

Example 4. Evaluation of the Efficacy of the Plasmid to Induce Succinic Acid Production The CRISPR/Cas9-based tool was tested for use in metabolic engineering. The goal was to improve succinic acid production in loΔura3+SA, which is strain SD108 previously engineered to produce succinic acid with a titer of 11.63 g/L in batch fermentation using shake flask. A cassette, which contained pyruvate carboxylase, malate dehydrogenase, fumarase and fumarate reductase expressed by strong constitutive promoters, was integrated into the genome of SD108. Because succinic acid production can further be increased by deletion of succinate dehydrogenase, succinate dehydrogenase subunits SDH1 and SDH2 were disrupted to create mutants loΔura3Δsdh1+SA and loΔura3Δsdh2+SA, respectively. For SDH1 disruption, 8 randomly picked colonies were sequenced, and 5 of which were correct (FIG. 6A). The actual SDH1 knockout efficiency should be higher since transformants of plasmid without KanMX marker were able to grow on selection YPAD plate with G418. For SDH2 disruption, 3 random colonies were picked for sequencing, and they were all correct (FIG. 6B).

Batch cultures using shake flasks were then performed to verify if these knockouts could enhance succinic acid production. loΔura3+SA, loΔura3Δsdh1+SA, and loΔura3Δsdh2+SA strains were tested in SC-URA medium containing 25.52 g/L calcium carbonate and 50 g/L glucose (FIG. 7). Strain loΔura3Δsdh1+SA grew significantly slower compared to strains loΔura3+SA and loΔura3Δsdh2+SA. Strains loΔura3+SA and loΔura3Δsdh2+SA consumed all glucose at 48 hours, whereas at 96 hours, strain loΔura3Δsdh1+SA consumed 22.6 g/L glucose. loΔura3+SA, loΔura3Δsdh1+SA, and loΔura3Δsdh2+SA strains produced succinic acid at concentrations of 6.27 g/L, 1.96 g/L, and 3.28 g/L at 96 hours, respectively. Nevertheless, if taking the slow growth of strain loΔura3Δsdh1+SA into account, it attained a succinic acid productivity of 0.17 g/L/OD$_{600}$ at 96 hr, which is 1.4-fold increase compared to strain loΔura3+SA.

In addition to minimal SC medium, batch cultures using rich YPAD medium containing 50 g/L glucose were also performed (FIG. 8). The same trend was observed in which strain loΔura3Δsdh1+SA grew slower and consumed less sugar compared to strains. Nevertheless, strain loΔura3Δsdh1+SA attained the highest succinic acid concentration of 3.11 g/L and the highest succinic acid productivity of 0.17 g/L/OD$_{600}$ at 48 hr, or disruption of SDH1 yielded 2.02-fold and 4.05-fold increases in succinic acid concentration and productivity compared to strain loΔura3+SA, respectively. In both media, SDH2 knockout did not help increase succinic acid production.

Figure 9A:
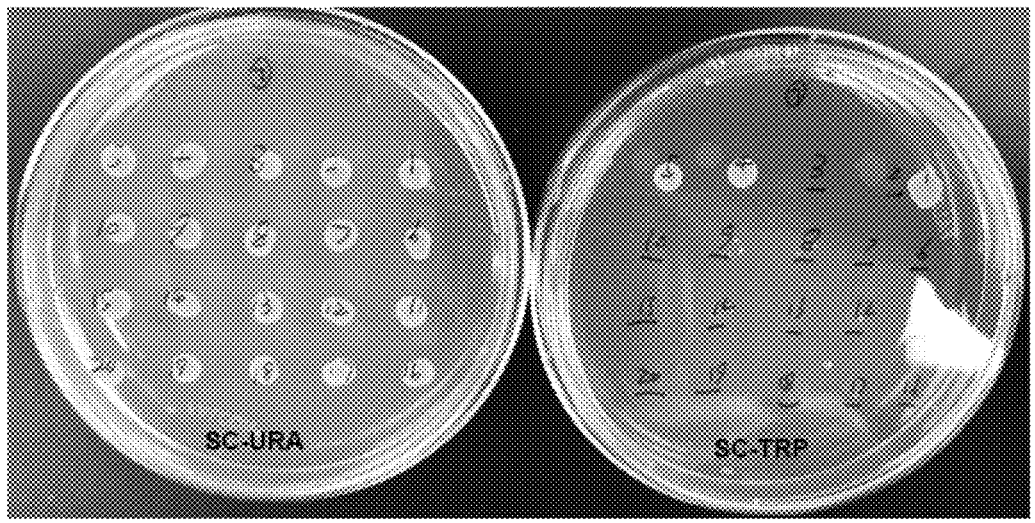
FIG. 9A discloses double-gene disruption of ADE2 and TRP1 on 20 randomly selected colonies streaked on SC-URA plate and SC-TRP plates.
Figure 9B:
FIG. 9B discloses double-gene disruption of ADE2 and HIS3 on 20 randomly selected colonies streaked on SC-URA plate and SC-HIS plates.

Example 5. Evaluation of the Efficacy of the Plasmid to Disrupt the Expression of Two Genes In addition to single-gene knockouts, the CRISPR/Cas9 system was tested for multiplex deletions. For double-gene knockout, ADE2 and TRP1, and ADE2 and HIS3 were deleted with efficiencies roughly estimated to be 57.5% and 79.3%, respectively (Table 2, Table 3 and FIG. 9).

TABLE 3

Calculation of double-gene knockout efficiencies

| Double-gene knockout | ADE2 disruption efficiency | Disruption efficiency screened by plating | Proportion of correct colonies verified by sequencing | Overall disruption efficiency |
|---|---|---|---|---|
| ADE2 and TRP1 | 84.6% | 17/20 | 4/5 | 57.5% |
| ADE2 and HIS3 | 83.5% | 19/20 | 5/5 | 79.3% |

Example 6. Materials and Methods

All the materials and methods used in Examples 1-5 are provided herein.

Strains, Media, and Chemicals.

The strains used in this study are listed in Table 4. *E. coli* transformants were grown at 37° C. in LB media supplemented with 100 μg/mL ampicillin. *S. cerevisiae* YSG50, *I. orientalis* SD108 and its mutants were propagated at 30° C. in YPAD media (1% yeast extract, 2% peptone, 0.01% adenine hemisulphate, and 2% dextrose). Yeast transformants were cultured or selected in the Synthetic Complete (SC) dropout media lacking uracil, tryptophan, leucine or with low concentration of adenine (~10 mg/L), (SC-URA, SC-TRP, SC-LEU, or SC-ADE). For SDH1 and SDH2 knockouts, yeast transformants were selected using YPAD supplemented with 100 μg/mL G418. DNA polymerase and restriction enzymes were purchased from New England Biolabs (Ipswich, MA). DNA extraction and purification kits were purchased from Zymo Research (Irvine, CA). All the other chemicals were purchased from Sigma (St. Louis, MO) and Fisher Scientific (Pittsburgh, PA). Oligonucleotides including gBlocks and primers were all synthesized by Integrated DNA Technologies (IDT, Coralville, IA).

TABLE 4

Strains and plasmids used in this study.

| Strains/plasmids | Features | Sources |
|---|---|---|
| Strains | | |
| *I. orientalis* SD108 | URA3Δ, host for plasmid in this disclosure | Present disclosure |
| *S. cerevisiae* YSG50 | ade2-1, ade3 Δ22, ura3-1, his3-11, 15, trp-1, leu2-3, 112, can1-100, used for in vivo assembly | Present disclosure |
| *E. coli* BW25141 | Cloning host | Provided by William Metcalf |
| Plasmids | | |
| pRS415 | *S. cerevisiae* plasmid containing LEU2 maker and ARS/CEN | New England Biolabs |
| pIo-UG | Derived from pRS415, containing IoURA3 and GFP cassette | Present disclosure |
| pIo-Cas9-BsaI | Derived from pRS415, containing IoURA3, iCas9 and sgRNA with BsaI sites | Present disclosure |
| pIo-Cas9-ADE2 | pIo-Cas9- BsaI with a N20 spacer sequence targeting *I. orientalis* ADE2 gene | Present disclosure |
| pIo-Cas9-X | pIo-Cas9- BsaI with a N20 spacer sequence targeting LEU2, HIS3, TRP1, SDH1, AND SDH2 | Present disclosure |

Plasmid Construction.

The plasmid pIo-UG was constructed using the DNA assembler method. In brief, the PCR-amplified fragments, GFP cassette (with TDH3p and Tef1at) and IoURA3 (with URA3p and ENO2t), were co-transformed with ApaI and NotI digested pRS415 backbone into *S. cerevisiae* for in vivo assembly via electroporation or lithium acetate-mediated methods. The isolated yeast plasmids were then transformed into *E. coli* for enrichment, and their identities were verified by restriction digestion or sequencing. The correctly assembled plasmids were subsequently transformed into *I. orientalis* SD108 for target gene expression.

CRISPR/Cas9 plasmids were constructed using DNA assembler from gBlocks containing promoter for sgRNA expression and the following fragments PCR amplified from previous constructs: promoter TEF1a; iCas9; terminator PGK1; *I. orientalis* URA3 expression cassette; *E. coli* helper fragment; and *S. cerevisiae* URA3 expression cassette flanked by XhoI recognition sites and CEN6/ARS4. The resulting plasmids were digested with XhoI to remove *S. cerevisiae* URA3 expression cassette and religated. The HR donor and spacer sequences were ordered as gBlocks and assembled into CRISPR/Cas9 plasmids by Golden Gate assembly method. Key primers, sgRNA promoters, and the spacer (N20) sequences are summarized in Table 5.

TABLE 5

List of the main primers and spacer sequences

| Name | Sequence (5' → 3') | SEQ ID NO |
|---|---|---|
| GFPcassette-F | TAACCTAAGGACTTAAATATTTGTACAAACATGTTCCATTGATTTAACCTGATCCAAAG | SEQ ID NO: 1 |
| GFPcassette-R | GGAACAAAAGCTGGAGCTCCACCGCGGTGGCGGCCGCTTGGCTAAAGAATAAGATGAACG | SEQ ID NO: 2 |
| 1oURA3 cassette-F | GTAATACGACTCACTATAGGGCGAATTGGTACCGGGCCCGTTGACATTGTCTAGCGGCA | SEQ ID NO: 3 |
| 1oURA3 cassette-R | TAAAAAATAGACATACCCCTTTTGGATCAGGTTAAATCAATGGAACATGTTTGTACAAAT | SEQ ID NO: 4 |
| ADE2-spacer | GAGACAGCATTGCAAAATGT | SEQ ID NO: 5 |
| LEU2-spacer | TATCTACTTTGGGGAGAGAG | SEQ ID NO: 6 |
| HIS3-spacer | CATTAGCCAAACATTCAGGG | SEQ ID NO: 7 |
| TRP1-tracer | CCAAGCTATGTCGAGCAAAG | SEQ ID NO: 8 |
| SDH1-spacer | ATAATCCTTTGCCATTGCGG | SEQ ID NO: 9 |
| SDH2-spacer | GCTGAAGGTGAATCCAGTGG | SEQ ID NO: 10 |

Transformation of *I. orientalis* and its Derived Mutants.

A fresh 2 mL overnight YPAD culture of *I. orientalis* was diluted to an initial $OD_{600}$ of 0.2. The cells were continuously grown until they reached $OD_{600}$ of 0.8-1. Cells were collected by centrifugation, washed twice with deionized water, and resuspended in 360 µL of transformation mixture containing 240 µL of 50% w/v PEG3350, 36 µl of 1 M lithium acetate, 50 µL of 2 mg/ml deoxyribonucleic acid from salmon testes (SS-DNA) that was boiled at 100° C. for 5 min and quickly chilled on ice, plasmid (1 µg), and deionized water. After mixing thoroughly, the suspension was subjected to heat shock for 1 hour at 42° C. Cells were collected by centrifugation and spread on appropriate plates.

Flow Cytometry Analysis.

The GFP expression was measured by flow cytometry as described elsewhere. Briefly, the transformed *I. orientalis* cells were cultured in SC-URA medium for ~24-120 h and then centrifuged for 2 min at 2,000×g to remove the supernatant. The cell pellets were resuspended in 10 mM phosphate-buffered saline (pH 7.4) and then analyzed by flow cytometry at 488 nm on a BD LSR II flow cytometer analyser (BD Biosciences, San Jose, CA). After flow cytometry analysis, the *I. orientalis* plasmids were extracted by Zymoprep Yeast Plasmid Miniprep II Kit and retransformed to *E. coli* for colony-counting. qPCR.

*I. orientalis* cultures were inoculated from plate and grown in YPAD media mid-log phase (OD 2-3). Total RNA was extracted using the Qiagen RNeasy kit (Venlo, Netherlands), and reverse transcription was performed with Bio-Rad iScript cDNA Synthesis Kit (Hercules, CA), with a prior denaturation step at 65° C. for 5 minutes to disrupt gRNA secondary structure. qPCR was performed using Bio-Rad iTaq Universal SYBR Green Supermix on a Roche Lightcycler 480 qPCR system. alg9 was used as the reference gene for relative quantification.

Double-Gene Knockout.

Following transformations, 20 randomly selected red colonies were streaked on nonselective SC-URA and selective SC-TRP or SC-HIS plates. After incubation for 2 days, 5 colonies that grew on SC-URA plate but did not on SC-TRP or SC-HIS plates were randomly chosen and sequenced for TRP1 or HIS3 deletion. The double-gene knockout efficiency was estimated to be the overall ADE2 disruption efficiency multiplied by TRP1 or HIS3 disruption efficiency screened by plating and proportion of correct colonies verified by sequencing.

Shake Flask Cultures.

Batch cultures using shake flasks were carried out as follows: a single colony grown on SC-URA plate was inoculated into 2 mL of YPAD medium and grown overnight. Then 100 µL of the stationary-phase cells were transferred into 2 mL of fresh SC-URA media or YPAD media containing 20 g/L of glucose and grown until saturation. An appropriate amount of cells was inoculated in SC-URA containing 25.52 g/L calcium carbonate and 50 g/L glucose or YPAD media containing 50 g/L glucose in 125 mL non-baffled shake flasks. Cells were grown at 30° C. and 250 rpm. The initial $OD_{600}$ was 0.2.

Example 7. Evaluation of the Incorporation of A Centromere-Like Sequence from *I. Orientalis* on Plasmid Stability ScARS was experimentally confirmed as functional for plasmid replication in *I. orientalis*, and the percentage of the cells carrying the ScARS-GFP containing plasmid was 55% of the entire population based on the flow cytometry analysis of the GFP expression at 5 days. Considering that in the benchmark system represented by *S. cerevisiae*, expressing GFP by the commercial vector pRS416 containing the native centromere resulted in a symmetric GFP peak representing >80% of the entire population, isolating a functional CEN sequence from *I. orientalis* genome can be important for stable plasmid segregation. It has been predicted that each of the 5 centromeres is a 35-kb gene desert containing a large inverted repeat. In silico GC3 analysis of the genome of *I. orientalis* SD108 was performed. Five long intergenic regions with sizes of 38.346.2 kb were identified to contain potential centromeres (Table 6 and Table 7).

TABLE 6

Centromere-containing loci predicted by in silico GC3 analysis

|  | IoCEN1 | IoCEN2 | IoCEN3 | IoCEN4 | IoCEN5 |
|---|---|---|---|---|---|
| Predicted CEN loci on chromosomes | 1463934-1510092 | 1451832-1492638 | 188014-226662 | 360477-403218 | 1093806-1132090 |
| Predicted CEN sizes (bp) | 46159 | 40807 | 38649 | 42742 | 38285 |

Figure 10:
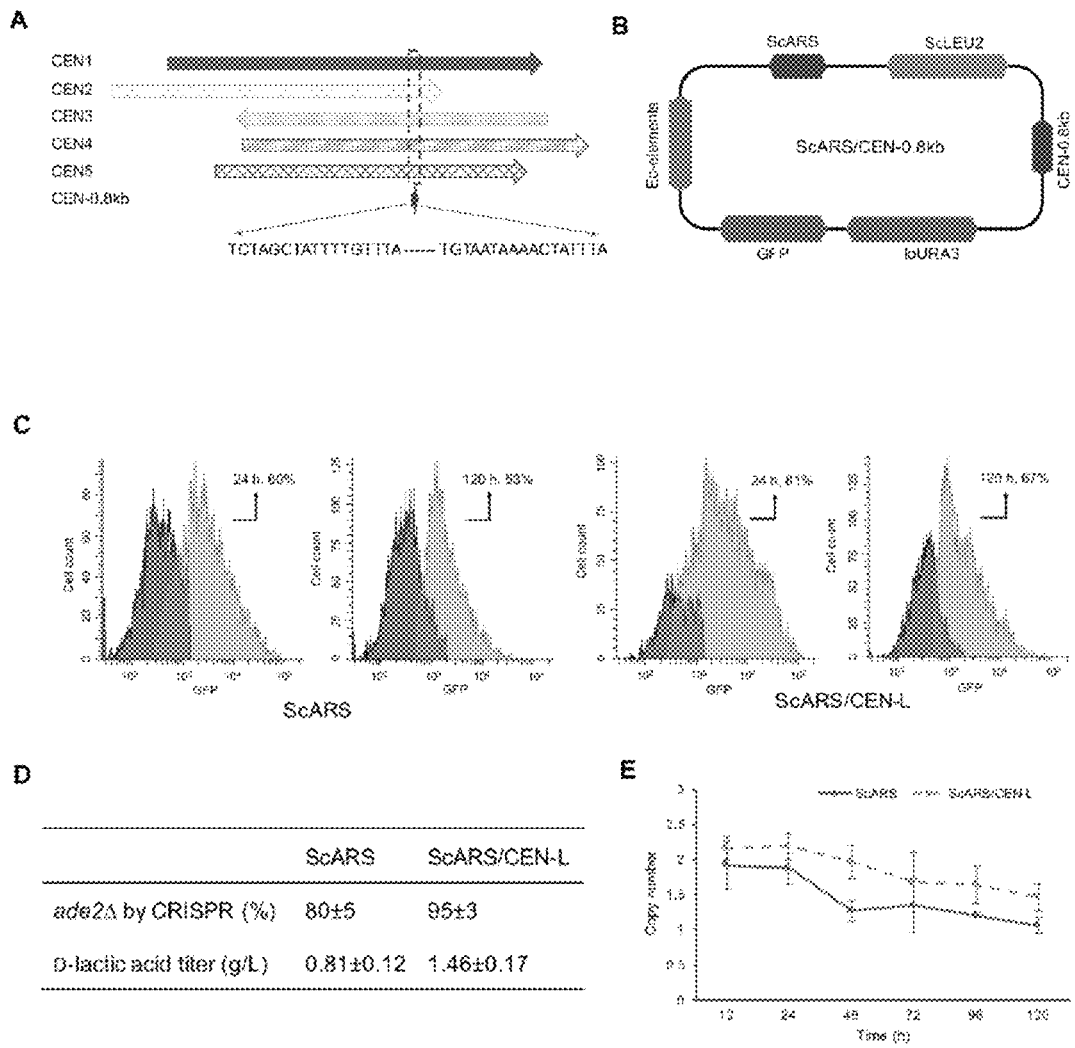
FIG. 10 panel A discloses alignment of the centromere sequences predicted by in silico GC3 analysis. TCTAGCT-ATTTTGTTTA is SEQ ID NO: 152; TGTAATAAAACTAT-TTA is SEQ ID NO: 153. Panel B discloses the plasmid map of ScARS/CEN-0.8 kb containing *I. orientalis* CEN-0.8 kb and URA3 selection marker, GFP expression cassette, *E. coli* elements (Ec-elements), *S. cerevisiae* ARS (ScARS), and LEU2 selection marker (ScLEU2). Panel C discloses GFP expression profiles by ScARS or ScARS/CEN-L harboring plasmids at 24 h and 120 h measured by flow cytometry. Panel D discloses ade2 knockout efficiencies by CRISPR/Cas9 and D-lactic acid productions using ScARS and ScARS/CEN-L plasmids. Panel E discloses copy number assay for ScARS and ScARS/CEN-L vectors. CEN-0.8 kb-2 was named as CEN-L.
Figure 11A:
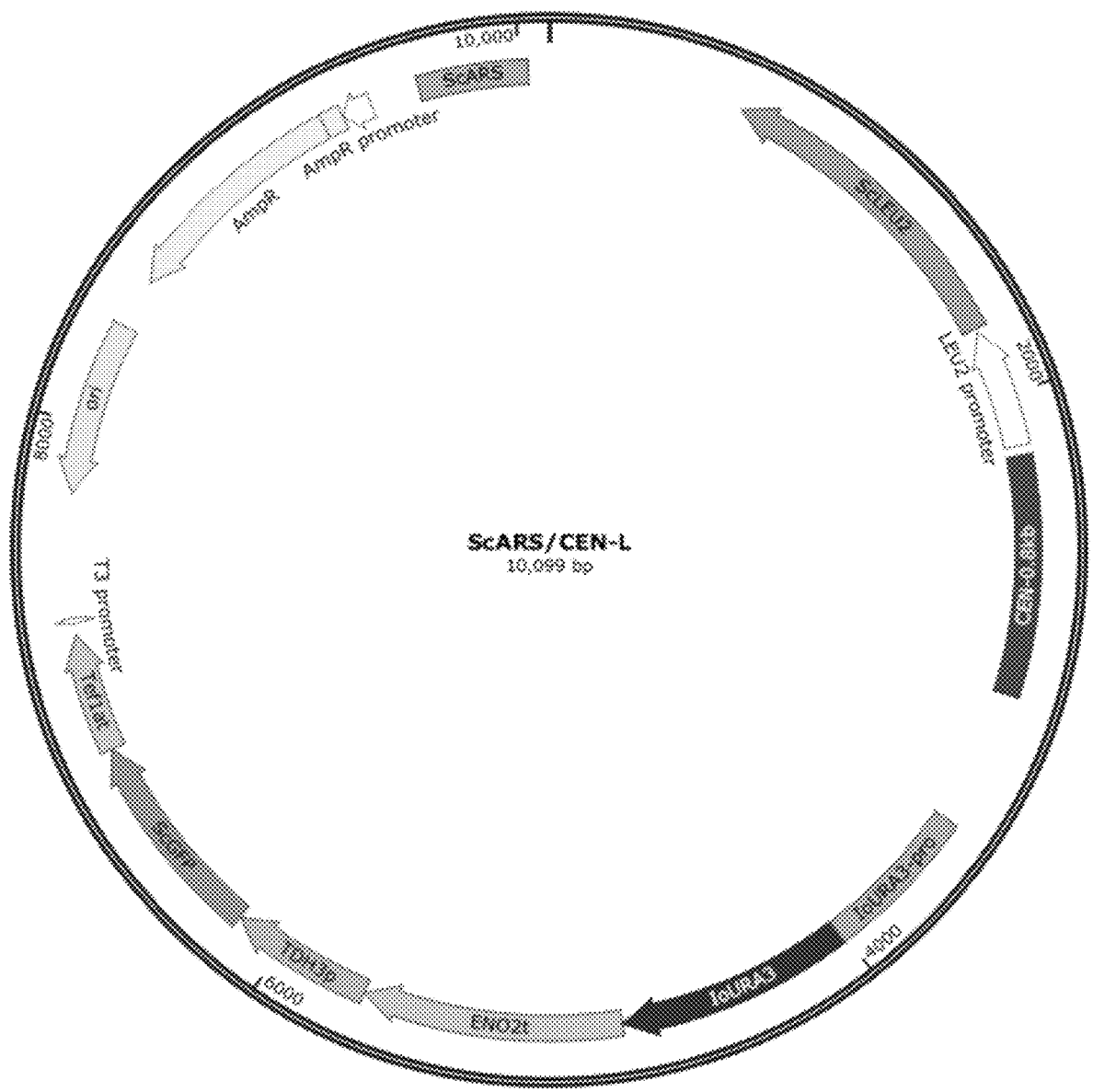
FIG. 11A discloses the map for the ScARS/CEN-L plasmid (ScARS/CEN-0.8 kb-2).
Figure 11B:
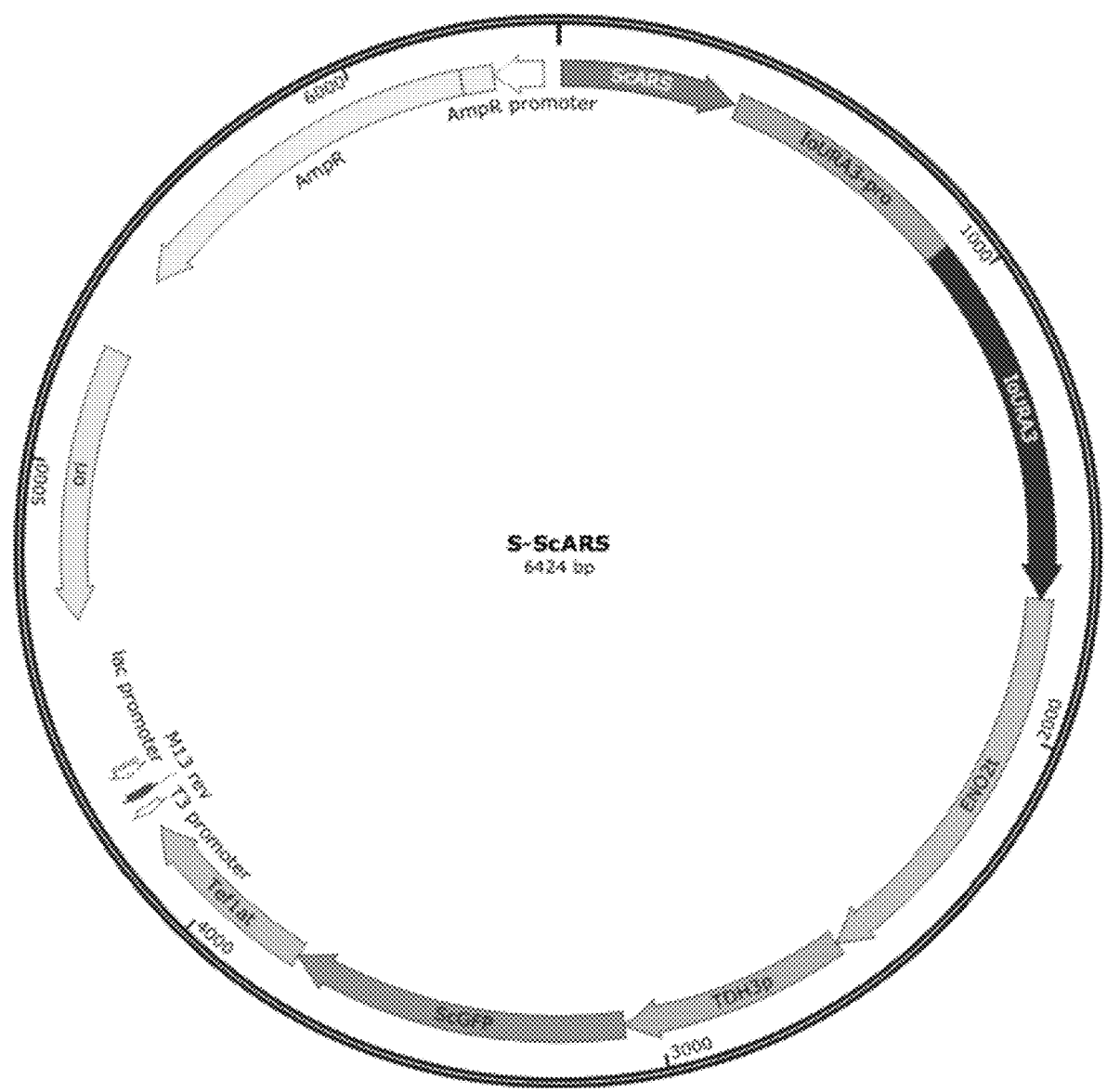
FIG. 11B discloses the map for the S-ScARS plasmid.
Figure 11C:
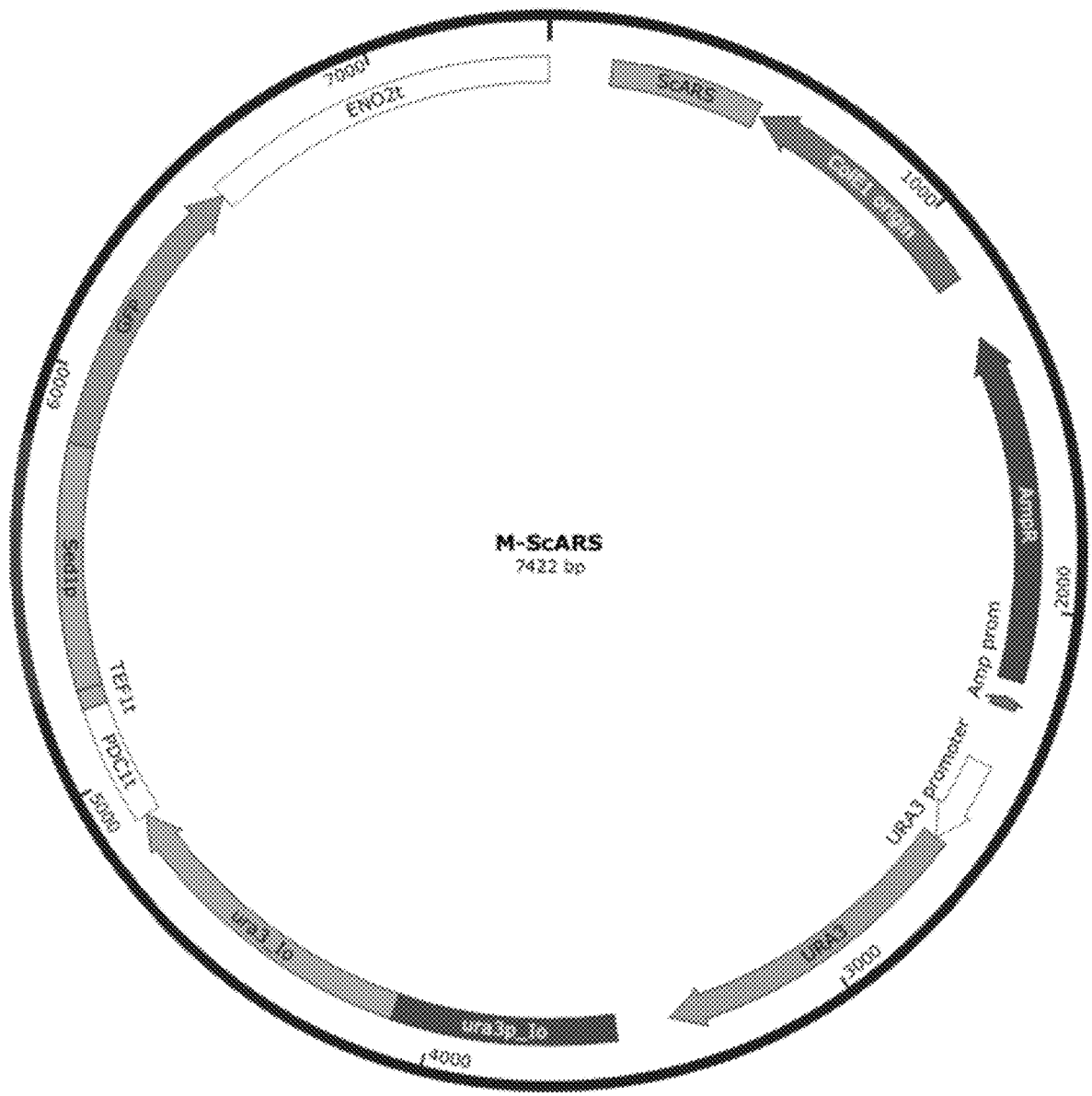
FIG. 11C discloses the map for the M-ScARS plasmid.
Figure 11D:
FIG. 11D discloses the map for the ScARS/CEN-L-Xylose plasmid.
Figure 12B:
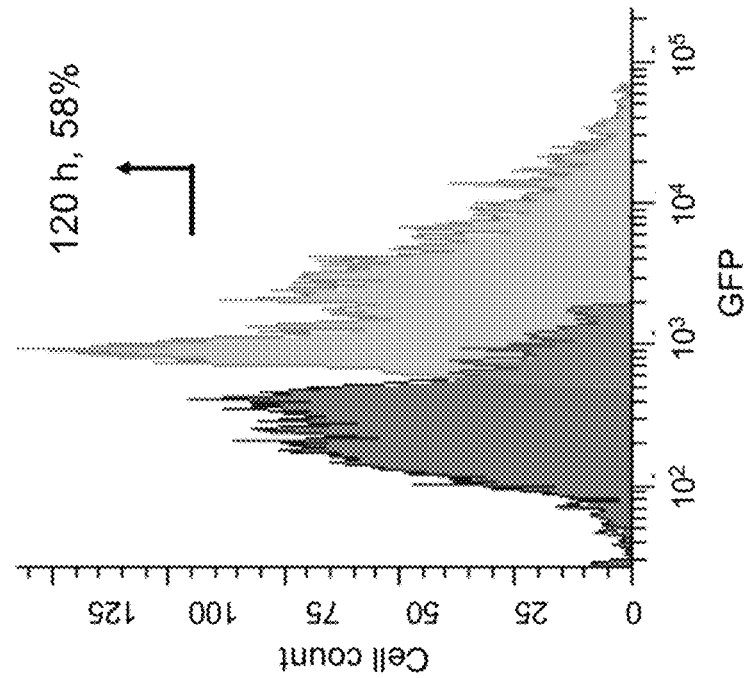
FIG. 12B discloses GFP expression profiles by the other nine colonies (CEN-0.8 kb-1 as an example) at 120h.
Figure 12A:
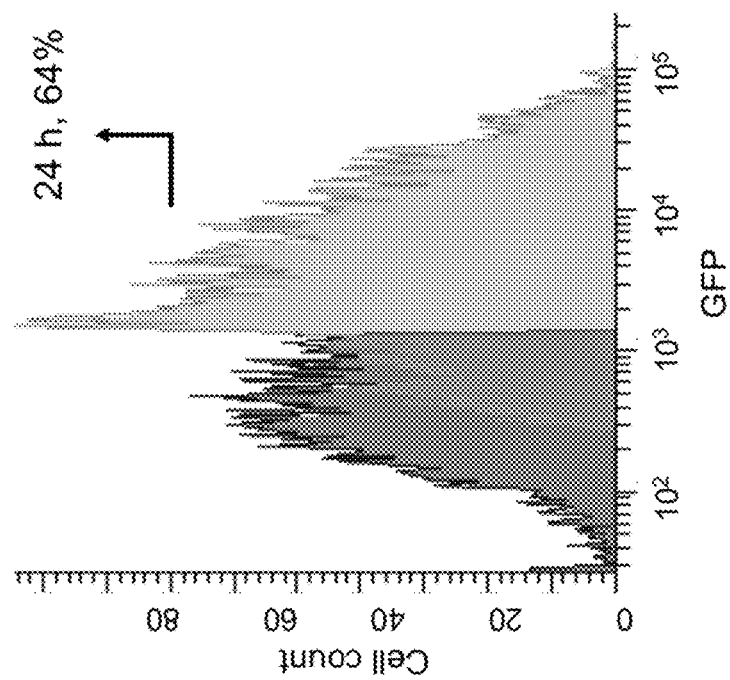
FIG. 12A discloses GFP expression profiles by the other nine colonies (CEN-0.8 kb-1 as an example) at 24h.

Due to the large sizes of these predicted sequences, integrating them to the plasmid for functional characterization was undesired. The five centromere sequences were aligned interactively, and an 811-bp conserved fragment (~2% of the original size) was obtained (FIG. 10A). The 811-bp fragment (CEN-0.8 kb) was amplified and integrated to ScARS-plasmid (FIG. 10B), and transformed into *I. orientalis* SD108 strain for functional characterization. It was shown that among the 10 randomly picked colonies, only CEN-0.8 kb-2 could express GFP at ratios of 81% and 67% at 24 h and 120 h, respectively (FIG. 10C), while the other nine colonies were associated with similar peaks (FIG. 12) to the cells harboring ScARS-plasmid (60% and 53% at 24 h and 120 h, respectively, FIG. 10C). After DNA sequencing and aligning the different CEN-0.8 kb fragments, there were a few nucleotide variants among them, which may be important for granting the function of CEN-0.8 kb. The nucleotide variants are CEN.8-1 (SEQ ID NO:154), CEN.8-2 (SEQ ID NO:155, CEN.8-3 (SEQ ID NO: 156), CEN.8-4 (SEQ ID NO: 157), CEN.8-5 (SEQ ID NO:158), CEN.8-6 (SEQ ID NO: 159), CEN.8-8 (SEQ ID NO: 160), CEN.8-9 (SEQ ID NO:161), CEN.8-10 (SEQ ID NO: 162). SEQ ID NO: 163 is a consensus of SEQ ID NOs: 154-162.

```
CEN0.8-1 (SEQ ID NO: 154)
TCTAGCTATTTTGTTTAGGTTGGGTAAAAACCTACGGAAAGACAATAGGAGCTTAGGCTATCTATTGA

TAGATCAATTATTTGTTTTAAGAACTATAGAATTAAAAACAAGGCAGTAGTTGTAGATTTTAAAGATTATTTAGAGTAGA

TAGATAGTAAAGGCTGTACTGAATATAAATGTGGATTTGCGGAACCAACAAGTGGCCTCCATCAAGCTATTTAAGTTATT

CTATTGGTATTTTACTAGAAAAGGAAGGCTAATCATTTTTCCAATGACGGTTCATATAATCCAAGTTTTAAATGGTTTGC

ATCATCATAATAGGGGTATCTAAAAGGCATAAATCGACGAAAGTGATAAAAATTACTTATTAAACGACGTATTTACATCC

ACGTTTTTGCTGGAAGTACTGAATCTGCCTACTGCTAGTTTGGGGAAGACAATAATACACAAAATAAAGACGATGATGAA

GATTCCAGTTTTTTTTAAAGATAAAAAAATAGATATATATGTATAATTGTATGAATAGTTTTAATAATAACTTATGTTGC

TATTTTGATAGCAATTCATTTTACTATTGAAAAGGTTACCCAGGCAAATAATATGTTTAGCACATCAGATTCTGTACTAA

TAATAATATAGACATATGCTATAACGTCAGGCAATACTTATGTGTATAGCGAAATAGTAAAGGGCTCGTCGTAAATCGTA

TGTTTTCACGACTTAGACTCATAAGACATGTCTAGAAGCCCAACCAATGAATTAGAGGACTGTTTGATATCAACATCCAG

TCACTTTGAGTGTAATAAAACTATTTA

CEN0.8-2 (SEQ ID NO: 155)
TCTAGCTATTTTGTTTAGGTTGGGTAAAAACCTACGGAAAGACAATTGGAGCTTAGGCTATCTATTGA

TAGATCAATTATTTGTTTTAAGAACTATAGAATTAAAAACAAGGCAGTAGTTGTAGATTTTAAAGATTATTTAGAGTAGA

TAGTAAAGGCTGTACTGAATATCAATGAGGATTTGCAGAACCAACAAGTGGCCTGCATCAAGCTATTTAAGTGATTCTAT

TGGTATTTTACTAGAAAAGGAAGGCTAATCATTTTTCCAATGACGGTTCATATAATCCAAGTTTTAAATGGTTTGCATCA

TCATAATAGGGGTATCTAAAAGGCATAAATCGACGAAAGTGATAAAAATTACTTATTAAACGACGTATTTACATCCACGT

TTTTGCTGGAAGTACTGAATCTGCCTACTGCTAGTTTGGGGAAGACAATAATACACAAAATAAAGACGATGATGAAGATT

CCAGTTTTTTTAAAGATAAAAAAATAGATATATATGTATAATTGTATGAATAGTTTTAATAATAACTTATGTTGCTATT

TTGATAGCAATTCATTTTACTATTGAAAAGGTTACCCAGGCAAATAATATGTTTAGCACATCAGATTCTGTACTAATAAT

AATATAGAGTTATGTTATAACGTCAGGCAATACTTATGTGTATAGCGAAATAGTAAATGGCAGATTGTAAACCGTATGTT

TTCACTACTCAGACTCATACGATATGTCTAGAAGCCCAACCAATGAATTAGAGGACTGTTTGATATCAACATCCAGTCAC

TTTGAGTGTAATAAAACTATTTA

CEN0.8-3 (SEQ ID NO: 156)
TCTAGCTATTTTGTTTAGGTTGGGTAAAAACCTACGGAAAGACAATAGGAGCTTAGGCTATCTATTGA

TAGATCAATTATTTGTTTTAAGAACTATAGAATTAAAAACAAGGCAGTAGTTGTAGATTTTAAAGATTATTTAGAGTAGA
```

TAGATAGTAAAGGCTGTACTGAATATAAATGTGGATTTGCGGAACCAACAAGTGGCCTCCATCAAGCTATTTAAGTTATT

CTATTGGTATTTTACTAGAAAAGAAAGGCTAATCATTTTTCCAATGAAGGTTCATATAATCCAAGTTTTAAATGGTTTGC

ATCATCATAATAGGGGTATCTGAAAGGCATAAATCAACGAAAGTGATAGAAATTACTTATTAAACAACGTATTTACATCC

ACGTTTTTTGCTGGAAGTACTGAATCTGCCTACTGCTAGTTTGGGGAAGACAATAATACACAAAATAAAGACGATGATGA

AGATTCCAGTTTTTTTTAAAGATAAAAAAATAGATATATATGTATAATTGTATGAATAGTTTTAATAATAACTTATGTTG

CTATTTTGATAGCAATTCATTTTACTATTGAAAAGGTTACCGGGGCAAATAATATGTTTAGCACATCAGATTCTGTACTA

ATAATAATATAGACATATGCTATAACGTCAGGCAATACTTATGTGTATAGCGAAATAGTAAAGGGCTCGTCGTAAATCGT

ATGTTTTCACGACTTAGACTCATAAGACATGTCTAGAAGCCCAACCAATGAATTAGAGGACTGTTTGATATCAACATCCA

GTCACTTTGAGTGTAATAAAACTATTTA

CEN0.8-4 (SEQ ID NO: 157)
TCTAGCTATTTTGTTTAGGTTGGGTAAAAACCTACGGAAAGACAATAGGAGCTTAGGCTATCTATTGA

TAGATCAATTATTTGTTTTAAGAACTATAGAATTAAAAACAAGGCAGTAGTTGTAGATTTTAAAGATTATTTAGAGTAGA

CAGTAAAGGCAGTACTGAATATCAATGAGGATTTGCAGAACCAACAAGTGGCCTGCATCAAGCTATTTAAGTGATTCTAT

TGGTATTTTACTAGAAAAGGAAGGCTAATCATTTTTCCAATGACGGTTCATATAATCCAAGTTTTAAATGTTTTGTATCA

TCATAATAGGGGTATCTGAAAGGCATAAATCAACGAAAGTGATAGAAATTACTTATTAAACAACGTATTTACATCCACGT

TTTTTGCTGGAAGTACTGAATCTGCCTACTGCTAGTTTGGGGAAGATAATAATACACAAAATAAAGACGATGATGAAGAT

TCCAGTTTTTTTTAAAGATAAAAAAATAGATATATATGTATAATTGTATGAATAGTTTTAATAATAACTTATGTTGCTAT

TTTGATAGCAATTCATTTTACTATTGAAAAGGTTACCGGGGCAAATAATATGTTTAGCACATCAGATTCTGTACTAATAA

TAATATAGAGTTATGTTATAACGTCAGGCAATACTTATGTGTATAGCGAAATAGTAAATGGCAGATCGTAAACCGTATGT

TTTCACTACTCAGACTCATACGACATGTCTAGAAGCCCAACCAATGAATTAGAGGACTGTTTGATATCAACATCCAGTCA

CTTTGAGTGTAATAAAACTATTTA

CEN0.8-5 (SEQ ID NO: 158)
TCTAGCTATTTTGTCTAGGTTGGGTAAAAACCTACGGAAAGACAATAGGAGCTTAGGCTATCTATTGA

TAGATCAATTATTTGTTTTAAGAACTATAGAATTAAAAACAAGGCAGTAGTTGTAGATTTTAAAGATTATTTAGAGTAGA

CAGTAAAGGCAGTACTGAATATCAATGAGGATTTGCAGAACCAACAAGTGGCCTGCATCAAGCTATTTAAGTGATTCTAT

TGGTATTTTACTAGAAAAGGAAGGCTAATCATTTTTCCAATGACGGTTCATATAATCCAAGTTTTAAATGTTTTGTATCA

TCATAATAGGGGTATCTGAAAGGCATAAATCAACGAAAGTGATAGAAATTACTTATTAAACAACGTATTTACATCCACGT

TTTTTGCTGGAAGTACTGAATCTGCCTACTGCTAGTTTGGGGAAGATAATAATACACAAAATAAAGACGATGATGAAGAT

TCCAGTTTTTTTTAAAGATAAAAAAATAGATATATATGTATAATTGTACGAATAGTTTTAATAATAACTTATGTTGCTAT

TTTGATAGCAATTCATTTTACTATTGAAAAGGTTACCGGGGCAAATAATATGTTTAGCACATCAGATTCTGTACTAATAA

TAATATAGACATATGCTATAACGTCAGGCAATACTTATGTGTATAGCGAAATAGTAAAGGGCTCGTCGTAAATCGTATGT

TTTCACGACTTAGACTCATAAGACATGTCTAGAAGCCCAACCAATGAATTAGAGGACTGTTTGATATCAACATCCAGTCA

CTTTGAGTGTAATAAAACTATTTA

CEN0.8-6 (SEQ ID NO: 159)
TCTAGCTATTTTGTTTAGGTTGGGTAAAAACCTACGGAAAGACAATAGGAGCTTAGGCTATCTATTGA

TAGATCAATTATTTGTTTTAAGAACTATAGAATTAAAAACAAGGCAGTAGTTGTAGATTTTAAAGATTATTTAGAGTAGA

CAGTAAAGGCAGTACTGAATATCAATGAGGATTTGCAGAACCAACAAGTGGCCTGCATCAAGCTATTTAAGTGATTCTAT

TGGTATTTTACTAGAAAAGGAAGGCTAATCATTTTTCCAATGACGGTTCATATAATCCAAGTTTTAAATGGTTTGCATCA

TCATAATAGGGGTATCTAAAAGGCATAAATCGACGAAAGTGATAAAAATTACTTATTAAACGACGTATTTACATCCACGT

TTTTGCTGGAAGTACTGAATCTGCCTACTGCTAGTTTGGGGAAGACAATAATACACAAAATAAAGACGATGATGAAGATT

CCAGTTTTTTTTAAAGATAAAAAAATAGATATATATGTATAATTGTATGAATAGTTTTAATAATAACTTATGTTGCTATT

TTGATAGCAATTCATTTTACTATTGAAAAGGTTACCGGGGCAAATAATATGTTTAGCACATCAGATTCTGTACTAATAAT

-continued

AATATAGAGTTATGTTATAACGTCAGGCAATACTTATGTGTATAGCGAAATAGTAAATGGCAGATCGTAAACCGTATGTT

TTCACTACTCAGACTCATACGACATGTCTAGAAGCCCAACCAATGAATTAGAGGACTGTTTGGTATCAACATCCAGTCAC

TTTGAGTGTAATAAAACTATTTA

CEN0.8-8 (SEQ ID NO: 160)
TCTAGCTATTTTGTTTAGGTTGGGTAAAAACCTACGGAAAGACAATTGGAGCTTAGGCTATCTATTGA

TAGATCAATTATTTGTTTTAAGAACTATAGAATTAAAAACAAGGCAGTAGTTGTAGATTTTAAAGATTATTTAGAGTAGA

TAGTAAAGGCTGTACTGAATATCAATGAGGATTTGCAGAACCAACAAGTGGCCTGCATCAAGCTATTTAAGTGATTCTAT

TGGTATTTTACTAGAAAAGGAAGGCTAATCATTTTTCCAATGACGGTTCATATAATCCAAGTTTTAAATGTTTTGTATCA

TCATAATAGGGGTATCTGAAAGGCATAAATCAACGAAAGTGATAGAAATTACTTATTAAACAACGTATTTACATCCACGT

TTTTTGCTGGAAGTACTGAATCTGCCTACTGCTAGTTTGGGGAAGATAATAATACACAAAATAAAGACGATGATGAAGAT

TCCAGTTTTTTTAAAGATAAAAAAATAGATATATATGTATAATTGTACGAATAGTTTTAATAATAACTTATGTTGCTAT

TTTGATAGCAATTCATTTTACTATTGAAAAGGTTACCGGGGCAAATAATATGTTTAGCACATCAGATTCTGTACTAATAA

TAATATAGACATATGCTATAACGTCAGGCAATACTTATGTGTATAGCGAAATAGTAAAGGGCTCGTCGTAAATCGTATGT

TTTCACGACTTAGACTCATAAGACATGTCTAGAAGCCCAACCAATGAATTAGAGGACTGTTTGATATCAACATCCAGTCA

CTTTGAGTGTAATAAAACTATTTA

CEN0.8-9 (SEQ ID NO: 161)
TCTAGCTATTTTGTTTAGGTTGGGTAAAAACCTACGGAAAGACAATAGGGGCTTAGGCTATCTATTGA

TAGATCAATTATTTGTTTTAAGAACTATAGAATTAAAAACAAGGCAGTAGTTGTAGATTTTAAAGATTATTTAGAGTAGA

TAGTAAAGGCTGTACTGAATATCAATGAGGATTTGCAGAACCAACAAGTGGCCTGCATCAAGCTATTTAAGTGATTCTAT

TGGTATTTTACTAGAAAAGGAAGGCTAATCATTTTTCCAATGACGGTTCATATAATCCAAGTTTTAAATGTTTGCATCA

TCATAATAGGGGTATCTAAAAGGCATAAATCGACGAAAGTGATAAAAATTACTTATTAAACGACGTATTTACATCCACGT

TTTTGCTGGAAGTACTGAATCTGCCTACTGCTAGTTTGGGGAAGACAATAATACACAAAATAAAGACGATGATGAAGATT

CCAGTTTTTTTAAAGATAAAAAAATAGATATATATGTATAATTGTACGAATAGTTTTAATAATAACTTATGTTGCTATT

TTGATAGCAATTCATTTTACTATTGAAAAGGTTACCGGGGCAAATAATATGTTTAGCACATCAGATTCTGTACTAATAAT

AATATAGACATATGCTATAACGTCAGGCAATACTTATGTGTATAGCGAAATAGTAAAGGGCTCGTCGTAAATCGTATGTT

TTCACGACTTAGACTCATAAGACATGTCTAGAAGCCCAACCAATGAATTAGAGGACTGTTTGATATCAACATCCAGTCAC

TTTGAGTGTAATAAAACTATTTA

CEN0.8-10 (SEQ ID NO: 162)
TCTAGCTATTTTGTTTAGGTTGGGTAAAAACCTACGGAAAGACAATTGGAGCTTAGGCTATCTATTGA

TAGATCAATTATTTGTTTTAAGAACTATAGAATTAAAAACAAGGCAGTAGTTGTAGATTTTAAAGATTATTTAGAGTAGA

TAGTAAAGGCAGTACTGAATATCAATGAGGATTTGCAGAACCAACAAGTGGCCTGCATCAAGCTATTTAAGTGATTCTAT

TGGTATTTTACTAGAAAAGGAAGGCTAATCATTTTTCCAATGACGGTTCATATAATCCAAGTTTTAAATGTTTTGTATCA

TCATAATAGGGGTATCTGAAAGGCATAAATCAACGAAAGTGATAGAAATTACTTATTAAACAACGTATTTACATCCACGT

TTTTTGCTGGAAGTACTGAATCTGCCTACTGCTAGTTTGGGGAAGATAATAATACACAAAATAAAGACGATGATGAAGAT

TCCAGTTTTTTTAAAGATAAAAAAATAGATATATATGTATAATTGTACGAATAGTTTTAATAATAACTTATGTTGCTAT

TTTGATAGCAATTCATTTTACTATTGAAAAGGTTACCGGGGCAAATAATATGTTTAGCACATCAGATTCTGTACTAATAA

TAATATAGACATATGCTATAACGTCAGGCAATACTTATGTGTATAGCGAAATAGTAAAGGGCTCGTCGTAAATCGTATGT

TTTCACGACTTAGACTCATAAGACATGTCTAGAAGCCCAACCAATGAATTAGAGGACTGTTTGATATCAACATCCAGTCA

CTTTGAGTGTAATAAAACTATTTA

SEQ ID NO: 163 is a Consensus of SEQ ID NOs: 154-162.
TCTAGCTATTTTGTTTAGGTTGGGTAAAAACCTACGGAAAGACAATAGGAGCTTAGGCTATCTATTGA

TAGATCAATTATTTGTTTTAAGAACTATAGAATTAAAAACAAGGCAGTAGTTGTAGATTTTAAAGATTATTTAGAG----

-continued

```
TAGATAGTAAAGGCTGTACTGAATATCAATGAGGATTTGCAGAACCAACAAGTGGCCTGCATCAAGCTATTTAAGTGATT

CTATTGGTATTTTACTAGAAAAGGAAGGCTAATCATTTTTCCAATGACGGTTCATATAATCCAAGTTTTAAATGGTTTGC

ATCATCATAATAGGGGTATCTGAAAGGCATAAATCAACGAAAGTGATAGAAATTACTTATTAAACAACGTATTTACATCC

ACGTTTTTTGCTGGAAGTACTGAATCTGCCTACTGCTAGTTTGGGGAAGACAATAATACACAAAATAAAGACGATGATGA

AGATTCCAGTTTTTTTTAAAGATAAAAAAATAGATATATATGTATAATTGTATGAATAGTTTTAATAATAACTTATGTTG

CTATTTTGATAGCAATTCATTTTACTATTGAAAAGGTTACCGGGGCAAATAATATGTTTAGCACATCAGATTCTGTACTA

ATAATAATATAGACATATGCTATAACGTCAGGCAATACTTATGTGTATAGCGAAATAGTAAAGGGCTCGTCGTAAATCGT

ATGTTTTCACGACTTAGACTCATAAGACATGTCTAGAAGCCCAACCAATGAATTAGAGGACTGTTTGATATCAACATCCA

GTCACTTTGAGTGTAATAAAACTATTTA
```

It was also observed that the spacing sequence between ScARS and CEN-0.8 kb-2 affected the CEN-0.8 kb-2 function. The currently used spacing sequence of ScLeu2 cassette with a size of 2.2-kb could guarantee a GFP+ population of >80% at 24 h. However, when ScARS and CEN-0.8 kb-2 were rearranged in tandem, the percentage of the GFP+ population decreased to 60% (see plasmids maps at FIG. 11).

Collectively, these observations provided the valuable information regarding CEN epigeneticity. In many eukaryotes, it is generally thought that CENs are epigenetically specified by their specialized chromatin structure and no conserved sequences or common features were found to predict CENs across species. The CenH3 has been proposed to be the epigenetic mark of CENs, and its post-translational modifications (e.g., phosphorylation, methylation, acetylation, and ubiquitylation) contribute to CEN function. Only one of the 0.8-kb sequence (CEN-0.8 kb-2) demonstrated the obvious benefit to plasmid stability.

The function of CEN-0.8 kb-2 was further investigated by evaluating the ade2 knockout efficiency via CRISPR/Cas9 and D-lactic acid production via overexpression of D-lactate dehydrogenase gene (IdhD) from *Leuconostoc mesenteroides* using plasmids harboring ScARS and ScARS/CEN-0.8 kb-2. Sequencing confirmation of ade2 knockout was conducted with the 8 bp deletion by integrating donor containing (50+50) bp homologous arms. GCAGTTGCAGACTCTGTTAGCGTTGAAAGCACCGAGACAGCATT GCAAAATGTTGGTT TGAAATTTGGTTTCCCATTTATGCTGAAGTCCAAAACTGAAGCATATGAT is SEQ ID NO: 164. Nucleotides 1-50 is a first homology arm, nucleotides 51 to 58 is the 8 bp deletion, and nucleotides 59-108 is a second homology arm. As shown in FIG. 10D and in FIG. 13, the ade2 knockout efficiency was 95% using pScARS/CEN-0.8 kb-2 (FIG. 13B), while it was only 80% for ScARS plasmid (FIG. 13A). Meanwhile, the D-lactic acid produced by an *I. orientalis* strain overexpressing IdhD by ScARS/CEN-0.8 kb-2 could reach 1.46 g/L in culture tube, which was around 1.8-fold higher than the level achieved with the corresponding ScARS vector. To elucidate if the gene expression was originated from plasmid stability, the copy number assay on the two GFP expressing vectors (i.e., ScARS and ScARS/CEN-0.8 kb-2) was carried out by quantitative PCR (qPCR). As shown in FIG. 10E, the copy number of ScARS/CEN-0.8 kb-2 plasmid was ~2.2 at 24 h, slightly higher than that of the ScARS plasmid (~1.9), indicating that CEN-0.8 kb-2 improved the plasmid stability and resulted in a higher gene expression level. However, the copy numbers of both plasmids decreased over time, suggesting that they were still not as stable as the reported CEN-containing plasmids in *S. cerevisiae* and *S. stipitis*. CEN-0.8 kb-2 was beneficial for improving the gene expression system, which was also proven useful for enhancing gene knockout efficiency and production of valuable chemicals in *I. orientalis*. To distinguish it from a fully functional CEN, CEN-0.8 kb-2 was renamed as centromere-like sequence, i.e., CEN-L hereafter.

TABLE 7

CENs sequences

| Sequence | | SEQ ID NO |
|---|---|---|
| CEN-0.8 kb | TCTAGCTATTTTGTTTAGGTTGGGTAAAAACCTACGGAAAGACAATTGGAGCTTAGGCTAT CTATTGATAGATCAATTATTTGTTTTAAGAACTATAGAATTAAAAACAAGGCAGTAGTTGT AGATTTTAAAGATTATTTAGAGTAGATAGTAAAGGCTGTACTGAATATCAATGAGGATTTG CAGAACCAACAAGTGGCCTGCATCAAGCTATTTAAGTGATTCTATTGGTATTTTACTAGAA AAGGAAGGCTAATCATTTTTCCAATGACGGTTCATATAATCCAAGTTTTAAATGGTTTGCA TCATCATAATAGGGGTATCTAAAAGGCATAAATCGACGAAAGTGATAAAAATTACTTATTA AACGACGTATTTACATCCACGTTTTTGCTGGAAGTACTGAATCTGCCTACTGCTAGTTTGG GGAAGACAATAATACACAAAATAAAGACGATGATGAAGATTCCAGTTTTTTTTAAAGATAA AAAAATAGATATATATGTATAATTGTATGAATAGTTTTAATAATAACTTATGTTGCTATTT TGATAGCAATTCATTTTACTATTGAAAAGGTTACCCAGGCAAATAATATGTTTAGCACATC AGATTCTGTACTAATAATAATATAGAGTTATGTTATAACGTCAGGCAATACTTATGTGTAT AGCGAAATAGTAAATGGCAGATTGTAAACCGTATGTTTTCACTACTCAGACTCATACGATA TGTCTAGAAGCCCAACCAATGAATTAGAGGACTGTTTGATATCAACATCCAGTCACTTTGA GTGTAATAAAACTATTTA | SEQ ID NO: 11 |
| CEN1-46159 bp | CTTTTGAATAATTTTCTAAATTCAAGTTAAGTTTAAGTAATTTGGGATACTATGACTAAGG ATGGTAAAAGAATTAGAAAAAAGTAAAAAAGGAAAATCAAGAATGTGCTGATTCGGAGAAA AGTGGAATTTAGGGAGAGAGAGAGCAAGGAATTTAAATACAATCTAGTTTCTCCGTGAAAT AGAAAACTCACCTCCTATAAGTGGTTTCCGTTTGACTAAAAATCACACAATGATGAAATAG | SEQ ID NO: 12 |

TABLE 7-continued

CENs sequences

| Sequence | SEQ ID NO |
|---|---|
| CCGAAATAGACAGGTTCCCCGTATTTTTCCGCAAAAAAAAGAAGCTATTTTTGAAATTG TTACAACAAAGCATAAGGGTGGGTGGTAAAGAGCGGAAAATAAAACTCTGTTTCTCTCTGC TTTTTCAATTTCAGCTTAATAGACTTTCAGGTAGTTTAGGTTTACAAACTTGCGAGTGGCA TATGCTAGGGAACACGTTACTTTGCACTTTAGACTTCTCCCTTTTATTAAAGGGAGGAGAA GACGATATTGGTATGTAAAAGTGGGTAATATTTACATAGCTGAAGAAGCTGCTCTTGAGAT CTTAATTGTCAAGTTAGTTTGAGTAAAGACAGGAACAACTGGAACTATCAATACAGAGACA GCCATGATATTTTGACTGAGTTTCCGCTCCAGATATAGTAAAAGAATGTTTCCGGTAATAT GTCTTGCTAATATGATAGGTGTGACCTGCATTGAAATACTAATAGTTCCCTATATTTTTC CGTTGTGTTACATTTTCCCCTGCGTGGCGCTCCCAATCAATTTCTACTCTGCTTGTGTTAT TCTCAGATGATGTTTCGGCCATTTTTGTGTAATTTCTTCTTGCAGTATTTTTATTTCCGGT GGGATGTTTAATATATCTCATTCTTCTGAAAAGAAAAAATTTTAATAGTAAACAATCCAAT GAGATAAGGACAGCCTTTTATGCCTATAGAGTTAACAACAACAAACAAACAAACATCAATT TTTTTACAATCTCTCCATCCTACCTTGGATAATTGTCACATACCACTTCTCTGGTAATGCC AAAAAGAGGAAAAAATATCCTAAAAATAGGTTGAAAATTAAATTGCCGCGCATGGCAA TGCAGTGTGTGCTGCCTTTTCAATCTGCAACTAGATAGAGTATCACTTTTTAATGGGACGA CAAAACGAACAACTGAATAGATAGTGTACATATTGAACTTATTTTTTTTGGATTACTTAG TGGTGGTTGTTGGGTTTACTGCCATTTAACAAAACACAACATGTTTAAACTTTGAGAGGTA GAGTGACATCGTTGAGAGATGGCTCCATCATTTCCATGTATGACCCTATTTTTGTTTTTT GTGTTTCTTTGTTTCTTGTTATTTTTTTATTTACACAAAAGCTTAATAATCTACAACCTT TGACGATTTTTGATTCTATCTCCGAATTCATGGTTTTGTTTGTTCCCGCTTTTTCCTGTTC CGCAGTGTTTCTCTTTTTTCCATGCACAAAAATCTATCCCCACTTTGGGTATATCACAGTA TTTCTTTAATTAGGAAAACCCAGTGTATAACATCAATCTCTGCTTTTTTGTTCATACTCTG GAACATATTTTGGTCTACTTATCTTTTTGATGCAGTGGAATACACTAAAATCAGAAGTATG AACCTTGTTGTCAGATGGGTTTGAATTTTAAACCCCTAGAATAGCCAGCTGCTAGTACTAT TGCTAACTCGGTATACATTTTTTTGGTGTTGCGGGAAAATTATATGCTACTGTATGGACAA AATTATATCCTTCCATCATGGATTAATTCAAGATAAAGAAAAAATACAAGCTATAATACTT CAGCAATCGCCGAGATCGGATATTCTACAAAAGATTGACATATTACCGCCTAAACAGCATG ACCAAGGCTGTTTGAACTTATTCCGAAACAAATTTTCAGGGCTGACATAGTCGTCTAGCTA GTTTTGCTGACAGTTAGACAAACCTGTAAATATTTAACTTGGTAAGGAGACTTGTTGGAAG GTTAACTCAAGCAGTGGAAACTAATGATTAGCACCAAGGTATCATTTTACCATCTCTACGA CAGTAGATCTCAGACCACCTTGGAACACCTTTATCGGAAGTCCTTGAATCGTCCTTTTTTT CAGTCCCTTTAGTTGAAACTCAACTAACAAAGTTAAACCAGACATTCTCTAATAAATTGTC CTAAAAAAAACACGAATGAAACTTTGCTAAAATAATAATATATGATATCTTCGAATCACAAT CATCCGTCGGTAATGAAGAGATCAATGAATGCTGAAATATTCAATGTTCTCTAGAAATTGA TAATTGCTAAGGAACAGTGTTGCTTGTTACCTATTATGGCCAAATTAAACAACTTATTCAA AGTTCAACAGTAACAAAACTGCGGTTAGATCAGATAGACAGACGAAGGTGCTTGATTTAAG TGATATAATAATGTCTTAAAAAAAAACACATCGGCTTTGTCGCTTCTATTGGGTGTATGAC ATTTGTGATCTTTACTGTCTGATATAAACGTGCAATGCTCTTCTTTTGCATCCACTGAACG TAAAAAACATGTAAGAAAAAAATACCTGAACTTTTCTTTTTCAACTCTAGTCTTGTTCTC GTTATATGCATAGCTTGATCTTTTTCTTTGCTTTCAGATGTGCTGATGACAAGAAAACAAA ACAAGTAGCTTCAATAAACGATCCTTAGACCAAATATTTTAAGTAATATCAGAGTCGCCAA TCTCTGTCTTCTTTTAAATACTGCAGCTACTTCTCTTTAGGGATATTAAATAGAATTATCT ATTTTATTGCTTATAATTTCACCAAATAAATTATTTTGAGCTGAATACAAAACGTGTTTTT CGTCAAGCTGTTAATAAAAATCCAACTATTCAGGGTCCTAGGAAACAAATATTCCTCTGCT AACCTCCGGAGTAAAAACTAAGCAGTGTCTTGTAATGGTTAGCAAAAGCAATAACGCACTA AAACTTAGGTTTATATGTGACAACCTAATTGAGACTGATATGTCTACATTTCTTTAAGTTC AACCATAGTCTCAAAAGTGTATTATAATAACTACGCCCTGGATACCCCTATTAGAAATGT TTTATTTTCTTTTCTGATTAACCTTTTCTATGTTCCCTATTAAAATTCTTTTAGCGGCAGT CCAGTCTATAGCTTTAATAATATTCAATGTAGAATCAGTTCACGTTAATATAACTCCTTAG CAATTATTGCTCTAAAAATAAAAGATTGGGTTGGTTTTCATTTAAGAAATTATTAGGTCA TACTAGTTTACGTAATAAACTATTTCAGCAATTCCCTGTTAGCTCAGTCGGTAGAGCGTTC GGCTTTTAAGATCTTCCAAGAAGTCGACCGAAATGTCCAGGGTTCGAGCCCCTGATAGGGA GATTTTTTCTTTTGAAGTTTTTTTATGTTATATATCTAACTTACATAACCTGTTATCACAA AAACCTATAATAATAAATCGAATACAAGCTAAGCAAATGCAAAAATAGTTATTTTGGACGT GATTTTTTTAAAACAAGGACTAGAATAGTTAACCTCAAAAAGATATTGCCACGACTAAGAT AGATTAATTACTTCTAGTAAGTTCATAGCGAACATTCATCTATTTGTTTACCATGTTACCT ATTCTGAACCTTGGCATAGCAGCATTGAATGGATGTCTAACAATTTGATACTTTAAACTTC CATTTTGCCTTGTATGCAATGCCAAGTAGTCTAGCATGAAACACTAAGTTAGTAAGTGCTC CTTTCTCTGTATCTTGTTATGTGCACACATCCATCTCACAATATAACCCTTTTGTAACCAT TGAACTAGTTAGGTCAAAATGTTAGCCAAGGATACAATTCTTTATAAGTTTCTGAATGTTG TAGAAAGTTGAAACCCAATTAATGCCATTAATGTTTTGCTTAAAAGCACTTAGTTGGGAG TCGCAACTCTTGTTTTGATTAAATGCATTTCGGAGTGACATGGTATTTGGTATTTTTCTAT ATTATTGTGTATACCATGTCCATTTGAACCTAATTTGGTGTAGTGCAGGCTTCCCCTTGTT GATAACCTATGTGATAGGTATTTAATATATTCTAGTTTATAGTCAGCGTTGAAGGCATAT TCTACACTGTTGCTATGACTAATGCATTCGCTTCCTGTAAGAAAGCTCGTTGAGATCATCT AAATTTTCAAAAACGACATAATAACATTTAAATTTACAAGAACAGCGGTATTCGACTTTAA TTAAGTGTTCCCAATATTACCTGATCAATCAGAATCTTTACTTAAATAAACAGTCTATGGT TGGACATCATGCAGTGTACCTTGACACATAATCGTTTGCCCCACCTATGAAATCAAACATT TGAATTCGGCTCTTCACTTGTATGATTAATCTCAACCTAAAAGGCTTTATTGCTAGTACAC ATCGAGCTGCTTCTCGACTATTGTCCATATGCCATTAAGATGGATTTTCTGAAAGCCACTA TAGACAGACACTCGATAATAGTACCTCCAATCCAACATTGCTAACTGCAACAAAAGTATTA CGAAACATGATCCACCAGATAGCTAGTAAACTTTCCTCCCTGGCACCAATAATTCACTTTT GTTTTATCCTGAAGCTTTCGACAAATTGAAGTATTCAAAGTTCTCTTTTATAGCCAAATTC CTAGTTCTTCCATTGTTTTCAGATGTGTTTTTTATTGCCAACCTATAGAAAATATTTTA ATTATTACAGTTTTTGTCTAAAAAAAGGCATGAGTTTGATATATCTGCTTCAAAAAAGCGG | |

TABLE 7-continued

CENs sequences

| Sequence | SEQ ID NO |
|---|---|
| ATTTCCAGACCAATACTAGCCTTCACCCCCTTTGTACTTGCTTCAGCAAACAAAAATTAGA GTGCCATCAAGCTAAAAGGCTAAAAATTATTATTTCAAAAATAAATTACTTTCTTATACTA GTTTCTCAAAATAAATTCCATTGGCATGTTTGTGGCAGCGAGGTATCACTTTCCAAGTTTT TTTCAGTTCATATATAGTTAACTTTGAGTTTTATCGCACAGTCGTCTGCTTTGTGGGTAGCGT TATGCTCTTCTAAGTATATGTACAGCCCACATCATCATTAGAAAGGGAGCATTGAAATCCA TCTGTATGTTGTTGCATTTATCGGCCCTTCAATGCCGATACCCAAGTGAATTGTTTCAAAT CTTCTATATGATAGTTCTTTGTAAATGTAGTTGAATCACATCTCTCGGGGAACCCTTCTTT TGTAGTTCTTGTTTTAGCCATTCCTTTTTAATCTTCCAAGTCACACACTTATCGCCAGCCA TATATAGCATACAGACAGGAAACATCTTGCAAACATCTTCTATTAGGAGGGGCTAATTTTT GGATGTTTTAGGCACTTATTGATTCAAACTTACTTAGAGACGCCTTTCACCCATCATACTAT CCAAGTTGCTTTAGTACTTGTTCGTATTCGCAACGTTTTCTGCCATCTTGTTTCATAGACC ACTAATTTTATGACTAAAACCATTAATGGCATCCAATGAGCTAAAAAAACATGCCAAAGTA CAAACTATAGTTTCAAACGAAAATTAGTTTGTTTTACGTTTCTTTAAAATAACGCACCCAT TGGAAAGTCGTTTGTTTTCAATTAAAAAAATCGACGGTGAATTCAGAGAAAGCCTTTGAG AGCAAATTATTTTTGCTCCTGACCTTTTTACATGAACTCTTTCTCACGGATTTCATTTAAT AACTACTGTTACACAAAAGTACAGGACTACTCGCCGATTTCCAATCTTTCTAGCCTACCAA ACACTAAAATTCAACCATGGTCAAATGCTTCCAAGAAATCTGATTTCTTGGAAAATCTGGA ACAAGAAGAACGTCATGCAAGATTAGTTTGTCAGAAGCAATAACGTCACCTCTTTCCCTGT AAACACCAGCCTTATTGACTGAGTGAATAATTATTGGAGCATAACTTTTGTTGGATAACAG CTTTGCATCATTAATAATATGAATCAAAGCACCTGTGTCAATAACAAATCGGGTCTTATTA TCCACAAGTTTTACCTCACCATCTTCAGTAGGCCTAACTTCCGATGCGACCTTTTCATCTC CTTCTGCTAACATTCCACCAGGTACGGTTCATTTTCGACTTCTGACAAGTTCACAATGCCA GCAAAGTTGGCCGAATCTTCTTTGCAGAATGTTTCTTAGAACAGTTATTCAGGGCGTCCTT TTCTTCTGCACTTAGGGCAACAGGTTTTTTGTGATTTTCCCTTTTACCTCTACTGGCCAGG TCAACAACGGATTTTTCTGGACTTTCCAAAGGCTCCACCCTGTACTGTCTGTATGCATAAT ACATGTCTTTGACGTTTGCAGACATCAACTTCTTCCTTTTAGAGGGAAGATAAGTTTCAAT TGCTTGCAAAAACGGAGCAGCAACAAGTTTTGGTATAACTGAACAAAACACTGTGGCCGCT AATAGTTTTGACTCCGGGACGTGATGGGATGCCAAGCTAAGATAGTTTTCCAGATCATTCA ACTTGGATGGATTGTTAATCTTGTTGTTCAACTCTCTAAAAATCTCAATCTTAAAACAATT CAACGATGCTATCTCATGGTTCAGCTTAGAATAAAGGGCTAAGCCATATTCATCTTCAAAC CTTTCATAGACATTGGATTCAAAATATGCTTTAATGGCGGCTGATAAAACGTTACCAAACA TGTTTGGTGGGACACTAATATAAGAAACATTGGCCTCACTGTCAGTAAAAAATAGATCGAA GTCGAAAGATGGGATTATTGTTAGAAGCGTTTTAGCACATCACATCTTAAAGACAGGCCAA TCCAGTTTATTCTTACTTTTAGTTCCTTTCGGGACTGCAAGCTTAGTGATGCATTTCTCAT ATGTTTCAAAAGTGACATCATTACTGATGACAGCAGTATCATCAATAATTTCAATGGTAGT TGACATTTCGTTAATGATTGGTAGGTAATAAATATTGGAAACTTGTGAGAAGTCCTGCACC TTCAGTATAAAGTTAATTATTAGATGAAATCTATTTAAAAAGCTACTTGTAGAAAGTTTGA ATGGAAAAAGTTTTACAATTACGTATATTTTTCCCCGACTCCCATTTTCATTTGCATTTTC GGTTATACGATCCTAGCAAAAGATGACCTGAAGGAACTGCACCATAGAGTTTACCGTTGCT TAGGTTTAAGGCAATACTAGCTTATGACCTGCAGTAAGCTGTAACCTCTGAAAACATGCT CCTTTAGATGTATGGATATAAGCCTTCATTGCTATTTAATAATAATCAAAAAAAAAAAAC AGTGAATCTGCTTGCTGGGCATTGCAGAAAAAATAAATGGTCATTTTAGGTTGGAAAGCCT GAGGAGTGTGTGTATTTGATGATTGCATACGCGGCAATACCACTATTAATAAGCACTGATA ACCATAGCTATAGCGGTTGTGGTAGTGGGGTCAGTCGCATAATGTTTTACGTAGTTAACTA GTCTTAACTGGAATCTTTGATTGCCAAGTGAAATTACACTAAATCACACTTTGTTCACTTG GTGAGCATACAACCCTACTGTAGTCCCCTTAAGCAGTGAAGAAAAAACAAAACAGTTTATA ATGAAGCTGGGTATATATAATACCAGCTGGAACGCTGAATTTCACTTTATAAGTCACGAAA TTTGGGACTTAATCATGCAGGAGCAGCATTCGTTAGTAAAACAAACTACGATCTAGTTAAA ATACTATGTAAATAGGCCACATCTGCAAAAAACTTTATAACGTGTTTATCGCAGGTAGTTTA TAAAGCCAGCATTACAGTACTTTTACCCAAATACCCCTTTTTATGAAGAAATTCACCTACAT ATACTCTTATATGGAATAAAAATTATTTTTACATTGATGTCTACCATGATGAATAGTGGCT TACAAGGAAGACTTTTGTACAAGGCTTGGTTTATCTTATCGTTTCGTAATTGAGAAAATTA GAGAATACGCACTTTTACAGTAGCGGTCGATATTATTGACTGGCTGCAACAGTCTTGGACC AGTTGATCTAATTTACTTAATTTCTCATTATTGCAGGTTTTGTTATGGTTCTTGACATAAT TATGTATCATCCTTGAATACAATCAGTTAATTTGTTCCCTATTATTTCGAAAGTATATAGA AAAGTTACATATCAGTGATCTATGATTTTAAGTACCATTACTAAGTCATTCTAGTAGTTGT CGAAATGAGAAAAGTCAAATTTGATAAATCGTGTCACTAATAGTGAATGACTCTAGTAATA GGTACAAGACTACTTGAACTACTAAATGCTATTGAACGTTCACAAATTAATGCAATGTGGT TCGAAGTTATCAGTGAGTGAAGAAGCAAGCAAGAAGAGAATCACTATGGTGAGAATCATCT TCCAACATTTGTTTAAGTTGTTTGTAGACTTTTTTAAATTCATCAAGTAATGATTTAGAAA CTAGTATTGCTTCTGAAATTGTATCCTGTTTACACTTAAAGATTCTACTTTTGATATCCAT ATTAAAGTTATAGGTTGAAATATCATTAAAAAAATTTATGTAGAATAGCATATGGAGAACA CGCTAAGTAAAAAATACTAACCGGATTGGACTCATCGTGATTGGTGAGGGTATTTATTGT TTGATTGGCTAATGCTTTAATTACCTCTTTCAACCGATTTCCAAATCTTTTTAATTTCTTC ATATTGAGATTAGATCATAGTATCAAAATACTGTTAACTTGCTAGTGGCCTATTTTAATTT GAAATTGATAAGGAACAAACAAGTAGATCACCAATGTAAGAGAAAACATTAAACAGATGTT CTTGGAGAACTAAGGCTTAAAGTACATAGGAGAGAAACGTGCAATAATCAGTCTCTAAAAT ACGTACCAGCAACAATTACAAAATGTGACGGACTTGGGGTAACGTGTCAAAATTATTTCCT TATTTGGGATCTTTTAACAGCTGAATCTTTTTAAAAATAATCACTAACCTTAACAATAGCA AAAACAGTGTATGTAACAATGATAATTATGATACACGTATTAGTAAGTACGCCATAGGTGT ATAATCACACGAGTAGACAATGGGTGTGGTGGAACTTAGTTGTAGTAGAAGCAGTAAATAG ATCTCTCTCTTCCGCCTTTTGCTGCTTTCACTCCCGATTAGGAGCTTTATTGTCTATCTAC TTGCACTTCCTTTTTCGGGACACATTCTGAAAAATCCCTTTCACATTATGAAAATGTTGCT GGTGGTGCGTATTTTAGAACCTGATTATTGCTTATTTGTATCTTATATATTTTATACACTA TTTCTCCGAGGCAGCTATAGAATGTTCCCTCTTTATGTAGTAATTGTTTAATCTAAAAATA | |

TABLE 7-continued

CENs sequences

| Sequence | SEQ ID NO |
|---|---|
| GCATTTTGAGGGATTTAATTATCTCCTAGAACTTCTGTCTAACCTTCTACAATCTTTTCA | |
| ACCTTCCATATAATTGCCCGATTAGGAAATAGGGAGATGGTCCTTTATCTGATCTCTTATA | |
| CTACCCCGTCGCTTTAGAAACTTCATCCCGAAGTTTATTATCTTTATCAATTGCTCTTGCA | |
| TTATCCCATAATGTTTTCTGTAAGTCTTCTGGGATCTCTAAAAATAATGAAAATGGGATGC | |
| TTGAACTATGACAAGGGTCACAATCTTTCTAGTAGACATCCAATGTATCGTTTGTTTCATC | |
| GATACCAGCTATACCGATAATCTCGGTCAGTCTACTTCTTGCTTCAGCTATCATTCTTGGG | |
| GGTACCTTGGGAAACTGTTTATCCGCTTGTAAGGATCTTCTAAGCCATCTGACATTGATTA | |
| CTCTATCCTTTTTATTCGTTTTCGGTAAATCAACTTCGTAGGCGTTGTCTGATATCTTCTT | |
| GACAACCTTGTAGGGTCCGTAGTATACCGGTTGTATTTTGTAATACAATCTATCACTACCG | |
| TATGCATCTTTGTGCAATAGTATCCAATCTCCAACTTCAAATGTCTCGTACACTCTCGACT | |
| TATTATGCTGTATTTCCTGGCTTCTTTGCGCTTCAATCATGTTTTCTTTCACATTTTCCAT | |
| GATGACTTTCATTTCTAATGCGAATTCTTCAGCTTTATTGCTGTACCTTCTACTTGAAACA | |
| CGACTGCTAGAAATAAACATTGGCGAGTCTGGTAAGTAACCATAGCAAACTTCAAATGGTG | |
| ATGAACTTATCGAGACTTGATGGGAACTGTTGTAGGCAAATTCGGCCATTGACAACCATTT | |
| GTCTCAACTGTAGAGATCGTTACTCGCATAATTCCTTAGTAATTGGTTTAAGATTCTATTT | |
| TTTCTTCCACTCTGGCCATCTGTTTGAGGGTGATTAGTGGTTGAGAAGAGTGATGATGTAC | |
| CAAGAATTCTATGTCATTATCTGAAACCATTCTTTTTGGAATCCCATGTAATTTAAAACAA | |
| TTTTCTACCATCAATTTCGCACATTGCTCTGCGGTTGCAGTTTTCCTAGTGGGGATGAAAT | |
| GTGCCATCTTCGTGAATCTATCCACCACTACCAAAATCATATCGTGTCCATTTTTGCATCT | |
| GGGGACACCTTTGACGAAATCCAAACTGATGTCTGTCCATCTTCCTTCAGGAATTGGAAGA | |
| GGGGAAAATAATCCTCTTTGACCAGTTGTCTCGGGTTTGGTTTTCTGGCAAACCGTACATC | |
| TTTGACAATATCCCTTCACGCTTTTTAGCATATTTGACCAGTAAAACATAGGGTGAAGTCT | |
| CATGTATGTTTTGAAATACCCGAAATGACCAGCAGAGTTACCGTCATGAGCGTTACCAATA | |
| ATTTCCTGAACCAACTTAGACTTAGGGGAGACTACTATTCTTCGATCATTTTCTCCTTTAA | |
| CCACCAAGAAATATAATAAATTATCCTCAATTGAATAATGTTTAGTGTAGTTATGGATTGA | |
| CTTCGGGATCGACAAATTTTCTTTTAAAATGTCGTATATCTCCTTAATTTCGTTGTCTTCT | |
| TCGTATGACTGGATAATCCGTTCTATCACTTCATGGTTTGGTGTTAACACCTATTTTATTG | |
| TGTTGATACTAACTTCATTTTCCTCGTCTGGGTACCTAGACAAAGCGTCTGCTACTGAATT | |
| AGTAGGACCTCAAGTATTGAATTTTGAAATCGTAATCAGCTAATCCTAGGAATGATTGAGC | |
| ATCTTTGGCATTTTTCGGAATTGGCCAACTCTTGATTTTGTCTATCTTAGCAGGGTCAGTC | |
| TGGATACCTCTGCTTGAAATGAGATGTCCTAAGAAACCTAAGGTTTTGAAGTAAAATGAGC | |
| ATTTCTTTTCTTCGCAATCAGCTTATTTCTCCTGAGCAATTCCAATATTTTTCTAATGTGA | |
| CTGTAGTGTTCTTCGACAGTCTTTGAGTAAATTATAATATCATCCAGGTACACCTGAACAA | |
| ATTGGTTCAAATAAGGTGCTAGAATCCTATTCATCATTCTTTGAAAAGTACTAGGGGCGTT | |
| GGTTAAACCGTAAGGCATCACAACCCACTCGTAGTGACCGTAATCTGTGGAAAATGCTATT | |
| TTTTCAATATCATCTTCTGCGATTCTGACCTGAAAGTAACCTGACATCAAATCCAACTTGG | |
| AAAATACTGAAGCTCCTCCAAAAAATGTGATTAATTTGTCGATTCGTGGTATTGGGAACTT | |
| GTCTTTTACCGTATTGTTATTCAGTAACCCATAGTCAACACACATTTTCATACTACCATCT | |
| TTCTTCTGGAACAAGTAACAAAAACTATTGAAAGAACTAGGGGCAGACTTGATAAAGGCT | |
| AGTTTCAACAGTTCATCAACCTGTTTATTCAGTTCTTGTTTCTCTGAATAGCTTGATTTGT | |
| ACTGGCGTCTGTATGTACTCTTGGTAGGTTCAATGAGTATAATTCTGTGAGTCAAATCCCT | |
| TTGGGGAGGTAAACTGGTGGGTTGGTCATTGGTCACCACATCTCTAAATTTTTCATGAATT | |
| TTATTTCTAATTCCAACAACACCACCGTAAGGTTCTTCTAAAACATTATTATTTTCTTTTT | |
| CTTCAACTGACTGCACAAACACTAATAATGGATAATTATCAACATTCTTTAAATTTCTTCT | |
| GACTGCACGCATAGATTTAATAGCTATAAGTTCATTTTCTTTTGTTTCTTCTAAGTCATTT | |
| CCGTTATTTAATTTTATTTCTTTTTGATATCTGGGATTTCAGGAGTTTCCGTTTCCTTTTC | |
| GATATTTTCCCAGTCAACTTTATTTCCATGATCTTTAACAAATGGGAAACCTAATATCATT | |
| TTATGGTTGATATCCTCTAAGACTAAGAACCTAATATTCTCATTTTGCCATTCGTCTCTTA | |
| GCTTGAACTACAGTTTTGTTTTTCTACTGAAGGTAGACTTGTGACAATATTGTGATCAAC | |
| TACCTTTATGGCCTCTAATTAGTTTATTTTCTTTGGCCCGTTTTTTACCACCATAACCAGC | |
| ACTATATAATCTAATAAAATTTTAGCTCCATTTAAAACCTTCCAAGTTCCGACCAAGGCAT | |
| AATCTGTACTTTATGTCGAGAAAGATAATTAAAACAGTAACCAATAAAACCACAGCCCTCT | |
| TTATCAGTTTCAAAGATGCCATTCAGGCCTAGTTAGCTGATTTATCAAATTCAGGATTTAG | |
| CTATTTCTAAATTTTGATAGTAAAGTTTATATTTGTTTTTGTTTAAAAGCGATCCCGCATG | |
| TCTATTTAGCTCAGTGTACAACTGATATTCCTGTAACTGTACCAGGTGATTTTGATTTCCA | |
| TTGTCCTTCATATGTTCTTTTATATAGGCTCTTTCAAAAACGGTTCAACTGATAACATCAC | |
| GATGGATATCTAAAGTGGAATTAATAGATCAAAGCAAGAGAGGATTTCCAAGGAATAGGGC | |
| AATTCTAGTATAGGAAGACTGTGGATTGTCGAGACAAACAAAAGTTGAGTTGTGAACCTTT | |
| TGTTTATGAGAAGTTCAATTCGCACTCCTTTTCTTTACAAGCTTGGGAATTCAGATAGAGA | |
| TAATACCTACATCTACTGAATATTAAGTGAACCAAAAATCACTGTAACAGCACTCAGTCAA | |
| CTAAAGTCGACTGTTTAAGCTCCTCTTTAGAAAGCCCCACTCGTCTCTAAATTAGTTTCTA | |
| TGCTATAAGCATCAGAGAGCTCCTCTAAGAATGTAAGAAAAGTGAAAAGCTTCTTTTGGTC | |
| TGATAGTTTTTTAATTAAACAGTTCAGTAACAGAAAAACTCGTTTTGAGCTTTTCCTTGTT | |
| AATCCACGACTTTGGATATACATTATATGCTAGGTCCTTTGTAATAACAATAGCTATT | |
| TTGGCATCGAGTTGTACAAGTTGACATTTCGTTTTATGTTGCTATTATTTAATAATATTAA | |
| GTGTTTCTTATCAAATGTATATAACCTTTGTCGGATGAATAACGAACCAAGTTACAAACCT | |
| AGCAATTGGACTCTTTCCGCTAGCCTTTGCTGGTTGACTTGAGAAGGTAGTTTTTCATGAT | |
| AAGTTGCACCCTGGCCATCTCTATGAAAATCAATATTTCAATAACTTATATACACTTATA | |
| ATGAACGCGCATTACTCAGACAAAGAAACAAGGACTTCTTGGAATTCCAAGTTGTGGTTGT | |
| TCAATTGAATCTTTATGTTTGACTTCTTCTTTATCCGCTTTATAGAAAACTTCCTGGGACA | |
| ACAAGGTTCGAACAAGAACATGAACAAGAACATGAACTTTTGCTCAATTAAACCCATTTGC | |
| TCTAATTCATTAATGAAGTGAAAAATAGGATTGGAAAGGTTTTTCGCTAGAGAAATCGCT | |
| TTTCTCAGCAGTCTTAAGTATCTGGCAATCACTGTGGTTCCCTTTGGTTTCAAAGTGTACA | |
| ATCGTTACCTCATAAAAGTTTTCAGTATGAATGAAATGATGTTTACTAGGGAACATAAACC | |
| ATTGGGATCTTTCTAGACTTAAACTGCCTTTTAAAAGCTGGGCCTTCAGAAACGATTCATC | |

TABLE 7-continued

CENs sequences

| Sequence | SEQ ID NO |
|---|---|
| ATAGGGAGTTTTGGAGCTTCCTTGGATGTGCTCCTTATGTAAACTATTCCTTAGTTCTCAA AAAAAAAAGCAAAAAGAACTGTAGTGATTTAACATCATCTGTAGGAATCTTTAGCTACATC TCTTCTCAGTTTTGTTCAATATGACTTTGTTTTGGAGATTAGCCTGTTTCTAAAAGTAAAC GTAGTTATGTTTCAAGGTGCTTTAGACAGCTTAGGGAGTGGATTTTCTGGAGATATGGCTT GCGCATGTCATGTGCCGAGTAGTCACCACGGGTCACCTCCTGGAAAAGTATAAACACGATC TCAAACTCGATTGGTTCTGAAAGGTTTTCATATGATAAGCTAAAAAATGGTTTTCGCGTTA AAGCTAGAATTGTCTGATTTCCTTCATCGATGTGAAGTGATCCAGTCTGACCACGCATAAA ATCCGGAATGGAAATCACACCAAAAGATGAGGAAATATCCAATTATGCTTAAATTGTCAAC TCAAACACAAGATGTCGCAGCAAACATTTGACGGGCTTGTAGGCTTTAAAACCAAGAATTC TGAAATAAAAACAGTACTAATTAGAACTTTATCATGAAGACACATGTATCATTTAATGCTC GACACCAGGTGATGACAAACAGCACCTCTCTGGTGAAAGGGATACAACAGTTCTGCCTTAT CTATCTGAAATAAAGGTGGAGTTTGTATTAGGAAAGAAAAAACATCGAGTTTATGTTGAT TCCTGATATTGTGAATGGAGTTGTACAATTTGATTAAAAGCCAGGTTTGAGTAGCATCCAA CTAATCTCTGGTGTGGCTATCAAACCAATGTGTTTTTGGAATTGATGCTGCATTCAACGTG TCAACATGCCAAGATTTTACGGCAAAAAACTATCAACCCTGAAAAAGATCTTGGTTGTGTG GGTGTTGACATATTGACAAGGATTGGGTGAGAAAGAAATAATATTAAGTGTAAACCGCAGC AAACAGTTTTGTCTCTCCATCATACACTACATATTTGATAATGTTTTACTTGCCAATGATG AGGATATATTTGACAGTATCTATTATATCTTGTATGAGGCGAGATGGAAAAGAAAAGACTA TTAATCTAAGCTTTGACAGTATGTTACCTATATCGTTAGGGGCTGATATCGAACCAGTCTT TAATGTAAAAACCTTACTTTAAATTACTTAAATTCAAGAGATGGAAGAGATGGAAGAAACC ACTGGAAAGGCTGAGCTTGATCAGACCAATTAAAAAAGACGGATATTTATCTCAGACAACT GACACTATACTATATAGAACACGGGATTATAGATGTGCTTAAAAACGAAGTAAAAGATATT GGGTACGAGCAGTTGTTGAGACCAAAGACGGCCACCAGCATCCATCCATTGAAAAGTCAAA ACACTCAAAAGAAAAGAGTTACTGGTATTAGAAGCAGAGATTTATTTGAAATTATATTGTT GGAGCCAAAGTCTATAGTTCCAGATCAATGGAAATTGGACAGTGTGTTTATTGGGTATAGA AAGAAATGTCTTATTTACGTCTATAATGTTGGGTTGTTCCCTGCCATAATTTGGTTGCTAT CGTTAATATTAGTCATTGTTAAGCAGCATTGCTTAAATATACTTTTTCTATAACTATATGG CGGTTTATAGTACAACATTCTAAGGATTCTTGAACTTTGGAAATCACCTCTGGAGCTTTTA AGATGCATCAGCATGTCTCATTCATCTGCAATATATCATGTGACCATGCTTTATGCTCAGG GAGAGTAGGGTATTTAGGATTTGATGAACCGTATAGAACTATAAAATTCTGCAACTATTCT CATGTTATATGCTGTTATATAAGCTCTACAAGTACAGATAACGCGTTTGCTTGAATTTTGT TCGTGCAGGAGTGTTTGTTATTTGATTAAGATGAGAAGAGAATCTATTATGTTTATCCTAA AGTTAGCCTAAATCTCGTTGCCCGAATGTTTACCGTGTAAAAGCTACTTTTTTTTACCACTT GGAGCATCATTTTAGGGTTGTTCTGTAAGCAGCTTAAGGTTATGTAAGGTCAAGTTTTTCT TGCCATTAGGGGACTTAGAATTGTTGAGAGTTAAAGAAGAAACGTAGTGTTATGTTTATGT TGAGAAATTCAACATTGACCTGAAAAAGACCCTAGTACATTGACTTACATAAACTAAACTA GATCATAATCGACAACGTTAGCTGGGAAGTTAGCTAGATTTCAACAAAAAACTTAGTATAA ACAATAAGTAAACCTTATAAATTATTGTTTTTTGCTCTCAGAGCAAATGGTAAGTTGCAC GCCCTTATACATACGCAAAATACATTAAACTCTTATAGAAAAAAAAAACTTGTGCTCTTAA AGGTCGGCCTAACAATCTTGCAAATAGCTATTTGGGCCAATAACACAACAATGCTCTGATA ATTCAGAAGAGTTCTGGTTGTTTGCAGAGGACTAGCCTCTTAATTATCAAAAGCATTTTGC CTGTTATTGTGGAACAATCATTAGCAATGTAATACATAAATCCTTTTGTTGCATTCTACTA AATTAAGCTGTTATTCACTCACATGACTCTACCCTTAGCAGCTGCTTGAATTCCATGTGTT GGATTTTCTTAGTATACGTTTCTACTAACTTCAGCAACGTCTAACCGTTTACCCTTATGCT TTGCATCAAATGACGGAGTCTCTGCAGCCTTTTCTGGATTCAGCTTTGGACTATGTGATTG CTGTCCCTTATGTTCCAGTTTTTTTCTTTTCATTTATTTGTTCGTTACCTACCCGTCCTTG AGCATTTTCATCAAAAGAAATCCGTGTGTGACTATTCCTCTTATAGTACATGATTTAAATA TATGAGACCCCCGTTAAAACAGCACTGTCTAAAGGATGCTTAAATAATAGATTCTAATCAC CAACTTGTTTGTACTCTCAGTTCAATGGTCCCTCTATCAGGGCTGACTCACCATGCTTAAT AAACATAACGCTAATTTCAACATTATCCCACACATTGGAGTTTTTTTTCCATCAAAAAAA TAATATATAAATAGCTTTCTTAGATTAGTGTATTCTTTTTCGCCTAATATTTGTGATGAGC TAAAAGATAGATCGATAAGGTCTAGCAAGAAAAGAGTCATTTAGTTCTCAAAGGTAACTGT TTTTTTTTTTCATGTCACAATGACCAATATTTAAAGTCGCTGATCTTGAAATTGCAAAAAA AAAAAGAAACACTATTCAACTAACACATACAACCTTTTTGTACATAAAAACAAGTAGCTTT TTCAAACAGCTACTTAAAATTCAGCTACATCGTGAAACTATTGGCTTTTCAGCTAGTTTGG TCCGACTGGAAACGTACGTCCTTTATAATTTTTTGTTGGACTTTTCTACTGGAGAATCTGA ATTTCGAGACCAAGTATTTAATTATATGTCCAAAAAGAACGTAATAATCTGGAAGTACGTC TTTACTACTCAAATTTTCAAACTTAATTTTACTGTGTGTATTGGATGAATCTTCCATAAAT ACAGTACTTTGTAAAACTAGAACTCTCTAAGATCCTGCATTTTCCCAGTTTAAAATATGTA CGGGTTGAAAACAGAAGAGTAATAGCCGTCTAACAAACTTTTGATATCCCTAAAGAAAACA TTTCTACGACAATATTATTTGTAATATTGGATAGCTTCCATTTCCGATCTTTTGCCGCACG AAACTCAAATCAAAAACATACAATTTTTGTAATGCAATAATGTAATCTTGATAATTTCTAA AAAAAACACCCAAAAGGTTTCATTGATCCATTCTGTAGGAATAAATCAGAAAAAAACATGT GCTTCTTTCTAAACTTTATCAAAATATTTGTCAAGCTATAGTTTTTATAGACACTCTTCTT TTTTCTTTCTCTCCACAGTCTAATCTACCAAACATTTTCTTAGAGAGTTATAATAAATGTC AAAACTCTATACAGACAATTATGTATGACTGTTATGCCTTTTCCTGAACTTATTTAAACAG TATGTTTCAGAAAACGTTTTGCGGCAAAGTCGAATTCGTGGTTCGCTTAGTTTATATTTCA TGTGGAAGTCATGTAAGCCTCTTGTTATAGGATAGTAAACGCCGGCTGTTTAAACAGGAA GGCTATAGCTTAAGGAATATCGTGCATCCATAAAATCATTTCTGTAAGGGCTCATATATAA GAAGTTGACGTCAACGAAAATCAATCAATAGGTGCAAATGGAACATTACGAAGTGATCTA TCGACCAGCAAGAAAAGTTTGCACCTTATGAGTATCCGGCAATTTCTCGGATTTTCATGTT TAGATCTCGTTGCAAATTTTCACTAAAGAGTGCTATGTCGAAACAGTGCTGAGGGTAATTT TTACAATTACCTAGAGGGTAAGATTAGGTACTAAGATGTGATGTCACTTTCAGAAATAGTG CTCACTTAAAGTTGTGTAACTGGCGATGGTTTCATTCGAAGCAAACTATAGTACATGTGCA TTTAAACCAGAAAGAGTACGATTCTTTTTAACTTTTGAGCATCTTTCATGATTGATCCGGC | |

TABLE 7-continued

CENs sequences

| Sequence | SEQ ID NO |
|---|---|
| ATAGTTTCGTTATCAGATTCAACACTGTAGATAGTTAACAATAGGCCAATTTCAGGATCAG TATTCATTTCTGATTGTTTGACAGCTATATTAAGACCTATGTTCTGAGTTAAGCACAGAAA TAACAATTAAAATTTATATCAGCATTAGTTATGGAAGACACCCTCAGTCATCATGGCACCA AAACAAAGATTAATAAGAAACCAGTTCAACTCCAACTGAATCTATTGATATCGATCTATAT AATTTGTGGATTCTTTTTAAGTTATCCAACTGCTGGACTAAATATGGGCATCACGTCAGGA ATTGTGCCTCTTGAACACCAGTTTTTATAGAATTTACAGCTACTATAAATATCTACATTGT GGCATAACGCTATTCCTTAACCACTGTTCTCCAATGTCAACTCATCTAGTATTTTTTATAT AAAATATCATTTCTTATTTTGTTCGCGCTGTTTGCAAAGAAATTTGTTTTACTATCATAAA ATTGATTAATTTGTCTCCCAAGACCTTTTACATGTATATCATTACTATTAATGTGCTTATT CGATAGTTATCCGCATATATTCTGAGTATCATCATACTTCGCTGGAAGTTTTCCAATATAT AATTTATTTTTTAGGTTCTATCGTTTTATTTACATATATATCAATGTTGTTTATTTATTGT TGATATTGAATAACTTATAAATCCATTAAAAAGGATATTGCATAATTCTCACTATTTGGTT CTCAATGAACAGAACTTATAAATATACTTGAAGTTATTGTTTTAGTTTTCTGTATACAGTA ACATTCCTAAATTCATTTAGTAAATTGAAATTATGCCATAAATAAGTTATCGACTCAGAG ACAGCTTTATAAAGATATTCCTAATCCTCTTACTAATAAAACAAAAGTTGCATTCACTATT TTTCTGGGAGAGTCTGATTCATTTTTGTTTTTGCTCAGGAAATTTAATCGTGTTATAATAT AAAAGAAGAATTTTCCTCAAGAGTACTCTTAGACATATTTATGGAGAATGAGTTTGTTTGC CTGAATGGTAAGTAGCTAAGAATCTATACTTTTTTCAGGGTTTTTTTATATTGACTTAA TGATTGGAATAATAAATCAGATTTGTAAAAAAATTGACGGAATTAGTTTGAGTGGCTTCCC ATGTAAATATGCTCTCTATCAGATATATTAAACATGAAAATTTATTATACCTCATTGTACT CTCGACATTAGTTAAATCTCCAAGTTCTTCCTGGCGCAATATATTTATATAATCATAATGG AGCTAATGAAAAGAATCTTGCTCAAGCTTGCTATCTATTTTTTGACTACTGGATTTAGCGA AATATAAGGTTATTGCTTTACAGAGGCCTTTACAAGATGGATACTCATGAATATTAAGAGA AGCTAGATTTGCGTACTTTATTAATGGTAGAATCTCTTAATAACAAGTATTCTTTAGTGAT GAGCTAAATAAAAATTATACGTCAAATAAATGCTACACAAATTTAGTTCTTGAGAGAATAG GAAATGTAGAGCTCGAGAAAATCGCATGAAAAGATGAAAAATGTTACGGTTGTTTATTAAT CCCATTTATTTTTGGGTAACTGTTTCTTATTTTCCTAATATTACTAGAAAAATATAATCCA GAAAGATGCTTTTGAGTTGGTTCCAGCCATGGCATCAAATATCGAAGGATTTTCTAATTAG CTCTATTTGACTAAAGCAAAACGAGAAAATACTCATCGTGTTTGTGATAGATGAAACACCT ATTTTGCTTCTATTGTATTTAAGGAAATTAGAAGGTCCACTTCAACATCTAGTTGGGCCAC AACCTTTCTGAATAATGCTTCTTTACCTGGTACTATAATTAGCAACCTTATACGGAATCTG TTAATGCGCACGTGCCCGAAACAAATGTGTCAATACATTACCTTCACTTATACATTTATA TTTTGTGCATGATATTTGGTTATATCTTCTAGTATCTCTTTAAATAGTTTTGTTACACCCA AGGTGACTGAATATTCGTACCAAACAGTCCTCTAATTCATTGCTTGGGCTTCTAGACATGT CGTATGAGTCTGAGTAGTGAAAACATACGATTTACAACCCGCCCTTTACTATTTCGCTATA CACATAGGTATTGCCTGACATTATAGCATATGTCGAAGTAAATATTATGGAATTTTTGTAT TAATAATTTTTATTTCAAAGTAATGTGATTTTCTAAGAGTTTGGTCAACAACGGGATCAA CAAGTAGTAAATATCCAAAGTGCTACTTTTCATTAAATTTTTTTTTTCCATTATTGACAAA TCTTTTTCTTTGCACAAACAGTTCCATTTTTAAAGCATCAGGAGCAAGAACTCTTTAGCCG CTGCTTTTCAAGAGGCTGCAGGAATTTGTTAGTGTCCTTGTTCAAATGAAGAATACTAACT TCAAACGAGGAGACCTAGTTCAAAGAATTACTATTATTGAAATTGTTCAATATACATAGCT TTTGCCCTTTATATCGTACTGTACATTTGCAAAGTTTTCAAACTAGGAAGCAGACCGTCTC TTGACTCTGTTTACAAAACCCGAAGCTATCTTTTTTAATTTTCCCTTTATGCGTAATACAA AACCTGGAAAAATAACGAGAAGTTTTTGCAATATTCGAAACTTTGCAAATTAACCCGGTCT GCAATATTTTTGAGCAGCTTTTCACTGTTAGCTTTACTCTCTTCATTTTTGTAAACATAA TGATGTCTTTAATGACTAGAAGGGGAACTTGTTATTATCGTAGCGCCACTTATCTCTACTA TATTTCAGTAGTGAAACTTTAGCCAGACAAAATTGTCCTAAACCTTTGGGATTGTTAAAA TCCCCTTTGAATTTCGTTTAACTATAAGTAATTATCCGAAGTCTACATTTACTATCATCCA TTTTTATATTGCCAAATACTTGATAGAAACTATAGATAGCTATGAAGTCTTCAACAAATCG ATTTTTTCCTCATAGCTTTCTTAATAACTTGCTGTTATATATTGTAATCCCAAAATATGAA ATTGTTGATTATAGCGCCCAGCTTCAAAGCCTTGACAAAAATACTGGAAATGATGCGTAAA CCATTGAGCTTTGTTTTGAGAATCTTCTTTTTGTTCTTTAGAATAAAAGGAAATAACTGTT TATATTATTCTTAACAGAAGGAAAAAGAAAGAGTTGTCAACGCGTACATATTTGTATAATA AAAGCTCCTTTTCAATAAACGTCTAAGGCGGAACTGATAGTATATTCATGCTTGAAATAAT TACTTTCGGGCTATTTCCGTCCATAAAGCGTCTCTAGAGGCCAGCATTTAACTTCTTATAA AATCAAAAATGGATTACTCTTACGTGATTTAATCACCAGCTCATGGAGGTCTTTTTTTTCA ATTGGGTGCTGTTTAGTAAAAAGTTAAGTTATATTTCCAGGCGACTTTAAGAAGGCTTCG CCTACCAAACACTAACCAAAACAAATAACAGAGACATAGACCAGCGGTATTCTCTCTTTTG CCTTATGCGTGAATTACTTAACCTTGCCTCGATGTAAGCTCTATCATTTTGAACATGTTTT TTTATGTTTTTACACAGACCCAATTTGATAAACTATAACTATATGTACACTTTATAAGCCA TTGATTTTAGTGTAAACGAGATCGAAAAAGAAACAGATGCTCCTCGGTAATTTCACAGAAG TCAATATCTGTTTTTTTTTGTACAACAATCAAGGAAAAAGTGGTTCACCGGTTTCAAATG CCAAATGCTAGAATTTGAGCGCCGAGTTTCATATTATATGAAGTTAGGTAATTCTAAAAAG TCTTTTTGCAAAATTAAGTATAAGTTTCCAAGTACTTCGAAAATAACATTCAGCGGCGTG CAGAGACATTAGGTAAAAGTAGTCGTTTCTGGCCAATGGTATATATATTTTGATGGTTTGA AATATTTTCCTCGGTTGTTCAATTAGAAGAGTTGAATTGGGGTGTAAAACAGTATAACATA CCTACTGATGTTATCATAAACATAATTTCCAACTCAGTAATATTTGTTTTTCTAAGAAATA GTGTATGTTCCACTTACAAACTCGACTTAAACAATTATACTGTCGCTTAACAAAACCAGTA GTCTTTGAACTTTTTGCAAGGATAAAGTGTTTTTTTGGGAATATATTTAGACTTGAGTTTC AATGCTCTGAAAAAGGCTATCACTTTCCTATCAAGGCAGAGAACAACTACATATAGAGAAA CAACATAAGTTAATGAGCATATATCAGCATCTTTGATTTAAACAGCTCTAGTATTGGAAGC AAAAATAAAAAATATTACTGTTTTGTAGCCTATATAATGCTTGCCTACAAAATGTTTTCTG TCATAATTGTAAAAGTTGTTTCGAATGGGCAAGCTAAGTCCCATGCCTTTTTATTTACAT CAGGAATATCTTTTCCGCTTCTCTAGAGAACGAAAAGTCGTGAGCGTCATAGGTGCAGCAG AAAAATAAAAAGTCAGTAGATTGAGTAGATTTTTGTTTACTTTCCCTTGAGTACTTGCGCC | |

TABLE 7-continued

CENs sequences

| Sequence | SEQ ID NO |
|---|---|
| CACTCAATGAGAGTTAAAGCAACTGATCATGCTGATTCTGATTGTTAAGAGAGATAATTTA<br>AACATTGGTGAATCGAAATGCGAACATCATTATGAGCCAAATGAAGCCAAACAGACTTGAT<br>CAGGCAACCTGTCAAAATTAAGGAGTTAGTATTTACTAATGCATATGGTTGTGTTTATATT<br>TCTTAGCATTCAAAAAGTGCACCCGTCCTTGGATATCTAGCTTAGTAGACACATGATGTTC<br>CCTACAAGTATCAGATTATTGCCTTGCTTAATTTAGTTTTTATGTTGTATTATATAAGTTC<br>TTTACAAAACTCCATTTTAAATACTTCCACATAGATTTCCAAAGTAGAGTTAATACTTGTC<br>AATATTTCCTAGTAATAACAATATCTATACCTCTCATCAGATTCGAGAAAATAGGAACG<br>TTCTATGTATTATAATCATGATTACTTTGTTGATATCAAGCTTGTTCGTGTTCTTGGATCG<br>ATTTGGCATTGTGCATTAGGCTTTGACGTAGTGACAAAGCTGCTTGGTTGAATATTCTTTC<br>AGGCACCTTTCTTGCTAGAGTTTGATCACAGTCTTTCCACAAGACATCATAAGTCTTTTCC<br>TTGCCTGATTCTTCTGACCATCCACCGATACCAGTCATTTCGTTGATTCTTGCCAACATCT<br>CACGCTCTGTTCTAGGCGGTTCCTGGTAAATATTGGGGTTTTCTTTATAGTATTTAATCCA<br>CTGTACATTTGATTCACGATCCTTCAAATTAATAACCAGTAAATCGACTTCATAAGCATTG<br>TCGTTTATTTTCTTGACTAGTCTGTATGGCCCATACTATACTGGTTGAATTTTTATGTACC<br>TTATATTCACACCAAAGGCATCTTGATGCACTAACACTAAATCACCAACTTTATATTCAAA<br>ATATCTTCTTTTTCTATTATGGTGTTTTCCTTGTTGCCCTTGCGCTTTACAATATTATCCA<br>GTGTTTGCTGTAAAATCAATTTCACACGTCTCACAAATTCTTCTGCGTTAGGTGAATATTT<br>GTTATCCTCCAAATCCCAGCTATTTACTTTTTTAATCATGTTCGATTCATACCCGTAGGC<br>GATTTCAAAAGGACTTGCTTTAATGGAATCTTGGTACGTTGAATTGTAACTAAGTTCACAC<br>ATAGATAGATGTTCATCCCAGAATAATTGATCGTTTGAAGAATATTTCCGAAGTAACTGAT<br>TAACAATCTTGTTGACTCTTTCGGTTTGACCATCAGTTTCTGGATGATCAGTAGTCAAGAA<br>TAGTAGAGAACTACCATTGAGATAATGTAATGTCTGCCAAAACTTATTCATAAACCGAATA<br>TCTTTGTCACTAAACAAACGAGCACATGCAGCAGCATTAAGTCTTTTGTGCGCTGGTATAA<br>AATGTGCCATTTTTGAAAAGCGATCGACAACAACCATGATCATATCGTAACCTGTTCTCGA<br>TCTAGGTAAGCCTGTAATGAAATCCATCGTAATGTCGGTCCAGCGACCTGTTGTGATTGGT<br>AAAGGGGAAAACAACCCTTGTCTTCTTCTGGTGTTAGTGTTGTGCTGTTGACAGATATGGC<br>AGGTTTCTACCCATTTTTGATTTGTCTCAACATAGATGACCAATAAAAACTATCTTTAAGA<br>TTCAAATAAGTTTTCCATGCACCAAAGTGACAAGCATCTTTGGAATCGTGTGCATTTTTGA<br>ATATTCTATACGGTAGTTTCTTGTAGTTTGGAATAACTACTCTAAAGAAATCTTGAGACTC<br>TAATGTCTTATAATAACGTACCTCATCTTGATAACAGAAATGTTTGATATGATTTTTTATC<br>TCAACTGGAACTTTTGTTTTCTCTCAAAGTTCTGAATATCAAGGCATAATTAGTATTTT<br>TTTTATAACCCGTAATAATTTCTTTTTTAACTCTTGATTGGCTTCGATAGTACCTAGTGT<br>CAAGGAATGTCTCTGTGTTTCATCCTCCTCTTTTTACGTCAATTCCAGCAACGCCAATTCG<br>ATTTTGGCTAGCGTTAACCTGTTTTAGTGGTTGTATGGGTATCTAGATAACGCATCAGCAG<br>CGGAATTGTTTTTCCCTGTAAGTAACGAATATCAAAATCAAACTGTGGTAAAAAGTCCAT<br>CCATCTAGCCACTCTAGTGGAGTCTATGAGATTTTGGTTTTTTAAGTAAATTAAACTCTTG<br>TGATCCGTCATAACAATGAAATGTCTTCCCATGAGATAATATCTCCATGTTCTTAATGCTT<br>CAACAACAGCCATAAATTCACGGTCATATATTCCATAATTCAGTTGACTTCCAACTAGCTT<br>CTTTGAACCGTAAGCAATCACACCTCGTCATTTACCTGTTTCGTCCAACTGTTCTAGAGTA<br>TAACCTAACGATACTCCACACGCATCGGTATGTAGAACAAATTTACAATTGCCTGACCAAC<br>TTGGGTGCACCAAGGTGGGACTTGATATCAAAGCGTTCTTTAGTTGATTGAAGGCTTCGTC<br>TTGTTCACTTGTCCATTTACTTTGTTTTGTCATGAACTTATGAATTGGATTGGCAATTTTG<br>GAATGCCCTTTAATAAACCTTCTATAGTACGAAGTTAAACCAATAAAACTTTGTGCTTCTT<br>TGATCGTGTTTGGCGTTGGCCAACTCTTTACCTTTTTAATTTTCTCGAGAGCGGTTTGAAT<br>ACAAATTGGTGTAATAACATGTCCTAAAAACCTAAATTCTTGATAAAAGAATCGGTATTTC<br>GACTTCTTCGTGATTAGTTTATGTTTTCTTAGTGTCGACAAAACTTCTTTCACGTGCTTAC<br>CGTGAGTTTCAACATCTTCGGAGTATATAAAAATGTCGTCTAAATACACTTGGACAAATCC<br>ATTTATTTTTTTAGACAAGACATTATTCATCATCTGTGGAAAAGTCGCAGATGCACTTGTT<br>AGTCCAGCCGGCATTACCATCCATTCATAATGGCCAAAGTAGAAAAAAGCCGTCTTCTCGAC<br>ATCTTCATCCGCAATTCTCACTTGGTAGTAACCAGGCATCAACTCTAACTTAGAATAGACT<br>TTTGCCTTACCAAATCTTGAAATCAATTGATCAATATCTGGAAGTGGAAACTTGTTCTTAA<br>CAGTATTATTGTTTAGAATCCTATAATCAACACACATACGCATAGTACCATCTTTCTTTCT<br>AACAAATAGCACTGGACTGTTAAAGGATTTGGAACTAGTTTTGATGAAACCTTGTTTGATT<br>AAAACTTCAACTTGTTTTGTTAGTTCCTGTTTCTCAGAGAAGCTTATTGGGATTTGTATTC<br>ATGGGTTAGTTAATATTATCAGGGTTTTCGACTTCGTCAACATCAATCGAGTAGATAAAG<br>TGAGATAGGATTCATTTCTCCTAACTAACTTATTAACGTACTTTTCTTGATATTGAGTGAA<br>ACGCTCGATAGAGGTGGATTGATATTTAAACCAGTTGATTTAATGGCATCAACACTCATTA<br>AAAAAAAAAATTTGAAATTAATTTATTGACACTTAGTCAATAGAGTTCCCAATATGAATAT<br>CTGGTGGTCACTGACCAACATGTAAAGCGACTTAATATCACTTATATTAATAGTTTCATTG<br>ACGTCTTTTCCAAATGGAATAGCTATAAAACCAATAACAATAGGATTTTTGATAATTGACG<br>CTATTCGAGGATTACCAAATTAACACTTTTTTGCCCTGCATGATTCACAAGCATTTTAAC<br>ATCATTTCCTTTGTTATGACTATTATGTGAAGAATAGTAGAAAACTGAATTATTTATGCTA<br>TTAGGATTTGCTGGTGGCTTAGTAAAACTAAAAAAAACTTGAATTTCTTGCCAACTTAAAA<br>TTATTATAAGCAGCTTTTAGGTCCATCAGGAGCCATGAATTTACTATTTTTGTCTCGTTC<br>CTATTTTTTAAAGTTGTTGGACCTTGGTCTGCGAGGGATGCCATTCAAATACAGATATA<br>ATCAGGCTTGTAGACTATCTTATCTCTGTATCTCTCATGGAAGCGCACTAAAATTTCGGAA<br>ACGGAAATAGCACCTAGGGTCTGTTGTAACAATTCCGTATTCCTCATTCCTTGTTCAATTG<br>TACTAAAATATTGAGCAATAGTAGGTTTCTCTTCAGCAACATCGAAAATAGTAGATATAGG<br>TACCCTAAGTTCTTCCTGCGAGCTCTTCGTTGGTTGATCTGACTTTCTTCTACACATAAAT<br>TTGATGATTTCCGTTTCGTGGCTTGTTTTCGCAATAGAAACAAATGTTTTTTTAATTTAG<br>CTTTAGAATTGTGTCAGCATTCTTTCAGTAAATCTTTATCAGTTAATTTAGTGGGGGACCT<br>CTCAGAACCTTTTTTTTTTTCAGGGTGATAACAGCGCATATAACCTTCTTATCATATGAT<br>AACCTACAATATTCATAATATATTCTAATTTGTGATAACCATTCCATTGCCGCGGCTCTTC<br>CTTTTAACGAAAGCAGTTTGCTAACATTCAGCAAAAGTTATTTTTTTACTTATAAACATGT<br>CGAGCATGCCTTTTTCTCTTGGCTGTTTGTGCACACTGCAGCCTTAGTTCATTTTATCATA | |

TABLE 7-continued

CENs sequences

| Sequence | SEQ ID NO |
|---|---|
| TATTTATGTCTTCCTGGTCGTTGTGTTCTCAATATATCCCTCTACAATCACCATATTAGTT<br>TGGATGTTAGGAAGTTGAATTGTACTAACTTGTTATCTTTATCTAATAAGAAGTCGAACAT<br>TGCAGGTACTACGTACTTGTTGGTTAATCTTTAAATTTTTTTTCTTTCTTTTAGTTCATTG<br>TTTCTAGATCTAAATAGAAATCATTCCATTGCTGTTTGCATGTTCTTTTCAGTTTACTTAC<br>TTCCATCTATTATTCTTATTGGCCCATTCCATCTTCTCCTATTAGAATGATTCTGCCAACT<br>AGACTATGCAAAAGTACATGTAGCCTAGTAGTGGTAAACACGTATGACTTTTCACTAGGA<br>CCAGTTCATTCTTTTGCTCTTCTTCGTTTCTTAGTTATAGCCTCCATGGTTGACCGCAGAA<br>TCATATAACTTCAAGCTATGAAGGTAACGCGGCGTTCTATACAATACATTTTTATATAACC<br>CACTGATAGTTAAATACCTGCCTACAGCAGAACCATTTATGATATAAATTTTGGATCAGTG<br>TTTAAAGATGCTTTGAATGATCTAAAACTTATTTCTGCCAATCTAAATGAAAAATCCGCCA<br>TATTATAGTTGAGTGACAGCCTAGTCCTTAAATCGCGTCTTTAAGTTTCTTCACATTTTTT<br>GCCTTCACAAATATAAGCACATCATTTCACCGTATGTTTTTTGTTCAAAATACTGAGTCGT<br>GCTGCAGGGAATTCATCTACAATCCTAACAATCTAAGTTTGTTAACTCCTATATACTATTC<br>CATTCGTTAATTTTATTTATTTTTTCTAAAACATATTAGATGGTGCGTAAACGATGTTTA<br>TCTTAGTAAATGGCTAATCAAAAGTATCTTATTTGCATTGAATAGAAAAAAGTTTAGGAAA<br>TTATTTAAACTTCGTTCATAGACAAGCTATATGTTCTTATTTATGTAGAGAAGTTATAAGC<br>TAATTATTTTTTTCAGCCATTATAAGTTTAAGCATATAACTGTGTTGAAAGCCACTAAATA<br>AGTGATAAAAAAAATCAAAAGACCTACTAGTATACAGAGTTAATTCTACATTTGCTACCCT<br>AATTATAAAAGAAACTATCGAGGTATTTCTGTATTTCTTCTGAACAATTGGGGTTTTAAG<br>TCTACCTACTTCTAAACCTTGATCATAGATACAATAGGTGCACAACACATACACGGTGTGT<br>GGTATATTATGAGCAGCCAATTCACCATTTTGAAAAGCTAAAACTCTGTACCATAACTTTC<br>AGTGGGATCCGTATTATCAAAACTATATTTAATAATCCTATGTGCTAACTAAAGCCTGGAA<br>GCTGTATATATAGTTTAGTTTTAATTCATAAAGTTTTTTCATTGGACTGCCGGAATGTC<br>ATGGGCCTTTAAAACATTCACTGCTTAACTGGTGTAGATTCTTTGTTACACTGTGCATTGT<br>TACTCGTCTTTCGTGTGAATTTCCCATCTCTATTCTAATACCTGTATTTTCTGTTTAGAT<br>TTTGGACATTGAGTTACACTACTCGCTTATATTTGTTGTAGCTAGTTTGAACTGAATCCTG<br>GAAGTTTATTATCTTTTTGTGTTCTCACACCACTTGCCAAGAGACTTGAGCCTGAAAAAAA<br>AGAATGAGTTGAAAAAAATGTAGGTTTTACACAATTTTAATCATTTTTCTTAAGTATGAAT<br>ATCAGCTGTCTTGTAAGATGTTTTCCATCAATAAGCTGAACTCACTTTATAGAGCACTGAA<br>TTTCATTTTTGTATAACAATTGGTTATTTCCTTTCAGTCTGGCACTCGCTTTTATTCATTT<br>TCCTAATAAATAGCTAATTCTGTTTCGATCAGGACTTCTAACTGTAGTGTACGACATCT<br>AATTCTAGAAAGGGTATTCTCACTTCCTAGTTAAGATGTGTATCATATTCTTTTATAAAAC<br>TAAAAGCACCTAGCCTATTGAGTTTATAATACTGAAAGTCTACTGAACTAGTCATCTTTGT<br>ACATTTCTTTAGACTTAGATCCAATCTTGTTGCTTTAGTTTATTTTCTATATAGTTATTTG<br>AATTAATCACAAGTATCTAACAAAAGGTCCATACTTACCGATTTGTGTAGTAGGATTTTTC<br>TTCTATTTCTTTGTAGGTAGTAGTGTTTCTAGGGGAAACCTTTCAAATTGGCCCTTCTGAG<br>TCTATTCTAGTTTGAAAAAAGCAAAGTTCTCACTAAATAACACATATTAATAATAGTCTTT<br>GCTACGGAACTAATTATTTCTTGATCTAAACTATTTTTGCTCCTGAATAGAAGGACCTAGT<br>TAATTTTTATATTAGGGCAGAAGAAATCAAAGAAAGAAGTTGAATAAAGAATAGGTATATT<br>TGTACTAAAGTTTGCTAAAAGCGATTTAGGTGGAGCTTCTTTTTATTTAAAAACCCCAATA<br>ATCTTAATAACAATAAAGGTCTTCCTGTAAACTTTTGAAAAATGTACCGGAGTATTTAAGT<br>TAAGTCCAAACCACGAGAATAGGTCAAAAGCTGCTACTTAGTTTATATTTCATTGCCTTTT<br>CAGTATCTCGAGACTTCTCCGCTGTCAATAATAAACAGTTGTCTAGCTATTTTGTTTAGGT<br>TGGGTAAAAACCTACGGAAAGACAATAGGAGCTTAGACTATCTATTGATAGATCAATTATT<br>TGTTTTAAGAACTATAGAATTAAAAACAAGGCAGTAGTTGTAGATTTTAAAGATTATTTAG<br>AGTAGATAGTAAAGGCTGTACTGAATATCAATGAGGATTTGCAGAACCAACAAGTGGCCTG<br>CATCAAGCTATTTAAGTGATTCTATTGGTATTTTACTAGAAAAGGAAAGCTAATCATTTTT<br>CCAATGACGGTTCATATAATCCAAGTTTTAAATGGTTTGCATCATCATAATAGGGGTATCT<br>AAAAGGCATAAATCGACGAAAGTGATAAAAATTACTTATTAAACGACGTATTTACATCCAC<br>GTTTTTGCTGGAAGTACTGAATCTGCCTACTGCTAGTTTGGGGAAGACAATAATACACAGA<br>ATAAAGACGATGATGAAGATTCCAGTTTTTTTCAAAGATAAAAAAATAGATATATATGTAT<br>AATTGTATGAATAGTTTTAATAATAACTTATGTTGCTATTTTGATAGCAATTCATTTTACT<br>ATTGAAAAGGTTACCCAGGCAAATAATATGTTTAGCACATCAGATTCTGTACTAATAATAA<br>TATAGAGTTATGTTATAACGTCAGGCAATACTTTATGTGTATAGCGAAATAGTAAATGGCAG<br>ATTGTAAACCGTATGTTTTTACTACTCAGACTCATACGATATGTCTAGAAGCCCAACCAAT<br>GAATTAGAGGACTGTTTGATATCAACATCCAGTCACTTTGAGTGTAATAAAACTATTTATA<br>TAGTTTGCTTCGAATGAAACCATCGCCAGTTACACAACTTTAAGTGAGCACTATTTCTGAA<br>AGTGACATCACATCTTAGTACCTAATCTTACCCTCTAGGTAATTGTAAAAATTACCCTCAG<br>CACTGTTTCGACATAGCACTCTTTAGTGAAAATTTGCAACGAGATCTAAACATGAAAATCC<br>GAGAAATTGCCGGATATTCATAAGGTGCAAACTTTTCTTGCTGGTCGATAGATCACTTCGT<br>AATGTTCCATTTGCACCTATTGATTGATTTTTCGTTGACGTCAACTTCTTATATATGAGCC<br>CTTATAGAAATGATTTTATGGATGCACGATTTTCCTTAAGCTATGACCTTCCTGTTTAAAA<br>CAGCCGGCGTTTACTATCCTATAACAAGAGGCTTACATGACTCCACATGAAATATAAACTA<br>AGCGAACCACGAATTCGACTTTGCCGCAAAACGTTTTCTGAAACATACTGTTTAAATAAGT<br>TCAGGAAAAGGCATAACAGTCATACATAATTGTCTGTATAGAGTTTTGACATTTATTATAA<br>CTCTCTAAGAAAATGTTTGGTAGATTAGACTGTGGAGAGAAAAGAAAAGAAGAGTGTCTA<br>TGAAAACTATAGCTTGACAAATATTTTGATAAAGTTTAGAAAGAAGCACATGTTTTTTTCT<br>GATTTATTCCTACAGAATGGATCAATGAAACCTTTTGGGTGTTTTTTTAGAAATTATCAA<br>GATTAAATTATTGCATTACAAAAATTGTATGTTTTTGATTTGAGTTTCGTGCGGCAAAAGA<br>TCGGAAATGGAAGCTATCCAATATTACAAATAATATTGTCGTAGAAATGTTTTCTTAGGG<br>ATATCAAAAGTTTGTTAGACGGCTATTACTCTTCTGTTTTCAACCCGTACATATTTTCAAC<br>TGGGAAAATGCAGGATCTTAGAGAGTTCTAGTTTTACAAAGTACTGTATTTATGGAAGATT<br>CATCCAATACACACAGTAAAATTAAGTTTGAAAATTTGAGTAGTAAAGACGTACTTCCAGA<br>TTATTACGTTCTTTTTGGACATATAATTAAATACTTGGTCTCGAAATTCAGATTCTCCAGT<br>AGAAAAGTCCAACAAAAAATTATAAAGGACGTACGTTTCCAGTCGGACCAAACTAGCTGAA | |

TABLE 7-continued

CENs sequences

| Sequence | SEQ ID NO |
|---|---|
| AAGCCAATAGTTTCACGATGTAGCTGAATTTTAAGTAGCTGTTTGAAAAAGCTACTTGTTT TTATGTACAAAAAGGTTGTATGTGTTAGTTGAATAGTGTTTCTTTTTTTTTTGCAATTTC AAGATCAGCGACTTTAAATATTGGTCATTGTGACATGAAAAAAAAAAACAGTTACCTTTGA GAACTAAATGACTCTTTTCTTGCTAGACCTTATCGATCTATCTTTTAGCTCATCACAAATA TTAGGCGAAAAGAATACACTAATCTAAGAAAGCTATTTATATATTATTTTTTTGATGGAA AAAAAAACTCCAATGTGTGGGATAATGTTGAAATTAGCGTTATGTTTATTAAGCATGGTGA GTCAGCCCTGATAGAGGGACCATTGAACTGAGAGTACAAACAAGTTGGTGATTAGAATCTA TTATTTAAGCATCCTTTAGACAGTGCTGTTTTAACGGGGGTCTCATATATTTAAATCATGT ACTATAAGAGGAATAGTCACACACGGATTTCTTTTGATGAAAATGCTCAAGGACGGGTAGG TAACGAACAAATAAATGAAAAGAAAAAAACTGGAACATAAGGGACAGCAATCACATAGTCC AAAGCTGAATCCAGAAAAGGCTGCAGAGACTCCGTCATTTGATGCAAAGCATAAGGGTAAA CGGTTAGACGTTGCTGAAGTTAGTAGAAACGTATACTAAGAAAATCCAACACATGGAATTC AAGCAGCTGCTAAGGGTAGAGTCATGTGAGTGAATAACAGCTTAATTTAGTAGAATGCAAC AAAAGGATTTATGTATTACATTGCTAATGATTGTTCCACAATAACAGGCAAAATGCTTTTG ATAATTAAGAGGCTAGTCCTCTGCAAACAACCAGAACTCTTCTGAATTATCAGAGCATTGT TGTGTTATTGGCCCAAATAGCTATTTGCAAGATTGTTAGGCCGACCTTTAAGAGCAAAAGT TTTTTTTTTTCTATAAGAGTTTAATGTATTTTGCGTATGTATAAGGGCGTGCAACTTACCA TTTGCTCTGAGAGCAAAAAAACAATAATTTATAAGGTTTACTTATTGTTTATACTAAGTTT TTTGTTGAAATCTAGCTAACTTCCCAGCTAACGTTGTCGATTATGATCTAGTTTAGTTTAT GTAAGTCAATGTACTAGGGTCTTTTTCAGGTCAATGTTGAATTTCTCAACATAACATAAC ACTACGTTTCTTCTTTAACTCTCAACAATTCTAAGTCCCCTAATGGCAAGAAAAACTTGAC CTTACATAACCTTAAGCTGCTTACAGAACAACCCTAAAATGATGCTCCAAGTGGTAAAAA AGTAGCTTTTACACGGTAAACATTCGGGCAACGAGATTTAGGCTAACTTTAGGATAAACAT AATAGATTCTCTTCTCATCTTAACCAAATAACAAACACTCCTGCACGAACAAAATTCAAGC AAACGCGTTATCTGTACTTGTAGAGCTTATATAACAGCATATAACATGAGAATAGTTGCAG AATTTTATAGTTCTATACGGTTCATCAAATCCTAAATACCCTACTCTCCCTGAGCATAAAG CATGGTCACATGATATATTGCAGATGAATGAGACATGCTGATGCATCTTAAAAGCTCCAGA GGTGATTTCCAAAGTTCAAGAATCCTTAGAATGTTGTACTATAAACCGCCATATAGTTATA GAAAAGTATATTTAAGCAATGCTGCTTAACAATGACTAATATTAACCATAGCAACCAAAT TATGGCAGGGAACAACCCAACATTATAGACGTAAATAACACATTTCTTTCTATACCCAATA AACACACTGTCCAATTTCCATTGATCTGGAACTATAGACTTTGGCTCCAACAATATAATTT CAAATAAATCTCTGCTTCTAATACCAGTAACTCTTTTCTTTTGAGTGTTTTGACTTTTCAA TGGATGGATGCTGGTGGCCGTCTTTGGTCTCAACAACTGCTCGTACCCAATATCTTTTACT TCGTTTTTAAGCACATCTATAATCCCGTGTTCTATATAGTATAGTGTCAGTTGTCTGAGAT AAATATCCGTCTTTTTTAATTGGTCTGATCAAGCTCAGCCTTTCCAGTGGTTTCTTCCATC TCTTCCATCTCTTGAATTTAAGTAATTTAAAGTAAGGTTTTTACATTAAAGACTGGTTCGA TATCAGCCCCTAACGATATAGGTAACATACTGTCAAAGCTTAGATTAATAGTCTTTTCTTT TCCATCTCGCCTCATACAAGATATAATAGATACTGTCAAATATATCCTCATCATTGGCAAG TAAAACATTATCAAATATGTAGTGTATGATGGAGAGACAAAACTGTTTGCTGCGGTTTACA CTTAATATTATTTCTTTCTCACCCAATCCTTGTCAATATGTCAACACCCACACAACCAAGA TCTTTTTCAGGGTTGATAGTTTTTTGCCGTAAAATCGTGGCATGTTGACACGTTGAATGCA GCATCAATTCCAAAAACACATTGGTTTGATAGCCACACCAGAGATTAGTTGGATGCTACTC AAACCTGGCTTTTAATCAAATTGTACAACTCCATTCACAATATCAGGAATCAACATAAACT CGATGTTTTTCTTTCCTAATACAAACTCCACCTTTATTTTCAGATAGATAAGGCAGAACT GTTGTATCCCTTTCACCAGAGAGGTGCTGTTTGTCATCACCTGGTGTCGAGCATTAAATGA TACATGTGTCTTCATGATAAAGTTCTAATTAGTACTGTTTTTATTTCAGAATTCTTGGTTT TAAAGCCTACAAGCCCGTCAAATGTTTGCTGCGACATCTTGTGTTTGAGTTGACAATTTAA GCATAATTGGATATTTCCTCATCTTTTGGTGTGATTTCCATTCCGGATTTTATGCGTGGTC AGACTGGATCACTTCACATCGATGAAGGAAATCAGACAATTCTAGCTTTAACGCGAAAACC ATTTTTTAGCTTATCATATGAAAACCTTTCAGAACCAATCGAGTTTGAGATCGTGTTTATA CTTTTTCCAGGAGGTGACCCGTGGTGACTACTCGGCACATGACATGCGCAAGCCATATCTCC AGAAAATCCACTCCCTAAGCTGTCTAAAGCACCTTGAAACATAACTACGTTTACTTTTAGA AACAGGCTAATCTCCAAAACAAAGTCATATTGAACAAAACTGAGAAGAGATGTAGCTAAAG ATTCCTACAGATGATGTTAAATCACTACAGTTCTTTTTGCTTTTTTTTTTGAGAACTAAG GAATAGTTTACATAAGGAGCACATCCAAGGAAGCTCCAAAACTCCCTATGATGAATCGTTT CTGAAGGCCCAGCTTTTAAAAGGCAGTTTAAGTCTAGAAAGATCCCAATGGTTTATGTTCC CTAGTAAACATCATTTCATTCATACTGAAAACTTTTATGAGGTAACGATTGTACACTTTGA AACCAAAGGGAACCACAGTGATTGCCAGATACTTAAGACTGCTGAGAAAAGCGATTTCTCT AGCGAAAAACCTTTCCAATCCTATTTTTTCACTTCATTAATGAATTAGAGCAAATGGGTTT AATTGAGCAAAGTTCATGTTCTTGTTCATGTTCTTGTTCGAACCTTGTTGTCCTAGGAAG TTTTCTATAAAGCGGATAAAGAAGAAGTCAAACATAAAGATTCAATTGAACAACCACAACT TGGAATTCCAAGAAGTCCTTGTTTCTTTGTCTGAGTAATGCCGTTCATTATAAGTGTATA TAAGATTATTGAAATATTGATTTTCATAGAGATGGCCAGGGTGCAACTTATCATGAAAAAC TACCTTCTCAAGTCAACCAGCAAAGGCTAGCGGAAAGAGTCCAATTGCTAGGTTTGTAACT TGGTTCGTTATTCATCCGACAAAGGTTATATACATTTGATAAGAAACACTTAATATTATTA AATAATAGCAACATAAAACGAAATGTCAACTTGTCAACTCGATGCCAAATAGCTATTGT TATTACAAAGGACCTACAGCATATAATGTATATCCAAAAGTCGTGGATTAACAAGGAAAAG CTCAAAACGAGTTTTTCTGTTACTGAACTGTTTAATTAAAAAACTATCAGACCAAAAGAAG CTTTTCACTTTTCTTACATTCTTAGAGGAGCTCTCTGATGCTTATAGCATAGAAACTAATT TAGAGACGAGTGGGCTTTCTAAAGAGGAGCTTAAACAGTCGACTTTAGTTGACTGAGTGC TGTTACAGTGATTTTTGGTTCACTTAATATTCAGTAGATGTAGGTATTATCTCTATCTGAA TTCCCAAGCTTGTAAAGAAAAGGAGTGCGAATTGAACTTCTCATAAACAAAAGGTTCACAA CTCAACTTTTGTTTGTCTCGACAATCCACAGTCTTCCTATACTAGAATTGCCCTATTCCTT GGAAATCCTCTCTTGCTTTGATCTATTAATTCCACTTTAGATATCCATCGTGATGTTATCA GTTGAACCGTTTTTGAAAGAGCCTATATAAAAGAACATATGAAGGACAATGGAAATCAAAA | |

TABLE 7-continued

CENs sequences

| Sequence | SEQ ID NO |
|---|---|
| TCACCTGGTACAGTTACAGGAATATCAGTTGTACACTGAGCTAAATAGACATGCGGGATCG<br>CTTTTAAACAAAAACAAATATAAACTTTACTATCAAAATTTAGAAATAGCTAAATCCTGAA<br>TTTGATAAATCAGCTAACTAGGCCTGAATGGCATCTTTGAAACTGATAAAGAGGGCTGTGG<br>TTTTATTGGTTACTGTTTTAATTATCTTTCTCGACATAAAGTACAGATTATGCCTTGGTCG<br>GAACTTGGAAGGTTTTAAATGGAGCTAAAATTTTATTAGATTATATAGTGCTGGTTATGGT<br>GGTAAAAAACGGGCCAAAGAAAATAAACTAATTAGAGGCCATAAAGGTAGTTGATCACAAT<br>ATTGCTACAAGTCTACCTTCAGTAGAAAAAACAAAACTGTAGTTCAAGCTAAGAAACGAAT<br>GGCAAAATGAGAATATTAGGTTCTTAGTCTTAGAGGATATCAACCATAAAATGATATTAGG<br>TTTCCCATTTGTTAAAGATCATGGAAATAAAGTTGACTGGGAAAATATCGAAAAGGAAACG<br>GAAACTCCTGAAATCCCAGATATCAAAAAGAAATAAAATTAAATAACGGAAATGACTTAGA<br>AGAAACAAAAGAAAATGAACTTATAGCTATTAAATCTATGCGTGCAGTCAGAAGAAATTTA<br>AAGAATGTTGATAATTATCCATTATTAGTGTTTGTGCAGTCAGTTGAAGAAAAAGAAAATA<br>ATAATGTTTTAGAAGAACCTTACGGTGGTGTTGTTGGAATTAGAAATAAAATTCATGAAAA<br>ATTTAGAGATGTGGTGACCAATGACCAACCCACCAGTTTACCTCCCCAAAGGGATTTGACT<br>CACAGAATTATACTCATTGAACCTACCAAGAGTACATACAGACGCCAGTACAAATCAAGCT<br>ATTCAGAGAAACAAGAACTGAATAAACAGGTTGATGAACTGTTGAAACTAGCCTTTATCAA<br>GTCTGCCCCTAGTTCTTTCAATAGTTTTTTGTTACTTGTTCCAGAAGAAAGATGGTAGTAT<br>GAAAATGTGTGTTGACTATGGGTTACTGAATAACAATACGGTAAAAGACAAGTTCCCAATA<br>CCACGAATCGACAAATTAATCACATTTTTTGGAGGAGCTTCAGTATTTTCCAAGTTGGATT<br>TGATGTCAGGTTACTTTCAGGTCAGAATCGCAGAAGATGATATTGAAAAAATAGCTTTTC<br>CACAGATTACGGTCACTACGAGTGGGTTGTGATGCCTTACGGTTTAACCAACGCCCCTAGT<br>ACTTTTCAAAGAATGATGAATAGGATTCTAGCACCTTATTTGAACCAATTTGTTCAGGTGT<br>ACCTGGATGATATTATAATTTACTCAAAGACTGTCGAAGAACACTACAGTTACATTAGAAA<br>AATATTGGAATTGCTCAGGAGAAATAAGCTGATTGCGAAGAAAAGAAATGCTCATTTTACT<br>TCAAAACCTTAGGTTTCTTAGGACATCTCATTTCAAGCAGAGGTATCCAGACTGACCCTGC<br>TAAGATAGACAAAATCAAGAGTTGGCCAATTCCGAAAAATGCCAAAGATGCTCAATCATTC<br>CTAGGATTAGCTGATTACGATTTCAAAATTCAATACTTGAGGTCCTACTAATTCAGTAGCA<br>GACGCTTTGTCTAGGTACCCAGACGAGGAAAATGAAGTTAGTATCAACACAATAAAATAGG<br>TGTTAACACCAAACCATGAAGTGATAGAACGGATTATCCAGTCATACGAAGAAGACAACGA<br>AATTAAGGAGATATACGACATTTTAAAAGAAAATTTGTCGATCCCGAAGTCAATCCATAAC<br>TACACTAAACATTATTCAATTGAGGATAATTTATTATATTTCTTGGTGGTTAAAGGAGAAA<br>ATGATCGAAGAATAGTAGTCTCCCCTAAGTCTAAGTTGGTTCAGGAAATTATTGGTAACGC<br>TCATGACGGTAACTCTGCTGGTCATTTCGGGTATTTCAAAACATACATGAGACTTCACCCT<br>ATGTTTTACTGGTCAAATATGCTAAAAAGCGTGAAGGGATATTGTCAAAGATGTACGGTTT<br>GCCAGAAAACCAAACCCGAGACAACTGGTCAAAGAGGATTATTTTCCCCTCTTCCGATTCC<br>TGAAGGAAGATGGACAGACATCAGTTTGGATTTCGTCACAGGTGTCCCCAGATGCAAAAAT<br>GGACACGATATGATTTTGGTAGTGGTGGATAGATTCACGAAGATGGCACATTTCATCCCCA<br>CTAGGAAAACTGCAACCGCAGAGCAATGTGCGAAATTGATGGTAGAAAATTGTTTTAAATT<br>ACATGGGATTCCAAAAAGAATGGTTTCAGATAATGACATAGAATTCTTGGTACATCATCAC<br>TCTTCTCAACCACTAATCACCCTCAAACAGATGGCCAGAGTGGAAGAAAAAATAGAATCTT<br>AAACCAATTACTAAGGAATTATGCGAGTAACGATCTCTACAGTTGAGACAAATGGTTGTCA<br>ATGGCCGAATTTGCCTACAACAGTTCCCATCAAGTCTCGATAAGTTCATCACCATTTGAAG<br>TTTGCTATGGTTACTTACCAGACTCGCCAATGTTTATTTCTAGCAGTCGTGTTTCAAGTAG<br>AAGGTACAGCAATAAAGCTGAAGAATTCGCATTAGAAATGAAAGTCATCATGGAAAATGTG<br>AAAGAAAACATGATTGAAGCGCAAAGAAGCCAGGAAATACAGCATAATAAGTCGAGAGTGT<br>ACGAGACATTTGAAGTTGGAGATTGGATACTATTGCACAAAGATGCATACGGTAGTGATAG<br>ATTGTATTACAAAATACAACCGGTATACTACGGACCCTACAAGGTTGTCAAGAAGATATCA<br>GACAACGCCTACGAAGTTGATTTACCGAAAACGAATAAAAAGGATAGAGTAATCAATGTCA<br>GATGGCTTAGAAGATCCTTACAAGCGGATAAACAGTTTCCCAAGGTACCCCCAAGAATGAT<br>AGCTGAAGCAAGAAGTAGACTGACCGAGATTATCGGTATAGCTGGTATCGATGAAACAAAC<br>GATACATTGGATGTCTACTAGAAAGATTGTGACCCTTGTCATAGTTCAAGCATCCCATTTT<br>CATTATTTTAGAGATCCCAGAAGACTTACAGAAAACATTATGGGATAATGCAAGAGCAAT<br>TGATAAAGATAATAAACTTCGGGATGAAGTTTCTAAAGCGACGGGGTAGTATAAGAGATCA<br>GATAAAGGACCATCTCCCTATTTCCTAATCGGGCAATTATATGGAAGGTTGAAAAAGATTG<br>TAGAAGGTTAGACAGAAGTTCTAGGAGATAATTAAATCCCTCAAAATGCTATTTTTAGATT<br>AAACAATTACTACATAAAGAGGGAACATTCTATAGCTGCCTCGGAGAAATAGTGTATAAAA<br>TATATAAGATACAAATAAGCAATAATCAGGTTCTAAAATACGCACCACCAGCAACATTTTC<br>ATAATGTGAAAGGGATTTTTCAGAATGTGTCCCGAAAAAGGAAGTGCAAGTAGATAGACAA<br>TAAAGCTCCTAATCGGGAGTGAAAGCAGCAAAAGGCGGAAGAGAGAGATCTATTTACTGCT<br>TCTACTACAACTAAGTTCCACCACACCCATTGTCTACTCGTGTGATTATACACCTATGGCG<br>TACTTACTAATACGTGTATCATAATTATCATTGTTACATACACTGTTTTTGCTATTGTTAA<br>GGTTAGTGATTATTTTAAAAAGATTCAGCTGTTAAAAGATCCCAAATAAGGAAATAATTT<br>TGACACGTTACCCCAAGTCCCTCAAAAAACTTTTTAGCCCTAGCTGGCCAAGTGGTTTGCG<br>CAGGGGGATAAGTTGGATTAGTAGGTGGTTCGGATTAGAACAAGGCATTTTCTTGACATTT<br>TTTTTTTATTATTCTGGCGATAAAATAGAGCAGAGGCGTAACATAAAAAAAAACCATTAGAT<br>GGTTTCATAAAGGGGATAGTGGGTATGTATTAAGTTTTCTCCCTATCATGCTATAACTTCA<br>GCAAATTTATTTTGGGCTTAATAATAACACTGACCATAGAAATCTATGGTTTCCAGAATAC<br>AGAAAGCTTTTTGGTCTACATGTTAATATACTAAATATTAAAGAGCGTATCGATAAATTT<br>CACAATCAAGGAGACAAACTGCAAAAATGCCAAACCAAAATTTCAGTATAATTAGAAGATA<br>CGTTTAATATTCTGTAATCCTAAACCTATTATCTCAGATATTCTACTATTTACATGTTAA<br>AACACAGACGATGGAGTTTGACTTATATGGTTAGGCGTATGTCCTTACATCCACACGAACG<br>TCTCTTCTAAGATCAGCCTCTGAGGATCACACTTTTACTTCGAAACATCACTCTGTAGTTG<br>CCAAGCTGATAATACTAACGAGAAGTATATTGTCAATTTTTGTAAGGAGAGGTCTACAACC<br>AAAGTGTCTTACTAATTTTTGATTTGCATTTGTCATACAGTCAAAAGTTTAGATAGTTTTA<br>GTAGAACTTTTCAGCAGTTCAGTACACACTTCAAAGGACTCAAAGGCGTTTTTTTTGGTGT | |

TABLE 7-continued

CENs sequences

| Sequence | SEQ ID NO |
|---|---|
| ACTGAACCCAACTAAGGATTAATTTTTACTATTTGTACGAATCAAGAGGCTAATCGATGTA
CCCATTATTCCATTGCTAATATGCGGTTAGTCATCATTTTTTGATAGTTGGTCAATGCCAG
ACAGAAACGAAAAGTTCTCTGATCTCCTGATCTCCTGTCTTGTTCTTTGCTTTCAGTTTTA
GGATCGACGGTGGCACATTGGTTCAAAATAAAAATGCTAATCTTGTCATACAGGAGAAATA
CTCCAGGGAATTAATTTAATATACATGAAATTATGTATAACCACAATCTAATAACAAAATG
AGAAATACCTCTTGCTATTGAGTTTTTTTTTATTTTTATTTTTAGTTTATACTTCTATC
TTTTGCATAAAAAAGAAACGAAACTTTTATGAAGCTTTCAATAAGCAAGGTTCATTGAGTA
TTGTATCAATTTGGAATATAACAGAGCGTTAATGAATTTTAAGCTCGAAGCATACGTGAGT
TATTTGCAGATAGCTTAGTGTTAAATAAAATTTGATGGCTGTAATGGAAGTAAATCTAAGC
TAACTCTCGTTTAAGTTCCTAATATGCATCTCCTTTTTTTTGATGTAATATGTTACATAAA
GATAAGACCGGTCATTTTAGGATATTTTAAATGAAAAGTAAGGTATAATCCATATTTATT
GGGATGGTTTGATCTGCACTGTATGTTTATTCCTGGTGACAAATTGAGCGGTCAATGTCTG
TGTCGTTTTACAAGCTTTTAGTTGGTGCCTCTATTTGACATTACTTTTTCAATGTTTTCAC
ATAACAAAGGATTCTCCAACCTGATTCCTTCATTTTCTTGTTTTCAATTTTATTTTTTGTG
ACCACTGCTGTTAAAAGAAGGTGTTCCTTATGTCCAGGCAGAGTGGTAGACGACAAACACT
GAATATTTTATTACAGTTATTGCAGGACCTTCAAAGTTGGTACGTATTTTTGCTCATATGC
TGAATCTACTTGGACATCACCGGAGATCAATTTTTTGCCGGTCTATCTTAAAATTCCATTA
AAGAAAGCTTTTCCTTTTTTGAAGGCTTTTCTGACAAAAAATGGTTGCTTAAATCAGCCGA
CTACCAATTCTAAAACGTTATGCAAGCAATTGCCACCAAGGAAAGTCTATCAATATTCTAT
GATCAGTAATATTGTGTTATTTATCAAAGGGATACAGGTAATCAAAACTTTTAGCCAGGTT
TTTATCAAGAATATTGCTTGAATCGAAAAGGCTCCTAACTTTTGTCATACTCATAGACATG
CAATATGCGGTCTCAAGTACCTCTGTGTCTAGGTACAATTTTCTGTGCAGACATCAGAGCT
TTTGTTTGCTCTGTTTGAAAGAAAAAAAAGATAGGAAAAATCCCTCAATTTCCTAACATTC
AGGTTAGCATTTGGATATCTATGATGTTACCCCAACTATTTATATTTGTGAGAATAAGCTG
TTTCAAGGAAACAAGTGAAATATTATGGAAGACACCGTAAAAATAAATGCAAAAATAGGTG
TATTTGCAGGTACCGAAACTGAGTAGTCAAAACAACATCGTTGAGTGATTCACCAACGAGG
ATATTAAATAGAACATATAACGCTGGACTGAAAATGTCTTTTTGGAGGTTTTTTTCATATG
CTACCGCTCTTACCACTTGATATGTTGCTATAACATTGAATCATTGCCTAACCAACATTTA
TTGAGTTTGCAAATGGCAGCCACAAGTCACGTGATTTGGTTATGTGCTTAGGTAGCTGTAT
TTTTTGAGACTTCTCAAAGAGGCCGTGCGGTTATCTACGGTTCAAAGAACATAGAGTATAG
ACACTTTGAGCCTGTTGCTTTTATAGAATTGGAGCATATGGCTCATTAGCAATTAAGTTAA
TCAACGAGTGAATGTGTACTAAGTATGGTTTTCTGAAATACTTACATAGTACATCGTCATA
CAGAAAGTACAATGCTTATGTTGTGACGAGCATGATGCATTTTAGGACAGGTACATTTAGGA
CAAAGGCCATACAGTTAACTTAGAAATGAGAGTCACGGTTCTTAAGAGTTATTTTACTTC
CTTAGGGGAAGCTGTGCATTGAACTCACAAAGAGGTTGGTAACACGATTATTACTAGCGGT
ATTATATGGCCAGGTTTCTTGTACTGTTGAAAATAGGAAAAGCTGTATAGATTCTTTTGAG
ACACATTAAAGTTCCAACAAACTCCACAGAGGAATATTTACTGCAGCCAGATTTTTTTCGT
AATATTCTTTTAACCTTTCTATTTAACCTACATTGACTAGGGCATATTTTACAGTTACATC
TAGCATTTGTTCCAGTAAAATACATTCAAGACTGTGTTTCTTTATGTAAGCTCATACCAGT
GCAGTTTATACGTGAGAATTTAACCAAGAGAGCTAGTTTCTAAAGTGGTACATTGAAGAAG
CTGGCTAGTGTAGATGTATGGCCATGGCGCATGCGCCACATTGTCATGTGACATTTTGGCA
GCATGCGCAGGTACTCTTTTTGGCAGAGCATTCGATAATATATTGACTAAGATGCCAACTA
AGATAAAGGCAGACAGGCTTTAAAACTCAAGATTCGTAGGGTGGAACACACAGTAGAAATT
TATGACAACACGAATGGGGGGTTAAGCTCCTGCTTCAGTTCTACGTGGAACATCCCCACTG
TCTACCAGCGAATAGTTGTAGAATACATAGACTTGTCTCGTGATGTAAGATAAGGTCTAAG
GACTCAATGATTGGCATCGAAGGAGAAACCTTAGCAGGAGCACAACACTCGATAACGGCCA
TGCTGAGTGGTTAGCTATAGCTAACCCATGGTTACATTTGTACGGGGTTTATTATTAGTTT
TCCGACCTGTGCTTCAAAATGAAGAAGCCTCAAAGATTACCTGGTATGGGTACTTTTCTAA
ATTCTCTTCAATTCTAGTGGTGAGATTAGGAACATCAAGCTATGAGTGAGATTAGGAACAT
CAAGCTGTGAGTGAGATTAGACCATCGGCCATATAGGTAAGACGTCTATACAAGTCAGCCA
ACTATGGGTGTGAGCAGTTCTTCTATGCGAATCGTGCTATTTGTCCGCCTTATATCCGTGA
AGTTTCCCCACTCTATAAACATGTGGACGCGGAAAAAATATTTTCCGTTTTCAGTGGCGTG
AAGATTCCCAGATTTTTCATTCTGCTTCAAGAATCTTGCATTTTGCCGTTTTGGCAATTAG
TCCTTCAAGGTTCTGTAGGATCACCACAGCGAACGTCGTTCTAGCTGACATTCTAACCGAG
AATATTCTTATGCGCTGAAACAGAGAAAGGGTGTTATGTCGAACAAATGGTATTGGAAATA
ATGTGTTTGGCTTGATCCCTTCCCCCATTGGGTCGGGCAATTGAAGCACACGGTGTAACTT
TCCGAGTTGCTGTATAGCTTAGCCACTCATATCTCTGGCAGCATCTAGCGGGTTTTGCACT
AACTGGAACAGCATGTACGTCGAAACGTCAAGAGGGTGCTGGGTTTTCAAGAGAGGGGGGG
CGGGGGCTTTGGCTGGAAAACAATAGAAACAACCCTACAAGACTCTGTAGGTGAGGCCACA
AGTGAAACAAATGACCATATCTGGAAAGCTTAAAACGTTTGCTTTTTCTTTGGACTCTAGG
ACACTTAACAATCTATCCCGCATTATTTCAAGACCTGGACAAATGATGGGAGTACATAGTT
ATGCTTCTAGAGTTTTGTAGCATGTCAACACCAAACTAGTGCGGCAGAGTTCCACCCGG
GTACGGAACTTCCTTTCCAATTTTCCGGGGTAGACCAATAAAACAGTAACTGCATTTAGGC
TGATCACCACCGGGACATAGCATACGCCAACACGCAGACACACACAGACCACCTTGTTACT
GTATATTACCTTGGTCTGTGTCGAAGATGCGCTGTTGCCACTGAACGTTGTGTTTCTCTCC
ACCACGAGAACAGAGGCGGCATAAACAACAAAAAAAAAACCGGGGTAAAGGAACCACGGC
TAACATGTAGCTGGCAATAAAAATTACCCTGCGGAAAAAAATGGAAATTTTTTAGTGGGGC
CAGAAAACTGCCGAAAACTGACCGAATTGGGAGAAATTATCCCCCACCAAAATATGTTCTG
AGCGGAAACCCCCGTGTTTTATTATTTTCCAGTAGGAACGCCGTGTCTCCCCACAAGTTT
GACAGCATGCTGTTTCTAATTGAACCTGTGTTTACTAATGGCTGCAGCAAGATAATGATGT
ATGTCCAACAAGAGATGTGCCTTTAATGGATGGCTGCTTGATGTCCATGAGGGCAATTTGT
TTCCCTGGGTTCCCCCGTCAGGAGGTTACCACAAGGGCAAGACTCCAGAACTTGACCAA
TTGCAGGTACAATGCAATTTTTTTTCCGCTCTCGCCGTTCAGACATGCTCCCATTTTTGC
TGACTCGGACTAAGTATGTGTGAGGCCGCATTTTCCTGTTTTTCCAACATTGGGTGATTTT
GTGTAGTCGAACACAAGGGTTTTTCCATTGCATATATTAATCCCATAGCTGGAAAGACGGG | |

TABLE 7-continued

CENs sequences

| | Sequence | SEQ ID NO |
|---|---|---|
| | TATTTAAACTCCCTAGTTTCCACCCTGGATATCTCTCAACACACCTAAGTTCAATCTTTTT TTTTTCCAAATTTCCTCTTCAACCACAAACAAATATACACTCACATATTCTAATACTATTT GTTTAAAAACAAAAGAAAGTACAAAAAAAAATTCACACAAAAG | |
| cEN2- 40807 bp | GTGTAATTATTTTATAAATTTTATTTATGATATACATAGTTAACCTTACTTTAGCAAGTTT TAAATCCAACCTATTATTTTTGTTTTACAACTTGATTTGAAATGAAATTTATCAAAGTCA GAACCTAGAAAATTGTAAGCCGAATTGGCTTTGAGTGCCCTATCAACAGATAAGACGAACA TACTCATCAATCAATAGACCATATATTTGTATTTCGAAGGCATATATGACTCACTCGTATG TCTCTTGCTATTAATTATCGATCTATTTCATCTAGCAAAATCAAAAAAAAAAGAAGCGCAG AGAAATGAATCAAATTTAGATATTCAAATTTGGAAGCGTTAGCACCGGGGCACTAAAACGA GAACAAACTCTAGACGCCGTGTTATATAGCAGCATATCTCGTTTTCAAACAGAACAGTAGC ATAAAATCGTCATTTTGCATTAAAAAGCATACGGGTCAGTAGAAATAAAATAGGAGATGTT ATCATCTAGGGAATAATAATTGGATATATATAATGAGCAAAATGTTTACTGGAAACAGAAT ACATGGGATGTTATTTCTTCGAAACACTACGTGGCTGCTATGACATATCAAGCTCGATTAT AAGATATTAATGACTGAAACATCAATAACGCATTGTGAGGGTGAAAACCACACAAGGAATA AGGAACGATTGAAAGGAACAGTACCGTTTGAAGTACCGGAAGTCAGTAATATCTTCATACA GTATTTTCCTGATCTATAACTAAGACGTGCTATTTCCTTTTTTTACTTCATGGACCAAAG TGGTCCTAGAAAAGGGGGAAAAGGCTCAATTTTCATTTTAATATTGGTACGGAAAAAGTTT CAGTTTGGTATATGCTTGAGAGAGTTTAAAATTTAGCCTTCAATACCCAGTGCTGCACTGA ATTTTCCGTCAGTTTACATTTACCCGCCATGTTTCTTTTCCACAATTTTAAAGTTTATGAT AATTTCTCAGACTCAGATCCACACGTCCATGGGATTGCATGCACTGCCGGACGCAATTTTT GTCAGATTAGTCATGCTTATCTGCAAACAGACCTGAAGTTTCACTATGGATACTTTAGACC AATAACGAGATTTGAATCACTGCCAAAAATCCTCCAATCAGCTTATTATTACTAGATAAGA TATGGTATGTTAAAGACTAACAAAAGTCAATAACACATAACTGTTTGCTATGTACTTTTA ATAGTTTAAACCACTAAATTGAAAAGGGAAAGACGAATGTCTTGCAAGTTCTGTTTTCTCC ATTCTCATTATATAATAGCTGCATAGTTAAATCTTTCAAGTCAAGAATTGAATATGGGCAC TATATATATGATATTGTCTTTCTTTAGAAGTAAAAGCCCAAAAAACCACAAAAATCGAATA CAGAGTTATGTCGGAAATTGGCTAACTCTCCGATGTAAATGATTGAAAACATCTTCATGAA AGCTGAGGAATGGGAAGGACAGTATCCGCCACGCAAAAAAAATTAAGCTAATGCCAGCACC CATGCTGGGAGTCGAACCCAGAATCTTTTGATTAGAAGTCAAACGCGTTAACCATTACGCT ACACGGGCATTGCTTGTTTTGTAAAGGGCTTGGAGTAACCTGTCGAAATTATTTCCTAATT TGGGATGTTTCGACGGTTGAATCTTTTTAAGAATAATCACTAATCTTATCAATATCTATAG TATTGTATGAAGGAATGATAATTGTGATATACGTATTAGTAAGTAGGCAATAGGTGTATTA GCTCACGAGTAGATAATGGGCGTGGTAGAAGTTAGTCGTAGTAGAAGTAGTAATAGATTTT TCTCTTCCTCCTTCTGCTGCTTTCACTCCCGATTAGGAGCTATATCAATTATATCAATTCT ATATAATAGGATATTATCCGTCTTATATACTTCACGCCCGCAACCTGGAATCACCCTCAGT TGCTACTCTTTTTTCGTATAGCAGACTCCTGTACGAGCTTATTACGTTTTAGGTCTTTATT TTTTTTAATATGCCAGTCCTGTCAACCCGTTGATAAATAATTTAACTTCCTACTCCGGATA CTTGACCCTTGTTAACCTCCCTATTCTAAAATCGAAACATTAACATCAGTATGTTATCGTC TATCTACTGGCACTTCCTTTTTTTTGGATCACACCCTGAAAAGCCCTCTCACATATCGAA AAAGGCTAAGAGTACCGAGTTGTGGCTATTTCTAACTTACAAATGTCTTAATGAACTTAAG CTTGGCAAAACCTTGTACGACTGGCCAATAATTATATCGATATCAAAAATATCCAATTCAA TGATAGCCTGTGTAAACTAGCTGAGCATGTTGCAGGTGCTTAATACGTGTATAAATGCACA TGTAGATAATGGATATATGGTGTTGACAGGCGTTACATTTACTTTAGAGATCCCTATTGCA ATTACCGATTGAACTATTATCAAAAGATCTTATACTAAATAACAAATAAAAACAAACTAAG TCAAAGGAACTAACTCGCTATTTAAAAGAACATCAGGTTTGTATCAATCTAGATTGATATA CGTAGGCTGACGTTTCAAAGAACAAGGGAAGAAAACATAACTAAATGAGCTAAAAATAGC TCGGCTCTAGTTCTGATTTACGCGTACGTATGCTGGACTAGCTGTATCGAGACTGTAAGGA TATCCTTAGTTTGATGTTTAGTGCTTTAATTATATATCTAAACAATTTTTATTTTGGGTGT CTGTTTCTTATTTTCCTAATATTACTAGAAAAATATATTCAAGGAAGGATGTTTTTGAGTT GGTTCCAGCCAAGGCATCAAATATCGAAGGATTTTCTAATTAGCTCTGTTTGACTAAAGCA AAACGAGAAAATACTCATCGTGTTTGTAATAGGTAAAGCATCTATTTTGCTTCTATTGTAT TTAAGGAAATTAGAAGGTCCACTTCAACATCTAGTTGGGTCACAACCTTTCTGTATAATAC TTCTTCACCAGGTACTATAATTATCAACCTTATACGGAATTTGTTAATGCGTACGTGTCCG AAGCAAAATCTTTCAGTACATTACTTTCACTTATACATTTTGTATATTTTGTGCATGATCT TTGATTATATCTTCTACTATCTCTTTAAATAGTTTTGTTGCACTCAAGGTGACTGGATGTT GATACCAAACAGTCCTCTAATTCATTGCTTGGGCTTCTAGACATGTCGTATACACATAGGTATTGCC AGTAAAAACATACGGTTTACAATCTGCCATTTACTATTTCGCTATACACATAGGTATTGCC TGACGTTATAACATAACTCTATATTATTATTAGTACAGAATCTGATGTGCTAAACATATTA TTTGCCTGGGTAACCTTTTCAATAGTAAAATGAATTGCTATCAAAATAGCAACATAAGTTA TTATTAAAACTATTCATACAATTATACATATATATCTATTTTTTATCTTTAAAAAAAACT GGAATCTTCATCATCGTCTTTATTTTGTGTATTATTGTCTTCCCCAAACTAGCAGTAGGCA GATCCAGTACTTCCAGCAAAAACGTGGATGTAAATACGTCGTTTAATAAGTAATTTTTATC ACTTTCGTCGATTTATGCCTTTTAGATACCCCTATTATGATGATGCAAACCATTTAAAACT TGGATTATATGAACCGTCATTGGAAAAATGATTAGCCTTCCTTTTCTAGTAAAATACCAAT AGAATCACTTAAATAGCTTGATGCAGGCCACTTGTTGGTTCTGCAAATCCTCATTGATATT CAGTACAGCCTTTACTATCTACTCTAAATAATCTTTAAAATCTACAACTACTGCCTTGTTT TTAATTCTATAGTTCTTAAAACAAATAATTGATCTATCAATAGATAGCCTAAGCCCCTATT GTCTTTCCGTAGGTTTTACCCAACCTAAACAAAATAGCTAGACAACTGTTTATTATTGAC AGCGGAGAAGTCTCGAGATACTGAAAAGGCAATGAAACATAAACTAAGTAGCAGCTTTTA CCTATTCTCGTGGTTTGGACTTAACTTAAATACTCTGGTACATTTTCAAAAGTTTACAGG AAGACCTTTATTGTTATTAAGTTTATGGGAGGTTTTTAAATAAAAAGAAGCTCCACCTAAA TCGCTTTTAGCAAACTTTAGTACAAATATACCTATTCTTTATTCAACTTCTTTCTTTGATT TCATCTGTCTTAATATAAAAAATTAACTAGGTCCTTCTATTCAGGAGCAAAAATAGTTTAG ATCAAGAAATAATTAGTTCCGTAGCAAAGACTATTATTAATATGTGTTATTTAGTGAGAAC | SEQ ID NO: 13 |

TABLE 7-continued

CENs sequences

| Sequence | SEQ ID NO |
|---|---|
| TTTGCTTTTTTCAAACTAGAATAGACTCAGAAGGGCCAATTTGAAAGGTTACCCCTAGAAA<br>CACTACTACCTACAAAGAAATAGAAGAAAAATCCTAATACACAAATCGGTAAGTATGGACC<br>TTTTGTTAGATACTTGTGATTAACTCGAATAACTATATAGAAAATAAACTAAAGCAACAAG<br>ATTGGATCTAAGTCTAAAGAAATGTACAAAGATGACTAGTTCAGTAGACTTTCAGTATTAT<br>AAACTCAATAGGCTAGGTGCTTTTAGTTTTATAAAAGAATATGATACACATCTTAACTAGG<br>AAGTGAGAATACCCTTTCTAGAATTAGATGTCGTACACACTACAGTTAGAAGTCCTGATCG<br>AAACAGAATTAGCTATTTATTAGGAAAATGAATAAAAGCGAGTGCCAGACTGAGAGGAAAT<br>AACCAAATGTTATACAAAAATGAAATTCAGTGCTCTATAAAGTGAGTTCAGCTTATTGATG<br>GAAAACATCCTACAAGACCGCTGATATTCATACTTAAGAAAAATGATTAAAATTGTGTAAA<br>ACTTACATTTTTTTTCAACTCATTCTTTTTTTTCAGGCTCAAGTCCCTTGGCAAGTGGTGT<br>GAGAACACAAAAGATAATAAACTTCCAGGATTCAGTTCAAACTAGCTACAACAAACATAA<br>GCGAGTAGTGTAACTCAATGTCCAAAATCTAAACAGAAAAATACAGGTATTAGAATAGAGA<br>TGGGAAATTCACACGAAAGACGAGTAGCAATGCACAGTGTAACAAAGAATCTACACCAGTT<br>AAGCAGTGAATGTTTAAAGGCCCATGACATTCCGGCAGTCCAATGAAAAAACTTTATGAA<br>TTAAAACTAAATTATATATATATAGCTTCCAGGCTTTAGTTAGCACATAGGATTATTAAAT<br>ATAGTTTTGATAATACGGATCCCACTGAAAGTTATGGTACAGAGTTTTAGCTTTTTCAAAT<br>GGTGAATTGGCTGCTCATAATATACCACACACCGTGTTTGTGTTGTGCACCTATTGTATCT<br>ATGATCAAGGTTTAGAAGTAGGTAGACTTAAAACCCCAATTGTTCAGAAGAAATACAAAAA<br>TACATCGATAGTTTCTTTTTATAATTAGGGTAGCAAGTGTAGAATTAACTCTGTATACTAG<br>TAGGTCTTTTGATTTTTTTATCACTTATTTAGTGGCTTTCAACACAGTTATATGCTTAAAC<br>TTATAATGGCTGAAAAAAATAATTAGCTTATAGCTTCTCTACATAAATAAGAACATATAGC<br>TTGTCTATGAACGAAGTTTAAATAGTTTCCTAAAATTTTTTCTATTCAATGCAAATAAGAT<br>ATTTTTGATTAGCCATTTCCTAAGATAAACATCGTTTACGCACCGTCTAATATGTTTTAGA<br>AAAAATAAAATAAAATTAACGAATGGAATAGTATATAGGAGTTAACAAACTTAGATTGTTA<br>GGATTGTAGATGAATTCCCTGCAGCACGACTCAGTATTTTGAACAAAAAACATACGGTGAA<br>ATGATGTGCTTATATTTGTGAAGGCAAAAAATGTGAAGAAACTTAGAGATGCGATTTAAGG<br>ACTAGGCTGTCACTCAACTATAATATGGCGGATTTTTCATTTAGATTGGCAGAAATAAGTT<br>TTAGATCATTCAAAGCATCTTTAAACACTGATCCAAAATTTATATCATAAACGGTTCTGCT<br>GTAGGCAGGTATTTAACTATCAGTGGGTTATATAAAAATGTATTATATAGAACGCCGCGTT<br>ACCTTCATAGCTTGAAGTTATATGATTCTGCGGTTAACCATGGAGGCTATAACTAAGAAAC<br>GAAGAAAAGCAAAAGAATGAACTGGTCCTAGTGAAAAGTCATACGTGTTTACCACTACTAG<br>GCTACATGTACTTTTTGCATAGTCTAGTTGGCAGAATCATTCTAATAGGAGAAGATGGAAT<br>GGGTCAATAAGAATAATAGATGGAAGTAAGTAAACTGAAAAGAACATGCAAACAGCAATGG<br>AATGATTTCTATTTAGATCTAGAAACAATGAACTAAAAGAAAGAAAAAAAATTTAAAGATT<br>AACCAACAAGTACGTAGTACCTGCAATGTTCGACTTCTTATTAGATAAAGATAACAAGTTA<br>GTACAATTCAACTTCCTAACATCCAAACTAATATGGTGATTGTAGAGGGATATATTGAGAA<br>CACAACGACCAGGAAGACATAAATATATGATAAAATGAACTAAGGCTGCAGTGTGCACAAA<br>CAGCCAAGAGAAATAGGCATGCTCGACATGTTTATAAGTAAAAAAATAACTTTTGCTGAAT<br>GTTAGCAAACTGCTTTCGTTAAAAGGAAGAGCCGCGGCAATGCAATGGTTATCACAAATTA<br>GAATATATTATGAATATTGTAGGGTATCATATGATAAGAAGGTTATATGCGCTGTTATCAC<br>CCTGAAAAAAAAAATGGTTCTGAGAGGTCCCCCACTAAATTAACTGATAAAGATTTACTGA<br>AAGAATGCTGACACAATTCTAAAGCTAAATTAAAAAAAACATTTGTTTCTATTGCGAAAAC<br>AAGCCACGAAACGGAAATCATCAAATTTATGTGTAGAAGAAAGTCAGATCAACCAACGAAG<br>AGCTCGCAGGAAGAACTTAGGGTACCTATACCTACTATTTTCGATGTTGCTGAAGAGAAAC<br>CTACTATTGCTCAATATTTTAGTACAATTGAACAAGGAATGAGGAATACGGAATTGTTACA<br>ACAGACCCTAGGTGCTATTTCCGTTTCCGAAATTTTAGTGCGCTTCCATGAGAGATACAGA<br>GATAAGATAGTCTACAAGCCTGATTATATCTGTATTTTGAATGGCATCCCTCGCAGACCAA<br>GGTCCAACAACTTTAAAAAAATAGGAACGAGACGAAAATAGTAAATTCATGGCTCCTGATG<br>GACCTAAAAAACTGCTTATAATAATTTTAAGTTGGTAAGAAATTCAAGTTTTTTTTAGTTT<br>TACTAAGCCACCAGCAAATCCTAATAGCATAAATAATTCAGTTTTCTACTATTCTTCACAT<br>AATATTCATAACAAAGGAAATGATGTTAAAATGCTTGTGAATCATGCAGGGCAAAAAAGT<br>GTTAATTTGGTAATCCTCGAATAGCGTCAATTATCAAAAATCCTATTGTTATTGGTTTTAT<br>AGCTATTCCATTTGGAAAAGACGTCAATGAAACTATTAATATAAGTGATATTAAGTCGCTT<br>TACATGTTGGTCAGTGACCACCAGATATTCATATTGGGAACTCTATTGACTAAGTGTCAAT<br>AAATTAATTTCAAAAAATTTAATGAGTGTTGATGCCGTTAAATCAACTGGTTTAAATATCA<br>ATCCACCTCCATCGAGCGTTTCACTCAATATCAAGAAAAGTACGTTAATAAGTTAGTTAGG<br>AGAAATGAATCCTATCTCACTTTTATCTACTCGATTGATGTTGACGAAGTCGAAAACCCTG<br>ATAATATTAACTAACCCATGAATACAAATCCCAATAAGCTTCTCTGAGAAACAGGAACTAA<br>CAAAACAAGTTGAAGTTTTAATCAAACAAGGTTTCATCAAAACTAGTTCCAAATCCTTTAA<br>CAGTCCAGTGCTATTTGTTAGAAAGAAAGATGGTACTATGCGTATGTGTTGATTATAGG<br>ATTCTAAACAATAATACTGCTAGGAACAAGTTTCCACTTCCAGATATTGATCAATTGATTT<br>CAAGATTTGGTAAGGCAAAAGTCTATTCTAAGTTAGAGTTGATGCCTGGTTACTACCAAGT<br>GAGAATTGCGGATGAAGATGTCGAGAAGACGGCTTTTTCTACTCTGGCCATTATGAATGGA<br>TGGTAATGCCGGCTGGACTAACAAGTGCATCTGCGACTTTTCCACAGATGATGAATAATGT<br>CTTGTCTAAAAAATAAATGGATTTGTCCAAGTGTATTTAGACGACATTTTTATATACTCC<br>GAAGATGTTGAAACTCACGGTAAGCACGTGAAAGAAGTTTTGTCGACACTAAGAAAACATA<br>AACTAATTACGAAGAAGTCGAAATGCAGATTCTTTTATCAAGAATTTAGGTTTTTAGGACA<br>AGTTGTTACACCAATTTGTATTCAAACCGCTCTCGAGAAAATAAAAAAGGTAAAGAGTTGG<br>CCAACACCAAAGACTGTCGAAGAAGCACAAAGGTTTATTGGTTTAACTTCGTATTATAGAA<br>GGTATATCAAAGGGCATTCCAAAATTGCTAATCCAATTCATAAGTTCATGACAAAACAAAT<br>TAAATGGACAAGTGAACAAGACGAAGCCTTCAACAAACTAAAGAAAGCTTTGATATCAAGT<br>CCCATCTTGGTGCACCCAAGCTGGTCAGGCAATTGTAAATTTGTTCTACATACCGATGCGT<br>GTGGAGTATCGTTAGGTTATACTCTAGAACAGTTGGACGAAACAGGTAAATGACGAGGTGT<br>GATTGCTTACGGTTCAAAGAAGCTAGTTGGAAGTCAACTGAATTATGGAATATATGACCGT<br>GAATTTATGGCTGTTGTTGAAGCATTAAGAACATGGAGATATTATCTCATGGGAAGACATT | |

TABLE 7-continued

CENs sequences

| Sequence | SEQ ID NO |
|---|---|
| TCATTGTTATGACGGATCACAAGAGTTTAATTTACTTAAAAAACCAAAATCTCATAGACTC CACTAGAGTGGCTAGATGGATGGACTTTTTACCACAGTTTGATTTTGATATTCGTTACTTA CAGGGAAAAAACAATTCCGCTGCTGATGCGTTATCTAGATACCCATACAACCACTAAAACA GGTTAACGCTAGCCAAAATCGAATTGGCGTTGCTGGAATTGACGTAAAAAGAGGAGGATGA AACACAGAGACATTCCTTGACACTAAGTACTATCGAAGCCAATCAAGAGTTAAAAAAAAAA ATTATTACGGGTTATAAAAAAATACTAATTATGCCTTGATATTCAGAACTTTGAGAGAGA AAACAAAAGTTCCAGTTGAGATAAAAAATCATATCAAACATTTCTGTTATCAAGATGAGGT ACGTTATTATAAGACATTAGAGTCTCAAGATTTCTTTAAAGTAGTTATTCCAAACTACAAG AAACTACCGTATAGAATATTCAAAATGCACACGATTCCAAAGATGCTTGTCACTTTGGTG CATGGAAAACTTATTTGAATCTTAAAGATAGTTTTTATTGGTCATCTATGTTGAGACAAAT CAAAAATGGGTAGAAACCTGCCATATCTGTCAACAGCACAACACTAACACCAGAAGAAGAC AAGGGTTGTTTTCCCCTTTACCAATCCCAACAGGCTACACTATCATTATGGTTATTGTCGA TCGCTTCTCAAAAATGACACATCTTATACCCACGCACAAAAGACTTAATGCTACTGCATGT GCTCGTTTGTTTAGTGACAAAGATATTCGGTTTATGAATAAGTTCTGGCAGACATTACATT ATCTCAATGGTAGTTCTCTATTATTTTCAACTACTAATCATCCAGAAACTGATGGTCAAAC TGAAAGATTCAACAAGATTGTTAATCAGTTACTTCGGAAATATTCTGCAAACGTTCAATTA TCCTGGAATGAGCATCTGTCTATGTGTGAACTTAGTTACAATTCAACGTACCAAGATTCCA TTAAAGCAAGTCCTTTTGAAATCGCCTACGGGTATGAATCGAACATGATTAAAAAAGTAA ATAGCTGGGATTTGGAGGATAACAAATATTCACCTAACGCAGAAGAATTTGTGAGACGTGT GAAATTGATTTTAGAGCAAACACTGGATAATATTGTAAAGCGCAAGGGCAACAAGGAAAAC ACCATAATAGAAAAGAAGATATTTTGAATATAAAGTTGGTGATTTTAGTGTTAGTGCATC AAGATGCCTTTGGTGTGAATATAAGGTACACAAAAATTCAACCAGTATGATATGGGCCATA CAGACTAGTCGAGAAAATAAACGGCAATGCTTATAAAGTCGATTTACCGGTTATTAATTTG AAGGATTGTGAATCAAATGTACAGTGGATTAAATACTATAAAGAAAACCCCAATATTTACC ACGAATCGCCTAGAACAGAGCGTGAGATGTTGGCAAGAATTAACGAACTGAGTGGTATCGG TGGATGGTCAGAAGAACCAGGCAAAGAAAAGACTTATGATGTCTTCTGGAAAGACTGTGAT CAAACTCTAGCAAGAAAGGTGCCTGAAAGAATATTCAACCAAGCAGCTTTGTCACTACGTC AAAGCCTAATGCACAATGCCAAATCGATCCAAGAACACGAACAAGCTTGATATCAACAAAG TAATCATGATTATAATACATAGAACGTTCCTATTTTCTCGAATCTGATGAGAGAGGTATAG ATATTGTTATTACTAGGAAATATTGACAAGTATTAACTCTACTTTGGAAATCTATGTGGAA GTATTTAAAATGGAGTTTTGTAAAGAACTTATATAATACAACATAAAAACTAAATTAAGCA AGGCAATAATCTGATACTTGTAGGGAACATCATGTGTCTACTAAGCTAGATATCCAAGGAC GGGTGCACTTTTTGAATGCTAAGAAATATAAACACAACCATATGCATTAGTAAATACTAAC TCCTTAATTTTGACAGGTTGCCTGATCAAGTCTGTTTGGCTTCATTTGGCTCATAATGATG TTCGCATTTCGATTCACCAATGTTTAAATTATCTCTCTTAACAATCAGAATCAGCATGATC AGTTGCTTTAACTCTCATTGAGTGGGCGCAAGTACTCAAGGGAAAGTAAACAAAAATCTAC TCAATCTACTGACTTTTTATTTTTCTGCTGCACCTATGACGCTCACGACTTTTCGTTCTCT AGAGAAGCGGAAAAGATATACCTGATGTAAATAAAAAGGCATGGGACTTAGCTTGCCCATT CGAAACAACTTTTTACAATTATGACAGGAAACATTTTGTAGGCAAGCATTATATAGGCTAC AAAACAGTAATATTTTTATTTTTGCTTTCAATACTAGAGCTGTTTAAATCAAAGATGCTG ATATATGCTCATTAACTTATGTTGTTTCTCTATATGTAGTTGTTCTCTGCCTTGATAGGAA AGTGATAGCCTTTTTCAGAGCATTGAAACTCAAGTCTAAATATATTCCCAAAAAACACTTT ATCCTTGCAAAAAGTTCAAAGACTACTGGTTTTGTTAAGCGACAGTATAATTGTTTAAGTC GAGTTTGCAAGTGGAACATACACTATTTCTTAGAAAAACAAATATTACTGAGTTGGAAATT ATGTTTATGATAACATCAGTAGGTATGTTATACTGTTTTCCACCCCAATTCAACTCTTCTA ATTGAATAACCGAGGAAAATATTTCAAACCATCAAAATATATATACCATTGGCCAGAAACG ACTACTTTTACCTAATGTCTCTGCACGCCGCTGAATGTTATTTTCGAAGTACTTTGGAAAC TTATACTTAATTTTGCAAAAGGACTTTTTAGAATTACCTAACTTCATATAATATGAAACTC GGCGCTCAAATTCTAGCATTTGGCATTTGAAACCGGTAAACCACTTTTTCCTTGATTGTTG TACAAAAAAAAACAGATATTGGCTTCTGTGAAATTACCGAGGAGCATCTGTTTCTTTTTC GATCTCGTTTACACTAAAATCAATGGCTTATAAAGTGTACATATAGTTATAGTTTATCAAA TTGGGTCTGTGTAAAAACATAAAAAAACATGTTCAAAATGATAGAGCTTACATCGAGGCAA GGTTAAGTAATTCACGCATAAGGCAAAAGAGAGAATACCGCTGGTCTATGTCTCTGTTATT TGTTTTGGTTAGTGTTTGGTAGGCGAAGCCTTCTTAAAGTCGCCTGGAAATATAACTTAAC TTTTTTACTAAACAGCACCCAATTGAAAAAAAAGACCTCCATGAGCTGGTGATTAAATCAC GTAAGAGTAATCCATTTTGATTTTATAAGAAGTTAAATGCTGGCCTCTAGAGACGCTTTA TGGACGGAAATAGCCCGAAAGTAATTATTTCAAGCATGAATATACTATCAGTTCCGCCTTA GACGTTTATTGAAAAGGAGCTTTTATTATACAAATATGTACGCGTTGACAACTCTTTCTTT TTCCTTCTGTTAAGAATAATATAAACAGTTATTTCCTTTTATTCTAAAGAACAAAAAGAAG ATTCTCAAAACAAAGCTCAATGGTTTACGCATCATTTCCAGTATTTTTGTCAAGGCTTTGA AGCTGGGCGCTATAATCAACAATTTCATATTTTGGGATTACAATATATAACAGCAAGTTAT TAAGAAAGCTATGAGGAAAAAATCGATTTGTTGAAGACTTCTACTATCTATAGTTTCTA TCAAGTATTTGGCAATATAAAAATGGATGATAGTAAATGTAGACTTCGGATAATTACTTAT AGTTAAACGAATTCAAAGGGGATTTTAACAAATCCCAAAGGTTAGGCAATTTTGTCTG GCCTAAAGTTTCACTACTGAAATACAGTAGAGATAAGTGGCGCTACGATAATAACAAGTTC CCCTTCTAGTCATTAAAGCATCATTATGTTTACAAAAATGAAGAGAGTAAAGCTAACAGT GAAAAGCTGCTCAAAAAATATTGCAGACCGGGTTAATTTGCAAAGTTTCGAATATTGCAAA AACTTCTCGTTATTTTTCCAGGTTTTGTATTACGCATAAAGGGAAATTAAAAAAGATAGC TTCGGGTTTTGTAAACAGAGTCAAGAGACGGTCTGCTTCCTAGTTTGAAAACTTTGCAAAT GTACAGTACGATATAAAGGGCAAAAGCTATGTATATTGAACAATTTCAATAATAGATTTC TTTGAACTAGGTCTCCTCGTTTGAAGTTAGTATTCTTCATTTGAACAAGGACACTAACAAA TTCCTGCAGCCTCTTGAAAAGCAGCGGCTAAAGAGTTCTTGCTCCTGATGCTTTAAAAATG GAGCTGTCTTTGTAAAGAAAAAGATTTGTCAATAATGGAAAAAAAATACTTAATGAAAGT AGCACTTTGGATATTTACTACTTGTTTGATCCCGTTGTTGGCCAAACTCTTAGAAAATTAC ATTACTTTGAAATAAATATTATTAATACAAAAAATTTCATAATATTTACTTCGACATATGC | |

TABLE 7-continued

CENs sequences

| Sequence | SEQ ID NO |
|---|---|
| TATAATGTCGGGCAATACCTATGTGTATAGCGAAATAGTAAAGGGCGGGTTGTAAATCGTA | |
| TGTTTTCACTACTCAGACTCATACGACATGTCTAGAAGCCCAAGCAATGAATTAGAAGACT | |
| GTTTGGTACCAATATTCAGTCACCTTGGGTGTAACAAAACTATTTAAAGAGATACTAGAAG | |
| ATATAACCAAATATCATGCACAAAATATAAATGTATAAGTGAAAGTAATGTATTGACACAT | |
| TTTGTTTCGGGCACGTGCGCATTAACAGATTCCGTATAAGGTTGATAATTATAGTACCTGG | |
| TGAAGAAGCATTATTCAGAAAGGTTGTAGCCCAACTAGATGTTGAAGTGGACCTTCTAATT | |
| TCCTTAAATACAATAGAAGCAAAATAGGTGTTTCACCTATCACAAACACGATGAGTATTTT | |
| CTTGTTTTGCTTTAGTCAAATAGAGCTAATTAGAAAATCCTTCGATATTTGATGCCTTGGC | |
| TGGAACCAACTCAAAAACATCTTTCTGGATTATATTTTTCTAGTAATATTAGGAAAATAAG | |
| AAACAGTTACCCAGAATAGATGGGATTAATAAACAACCGTAACATTTTTTATCTTTTCAT | |
| GCGATTTTCTCGAGCTTTACATTTTCTATTCTCTCAAGAGCCAAGTTTGTGTAGCATTTGC | |
| TTGGCCTATAATTTTTATTTAGCTCAACGCTAAAGAATACTTGTTATTGAAAAATACCACC | |
| AGTAATAAAGTACGCAAATATAGCTTCTCTAAATATTCATGAGTATCCACCTTGTAAAGGC | |
| CTCTGTAGAAAATAACCTTATATTTGGCTAATAATTCTCACCTTAAACAGTTTCAAAAT | |
| CATATAAATGGGGTTCGTAGAAAGGTGAACAAAATAACCCAATATATCAATAACTCATGAT | |
| CCAATTTGTTCATCAGCTAGATAATTATCTAGCTGATGAATACTACTTTTCCCTAGACTCG | |
| TTAAGATTTTTCAAAATATATTGCGCCAGGGAAACTATACGTTGTACTGTTAACATTAAAA | |
| TTAAAGTATGGAATAAAAAAGTTTGTTAGTTCAATATATGATTGATAGATCTGTTTGCAAA | |
| GTAAAAACGGTTTCGATATATAACTAAAGCATTAAACATCAAACTAAAAACATCTTTATCA | |
| GTCTCAAAGAGGCCCCGGAGGCCGAACGGGGAAACCAATGTCTAAAACATATAGTTGTGTT | |
| GACAATTCTTTCTTCAAAGGTTATTTCACATATTTACATCTAGCATAGTACATATTTTTAA | |
| TTCCCTATAATAACCAGTATATATCCTTTTTTAAACTATTTTCATATGTTGTGTTATACCT | |
| TTTGATAATAGTTCAATTTATAGTTCTTATTCCAGAATTCCAGAGTTGAATTAACAGAGTG | |
| CTGCAAACTGTATTTTTAAACTTTATTTATTCCAAAGGCACAACAGTACAAACTCATAATT | |
| CCGTTTTTGAGGAAAGCTTTTCATTGTTTTATCCTTAGCAAAATAGTCTTTTTTATCATTG | |
| TTGTTTATGCTACATTATAGGAGTCATACGTGGGATTATTTAGTCGAAGCTTAAGCTGATT | |
| TGACAAACACCTTAAAGTTACCATGAGAGCTCCTTTAGTATATAGTTCTTTTGTGGTCATC | |
| TATAATATATGCCAAATAGAATCGGTTTACCCTGAAATGATCTTTAAATAATAATAGTCTA | |
| TAGAGCTATTTTAGTCTCACTTATATACAGTTTTATCTTCACAAAAGTTTGAACACCTTCT | |
| TGTAGCACATTTTTGAACAGCTTACCAATTAGTTGCAGCATCTATCTGTGTTACTCTGAAA | |
| AAATCAACTACTAAAAATTTGGATTTCAGCAGTGAAGGTTTATCTAGTTGTCAAGCATTAT | |
| TTCTAAAGAGGTTCAATCTCACGTAAGTCTATTTCTAACTACTATTCTATAAAAGGAAGCT | |
| TAAGCAATAAACAAAGTGAAATTATTCTCACTGTAGATATGTCGCATTTTACCCGCTCCAG | |
| GAACTCCCAAATAGTCTAAAAGAATTCTAAAACTCAACCTTGAAAGACAGCTATTAACTAA | |
| AATTTCACAATTTTAAATTCTAAAAAATAATGCGTTTGAGGCCAACAGGAATCGAACCTGC | |
| AACCCTTCGATCTGGAGTCGAAAGCTCTACCATTGAGCCATAGCCCCAACACCTTGGGATA | |
| AGAGTGTTGCTACTGATGCGTACTTTAGAATCTGATTATTGCTTATTTTTATCTTATATAT | |
| TTTTATATGTTAATTCTCTGAAAACATATATGGAATGTCCTCTGTTTAAATAGTAATTCTT | |
| TAATTTAAAAATAGCATTTTGAGGGATTTAATTATCTTCTAGAACTTCTGTTTAACCTTCT | |
| ACAACCTTCTTCAACCTTCTATATGATTACCCGATGAGGAAATAGAGAGATAGTCCTTTGT | |
| CTGATCTCTTACATTACCCCGCGCTTTAGAAACTTCGTACCGAAGTTTATTGTCCTTATC | |
| AATTGCTTTTGCATTATCCCATAAAGTTCTCTGTAAATCTTCTGGGATCTCTAAAAATAAT | |
| GAAAATGGGATGCTTGAACTATGACAAGGGTCACAATCTTTCCAGTAGACATCCAATGTAT | |
| CGTTTGTTTCGTCGATACCAGCTATACCGATAATCTCGGTCAGTCTACTTCTTGCTTCAGC | |
| TATTGTTCTTGGGGTACCTTGGGAAACTGTTTATCCGCTTGTAAGAATCTTCTAAGCCATC | |
| TGACATTGATTACTCTATCCTTTTTATTCGTTTTCGGTAAATCAACTTCGTAGGCGTTGTC | |
| TGATATCTTCTTGACAACCTTGTAGGGTCCGTAGTATACCGGTTGTATTTTGTAATACAAT | |
| CTATCACTACCATATGCATCTTTGTGTAATAGTATCCAATCTCCAACTTCAAATGTTTCGT | |
| ACACTCTCGACTTATTATGCTGTGTTTCCTGGCTTCTTTGCGCTTCAATCATGTTTTCTTT | |
| CACATTTTCCATGATGATTTTCATTTCTAATGCGAATTCTTCAGCTTTATTGCTGTACCTT | |
| CTACTTGAAACACGACTGCTAGAAATAAACATTGGCGAGTCTGGTAAGTAACCATAGCAAA | |
| CTTCAAATGGTGATGAACCGATCGAGACTTGATGGGAACTATTGTAGGCAAATTCGGCCAT | |
| TGACAACCATTTGTCCCAACTGCAGAGATCGTTACTCGCATAATTTCTTAGTAATTGGTTT | |
| AAGATTCTGTTCGTTCTTTCTGTTTGGGGGTGATTAGTGGTTGAGAAGAGCGATGATGTAC | |
| CAAGAATTCTATGTCATTATCTGAAACCATTCTTTTTGGAATCCCATGTAATTTAAAACAA | |
| TTATCTACCATCAATTTTGCACATTGCTCTGCGGTTGCAGTTTTCCTAGTGGGGATGAAAT | |
| GTGCCATCTTCGTGAATCTATCCACCACTCCCAAATCATATCGTGTCCATTTTTGCATCT | |
| GGGGACACCTGTGAGGAAATCCAAACTATGTCTGTCCATCTTCCTTCAGGAATCGGAAGAG | |
| GGGAAAATAATCCTCTTTGACCAGTTGTCTCGGGTTTAGTTTTCTGGCAAACCGTACATCT | |
| TTGACAATATCTCTTCACGCTTTTTAGCATATTTGGCCAGTAAAACATAGGGTGAAGTCTC | |
| ATGTATGTTTGAAATACCCAAAATGACCAGCAGAGTTACCGTCATGAGCGTTACCAATAA | |
| TTTCCTGAACCAACTTAGACTTAGGGGAGACTACAATTCTTCGATCATTTCCTCCTTTAAC | |
| CACTGAGAAATATAGTAAATTATCCTCAATTGAATAATGTTTGATGTGGTTATGGATTGAC | |
| TTCGGGACCGGCAAATTCTCTTTAAAATGTCGTATATCTCCTTAATTTCGTTGTCTTCATC | |
| GTACGACTTATTGATCCGTTCTAGCAGTTCCTGATTTGGTGTTAACACCGATTCTATTGTG | |
| TTGATACCAACTTCTTTCTCCTCGTAGGGGTACCTAGACAAAGCGTCTGCTACTGAATTAG | |
| TAGGACCTTTCACGTACTGAATGGTGAAATCGTAATCAGCTAAATAATCCAACCATCTGAC | |
| CACTCTATGGCTATCTATTGCATTCTGTCGCTTTAAATAGACCAACGATCTGTGATCTGTT | |
| TTCAATACAAAGTGCCGATTTAATAAATAGTAACGCCAGTTCTTTAATGCTTCGACAACAG | |
| CGAGAAATTCACGGTCATATATTGAATAATTTAATTCTGAACCTATTAATTTCCTGGAGCC | |
| ATAGGCTATTACACCACATAATTCTCCATCTGGATCGAGCTGTTCTAACACGTACCCTAAT | |
| GCAGTACCACAAGCACCTGTGTGTACCACAGATGTATAACCATCTTCCCAAATAGGATGTA | |
| CTAAAATTGGGGTATTAATCAACTTTCCTTTCAGCTCTTCGAATGGTTTATCTTGAGGTTC | |
| CTTCCAAACACATTTCTTATTTGCGAATTCCATTATAGGAGATGCAATCTTAGAATGATCT | |
| TTGATAAATCTTCGATAATAACCAGCTAATCCCAGGAATGATTGAGCATCTTTGGCGTTTT | |

TABLE 7-continued

CENs sequences

| Sequence | SEQ ID NO |
|---|---|
| TCGGAATTGGCCAACTCTTGATTTTGTCTATCTTAGCAGGGCCAGTCCGGATACCTCTGCT<br>TGAAATGAGATGTCCTAAGAAACCTAAGGTTTTGAAGTAAAATGAACATTTCTTTTTCTTC<br>GCAATCAGCTTATTTCTCCTGAGCAATTCCAATATTTTCCCAGTGTTACTGTAGTGTTCTT<br>CGACAGTCTTTGAGTAAATTATAATATCATCCAGGTACACCTGAACAAATTGGTTCAAATA<br>AGGTGCTAGAATCCTATTCATCATTCTTTGAAAAGTACTAGGGGCGTTGGTTAAACCGTAA<br>GGCATCACAACCCACTCGTAGTGACCGTAATCTGTGGAAAATGCTGTTTTTTCAATATCAT<br>CTTCTGCGATTCTGACCTGAAAGTAACCTGACATCAAATCCAACTTGGAAAATACTGAAGC<br>TCCTCAAAAAATGTGATTAATTTGTCGATTCGTGGTATTGGGAACTTGTCTTTTACCGTA<br>TTGTTATTCAGTAACCCATAGTCAACACACATTTTCATACTACCATCTTTCTTCTGGAACA<br>AGTAACAAAAACTATTGAAAGAACTAGGGGCAGACTTGATAAAGGCTAGTTTCAACAGTT<br>CATCAACCTGTTTATTCAGTTCTTGTTTCTCTGAATAGCTTGATTTGTACTGGCGTCTGTA<br>AGTACTCTTGGTAGGTTCAATGAGTATAAGTCTGTGAGTCAAATCCCTTTGGGGAGGTAAA<br>CTGGTGGGTTGGTCATTGGTCACCACATCTCTAAATTTTTCATGAATTTTCTTTCTAATTC<br>CAACAACACCACCGTAAGGTTCTTCTAAAACATTATTATTTCTTTTTCTTCAACTGACTG<br>CACGCATAGATTTAATAGCTATAAGTTCATTTTCTTTGTTTCTTCTAAGTCATTTCCGTT<br>ATTTAATTTTATTTCTTTTTGATATCTGGGATTTCAGGAGTTTCCGTTTCCTTTTCGATAT<br>TTTCCCAGTCAACTTTATTTCCATGATCTTTAACAAATGGGAAACCTAATATCATTTTATG<br>GTTGATATCCTCTAAGACTAAGAACCTAATATTCTCATTTTGCCATTCGTCTCTTAGCTTG<br>AACTACAGTTTTGTTTTTTCTACTGAAGGTAGACTTGTAGCAATATTGTGATCAACTACCT<br>TTATGGCCTCTAATTAGTTTATTTTCTTGGCCGTTTTTTACCACCATAACCAGCACTAT<br>ATAATCTAATAAAATTTTAGCTCCATTTAAAACCTTCCAAGTTCCGACCAAGGCATAATCT<br>GTACTTTATGTCGAGAAAGATAATTAAAACAGTAACCAATAAAACCACAGCCCTCTTTATC<br>AGTTTCAAAGATGCCATTCAGGCCTAGTTAGCTGATTTATCAAATTCAGGATTTAGCTATT<br>TCTAAATTTTGATAGTAAAGTTTATATTTGTTTTTGTTTAAAAGCGATCCCGCATGTCTAT<br>TTAGCTCAGTGTACAACTGATATTCCTGTAACTGTACCAGGTGATTTTGATTTCCATTGTC<br>CTTCATATGTTCTTTTATATAGGCTCTTTCAAAAACGGTTCAACTGATAACATCACGATGG<br>ATATCTAAAGTGGAATTAATAGATCAAAGCAAGAGAGGATTTCCAAGGAATAGGGCAATTC<br>TAGTATAGGAAGACTGTGGATTGTCGAGACAAACAAAAGTTGAGTTGTGAACCTTTTGTTT<br>ATGAGAAGTTCAATTCGCACTCCTTTTCTTTAAAAGCTTGGGAATTCAGATAGAGATAATA<br>CCTACATCTACTGAATATTAAGTGAACCAAAAATCACTGTAACAGCACTCAGTCAACTAAA<br>GTCGACTGTTTAAGCTCCTCTTTAGAAAGCCCCACTCGTCTCTAAATTAGTTTCTATGCTA<br>TAAGCATCAGAGAGCTCCTCTAAGAATGTAAGAAAAGTGAAAAGCTTCTTTTGGTCTGATA<br>GTTTTTTAATTAAACAGTTCAGTAACAGAAAAACTCGTTTTGAGCTTTTCCTTGTTAATCC<br>ACGACTTTTGGATATACATTATATGCTAGGTCCTTTGTAATAACAATAGCTATTTTGGC<br>ATCGAGTTGTACAAGTTGACATTTCGTTTTATGTTGCTATTATTTAATAATATTAAGTGTT<br>TCTTATCAAATGTATATAACCTTTGTCGGATGAATAACGAACCAAGTTACAAACCTAGCAA<br>TTGGACTCTTTCCGCTAGCCTTTGCTGGTTGACTTGAGAAGGTAGTTTTTCATGATAAGTT<br>GCACCCTGGCCATCTCTATGAAAATCAATATTTCAATAATCTTATATACACTTATAATGAA<br>CGCGCATTACTCAGACAAAGAAACAAGGACTTCTTGGAATTCCAAGTTGTGGTTGTTCAAT<br>TGAATCTTTATGTTTGACTTCTTCTTTATCCGCTTTATAGAAAACTTCCTGGGACAACAAG<br>GTTCGAACAAGAACAAGAACAAGAACATGAACTTTTGCTCAATTAAACCCATTTGCTCTAA<br>TTCATTAATGAAGTGAAAAAATAGGATTGGAAAGGTTTTTCGCTAGAGAAATCGCTTTTCT<br>CAGCAGTCTTAAGTATCTGGCAATCACTGTGGTTCCCTTTGGTTTCAAAGTGTACAATCGT<br>TACCTCATAAAAGTTTTCAGTATGAATGAAATGATGTTTACTAGGGAACATAAACCATTGG<br>GATCTTTCTAGACTTAAACTGCCTTTTAAAAGCTGGGCCTTCAGAAACGATTCATCATAGG<br>GAGTTTTGGAGCTTCCTTGGATGTGCTCCTTATGTAAACTATTCCTTAGTTCTCAAAAAAA<br>AAGCAAAAGAACTGTAGTGATTTAACATCATCTGTAGGAATCTTTAGCTACATCTCTTCT<br>CAGTTTTGTTCAATATGACTTTGTTTGGAGATTAGCCTGTTTCTAAAAGTAAACGTAGTT<br>ATGTTTCAAGGTGCTTTAGACAGCTTAGGGAGTGGATTTTCTGGAGATATGGCTTGCGCAT<br>GTCATGTGCCGAGTAGTCACCACGGGTCACCTCCTGGAAAAGTATAAACACGATCTCAAAC<br>TCGATTGGTCTGAAAGGTTTTCATATGATAAGCTAAAAATGGTTTTCGCGTTAAAGCTA<br>GAATTGTCTGATTTCCTTCATCGATGTGAAGTGATCCAGTCTGACCACGCATAAAATCCGG<br>AATGGAAATCACACCAAAAGATGAGGAAATATCCAATTATGCTTAAATTGTCAACTCAAAC<br>ACAAGATGTCGCAGCAAACATTTGACGGGCTTGTAGGCTTTAAAACCAAGAATTCTGAAAT<br>AAAAACAGTACTAATTGGAACTTTATCATGAAGACACATGTATCATTTAATGCTCGACACC<br>AGGTGATGACAAACAGCACCTCTCTGGTGAAAGGGATACAACAGTTCTGCCTTATCTATCT<br>GAAAATAAAGGTGGAGTTTGTATTAGGAAAGAAAAAACATCGAGTTTATGTTGATTCCTGA<br>TATTGTGAATGGAGTTGTACAATTTGATTAAAAGCCAGGTTTGAGTAGCATCCAACTAATC<br>TCTGGTGTGGCTATCAAACCAATGTGTTTTTGGAATTGATGCTGCATTCAACGTGTCAACA<br>TGCCAAGATTTTACGGCAAAAACTATCAACCCTGAAAAAGATCTTGGTTGTGTGGGTGTT<br>GACATATTGACAAGGATTGGGTGAGAAAGAAATAATATTAAGTGTAAACCGCAGCAAACAG<br>TTTTGTCTCTCCATCATACACTACATATTTGATAATGTTTTACTTTGGGTATAGAAAGAAA<br>TATTTGACAGTATCTATTATATCTTGTATGAGGCGAGATGGAAAAGAAAAGACTATTAATC<br>TAAGCTTTTACAGTATGTTACCTATATCGTTAGGGGCTGATATCGAACCAGTCTTTAATGT<br>AAAAACCTTACTTTAAATTACTTAAATTCAAGAGATGGAAGAGATGGAAGAAACCACTGGA<br>AAGGCTGAGCTTGATCAGACCAATTAACAAAGACGGATATTTATCTCAGACAACTGACACT<br>ATACTATATAGAACACGGGATTATAGATGTGCTTAAAAACGAAGTAAAAGATATTGGGTAC<br>GAGCAGTTGTTGAGACCAAAGACGGCCACCAGCATCCATCCATTGAAAAGTCAAAACACTC<br>AAAAGAAAAGAGTTACTGGTATTAGAAGCAGAGATTTATTTGAAATTATATTGTTGGAGCC<br>AAAGTCTATAGTTCCAGATCAATGGAAATTGGACAGTGTGTTTATTGGGTATAGAAAGAAA<br>TGTGTTATTTACGTCTATAATGTTGGGTTGTTCCCTGCCATAATTTGGTTGCTATCGTTAA<br>TATTAGTCATTGTTAAGCAGCATTGCTTGAATATACTTTTTCTATAACTATATGGCGGTTT<br>ATAGTACAACATTCTAAGGATTCTTGAACTTTGGAAATCACCCCTGGAGCTTTTAAGATGC<br>ATCAGCATGTCTCATTCATCTGTAATATATCATGTGACCATGCTTTATGCTCAGGGAGAGT<br>AGGGTATTTAGGATTTGATGAACCGTATAGAACTATAAAATTCTGCAACTATTCTCATGTT | |

TABLE 7-continued

CENs sequences

| Sequence | SEQ ID NO |
|---|---|
| ATATGCTGTTATATAAGCTCTACAAGTACAGATAACGCGTTTGCTTGAATTTTGTTCGTGC<br>AGGAGTGTTTGTTATTTGGTTAAGATGAGAAGAGAATCTATTATGTTTATCCTAAAGTTAG<br>CCTAAATCTCGTTGCCCGAATGTTTACCGTGTAAAAGCTACTTTTTTTACCACTTGGAGCA<br>TCATTTTAGGGTTGTTCTGTAAGCAGCTTAAGGTTATGTAAGGTCAAGTTTTTCTTGCCAT<br>TAGGGGACTTAGAATTGTTGAGAGTTAAAGAAGAAACGTAGTGTTATGTTTATGTTGAGAA<br>ATTCAACATTGACCTGAAAAGACTCTAGTACATTGACTTACATAAACTAAACTAGATCAT<br>AATCGACAACGTTAGCTGGGAAGTTGGCTAGATTTCAACAAAAAACTTAGTATAAACAATA<br>AATAAACCTTATAAATTATTGTTTTTTTGCTCTCAGAGCAAATGGTAAGTTGCACACCCTT<br>ATACATACGCAAAATACATTAAACTCTTATAGAAAAAAAAAACTTGTGCTCTTAAAGGTCG<br>GCCTAACAATCTTGCAAATAGCTATTTGGGCCAATAACACAACAATGCTCTGATAATTCAG<br>AAGAGTTCTGGTTGTTTGCAGAGGACTAGCCTCTTAATTATCAAAGCATTTTGCCTGTTA<br>TTGTGGAACAATCATTAGCAATGTAATACATAAATTCCTTTTGTTGCATTCTACTAAATTAA<br>GCTGTTATTCACTCACATGACTCTACCCTTAGCAGCTGCTTGAATTCCATGTGTTGGATTT<br>TCTTAGTATACGTTTCTACTAACTTCAGCAACGTCTAACCGTTTACCCTTATGCTTTGCAT<br>CAAATGACGGAGTCTCTGCAGCCTTTTCTGGATTCAGCTTTGGACTATGTGATTGCTGTCC<br>CTTATGTTCCAGTTTTTTTCTTTTCATTTATTTGTTCGTTACCTACCCGTCCTTGAGCATT<br>TTCATCAAAAGAAATCCGTGTGTGACTATTCCTCTTATAGTACATGATTTAAATATATGAG<br>ACCCCCGTTAAAACAGCACTGTCTAAAGGATGCTTAAATAATAGATTCTAATCACCAACTT<br>GTTTGTACTCTCAGTTCAATGGTCCCTCTATCAGGGCTGACTCACCATGCTTAATAAACAT<br>AACGCTAATTTCAACATTATCCCACACATTGGAGTTTTTTTTTCCATCAAAAAAATAATAT<br>ATAAATAGCTTTCTTAGATTAGTGTATTCTTTTTCGCCTAATATTTGTGATATGAGCTAAA<br>AGATAGATCGATAAGGTCTAGCAAGAAAAGAGTCATTTAGTTCTCAAAGGTAACTGTTTTT<br>TTTTCATGTCACAATGACCAATATTTAAAGTCGCTGATCTTGAAATTGCAAAAAAAAAAGA<br>AACACTATTCAACTAACACATACAACCTTTTTGTACATAAAAACAAGTAGCTTTTTCAAAC<br>AGCTACTTAAAATTCAGCTACATCGTGAAACTATTCACTTTTCAGCTAGTTTGGTCCGACT<br>GGAAACGTACGTCCTTTATAATTTTTTGTTGGACTTTTCTACTGGAGAATCTGAATTTCGA<br>GACCAAGTATTTAATTATATGTCCAAAAAGAACGTAATAATCTGGAAGTACGTCTTTACTA<br>CTCAAATTTTCAAACTTAATTTTACTGTGTGTATTGGATGAATCTTCCATAAATACAGTAC<br>TTGGTAAAACTAGAACCCTCTAAGATCCTGCATTTTCCCAGTTTAAAATATGTATGGGTTG<br>AAAACAGAAGAGTAATAGCCGTCTAACAAACTTTTGATATCCCTAAAGAAAACATTTCTAC<br>GACAATATTATTTGTAATATTGGATAGCTTCCATTTCCAATCTTTTGCCGCACGAAACTCA<br>AATTAAAAACATACAATATTTGTAATGCAATAATGTAATCTTGATAATTTCTAAAAAAAAA<br>ACACCCAAAAGGTTTCATTGATCCATTCTGTAGGAATAAATCAGAAAAAAACAGTGTGCTT<br>CTTTCTAAACTTTATCAAAATGTTTGTCAAGCTATAGTTTTTATAGACACTCTTCTTTTTT<br>CTTTCTCTCCACAGTCTAATTTACCAAACATTTTTTATAGAGTTATAATAAATGTCAAAA<br>CTCTATACAGACAATTATGTATGACTGTTATGCCTTTTCCTGAACTTATTTAAACAGTACG<br>TTTCAGAAAACGTTTTGCGGCAAAGTCGAATTCGTGGTTCGCTTAGTTTATATTTCATGTG<br>GGAGTCATGTAAGCCTCTCGTTATAGGATAGTAGACGCCGGCTGTTTTAAACAGGAAGGCT<br>ATAGCTTAAGGAAAATCGTGCATCCATAAAATCATTTCTGTAAGGGCTCATATATAAGAAG<br>TTGACGTCAACGAAAAATCAATCAATAGGTGCAAATGGAACATTACGAAGTGATCTATCGA<br>CCAGCAAGAAAGTTTGCACCTTATGAGTATCTGGCAATTTCTCGGATTTTCATGTTTAGA<br>TCACGTTGCAAATTTTCACTAAATAGTGCTATGTGGAAACAGTGCTGAGGGTAATTTTTAC<br>AATTACCTAGAGAGTAAGATTAGGTACTAAGATGTGATGTCACTTTCAGAAATAGTGCTCA<br>CTTAAAGTTGTGTAACTGGCGATGGTTTCATTCGAAGCAAACTATAGTACAGGTGCGTTTA<br>AACCAAAAAGAGTACGATTCTTTTTAAATTTTGAGCATCTTTCATGATTGAGTTAGCATAG<br>TTTCGTTATCAGATTCAACACTGTAGATAGTTAACAATAGGCCAATTTCAGGATCAGTATT<br>TATTTCTGATTGTTTGACAGCTATATTTAGACCTATGTTCTGAGTTAAGCACAGAAATAAC<br>GATTAAAATTTATATCAGCATTAGTTATGGAAGACACCCTCAGTCATCATGGCACCAAAAC<br>AAAGATTAATAAGAAACCAGTTCAACTCCAACTGAATCTATTGATTCGATCTATATAATT<br>TGTGGATTCTTTTTAAGTTATCCAACTGCTGGACTAAATATGGGCATCACGTCAGGAATTG<br>TGCCTCTTGAACACCAGTTTTTATAGAATTTACAGCTACTATAAATATCTACATTGTGGCA<br>TAACGCTATTCCTTAACCACTGTTCTCCAATGTCAACTCATCTAGTATTTTTTATATAAAA<br>TATCATTTCTTATTTTGTTCGCGCTGTTTGCAAAGAAATTTGTTTTACTATCATAAAATTG<br>ATTAATTTGTCTCCCAAGACCTTTTACATGTATATCATTACTATTAATGTGCTTATTCGAT<br>AGTTATCCGCATATATTCTGAATATCATCATACTTCGCTGGAAGTTTTCCATTATATAAAT<br>TATTTTTTAGGTTCTATCGTTTTATTTACATATATATCAATGTTGTTTATTTATTGTTGAT<br>ATTGAATAACTTTTAAGTCCATTAAAAAGGATATTGCATAATTCTCACTATTTGGTTCTCA<br>ATGAACAGAATTTGTAAATATACTTGAAGTTATTTTTTCAGTTTTCTGTATATAGTGACAT<br>TCCTAAACTCATTTAGTAAATTGAAATTAGGCCATAACTAGATTTATCGACTCAGAGACAG<br>CTTTATAAAGATATTCCTAATCCTCTTACTAATAAAACAAAAATTGCATTCACTTTTTTTC<br>TGGGAGAGTCTGATTCATTTTGTTTTGCTCAGGAAATTTAATCGTGTTATAATATAAAA<br>GAAGAATTTTTCTCAAGAGTACTCTTAGACATATTTATGGAGAATGAGTTTGTTTGCCTGA<br>ATGGTAAAGTAGCTAAGAATCTTTACTTTTTTCAGGGTTTTTTTTATCTTGACTTAATGAT<br>TGGAATAATAAATTAGATTTGTAAAAAAATTGACGGAATTAGTTTGAGTGGCTTCCCATGT<br>AAATATGCTCTCTATCAGATATATTAAACATGAAAATTTATTATACCTCATTGTACTCTCG<br>ACATTAGTTAAATCTCCAGTTCTTCCTGGCGCAATATATTTATATAATCATAATGGAGCT<br>AATGAAAAGAATCTTGCTCAAGCTTGCTATCTATTTTTTGACTACTGGATTTAGCGAAATA<br>TAAGGTTATTGCTTTACAGAGGCCTTTACAAGATGGATACTCATGAATATTTAGAGAAGCT<br>ATATTTGCGTACTTTATTACTGGTGGTATTTTTCAATAACAAGTATTCTTTAGCGTTGAGC<br>TAAATAAAAATTATAGGCCAAGCAAATGCTACACAAACTTGCCTTGAGAGAATAAAAA<br>TGTAAAGCTCGAGAAAATCGCATGAAAAGATAAAAAATGTTACGGTTGTTTATTAATCCCA<br>TCTATTTCTGGGTAACTGTTTCTTATTTTCCTAATATTACTAGAAAAATATAATCCAGAAA<br>GATGTTTTGAGTTGGTTCCAGCCAAGGCATCAAATATCGAAGGATTTTCTAATTAGCTCT<br>ATTTGACTAAAGCAAAACAAGAAAATACTCATCGTGTTTGTGATAGGTGAAACACCTATTT<br>TGCTTCTATTGTATTTAAGGAAATTAGAAGGTCCACTTCAACATCTAGTTGGGCTACAACC | |

TABLE 7-continued

CENs sequences

| Sequence | SEQ ID NO |
|---|---|
| TTTCTGAATAATGCTTCTTCACCAGGTACTATAATTATCAACCTTATACGGAATCTGTTAA<br>TGCGCACGTGCCCGAAACAAAATGTGTCAATACATTACTTTCACTTATACATTTATATTTT<br>GTGCATGATATTTGGTTATATCTTCTAGTATCTCTTTAAATAGTTTTGTTACACCCAAGGT<br>GACTGAATATTGGTACCAAACAGTCTTCTAATTCATTGCTTGGGCTTCTAGACATGTCGTA<br>TGAGTCTGAGTAGTGAAAACATACGATTTACAACCCGCCCTTTACTATTTCGCTATACACA<br>TAGGTATTGCCCGACATTATAGCATATGTCGAAGTAAATATTATGAAATTTTTTGTATTAA<br>TAATATTTATTTCAAAGTAATGTAATTTTCTAAGAGTTTGGCCAACAACGGGATCAAACAA<br>GTAGTAAATATCCAAAGTGCTACTTTTCATTAAGTATTTTTTTTCCATTATTGACAAATCT<br>TTTTCTTTACAAAGACAGCTCCATTTTTAAAGCATCAGGAGCAAGAACTCTTTAGCCGCTG<br>CTTTTCAAGAGGCTGCAGGAATTTGTTAGTGTCCTTGTTCAAATGAAGAATACTAACTTCA<br>ACCGAGGAGACCTAGTTCAAAGAATTACTATTATTGAAATTGTTCAATACACATAGCTTTT<br>GCCCTTTATATCGTACTGTACATTTGCAAAGTTTTCAAACTAGGAAGCAGACCGTCTCTTG<br>ACTCTGTTTACAAAACCCGAAGCTATCTTTTTTAATTTTCCCTTTATGCGTAATACAAAAC<br>CTGGAAAAATAACGAGAAGTTTTTGCAATATTCGAAACTTTGCAAATTAACCCGGTCTGCA<br>ATATTTTTTGAGCAGCTTTTCACTGTTAGCTTTACTCTCTTCATTTTTGTAAACATAATGA<br>TGTCTTTAATGACTAGAAGGGGAACTTGTTATTATCGTAGCGCCACTTATCTCTACTGTAT<br>TTCAGTAGTGAAACTTTAGGCCAGACAAAATTGTCCTAAACCTTTGGGATTTGTTAAAATC<br>CCCTTTGAATTTCGTTTAACTATAAGTAATTATCCGAAGTCTACATTTACTATCATCCATT<br>TTTATATTGCCAAATACTTGATAGAAACTATAGATAGCTATGAAGTCTTCAACAAATCGAT<br>TTTTTCCTCATAGCTTTCTTAATAACTTGCTGTTATATATTGTAATCCCAAAATATGAAAT<br>TGTTGATTATAGCGCCCAGCTTCAAAGCCTTGACAAAAATACTGGAAATGATGCGTAAACC<br>ATTGAGCTTTGTTTTGAGAATCTTCTTTTTGTTCTTTAGAATAAAAGGAAATAACTGTTTA<br>TATTATTCTTAACAGAAGGAAAAAGAAAGAGTTGTCAACGCGTACATATTTGTATAATAAA<br>AGCTCCTTTTCAATAAACGTCTAAGGCGGAACTGATAGTATATTCATGCTTGAAATAATTA<br>CTTTCGGGCTATTTCCGTCCATAAAGCGTCTCTAGAGGCCAGCATTTAACTTCTTATAAAA<br>TCAAAAATGGATTACTCTTACGTGATTTAATCACCAGCTCATGGAGGTCTTTTTTTTCAAT<br>TGGGTGCTGTTTAGTAAAAAAGTTAAGTTATATTTCCAGGCGACTTTAAGAAGGCTTCGCC<br>TACCAAACACTAACCAAAACAAATAACAGAGACATAGACCAGCGGTATTCTCTCTTTTGCC<br>TTATGCGTGAATTACTTAACCTTGCCTCGATGTAAGCTCTATCATTTTGAACATGTTTTTT<br>TATGTTTTTACACAGACCCAATTTGATAAACTATAACTATATGTACACTTTATAAGCCATT<br>GATTTTAGTGTAAACGAGATCGAAAAAGAAACAGATGCTCCTCGGTAATTTCACAGAAGCC<br>AATATCTGTTTTTTTTTTGTACAACAATCAAGGAAAAAGTGGTTCACCGGTTTCAAATGCC<br>AAATGCTAGAATTTGAGCGCCGAGTTTCATATTATATGAAGTTAGGTAATTCTAAAAAGTC<br>CTTTTGCAAAATTAAGTATAAGTTTCCAAAGTACTTCGAAAATAACATTCAGCGGCGTGCA<br>GAGACATTAGGTAAAAGTAGTCGTTTCTGGCCAATGGTATATATATTTTGATGGTTTGAAA<br>TATTTTCCTCGGTTGTTCAATTAGAAGAGTTGAATTGGGGTGTAAAACAGTATAACATACC<br>TACTGATGTTATCATAAACATAATTTCCAACTCAGTAATATTTGTTTTTCTAAGAAATAGT<br>GTATGTTCCACTTGCAAACTCGACTTAAACAATTATACTGTCGCTTAACAAAACCAGTAGT<br>CTTTGAACTTTTTGCAAGGATAAAGTGTTTTTTGGGAATATATTTAGCTTGAGTTTCAAT<br>GCTCTGAAAAAGGCTATCACTTTCCTATCAAGGCAGAGAACAACTACATATAGAGAAACAA<br>CATAAGTTAATGAGCATATATCAGCATCTTTGATTTAAACAGCTCTAGTATTGAAAGCAAA<br>AATAAAAAATATTACTGTTTTGTAGCCTATATAATGCTTGCCTACAAAATGTTTCCTGTCA<br>TAATTGTAAAAGTTGTTTCGAATGGGCAAGCTAAGTCCCATGCCTTTTTATTTACATCAG<br>GTATATCTTTTCCGCTTCTCTAGAGAACGAAAAGTCGTGAGCGTCATAGGTGCAGCAGAAA<br>AATAAAAAGTCAGTAGATTGAGTAGATTTTTGTTTACTTTCCCTTGAGTACTTGCGCCCAC<br>TCAATGAGAGTTAAAGCAACTGATCATGCTGATTCTGATTGTTAAGAGAGATAATTTAAAC<br>ATTGGTGAATCGAAATGCGAACATCATTATGAGCCAAATGAAGCCAAACAGACTTGATCAG<br>GCAACCTGTCAAAATTAAGGAGTTAGTATTTACTAATGCATATGGTTGTGTTTATATTTCT<br>TAGCATTCAAAAAGTGCACCCGTCCTTGGATATCTAGCTTAGTAGACACATGATGTTCCCT<br>ACAAGTATCAGATTATTGCCTTGCTTAATTTAGTTTTTATGTTGTATTATATAAGTTCTTT<br>ACAAAACTCCATTTTAAATACTTCCACATAGATTTCCAAAGTAGAGTTAATACTTGTCAAT<br>ATTTCCTAGTAATAACAATATCTATACCTCTCTCATCAGATTCGAGAAAATAGGAACGTTC<br>TATGTATTATAATCATGATTACTTTGTTGATATCAAGCTTGTCGTGTTCTTGGATCGATT<br>TGGCATTGTGCATTAGGCTTTGACGTAGTGACAAAGCTGCTTGGTTGAATATTCTTTCAGG<br>CACCTTTCTTGCTAGAGTTTGATCACAGTCTTTCCACAAGACATCATAAGTCTTTTCCTTG<br>CCTGATTCTTCTGACCATCCACCGATACCAGTCATTTCGTTGATTCTTGCCAACATCTCAC<br>GCTCTGTTCTAGGCGGTTCCTGGTAAATATTGGGGTTTTCTTTATAGTATTTAATCCACTG<br>TACATTTGATTCACGATCCTTCAAATTAATAACCAGTAAATCGACTTCATAAGCATTGTCG<br>TTTATTTTCTTGACTAGTCTGTATGGCCCATACTATACTGGTTGAATTTTTGTGTACCTTA<br>TATTCACACCAAAGGCATCTTGATGCACTAACACTAAATCACCAACTTTATATTCAAAATA<br>TCTTCTTTTTCTATTATGGTGTTTTCCTTGTTGCCCTTGCGCTTTACAATATTATCCAGTG<br>TTTGCTCTAAAATCAATTTCACACGTCTCACAAATTCTTCTGCGTTAGGTGAATATTTGTT<br>ATCCTCCAAATCCCAGCTATTTACTTTTTTTAATCATGTTCGATTCATACCCGTAGGCGAT<br>TTCAAAAGGACTTGCTTTAATGGAATCTTGGTACGTTGAATTGTAACTAAGTTCACACATA<br>GATAGATGTTCATCCCAGAATAATTGATCGTTTGAAGAATATTTCCGAAGTAACTGATTAA<br>CAATCTTGTTGACTCTTTCGGTTTGACCATCAGTTTCTGGATGATTAGTAGTTGAAAATAA<br>TAGAGAACTACCATTGAGATAATGTAATGTCTGCCAGAACTTATTCATAAACCGAATATCT<br>TTGTCACTAAACAAACGAGCACATGCAGTAGCATTAAGTCTTTTGTGCGTGGGTATAAGAT<br>GTGTCATTTTTGAGAAGCGATCGACAATAACCATAATGATAGTGTAGCCTGTTGGGATTGG<br>TAAAGGGGAAAACAACCCTTGTCTTCTTCTGGTGTTAGTGTTTGTGCTGTTGACAGATATGG<br>CAGGTTTCTACCCCATTTTTGATTTGTCTCAACATAGATGACCAATAAAAACTATCTTTAAG<br>ATTCAAATAAGTTTTCCATGCACCAAAGTGACAAGCATCTTTGGAATCGTGTGCATTTTTG<br>AATATTCTATACGGTAGTTTCTTGTAGTTTGGAATAACTACTTTAAAGAAATCTTGAGACT<br>CTAATGTCTTATAATAACGTACCTCATCTTGATAACAGAAATGTTTGATATGATTTTTTAT<br>CTCAACTGGAACTTTTGTTTTCTCTCTCAAAGTTCTGAATATCAAGGCATAATTAGTATTT | |

TABLE 7-continued

CENs sequences

| Sequence | SEQ ID NO |
|---|---|
| TTTTTATAACCCGTAATAATTTTTTTTTTTAACTCTTGATTGGCTTCGATAGTACTTAGTG TCAAGGAATGTCTCTGTGTTTCATCCTCCTCTTTTTACGTCAATTCCAGCAACGCCAATTC GATTTTGGCTAGCGTTAACCTGTTTTAGTGGTTGTATGGGTATCTAGATAACGCATCAGCA GCGGAATTGTTTTTTCCCTGTAAGTAACGAATATCAAAATCAAACTGTGGTAAAAAGTCCA TCCATCTAGCCACTCTAGTGGAGTCTATGAGATTTTGGTTTTTTAAGTAAATTAAACTCTT GTGATCCGTCATAACAATGAAATGTCTTCCCATGAGATAATATCTCCATGTTCTTAATGCT TCAACAACAGCCATAAATTCACGGTCATATATTCCATAATTCAGTTGACTTCCAACTAGCT TCTTTGAACCGTAAGCAATCACACCTCGTCATTTACCTGTTTCGTCCAACTGTTCTAGAGT ATAACCTAACGATACTCCACACGCATCGGTATGTAGAACAAATTTACAATTGCCTGACCAG CTTGGGTGCACCAAGATGGGACTTGATATCAAAGCTTTCTTTAGTTTGTTGAAGGCTTCGT CTTGTTCACTTGTCCATTTAATTTGTTTTGTCATGAACTTATGAATTGGATTAGCAATTTT GGAATGCCCTTTGATATACCTTCTATAATACGAAGTTAAACCAATAAACCTTTGTGCTTCT TCGACAGTCTTTGGTGTTGGCCAACTCTTTACCTTTTTTATTTTCTCGAGAGCGGTTTGAA TACAAATTGGTGTAACAACTTGTCCTAAAAACCTAAATTCTTGATAAAAGAATCTGCATTT CGACTTCTTCGTAATTAGTTTATGTTTTCTTAGTGTCGACAAAACTTCTTTCACGTGCTTA CCGTGAGTTTCAACATCTTCGGAGTATATAAAAATGTCGTCTAAATACACTTGGACAAATC CATTTATTTTTTAGACAAGACATTATTCATCATCTGTGGAAAAGTCGCAGATGCACTTGT TAGTCCAGCCGGCATTACCATCCATTCATAATGGCCAGAGTAGAAAAAGCCGTCTTCTCGA CATCTTCATCCGCAATTCTCACTTGGTAGTAACCAGGCATCAACTCTAACTTAGAATAGAC TTTTGCCTTACCAAATCTTGAAATCAATTGATCAATATCTGGAAGTGGAAACTTGTTCCTA GCAGTATTATTGTTTAGAATCCTATAATCAACACACATACGCATAGTACCATCTTTCTTTC TAACAAATAGCACTGGACTGTTAAAGGATTTGGAACTAGTTTTGATGAAACCTTGTTTGAT TAAAACTTCAACTTGTTTTGTTAGTTCCTGTTTCTCAGAGAAGCTTATTGGGATTTGTATT CATGGGTTAGTTAATATTATCAGGGTTTTCGACTTCGTCAACATCAATCGAGTAGATAAAA GTGAGATAGGATTCATTTCTCCTAACTAACTTATTAACGTACTTTTCTTGATATTGAGTGA AACGCTCGATGGAGGTGGATTGATATTTAAACCAGTTGATTTAACGGCATCAACACTCATT AAATTTTTGAAATTAATTTATTGACACTTAGTCAATAGAGTTCCCAATATGAATATCTGG TGGTCACTGACCAACATGTAAAGCGACTTAATATCACTTATATTAATAGTTTCATTGACGT CTTTTCCAAATGGAATAGCTATAAAACCAATAACAATAGGATTTTTGATAATTGACGCTAT TCGAGGATTACCAAATTAACACTTTTTTTGCCCTGCATGATTCACAAGCATTTTAACATCA TTTCCTTTGTTATGAATATTATGTGAAGAATAGTAGAAAACTGAATTATTTATGCTATTAG GATTTGCTGGTGGCTTAGTAAAACTAAAAAAAACTTGAATTTCTTACCAACTTAAAATTAT TATAAGCAGTTTTTTAGGTCCATCAGGAGCCATGAATTTACTATTTTCGTCTCGTTCCTAT TTTTTTAAAGTTGTTGGACCTTGGTCTGCGAGGGATGCCATTCAAAATACAGATATAATCA GGCTTGTAGACTATCTTATCTCTGTATCTCTCATGGAAGCGCACTAAAATTTCGGAAACGG AAATAGCACCTAGGGTCTGTTGTAACAATTCCGTATTCCTCATTCCTTGTTCAATTGTACT AAAATATTGAGCAATAGTAGGTTTCTCTTCAGCAACATCGAAAATAGTAGGTATAGGTACC CTAAGTTCTTCCTGCGAGCTCTTCGTTGGTTGATCTGACTTTCTTCTACACATAAATTTGA TGATTTCCGTTTCGTGGCTTGTTTTTCGCAATAGAAACAAATGTTTTTTTAATTTAGCTTT AGAATTGTGTCAGCATTCTTTCAGTAAATCTTTATCAGTTAATTTAGTGGGGACCTCTCA GAACCATTTTTTTCAGGGTGATAACAGCGCATATAACCTTCTTATCATATGATACCCTAC AATATTCATAATATATTCTAATTTGTGATAACCATTGCATTGCCGCGGCTCTTCCTTTTAA CGAAAGCAGTTTGCTAACATTCAGCAAAAGTTATTTTTTACTTATAAACATGTCGAGCAT GCCTTTTCTCTTGGCTGTTTGTGCACACTGCAGCCTTAGTTCATTTTATCATATATTTAT GTCTTCCTGGTCGTTGTGTTCTCAATATATCCCTCTACAATCACCATATTAGTTTGGATGT TAGGAAGTTGAATTGTACTAACTTGTTATCTTTATCTAATAAGAAGTCGAACATTGCAGGT ACTACGTACTTGTTGGTTAATCTTTAAATTTTTTTCTTTCTTTTAGTTCATTGTTTCTAG ATCTAAATAGAAATCATTCCATTGCTGTTTGCATGTTCTTTTCAGTTTACTTACTTCCATC TATTATTCTTATTGACCCATTCCATCTTCTCCTATTAGAATGATTCTGCCAACTAGACTAT GCAAAAAGTACATGTAGCCTAGTAGTGGTAAACACGTATGACTTTTCACTAGGACCAGTTC ATTCTTTTGCTTTTCTTCGTTTCTTAGTTATAGCCTCCATGGTTAACCGCAGAATCATATA ACTTCAAGCTATGAAGGTAACGCGGCGTTCTATATAATACATTTTTATATAACCCACTGAT AGTTAAATACCTGCCTACAGCAGAACCGTTTATGATATAAATTTTGGATCAGTGTTTAAAG ATGCTTTGAATGATCTAAAACTTATTTCTGCCAATCTAAATGAAAAATCCGCCATATTATA GTTGAGTGACAGCCTAGTCCTTAAATCGCATCTCTAAGTTTCTTCACATTTTTTGCCTTCA CAAATATAAGCACATCATTTCACCGTATGTTTTTTGTTCAAAATACTGAGTCGTGCTGCAG GGAATTCATCTACAATCCTAACAATCTAAGTTTGTTAACTCCTATATACTATTCCATTCGT TAATTTTATTTTATTTTTTCTAAAACATATTAGACGGTGCGTAAACGATGTTTATCTTAGG AAATGGCTAATCAAAAATATCTTATTTGCATTGAATAGAAAAAATTTTAGGAAACTATTTA AACTTCGTTCATAGACAAGCTATATGTTCTTATTTATGTAGAGAAGCTATAAGCTAATTAT TTTTTTCAGCCATTATAAGTTTAAGCATATAACTGTGTTGAAAGCCACTAAATAAGTGATA AAAAAATCAAAAGACCTACTAGTATACAGAGTTAATTCTACACTTGCTACCCTAATTATAA AAAGAAACTATCGATGTATTTTTGTATTTCTTCTGAACAATTGGGGTTTTAAGTCTACCTA CTTCTAAACCTTGATCATAGATACAATAGGTGCACAACACAAACACGGTGTGTGGTATATT ATGAGCAGCCAATTCACCATTTTGAAAAGCTAAAACTCTGTACCATAACTTTCAGTGGGAT CCGTATTATCAAAACTATATTTAATAATCCTATGTGCTAACTAAAGCCTGGAAGCTATATA TATATAATTTAGTTTTAATTCATAAAGTTTTTTCATTGGACTGCCGGAATGTCATGGGCCT TTAAAACATTCACTGCTTAACTGGTGTAGATTCTTTGTTACACTGTGCATTGCTACTCGTC TTTCGTGTGAATTTCCCATCTCTATTCTAATACCTGTATTTTTCTGTTTAGATTTTGGACA TTGAGTTACACTACTCGCTTATGTTTGTTGGAGCTAGTTTGAACTGAATCCTGGAAGTTTA TTATCTTTTTGTGTTCTCACACCACTTGCCAAGGGACTTGAGCCTGAAAAAAAAGAATGAG TTGAAAAAAATGTAAGTTTTACACAATTTTAATCATTTTTCTTAAGTATGAATATCAGCG GTCTTGTAGGATGTTTCCATCAATAAGCTGAACTCACTTTATAGAGCACTGAATTTCATT TTTGTATAACATTTGGTTATTTCCTCTCAGTCTGGCACTCGCTTTTATTCATTTTCCTAAT AAATAGCTAATTCTGTTTCGATCAGGACTTCTAACTGTAGTGTGTACGACATCTAATTCTA | |

TABLE 7-continued

CENs sequences

| Sequence | SEQ ID NO |
|---|---|
| GAAAGGGTATTCTCACTTCCTAGTTAAGATGTGTATCATATTCTTTTATAAAACTAAAAGC | |
| ACCTAGCCTATTGAGTTTATAATACTGAAAGTCTACTGAACTAGTCATCTTTGTACATTTC | |
| TTTAGACTTAGATCCAATCTTGTTGCTTAGTTTATTTTCTATATAGTTATTCGAGTTAAT | |
| CACAAGTATCTAACAAAAGGTCCATACTTACCGATTTGTGTATTAGGATTTTTCTTCTATT | |
| TCTTTGTAGGTAGTAGTGTTTCTAGGGGTAACCTTTCAAATTGGCCCTTCTGAGTCTATTC | |
| TAGTTTGAAAAAAGCAAAGTTCTCACTAAATAACACATATTAATAATAGTCTTTGCTACGG | |
| AACTAATTATTTCTTGATCTAAACTATTTTTGCTCCTGAATAGAAGGACCTAGTTAATTTT | |
| TTATATTAAGACAGATGAAATCAAAGAAAGAAGTTGAATAAAGAATAGGTATATTTGTACT | |
| AAAGTTTGCTAAAAGCGATTTAGGTGGAGCTTCTTTTTATTTAAAAACCTCCCATAAACTT | |
| AATAACAATAAAGGTCTTCCTGTAAACTTTTGAAAAATGTACCAGAGTATTTAAGTTAAGT | |
| CCAAACCACGAGAATAGGTTAAAAGCTGCTACTTAGTTTATGTTTCATTGCCTTTTCAGTA | |
| TCTCGAGACTTCTCCGCTGTCAATAATAAACAGTTGTCTAGCTATTTTGTTTAGGTTGGGT | |
| AAAAACCTACGGAAAGACAATAGGAGCTTAGGCTATCTATTGATAGATCAATTATTTGTTT | |
| TAAGAACTATAGAATTAAAAACAAGGCAGTAGTTGTAGATTTTAAAGATTATTTAGAGTAG | |
| ATAGATAGTAAAGGCTGTACTGAATATCAATGAGGATTTGCAGAACCAACAAGTGGCCTGC | |
| ATCAAGCTATTTAAGTGATTCTATTGGTATTTTACTAGAAAAGGAAGGCTAATCATTTTTC | |
| CAATGACGGTTCATATAATCCAAGTTTTAAATGGTTTGCATCATCATAATAGGGGTATCTA | |
| AAAGGCATAAATCGACGAAAGTGATAAAAATTACTTATTAAACGACGTATTTACATCCACG | |
| TTTTTGCTGGAAGTACTGAATCTGCCTACTGCTAGTTTGGGGAAGACAATAATACACAAAA | |
| TAAAGACGATGATGAAGATTCCAGTTTTTTTTAAAGATAAAAAATAGATATATATGTATA | |
| ATTGTATGAATAGTTTTAATAATAACTTATGTTGCTATTTTGATAGCAATTCATTTTACTA | |
| TTGAAAAGGTTACCCAGGCAAATAATATGTTTAGCACATCAGATTCTGTACTAATAATAAT | |
| ATAGAGTTATGTTATAACGTCAGGCAATACTTATGTGTATAGCGAAATAGTAAATGGCAGA | |
| TTGTAAACCGTATGTTTTTACTACTCAGACTCATACGACATGTCTAGAAGCCCAAGCAATG | |
| AATTAGAGGACTGTTTGGTATCAACATCCAGTCACCTTGGGTGTAATAAAACTTATTTAAA | |
| GAGATAGTAGAAGATATAATCAAAGATCATGCACAAAATATAAATGTATAAGTGAAAGTAA | |
| TGTATTGACACATTTTGCTTCGGGCACGTGCGCATTAACAGATTTTGTATAAGGTTGATAA | |
| TTATATGTACCTGGTGAAGAAGCATTATTCAGAAAGGTTGTAGCCCAACTAGATGTTGAAGT | |
| GGACCTTCTAATTTCCTTAAATACAATAGAAGCAAAATAGATGCTTTACCTATTACAAACA | |
| CGATGAGTATTTTCTCGTTTTGCTTTAGTCAAACAGAGCTAATTAGAAAATCCTTCGATAT | |
| TTGATGCCTTGGCTGGAACCAACTCAAAAACATCTTTCTGGATTATATTTTCTAGTAATA | |
| TTAGGAAAATAAGAAACAGACACCCAAAATAAAAATTGTTTAGATATATAATTAAAGCACT | |
| AAACATCAAACTAAGGATATCCTTACAGTCTCGATACAGCTAGTCCAGCATACGTACGCGT | |
| AAATCAGAACTAGAACCGAGCTATTTTTTAGCTCATTTAGTTATGTTTTCTTCCCTTGTTC | |
| TTTGAAACGTCAGCCTACGTATATCAATCTAGATTGATACAAACCTGATGTTCTTTTAAAT | |
| AGCGAGTTAGTTCCTTTGACTTAGTTTGTTTTTATTTGTTATTTAGTATAAGATCTTTTGA | |
| TAATAGTTCAATCGGTAATTGCAATAGGGATCTCTAAAGTAAATGTAACGCCTGTCAACAC | |
| CATATATCCATTATCTACATGTGCATTTATACACGTATTAAGCACCTGCAACATGCTCAGC | |
| TAGTTTACACAGGCTATCATTGAATTGGATATTTTTGATATCGATATAGTTATTGGCCAGT | |
| CGTACAAGGTTTTGCCAAGCTTAAGTTCATTAAGACATTTGTAAGTTAGAAATAGCCACAA | |
| CTCGGTACTCTTAGCCTTTTTCGATATGTGAGAGGGCTTTTCAGGGTGTGATCCAAAAAAA | |
| AAGGAAGTGCCAGTAGATAGACGATAACATACTGATGTTAATGTTTCGATTTTAGAATAGG | |
| GAGGTTAACAAGGATCAAGTATCCGGAGTAGGAAGTTAAATTATTTATCAACGGGTTGACA | |
| GGACTGGCATATTAAAAAAAATAAAGACCTAAAACGTAATAAGCTCGTACAGGAGTCTGCT | |
| ATACGAAAAAGAGTAGCAACTGAGGGTGATTCCAGGTTGCGGGCGTGAAGTATATAAGAC | |
| GGATAAATATCCTATTATATAGAATTGATATAATTGATATAGCTCCTAATCGGGAGTGAAAG | |
| CAGCAGAAGGAGGAAGAGAAAAATCTATTACTACTTCTACTACGACTAACTTCTACCACGC | |
| CCATTATCTACTCGTGAGCTAATACACCTATTGCCTACTTACTAATACGTATATCACAATT | |
| ATCATTCCTTCATACAATACTATAGATATTGATAAGATTAGTGATTATTCTTAAAAAGATT | |
| CAACCGTCAAAACATCCCAAATTAGGAAATAATTTCGACACCTTTCTCCTGGACCCTAATA | |
| TTTCATCAGTTTCCGATATAGTGTAACGGCTATCACGGTCCGCTTTCACCGGGCAGACCCG | |
| GGTTCGACTCCCGGTATCGGAACATTTTATGCCTGGTTAGCTCAATCGGTAGAGCGTTTGA | |
| CTCTTAAGATTTCTTCTTATAAAGAAGTGCAATCAAAAGGCTGCGGGTTCGAGCCCCGCAT | |
| CGGGCTTAATTTTTTATGTTTTTGCTTGGTTGTTACTCACAGTATAGAACAGCTCTAGGTT | |
| CATTTATTATTTTATCCTCCTTTTTTATTAATTACTCTTTTATCAAGAAAAGTTCAGTTAA | |
| GAAGCACTTTATAGAAGAACTTGCTTAAGGGTGCAAGGAAAGAAATGCTGTCAATGAGTGA | |
| TCTGCCAGATGAAGATATTCTAAGTTTGTATATGTCTTATAATAATGCCAAGGAAAAGGAA | |
| GGGGAGATTTTGGAACTCATTCGAAATCGAGTCAGATTAAGGAGTAGCATTGACCATCTTG | |
| TGAAGGTGTTACGGGCAGATGGTAATGTTAGACGAAGTGTTATGAAGATATTTGAAAAACC | |
| TCTATGGAAGACTGAACGATAGTAAAATTAGAAAAAAAGATAAGAAGATAGGCGACAAG | |
| ATTTCCAATGAAATCACACGCTTAGATCGAAAATATGCAAAACTAAGTCTGAAGTATGACT | |
| TATTGAAGGCTGAACATTCAGTTTTGGAGAATGAACTGGCAAAGCTACAGACGAATTATGA | |
| AGGGCTTTCCAGCGACACATACACACCACAGGGTGGTAAAGTAATTGGTAGAAAGATTCAA | |
| TTCAAAAGTTGAGCAGAAAGAGGTAAGTCTGTTATTCAATGTTTATAGTATGTATATGTA | |
| CACAATATAAAGAAGAAAATCCTTTTGTATTCACTTAAGCTGTTTTGAAGCATAGTATTG | |
| CATAGTTTTCAATGTACAGATAGATGAAACCTTTTGGTTCATGAGAAATGCTTGAACAAAA | |
| TGATTTGCCTACTATAACATGCCAAGGAGAACCCAACTCCTCGTCCAACTTGGTTTTTATC | |
| GCAGTGGCTAATTGACTTGGCTGTGTTTTATGTTCATTATACAGGGATGATAAAATATCGA | |
| CAATGTGTGTTTTTGTCTCGTCGTCTAAATCTGTGGATTTGACATTGATGTTTTCCGATGA | |
| CATAATCTTGGCTGAGGGAAGTTGAGGTCTGAAGGTTTACAATTTAAAGGTGATTGTGTTT | |
| GGTATGATATTCAATGTGCTCGATTTCATTTCATCTCCTGCCACGTCTTATAGAAATTGAG | |
| GAAAAAAAGAGTCACGTGCCGAAGAAGAAATTTACAGTGAAACAGTGAGATCGTTAAG | |
| AAATTCTTAGATATATACATATATACAGTGTTAAAGGACAGAATGTAAGTAACAACGCT | |

TABLE 7-continued

CENs sequences

| | Sequence | SEQ ID NO |
|---|---|---|
| ECN3 - 38649 bp | TTAAAGGTAAGACTAGCTTTGCCCAAAAAAAAAAATTATTACTGTTTGACTGTCGTGTCTA<br>CTCTGGATGCCCTTAGTGTGCCTTGTTTTGAGGTTCACATTCAAAGTCATGAGGTCTCCTA<br>AATATTATGCGATTTTGTTTATTGCCCCTTGTGGTTTATTGTTTCCTTTTTCCACACATAA<br>AAAAACCCGCATTTAAAAAAATTTAAAAAAACGTCAGCTACAGGATTCGAACCTGTGCGGC<br>CAAAGGCCAAAAGATTTCAAGTCTTTCTCCTTAACCACTCGGACAAACTGACTCTTTTTC<br>TTTGAAAGTGTTGCTGGTGGTACGTACTTTAGAATCTGTTTATTGCTTGTTTATATCTTAT<br>ATATTTTTATACGTTAATTCTCTGAGAACATATATAGAATGTCCTCTGTTTAAATAGTAAT<br>TCTTTAATTTAAAAATAGTTTTTTTGAGGGATTTAATTATCTTCCAGAACTTTTGTTTAAC<br>CTTCTATAATCTTCTTCAACCTTCTATATGATTACCCGATTAAGAAATAGAGAGATAGTCC<br>TTTGTCTGATCTTTTACATTCTCTGTAAAGGACTTGGTGTAGGGTGTCGAAATTATTTCCT<br>AATTTGGAATGTTTTGATGGTTGAATCTTTTCAAGAATAGTTAATAATCTTATCAATATCT<br>ATAGTATTGTATGAAGGAATGATAATTGTGATATACGTATTAGTAAGTACGCAATATGTGT<br>ATAATCGCACGAGTAGACAATGGGCGTGGTGGAAGTTAGTCGTAGTAGAAGTAGTAATAGA<br>TTTCTCTCTTCCTCCTTCTGCTGCTTTCACTCCCGATTAGGAGCTATATCAGCTATATCAA<br>TTCTATATAACAGGATATTGTCTGTCTTATATACTTCACGCCCGCAACCTGGAATCACCCT<br>CAGTTGCTGCTCTTTTTTGGAACACAACCTAAAAAAAATTCCTTTCATACCTTGATTAGGA<br>CGATGAGTAACGTCTCGAATTATTTTGAAAATTAGGAACCAGCTACTTCTTTATTCTGTA<br>AATAAATTTACCTTCTTAATCTTATCAATAGGAGCCTCTCTACGTGAATCCAAAACAGTAC<br>ACAACTAATATTAATATAAATAACAGCTTATTCCCTTTTACCTAGCTTTTTTCCTAAGAG<br>TTATTTTCTGTAAGTTATTTCAACAATAGTTCACTCAATAACTTTAACATGAATATTCAAA<br>GAAAAACTATTACGTGTCAACACTATCTCACTCACTACACACCCAATATTTCTATAAATAT<br>CAAATTACTCTTTCTTGCTTAACTTGTTTTTTGTTAGCTTATATGTTATTTTGTAAAAGTT<br>CTTTTAGCGATAGTTTTTGAATGAATTGCTATAGAGGAGCCTGTTTAAAAGAATTTATAAT<br>AAGGAGTTGGAAAAGTTAAATGTTATGTATGCGTGATATTCCGATGAAAGCTCAGTTTAAC<br>GGACGAATTTTGGGAGAGTTAACTATACCCTTAAAATTTCTAATCTTAGTATTGATAAATC<br>CTTCTAAGTAATCAGCTATAAAATTCAAGAAGATTTTCTTTCCATATCTGGTAAAGACTTT<br>ATATACCTACTAAACATGAAACCAACAAGTTATTATCGGAGTATCAACCAACCGATTAGTA<br>CCAAATGGTTAACCTGCTTTTTAAGAAGTAAGTTATTTGATTTGGGATTTGATACTGTATA<br>TCAAGGACTCAAAATTTTCCATGAGAAACTATGTTACTAGACTGCTGTTTGTTCTGGGTTA<br>TCGGTTTTTCCATTCAAATTTTCATTGGCAAAAGAAACATCTTAGTCTTTCCTTAGAACC<br>TTCCAAAACATTACTTTTCACTTTAAATGTCAGCAATACAATCTTTAAATACATAACTACT<br>GCTTGTTCTTTGTAATAGAATTGGTAACTTGAGGTTCGGTTGCACAAATGTAATTGCGGTG<br>TTATAGCTACTAACAAGTGATAAAAAACGTTTTTTTGTAATAAGTATGCAACATTTGCCAG<br>ATCACAGAGACATAGTTACAGACTTCGCAATTGAGGCTTTCTCGGAGATTTTTTGCTGGAG<br>AATATAGATATAATTTGTTCCTGAGCAGTTAGACATTGGCCGTCTTTCTGGAGGGTTTTTC<br>AAAAACTTCATAGATACTTAAAATGAAATTCCACCACTTAAACGAAGAAAGGGAGACTTCT<br>TGAAATTCTAAATTTTTGTTGATAAATGGTAGGCTCTTTATGTTTGGCTTTTGCTTTAATA<br>GTTTTCTAAAAAAGCTCTAGAACAGGTAGGTGCGATCAGGAACATGAGCTTTACTCAATTA<br>TAACCACGTACTCCAATTACTTAAGGAAGTGATAATGTAAGATCCAAGAGTTCCTCACTAA<br>AGAGATTGTTTTAATTGTCAAAATTCTAGAAAGCACGAAGAATTCCTTTGCTTACATTGT<br>GTATGTGCGTTACCTTAAAAATGTTTTCGATGTGGTTGAACCAATGCATTTGGCATTGACC<br>GACTGGGACGCAGAAAACAAATTTGGCATCTTACCACACGTCTGGTATCAACTAAGAACTC<br>AGACTGAAAAAATGTCACACTCTAGGGATTTATTTAACTTTTATGGAGGGGTTCCTCACGT<br>TTATTATATTCTGTAGCTTTTGAATTTGCAAAACCAAAGTGATTTATAAGAATATTTAGCA<br>AACTTTTACTACTTATTTGCTCCGTTTTGCTCAATACTTCCATTTAAAAAGGATTAGTTTC<br>TTCTTAAAGGTAAATGCAGTTTTACGCCCTGAAACGCTAGGAAATTTAGCTGGAGAGTATC<br>TTACAAAAATACGATTGATGTTAGTCATGTAGTAGAGAACTCATAAAAAGCTAGCTTTTTG<br>AAGAAATTTAGCTTGGTTTTGGTATATATTGTTATTCAAAGGTTCCATTCGTAATGCAT<br>GATATTCGTTGTTAGGTCAAAATTTGCATTATCTTTACTTGTTTCATCAACGCAATCTTCG<br>AGTTTATCATATGCAAAGTCATGATGCGAACTACACTAAAAGATAAAGAGACATCCCGCT<br>ATGCTAAAATTGTTAAATCCAAAGGAATATATTTCAACAAGCAGCGTTACGCTTGTGGACG<br>TTAAAACTAAGCGCCTTGAAGTAAAAATAGTTTTAATCCGATTTTTATCACTAATACATTC<br>CGATCGTTTAGAGATTCACACAAAAAATGGCAGACCAATAGCACTTTTCTTATTCGTAGAA<br>TATGTCAGATTTTTTGAACAATTTGGAAGGTAAAAAAACAAAGGTGGTATTTATAGTGGGA<br>AGAAAGAGACAACGAGTTCGTATTAGGTGCAGATATTGCGTGCAGTTTCATTCAGTTTGAA<br>CAAAAGCCTGGTTTGGTCGTTAAATTTAAACAACCGCTTGCAGAACCATCAAACCAACATG<br>TCTTTGGAGTGGATGTTATATCCAGTGGCACAAGACTCTGAGATTTTAATCTAATAACAGT<br>CGTACATATCAATGAAAAAAGCGAAAACTCACGCTTGGTTCGTTCTGCTTTCTTCCGGAA<br>AGTGAATCAGCTGGTAACTAGAGCCTTTTTATTATGGAATTATGTGAACTTTTGAAGGAGT<br>GTTTACCCAAGATGAGTCTTTTCCAAATTCACGCCATATTGTTACAGACAATTTTAAAGCG<br>TCACAAAACACTATTATAAGTCATTTTGAGACCGATAGGGTTGCTGCAAGTATATATAGAT<br>ATAAACCATTACACGCTTCATGTGCCAAAAAGGTTTAGCTTGAAAAACTTTAGAGGTATAA<br>AATATATGTTGGGAAAACCATGTCGGATTCTGCCTTTGGGCATATTTTACCTATTACTTTT<br>TTCTCGGTAATGTACTAAATATTTGGGAGGCAATACAGAAGAGTCTCTTAGATTGGTAAAA<br>AAATAGCTAATTCTGATGCATTGCCATTGCCGGGGCAGCCAAAATTAGAGAACGCTTACCA<br>AGTTTTTCATAGATGCTCACAAATAAAGGAGACTGCCATCATCTATTGGAGCATCTGCGAA<br>TGAATTGGAAAAAAAGATTCGATCAGAGATGGAGAGAATCTTTATTTCCGTATGAAAACGT<br>TTAGTACGGCCTTTTCATCTTGACAGCACCCAATAGTGAATTATACGCAATTCTTTGAAG<br>ATACAATACAAGATAAAAGAAATCCTCTAATGTTCTTTTCAAGTTTCTTCATTCAAGTTTT<br>TTAAAAAAACAGTAATAAATTTGTTCTGGGAATACCATCTTCAGCGGTTGATTCCAGTTTT<br>TGTGTGTTCATGAAAGTAGCATAGCCCTCTACGTTTTGTAATGAACTAAACGGCTCTTAGA<br>AACTTGATACTAGTATTGAAACAGAAGTATGATAGTGTTTAAACACAGACATCTCCCTGAT<br>TCGGTTGGTGATTCTCACGTACGTTGTTGGTGCATTATAAAAAATTGTTTTTTGAGAAGAG<br>AAGAGAAAACACGCTGTTGAAAAGCAAACTAATCAATAACCATGAATATGAAAAATATCAAC | SEQ ID NO: 14 |

TABLE 7-continued

CENs sequences

| Sequence | SEQ ID NO |
|---|---|
| AGGAGAAAGGTTGAACTCTTTGCCCTCAATGAGCATTTTTGTATGAGGCGAGATGGAAAAG AAACGAATATTTATACAAACTTTGGTAGCACGTCACCTCTATCATCTAGGGTTGTTTGAAT ATATATTTTCTGTAGTGGTGTGGTGGTTACAGTATTACTTTTTCAAGATCCATAGATTTT GGAAATCACTTCTTGAAATTTTTTAAAATGCTGTTAAATACCTCCTTTGTTTGCTGCATAG GCCTGCCAGTGTTTATTTAAAATGAGTAAAATATTCAAGTTTCGTGTAGTTATGAGTAGTT TTGATGTAAGTGCCAGAATACCTTTTCATTAAAGTCTCTTTCATGACTAATCACAGAATCC TTTCATGGTTGTTTTCTAATAAACATAAACATGTCCACAACCAATTTTTCTTATCTTTACA AAGGACTTGAACTTATCGAAATCTGGTAGAGGGATTTAATGTTATTGAGCAGCTCAATATT TTATTATTAACCTGAAAAAAACCCTATCATAGCAACTAGAAAAACTTAAACGAAGTCCTGA TTAGCAATATTAACTGGGAGGTTAACTGAACTTTAGCAAGCGACTTAGTATAAAGAACATA TGAGCCTCACAAATTATTCGTTTTATTAAAAGGTAGAATCTGTTTACTTAATATTAATCAT GCCAACCCACAGCTAACCCTTATAGTAGTAGAATAACTTTTGCCTATAACGATCTATGTAG AAATATTGTGAATATCATGTTGAAATAGACAATGTATAACATTGGCAAAATAAATCACACC TTGGAAATCAATAAATATTCAAAGCAAAAGCATTTGTTATTTGAACTAGTAAATTAGTAAA ACGCTCGGATAATTCAGAACAGTTCTAGCCCTTTGCAAATCAGCTAACAATTTTTTACGCA ATAGAAAAATGGTGCATACTTTGGGTGTAGGATATCTTTAGAAAGGTAATACATAAAGCAT TTTAGCTCGTTCTATTAAATTGCTTTGTGGTTTACCCAATTAAGTTTATTGTTACAGCTGT ATGTGAGTTGTAGTTCTTCCCCTACGTGTGGGATATTTGTTTAATTAGTTGTGTTGATCTA TCCTTTTTTGCCTTTTGAGAAAGTTTTGCTGATATAGCGGCAACGTTTTTTCAAATAGATA TCAGTTGCCTTCAAATGACAAAATATCTGCAGCCCTTGCAGAATGCCGTTCTGTACTAAGT AATTGATGCCCCTTACGGCCAAATATTGTTCTTTTATTTCTTTACTGGTAACAGCCATCTT TGCAGGTTATCACCAGAGGAATTCTGCTTGTGTAATTGTTTCTCTTATAGTGCTCGCTTCA AATAGATCAAAACCACGTCCTCCAGCATTAACATTTTCTAAAGAACACCTACACAACCGCT TCTCATCAGCAACTTATTCATACTTTGACTTTGAGATTTTAGCGATAACAAGAGCCCTGTA GTGCTGAATAATTGTAATGTTAGAGCTAACAATAATTGAAATATTGTGTACCACTTATTTC ATCAAAGAAAAATAAGATATAGATAACCTTCTTGTCTCTGTATATTCTTATTCAAGTAAA AACTTTTGATATGGAGTCAAAGGTGAATCGACAAGGTTTAACAGGTGAAGAGTCAAATCGC AGAACCATTGTTCCTTGCGCGAAATGCAAGAAAAAAGGGTTTTTAGAGGCCACACACCTTT TTTTAATATCATAAGAATCAGTATCTTTAGCGTCTATCAGATTAAAAGAGTAATCATTGTT CAATAAACAGTTACAGTATTATTCTATATAAAAACAACTAGCTTTTTCTCTGTTTTTAAAA GTTAACTACATCATGAACCCATCCAAATTGTATTCATGCAGTGTTGACACTGGTCCAAATA GAAGCCCTATGCAATTTTCTGATCGACTGATCCACCAGAGAATCAAGAGCAAATTCTGTCC CACATCTGCATGAAAACGAAGTAATTAGAAAGTACACATTTACTACTCAAGTTTTCAGACT TTCTTATAGTATGCATATTAGATGCACCTGAGAAAAGTACATGTAGCATGGTGGCAAACAC TAGGCGAGTGTTGCTTCTTTGTATAATAATTCATCCCCTGGAATAATCGTCAGGTTAATGG AAAATTGAGCTGTGTGCCATAAATAGTCGACGAGCAAGTGAAGAAATTTTCCATTCTACAT TTACAGTGTTACGTCCATTCTTTTGTATATATTTTGTACTAACTAATTTTGTACCAAAA GTACAGGACTTCCAAAATATTTTACACAAGCTATTTCAAACAAGACAGCTAAAGTTTAAGA AAAGTTATTCGGTTATGTAAGATCTTATACACATGAATTTGACTTCAATACAAGCTACTAA ACCAATCAATGGGAGCTAACACAACACCTTGAAAATGATCTGCCAATAAACAAGAAAAGAT TAATGCTAAGCTTAATTAAGAAAGAATTGTTTCTTTCCAAAATATAGACATATGTCAAGCT TTATTACCTTTGAAATTCTCATCGTATATAGCTTTTGTTTTTCATCATGCCATACATTTCC AAAAGATTTCTGGTAAGTAATAACACCGTCTCTTGAGCTTATTTTCCAAGTACGAAGTTAC TTTTTGCTTTCACCTAACTAAAAATACCAAACTAGAGCAGTAACAAGAAGGTTCTACAAAA CTTGGATCCAAATAAATTTTTTCTATGTTTTCTCAAACTTTGCAAACAAACTCCGTCTGCA ATATAGCTTTTACTCAGCCTCTTTAGTGATAGCTCTAGTGTCTTCATTTTTGAAATCATAA TATTTTGGACAAGTGGAAAAGAAAAAAAAAATATTACAGCGTCAGTTACTCTTCCCTCTGTT CCATTAGAACAGGTTTAGAAGAACAGCATAGATTACTTCAGTTTTTTTTCAGCTTATAAGT AATTATCAATGTTTATATTTGCTATTATTTACGCGTATGTTAGTTAAAGATCTACAAACAC TTTCGATAGCTATGAATTCTTCAACAAGTCTGTTTTTCTTAGTTGCTTTCTTAGTTGCATC CTGCTATATGTTGCATTCCCTTAGTATGAAACTATATTTTATACTGCCAGACTTCAACCCG ACGGCAAAAGTATTGGAGATGAGAATTAAACCTTGAACTCTGTTTTCTTGACGCCCCCTTG TTTTCTTTAAAACAAAGAGAAATAACTTGTTTTGTATTATTTGTAGCAGGTGTAATTCATA CATATCTGAGATAGAGTTGAAAATATACTTATGCGTGAAATGATTGCTTTTATTCACTTTT AATGTAAGAAGCATTTTTTGAGAGCACCCTTTAAATGTTAGTAGGATCAGCAATAAGTTAC TTTTACGTGGTTCTTTCGCCAGCCTATGAGAATCATTCTCTTTTTTTCAGTAGGGTACCGT TGAATAAAATTGTGTAACCTTTAAGCGATTTTAAGAAGTCTTTGTTCATTAATCACAAAGC AGAGACATTTATGTCTCCCTTCTACATGTGGGTCACCTAACACTCCTGTTGAAAAAGAATT ATAATGTTGAGAAATCTTAAATTTAAGTACGATGATTTTTAACCTGCAAAAACCACTGATG TTTGTTGGCACGTATTGACTCTACTTTGGATATCCATACTAAATTTATAGATTGAACTGCT TATAAAAGAATGTATATTAAATTACATATAAAAACAAACTAAGCAAAAGAAATAAACATCA GAATAAAGAAATTGTTAGGGCCTGATTACGGCAAATCGGCACACTGGACCGGCTTGGTCTT AGTGAGATCAATATAGAAATCTGCCGATTGGTCTATGTTTTAATTACCTATTTCAGAAATT CTAGTGTAAAGGGATCGCAAAGGAAACAGATATTTCCCTGTGGTATGATAGAATTGATTTT CTGTTTCTTTTACAAAGCGCATAAGGAAAATGGCAATGGTTTCACATGTTGAATATTAAA ATGGTAATGCTGAATTTTATATTCTGAAGAGTCACGTAAATTTAAGCAGTGCTTTTGCAA AATTAAGTTTGAGTCCGCAAAGTAGTTGGAGAACAACATTTAGTAGCGGGTAAGAACATAA CATAAGTAGTCATTTCTGCCGAATGGCTTATAAACGTTAATGGTCTATGATACCATCCTCG GTTATTTGGTTGGAAAAGTCGAATTGTGGTAAAAAAAACAATACTCGCTGGTGTTATCATA AACCTAACTTTCAACTCAGTAGTACTTAGTTTTGCATAAAACTGCATGTCTTCCACTCGCA AACCAAATTTGAAAAAATTGGCGTGTCGCCAGACAAAACTTATAGTCCTAGATTTTTTGC AATAAAAAGGAAGTTTCAAGAAAAATATTTATGTGTGAATTTCAATGCTATAACGAAGGGT AACATTTTCAATTTTTTATTATCTATCACAATTTCTTCCAATACTCAAAGAGCTTACAAG CGCCTAACTATGTTGACTCATCTTGTTGACGTGGACAATTAAAGCCTTCACCAATAGGCGG TATAAACACCCAGGTTAGGCCCAATGAGGCTTAACAGATTGAATTGGGCGTACTGTTTGAC | |

TABLE 7-continued

CENs sequences

| Sequence | SEQ ID NO |
|---|---|
| TTAGGAAGTTACTATTCCCTAACTCATATAGTTATGTTTACATTTCTTATCCTTCAATGGT<br>AAACGGAGCTGTGTGTTTCTAGCTTAGTGCATACCTAATACTCATTGAGATATTATGTTAA<br>ATTGCATTTTCTAATGTGAGTCCATGTATTATCCAATAAAACTTTTAATATGGCTATTCAA<br>AGTACAAATAAAACATGTCAATATAGAGTAACTATATTGTTTCGTTAGCAATAACAATACC<br>AGTTATTCCCTATAATAATCTACACACTTCTCTAAGAACGCGGGCTAGCACTTTGGGTAGC<br>ACTTTCAGAAACTTCTAACCCACTTAGGGAATTTTTTTAAGCATATAAAATTGACCACTTT<br>ATTTTTCGCAGAGTTTTCGTAAATCTATTTCGCAAGAATTATCAAATAGCTCTTTGACAAA<br>CCAAGAAGTACCGCAGTATACTAGTTAAACCTTATAATAAAATTTATCACTGCCATAAACA<br>TCCTTGTGTAATAATATGCGACTACAAACTTCCAACGTTCCGTAAACTCTAAATCCACTTT<br>ATTATTTTCTGCACTTCTTTATGCTTCTAACATGCATACTTTGTTCACATTTTTTAAAAA<br>AGTGTGCATATCCAATGAAGACTCTTCAACCTTATTGCTATCTCTTGGACCTAAAAAAACA<br>TTAGAGAGTCTAGTAGATGATAATCTCTTTTGTCCAATTTCAACAACACAGACAACACGAC<br>ATGTACCCCCATAAACTCGACGTTAGGCAATGGTAAACATCATGTTGTTGTTACTTTTATG<br>TAACAGTTCACCTCCTAAGAAACTGTAAATTAATGGAAAAATAAATTGTGAATTGGGGATA<br>GTTGAGCAAGAGAAAATTTTTGTTTCCATCTTTTTAATGGTATGTCTATTCTTTGTATAG<br>CGTCCATTACCAAAATCTAGGTGTTTTCTAAAACCATGCTATTCCAATATGTGGAGCCTAA<br>TAAATACAAAACAATAAGGGGCAAAGCAATACTATATGGAAATCTCTCACGGCTATATGGA<br>AGAAACAAAAAAAACAAGACGAATTTTAACTTTCAGGGGACAATTGGGGATAAACTGCCA<br>AGAATGTTATAATAAGAAGACACATTGATCAACAAAACACGCAAATCAGAAATTAACCGAT<br>ACTCATACAGCAATAAACACTGTTTTAAAAGAATAGAAAAACACTGGAAAACATTAGCTCGA<br>GGAAGACAAGAAAATAGGCTCAGTAGAGTTTGGGAGCCTTTATCCAGTTTCCATGTATTGT<br>ATATTGAAAATAAAGATGCGATCATACATCCAAGTAGCGATTTCACATTCTAAAATTAAGA<br>GAAGGTAGAGGACAGAATCTATTGACTACAAATAGATGAGATATTTAGCATTATATATGAT<br>GTCAAATTCTTTTCAAATTGCATGTTTGGGATTTTTTGTATGGCTGCCTCCAGGCTAAAAC<br>TCAAAAGAACAATATTGAAAGAACAGCGTGTAGCTCTCTTGCAGGCTATTTTGGGCGGATA<br>TTTATATCATGGGTTATATATTGCACATTGGCATCTTAAAGACTCGTAAGCGAAATAGAGA<br>AACCATTTGTAGTGAGTTTTTGTCATTACAGTGGGACTATATCGCCATTTATTAAGAATTT<br>GTTGAGAGATAGAGGCAGCAGACTAAGGTACTACGAGGTGAACTGAATAAAAATCAAGTGA<br>TGGCTAGACAAAATATGCCGGCCTTTTTTCTAAATATATTGGTGTTCAGTAATTTATTATT<br>TGAAAGCAAACAAAAGTTCATCACAAGTTATCCAAAATTAGGAATTTCCTTGTAGAGATTG<br>CCTCTAGGAAGTGCAAATGTAGCCTAGAGCAGGCTCGATCACTTCAGCTACTCAATGAAAG<br>GCTGGTAACTGCTCCTGTCTTAGCACTAACAATAATCGAAGAATGATACAACTTTAAAACC<br>ATCGCAATTGATATGTGGAACATTAAGGCAATTAAAACCAAGTATCAAGTTGTTGGCTGTA<br>CGGCAATACGGATCAAAAAGATTATTATATGCCAAATTTTGATCTTCATCAAGAAAAGAAT<br>TTCAAACGATCGTAAAGCTCTAAATAAATTAAGAAGCTTACCTCTTCTAAAAACTATTTCT<br>TGATTTAGACTGATCACCATTCGTTCGCATATCTGGAAAATCAGAAACAGTTCCGAGAAGG<br>TGTATTAGCCAGATGGCTATTTTTTATCGTCCAATACGGGTCGACATTCAGTGTATTAAAA<br>GGCACCCTGACAAGACACTAGATACCTTATTTCGATGACTGATGATTTTGAAGCTGAATGA<br>AATTGCCCTCTTGAAGAAAACATGACAGTCATTCAAGGGCATGGAAACAGAGGTTTCAACT<br>GAGGTATGTGAATGACAAAGCCTTTTGAATCCTGAAATACGTTGCGTGAAAAAGACGGTTC<br>ACCGAATAAATGAGAATTAAACTTAAAGTTCCTATCTCCCTGAGAAAATTTTATTTTATCT<br>GGTAATCGGATGTAACGAGTATTCTCGCATATTTGAACCTAGCAAAGATATTGGGGGAAAA<br>GACACAATTTGTCAACGCCATTATGACATCACAAGACGTTATTTTAATACCTTTAAAATCT<br>AAAAATTACTATCAAGAAGTTTCGTTTGAAATTGTATGATTGAGAACCAAAAAATATGTAG<br>ATATATGTGCGCTGTGTGCATAGATCCAAACCAACCAATATTGCCATACTTGGGGTTTTTT<br>GGATGATTGTTTCAGATAGAGGGGTAACATCTACCAGTACATTCTACAAAATTTTCAACAA<br>AAAAGGGATCATCAGTCCTGCTATATACTACCATTCATTCAGAAATGAAAGACCAGCCGAA<br>AATGATAAGAGCTACAACGCTCTATTTTACTTGAGAAAACTATTTTATCAAGAACACGCTA<br>GATTGGAATATCATCGGTTTGCAAAAGAATTCAGTCATTATTTAACTTATTTTGAAGGTAT<br>TGGCGCATTCCTGTTTAATATAGATTTCTTCAGTATCCAGAACAGCACCAATTTTGTCGTT<br>GACTATTATATATTATATCATTAAAATCAACGATAAGAACAAAAAAGGAGCCAGATATTTG<br>ACAAAAATCCACCGCTAGACACAAGGTTAACTAAAAGGCACAAACGGGATATAAGAAGACG<br>GATGTACCGGCACAACTAGGACGTGCATTATCAAGTGATAGCCAACATTTTTGTATAAATA<br>ATACGTTAGTTTACCTTTCTCTGCTAACTTATAACAATCTACTCCTGTAGTACCTCGGGCC<br>ATGCACGTCAGTGATAGAACTTGACTCATTCCCATTTGAGGTTGGTTTACATACATACAAA<br>AAAAAGTATTATGCTACACAATCAATGGTTAAAAAAGTGCAATAGTAACAACGATTGGTAT<br>CAAACAATGTTAAAATTACGCGCAACCATTGGAATTGCTGAATTTGGGTAATAGTCTCAGA<br>CGTTGCAAGATTATGGAAAAGGCACACCTCTGCCCTGTTCCCTCCACTCTAGCGTATACGCA<br>ATTTAATTAATTTCCAACTTCGTTACAATCATCATTGATGGCATAAACCAACTGATTTAAG<br>CCTGAAAGAACCAAAGAATATTCTTTTCCAAGGTGTGATAATGCTACAGATTGTTTCCTTC<br>TTGTCCAGATAGATGGGTCACTTTCTTTTCCTTCGACGATACAACTGTTGAAAAAATTAAA<br>ATACGCTCGTGTAGCTTGCCAGCAATAAACTTTTAGAATTTTTGACAGCCACATTTGCTCT<br>CCTACTGCAGTCAAATATATCTTTGGAAAACCAAATATTACTACCTAAATCACCAGCGATC<br>TATCATATCATTACTTTTTCTTTATGTGAGAATCCCGAATTGGCGTTTATTGTATTTCAAT<br>ATTTTTAAGGTCTGATTACTTTTTAGGGGATCAGTAAGGAACCTCTTTTGGACTATTCAG<br>GTTAAAACACAACATTTACTTGCATCTTTCCTTTAGTTTTCGATTTTCAACTACTTCGGGCG<br>TCTTAAATAGTTCGCAGTTTCGAAGTTGTTTATACTCTTATAGGTAATGAGAACATACACA<br>TTAACTCATTGTGTTAAAAATAACCCCCTGGCAAGTAGGGTAAGTGAAAGTAGACCCAAAT<br>GATTTTTCTTTCTCTAGATAAGTGCTGCTCGTCCAAAACTTAAAAGGAAAATATAATAAAC<br>GCGAAACTTTTGACAAGCTCATGCAATTAGTGGAAAATGAGAGCTATCCATGAGAATAACT<br>TTCAAATGATGCTCAGTGAGGAATAGCAAAGGCCCTTTAAGGAAAAAAAACCCTTTTGAAT<br>CCAGACATCTCTGTAACATATGAAATACAAAGATCCGGGTTGACATTTACATTTACTTCAA<br>GATCACAGAAACAGTTTGTTTTTAAGTTACGTTTAACTTCTTTTCAATGATCAAAATAGAA<br>TATAAAAAAAGCTCTTAAGGCTGTCAAGCTAGATTAAGAGTATTGGAGCGGTATAAGAGGC<br>CATTATAGCAATAGCACAAAGTAGTTTTAATGTACAGATTAAAGTAACAGCCAAAAAAAGA | |

TABLE 7-continued

CENs sequences

| Sequence | SEQ ID NO |
|---|---|
| TCCCTTTAGCTCAATGAGAATACATCTTGTATAATCATTTTTTGAAAACTTCATTAGAATT | |
| TCAAATCATGGGATATTTTAAGAGCTCGCCAAAAAGAATTTACTGGCATGTATCAGTTCTA | |
| CCTTGGATAGCTATTAAAAGTTTTATTGGATAATACATGAACTCACATTAGAAAATGCAAT | |
| TTAACATAATATCTCAATGAGTATTAGGTATGCACTAAGCTAGAAACACACAGCTCCGTTT | |
| ACCATTGAATGATAAGAAATGTAACTATATGAGTCAGGGAATAGTAACTTCCTAAGTCAAA | |
| CAGTACGCCCAATTCAATGTGTTAAGCCTCATTGGGCCTAACCTGGGTTTATACCGCCTAT | |
| TGGTGAACGCTTTAATTGTCTACGTCAACAAAACTGATATAGGTAGTTTCACGTTGCAGAA | |
| CCCTCTGGGGAGGAAAGCCTGCATTTTCCAGCCCATATTTTTTATGTCCACTTTTCCTGTC | |
| TGTATTCCTTAAGATCTTTCCTGTCTCCTATTGTTAATCGTTGAAGATGCATATGGGAAAA | |
| ATCATGATGCTATAACTTAGCATATTTCAGGCAGGTATATTGAAGTTAATTTTATTACTAC | |
| AAATAAAGATTTTCACATAAATAAGCTCGAAATATTCTCACCGACTTATGTCACTCGGCAT | |
| TAGATGTGATATTTTGATTACTTTGAATGTGCACATGGATTTCTAAATGGCAAACTTGTTG | |
| ATATATGTAATCAAAACATTGGCCAATCGGGCAACAAACACGCTTATCAGGCCCAATGAGG | |
| CTAATCGGACAGAATTCCGCGAAATAGCAGAATCAAGATCTTGCTATTTCCCAATCTTGAT | |
| AGTTATTTTACATTGCGTAGCTTAACGATACAAACCTACCTACGCGTACCTAACTTGTTA | |
| CAGACTTAGTATATTCCTATAGGTATGAGTTTATTTCCTTTTGCTTAATTTGTTTTGATAT | |
| GTAGTTTAATATTGAAACCTGTAAACAGCGGTTTATCAGAATAACACCCATAAATATTTAA | |
| CCTCCTAATAAACTAGTCCTCAGTTTTTGTTTTTTCCTCACTTTCAAGGGGGCTGTCGTGG | |
| CGTAATCAGGTCTGGAAACAATAGCTTCACTTAATACATAATATATGTTCTATAAAAAAGA | |
| AGCAAAAACAAATGCTCTCACTCAGAGTCGAACTGAGGATCGCTACATTACTAGTGTAGCG | |
| CCTTACCAACTTGGCCATAAGAGCTTTGTTGTGGCTGTAAAATCGCACAAGTAGACAATCG | |
| GCATAGTGGAAGTTAGTTCTAGTAAAAGTAGTAACAGATGTCTCTCTTCCTCCATCTGCTC | |
| CTTTTACTCCCGATTAGGAACTATATCAGCTATATCAATTCTATATAACAGGATATCGTCT | |
| GCCTTATATACTTCACGCCCGCAACCTGGAATCACCCTCAGTTGCTACTCTTTTTCGTATA | |
| GCAGATTTCTGTACGAGCTTATTACGTTTTAGGTCTTTATTTTTTTTATGCAGTTTTTTTT | |
| TTTTTTTTTTTTTTTTATTACTTTATTATGTTTTGTCTTTATTTTTTTGGATCACACCT | |
| TGAAAAGCCCTCTCACATATCGAAAAAGGCCAAGAGTACCGAGTTGTGGCTATTTCTAACT | |
| TACAAATGTCTCAATGAACTTAAGCTTGGCAAAAAACCTTGTACGACTGGTCAATAATTAT | |
| ATCGATATCAAAATATCCAATTCAATGATAGCCAGTGTAAACTAGCTGAGCATGTTGCAGG | |
| TGCTTAATACGTGTATAAATGCACATGTATACAATGGGTATATGGTGTTGACAGGTGTTAC | |
| ATTTACTTTAGAGATCCCTATTGCAATTACTGATTGAACTATTATCAAAAGATCTTATACT | |
| AAATAACAAATAAAAACAAACTAAGTCAAAGGAACTAACTCGCTATTTAAAAGAACATCAG | |
| GTTTGTATCAATCTAGATTGATACACGTAGGCTGACGTTTCAAAGAACAAGGGAAGAAAAC | |
| ATAACTAAATGAGCTAAAACATAGCTCGGCTCTAGTTCTGATTTACGCGTACGTATGCTGG | |
| ACTAGCTGTATTGAGACTGATAAGGATATCCTTAGTTTGATGTTTAGTGCTTTAATTATAT | |
| ATCTAAACAATTTTTATTTTGGGTGTCTGTTTCTTATTTTCCTAATATTACTAGAAAAATA | |
| TATTCCAGGAAGATGTTTTGAGTTGGTTCCAGCCAAGGCATCAAATATCGAAGGATTTTC | |
| TAATTAGCTCTGTTTGACTAAAGCAAAACGAGAAAATACTCATCGTGTTTGTAATAGGTAA | |
| AGCATCTATTTTGCTTCTATTGTATTTAAGGAAATTAGAAGGTCCACTTCAACATCTAGTT | |
| GGGTCACAACCTTTCTGTATAATACTTCTTCACCAGGTACTATAATTATCAACCTTATACA | |
| AAATCTGTTAATGCGCACGTGCCCGAAGCAAAATGTGCAATACATTACTTTCACTTATAC | |
| ATTTATATTTTGTGCATGATCTTTGATTATATCTTCTACTATCTCTTTAAATAAGTTTTAT | |
| TACACCCAAGGTGACTGGATGTTGATACCAAACAGTCCTCTAATTCATTGCTTGGGCTTCT | |
| AGACATGTCGTATGAGTCTGAGTAGTAAAAACATACGGTTTACAATCTGCCATTTACTATT | |
| TCGCTATACACATAGGTATTGCCTGACGTTATAACATAACTCTATATTATTATTAGTACAG | |
| AATCTGATGTGCTAAACATATTATTTTGCCTGGGTAACATTTTCAATAGTAAAATGAATTGC | |
| TATCAAAATAGCAACATAAGTTATTATTAAAACTATTCATACAATTATACATATATATCTA | |
| TTTTTTTATCTTTAAAAAAAAAACTGGAATCTTCATCATCGTCTTTATTTTGTGTATTATTG | |
| TCTTCCCCAAACTAGCAGTAGGCATATTCAGTACTTCCAGCAAAAAAACGTGGATGTAAAT | |
| ACGTGCGTTTAATAAGTAATTTTTATCACTTTCGTCGATTTATGCCTTTTAGATACCCCTAT | |
| TATGATGATGCAAACCATTTAAAACTTGGATTATATGAACCGTCATTGGAAAAATGATTAG | |
| TCTTCCTTTTCTAGTAAAATACCAATAGAATAACTTAAATAGCTTGATGCAGGCCACTTGT | |
| TGGTTCCGCAAATCCACATTTATATTCAGTACAGCCTTTACTATCTATCTACTCTAAATAA | |
| TCTTTAAAATCTACAACTACTGCCTTGTTTTTAATTCTATAGTTCTTAAAACAAATAATTG | |
| ATCTATCAATAGATAGCCTAAGCTCCTATTGTCTTTCCGTAGGTTTTTATCCAACCTAAAC | |
| AAAATAACTAGACAACTGTTTATTATTGACAGCGGAGAAGTCTCGAGATACTGAAAAGGCA | |
| ATGAAACATAAACTAAGTAGCAGCTTTTGACCTATTCTCGTGGTTTGGACTTAACTTAAAT | |
| ACTCCGGTACATTTTTCAAAAGTTTACAGGAAGACCTTTATTGTTATTAAGATTATTGGGG | |
| TTTTTAAATAAATAGAAGCTCCACCTAAATCGCTTTTAGCAAACTTTAGTACAAATATACC | |
| TATTCTTTATTCAACTTCTTTCTTTGATTTCTTCTGCCCTAATATAAAAAATAACTAGGTC | |
| CTTCTATTCAGGAACAAAAATAGTTTAGATCAAGAAATAATTAGTTCCATAGCAAAGACTA | |
| TTATTAATATGTGTTATTTAGCGAGAAATTTTCTTTTTCAAACTAGAATAGACTCAGAAGG | |
| GCCAATTTGAAAGGTTACCCCTAGAAACACTACCACCTACAAAGAAATAGAAGAAAAATCC | |
| TAATACACAAATCGGTAAGTATGGACCTTTTGTTAGCTACTTGTGATTAATTCAAATAACT | |
| ATATAGAAAATAAACTAAAGCAACAAGATTGGATCTAAGTCTAAAGAAGTGTACAAAGATG | |
| ACTAGTTCAGTAGACTTTCAGTATTATAAACTCAATAGGCTAGGTGCTTTTAGTTTTATAA | |
| AAGAATATGATACACATCTTAACTAGGAAGTGAGAATACCCTTTCTAGAATTAGATGTCGT | |
| ACACACTACAGTTAGAAGTCCTGATCGAAACAGAATTAGCTATTTATTAGGAAAATGAATA | |
| AAAGCGAGTGCCAGACTGAGAGGAAATAACCAAATGTTATACAAAAATGAAATTCAGTGCT | |
| CTATAAAGTGAGTTCAGCTTATTGATGGAAAACATCCTACAAGACCGCTGATATTCATACT | |
| TAAGAAAAATGATTAAAATTGTGTAAAACTTACATTTTTTTTCAACTCATTCTTTTTTTTC | |
| AGGCTCAAGTCTCTTGGCAAGTGGTGTGAGAACACAAAAAGATAATAAACTTCAGGATTC | |
| AGTTCAAATTAGCTACAACAAATATAAGCGAGTAGTGTAACTCAACGTCCAAAATCTAAAC | |
| AGAAAAAATACAGGTGTTAGAATAGAGATGGGAAATTCACACGAAAGACGAGTAACAATGCA | |
| CAATGTAACAAAGAATCTACACCAGTTAAGCAGTGAATGTTTTAAAGGCCCATGACATTCC | |

TABLE 7-continued

CENs sequences

| Sequence | SEQ ID NO |
|---|---|
| GGCAGTCCAATGAAAAAACTTTATGAATTAAAACTAAATTATATATATATAGCTTCCAGGC<br>TTTAGTTAGCACATAAGATTATTAAATATAGTTTTGATAATACGGATCCCACTGAACGTTA<br>TGGTACAGAGTTTTAGCTTTTCAAAATGGTGAATTGGCTGCTCATAATATACCCCACACCG<br>TGTTTGTGTTGTGCACCTATTGTATCTATGATCAAGGTTCAGAAGTTGGTAGACTTAAAAC<br>CCCAATTATTCAGAAGAAATACAGAGATACATCGATAGTTTCTGTCTAAAATTAGGGTAGC<br>AAATGTAGAATTAACTCTGTATACTAGTAGGTCTTTTGATTTTTTTATCACTTATTAAGTT<br>TCTTTGAACATCGTTATATGCTTGAACTTATAATGGCTGATAAAAATAATTAGCTTATAAC<br>TTCTCTACATAAATAAGAATATATAGCTTGTCTATGAACGAAGTTTAAATAATTTCCTAAA<br>CTTTTTTCTATTCAATGCAAATAAGATACTTTTGATTAGCCATTTACTAAGATAAACATCG<br>TTTACGCACCATCTAATATGTTTTAGAAAAAATAAAATAAAATTAACGAATGGAATAGTAT<br>ATTGGAGTTAACAAACTTAGATTGTTAGGATGGTAGATGAATTCCCTGCAGCATGACTCAG<br>TATTTTGAACAAAAAACATACGGTGAAATGATGTGCTTATATTTGTGAAGGCAAAAAATGT<br>GAAGAAACTTAAAGACGCGATTTAAGGACTAGGCTGTCACTCAACTATAATATGGCGGATT<br>TTTCATTTAGATTGGCAGAATAAGTTTTAGATCATTCAAAGCATCTTTAAACACTGATCC<br>AAAATTTATATCATAAATGGTTCTGCTGTAGGCAGGTATTTAACTATCAGTGGGTTATATA<br>AAAATGTATTATATAGAACGCCGCGTTACCTTCATAGCTTGAAGTTATATGATTCTGCGGT<br>CAACCATGGAGGCTATAACTAAGAAACGAAGAAGAGCAAAAGAATGAACTGGTCCCAGTGA<br>AAAGTCATACGTGTTTACCACTACTAGGCTACATGTACTTTTTGCATAGTCTAGTTGGCAG<br>AATCATTCTAATAGGAGAAGATGGAATGGGTCAATAAGAATAATAGATGGAAGTAAGTAAA<br>CTGAAAAGACCATGCAAACAGCAATGGAATGATTTCTATTTAGATCTAGAAACAATGAACT<br>AAAAGAAAGAAAAAAATTTAAAGATTAACCAACAAGTACGTAGTACCTGCAATGTTCGACT<br>TCTTATTAGATAAAGATAACAAGTTAGTACAATTCAACTTCCTAACATCCAAACTAATATG<br>GTGATTGTAGAGGGATATATTAAGAACACAACGACCAGGAAGACATAAATATATGATAAAA<br>TGAACTAAGGCTGCAGTGTGTACAAACACAGCCAAGAGAAAAAGGCATGCTCGACATGTTT<br>ATAAGTAAAAAAATAACTTTTGCTGAATGTTAGCAAACTGCTTTCGTTAAAAGGAAGAGCC<br>GCGGCAATGGAATGGTTATCACAAATTAGAATATATTATGAATATTGTAGGGTATCATATG<br>ATAAGAAGGTTATATGCGCTGTTATCACCCTGAAAAAAAAAGGTTCTGAGAGGTCCCCCA<br>CTAATTAACTGATAAAGATTTACTGAAGAACCCACGGCCTAATTCTAAAGCTAAACTGAGA<br>AAAACAAGTCACGAAACAGAAATCATCAAATTTGTGTGTAAAAGAAAGTCAGATCAACCAA<br>CAAAGAGCTCTCAGGAAGAACTTAGGGTACCTATACGTACTATTTTCGATGTTGCTGAAGA<br>GAAACCTACTATTGCTCGATATTTTAATACAATTGAACAAAGAATGAGAAACACAGAATTG<br>TTACAACGGAGCCTAGGTGCTATTTCATGAGAGATACAGAGATAAAATAGCCTACCAATCT<br>GGCTATATCAGTACTTTGAATGGCATCCCTTGAATAGCAAGGTCCAACAACTTAAATCAAC<br>TGGTATAAACCACAACTCAGAGTTATCAATCAGCTACTTTCAATATCAAGAAAGGTGTGTT<br>AACAAGTTGGTTAAGAGAAATGAATCTTATCTCGCTTTTATCTACTCGATTGTGGATAAAT<br>ATGTGGAGAAAACGGCTTTTTCTACTGATTTTGACCATTACGAATGGATGATAATGCCGGT<br>TGGACTAACAAATGCACCTGCGACTTTTCAACAGATGATGGATAATGTCTTGCCTGAAGA<br>ATAGATCGATTTGTCCAAGTGTATTTAGACGACATTTTTATATACTCCGAAGATGTTGAAA<br>CTCACGGTAAGCACGTGAAAGAAGTTTTGTCGACACTAAGAAAACATAAACTAATTACGAA<br>AAAGTCGAAATGCAGATTCTTTTATCAAGAATTTAGGTTTTTAGGACCAGTTGTTACACCA<br>ATTTGTATTCAAACCGCTCTAGAGAAAATAAAAAAGGTAAAGAGTTGGCCAACACCAAAGA<br>CTGTCAAAGAAGCACAAAGTTTTATTGGTTTAACTTCGTACTATAGAAGGTTTATTAAAGG<br>GCATTCCAAAATTGCTAATCCAATTCATAAGTTCATAACAAACAAAGTAAATGGACAAGT<br>GAACAAGACGAAGCCTTCAATCAACTAAAGAACGCTTTGATATCAAGTCCCACCTTGGTGC<br>ACCCAAGTTGATCAGGCAATTGTAAATTTGTTCTACATACCGATGCGTGTGGAGTATCATT<br>AGGTTATACTCTAGAACAGTTGGACGAAACAGGTAAATGACGAGGTGTAATTGCTTACGGT<br>TCAAAGAAGCTAGTTGGAAGTCAACTAAATTATGGAATATATGATCGTGAATTTATGGCTA<br>TTGTTGAAGCATTAAGAACATGGAGATATTATCTCATGGGAAGACATTTCATTGTTATGAC<br>GGATCACAAGAGTTTAATTTACTTAAAAAACCAAATCTCATAGACTCCACTAAAGTGGCT<br>AGATGGATGGACTTTTTACCACAGTTTGATTTTGATATTCGTTACTTACAGGGAAAAAACA<br>ATTCCGCTGCTGATGCGTTATCTAGATACCCATATAACCACGAAAACAACTTAACGCTAGC<br>CAAAATCAAATTGGCGTTGCTGGAATTGACGTAAAAAGAGGAGGATGAAACACAGAGACAT<br>TCCTTGACACTAGGTATTATCGAAGCCCATCAAGATTTAAAAAAAGAAATTATTACGAGTT<br>ATAAAAAAGATACTAATTATGCCTTGATATTCAGAACTTTGAGAGAGAAAACAAAAGTTCC<br>AGTTGAGATAAAAAATCATATCAAACATTTCTGTTATCAAGATGATGTACTTTATTATAAG<br>ACATTAGAGTCTCAAGATTTCTTTAGAGTAGTTATTCCAAACTACAAGAAACTACTGTATA<br>GAATATTCAAAAATGCACACGATTCCAAAGATGCTCGTCACTTTGGTGCATGGAAAACTTA<br>TTTGAATCTCAAAGATAGTTTTTATTGGTCATCTATGTTGGCACAAATTAGAAAATGGGTA<br>GAAACCTGTCGTATCTGTCAACAGCACAACACCAACACTAGAGGAAGACAAGGGTTGTTTT<br>CCCCTTTACCAATCCCAACAGGTCGCTGGACCGACATTACGATGGATTTCATTACAGGCTT<br>ACCTAGATCGGGAACAGGTTACGATATGATCATGGTTGTTGTTGATCGCTTTTCAAAAATG<br>GCACATTTTATACCAACGCACAAAAGACTTAATGCTGCAGCATGTCTCGTTTGTTTAGTG<br>ACAAAGATATTCGGTTTATGAATAAGTTCTGGCAAACATTACATTATCTCAATGGTAGTTC<br>TCTATTATTTTAACTACTGATCATCCAGAAACTGATGGTCAAACCGAAAGAGTCAACTAGA<br>TCGTTAATCAGTTACTTCGGAAATATTCTTCAAACGATCAATTATCCTGGAATGAGCATCT<br>ATCTATGTGTGAACTTAGTTACAATTCAACGTACCAAGATTCCATTAAAGCAAGTCCTTTT<br>GAAATCGCCTACGAGTATGAACCGAACATGATTAGAAAAGTAAATAGCTGGGATTTGGAGG<br>ATAACAAATATTCACCTAACGCAGAAGAATTTGTGAGACGTGTGAAATTGATTTTACAGCA<br>CACTGGATAATATTGTAAAGCACAATGGCGACAAGGAAAACACCATAATAGAAAAGAAGA<br>TACTTTGAATATAAAGTTGGTGACTTAGTGTTAGTGCATCAAGATGCCTTTGGTGTGAAATA<br>TAAGGTACACAAAAATTCAACCAGTATGATATGGGCCATACAGACTAGTCTGAGAAAATAAA<br>CGGCAATGCTTATAAAGTCGATTTACCGGTTATTAATTTGAAGGATCGTGAATCAAATGTA<br>CAGTGGATTGAATACTATAAAGAAAACCCCAATATTTACCAGGAACCGCCTAGAACAGAGC<br>GTGAGATGTTGGCAAGAATTAACGAACTGAGTGGTATCGGTGGATGGTCAGAAGAACCAGG<br>CAAAGAAAAGACTTATGATGTCTTCTGGAAAGACTGTGATCAAACTCTAGCAAGAAGGTA | |

TABLE 7-continued

CENs sequences

| Sequence | SEQ ID NO |
|---|---|
| CCTGAACGAATATTCAATCAAGCAGATTTGTCACTACGTCAAAGCCTAATGTACAATGCCA AATTGATCCAAGAACACGAACAGGTTTGATATCAATAAAGTAATCATGATTATAATATATA GAACGTTCCTATTTGTCTCTCAGCTGAAGAAAAAAAAATACAGATATTGCTCCTACCAAAA CACAAAACATATTGTTTTTTGATTGAAATAAGTTAGCCACTCTCGATTTAAAGAAATACAA ATTGAGCTCATAAAAAAATTATTGTTACTGCCAGGATCCACCTACATTTATTATTCTAATC TGGTTTAATGTTTTGCAGCTTCATTGGTTCAGGCCCCCATCCGGAATTATTCCAGGTTGCG GGCGTGAAGTATATAAGGCAGACGATATCCTGTTATATAGAATTGATATAGCTGATATAGT TCCTAATCGGGAGTAAAAGGAGCAGATGGAGGAAGAGAGACATCTGTTACTACTTTTACTA GAACTAACTTCCACTATGCCGATTGTCTACTTGTGCGATTTTACAGCCACAACAAAGCTCT TATGGCCAAGTTGGTAAGGCGCTACACTAGTAATGTAGCGATCCTCAGTTCGACTCTGAGT GAGAGCATTTGTTTTTGCTTCTTTTTTATAGAACATATATTATGTATTAAGTGAAGCTATT GTTTCCAGACCTGATTACGCCACGACAGCCCCTTGAAAGTGAGGAAAAAACAAAAACTGAG GACTAGTTTATTAGGAGGTTAAATATTTATGGGTGTTATTCTGATAAACCGCTGTTTACAG GTTTCAATATTAAACTACATATCAAAACAAATTAAGCAAAAGGAAATAAACTCATACCTAT AGGAATATACTAAGTCTGTAACAAGTTAGGTACGCGTAGGTAGGTTTGTATCGTTAAGCTA CGCAATGTAAAAATAACTATCAAGATTGGGAAATAGCAAGATCTTGATTCTGCTATTTCGC GGAATTCTGTCCGATTAGCCTCATTGGGCCTGATAAGCGTGTTTGTTGCCCGATTGGCCAA TGTTTTGATTACATATATCAACAAGTTTGCCATTTAGAAATCCATGTGCACATTCAAAGTA ATCAAAATATCACATCTAATGCCGAGTGACATAAGTCGGTGAGAATATTTCGAGCTTATTT ATGTGAAAATCTTTATTTGTAGTAATAAAATTAACTTCAATATACCTGCCTGAAATATGCT AAGTTATAGCATCATGATTTTTCCCATATGCATCTTCAACGATTAACAATAGGAGACAGGA AAGATCTTAAGGAATACAGACAGGAAAAGTGGGCATAAAAAATATGGGCTGGAAAATGCAG GCTTTCCTCCCCAGAGGGTTCTGCAACGTGAAACTACCTATATCAGTTTTGTTGACGTAGA CAATTAAAGCGTTCACCAATAGGCGGTATAAACCCAGGTTAGGCCCAATGAGGCTTAACAC ATTGAACTGGGCGTACTGTTTGACTTAGGAAGTTACTATTTCCTGACTCATATAGTTACAT TTCTTATCATTCAATGGTAAACGGAGCTGTGTGTTTCTAGCTTAGTGCATACCTAATACTC ATTGAGATATTATGTTAAATTGCATTTTCTAATGTGAGTTCATGTATTATCCAATAAAACT TTTAATAGCTATCCAAGGTAGAACTGATACATGTCAGTAAATTCTTTTTGGCGAGCTCTTA AAATATCCCATGATTTGAAATTCTAATGAAGTTTTCAAAAAATGATTATACAAGATGTATT CTCATTGAGCTAAAGGGATCTTTTTTTGGCTGTTACTTTAATCTGTACATTAAAACTACTT TGTGCTATTGCTATAATGGCCTCTTATACCGCTCCAATACTCTTAATCTAGCTTGACAGCC TTAAGAGCTTTTTTTATATTCTATTTTGATCATTGAAAAGAAGTTAAACGTAACTTAAAAA CAAACTGTTTCTGTGATCTTGAAGTAAATGTAAATGTCAACCCGGATCTTTGTATTTCATA TGTTACAGAGATGTCTGGATTCAAAAGGGTTTTTTTTCCTTAAAGGGCCTTTGCTATTCCT CACTGAGCATCATTTGAAGGTTATTCTCATGGATAGCTCTCATTTTCCACTAATTGCATGA GCTTGTCAAAAGTTTCGCGTTTATTATATTTTCCTTTTAAGTTTTGGACGAGCAGCACTTA TCTAGAGAAAGAAAAATTATTTGGGTCTACTTTCACTTACCCTACTTGCCAGGGGGTTATT TTTAACACAATGAGTTAATGTGTATGTTCTCATTACCTATAAGAGTAAAACAACTTCGAAA CTGCGAACTATTTAAGACGCCCGAAGTAGTTGAAATCGAAACTAAAGGAAAGATGCAAGT AAATGTTGTGTTTTAACTTGAATAGTCCAAAAGAGGTTCCTTACTGATCCCCTAAAAAAGT AATCAGACCTTAAAAATATTGAAATACAATAAACGCCAATTCGGGATTCTCACATAAAGAA AAAAGTAATGATATGATAGATCGCTGGTGATTTAGGTAGTAATATTTGGTTTTCCAAAGAT ATATTTGACTGCAGTAGGAGAGCAAATGTGGCTGTCAAAAATTCTAAAAGTTATTGCTGGC AAGCTACACGAGCGTATTTTAATTTTTTCAACAGTTGTATCGTCGAAGGAAAAGAAAGTGA CCCATCTATCTGGACAAGAAGGAAACAATCTGTAGCATTATCACACCTTGGAAAAGAAATAT TCTTTGGTTCTTTCAGGCTTAAATCACTTGGTTTATGCCATCAATGATGATTGTAACGAAG TTGGAAATTAATTAAATTGCGTATACGCTAGAGTGAGGGAACAGGGCAGAGGTGTGCCTTT TCCATAATCTTGCAACGTCTGAGACTATTACCCAAATTCAGCAATTCCAATGGTTGCGCGT AATTTTAACATTGTTTGATACCAATCGTTGTTACTATTGCATTTTTTAACCATTGATTGT GTAGCATAATACTTTTTTTTGTATGTATGTAAACCAACCTCAAATGGGAATGAGTCAAGTT CTATCACTGACATGCATGGCCCGAGGTACCACAGGAGTAGATTGTTATAAGTTAGCAGAGA AAGGTAAACTAACGTATTATTTATACAAAAATGTTGGCTATCACTTGATAACGCACGTCCT AGTTGTGCCGGTACACCCGTCTTCTTATATCCCGTTTGTGCCTTTTAGTTAACCTTGTGTC TAGCGGTGGATTTTTGTCAAATATCTGGCTCCTTTTTTGTTCTTATCGTTGATTTTAATGA TATAATATATAATAGTCAACGACAAATTGGTGCTGTTCTGGATACTGAAGAAATCTATAT TAAACAGGAATGCGCCAATACCTTCAAAATAAGTTAAATAATGACTGAATTCTTTTGCAAA CCGATGATATTCCAATCTAGCGTGTTCTTGATAAAATAGTTTTCTCAAGTAAAATAGAGCG TTGTAGCTCTTATCATTTTCGGCTGGTCTTTCATTTCTGAATGAATGGTAGTATATAGCAG GACTGATGATCCCTTTTTTGTTGAAAATTTTGTAGAATGTACTGGTAGATGTTACCCCTCT ATCTGAAACAATCATCCAAAAAACCCCAAGTATGGCAATATTGGTTGGTTTGGATCTATGC ACACAGCGCACATATATCTATATATTTTTTGGTTCTCAATCATACAATTTCAAACGAAACT TCTTGATAGTGATTTTTAGATTTTAAAGGTATTAAAATAACGTCTTGTGATGTCATAATGG CGTTGACAAATTGTGTCTTTTCCCCCAATATCTTTGCTAGGTTCAAATATGCGAGAATACT CGTTACATCCGATTACCAGATAAAATAAAATTTTCTCAGGGAGATAGAAACTTTAAGTTTA ATTCTCATTTATTCGGTGAACCGTCTTTTTCACGCAAAGTATTTCAGGATTCAAAAGGCTT TGTCATTCACATACCTCAGTTGAAACATCTGTTTCCATGCCCTTGAATGACTGTCATGTTT TCTTCAAGAGGGCAATTTCATTCAGCTTCAAAATCATCAGGCATCGAAATAAGGTATCTAG TGTCTTGTCAGGGTGCCTTTTAATACACTGAATGTCGACCCGTATTGGACGATAAAAAATA GCCATCTGGCTAATACACCTTCTCGGAACTGTTTCTGATTTTCCAGATATGCGAACAAATG GTGATCAGTCTAAATCAGGAAATAGTTTTAGAAGAGGTAAGCTTCTTAATTTATTTAGAG CTTTACGATCGTTTGAAATTCTTTTCTTGATGAAGATCAAAATTTGGCATATAATAATCTT TTTGATCCGTATTGCCGTACAGCCAACAACTTGATACTTGGTTTTAATTGCCTTAATGTTC CACATATCAATTGCGATGGTTTTAAAGTTGTATCATTCTTCGATTATTGTTAGTGCTAAGA CAGGAGCAGTTACCAGCCTTTCATTAAGTAGCTGAAGTGATCGAGCCTGCTCTAGGCTACA TTTGCACTTCCTAGAGGCAATCTCTACAAGGAAATTCCTAATTTTGGATAACTTGTGATGA | |

TABLE 7-continued

CENs sequences

| Sequence | SEQ ID NO |
|---|---|
| ACTTTTGTTTGCTTTCAAATAATAAATTACTGAACACCAATATATTTAGAAAAAAGGCCGG CATATTTTGTCTAGCTATCACTTGATTTTTATTCAGTTCACCTCGTAGTACCTTAGTCTGC TGCCTCTATCTCTCAACAAATTCTTAATAAATGGCGATATAGTCCCACTGTAATGACAAAA ACTCACTACAAATGGTTTCTCTATTTTGCTTACGAGTCTTTAAGATGCCAATGTGCAATAT ATAACCCTTGATATAAATATCCGCCCAAAATAGCCTGCAAGAGAGCTACACGCTGTTCTTT CAATATTGTTCTTTTGAGTTTTAGCCTGGAGGCAGCCATACAAAAAATCCCAAACATGCAA TTTGAAAAGAATTTGACATCATATATAATGCTAAATATCTCATCTATTTGTAGTCAATAGA TTCTGTCCTCTACCTTCTCTTAATTTTAGAATGTGAAATCGCTACTTGGATGTATGATCGC ATCTTTATTTTCAATATACAATACATGGAAACTGGATAAAGGCTCCCAAACTCTACTGAGC CTATTTTCTTGTCTTCCTCGAGCTAATGTTTTCCAGTGTTTTCTATTCTTTTAAAACAGTG TTTATTGCTGTATGAGTATCGGTTAATTTCTGATTTGCGTGTTTTGTTGATCAATGTGTCT TCTTATTATAACATTCTTGGCAGTTTATCCCCAATTGTCCCCTGAAAGTTAAAATTCGTCT TGTTTTTTTGTTTCTTCCATATAGCCGTGAGAGATTTCCATATAGTATTGCTTTGCCCCT TATTGTTTTGTATTTATTAGGCTCCACATATTGGAATAGCATGGTTTTAGAAAACACCTAG ATTTTGGTAATGGACGCTATACAAAGAATAGACATACCATTAAAAAGATGGAAACAAAAAA TTTTCTCTTGCTCAACTATCCCCAATTCACAATTTATTTTTCCATTAATTTACAGTTTCTT AGGAGGTGAACTGTTACATAAAAGTAACAACAACATGATGTTTACCATTGCCTAACGTCGA GTTTATGGGGTACATGTCGTGTTGTCTGTGTTGTTGAAATTGGACAAAAGAGATTATCAT CTACTAGACTCTCTAATGTTTTTTAGGTCCAAGAGATAGCAATAAGGTTGAAGAGTCTTC ATTGGATATGCACACTTTTTAAAAAATGTGAACAAAGTATGCATGTTAGAAGCATAAAGA AGTGCAGAAAAATAATAAAGTGGATTTAGAGTTTACGGAATGTTGGAAGTTTGTAGTCGCA TATTATTCACAAGGATGTTTATGGCAGTGATAAATTTTATTATAAGGTTTAACTAGTATA CTGCGGTACTTCTTGGTTTGTCAAAGAGCTATTTGATAATTCTTGCGAAATAGATTTACGA AAACTCTGCGAAAAATAAAGTGGTCAATTTTATATGCTTAAAAAAATTCCCTAAGTGGGTT AGAAGTTTCTGAAAGTGCTACCCAAAGTGCTAGCCCGCGTTCTTAGAGAAGTGTGTAGATT ATTATAGGGAATAACTGGTATTGTTATTGCTAACGAAACAATATAGTTACTCTATATTGAC ATGTTTTATTTGTACTTTGAATAGCCATATTAAAAGTTTTATTGGATAATACATGGACTCA CATTAGAAAATGCAATTTAACATAATATCTCAATGAGTATTAGGTATGCACTAAGCTAGAA ACACACAGCTCCGTTTACCATTGAATGATAAGAAATGTAACTATATGAGTCAGGAAATAGT AACTTCCTAAGTCAAACAGTACGCCCAATTCAATCTGTTAAGCCTCATTGGGCCTAACCTG GGTGTTTATACCGCCTATTGGTGAATGCTTTAATTGTCCACGTCAACAAGATGAGTCAACA TAGTTAGGCGCTTGTAAGCTCTTTGAGTATTGGAAGAAATTGTGATAGATAATAAAAAAAT TGAAAATGTTACCCTTCGTTATAGCATTGAAATTCACACATAAATATTTTTCTTGAAACTT CTTTTTATTGCAAAAAAATCTAGGACTATAAGTTTTGTCTGGCGACACGCCAATTTTTTC AAATTTGGTTTGCGAGTGGAAGACATGCAGTTTATGCAAAACTAAGTACTACTGAGTTGA AAGTTAGGTTTATGATAACACCAGCGAGTATTGTTTTTTTTACCACAATTCGACTTTTCCA ACCAAATAACCGAGGATGGTATCATAGACCATTAACGTTTAGAAGCCATTTGGCAGAAATG ACTACTTATGTTATGTTCTTACCCGCTACTAAATGTTGTTCTCCAACTACTTTGCGGACTC AAACTTAATCTTGCAAAAGCACTGCTTAAATTTACGTGACTCTTCAGAATATAAAAATTCA GCATTACCATTTTAATATTCAACATGTGAAACCATTGCCATTTTTCCTTATGCGTTTTGTA AAAGAAACAGAAAATCAATTCTATCATACCACAGGGAAATATCTGTTTCCTTTGCGATCCT TTTACACTAGAATTTCTGAAATAGGTAATTAAAACATAGACCAATCGGCAGATTTCTATAT TGATCTCACCAAGACCAAGCCGGTCCAGTGTGCCGATTTGCCGTAATCAGGCCCTAACAAT TTCTTTATTCTGATGTTTATTTCTTTTGCTTAGTTTGTTTTTATATGTAATTTAATATACA TTCTTTTATAAGCAGTTCAATCTATAAATTTAGTATGGATATCCAAAGTAGAGTCAATACG TGCCAACAAACATCAGTGGTTTTTGCAGGTTTAAATTATCGTACTTAAATTTAAGATTTCT CAACATTATAATTCTTTTTCAACAGGAGTGTTAGGTGACCCACATGTAGAAGGGAGACATA AATGTCTCTGCTTTGTGATTAATGAACAAAGACTTCTTAAAATCGCTTAAAGGTTACACAA TTTTATTCAACGGTACCCTACTGAAAAAAAGAGAATGATTCTCATAGGCTGGCGAAAGAAC CACGTAAAAGCAACTTATTGCTGATCCTACTAACATTTAAAGGGTGCTCTCAAAAAATGCT TCTTACATTAAAAGTGAATAAAAGCAATCATTTCACGCATAAGTATATTTTCAACTCTATC TCAGATATGTATGAATTACACCTGCTACAAATAATACAAAACAAGTTATTTCTCTTTGTTT TAAAGAAAACAAGGGGGCGTCAAGAAAACAGAGTTCAAGGTTTAATTCTCATCTCCAATAC TTTTGCCGTTGGGTTGAAGTCTGGCAGTATAAAATATAGTTTCATACTAAGGGAATGCAAC ATATAGCAGGATGCAACTAAGAAAGCAACTAAGAAAACAGACTTGTTGAAGAATTCATAG CTATCGAAAGTGTTTGTAGATCTTTAACTAACATACGCGTAAATAATAGCAAATATAAACA TTGATAATTACTTATAAGCTGAAAAAAAAACTGAAGTAATCTATGCTGTTCTTCTAAACCTG TTCTAATGGAACAGAGGGAAGAGTAACTGACGCTGTAATATTTTTTTTTTCTTTTCCACTT GTCCAAATATTATGATTTCAAAAATGAAGACACTAGAGCTATCACTAAAGAGGCTGAGTA AAAGCTATATTGCAGACGGAGTTTGTTTGCAAAGTTTGAGAAAACAAAAAAAATTTATTTG GATCCAAGTTTTGTAGAACCTCTTGTTACTGCTCTAGTTTGGTATTTTAGTTAGGTGAA AGCAAAAAGTAACTTCGTACTTGGAAAATAAGCTCAAGAGACGGTGTTATTACTTACCAGA AATCTTTTGGAAATGTATAGCATGATGAAAACAAAAGCTATATTCGATGAGAATTTCAAA GGTAATAAAGCTTGACATATGTCTATATTTTGGAAAGAAACAATTCTTTCTTAATTAAGCT TAGCATTAATCTTTTCTTGTTAATTGGCAGATCATTTTCAAGGTGTTGTGTTAGCTCCCAT TGATTGGTTTAGTAGCTTGTATTGAAGTCAAATTCATGTGTATAAGATCTTACATAACCGA ATAACTTTTCTTAAACTTTAGCTGTCATGTTTGAAATAGCTTGTGTAAAATATTTTGGAAG TCCTGTACTTTTGGTACAAAATTAGTTGTAGTACGAAATATATACAAAAGAATGGACGTAA CACTGTAAATGTAGAATGGAAAATTTCTTCACTTGCTCGTCGACTATTTATGGCACACAGC TCAATTTTCCATTAACCTGACGATTATTCCAGGGGATGAATTTATACAAAGAAGCAACA CTCGCCTAGTGTTTGCCACCATGCTACATGTACTTTTCTCAGGTGCATCTAATATGCATAC TATAAGAAAGTCTGAAAACTTGAGTAGTAAATGTGTACTTTCTAATTACTTCGTTTTCATG CAGATGTGGGACAGAATTTGCTCTTGATTCTCTGGTTGATCAGTCGATCAGAAAATTGCAT AGGGCTTCTATTTGGACCAGTGTCAACACTGCATGAATACAATCTGGATGGGTTCATGATG TAGTTAACTTTTAAAAACAGAGAAAAAGCTAGTTGTTTTATATAGAATAATACTGTAACT | |

TABLE 7-continued

CENs sequences

| Sequence | SEQ ID NO |
|---|---|
| GTTTATTGAACAATGATTACTCTTTTAATCTGATAGACGCTAAAGATACTGATTCTTATGA TATTAAAAAAAGGTGTGTGACCTCTAAAAACCCTTTTTTCTTGCATTTCGCGCAAGGAACA ATGGTTCTGCGATTTGACTCTTCACCTGTTAAACCTTGTCGATTCACCTTTGACTCCATAT CAAAAGTTTTTACTTGAATAAGGATATACAGAGACAAGAAGGTTATCTATATCTTATTTTT TCTTTGATGAAATAAGTGGTACACAATATTTCAATTATTGTTAGCTCTAACATTACAATTA TTCAGCACTACAGGGCTCTTGTTATCGCTAAAATCTCAAAGTCAAAGTATGAATAAGTTGC TGATGAGAAGCGGTTGTGTAGGTGTTCTTTAGAAAATGTTAATGCTGGAGGACGTGGTTTT GATCTATTTGAAGCGCGCACTATAAGAGAAACAATTACACAAGCAGAATTCCTCTGGTGAT AACCTGCAAAGATAGCTGTTACCAGTAAAGAAATAAAAGAACAATATTTGGCCGTAAGGGG CATCAATTACTTAGTACAGAGCGGCATTCTGCAAGGGCTGCAGATATTTTGTCATTTGAAG GCAACTGATATCTATTTGAAAAAACGTTGCCGCTATATCAGCAAAACTTCCTCAAAAGGCA AAAAAGGATAGATCAACACAACTAATCAAACAAATATCCCACACGTAGGGGAAGAACTACA ACTCACATACAGCTGTAACAATAAACTTAATTGGGTAAACCACAAAGCAATTTAATAGAAC GAGCTAAAATGTTTTATGTATTACCTTTCTAAAGATATCCTACACCCAAAGTATGCACCAT TTTTCTATTGCTTAAAAAATTGTTAGCTGATTTGCAAAGGGCTAGAACTGTTCTGAATTAT CCGAGCGTTTTACTAATTTACTAGTTCAAATAACAAATGCTTTTGCTTTGAATATTTATTG ATTTCCAAGGTGTGATTTATTTTGCCAATGTTATACATTGTCTATTTCAACATGATATTCA CAATATTTCTACATAGATCGTTATAGGCAAAAGTTATTCTACTACTATAAGGGTTAGCTGT GGGTTGGCATGATTAATATTAAGTAAACAGATTCTACCTTTTAATAAAACGAATAATTTGT GAGGCTCATATGTTCTTTATACTAAGTCGCTTGCTAAAGTTCAGTTAACCTCCCAGTTAAT ATTGCTAATCAGGACTTCGTTTAAGTTTTTCTAGTTGCTATGATAGGGTTTTTTTCAGGTT AATAATAAAATATTGAGCTGCTCAATAACATTAAATCCCTCTACCAGATTTCGATAAGTTC AAGTCCTTTGTAAAGATAAGAAAAATTGGTTGTGGACATGTTTATGTTTATTAGAAAACAA CCATGAAAGGATTCTGTGATTAGTCATGAAAGAGACTTTAATGAAAAGGTATTCTGGCACT TACATCAAAACTACTCATAACTACACGAAACTTGAATATTTTACTCATTTTAAATAAACAC TGGCAGGCCTATGCAGCAAACAAAGGAGGTATTTAACAGCATTTTAAAAAATTTCAAGAAG TGATTTCCAAAATCTATGGATCTTGAAAAAGTAATACTGTAAACCACCACACCACTACAGA AAATATATATTCAAACAACCCTAGATGATAGAGGTGACGTGCTACCAAAGTTTGTATAAAT ATTCGTTTCTTTTCCATCTCGCCTCATACAAAAATGCTCATTGAGGGCAAAGAGTTCAACC TTTCTCCTGTTGATATTTTCATATTCATGGTTATTGATTAGTTTGCTTTTCAACAGCGTGT TTTCTCTTCTCTTCTCAAAAAACAATTTTTTTATAATGCACCAACAACGTACGTAGAATCA CCAACCGAATCAGGGAGATGTCTGTGTTTAAACACTATCATACATCTGTTTCAATACTAGT ATCAAGTTTCTAAGAGCCGTTTAGTTCATTACAAAACGTAGAGGGCTATGCTACTTTTATG AACACACAAAAACTGGAATCAACCGCTGAAGATGGTATTCCCAGAACAAATTTATTACTGA TTTTTTAAAAAACTTGAATGAAGAAACTTGAAAAGAACATTAGAGGATTTCTTTTATCTTG TATTGTATCTTCAAAGAATTGCGTATAATTTCACTATTGGGTGCTGTCAAGATGAAAAGGC CGTACTAAACGTTTTCATACGGAAATAAAGATTCTCTCCATCTCTGATCGAATCTTTTTTT CCAATTCATTCGCAGATGCTCCAATAGATGATGGCAGTCTCCTTTATTTGTGAGCATCTAT GAAAAACTTGATAAGCGTTCTCTAATTTTGGCTGCCCCGGCAATAGCAAGTCATCAGAATT AGCTATTTTTTACCAATCTAAGAGACTCTTCTGTATTGCCTCCCAAATATTTAGTACATT ACCGAGAAAAAAGTAATAGGTAAAATATGCCCAAAGGCAGAATCCGACATGGTTTTCCCAA CATATATTTTATACCTCTAAAGTTTTTCAAGCTAAACCTTTTTGGCACATGAAGCGTGTAA TGGTTTATGTTATATATAATTTGCAGCAACCCTATCGGTCTCAAATGACTTATAATAGTG TTTTGTGACGCTTTAAAATTGCCTGTAACAATATGGCGTGAATTTGGAAAAGACTCATCTT GGGTAAACACTCCTTCAAAGGTTCACATAATTCATAATAAAAAGGCTCTAGTTACCAACT GATTCACTTTCCGGAAGAAAGCAGAACGAACCAAGCGTGAGTTTTCGCGTTTTTTCATTGA TATGTACGACTGTTATTAGATTAAAATCTCAGAGTCTTGTGCCACTGGATATAACATCCAC TCCAAAGACATGTTGGTTTGATGGTTCTGCAAGCGGTTGTTTAAATTTAACGACCAAACCA GGCTTTTGTTCAAACTGAATGAAACTGCACGCAATATCTACGTCTAATACGAACTCGTTGT CTCTTTCTTCCCACTATAAATACCACCTTTGTTTTTTTACCTTCCAAATTGTTCAAAAAAT CTGACATATTCTACGAATAAGAAAAGTGCTATTGGTCTGCCATTTTTTGTGTGAATCTCTA AACGATCGGAATGTATTAGTGATAAAAATCGGATTAAAACTATTTTTACTTCAAGGCGCTT AGTTTTAACGTCCACAAGCGTAACGCTGCTTGTTGAAATATATTCCTTTGGATTTAACAAT TTTAGCATAGCGGGATGTCTCTTTATCTTTTAGTGTAGTTCGCATCTATGACTTTGCATAT GATAAACTCGAAGATTGCGTTGATGAAACAAGTAAAGATAATGCAAATTTTGACCTAACAA CGAATATCATGCATTACGAATGGAACCTTTTGAATAACAATATATACCAAAAACCAAGCTA AATTTCTTCAAAAAGCTAGCTTTTTATGAGTTCTCTACTACATGACTAACATCAATCGTAT TTTTGTAAGATACTCTCCAGCTAAATTTCGTAGCATTTCGGGGCGTAAAACTGCATTTACC TTTAAGAAGAAACTAATCCTTTTTAAATGGAAGTATTGAGCAAAACGGCGCAAATAAGTAG TAAAAGTTTGCTAAATATTCTTATAAATCACTTTGGTTTTGCAAATTCAAAAGCTACAGAA TATAATAAACGTGAGGAACCCCTCCATAAAAGTCAAATAAATCCCTAGAGTGTGTCATTTT TTCAGTCTGAGTTCTTAGTTGATACCAGACGTGTGGTAAGATGCAAATTTGTTTTCTGCG TCCCAGTCGGTCAATGCCAAATGCATTGTTTCAACCACATCGAAAACATTTTTAAGGTAAC GCACATACACAATGTAAGCAAAGGAATCCTTCGTGCTTTCTAGAATTTTGACAATTAAAAA CAATCTCTTTAGTGAGGAACTCTTGGATCTTACATTATCACTTCCTTAAGTGATTGGAATA CGTGGTTATAATTGAGTAAAGCTCATGTTCCTGATCGCACCTACCTGTTCTAGAGCTTTTT TAGAAAACTATTAAAGCAAAAGCCAAACATAAAGAGCCTACCATTTATCAACAAAAATTTA GAATTTCAAGAAGTCTCCCTTTCTTCGTTTAAGTGGTGGAATTTCATTTTAAGTATCTATG AAGTTTTTGAAAAACCCTCCAGAAAGACGGCCAATGTCTAACTGCTCAGGAACAAATTATA TCTATGTTCTCCAGCAAAAAATCTCCGAGAAAGCCTCAATTGCGAAGTCTGTAACTATGTC TCTGTGATCTGGCAAATGTTGCATACTTATGACAAAAAAACGTTTTTTATCACTTGTTAGT AGCTATAACACCGCAATTACATTTGTGCAACCGAACCTCAAGTTACCAATTCTATTACAAA GAACAAGCAGTAGTTATGTATTTAAAGATTGTATTGCTGACATTTAAAGTGAAAAGTAATG TTTTGGAAGGTTCTAAGGAAAGACTAAGATGTTTCTTTTTGCCACTGAAAATTTGAATGGA AAAACCGATAACCCAGAACAAACAGCAGTCTAGTAACATAGTTTCTCATGGAAAATTTTGA | |

TABLE 7-continued

CENs sequences

| | Sequence | SEQ ID NO |
|---|---|---|
| | GTCCTTGATATACAGTATCAAATCCCAAATCAAATAACTTACTTCTTAAAAAGCAGGTTAA<br>TCATTTGGTACTAATCGGTTGGTTGATACTCCGATAATAACTTGTTGGTTTCATGTTTAGT<br>AGGTATATATAGTCTTTATTTGAATTCAAAAAGCTCGACTGTAGTAGATCACTATAATACA<br>GCATGGAAACTAACTGGGGTTGTAAAAAATTTATTCCGAGGCTTGCAAAGGAAACAGAACC<br>AATTGAACTACTTCATTGGCTTGGTTCCCAGAGTGACGCAAGCTTCACATGTTTAATTGTT<br>TTCCTGGTGAAAAGGGCATATTAAGTATGGTTGAAAATGAGACCCTGTATCATATCTGAAA<br>ATGCCAAAAATCAGACAAAGTTTATTTCTCAGCATTTGTTTATCTCGACAATATCGAAATT<br>TCCCCAACTAAATCTGCCAGTTTTCTTGGTTATTTTATCTGAGGGGAAAGTTTGATTTTGC<br>TCTCTGGCCCTAACGGCCCGCCAATATATAAATTTCATGGTACGGCAGGAAGAGCAGAAGA<br>TTGAAACATATGAGATTGAAACGTTTGCTTTTTTATTTTGCCAGAAATTGTGGTTTTCAAC<br>TGGTTAAAGTTTTTATAATTACAAGTGACAAATGTTTTAATTAACTATGTCAGCAATAGTT<br>AGTTATCACAACCCCAAACCAACAATTTTAACAAATAGTTCAACTTTCATTGTTTCCTTTA<br>AAAATCCTTTGCCTTTATCATAAATCGAGTTGAGCAAACTATTATACTTAATTTGAATACC<br>GCCACATAATTTGTAGCCCTCCAGCAGAATTTATGCAGGTCAACATGGCACTAACATTCTT<br>ATGTTGAGATAGGTAATTAAAACATTAACCTATTTATGGGCATTTTATCGATCTCACTAGG<br>GCCAGTCCGATCTTGTGAGACAATTTTCCTTAATCAAAGTCCCGCTATTTTCCAATCCTGA<br>TAAGTATCACTATATAATGTAGCTCAAAAGTCTGTGTCGAGATTTTAGAAGACTAGTTCCC<br>TCAAAAGGCAATTCTCCAAATCTAATCACACCAAAAAATTAAATAATACATTTTTCCAAAA<br>AAAACAAATGCTCTCACTCAGAGTCGAACTGAGGATCGCTACATTACTAGTGTAGCGCCTT<br>ACCAACTTGGCCATAAGAGCTTTGTTGATCCTCTAATTGACCATGAGTAAACTGTTCTAAT<br>TATTGCTAAACTGAATATAGTCACATCTACAGTTTAATATTTTAGTATAGAAATGTTTTTT<br>TCATACTTTACAGATGAGTAAGCAAATCTGGTTAATGCAACGTAATTATCGTTTAGATAAG<br>TAACTTTAACACTGGCCAATCAAACCACTGGCATCATTATCACTCTCAATGAGGATATACA<br>AATTAATTTAGATTTTTTATCGGAAGTTTGAAGCTTAGTTATTCTTGTGTTAATATGTTGTT<br>ATTTGCGAGAGTGAGAATGATATTTGTAATTCGGCTGGTTAATGCTTCAATCAGCCTTTTG<br>AATAAATAAAAAATAAAACTGATTCGTATAGATATATCCAAGGAACATAATTTTGCGTGAA<br>ATTAGAGGAAAATAGGCCAAATATGTAGCAATCAAGCAAAGGTTATTGACACGACGCTTAA<br>AATCTTGAGGGAGATCAGGCAAAGGACTATCTCCCTACTTCATAATCAGGTAATCATATAA<br>AAGGTTGAAGAAGATTATAGAAGGTTAAACAGAAGTTCTAGAAGATAATTATATCCTTCAA<br>AATGCTATTTTTAAATTAAAGAATTACTATTTAAACAGAGGACATTCCATATATGTTCTCA<br>GAGAATTAACGTATAAAAATATATAAGATATAAACAAGCAATAATCAGATTCTAAAGTACT<br>CATCACCAGCAACAATTTCAATTTTAAGAAAAGGTCCCTTGGCCCAGTTGGTTAAGGCGTG<br>GTGCTAATAACGCCAAGATCAGCAGTTCGATCCTGCTAGGGACCAATCTTTCATTTGGGCG<br>TGTGGCGTAGTTGGTAGCGCGTTCGCCTTGCAACCGAAAGGTCATCGGTTCGACTCCGGTC<br>TCGTCCATTTCTTTTTAAAATTTTTTAAACGAAAAT | |
| CEN4-<br>42742<br>bp | CTTTTGAATAATTTTTTTTTGATAAAATTAAGTTAAATTAGGGTGATTTGAGAATGTGTGA<br>ATGTGTGTGATAAAAGAATAAAACAAAAGCTAAAAAAAAGGAAAATTAGCATACCAACAAT<br>ACGGAGAAAAGTGATATTAGGAGGGGGGAGCACGGAATTTAAATACAATTTAGTTTCTCCG<br>TAAATGGGGAAAATCCGCCTCTGGAAATGGTTTCCGTTTTACTGAAAATCACCCAATGTTG<br>GAAAGGCCGAAATAGCCAGGTTCCCCATATTTTTTCCGAAAAAAAAACGGAAGCCATTTTC<br>AAAATTGTTACGAAAAAGTAATGGGGACGGGGGGTGGGGAGCGGAAAGGGACACTTTGTTT<br>TTATTATTTTTTTTTTTTCATCTACAACGGCAATATTTTATCAAGTATCTTGGGTTTACC<br>TGTTTGTGTTTACCACACGTTAAGAGGAGTATTTACTTTGTCATCAAGTTCTCCCGTCTGA<br>GCATTCGGCGAGGTGGATGACTGTGTGCCTAAATGCCCGACATCGGTGTATGAATGAGGAG<br>ATCGTCCATACAACTGGACAAGCCGTCCACGAGGTCCCGACTATCACGTTGGGTCAGGTAA<br>ACCCAAGTCGACTAGAGCCGTCAGTAGAGAGAGTGGCTTCACTTTTTTTCTCCCCACTATG<br>TACCATACAAATGTGGAGAGAGGGAAACACGGCATTTTAGAAAACGGGGTTTCCGCTCCGA<br>ATATGGAAAAAACTGTTTCCGGCGGCAGCTCTTGCCATTATGATAGGTGAGACCTACATGG<br>AAATACGGATATTTCCCCATATTTTTCCGCTGTGTTTCGTTTTTTCCCTTTTCCCTTTTCC<br>CTTTTCCCAGCGCGCCGCCCCCAAGCCATTTCCACTCAGCCCGGGTTATTATCAAGTGGA<br>GAATTTCTACACTTTCTGTGTGTTTTGCTCTTATGGTTTTTTCCGTCTCTTGTGGGATGTT<br>TAATGCACCTCACTCCTCTAAAAATAAAAGGAAAATTTTTTAGTTTGAACAACATGGGCGG<br>ATTATATCAACCCCCGACGCTCTCAGAGTTGACAAGGACAAACATACACCAGTTATTTCTA<br>CTGTTTCTCCATTCTACCCCGGATAATTGACAGATGGGATTTCCCCGATAATCTTCACAAA<br>GAGCAGATGAAGGAAAAAATAGCATGAAAAATTAAAATTGCCGCGCCTGTGTGCGAAATGC<br>GTGCCGCCAGGCTCACTCTGCAATTGGGTGAAATGCCACTCTTGAATGAGGCACAAAAAAC<br>AGAGAAATGAATGGGCAATGTACATGTTCAATTTAATTGTCCGGTTTGGTTAACAGGTGGG<br>GATCGGGCTGTACCGTCCTTTACAAAACATATAACATGTTTAATCTTTGAGAGGCATAGAG<br>AGAATTTTATTTGAGGAACGGTCCCTTCATTTCCAGATATGACCTTATTTTTGTATTTTTT<br>GTTTCCTGTCAATTTGTTTATTTACATGCAGGCTTAGTAATGTACAACATTCTACGATTAT<br>TGATGCTATCCCCACATTGATAGCCTTGGTTGGCCCCGCTTTTTCCCGTTCTGCTGTGTAC<br>CTCTTTTTTCATCTTCCACAGAAATCTATCCCCACTTTGGGTATATCACAGTATATCTTT<br>TATTAGGAAACCCAGTGTATAATATCAATCTCTGCTTTTTTGTTCATACCCCTAAACATA<br>ATTTGGTCTACTTATCTTTTGATGCAGTAGAATATACTAAAATCAAAAGTATGAACCTTG<br>TTGTCAGATGGGTTCGAATTTTAAACCCCTAAAATCCCCAGCTGCTAGTACTATTGCTAAC<br>TCGGTATACATGTTTTTGCGTTACGAAAAATTATATGCTACTGTATGGACAAAATTATAT<br>CCTTCCATCATGGATTAATTCAAGATAAAGGAAAAATACAAGCTATAATACCTCAGCAATC<br>GCCGAGATCGGATATTCTACAAAAGATTGGCATATTACCGCCTAAACAGCGTGACCAAGGC<br>TGTTTGAACTTATTCCGAAACAAATTTCCAGGGCTGACATATCGTCTAGCTAGTTTTGCT<br>GACAGTTAGACAAACCCGTAAATATTTAGCTGGGTAAGGAGACATGTTGGAAGGTTAACTC<br>AAGCAGTGGAACTAATGATTAGCAGCAAGGTATCATTTTACCATCTCTACGACAGTAGAT<br>CTCAGACCACCTTGAAACACCTTTATCGGAAGTCCTTGAATCGTCCTTTTTTTCAGTCCCT<br>TTAGTTGAAGTTCAACTAACAAAGTTAAACCAGACATTCTTTAATAAATTGTCCTAAAAAA<br>ACACGAATGAAACTTTGCTAAAATAATAATATATGATATCTTCGAATCACAATCATCCGTC | SEQ ID NO: 15 |

TABLE 7-continued

CENs sequences

| Sequence | SEQ ID NO |
|---|---|
| GGTAATGAAGAGATCAATTAATGCTGAAATATTCAATGTTCTTTAGAAATTGATAATTGCT
AAGGAACAGTGTTGCTTGTTACCAATTATGGCCAAATTAAACAGCTTATTCAAAGTTCAAC
AGCAACAAAACTGCGGTTAGATCAGATAGACAGACGAAGGTGCTTGATTCAAGTGATATAA
TAATGTCCTTAAAAAAAACACATCAGCTTTGTCGCTTCTATTGGGTGTATGACATTTGTGA
TCCTTACTATCTGATATAAACGTGCAATGATCTTCTTTTGCATCCACTGAACGTAAAAAAC
ATGTAAGAAAAAAATACCTGAACTTTTCTTTTTTCAACTCTACTCTTGTTCTCGTTATATG
CATAGCTTGATCTTTTCTTTGCTTTCAGATGTGCTGATGACAAGAAAACAAAACCTGTAG
CATCAATAAACGAACCTTAGACCAAACTACGCAAGATGACATTTGAACAACAACTCATAGG
AATACCAGCATGTACGCATTCGGCTAAATTTATTTCCTTTTAGTATCACAAGTTAGTAACC
TGCTAGTTCCTTACCAGTATGAGAACCACGTAAATTTCGAGACAAATTTGAAGCACCAATT
TTGTGAGTATCACAATAGTGGCTAATCGTAGTTCTTTGTTGGATGCTGTAATTACTAATTT
TCATCCTAACAAACAATAAGAGTAGTTTTTTTGTCGCCTATTCACTAAATAGCATTTTTTG
AACTAAATCCATATATTTTATCAAGCAGTTAACAAAAAGGCAGGCATTGAGAATTTTAGAA
AATCAATATTACTGTGGTAACCCCCACAACAAAATCAACTAACTTATAGTAATAGTAAGTG
GAAAATATTTTAGATGGTTAGTCCTACTAATGCCGCCTCACGCTCGAAAGATTAAGAAACC
GGCCAGCTTGTATTTGAATAAGAAAATATATCAGCTTATGCATATTCAAATAACATCGACA
CCTAAAAATTCGAATAGGCTCAACAATCTCAATGGTTGGAAGAAGTTACCATACATATTCA
TTTAGCCTTCGACTTGTCAGGTTATTTATTTATTATGGGATATTTTCATACCTGTGGCCAT
TGAAACAGTAGCAAAAACAATATCGCGGTGAAACACCAACTCCCAAATCAAAACCAAATGG
AAATATATAACTAACTTGTACTAGGTTTTATTAAAATGATTCCCAATCTCAAAAGTGCCAC
TTAGAAAATTATTGCCTGAAGGGTCCAAATGAACCATGGAAAATAAGTTTCGATCTCGGCC
AACTACATAAAAATAAATTCCCTTTTCAATAAGCACCAGATAAATCTCAATACTATGAAAA
CCAAGAGTATATATATGTAAATTCTGCAATTTCAAAAAAAAATTAAAATGATCGAACCCAG
GATCGAACTGGGGACGTTATGCGTGTTAAGCATATGCCATAACCAACTAGACCATCCGACC
ACTTATGAGCTAGAAATGTTGCTGGTGGGACCTACTTTAGAATCTGATTATTGCTTATTTA
TATCTTATATATTTTTATACGTTAATTCTCTGAGAACATAAATGGAATGTCCTCTGTTTAG
ATAGCAATTCTTTAATTTACAAATAGCATTTTGAAGAATTTAATTATCTTCTAGAACTTCT
GTTTAACCTTCTATAATCTTCTTCAACCTTCTATATTATTACCCGATTAGGAAATAGAGAG
GTAGTCCTTTGTCTGATCTCTTACATTACCCCGCCGCTTTAGAAACTTCGTCCCGGAGTTT
ATTATCATTATCAATTGCTTTTGCATTATCCCATAAAGTTTTCTGTAAATCTTCTAGGATC
TCTAAAAATAATGAATATGGGATGCTTGAACTATGACAAGGGTCACAATCTTTCCAGTAGA
CATCCAATGTATCGTTTGTTTCGTCGATACTAGCTATACCGATAATCTCGGTCAGTCTACT
TCTTGCTTCAGCTATCATTCTTGGGGGTACCTTGGAAAACTGTTTATCCGCTTGTAAGGAT
CTTCTAAGCCATCTGACATTGATTACTCTATCCTTTTTATTCGTTTTCGGTAAATCAACTT
CGTAGGCGTTGTCTGATATCTTCTTGACAACCTTGTAGGGTCCGTAGTATACCGGTTGTAT
TTTGTAATACAATCTATCACTACCATATGCATCTTTGTGTAATAGTATCCAATCTCCAACT
TCAAATGTTTCGTACACTCTCGACTTATTATGCTGTGTTTCTGACTTCTTTGCGCTTCAA
TCATGTTTTCTTTCACATTTTCCATGATGACTTTCATTTTTAATGCGAATTCTTCAGCTTT
GTTGCTGACCTTCTACTTGAAACACGACTGCTAGAAATAAACATTGGCGAGTCTGGTAAGT
AACCATAGCAAACTTCAAATGGTGATGAACTTATCGAGACTTGATGGGAACTGTTGTAGGC
AAATTCGGCCATTGACAACCATTTGTCTCAACTGTAGAGATCGTTACTCGCATAATTCCTT
AGTAATTGGTTTAAGATTCTGTTCGTTCTTTCTGTTTGACCATCTGTTTGAGGGTGATTAG
TGGTTGAGAAGAGTGATGATGTACCAAGAATTCTATGTCATTATCTGAAACCATTCTTTTT
GGAATCCCATGTAATTTAAAACAATTTTCTACCATCAATTTCGCACATTGCTCTGCGGTTG
CAGTTTTCCTAGTGGGGATGAAATGTGCCATCTTCGTGAATCTATCCACCACTCCCAAAAT
CATATCGTGTCCATTTTTGCATCTGGGGACACCTGTGATGAAATCCAAACTATGTCTGTCC
ATCTTCCTTCAGGAATCGGAAGAGGGGAAAATAATCCTCTTTGACCAGTTGTCTCGGGTTT
GGTTTTCTGGCAAACAGTACATCTTTGACAATATCTCTTCACGCTTTTTAGCATATTTGGC
CAGTAAAACATAGGGTGAAGTCTCACGTATGTTTTGAAATACCCGAAATGACTAGCGGAGT
TACCACCATGTGCGTTACCAATGATTTCCTGAACCAACTTAGACTTAGGGGACACTACTAT
TCTTCGATAATTTCCTCCTTTAACCACCAAGAAATATAATAAATTATCATCAATTGAATAA
TGTTTGACGTGGTTATGGATTGACTTCGGGATCGGCATATTTCTTTTAAAATCTCGTATA
TCTCCTTAATTTCGTTGTCTTCATCGTACGACTGGATAATCTGTTCTAGGAGTTCCTGATT
TGGTGTTAACACCTATTCTATTGTGTTGATACTAACTTCATTTTCCTCGTCTGGGTACCTA
GACAAAGCGTCTGCTACTGAATTAGTAGGACCTCAAGTATTGAATTGTGAATTCGTAATCA
GCTAATCCTAGGAATGATTGAGCACATTTGGCGTTTTTCGGAATTGGCCAACTCTGGATTT
TGTCTATCTTAGCAGGGTCAGTCTGGATACCTCTGCTTGAAATGAGATGTCCTAAGAAACC
TAAGGTTTTGAAGTAAAATGAGCATTTCTTTTTCTTAGTAATCAGCTTATTTCTCCTGAGC
AATTCCAGTATTTTTCTAATGTGATTGTAGTGTTCTTCAATAGTCTTGGAGTAAATTATAA
TATCATCCAGGTACACCTGAACAAATTGGTTCAAATAAGGTGCTAGAATCCTATTCATCAT
TCTTTGGAAAGTACTAGGGGCGTTGGTTAAACCGAAAGGCATCACAACCCACTCGTAGTGA
CCGTAATCTGTGGAAAAGGCTGTTTTTTCCATATCATTTTCTGCGATGCTGACCTGAAAGT
ACCCTGACATCAAATCCAACTTGGAAAATACTGAAGCTCCTCCAAAACATGTGATTAATTC
GTCGATTCGTGGTATTGGGAACTTGTCTTTTACCGTATTGTTATTTAATAACCTATAATCA
ACACACATTCTCATACTACCATCTTTCTTCTTGACAAGTAACAAAGGACTATTGAAAGAAC
TAGGGGCAGACTTGATAAAGGCTAGTTTCAACAGTTCATCAACCTGTTTATTCAGTTCTTG
TTTCTCTGAATAGCTTGATTTGTACTGGCGTCTGTAAGTACTCTTGCTAGGTTCAATGCAT
ATAAGTCTGTGAGTCAAATCCCTTTGAGGAGGTAAATCGGTAGGTTGGTCATTGGTCACCA
CATCTCTAAATTCTTCATGAATTTTATTTCTAATTCCATCAACACCATTGTAAGGTTCTTC
TAAAACATTATTATTTTCTTTTACTTCAACTGACTGCACAAACAGTAATAATGGAAGATTA
TCAACATTCTTTAAATTTCTTCTAACTGCACGCATGGAGTTGATACCTATAAGTTCATTTT
CTTTTGTTTCTTTTGAGCCGTTTTCGTCGCTTGACTCTATTTGTTCTTCGATATCTAGGAT
TTCAGGAGTTTCCGTTTCCTTTTCGATATTTTCCCAGTCAACTTTGTTTCCATGATCTTTA
ACAAATGGGAAACCTAATATCATTTTATGGTTGATATTCTCTAAGACTAAGAATCTAATAT
TCTCATTTTGCCATTCGTCTCTTAGCTTAAATTGTAATTCTAAGGTTAATTCTCCTTTAAC | |

TABLE 7-continued

CENs sequences

| Sequence | SEQ ID NO |
|---|---|
| GCTGATCGTTTTCTTATTAGCGGCGACAACATCTTCAAATTCGGTAGGCTCTAAATAATTT | |
| TCTAATTGATGTGATTTAACAAATTCGTAATCCAAAAAGTTTCTTGACGCACCGCTGTCAA | |
| CTAAAGCAACACATTCCTTAAATAATTCGTTTTTAACTTTCAAAAGCGGAAGTTCTTTCCT | |
| ATCCATGTAAACGTTCAAAACACTTAAATTTTCTATATCCTTGTTATTTAGTATATACTTG | |
| TCAAACTTAGTAGAGTGTTGAATCTCGTTCTTTAATTGCAGATTTGCATTTTCTATTGTAG | |
| GTGTGTTTATAGCAATATGGGAACCAACCACCTTTTGGTTCCTAACTAATTTAAATTTTCT | |
| CTGTCTTGTTTTCTACCAGTGTAACCACCATTATAGTTTCTGTTGTAATTCTTGTTTCTTT | |
| TATAACTGTCAAAATTCCGACCACGATAATTTTTATTTTTAATGGAGTCTATTTCCATTGG | |
| TTCACCTCTCCATCTATCTTGATGCGAGAATCTAAAGTCTCTAGCTCTGGGTGCTGAGTCC | |
| TTCTCAAAGTCTCTTGCTAAAAATTTGGCTTCAGCAAGCGAGTTTGGTCTATGTTGGAATA | |
| CGCGTCCTCTAATTTCTGCACGTAATCCTTGCACAAACCTATCTCTGGTGGCCCATTCGTT | |
| TTCATACTCACCTGGGAGTAAGGTCCGGTACCCTTCAAATTCCTGGATAAATTGTTCCACG | |
| GAATTTTTACCTTGGTGACAGCCATTGTATTTTGCTGCCACTTGTCTCAACTCAAATTCGT | |
| CTGTTGGACAGAATTCGAGTGTAAACTCTTCGACAAATTGATGCCATAAAGGTAATTCGGA | |
| GTTTCCATACCTGTTAGTGAACCAGGCGAGAGCGGATCCATCGAGGTTGAGCATTGCGGTT | |
| GCTACCTTAAATAATTCTGTGACATCCTTTCCCATACTTTCTTGTAGTTTAAAGGCCATGT | |
| CAAGTTTGAACAGAAATTGTTGGGCTAAACGAACAGAGTTCTTTTCGTTACCCTTGAATAC | |
| CATGTTTAAGTTAACTTGCGACGGGTTAGAACCTGCATGCATCGCGTTAACTTCTGAATTC | |
| ATGTTGTTTAATTTCTTTGTTGAACTTTTCTAACTAGCCGGTGCTACCAATTGAAAGTGTT | |
| GCTGGTGTTGCGTACTCTAGAATCTGATTCTTGCTTATTTATATCTTATATATTTTTATAC | |
| GTTAATTCTCTGAGAACATATATGGAATATCCTCTGTTTAAATAGTAAATCTTTAATTTAA | |
| AAATAGCATTTTGAGGGATATAATTATCTTCTAGAACTTCTGTTTAACCTTCTACAATCTT | |
| CTTCAACCTTCTATATGATTACCCGATGAGGAAATAGAGAGATAGTCCTTTGTCTGATCTC | |
| TTACATTTTTGAAAGTTTTGCTAGTGGTGCGTACTCTAGAATCTGATTCTTGCTTATTTAT | |
| ATCTTATATATTTTTATACGTTAATTCTCTGAGAACATATATGGAATATCCTCTGTTTAAA | |
| TAGTAAATCTTTAATTTAAAAATAGCATTTTGAGGGATATAATTATCTTCTAGAACTTCTG | |
| TTTAACCTTCTACAATCTTCTTCAACCTTCTATATGATTACCCAATTAGGAAATAGAGAGG | |
| TAGTCCTTTGTCTGATCTCTTACAGTTTTTAATAGGACTTGGAATAAGGTGTCAAAATCAT | |
| TTCCTAGTTCTGGATGTTTCTACGGTTAAATCTTTTATCAAAAAAGTAATCATAGCCTTAT | |
| CCATAGTTACAGTATTGTTTATAACAATGATAATTGTGATACACGTGTTAGTAAGTACGCA | |
| ATAGGTGTATAACCGCACGAGTAGACAATAAGCGTGGTGGAAGTTAGTCGTAGTAGAAGTA | |
| GTAATCTATTTCTCTCTTTTTTCTTCTGCCGCTTCCACTCCCGATTAGGACCTATATCAGC | |
| TATATCAATTCTATATAACGGAATATCGTCTGTCTTTTGTACTTCACGCCCGCAACCTGGA | |
| ATCACCCTCGGTTGCTACTCTTTTTCGTATAGCAGACTCCTGTACGAGCTTATTACGTTTT | |
| AGGTCTATTTTGTTTTACTATGCCAGTTCTGTCATAACCCGTTGATGAATGATAATTAATT | |
| TATGCCAATGACAGTGTCTCCGACGGCTTCTCCATGCCTATGCCCTACATGATCAACGGGA | |
| CTAACTCTCTTTGCTTCCTACTCCGGATACTTGACCCTTGTTAACTTCCCTTATTCTAAAA | |
| TCGAAACCTTAACATCAGTATGTTATCGTCTACCTACTGGCACTTCCTTTTTTGGAACACA | |
| TCCTGAAAAATCCCTTTCACTACCCCGGCTCTTGGGAAACATCGCCCCGATGTTCCTCAAA | |
| ACGGTGCAACAAAATAACTGGATAATCCCGGATGGGGGCACTGAACCAATGAAGCTGCAAA | |
| ACATTAAACCAGATTAGAATAATAAATGTAGGTGGATCCTGGCAGTAACAATAATTTTTTT | |
| ATGAGTTCAATTTGTATTTCTTTAAATCGAGAGTGGCTAACTTATTTCAATCAAAAACAA | |
| TATGTTCTATGTTTTGGTAGGAGCAATATCTGTATTTTTTTCTTCAGCTGAGGGACAAAT | |
| AGGAACGTTCTATGTATTATAATTATGATTACTTTGTTGATATCAAACTTGTTCGTGTTCT | |
| TGAATTAATTCGGCTTTGTACATTGGACTTTGACGTAGTGACAAAGCTGCTTGGTTGAATA | |
| TTCTTTCAGGCACCTTTCTTGCTAGAGTTTGATCACAGTCTTTCCAGAAGACATCATAAGT | |
| CTTTTCTTTGCCTGGTTCTTCTGATCATCCACCGATACCACTCAGTTCGTTAATTCTTGCC | |
| AACATCTCACGCTCTGTTCTAGGCGGTTCCTGGTAAATATTGGGGTTTTCTTTATAGTATT | |
| TAATCCACTGTACATTTGATTCACGATCCTTCAAATTAATAACTGGTAAATCGACTTTATA | |
| AGCATTGCCGTTTATTTTCTCGACTAGTCTGTATGGCCCATATCATACTGGTTGAATTTTT | |
| GTGTACCTTATATTCACACCAAAGGCATCTTGATGCACTAACACTAAGTCACCAACTTTAT | |
| ATTCAAAGTATCTTCTTTTTCTATTATGGTGTTTTCCTTGTCGCCCTTATGCTTTACAATA | |
| TTATCCAGTGTGCTGTAAAATCAATTTCACACGTCTCACAAATTCTTCTGCGTTAGGTGAA | |
| TATTTGTTATCCTCCAAATCCCAGCTATTTACTTTTCTAATCATGCTCGGTTCATACTCGT | |
| AGGCGATTTCAAAAGGACTTGCTTTAATGGAATCTTGGTACGTTGAATTGTAACTAAGTTC | |
| ACACATAGACAGATGCTCATTCCAGGATAATTGAACGTTTGCAGAATATTTCCGAAGTAAC | |
| TGATTAACAATCTTGTTGAATCTTTCAGTTTGACCATCAGTTTCTGGATGATTAGTAGTTG | |
| AAAATAATAGAGAACTACCATTGAGATAATGTAATGTCTGCCAAAACTTATTCATAAACCG | |
| AATATCTTTGTCACTAAACAAACGAGCACATGCAGCAGCATTAAGTCTTTTGTGCGCTGGT | |
| ATAAAATGTGCCATTTTTGAAAAGCGATCGACAACAACCATAATGATAGTGTAGCCTGTTC | |
| TCGATCTAGGTAAACCTGTAATGAAATCCATCGTAATGTCGGTCCAGCGACCTGTTGGGAT | |
| TGGTAAAGGGGAAAACAACCCTTGTCTTCCTCTAGTGTTGGTGTTGTGCTGTTGACAGATA | |
| CGACAGGTTTCTACCCATTTTCTAATTTGTGCCAACATAGATGGCCAATAAAAACTATCTT | |
| TAAGATTCAAATAAGTTTTCCATGCACCAAAGTGACCAGCATCTTTGGCATCGTGTGCATT | |
| TTTGAATATTCTATACGGTAGTTTCTTGTAGTTTGGAATAACTACTCTAAAGAAATCTTGA | |
| GACTCTAATGTCTTATAATAAAGTACCTCATCTTGATAACAGGAATGTTTGATATGATTTT | |
| TAATTTCAACTGGAACTTTTGTTTTATCTCTCACAGTTCTAAATATCAAGGCATAATTATT | |
| ATCTTTTTTATAACCCGTAATAATTTCCCTTTTTGATTTTTGATTAGCTTCGATAGTACCT | |
| AGTGTCAACGAATGTTTCTGTGTTTTATTCTCCTCTTCTTGAGTCAATTCTAGCAACGCCA | |
| GTTCGATTTTGGCTAGCGTTAAGTTGTTTTCGTGGTTGTATGGGTATCTAGATAATGCATT | |
| AGCAGCGGAATTGTTTTTTCCCTGTAAGTAACGAATATCAAAATCAAACTGTGGTAAAAAG | |
| TCCATCCATCTAGCCCACTCCAGTGGAGTCTATGAGATTTTGGTTTTTAAGTAAATTAAAC | |
| TCTTGTGATCCGTCATAACAATGACATGTCTTCCCATGAGATAATATCTTCATGTTCTTAA | |
| TGCTTCAACAACAGCCAAAAATTCACGATCATATATTCCATGATTCAGTTGACTTCCAACT | |
| AGCTTCTTTGAACCGTAAGCAATCACACCTCGTCATTTACCTGTTTCGTCCAACTGTTCTA | |

TABLE 7-continued

CENs sequences

| Sequence | SEQ ID NO |
|---|---|
| GAGTATAACCTAACGATACTCCACACGCATCGGTATGTAGAACAAATTTACAATTGCCTGA<br>CCAACTTGGGTGCACCAAGGTGGGACTTGATATCAAAGCGTTCTTTAGTTGGTTGAAGGCT<br>TCGTCTTGTTCACTTGTCCATTTAATTTGTTTTGTCATGAACTTATGAATTGGATTGGCAA<br>TTTTGGAATGCCCTTTAATAAACCTTCTATAGTACGAAGTTAAACCAATAAAACTTTGTGC<br>TTCTTTGATCGTGTTTGGCGTTGGCCAACTCTTTACCTTTTTTATTTTCTCTAGAGCGGTT<br>TGAATACAAATTGGTGTAACAACTTGTCCTAAAAACTTAAATTCTTGATAAAAAAATCTGC<br>ATTTCGACTTCTTCGTAATTAGTTTATGTTTTCTTAGTGTCAACAAAACTTCTTTCACGTG<br>CTTACCGTGAGTTTCAACATCTTCGGAGTATATAAAAATGTCGTCTAAATAGACTTGGACA<br>AATCGATCTATTCTTTCAGGCAAGACAGTATCCATCATCTGTTGAAAAGTCGCAGGTGCGC<br>TTGTTAGTCCAGCCGGCATTACCATCCATTCATAATGGCCAAAATCAGTAGAAAATGCCGT<br>TTTCTCCACGTCTTCATCAGCAATTCTCACTTGGTAGTAACCAGGCGTCAACTCTAACTTA<br>GAATAGACTTTTGCCTTACCAAATCTTGAAATCAATTGATCAATATCTGGAAGTGGAAACT<br>TGTTCCTAGCAGTATTATTGTTTAGAATCCTATAATCAACACACATACGCATAGTACCATC<br>TTTCTTCTTAACAAATAGCACTGGACTGTTAAAAGGTTTGGAACTAGTTTTGATGAAACCT<br>TGTTTGATTAAAACTTCAACTTGTTTTGTTAGTTCCAGTTTCTCAGAGAAGCTTAATTGGT<br>ATTGTTTTTTTCAAAGAGAACTCATTAGGGTAATACAAGGCAACATATGCCCGCATCTTTT<br>CTTTGGCGGTAGTTCAGTTGATGGATCTCAAGTAAACTTTTCAAGTGTTTCCTTTTTCAAT<br>CCTCTTGCATGATTTGCGTCTAGGGGTCGATATTTAAATCAGCTTTGGCTTTATCGATATC<br>AGGACTTACTAAATACCCTAAAGTTAGATCACTAAATTGCCTCTTGATAAATGGGTTTCCC<br>AACATGAATAGCGCATGCTCAGTATCAAACATTTAAAATGACCTAACCTCCACTTATACTGA<br>TAGTTTCTTTGACTACCTCAAAAGGGACAATTACGTCTGCGATAGCAACACCAGAGTTTCC<br>GATAATCTTTACTGTTATTGATCCATCGAGCTTGGCCTTTTGCTAAACACATGAACTTCCT<br>CAACAGTTTTATTAATAACTGTAAAAGTGGTTCTGGAGCAACCAAAATGTCATCTGCATAT<br>TTGATATAAACGACACCACAAATTAATTTTGGTTTTTCTTTTTTGGGATGGTCATAATGTG<br>AGTGTGGGATGGCATCCACTCATTTTTCGGACATTTATACTTACTATGAAAGTTCCTTTTC<br>GTATTTCGCATCATTATCATGCCCTTTAACATCCTCTTATAAATACTATTTGAATAAAGGA<br>ACATGAAATTATCCATGATACATTAGGTTGCCGATGGCTGAAAAGGCATGAAATAAATTGA<br>GTTCTTTGGCGGACTTTGTTCTATAAGGGAAACCATTTAAATCATTGTATAAGTGCCCATG<br>TAGCTTCTTGCATGTCTATATCTCCAATAGACTCGCCCCAACATGGTTAAAACACACATCA<br>AGCTTTTATGTTAGACTGCAACAATCTCACCCCCATTAACTGCTCAATATCGGTAAGGCCA<br>TCAAGGAATAGTGGTCAACTCTTAATGTCAGAAATAGCGACGTATATAGACACTTTAAAGT<br>TTTCTTTATAGCCTCTCATCGATTGACCTGGTTTCAATCGACACAATTACTTGACAATATT<br>CACCACAGAGTCTCTGTCTTTGTCGACAGGAACAAAGCGTTTCAGAATCTATCTTCAAATT<br>TAGACCAACTAAAATCCAGTATTTGCTAGTTCATATGCATTTGAGAAGTGTGTAATTTACG<br>TTCGTTATTTTTCAAACCTGCAACAGCCCTTATAACTTTTCTGACATCTGGTAGCCCATAT<br>GTAGCAAATTCTCTTCCAATGTCTGCTGACCATTCTATGCCTCTAGCCCTTATATCCAGTA<br>ATGGAAATCCGGGGCCTTTCTAGTCTGGAATTAATCAGAGAAGTTGGGTGGTTTTGTATAA<br>TTTTATTCTGCATTGAACATAGTTGAGTTTTGTTCTCGTTTTATCGATTTAGCTTTGATAA<br>ATCAGCTAGTTGTTCTTATCCCATTGCAATCATATAAGGCAATAAGATAAACTGTTTTACC<br>ATTGTCCAAAATGCAAATATTCAATATAGTTTAGTTTCTAAAAGCAGCCAATAAATACATG<br>TCAAGCAAATACAATACTGCCTTGATGTGCCCTAATTCTACTTCAGATAACCATGTTACAC<br>GTTATAGATTGAACGTTTAAAAGAGTTACTTCAAAATACCACATAAAAAGAACCCAAGGAA<br>AAGAAAATAATCTACAACCTTTATTGATATCATGTGATACAGCAGGTATGTCGACACACAT<br>TATGCACTGATGGCAACTAGCTAATGACAACTAGTAATATGTTTTGTGTTTAGTTAGAGAT<br>GATATCATTATTTATTGTGGCGCCAAACCGACAATTGATAAGAGAGGTAACTCCGCTCTTA<br>CTGTAGCTTTTAATACGCATATTATTTAGAAATCCCTTAGTAATCAAGTGTCGAACTAAAT<br>ATGGATATCGTACCATCAATAGCTGATTGATCGGACCTAGTCATCCATATTGCTCTCCAAG<br>AGTTATATATTAGTGTATAAATTAACTACTGTGGCTGAAAATTACAACTTTCAAATACACA<br>ACCAACGTTGCAGGTTTGTTGTGATAAAAAGTGTAACTTGATGTGGGGTTGCACTGTATAG<br>TTTTGATGTTATACTGCCATTAATTGGGATATAAAATGTTTACCACCACCAACATGTGTCA<br>TCTGATAAACCACAGACCAGCAACAAATCTGGCACTTGAAGGTTTGTTGTAAAGCTTTTG<br>TTGCTAAAATTGGAGAGGTATTTTTCCCTGATAAGGAGAATTCAGACCGTCTTTTTGGAAG<br>TATCTTGAAAACCTTGTGATACTTATTTCGAACGCCCACCACTTGGACGGAGAAAGGATA<br>ATGACTTCTTGCGATTTTACAATTTTGCTGATAAATTAAAGGCCTTTCATGGTAGCTTTTG<br>TGGGAACGGCTCTACGGAAAAGTTCTTGAGACATCCAGGTTTGACAAAAAGATAAAGTCTA<br>CTAAATCTATTTACAGGCCCCAATTGATTAAAAAGGTGAAAATATAGGTTTTACAAAGCT<br>CTTCTGTAAATGTATTGTTTCGGATTACAATACATTTTTAGCAAGCACGGAAATTCCCTTT<br>TGTTACAATATACAGGAGTGTTCGTTAAGGAAAGGTTTTGACGTGGATGGAATGATGCACC<br>TGTAACATATCGGTGGAAACACAAGAAACCATATGGGCCTTTTACCAGACTAAGAGCATCT<br>TTTAAATATTCAGTTTATAGACATGGTGCATCTTTCAGAGTGACAGAACATCTTTGGGGGA<br>GTTACTCACGTATATTATTCTATAGATTTTAGGATTTCAAGGATCCACTGTGAGCTAATAG<br>GATTGGTAGTGGGCTTGTGCTACAAATTTGCTCAGTTTTGCTCGATGTCGCCAACCTTAAA<br>AACATTAATGTGTTTTTAAGGATTAACGCAGTTCCGTGCTCCGTTATGATGGAAAGGTTAA<br>AGGGAAAGTAACCTATAGTTTTGGTTTGTATCAGCCATGTTCTAGCTCGGAAGTCAACGAA<br>CAAGCTGTTTGGAAAAATCTAGCATTGTTTTTGATTTCTTCATCAATGTGATTATTAGGCC<br>CGAATCGTTTACGGCCGTAGTTATTAAGACATATTATACTAGAAAGATAAAAGGATATCCC<br>ATTATGCATATATTGTTAACTCGAACGGAAGAGATCAAATCAACCATTTGAGTGTTTACAA<br>AGACAATGGCAAAACAACAGCACTCCTCTTAAGAACACGATGTGGCACCTTCGCTTAACCT<br>TTTGGAAAGTAAAGGTAGTGTTTGTAGTAAAAAAGAAGGGAAGAAGATATTGAGATTGTG<br>TTATATCCGGATATTGTGAACAAAGTCACACAGTCGCCCAAATTCATGGTTTAATTGTAG<br>AGCTTATCCAGTCAGTATGTTTCTGGAATTGATGCTGTATTCAATGTGACAACATGCCAAT<br>ATTTCAAATCTATGACAGATGTATATATGAATGACATAAACGAAAAATCCATTGTTGAGT<br>ATGGTTATTTCTGCAAAATAAATCAGCAGGTAATTATGGTATTTGTATTACGAAATTAAGT<br>GAACTGCTCAAGAAATCTTTCTAAGATGAGCTTTTGCCACAATAGCGTTACATTTTTTAGA<br>TGGTTTTGAAACTTCACACAAAAGTCTTGCAAGACAATTTTGACCTAATAGAGTTGCTGCT | |

TABLE 7-continued

CENs sequences

| Sequence | SEQ ID NO |
|---|---|
| GTAAAGTTTCTACGGCACAAAACTATCAACCTTGAAAAAAATCTCGATTGTGTTGGTGTTG ACACATTGACAAGGTTTAGGTGAGAAAGAAATATTATGAAGTGTAAACCGCAGCAAACAGT TTTGTCTCTCCATCATACACCCCATATTTGATAATGTTTTACTTGTCAATGATCGGAATAT ATTTGACAGTATCTATTGTGTGTGGAACAAAAAAGGGAAAACTAGATATGCGCCTTTTGAC ATCTACGAAAAGAAAAGTCCACCGTGAAAAGCTTTGGAAATATAAAACATAAATTGGGTGA ACCATCTCCAAAGCTGTTTCTTTATTATTCGTTTAGAAGTGTTAGAAGTCTGGTACTTTTG GCATAAAACCAGTTAGGAAATATATAGGAAAGAATGGACGTAACATTAAAAATGTATCAGG AAAAATTTTTTACTTGCTCGTGGATTATTTATGACTCACAGCTTAGTTTTCCATTTCCCCG ATAATACTCCCAGAGGGTGAATTGCTATAAAAAAGTAACATTCGCATAGTATTTGCCACTG TGCTACATGCACTTTTCTCATTATATTACTTTTTTTACATTACTAGTTTTATATGAAGTGT ACAGGACTACTTGCATTATCTAAAAGCAGGTATTATTAAAGCATGTTCTTATCTGGGTTTT GTTACCAGATTCAAGTCGTTATAACAACTCATGAAGCTTACACTGATATATTTATTAGTGA ACAATGGAAAGATACAACCATATAACGATATCGAGAAATTCAAGTTGTTATTAGTTGATTT ATACAAACCACTAGAAAAAGTGTCATTTCCAATTAATAACTGCATCGCGACAGAAAACTT AGTTAAAGACTATATCAATCATATAGAAAGATAATGAAAAAAAATTCAAAAAAATTCCTCC ACACAAAGCAACGGAACTTGTAGCTGGTAAAACAATAAAGCTGCTGTTATACGGTGCCATT GAATGTGTAAACACAAGTGGGTATTTATTTTAAAATGATAGTAGTGTCCAGAAGGTCATCA TAGATATCATTGAAAAGGTCAGGACAACTCCGACTTTCTGTAAACTGTCAATAAGTTTCTA GACCTTCACTTTTTAAATGGGGATAAGAGAAAATGCATATAGACAAACAAACAAATACCTT GTGAGAAGAAAACAGCTATAGTATACCTACTAGAAGTGCTTGATTGTAAGGCCGAATATAC ATATCCATCCGAAATAGCATTTGGATCATTAATAATCATTTATTTAGACAATAAAGGATCT AATAAAATCCGCCATAAATGTGTCAGAGGCTAGTATCTAAGAATTAGTATGTAAATATCTG ACAGACTTATCAAGTGGAACTCACTGCAAGACTTTAACTTATTCAACGAAATTGGGGACTT AATCAAATTTGGAACGATATTGTATACTCCCCATTAATTACTCTTGGCTGGATTGTATATG GATCGGTGGAAGACCGGATTTTATATAATGGCATTATGAGCTATAGTTCCTTGGAAAAAAA CGAGTTTAAGGATGAAAATAAAGATATTATAGTCAATTTCGTTGTAGTAATTAATAAAAAA GGTCAAAGTGTCCAAGGATGTGTTCAAGGAGTGTTCAACCAGATATAACAGTCTCACGCAG AACCCAATCAGGAAAATACGCTTTGAAATGGAAAGCATCGCAAACAAAAAAGCCTGATTTT CTTGTGAATGATTTCACAAAAAGTCCAAACATATCTTGCTTAATAACTAGCTTTTGTCAAA AAAAACTGATCTTCTAAGGTAGAAATCCATCAATTATGGATGAAACACGGAACTCATTTGT TGAAAAACGCACTAGAAACAAGCAACTGTAATTAACGTTTATGTGAAATCTTAGATACACA AGTGCCTAACGGCTGAGAAGGCCACAGTTATGTTTTCCGATAGTTGAAAAGTGCTATTCAT AAGCTGTCAAAACAAAATCATGAGACACATCTAACAAATACAATTATACAAATTCAGAAGT TATATAATACAATCCATCTAAGACCTCGTTACTACATTGTGGTAATGGATTAATTGATGGA GCTATATGGCAAATCAAAAAGTTAGAACTAACAAAGGAAGGGGATAGACAAACAATGTAA CTGACTATTGTAAATAATGATAGTAACAGTTCACAGTCTAAAAATCAGAGGGAAAAACTTT GTAAGAAGAAGAAAATAAGTATATTACTATTATTATCTCAAGCTTTTATATGTCAAAAACG AATGCGATGTTTTGAGGAGGAATATTTATAGACCTGGCAAGCATCTGATTCGTAAAATTAT TTCGCAAGACCAAACTGAATGTACTGTACAATGAATCATTATTAAGATGTCCGAAATGAGT TAGCTGAAACTAAGGAATTACCAGATGACTCAGTGGACAAACAAGGTATTGAAGAAATAAT ACCGGTGTCGGAATATGACGAACCAAAAAAATGATCAACCCAATTTAAACCATTTACGGCA CACGGCTTAAGACAGAGGCAAACAAAAAAGGCAGCATTTAACCAAGAGAGCATAATGGCCG ATGCCGAGACTAATGACATTCCTTTTTTTTCAAAGACAAATAACAAATAAAATTTTCTGGG AAAGTCAAATCTGTATAAACACAATGCACCTGGTACTATTTTATCTATTTATCAATTGCCT GTATCTCAAGTCTCGAGAAGAGACGAAAACCAACATTGGGGTTACTTTTATGGAAGACATT ATAGGAGTCTATGCGCGCATAATAACTGAGAACCAAAATCACCAAAGTCTAATATAAAAAT TTCGCAAAAGGAAAGTAAAAACGATGTAAGCGCCGACTAAGAAATACACCATTCCCAAAGG TCAAAAACAACACTGGTAACAAAATATTTGCACAATAGAGAAAGTTGTTGCATGTGTCGAA TATTTTTTATGGATTAACAATAATGGTTAAGATAGTGTATGATGAGATGATCAAAGAAAAA AACAAGTTTCCCACAGACTCAACGATATTTTTTGATTTGAAATTAGGAAACCATATACTAT AATCCAATTACCGAAATTTTCATGAGTAAGCTACTATCCTTGTTAAGTGTTATTAGACCAG ACATTAAATACGCTGCAAGATATTTTGCAAACTGTACTTTCACGTCTGAAAATGTATTAAG ATAATGCATGCAAGTACTCAGATATTTCATTGCAACAAAACATTAAAGTTTTGTTTGACAA TGAAAACAAATATGAAGAGTTAATTTCATTCTCTAACTCGGGCAACTCTACTAGTAATTCG AAATCTATACCGATCAAAAGAGCGTGCTTATGTTTGTTAAAGGACTTATAATGTGAAGATC AGCAAAAAAACTAATTAGTAGTCACACAACTTTATCATTATAAATCAGTATTTAGCTGAA GAAGACTGTGAAATTAAAAAAAAACGAAACAGCAGTTAATTTAGCTAAAGTACACAAAATA CATATCACTGTCAATACTCAGAATTTTTCAAGAAATGGATACCTGAACTATGGATAATAAT TCACAACGTCATGATCAAGGAGTAGTGTGTAAAGAGTAATAATAGAAGCACGAACTCATAT TGTAAGGAAACATCTTAATGGTAAAAAAAATGGAGGCTGAAACCTTGTCATTTATATGGA GACTATTCATACTACATGAGGAAAACCAGGTACTTATATATCTAGGCCCCCTATATATAGA GAAAGAATGGTGAAGACATAATATTTACTGCGAGTGATGTGAGGCTGGTTGATAGTGAAAT CATTAAGGAAAATACCAGGAAGTATTTTAAATAACTCGATTGAAGAACTTGCCTGTAGTTC TCTCCTTGGAGTCAATAAAAGTACTGCCCAAGGGAACATCAGCAAGAAGATATCTAGTAAG GTATTTGTGTACGATTACGTGAGAGACCGAAGAATCCATACAAGTTTGAAGTATGGCTTCC TAAATTTTCTATCTGGGTCTATTTCTAATTATAGGTGAGTTGGTTTTGCTCAAGTGGCACA TGTATGAGTGTCCTTGTAATTATGAATTCACTTATTACTTTTATTCTTCTCCGCTTTGAAT CAGTTATATAATAAAGCCTAGTTTACCTCTTTAAAAATGCAAAGTAACCAAAAAAAAGGT GCTAGCTATATCACATGTTATTTTCACCGTTTTCTTTGGTATACCCACAGTTTTAGATAAT TTATTTTAAGCAAAAATAAATGAATAGTTTAATTGATATCACACTTTGTTAGAAGTAAAAG TTTAGACAGAGGTATTTTAACTCATGATACTCGATGAAGTTCATTATAGAACCGCATTTGT AAGCTTCGAGATTTGGTTCAAATTATAAAAAAAATCGAAAGAAATACCTCATTACCCAAAT CTGGAACAGCATGCATTGATAGGGCCGGAAATTTATTTATTAAGTTACATGTTAGAAAAAA GTGAACAGTCAGAACTTAGTTCAATACGCGGTAAATATGTTAAATAAATTTTACTTGGTTT GCATTTTTTCACTTTTCAGTATCTCAATAACTATCCCTTATTATCAATGAAAATCTATCTA | |

TABLE 7-continued

CENs sequences

| Sequence | SEQ ID NO |
|---|---|
| GTTATTTTGTTTAAGTTGGATAAAAATCTACGGAAAGACATTACTACTTGAAGGTATCTAT TGATAGATCAATTATTTGTTTTAAGAACTATAGAATTAAAAACAAGGCAGTAATGGTAGAT TTTAAAGATTATTTAGAGTAGATAGATAGTAAAGGCTGTACTGAATATAAATGTGGATTTG CAGAACCAATAAGTGACCTGTAATCAAGCTACTTAAGTAATTCTAATGGTATTTTACCACA GGAAAGCTAATCCTTTTCCCAATGACGGTTCATATGATCCAAGTTTTAAATGTTTTGTATC ATCATATCATAATAGGGGTATTTGAAAGGCATAGATCGACGAAAGTGATAAAAATTACTTA TTAAACGACGTATTTACATCCACGTTTTTGCTGGAAGTACTGAATCTGCCTACTGCTAGTT TGGGGAAGACAATAATACACAAAATAAAGACAATGATGAAGATTCCAGTTTTTTTTAAAGA TAAAAAAATAGATATATATGTATAATTGTATGAATAGTTTTAATAATAACTTATGTTGCTA TTTTGATAGCAATTCATTTTACTATTGAAAAGGTTACCCAGGCAAATAATATGTTTAGCAC ATCAGATTCTGTACTAATAGTAATATAGAGTTATGCTATAACGTCAGGCAATACTTATGTG TATAGCGAAATAGTAAATGGCAGATTGTAAACCGTATGTTTTCACTACTCAGACTCATACG ACATGTCTAGAAGCCCAAGCAATGAATTAGAGGACTGTTTGGTATCAACATCCAGTCACCT TGGGTGTAATAAAACTTATTTAAAGAGATAGTAGAAGATATAATCAAAGATCATGCACAAA ATATAAATGTATAAGTGAAGGTAATGTATTGACACATTTTGCTTCGGGCACGTGCGCATTA ACAGATTTTGTATAAGGTTGCTAATTATAGTACCTGGTGAAGAAGCATTATTCAGAAAGGT TGTGGCCCAACTAGATGTTGAAGTGGACCTTCTACTTTCCTTAAATACAATAGAAGCAAAA TAGATGCTTTACCTATCACAAACACGATGAGTATTTTCTCGTTTTGCTTTAGTCAAATAGA GCTAATTAGAAAATCCTTCGATATTTGATGCCTTGGCTGGAACCAACTCAAAAACATCTTC TTGGAATATATTTTCTAGTAATATCGGGAAAATAAGAAACAGTTACCCAGAAATAAATGG GATTAATAAACAACCGTAACATTTTTTATCTTTTCATGCGATTTACTCGAGCTCTACATTT TCTATTACCTCAAGAACTAAATTTGTGTAGCATTTATTTGACGTATAATTTTTATTTAGCT CATCACTAAAGAATACTTGTTATTAAGAGATTCTACCATTAATAAAGTACGCAAATCTAGC TTTTCTGAAGTCTTGTTAACTTTTAATCTCATAAATGCATAAATAACATATCAGATGTATC GTATTTAAATAAATATAATGCACATGATTTAGGAAAAAAAAAAACCATTTGTCCTCAAACA AAAGAGTAGATCAGACATAAAAAATTGAAGAGATTTCATTCTTTTTAAGATATCTGTTTTT GGTTCAATAATTGACTAATCTATCAAGTAAATTAAGTAAGAGTGTTTATATAATCCTCTTA TAAACTGTTGCTGTGATGTCAGTCTGACTAATTCTATCATCTGTGATTAATATCTGCTTAG CATCACTGAATTAATTTATATTATTAGTTGTTATCATCTATTGTTCATCAGACATTTGTTT TTTTAATGTAAGCTAATACACTTATGATGTGAGTAAGTGACGTGCAACAGTTACGTCCAAG ATATTGCTATGAATATAAAGCCCTTTTCAGTTCAATATTTTTTTACACATTATCAAAACTA TTTGATCAACAGATTGACAGCCAATTCCGAAGATGAAGTTTTAATATTAAACTTTTGAAAG CAAAAATCCCACAACTAAGAGTGTTCTTTGCCAAATAATAGTTCAAGCGTAGCCCATGGCA AAAACATTGGAATTAAAAAATCTCCGAGACCGGGAATTGAACCCGGGTCTCCCGCGTGACA AGCGGAAATTCTAGCCACTAAACTATCTCGGACAACTGCGCAAGCCCGGAATCGAACCAGG GGCTCAACGATGGCAACGTTGAATTTTACCACTAAACCACTTGCGCTTGTTGAGTTCTGAA AGTGTTGCTGGTGGTGGGTACTTTAGAATCTGATTATTGCTTATTTATATCTTATATATTT TTATACGTTAATTCTCTGAGAACATATAGGGAATATCCTCTGTTTAGATAGCAATTTTTAA TTTACAAATAGCATTTTGAGGAATTTAATTTATCTTCTAGAACTTCTGTTTAACCTTCTATA ATCTTCTTCAACCTTCTATATTATTACCCGATTAGGAAATAGAGAGATAGTCCTTTGTCTG ATCTTTTACATTACCCCGCCGCTTTAGAAACTTCGTCCCGGAGTTTATTATCATTATCAAT TGCTTTTGCATTATCCCATAAAGTTTTCTGTAAATCTTCTGGGATCTCTAAAAATAATGAA TATGGGATGCTTGAACTATGACAAGGGTCACAATCTTTCCAGTAGACATCCAATGTATCGT TTGTTTCGTCGATACCAGCTATACCGATAATCTCGGTCAGTCTACTTCTTGCTTCAGCTAT TGTTCTTGGGGTACCTTGGGAAACTGTTTATCCGTTTGTAAGAATCTTCTAAGCCATCTGA CATTGATTACTCTATCCTTTTTATTCGTTTTCGGTAAATCAACTTCGTAAGCGTTGTCTGA TATCTTTTTGACAACCTTGTAGGGTCCGTAGTATACCGGTTGTATTTTGTAATACAATCTA TCACTACCATATACATCTTTGTGTAATAATATCCAATCTCCAGCTTCAAATGTTTCGTACA CTCTCGACTTATTATGCTGTGTTTCCTGACTTCTTTGCGCTTCAATCATGTTTTCTTTCAC ATTTTCCATGATGACTTTCATTTTTAATGCGAATTCTTCAGCTTTATTGCTGTACCTTCTA CTTGAAACACGACTGCTAGAAATAAACATTGGCGAGTCTGGTAAGTAACCATAGCAAACTT CAAATGGTGATGAACCTATCGAGACTTGATGGGAACTATTGTAGGCAAATTCGGCCATTGA CAACCATTTGTCCCAACTGTAGAGATCGTTACTATCATAATGTCTCTGTTATTGGTTTAAG ATTCTGTTCGTTCTTTCCGTTTGACCATCTGTTTGAGGGTGATTAGTGGTTGAGAAGAGTG ATGATGTACCAAGAATTCTATGCCATTATCTGAAACCATTCTTTTTGGAATCCAATGTAAT TTAAAACAATTGTCTACTATCAATTTTGCACATTGCTCTGCGGTTGCAGTTTTCCTAGTGG GGATGAAATGCCATCTTCGTGAATCTATCCACCACTACCAAAATCATATCGTGTCCATT TTTGCATCTGGGAACACCTGTGACGAAATCCAAACTGATGTCTGTCCATCTTCCTTCAGGA ATTGGAAGAGGGGAAAATAATCCTCTTTGACCAGTTGTCTCGGGTTTGGTTTTCTGGCAAA CCGTACATCTTTGACAATATCTCTTCACGCTTTTTAGCATAATTGGCCAGTAGAACATAGG GTGAAGTCTCATGTATGTTTGAAATACCCAAAATGACCAGCAGAGTTACCGTCATGAGCG TTACCAATAATTTCCTGAGCCAACTTAGACTTAGGGGAGACTACAATTCTTCGATCATTTC CTCCTTTAACCACTGAGAAATATAGTAAATTATCCTCAATTGAATAATGTTTGATGTGGTT ATGGATTGACTTCGGGATCGGCAAATTCTCTTTTAAAATGTCGTATATCTCCTTAGTTTCG TTGTCTTCATCGTACGACTTAATGATCCGTTCTAGAAGTTCCTGATTTGGTGTTAACACCG ATTCTATTGTGTTGATACCAACTTCATTTTCCTCGTAGGGGTACCTAGACAAAGCGTCTGC TACTGAATTAGTAGGACCTCAAGTATTGAATTGTGAATTCGTAATCAGCTAATCCTAGGAA TGATTGAGCATCTTTGGCGTTTTTCGGAATTGGCCAGCTCTTGATTTTGTCTATCTTAGCA GGGTCAGTCTGGATACCTCTGCTTGAAATGAGATGTCCTAAGAAACCTAAGGTTTTGAAGT AAAATGAGCATTTCTTTTTCTTCGCAATCAGCTTATTTCTCCTGAGCAATTCCAATATTTT TCTAATGTGACTGTAGTGTTCTTCAACAGTCTTTGAGTAAATTATAATATCATCCAGGTAC ACCTGAACAAATTGGTTCAAATAAGGTGCTAGAATCCTATTCATCATTCTTTGGAAAGTAC TAGGGGCGTTGGTTAAACCGAAAGGCATCACAACCCACTCAAAGTGACCGTAATCTGTGGA AAATGCTGTTTTTTCAATATCATCTTCTGCGATTCTGACTTGAAAGTAACCTGACATCAAA TCCAACTTGGAAAATACTGAAGCTCCTCCAAAACATGTGATTAATTTGTCGATTCGTGGTA | |

TABLE 7-continued

CENs sequences

| Sequence | SEQ ID NO |
|---|---|
| TTGGGAACTTGTCTTTTACCGTATTGTTATTTAATAACCTATAATCAACACACATTCTCAT ACTACCATCTTTCTTCTTGGCAAGTAACAAAGGACTATTGAAAGAACTAGGTGCAAACTTG ATAAAGGCTAGTTTCAACAGTTCATCAACCTGTTTATTCAGCTCTTGTTTCTCTGAATAGC TTGATTTGTACTGGCGTCTGTATGTACTCTTGGTAGGTTCAATGAGTATAATTCTGTGAGT CAAATCCCTTTGGGGAGGTAAACTGGTAGGTTGGTCATTGGTCACCACATCTCTAAATTCT TCATGAATTTTCTTTCTAATTCCATCAACACCATCGTAAGGTTCTTCTAAAACATTATTAT TTTCTTTTACTTCAACTGACTGCACAAACAGTAATAATGGATAATTATCAACATTCTTTAA ATTTCTTCTAACTGCACGCATGGAGTTGATACCTATAAGTTCATTTTTTTTGTCTCTTCAA TTTTTTCATTATCATTAATTGTTTTGCAAGTACTCTCTAAGTTAATATATATCCCGTAACC TTAATTCTTCTTCAAAAAGTAGAGCTTCTAGCGCCACTAATTCTTTTTTATTTCTCTTTCG ATCATCCTTAGCCCTATAATCTTTAATAAAGAGGAGACTGAAAATTATTTTATGATTGGTA TTCTTCAAAAGCAAACATTTGTTGTCTTTATTGCGCCCATTATATTTTAAAACAAGTTGCG GTCTTAAAATCAATTTAGCTCTATGTGTAATTGCTTTCTTATTAGCGGATATAACAACTTC AAATCTAGTAGACTTTGAAAAACTCTCTCATGGATGTAACCTAACAAATACATAATCCTTA ATGTTTCTTGGCGCGCTGTCATCAACTAAAGCAACAGAATACCTAAACAGTCTCTCTTTCA AAATCTCTTCTATTGCGAGACAGAGTTTTCTTAATAAAATCAAAATCCTTAGTTTTGCTTC TCTATCTGAATTCTGGGGCGAAACCACCTTTAAGCGTTTAGCAAAATGAAACCATAAAAG TAGTCTTAAATTGAAAATACTTTATTTGTTAGTATACCAAGTAAGGACCGATTCAACAAGG ACTAATACCTCCATCTCCAAACTAGGAAAAGTACGTGACTTGCTTTCTAATCCATTTCTGT GTGTAGCTTAAAATTGGTAACCAATCTATTAACAAATGTTATGACAAGCGCCTATATTTTG TTGTTACATTTGAAAAACATTTTTAAGTCTAGTAGGAATAAGTTGGAACCTGCGTTCATCG CTTTCACTTCGAAAATCTCTTTATTGGTCTCTTGGACCCTAAAACCTCCGATACTAGCAGT TGTAAGTGTTATTGGCAGAATTTCGACTAGACATTACTTATAGCGTTTTTTGTTTTATGTC ATTTATTTATTGATTATACTGCTTATACACTTTATATATTATAATTTATTCAATATAATTA ATTCAAACTACATATGTGAATTTTGAATACCTTAGACTGAAGTTCAAAATCAAAGACTGAT GTGAGCTTGCAACCCGAAAAAGCAAACTTTCACTGATTGATCATCCATGGGCTGCAACTGA AAGGCACGTAGATTTGTTTTTCTCTAAGGACAGTACATGCTAGGTTTGTGGGAAATGAGGA AAGCTTTGTGTACGCCAACTTACACGCAGGAGGAGAAATTTGGAAAATACCCTATATAGTT TATAAACAATAAGTTCTTTGTTCCATCTAGCAAAACCTAGACCAGTCGAGATAATACACAT ATACATAAGTCATTTTCCATGATGTTATTTCATCAGAGGTAATTATTACATTCTAAAATTA ATGCCAACGACATAGTGATTTAAAAGTGAGAGGTTTTTTCAGGCGTTGAACTTTAAGTTTG AGTATTTTTTCAAAACTTTTTTTTGAAAAAACCCTTCTAGGGATAGTGCAGTTTTAAGTCG GGTTTACAAGAAGCATTTAAACTAGTTGATGAATATTTGAATATTACTGTCAGTGTTTCTG CACGATGCTAAATGTTATTCTCAAAGTACTTTGGAAGCTCATACTTAATTTTGCAAAAGGA CTTTTTAGAATTATCTAACTTCATATAATATGAAACTCAGCGCTCAAATTCTACCATTCGG CATTTGAAACCGGTGAACCACTTTTTCCTTGATTGTTGTACAAAAAAACAGATATTGACT TCTGCGAAATTACCGAGGAGCATCTGTTTCTTTTTCGATCTCGTTTACACTAAAATCAATG GCTTATAAAGTGTACATATAGTTATAGTTTATTAAATTGGGTCTGTGTAAAAACATAAAAA AACATGTTCAAATGATAGAGCTTACATCGAAGCAAGGTTAAGTGATTTACGCATAAGGCA AAAGAGAGAATACCGCTGGTCTATGTCTCTGTTATTTGTTTTGGTTAGTGTTTGGTAGAGG AAACCTTCTTAAAGTCGCCTGGAAATATAACTTAACTTTTTTTACTAAACAGCACCCAATTG AAAAAAAAAGACCTCCATGAGCTGGTGATTAAATCACGTAAGAGTAATCCATTTTTGATTT TATAAGAAGTTAAATGCTGGCCTCTAGAGACGCTTTATGGACGGAAATAGCCCGAAAATAA TTATTTCAAGCATGAATATACTATCAGTTCCGCCTTAGACGTTTATTGAAAAGGAGCTTTT ATTATACAAATATGTACGCGTTGACAACTCTTTCTTTTTCCTTCTGTTAAGAATAATATAA ACGGTTATTTCCTTTTATTCTAAAGAACAAAAGGAAGCTCCTCAAAACAAAGCTGAAGGTT TACGCATCATTTCGAGTATATTTGTCAGGGCTTTGAAGCCGGGCGCTATAATCAACAATTT CATATTTTGGGATTACAATATATAACAGCAATTTATTAAGAAAGCTATGAGGAAAAAATCG ATTTGTTGAAGACTTCATAGCTATCTATAGTTTCTATCAAGTATTTGGCAATATAAAAATG GATGATAGTAAATGTAGACTTCGGATAATTACTTATAGTTAAACGAAATTCAAAGGGGATT TTAACAAATCCCAAAGCTTTAGGACAATTTTGGCTGGCCTAAAGTTTCACTACTGAAATAC AGTAGAGATAAGTGGCGCTACGATAATAACAAGTTCCCCTTCTAGTCATTCAAAACATTAT GTTTACAAAAATGAAGAGAGTAAAGCTAACAGTGAAAAGCTGCTCAAAAAATATTGCAGAC CGGGTTAATTTGCAAAGTTTCGAATATTGCAAAACTTCTCGTTATTTTTCCAGGTTTTGT ATTACGCATAAAAGGAAAATTAAAAAAGATAGCTTCGGGTTTTGTAAACAGAGTCAAGAGA CGGTCTGCTTCCTAGTTTGAAAACTTTGCAAATGTACAGTACGATATAAAGGGCAAAAGCT ATGTATATTGAACAATTTCAATAATAGTAATTCTTTGAACTAGGTCTCCTCGTTTGAAATT AGTGTACTTCATTTAACCAAGAACAGTAACAAATTTCTGCAGCCTCCTGAAAAGCAGCGGC TAAAGAGTTCTTGCTCCTGATGCTTTAAAAATGGAACTGTTTGTGCAAAGAAAAAGATTTG TCAATAATGGAAAAAAAAATTTAATGAAAAGTAGCACTTTGGATATTTACTACTTGTTTG ATCCCGTTGTTGGCCAAACTCTTAGAAAATCACATTACTTTGAAATAAAAATTATTAATAC AAAAGATTCCATAATATTTACTTCGACATATGCTATAATGTCAGGCAATACCTATGTGTAT AGCGAAATAGTAAAGGGCGGGTTGTAAATCGTATGTTTTCACTACTCAGACTCATACGACA TGTCTAGAAGCCCAAGCAATGAATTAGAGGACTGTTTGATACGAATATTCAGTCACCTTGG GTGTAACAAAACTATTTAAAGAGATACTAGAAGATATAACCAAATATCATGCACAAAATAT AAATGTATAAGTGAAGGTAATGTATTGACACATTTTGTTTCGGGCACGTGCGCATTAACAG ATTCCGTATAAGGTTGATAATTATAGTACCTGGTGAAGAAGCATTATTCAGAAAGGTTGTA GCCCAACTAGATGTTGAAGTGGACCTTCTAATTTCCTTAAATACAATAGAAGCAAAATAGG TGTTTCACCTATCACAAACACGATGAGTATTTTCTTGTTTTGCTTTAGTCAAATAGAGCTA ATTAGAAAATCCTTCGATATTTGATGCCTTGGCTGGAACCAACTCAAAAACATCTTTCTGG ATTATATTTTCTAGTAATATTAGGAAAATAAGAAACAGTTACCCAGAAATAGATGGGATT AATAAACAACCGTAACATTTTTTATCTTTTCATGCGATTTTCTCGAGCTTTACATTTTCTA TTCTCTCAAGAGCCAAGTTTGTGTAGCATTTGCTTGGCCTATAATTTTTATTTAGCTCAAC GCTAAAGAATACTTGTTATTGAAAAATACCACCAGTAATAAAGTACGCAAATATAGCTTCT CTAAATATTCATGAGTATCCATCTTGTAAAGGCCTCTGTAAAGCAATAACCTTATATTTCG | |

TABLE 7-continued

CENs sequences

| Sequence | SEQ ID NO |
|---|---|
| CTAAATCCAGTAGTCAAAAAATAGATAGCAAGCTTGAGCAAGATTCTTTTCATTAGCTTCA<br>TTATGATTATATAAATATATTGCGCCAGGAAGAACTTGGAGATTTAACTAATGTCGAGAGT<br>ACAATGAGGTATAATAAATTTTCATGTTTAATATATCTGATAGCGAGCATATTTACATGGG<br>AAGCCACTCAAACTAATTCCGTCAATTTTTTTACAAATCTAATTTATTATTCCAATCATTA<br>AGTCAAGATAAAAAAAACCCTGAAAAAGTATAGATTCTTAGCTACTTTACCATTCAGGCA<br>AACAAACTCATTCTCCATAAATATGTCTAAGAGTACTCTTGAGAAAAATTCTTCTTTTATA<br>TTATAACACGATTAAATTTCCTGAGCAAAAACAAAAATGAATCAGACTCTCCCAGAAAAAT<br>AGTGAATGCAATTTTTGTTTTATTAGTAAGAGGATTAAGAATATCCTTATAAAGCTATCTC<br>TGAGTCGATAAATCTATCTATGGCCTAATTTCAATTTACTAAATGAGTTTAGGAATGTCAC<br>TATATACAGAAAACTGAAAAATAACTTCAAGTATATTTACAAATTCTGTTCATTGAGAAC<br>CAAATAGTGAGAATTATGCAATATCCTTTTTAATGGATTTATAAGTTATTCAATATCAACA<br>ATAAATAAACAACATTGATATATATGTAAATAAAACGGTAGAACCTAAAAAATAATTTATA<br>TAATGAAAACTTCCAGCGAAGTATGATGATATTCAGAATATATGCGGATAACTGTCGAAT<br>AAGCACATTAATAGTAATGATATACATGTAAAAGGTCTTGGGAGACAAATTAATCAATTTT<br>ATGATAGTAAAACAAATTTCTTTGCAAACAGCGCGAACAAAATAAGAAATGATATTTTATA<br>TAAAAAATACTAGATGAGTTGACATTGGAGAACAGTGGTTAAGGAATAGCGTTATGCCACA<br>ATGTAGATATTTATAGTAGCTGTAAATTCTATAAAAACTGGTGTTCAAGAGGCACAATTCC<br>TGACGTGATGCCCATATTTAGTCCAGCAGCTGGATAACTTAAAAAGAATCCACAAATTATA<br>TAGATCGATATCAATAGATTCAGTTGGAGTTGAACTGGTTTCTTATTAATCTTTGTTTTGG<br>TGCCATGATGACTGAGGGTGTCTTCCATAACTAATGCTGATATAAATTTTAATCGTTATTT<br>CTGTCCTTAACTCAGAACATAGGTCTAAATATAGCTGTCAAACAATCAGAAATAAATACTG<br>ATCCTGAAATTGGCCTATTGTTAACTATCTACAGTGTTGAATCTGATAACGAAACTATGCC<br>GGATCAATCATGAAGATGTTCAAGCGTTAAAAAGAATCGTACTCTTTTTGGTTTAAACGC<br>ACCTGTACTATAGTTTGCTTTGAATAAAACCATCGCCAGTTACCCAACTTTAAGTGAGCAC<br>TATTTCTGAAAGTGACATCACATCTTAGTACCTAATCTTACTCTCTAGGTAATTGTAAAAA<br>TTACCCTCAGCACTGTTTCGACATAGCACTCTTTAGTGAAAATTTGCAACGTGATCTAAAC<br>ATGAAAATCCGAGAAATTGCCGGATACTCATAAGGTGCAAACTTTTCTTGCTGGTCGATAG<br>ATCACTTCGTAATGTTCCATTTGCACCTATTGATTGATTTTTCGTTGACGTCAACTTCTTA<br>TATATGAGCCCTTACAGAAATGATTTTATGGATGCACGATATTCCTGTTTAAAACAGCCGG<br>CGTTTACTATCCTATAACAAGAGGCTTACATGACTCCCACATGAAATATAAACTAAGCGAA<br>CCACGAATTCGACTTTGCCGCAAAACGTTTTCTGAAACATACTGTTTAAATAAGTTCAGGA<br>AAAGGCATAACAGTCATACATAATTGTCTGTATAGAGTTTTGACATTTATTATAACTCTCT<br>AAGAAAATGTTTGGTAGATTAGACTGTGGAGAGAAAGAAAAAGAAGAGTGTCTATAAAAA<br>CTATAGCTTGACAAATATTTTGATAAAGTTTAGAAAGAAGCACATGTTTTTTTCTGATTTA<br>TTCCTACAGAATGGATCAATGAAACCTTTTGGGTGTTTTTTTTAGAAATTATCAAGATTAA<br>ATTATTGCATTACAAAAATTGTATGTTTTTGATTTGAGTTTCGTGCGGCAAAAGATTGGAA<br>ATGGAAGCTATCCAATATTACAAATAATATTGTCGTAGAAATGTTTTCTTTAGGGATATCA<br>AAAGTTTGTTAGACGGCTATTACTCTTCTGTTTTCAACCCGTACATATTTTAAACTGGGAA<br>AATGCAGGATCTTAGAGAGTTCTAGTTTTACAAAGTACTGTGTCTATGGAAGATTCATCCA<br>ATACACACAGTAAAATTAAGTTTGAAAATTTGAGTAGTAAAGACGTACTTCCAGATTATTA<br>CGTTCTTCTTAGACATATAATTAAATACTTGGTCTCGAAATTCAGATTCTCCAGTAGAAAA<br>GTCCAACAAAAATTATAAAGGACGTACGTTTCCAGTCGGACCAAACTAGCTGAAAAGCCA<br>ATAGTTTCACGATGTAGCTAAATTTTAAGTAGCTGTTTGAAAAAGCTACTTGTTTTTATGT<br>ACAAAAAGGTTGTATGTGTTAGTTGAATAGTGTTTCTTTTTTTTTTGCAATTTCAAGATC<br>AGCGACTTTAAATATTGGTCATTGTGACATGAAAAAAAAAACAGTTACCTTTGAGAACTAAA<br>TGACTCTTTTCTTGCTAGACCTTATCGATCTATCTTTTAGCTCATCACAAATATTAGGCGA<br>AAAAGAATACACTAATCTAAGAAAGCTATTTATATATTATTTTTTTGATGGAAAAAAAAAC<br>TCCAATGTGTGGGATAATGTTGAAATTAGCGTTATGTTTATTAGGCATGGTGAGTCAGCCC<br>TGATAGAGGGACCATTGAACTGAGAGTACAAACAAGTTGGTGATTAGAACCTATTATTTAA<br>GCATCCTTTAGACAGTGCTGTTTTAACGGGGGTCTCATATATTTAAATCATGTACTATAAG<br>AGGAATAGTCACACACGGATTTCTTTTGATGAAAATGCTCAAGGACGGCTAGGTAACAAAC<br>AAATAAATGAAAAGAAAAAAACTGGAACATAAGGGACAGCAATCACATAGTCCAAAGCTGA<br>ATCCAGAAAAGGCTGCAGAGACTCCGTCATTTGATGCAAAGCATAAGGGTAAACGGTTAGA<br>CGTTGCTGAAGTTAGTAGAAACGTATACTAAGAAAATCCAACACATGGAATTCAAGCAGCT<br>GCTAAGGGTAGAGTCATGTGAGTGAATAACAGCTTAATTCAGTAGAATGCAACAAAAGGAT<br>TTATGTATTACATTGCTAATGATTGTTCCACAATAACAGGCAGCATGCTTTTGATAATTAA<br>GAGGCTAGTCCTCTGCGGATAACTAGAGCTCTTCTGAATTATCAGAGTATTGTTGTGTTAT<br>TGGTCCATATAGCTTTTGCAAGATTGTTAGGCCGACCTTTAAGAGCACAAGTTTTTTTTT<br>CTATAAGAGTTTAATGTATTTTGCATATGTATAAGGGCGTGCAACTTACCATTTGCTCTGA<br>GAGCAAAAAAACAATAATTTATAAGGTTTATTTTTTGTTTATACTAAGTTTTTTGTTAAAA<br>TCTAGCCAACTTCCCAGCTAACATTGTCGATTATGATCTAGTTTAGTTTATGTAAGTCAAT<br>GTACTAGGGTCTTTTTCAGGTCAATGTTGAATTTCTCAACATAAACATAACACTACGTTTC<br>TTCTTTAACTCTCAACAATTCTAAGTCCCCTAATGGCAAGAAAAACTTGACCATACATAAT<br>CTTAAGCTGCTTACAGAACAACCCTACAATGATGCTCCAAGTGGTAAAAAGTAACTTCTA<br>AACGGTAAACATTCGGGCAATGAGATTTAGGCTAACTTTAGGATTAACATAATAGATTCTC<br>TTCTCATCTTAACCAACTTATAAACACTTCTGCACGAATAAAATTCACGCAAACGCGTTAT<br>CTGTACTTGTAGAGCTTATATAACAGCATATAACATGAGAATAGTTGCAGAATTTTATAGT<br>TCTATACGGTTCATCAAATCCTATATACCCTACTCTCCCTGAGCATAAAGCATGGACACAT<br>GATATATTGCAGACGAATGACACATGCTGATGCATCTTAAAATGCTCCAGGAGTGATTTCC<br>AAAGTTCAAGAATCCTTAGAATGTTGTACTATAAACCGCCATATAGTTTATAGAAAAAGTAT<br>ATTCAAGCAATGCTGCTTAACAATGACTAATATAAACACAGTCCAATTTCCATTGATTTGG<br>AACTATAGTTTTTGGTTCAACAATATAATTTCAAATAAATCTCTGCTTCCAATACCAGTA<br>ACTCTTTTCTCTTGAGTGTTTTGACTTTTCAATGGATGGATGTTGGTGGCCGCCTTTGATC<br>TCAACAAATGCTCATACCCAATACCTTTTACTTCGTTTTTGAGCACATCTATAATCCCGTG<br>TTCTGTATAGTATAGTGTCAGTCGTCTGAGATAAATATCCGTCTTTTTTAATTGGTCTGAT | |

TABLE 7-continued

CENs sequences

| Sequence | SEQ ID NO |
|---|---|
| CAATCTCAGCATTTCCAGTGGTTTCTTCCATTTCTTCCATCTCTTGAATTTAAGTAATTTA<br>AAGTAAGGTTTTTACATTAAAAACTGGTTCGATATCAGCCCTTAACGATATAGGTAACATA<br>CTATCAAAGCTTAGATTAATTGTACTTTCTTTTTCATCTCGCCTTATACAAGACATAATCG<br>ATACTGTCAAATATATCCCGATTATTGACAAGTAAAACATTATCAAATATGGGGTGTATGA<br>TGGAGAGACAAAACTGTTTGCTGCGGTTTACACTTCATAATATTTCTTTCTCACCTAAACC<br>TTGTCAATGTGTCAACACCAACACAATCGAGATTTTTTTCAAGGTTGATAGTTTTGTGCCG<br>TAGAAACTTTACAGCAGCAACTCTATTAGGTCAAAATTGTCTTGCAAGACTTTTGTGTGAA<br>GTTTCAAAACCATCTAAAAAATGTAACGCTATTGTGGCAAAAGCTCATCTTAGAAAGATTT<br>CTTGAGCAGTTCACTTAATTTCGTAATACAAATACCATAATTACCTGCTGATTTATTTTGC<br>AGAAATAACCATACTCAACAATGGATTTTTTCGTTTATGTCATTCATATATACATCTGTCA<br>TAGATTTGAAATATTGGCATGTTGTCACATTGAATACAGCATCAATTCCAGAAACATACTG<br>ACTGGATAAGCTCTACAATTAAACCATGAATTTGGGCGGACTGTGTGACTTTGTTCACAAT<br>ATCCGGATATAACACAATCTCAATATCTTCTTCCCTTCTTTTTTTACTACAAACACTACCT<br>TTACTTTCCAAAAGGTTAAGCGAAGGTGCCACATCGTGTTCTTAAGAGGAGTGCTGTTGTT<br>TTGCCATTGTCTTTGTAAACACTCAAATGGTTGATTTGATCTCTTCCGTTCGAGTTAACAA<br>TATATGCATAATGGGATATCCTTTTATCTTTCTAGTATAATATGTCTTAATAACTACGGCC<br>GTAAACGATTCGGGCCTAATAATCACATTGATGAAGAAATCAAAAACAATGCTAGATTTTT<br>CCAAACAGCTTGTTCGTTGACTTCCGAGCTAGAACATGGCTGATACAAACCAAAACTATAG<br>GTTACTTTCCCTTTAACCTTTCCATCATAACGGAGCACGGAACTGCGTTAATCCTTAAAAA<br>CACATTAATGTTTTAAGGTTGGCGACATCGAGCAAAACTGAGCAAATTTGTAGCACAAGC<br>CCACTACCAATCCTATTAGCTCACAGTGGATCCTTGAAATCCTAAAATCTATAGAATAATA<br>TACGTGAGTAACTCCCCCAAAGATGTTCTGTCACTCTGAAAGATGCACCGTGTCTATAAAC<br>TGAATATTTAAAAGATGCTCTTAGTCTGGTAAAAGGCCCATATGGTTTCTTGTGTTTCCAC<br>CGATATGTTACAGGTGCATCATTCCATCCACGTCAAAACCTTTCCTTAACGAACACTCCTG<br>TATATTGTAACAAAAGGGAATTTCCGTGCTTGCTAAAAATGTATTGTAATCCGAAACAATA<br>CATTTACAGAAGAGCTTTGTAAAACCTATATTTTCACCTTTTTAATCAATTGGGGCCTGTA<br>AATAGATTTTAGTAGACTTTATCTTTTTGTCAAACCTGGATGTCTCAAGAACTTTTCCGTA<br>GAGCCGTTCCCACAAAAGCTACCATGAAAGGCCTTTAATTTATCAGCAAATTGTAAAATC<br>GCAAGAAGTCATTATCCTTTCTCCGTCCAAGTGGTGGGCGTTCGAAATAAGTATCCACAAG<br>GTTTTCAAGATACTTCCAAAAAGACGGTCTGAATTCTCCTTATCAGGGAAAAATACCTCTC<br>CAATTTTAGCAACAAAAGCTTTACAACAAACCTTCAAGTGCCAGATTTGTTGCTGTGTCTG<br>TGGTTTATCAGATGACACATGTTGGTGGTGGTAAACATTTTATATCCCAATTAATGGCAGT<br>ATAACATCAAAACTATACAGTGCAACCCCACATCAAGTTACACTTTTTATCACAACAAACC<br>TGCAACGTTGGTTGTGTATTTGAAAGTTGTAATTTTCAGCCACAGTAGTTAATTTATACAC<br>TAATATATAACTCTTGGAGAGCAATATGGATGACTAGGTCCGATCAATCAGCTATTGATGG<br>TACGATATCCATATTTAGTTCGACACTTGATTACTAAGGGATTTCTAAATAATATGCGTAT<br>TAAAAGCTACAGTAAGAGCGGAGTTACCTCTCTTATCAATTGTCGGTTTGGCGCCACAATA<br>AATAATGATATCATCTCTAACTAAACACAAAACATATTACTAGTTGTCATTAGCTAGTTGC<br>CATCAGTGCATAATGTGTGTCGACATACCTGCTGTATCACATGATATCAATAAAGGTTGTA<br>GATTATTTTCTTTTCCTTGGGTTCTTTTTATGTGGTATTTTGAAGTAGCTCTTTTAAACGTT<br>TCAATCTATAACGTGTAACATGGTTATCTGAAGTAGAATTAGGGCACATCAAGGCAGTATT<br>GTATTTGCTTGACATGTATTTATTGGCTGCTTTTAGAAACTAAACTATATTGAATATTTGC<br>ATTTTTGGACAATGGTAAAACAGTTTATCTTATTGCCTTATATGATTGCAATGGGATAAGAA<br>CAACTAGCTGATTTATCAAAGCTAAATCGATAAAACGAGAACAAAACTCAACTATGTTCAA<br>TGCAGAATAAAATTATACAAAACCACCCAACTTCTCTGATTAATTCCAGACTAGAAAGGCC<br>CCGGATTTCCATTACTGGATATAAGGGCTAGAGGCATAGAATGGTCAGCAGACATTGGAAG<br>AGAATTTGCTACATATGGGCTACCAGATGTCAGAAAAGTTATAAGGGCTGTTGCAGGTTTG<br>AAAAATAACGAACGTAAATTACACACTTCTCAAATGCATATGAACTAGCAAATACTGGATT<br>TTAGTTGGTCTAAATTTGAAGATAGATTCTGAAACGCTTTGTTCCTGTCGACAAAGACAGA<br>GACTCTGTGGTGAATATTGTCAAGTAATTGTGTCGATTGAAACCAGGTCAATCGATGAGAG<br>GCTATAAAGAAAACTTTAAAGTGTCTATATACGTCGCTATTTCTGACATTAAGAGTTGACC<br>ACTATTCCTTGATGGCCTTACCGATATTGAGCAGTTAATGGGGGTGAGATTGTTGCAGTCT<br>AACATAAAAGCTTGATGTGTGTTTTAACCATGTTGGGGCGAGTCTATTGGAGATATAGACA<br>TGCAAGAAGCTACATGGGCACTTATACAATGATTTAAATGGTTTCCCTTATAGAACAAAGT<br>CCGCCAAAGAACTCAATTTATTTCATGCCTTTTCAGCCATCGGCAACCTAATGTATCATGG<br>ATAAATTTCATGTTCCTTTATTCAAATAGTATTTATAAGAGGATGTTAAAGGGCATGATAAT<br>GATGCGAAATACGAAAAGGAACTTTCATAGTAAGTATAAATGTCCGAAAAATGAGTGGATG<br>CCATCCCACACTCACATTATGACCATCCCAAAAAAGAAAAACCAAAATTAATTTGTGGTGT<br>CGTTTATATCAAATATGCAGATGACATTTTGGTTGCTCCAGAACCACTTTTACAGTTATTA<br>ATAAAACTGTTGAGGAAGTTCATGTGTTTAGCAAAAGGCCAAGCTCGATGGATCAATAACA<br>GTAAAGATTATCGGAAACTCTGGTGTTGCTATCGCAGACGTAATTGTCCCTTTTGAGGTAG<br>TCAAAGAAACTATCAGTATAAGTGAGGTTAGGTCATTTTAAATGTTTGATCTGAGCATGC<br>GCTATTCATGTTGGGAAACCCATTTATCAAGAGGCAATTTAGTGATCTAACTTTAGGGTAT<br>TTAGTAAGTCCTGATATCGATAAAGCCAAAGCTGATTTAAATATCGACCCCTAGACGCAAA<br>TCATGCAAGAGGATTGAAAAAGGAAACACTTGAAAAGTTTACTTGAGATCCATCAACTGAA<br>CTACCGCCAAAGAAAAGATGCGGGCATATGTTGCCTTGTATTACCCTAATGAGTTCTCTTT<br>GAAAAAAACAATACCAATTAAGCTTCTCTGAGAAACTGGAACTAACAAAACAAGTTGAAGT<br>TTTAATCAAACAAGGTTTCATCAAAACTAGTTCCAAACCTTTTAACAGTCCAGTGCTATTT<br>GTTAAGAAGAAAGATGGTACTATGCGTATGTGTGTTGATTATAGGATTCTAAACAATAATA<br>CTGCTAGGAACAAGTTTCCACTTCCAGATATTGATCAATTGATTTCAAGATTTGGTAAGGC<br>AAAAGTCTATTCTAAGTTAGAGTTGACGCCTGGTTACTACCAAGTGAGAATTGCTGATGAA<br>GACGTGGAGAAAACGGCATTTTCTACTGATTTTGGCCATTATGAATGGATGGTAATGCCGG<br>CTGGACTAACAAGCGCACCTGCGACTTTCAACAGATGATGGATACTGTCTTGCCTGAAAG<br>AATAGATCGATTTGTCCAAGTCTATTTAGACGACATTTTTATATACTCCGAAGATGTTGAA<br>ACTCACGGTAAGCACGTGAAAGAAGTTTTGTTGACACTAAGAAAACATAAACTAATTACGA | |

TABLE 7-continued

CENs sequences

| Sequence | SEQ ID NO |
|---|---|
| AGAAGTCGAAATGCAGATTTTTTTATCAAGAATTTAAGTTTTTAGGACAAGTTGTTACACC<br>AATTTGTATTCAAACCGCTCTAGAGAAAATAAAAAAGGTAAAGAGTTGGCCAACGCCAAAC<br>ACGATCAAAGAAGCACAAAGTTTTATTGGTTTAACTTCGTACTATAGAAGGTTTATTAAAG<br>GGCATTCCAAAATTGCCAATCCAATTCATAAGTTCATGACAAAACAAATTAAATGGACAAG<br>TGAACAAGACGAAGCCTTCAACCAACTAAAGAACGCTTTGATATCAAGTCCCACCTTGGTG<br>CACCCAAGTTGGTCAGGCAATTGTAAATTTGTTCTACATACCGATGCGTGTGGAGTATCGT<br>TAGGTTATACTCTAGAACAGTTGGACGAAACAGGTAAATGACGAGGTGTGATTGCTTACGG<br>TTCAAAGAAGCTAGTTGGAAGTCAACTGAATCATGGAATATATGATCGTGAATTTTTGGCT<br>GTTGTTGAAGCATTAAGAACATGAAGATATTATCTCATGGGAAGACATGTCATTGTTATGA<br>CGGATCACAAGAGTTTAATTTACTTAAAAAACCAAAATCTCATAGACTCCACTAGAGTGGC<br>TAGATGGATGGACTTTTTACCACAGTTTGATTTTGATATTCGTTACTTACAGGGAAAAAAC<br>AATTCCGCTGCTGATGCGTTATCTAGATACCCATACAACCACGAAAACAACTTAACGCTAG<br>CCAAAATCGAACTGGCGTTGCTAGAATTGACTCAAGAAGAGGAGAATAAAACACAGAAACA<br>TTCGTTGACACTAGGTACTATCGAAGCTAATCAAAAATCAAAAAGGGAAATTATTACGGGT<br>TATAAAAAGATAATAATTATGCCTTGATATTTAGAACTGTGAGAGATAAAACAAAAGTTC<br>CAGTTGAAATTAAAAATCATATCAAACATTTCTGTTATCAAGATGAGGTACTTTATTATAA<br>GACATTAGAGTCTCAAGATTTCTTTAGAGTAGTTATTCCAAACTACAAGAAACTACCGTAT<br>AGAATATTCAAAAATGCACACGATGCCAAAGATGCTGGTCACTTTGGTGCATGGAAAACTT<br>ATTTGAATCTTAAAGATAGTTTTTATTGGCCATCTATGTTGGCACAAATTAGAAAATGGGT<br>AGAAAACCTGTCGTATCTGTCAACAGCACAACACCAACACTAGAGGGAAGACAAGGGTTGTTT<br>TCCCCTTTACCAATCCCAACAGGTCGCTGGACCGACATTACGATGGATTTCATTACAGGTT<br>TACCTAGATCGAGAACAGGCTACACTATCATTATGGTTGTTGTCGATCGCTTTCAAAAAT<br>GGCACATTTTATACCAGCGCACAAAAGACTTAATGCTGCTGCATGTGCTCGTTTGTTTAGT<br>GACAAAGATATTCGGTTTATGAATAAGTTCTGGCAGACATTACATTATCTCAATGGTAGTT<br>CTCTATTATTTTCAACTACTAATCATCCAGAAACTGATGGTCAAACTGAAAGATTCAACAA<br>GATTGTTAATCAGTTACTTCGGAAATATTCTGCAAACGTTCAATTATCCTGGAATGAGCAT<br>CTGTCTATGTGTGAACTTAGTTACAATTCAACGTACCAAGATTCCATTAAAGCAAGTCCTT<br>TTGAAATCGCCTACGAGTATGAACCGAGCATGATTAGAAAAGTAAATAGCTGGGATTTGGA<br>GGATAACAAATATTCACCTAACGCAGAAGAATTTGTGAGACGTGTGAAATTGATTTTACAG<br>CACACTGGATAATATTGTAAAGCATAAGGGCGACAAGGAAAACACCATAATAGAAAAGAA<br>GATACTTTGAATATAAAGTTGGTGACTTAGTGTTAGTGCATCAAGATGCCTTTGGTGTGAA<br>TATAAGGTACACAAAAATTCAACCAGTATGATATGGGCCATACAGACTAGTCGAGAAAATA<br>AACGGCAATGCTTATAAAGTCGATTTACCAGTTATTAATTTGAAGGATCGTGAATCAAATG<br>TACAGTGGATTAAATACTATAAAGAAAACCCCAATATTTACCAGGAACCGCCTAGAACAGA<br>GCGTGAGATGTTGGCAAGAATTAACGAACTGAGTGGTATCGGTGGATGATCAGAAGAACCA<br>GGCAAAGAAAAGACTTATGATGTCTTCTGGAAAGACTGTGATCAAACTCTAGCAAGAAAGG<br>TGCCTGAAAGAATATTCAACCAAGCAGCTTTGTCACTACGTCAAAGTCCAATGTACAAAGC<br>CGAATTAATTCAAGAACACGAACAAGTTTGATATCAACAAAGTAATCATAATTATAATACA<br>TAGAACGTTCCTATTTGTCCCTCAGCTGAAGAAAAAAAATACAGATATTGCTCCTACCAAA<br>ACATAGAACATATTGTTTTTTGATTGAAATAAGTTAGCCACTCTCGATTTAAAGAAATACA<br>AATTGAACTCATAAAAAAATTATTGTTACTGCCAGGATCCCACCTACATTTATTATTCTAAT<br>CTGGTTTAATGTTTTGCAGCTTCATTGGTTCAGTGCCCCATCCGGGATTATCCAGTTATT<br>TTGTTGCACCGTTTTGAGGAACATCGGGGCGATGTTTCCCAAGAGCCGGGGTAGTGAAAGG<br>GATTTTTCAGGATGTGTTCCAAAAAAGGAAGTGCCAGTAGGTAGACGATAACATACTGATG<br>TTAAGGTTTCGATTTTAGAATAAGGGAAGTTAACAAGGGTCAAGGTATCCGGAGTAGGAAGC<br>AAAGAGAGTTAGTCCCGTTGATCATGTAGGGCATAGGCATGGAGAAGCCGTCGGAGACACT<br>GTCATTGGCATAAATTAATTATCATTCATCAACGGGTTATGACAGAACTGGCATAGTAAAA<br>CAAAATAGACCTAAAACGTAATAAGCTCGTACAGGAGTCTGCTATACGAAAAAGAGTAGCA<br>ACCGAGGGTGATTCCAGGTTGCGGGCGTGAAGTACAAAAGACAGACGATATTCCGTTATAT<br>AGAATTGATATAGCTGATATAGGTCCTAATCGGGAGTGGAAGCGGCAGAAGAAAAAGAGA<br>GAAATAGATTACTACTTCTACTACGACTAACTTCCACCACGCTTATTGTCTACTCGTGCGG<br>TTATACACCTATTGCGTACTTACTAACACGTGTATCACAATTATCATTGTTATAAACAATA<br>CTGTAACTATGGATAAGGCTATGATTACTTTTTTGATAAAAGATTTAACCGTAGAAACATC<br>CAGAACTAGGAAATGATTTTGACACCTTATTCCAAGTCCTATTAAAAACTGTAAGAGATCA<br>GACAAAGGACTACCTCTCTATTTCCTAATTGGGTAATCATATAGAAGGTTGAAGAAGATTG<br>TAGAAGGTTAAACAGAAGTTCTAGAAGATAATTATATCCCTCAAAATGCTATTTTTAAATT<br>AAAGATTTACTATTTAAACAGAGGATATTCCATATATGTTCTCAGAGAATTAACGTATAAA<br>AATATATAAGATATAAATAAGCAATAATCAGATTCTAGAGTACGCACCACTAGCAAAACTT<br>TCAAAATATAAGCAATGCCCGTGTAGCGTAATGGTTAACGCGTTTGACTTCTAATCAAAAG<br>ATTCTGGGTTCGACTCCCAGCATGGGTCAGGCATGTGCTTAATATTTTTTATTTTTATT<br>AATTTTTCAACCAGCAAAACCAAGTTTTTTAACTGAATAAAAGAATGTTTGGCCACTTCT<br>CTATGTGTCATTTGTCTTTTTGATGGGTTATTTCTATCAAAG | |
| cEN5-<br>38285<br>bp | CTCACAGCAAACACAAAAATATCACAAGATCGCTATGTATGTAGTCGATAGGTTGTCATGA<br>TTACTATTCATCTAAACACCTAGACATGTAGAGCCTATTAGAGTAAGCTCACTAATTTTGA<br>CTTTGAATCCTCCAAAGAGTTACAAACCAAAAATAATTTTGGGAAAATTACTCCGGCCTA<br>ATTCTTTGTCGGTATATCAAGGAAGGAAAACTCCAATGGTTTAAAAGACTAGGATAAAACT<br>AATAAGGGACATTATAAAATCTAAAACTTAAAACTTGTCCCCATTTTGATTATCAGGTTA<br>TTTTTGACATAAAAATCTTCTCTAATGTTTCGTCTCGTCCAAAATTGAATGCTTTGAATAG<br>AGTGAACAGGAATAATTATTAACACAGAAAGCCTAACTGTACACAGGAACATCTATAAG<br>TAGAATTACGTATGTCAACCTATAAAAAGGGGTCCAAAGTTGACAACTCAATATCTAAATC<br>TTGCACGATTAAGAGGTTGGTTTTTATAACCTTTTTAGGGTAACCAGAATGCCATCTACTT<br>CAAGCAGAAAAGAAATGTAAAAACACCCGTTTTTAATGGCTAATCTGATACTCTTCAGAA<br>AAGATTTATGAAGAACCAGCCGTAAAAGTCTCAAAATTTATTCGGATAGTAATTCCATTCA<br>ATACAAATAAATTGAAAAAAATCAAGCCCGATGCGGGGCTCGAACCCGCAGCCTTTTGATT | SEQ ID NO: 16 |

TABLE 7-continued

CENs sequences

| Sequence | SEQ ID NO |
|---|---|
| GCACTTCTTTATAAGAAGAAATCTTAAGAGTCAAACGCTCTACCGATTGAGCTAACCAGGC ATAAAATGTTCCGATACCGGGAGTCGAACCCGGGTCTGCCCGGTGAAAGCGGACCGTGATA GCCGTTACACTATATCGGAAACTGATGAAATATTAGGGTCCAGGAGAAAGGTGTCGAAATT ATTTCCTAATTTGGGATGTTTTGACGGTTGAATCTTTTTAAGAATAATCACTAATCTTATC AATATCTATAGTATTGTATGAAGGAATGATAATTGTGATATACGTATTAGTAAGTAGGCAA TAGGTGTATTAGCTCACGAGTAGATAATGGGCGTGGTAGAAGTTAGTCGTAGTAGAAGTAG TAATAGATTTTTCTCTTCCTCCTTCTGCTGCTTTCACTCCCGATTAGGAGCTATATCAATT ATATCAATTCTATATAATAGGATATTATCCGTCTTATATACTTCACGCCCGCAACCTGGAA TCACCCTCAGTTGCTACTCTTTTTCGTGTAGCAGACTCCTGTACGAGCTTATTACGTTTTA GGTCTATTTTGTTTTACTATGCCAGTTCTGTCATAACCCGTTGATGAATGATAATTAATTT ATGCCAATGACAGTGTCTCCGACGGCTTCTCTATGCCTATTCTTACATGATCAACGGGGCT AACTCTCTTTGCTTCCTACTCCGGATACTTGACCCTTGTTAACTTCCCTTATTCTAAAATC GAAACCTTAACATCAGTATGTTATCGTCTATCTACTGGCACTTCCTTTTTTGGAACACATC CTGAAAAATCCCTTTCACTACCCCGGCTCTTGGGAAACATCGCCCCGATGTTCCTCAAAAC GGTGCAACAAAATAACTGGATAATCCCGGATGGGGGCACTGAACCAATGAAGCTGCAAAAC ATTAAACCAGATTAGAATAATAAATGTAGGTGGATCCTGGCAGTAACAATAATTTTTTTAT GAGCTCAATTTGTATTTCTTTAAATCGAGAGTGGCTAACTTATTTCAATCAAAAAACAATA TGTTCTATGTTTTGGTAGGAGCAATATCTGTATTTTTTTCTTCAGCTGAGGGACAAATAG GAACGTTCTATGTATTATAATTATGATTACTTTGTTGATATCAAACTTGTTCGTGTTCTTG AATTAATTCGGCTTTGTACATTGGACTTTGACGTAGTGACAAAGCTGCTTGGTTGAATATT CTTTCAGGCACCTTTCTTGCTAGAGTTTGATCACAGTCTTTCCAGAAGACATCATAAGTCT TTTCTTTGCCTGGTTCTTCTGACCATCCACCGATACCACTCAGTTCGTTAATTCTTGCCAA CATCTCACGCTCTGTTCTAGGCGGTTCCTGGTAAATATTGGGGTTTTCTTTATAGTATTTA ATCCACTGTACATTTGATTCACGATCCTTCAAATTAATAACGGTAAATCGACTTTATAAG CATTGCCGTTTATTTTCTCGACTAGTCTGTATGGCCCATATCATACTGGTTGAATTTTTGT GTACCTTATATTCACACCAAAGGCATCTTGATGCACTAACACTAAGTCACCAACTTTATAT TCAAAGTATCTTCTTTTTCTATTATGGTGTTTTCCTTGTCGCCCTTGTGCTTTACAATATT ATCCAGTGTGCTGTAAAATCAATTTCACACGTCTCACAAATTCTTCTGCGTTAGGTGAATA TCTGTTATCCTCCAAATCCCAGCTATTTACTTTTCTAATCATGTTCGATTCATACCCGTAG GCGATTTCAAAAGGACTTGCTTTAATGGAATCTTGGTACGTTGAATTGTAACTAAGTTTAC ACATAGATAGATGTTCATCCCAGAATAATTGATCGTTTGAAGAATATTTCCGAAGTAACTG ATTAACGATCTAGTTGACTCTTTCGGTTTGACCATCAGTTTCTGGATGATTAGTAGTCGAA AATAGTAGAGAACTACCATTGAGATAATGTAATGTTTGCCAGAACTTATTCATAAACCGAA TATCTTTGTCACTAACTATTCTTTGTGGGACACCGTGTAACTTGATAACATTGTCACTAAA CAAACGAGCACATGCTGCAGCATTAAGTCTTTTGTGCGCTGGTATAAAATGTGCCATTTTT GAAAAGCGATCAACAACAACCATGATCATATCGTAACCTGTTCCCGATCTAGGTAAACCTG TAATGAAATCCATCGTAATGTCGGTCCAGCGACCTGTTGGGATTGGTAAAGGGGAAAACCA CCCTTGTCTTCCTCAGTGTTGGTGTTGTGTTGTTGACAGATATGGCAGGTTTCTACCCATT TTTGATTTGTCTCAACATAGATGACCATTAAAAACTATCTTTAAGATTCAAATAAGTTTTC CATGCACCAAAGTGACAAGCATCTTTGGAATCGTGTGCATTTTGAATATTCTATACGGTAG TTTCTTGTAGTTTGGAATAACTACTCTAAAGAAATCTTGAGCTCTAATGTCTTATAATAA CGTACCTCATCTTGATAACAGAAATGTTTGATTTGATTTTTTATCTCAACTGGAACTTTTG TTTTATCTCTCAAAGTTCTGAATATCAAGGCATAATTAGTATCTTTTTTATAACCCGTAAT AATTTCTTTTTTTAAATCTTGATGGGCTTCGATAATACCTAGTGTCAAAGAATGTATCTGT GTTTCATGCTCCTCTTTTTACGTCAATTCCAGCAACGCCAATTCGATTTTGGTTAGCGTTA AGTTGTTTTCGTGGTTATATGGGTATCTAGATAACGCATCAGCGGCAGAATTGTTCTTTCC CTGTAAGTAACAAATATCAAAATCAAATTGTGGTAAAAAGTCCATCCATCTAGCCACTCTA GTGGAGTCTATAAGATTTTGGTTTTTTAAGTAAATTAAACTTTTGTGATCCGTCATAACAA TGACATGTCTTCCCATGAGATAATATCTTCATGTTCTTAATGCTTCAACAACAGCCAAAAA TTCACGATCATATATTCCATGATTCAGTTGACTTCCAACTAGCTTCTTTGAACCGTAAGAA ATCACATCTCGTCATTTACCTGTCTCGTCCAACTTTTCTAGAGTATAACCTAATGATACTC CACACGCATCGGTATTTAGAACAAATTTACAATTGCCTGACCAGCTTGGGTGCACCAAGAT GGGACTTGATATCAAAGCTTTCTTTAGTTTGTTGAAGGCTTCGTCTTGTTCACTTGTCCAT TTAATTTGTTTTGTCATGAACTTATGAATTGGATTGGCAATTTTGGAATGCCCTTTAATAA ACCTTCTATAGTACGAAGTTAAACCAATAAAACTTTGTGCTTCTTTGATCTTGTTTAGCGT TGGCCAACTCTTTACCTTTTAATTTTCTCGAGAGCGGTTTGAATACAAATTGGTGTAACA ACATGTCCTAAGAACCTAAATTCTTGATAAAAGAATCTGCATTTCGACTTCTTCGTAATTA GTTTATGTTTCTTAGTGTCGACAAAACTTCTTTCACGTGCTTACCGTGAGTTTCAACATC TTCGGAGTATATAAAAATGTCGTCTAAATACACTTGGACAAATCCATTTATTTTTTTAGAC AAGACATTATTCATCATCTGTGGAAAAGTCGCAGATGCACTTGTTAGTCCAGCCGGCATTA CCATCCATTCGTAATGGCCAAAATCAGTAGAAAATGCCGTTTTCTCCACGTCTTCATCAGC AATTCTCACTTGGTAGTAACCAGGCGTCAACTCTAACTTAGAATAGACTTTTGTCTTACCA AATCTTGAAATCAATTGATCAATATCTGGAAGTGGAAACTTGTTCTTAACAGCATTATTGT TTAAAATCCTATAATCAACACACATACGCATAGTACCCATCTTTCTTTTTAACAAATAGCAC TGGACTGTTAAAAGGTTTGGAACTAGTTTTGATGAAACCTTGTTTGATTAAAACTTCAACT TGTTTTGTTAGTTCCAGTTTCTCAGAGAAGCTTAATGGGTATTGTTTTTTCCAAAGAGAAC TCATTAGGGTAAGACAAGGCAACATATGCCCGCATCTTTTCTTTGGCGGTAGTTCAGTTGG TGGATCTCAAGTAAACTTTTCAAGTGTTTCCTTTTTCAATCCTCTTGCATGATTTGCGTCT AGGGGCCGATATTTAAATCAGCTTTGGCTTTATCGATATCGGGACTTACTAAATACCTTAA AGTTAGATCACTAAATTGCCTCTTGATAAATGGGTTTCCCAACATGAATACCACATGCTCA GTATCAAACATTTAAAATGACCTAACCTCACTTATACTGATAGTTTCTTTGACTACCTCAA ATGGGACAATTACGTCTGCGATAGCAACACCAGAGTTTCCGATAATCTTTACTGTTATTGA TCCATCGAGCTTGGCCTTTTGCTAAACACATGAACTTCCTCAACAGTTTTATTAATAACTG TAAAAGTGGTTCTGGAGCAACCAAAATGTCATCTGCATATTTGATATAAACGACACCACAA ATTAATTTTGGTTTTTCTTTTTTGGGATGGTCATAATGTGAGTGTGGGATGGCATCCACTC | |

TABLE 7-continued

CENs sequences

| Sequence | SEQ ID NO |
|---|---|
| ATTTTTTGGACATTTATACTTACTATGAAAGTTCCTTTTCGTATTTCGCATCATTATCATG<br>CCCTTTAACATCCTCTTATAAATACTATTTGAATAAAGGAACATGAAATTATCCATGATAC<br>ATTAGGTTACCGATGGCTGAAAAGGCATGAAATAAATTGAGTTCTTTGGCGGACTTTGTTC<br>TATAAGGGAAACCATTTAAATGATTGTATAAGTGCCCATGTAACTTCTTGCATGTGTATAT<br>CTCCAATAGACTCGCCTCAACATGGTTAAAACACACATCAAGCTTTTATGTTAGACTGCAA<br>CAATCTCACCCCCATTAACTGCTCAATATCGGTAAGGCCATCAAGGAATAGTGGTCAACTC<br>TTAATGTCAGAAATAGCGACGTACATAGACACTTTAAAGTTTTCTTTATAGCCTCTCATCG<br>ATTGACCTGGTTTCAATCGACACAATTACTTGACAATATTCACCACAGAGTCTCTGTCTTT<br>GTCGACAGGAACAAAGCGTTTCAGAATCTATCTTCAAATTTAGACCGACTAAAATCCAGTA<br>TTTGCTAGTTCATATGCATTTGAGAAGTGTGTAATTTACGTTCGTTATTTTTCGAACCTGC<br>AACAGCCCTTATAATTTTTCTGACATCTGGTAGCCCATATGTAGCAAATTCTCTTCCAATG<br>TTTGCTGACCATTCTATGCCTCTAGCCCTTATATCCAGTAATGGAAATCCGGGGCCTTTCT<br>AGTCTGAAATTAATCAGAGAAGTTGGGTGGTTTTGTATAATTTTATTCTGCATTGAACATA<br>GTTGAGTTTTGTTCTCGTTTTATCGATTTAGCTTTGATAAATCCGCTAGTTATTCTTCTCC<br>CATTGCAATCATATAAGACAATAAGATAAACTGTTTTACCATTGGCCAAAATGCAAATATT<br>CAATATAGTTTAGTTTCTAAAAGCAGCCAATAAATACATGTCAAGCAAATACAATACTGCC<br>TTGACGTGCCCTAATTCTACTTCAGATAACCATGTTACACGTTATAGATTGAACGTTTAAA<br>AGAGTTACTTCAAAATACCACATAAAAAGAACCCAAGGAAAAGAAAATAATCTACAACCTT<br>TATTGATATCATGTGATACAGCAGGTATGTCGACTCACATTATGCACTGATGGCAACTAGC<br>TAATGACAACTAGTAATATGTTTTGCGTTTAGTTAGAGATGATATCATTATTTATTGTGGC<br>GCCAAACCGACAATTGATAAGAGAGGTAACTCCGCTCTTACTGTAGCTTTTAATACGCATA<br>TTATTTAGAAATCCCTTAGTAATCAAGTGTCGAACTAAATATGGATATCGTACCATCAATA<br>GCTGATTGATCGGACCTAGTCATCCATATTGCTCTCCAAGAGTTATATTTTAGTGTATAAA<br>TTAACTACTGTAGCTGAAAATTACAACTTTCAAATACACAACCAACGTTGCCGGTTTGTTG<br>TGATAAAATGTGTAACTTGATGTGAGGTTGCACTGTATAGTTTTGATGTTATACTGCCATT<br>AATTGGGATATAAAATGTTTACCACCACCAACATGTGTCATCTGATAAACCACAGACACAG<br>CAACAGATCTGGCACTTGAAGGTTTGTTGTAAAGCTTTTGTTGCTAAAATTGGAGAGGTAT<br>TTTTCCCTGATAAGGAGAATTCAGACCGTCTTTTTGGAAGTATCTTGAAAACCTTGTGGAT<br>ACTCATTTCGAACGCCCACCCACTTGGACGGAGAAAGGATGATGACTTCTTGCGATTTTACA<br>TTTTTGCTGATAAATTAAAGGCCTTTCATGGTAGCTTTTGTGGGAACGGCTCTACGGAAAA<br>GTTCTTGAGACATCCAGGTTTGACAAAAAGATAAAGTCTACTAAAATCTATTTACAGGCCC<br>CAATTGATTAAAAAGGTGAAAATATAGGTTTTACAAAGCTCTTCTGTAAATGTATTGTTTC<br>GGATTACAATACATTTTTAGCAAGCACGGAAATTCCCTTTTGTTACAATATACAGGAGTGT<br>TCGTTAAGGAAAGGTTTTGACGTGGATGGAATGATGCACCTGTAACATATCGGTGGAAACA<br>CAAGAAACCATATGGGCCTTTTACCAGACTAAGAGCATCTTTTAAATATTCAGTTTATAGA<br>CACGGTGCATCTTTCAGAGTGACAGAACATCTTTGGGGGAGTTACTCACGTATATTATTCT<br>ATAGATTTTAGGATTTCAAGGATCCACTGTGAGCTAATAGGATTGGTAGTGGGCTTGTGCT<br>ACAAATTTGCTCAGTTTTGCTCGATGTCGCCAACCTTAAAAACATTAATGTGTTTTTAAGG<br>ATTAACGCAGTTCCGTGCTCCGTTATGATGGAAAGGTTAAAGAGAAAGTAACCTATAGTTT<br>TGGTTTGTATCAGCCATGTTCTAGCTCGGAAGTCAACGAACAAGCTGTTTGGAAAAATCCA<br>GCATTGTTTTTGATTTCTTCATCAATGTGATTATTAGGCCCGAATCGTTTACGGCCGTAGT<br>TATTAAGACATATTTATACTAGAAAGATAAAAGGATATCCCATTATGCATATATTGTTAACT<br>CGAACGGAAGAGATCACATCAACCATTTGAGTGTTTACAAAGACAATGGCAAAACAACAGC<br>ACTCCTCTTAAGAACACGATGTGGCACCTTCGCTTAACCTTTTGGAAAGTAAAGGTAGCGT<br>TTGTAGTAAAAAAGAAGGGAAGAAGATATTGAGATTGTGTTATATCCGGAAATTGTGAAC<br>AAAGTCACACAGTCCGCCCAAATTCATGGTTTAATTGTAGAGCTTATCCAGTCAGTATGTT<br>TCTGGAGTTGATGCTGTATTCAATGTGACAACATGCCAATATTTCAAATCTATGACAGATG<br>TATATATGAATGACATAAACGAAAAAATCCATTGTTGAGTATGGTTATTCTGCAAAATAA<br>ATCAGCAGGTAATTATGGTATTTGTATTACGAAATTAAGTGAACTGCTCAAGAGATCTTTC<br>TAAGATGAGCTTTTGCCACAATAGCGTTACATTTTTTAGATGGTTTTGAAACTTCACACAA<br>AAGTCTTGGAAGACAATTTTTGACCTAATAGAGTTGCTGCTGTAAAGTGTCTACGGCACAAA<br>ACTATCAACCTTGAAAAAAATCTCGATTGTGTTGGTGTTGACACATTGACAAGGTTTAGGT<br>GAGAAAGAAATATTATGAAGTGTAAACCGCAGCAAACAGTTTTGTCTCTCCATCATACACC<br>CCATATTTGATAATGTTTTACTTGTCAATGATCGGGATATATTTGACAGTATCTATTATAT<br>CTTGTATGTGGCGAGATGGAAAGAAAAGACTATTAATCTAAGCTTTGACAGTATGTTACC<br>TATATCGTTAAGGGCTGATATCGAACCAGTTTTTAATGTAAAAACCTTACTTTAAATTACT<br>TAAATTCAAGAGATGGAAGAGGTCGAAGAAACCACTGGAAATGTTGAGATTGATCAGACCA<br>ATTAAAAAAGACGGATATTTATCTCAGACAACTGACACTATACTATATAGAACACGGGATT<br>ATAGATGTGCTTAAAAACGAAGTAAAAGATATTGGGTACGAGCAGTTGTTGAGACCAAAGA<br>CGGCCACCAGCATCCATCCATTGAAAGTCAAAACACTCAAAAGAAAAGAGTTACTGGTAT<br>TAGAAGCAGAGATTTATTTGAAATTATATTGTTGGAGCCAAAGTCTATAGTTCCAGATCAA<br>TGGAAATTGGACAGTGTGTTTATTGGGTATAGAAAGAAATGTGTTATTTACGTCTATAATG<br>TTGGGTTGTTCCCTGCCATAATTTGGTTGCTATCGTTAATATTAGTCATTGTTAAGCAGCA<br>TTGCTTGAATATACTTTTTCTATAACTATATGGCGGTTTATAGTACAACATTCTAAGGATT<br>CTTGAACTTTGGAAATCACCTCTGGAGCTTTTAAGATGCATCAGCATGTCTCATTCATCTG<br>CAATATATCATGTGACCATGCGTTTATGCTCAGGGAGAGTAGGGTATTTAGGATTTGATGAA<br>CCGTATAGAGCTATAAAATTCTGCAACTATTCTCATGTTATATGCTGTTATATAAGCTCTA<br>CAAGTACAGATAACGCGTTTGCTTGAATTTTGTTCGTCAGGAGTGTTTGTTATTTGGTTA<br>AGATAAGAAGAGAACCTATTATGTTTATCCTAAAGTTAGCCTAAATCTTGTTGCCCGAATG<br>TTTACCGTGTAAAAGCTACTTTTTTTACCACTTGGAGCATCATTTTAGGGTTGTTCTGTAA<br>GCAGCTTAAGGTTATGTAAGGTCAAGTTTTTCTTGCCATTAGGGGACTTAGAATTGTTGAG<br>AGTTAAAGAAGAAACTTAGTGTTATGTTTATGTTGAGAAATTCAACATTGACCTGAAAAAG<br>ACCCTAGTACATTGACTTACATAAACTAAACTAGATCATAATCGACAACGTTAGCTGGAAA<br>GTTAGCTAGATTTCAACAAAAAAACTTAGTATAAACAATAAGTAAACCTTATAAATTATTG<br>TTTTTTTGCTCTCAGAGCAAATGGTAAGTTGCACGCCCTTATACATACGCAAAATACATTA | |

TABLE 7-continued

CENs sequences

| Sequence | SEQ ID NO |
|---|---|
| AACTCTTATAGAAAAAAAAACTTGTGCTCTTAAAGGTCGGCCTAACAATCTTGCAAATAGC<br>TATTTGGGCCAATAACACAACAATGCTCTGATAATTCAGAAGAGTTCTGGTTGTTTGCAGA<br>GGACTAGCCTCTTAATTATCAAAAGCATTTTGCCTGTTATTGTGGAACAATCATTAGCAAT<br>GTAATACATAAATCCTTTTGTTGCATTCTACTAAATTAAGCGGTTATTCACTCACATGACT<br>ACCCTTAGCAGCTGCTTGAATTCCATGTGTTGGATTTTCTTAGTATACGTTTCTACTAACT<br>TCAGCAACGTCTAACCGTTTACCCTTATGCTTTGCATCAAATGACGGAGTCTCTGCAGCCT<br>TTTCTGGATTCAGCTTTGGACTATGTGATTGCTGTCCCTTATGTTCCAGTTTTTTCTTTT<br>CATTTATTTGTTCGTTACCTACCCGTCCTTGAGCATTTTCATCAAAAGAAATCCGTGTGTG<br>ACTATTCCTCTTATAGTACATGATTTAAATATATGAGACCCCCGTTAAAACAGCACTGTCT<br>AAAGGATGCTTAAATAATAGGTTCTAATCACCAACTTGTTTGTACTCTCAGTTCAATGGTC<br>CCTCTATCAGGGCTGACTCACCATGCTTAATAAACATAACGCTAATTTCAACATTATCCCA<br>CACATTGGAGTTTTTTTTCCATCAAAAAAATAATATATAAATAGCTTTCTTAGATTAGTG<br>TATTCTTTTTCGCCTAATATTTGTGATGAGCTAAAAGATAGATCGATAAGGTCTAGCAAGA<br>AAAGAGTCATTTAGTTCTCAAAGGTAACTGTTTTTTTTCATGTCACAATGACCAATATTT<br>AAAGTCGCTGATCTTGAAATTGCAAAAAAAAAGAAACACTATTCAACTAACACATACAAC<br>CTTTTTGTACATAAAAACAAGTAGCTTTTTCAAACAGCTACTTAAAATTTAGCTACATCGT<br>GAAACTATTGGCTTTTCAGCTAGTTTGGTCCGACTGGAAACGTACGTCCTTTATAATTTTT<br>TGTTGGACTTTTCTACTGGTGAATCTGAATTTCGAGACCAAGTATTTAATTATATGTATAA<br>GAAGAACGTAATAATCTGGAAGTACGTCTTTACTACTCAAATTTTCAAACTTAATTTTACT<br>GTGTGTATTGGATGAATCTTCCATAAATACAGTACTTGGTAAAACTAGAACCCTCTAAGAT<br>CCTGCATTTTCCCAGTTTAAAATATGTACGGGTTGAAAACAGAAGAGTAATAGCCGTCTAA<br>CAAACTTTTGATATCCCTAAAGAAAACATTTCTACGACAATATTATTTGTAATATTGGATA<br>GCTTCCATTTCCGATCTTTTGCCGCACGAAACTCAAATCAAAAACATACAATTTTTGTAAT<br>GCAATAATGTAATCTTGATAATTTCTAAAAAAAACACCCAAAAGGTTTCATTGATCCATTC<br>TGTAGGAATAAATCAGAAAAAACATGTGCTTCTTTCTAAACTTTATCAAAATATTTGTCA<br>AGCTATAGTTTTTATAGACACTCTTCTTTTTTCTTTCTCTCCACAGTCTAATCTACCAAAC<br>ATTTTCTTAGAGAGTTATAATAAATGTCAAAACTCTATACAGACAATTATGTATGACTGTT<br>ATGCCTTTTCCTGAACTTATTTAAACAGTATGTTTCAGAAAACGTTTTGCGGCAAAGTCGA<br>ATTCGTGGTTCGCTTAGTTTATATTTCATGTGGGAGTCATGTAAGCCTCTTGTTATAGGAT<br>AGTAAACGCCGGCTGTTTAAACAGGAATATCGTGCATCCATAAATCATTTCTGTAAGGG<br>CTCATATATAAGAAGTTGACGTCAACGAAAATCAATCAATAGGTGCAAATGGAACATTAC<br>GAAGTGATCTATCGACCAGCAAGAAAAGTTTGCACCTTATGCGTATCCGGCAATTTCTCGG<br>ATTTTCATGTTTAGATCACGTTGCAAATTTTCACTAAAGAGTGCTATGTCGAAACAGTGCT<br>GAGGGTAATTTTTACAATTACCTAGAGGGTAAGATTAGATACTAAGATGTGATGTCACTTT<br>CAGAAATAGTGCTCACTTAAAGTTGGGTAACTGGCGATGGTTTTATTCGAAGCAAACTATA<br>GTACAGGTGCGTTTAAACCAAAAAGAGTACGATTCTTTTTAACGCTTGAACATCTTTCATG<br>ATTGATCCGGCATAGTTTCGTTATCAGATTCAACACTGTAGATAGTTAACAATAGGCCAAT<br>TTCAGGATCAGTATTTATTTCTGATTGTTTGACAGCTATATTTAGACCTATGTTCTGAGTT<br>AAGCACAGAAATAACGATTAAATTTATATCAGCATTAGTTATGGAAGACACCCTCAGTCA<br>TCATGGCACCAAAACAAAGATTAATAAGAAACCAGTTCAACTCCAACTGAATCTATTGATA<br>TCGATCTATATAATTTGTGGATTCTTTTTAAGTTATCCAGCTGCTGGACTAAATATGGGCA<br>TCACGTCAGGAATTGTGCCTCTTGAACACCAGTTTTTATAGAATTTACAGCTACTATAAAT<br>ATCTACATTGTGGCATAACGCTATTCCTTAACCACTGTTCTCCAATGTCAACTCATCTAGT<br>ATTTTTTATATAAAATATCATTTCTTATTTTGTTCGCGCTGTTTGCAAAGAAATTTGTTTT<br>ACTATCATAAAATTGATTAATTTGTCTCCCAAGACCTTTTACATGTATATCATTACTATTA<br>ATGTGCTTATTCGATAGTTATCCGCATATATTCTGAATATCATCATACTTCGCTGGAAGTT<br>TTCCATTATATAAATTATTTTTTAGGTTCTATCGTTTTATTTACATATATATCAATGTTGT<br>TTATTTATTGTTGATATTGAATAACTTATAAATCCATTAAAAAGGATATTGCATAATTCTC<br>ACTATTTGGTTCTCAATGAACAGAACTTATAAATACTTGAAGTTATTGTTTTAGTTTTTC<br>TGTATACAGTAACATTCCTAAATTCATTTGGTAAATTGAAATTATGCCATAAATAAGTTTA<br>TCGACTCAGAGACAGCTTTATAAAGATATTCCTAATCCTCTTACTAATAAAACAAAAGTTG<br>CATTCACTATTTTCTGGGAGAGTCTGATTCATTTTTGTTTTTGCTCAGGAAATTTAATCG<br>TGTTATAATATAAAAGAAGAATTTTTCTCAAGAGTACTCTTAGACATATTTATGGAGAATG<br>AGTTTGTTTGCCTGAATGGTAAAGTAGCTAAGAATCTATACTTTTTCAGGGTTTTTTTA<br>TCTTGACTTAATGATTGGAATAATAAATTAGATTTGTAAAAAAATTGACGGAATTAGTTTG<br>AGTGGCTTCCCATGTAAATATGCTCTCTATCAGATATATTAAACATGAAAATTTATTATAC<br>CTCATTGTACTCTCGACATTAGTTAAATCTCCAAGTTCTTCCTGGCGCAATATATTTATAT<br>AATCATAATGGAGCTAATGAAAAGAATCTTGCTCAAGCTTGCTATCTATTTTTTGACTACT<br>GGATTTAGCGAAATATAAGGTTATTGCTTTACAGAGGCCTTTACAAGATGGATACTCATGA<br>ATATTAAGAGAAGCTAGATTTGCGTACTTTATTAATGGTAGAATCTCTTAATAACAAGTAT<br>TCTTTAGTGATGAGCTAAATAAAAATTATACGTCAAATAAATGCTACACAAATTTAGTTCT<br>TGAGGTAATAGAAAATGTAGAGCTCGAGTAAATCGCATGAAAAGATGAAAAATGTTACGGT<br>TGTTTATTAATCCCATTTATTTCTGGGTAACTGTTTCTTATTTTCCTAATATTACTAGAAA<br>AATATAATCCAGAAAGATGTTTTGAGTTTGTTCCAGCCATGGCATCAAATATCAAAGGAT<br>TTTCTAATTAGTTCTATTAGACTAAAGCAAAGCGAGAAAATACTCATCGTGTTTGTGATAG<br>GTGAAACACCTATTTTGCTTCTATTGTATTTAAGGAAATTAGAAGGTCCACTTCAACATCT<br>AGTTGGGCTACAACCTTTCTGAATAATGCTTCTTCACCAGGTACTATAATTATCAACCTTA<br>TACGGAATCTGTTAATGCGCACGTGCCCGAAACAAAATGTGTCAATACATTACTTTCACTT<br>ATACATTTATATTTTGTGCATGATATTTGGTTATATCTTCTAGTATCTCTTTAAATAGTTT<br>TGTTACACCCAAGGTGACTGAATATTGGTACCAAACAGTCTTCTAAATTCATTGCTTGGGCT<br>TCTAGACATGTCGTATGAGTCTGAGTAGTCGAAAACATACGATTTACAACCCGCCCTTTACT<br>ATTTCGCTATACACATAGGTATTGCCTGACATTATAGCATATGTCGAAGTAAATATTATGG<br>AATCTTTTGTATTAATAATATTTATTTCAAAGTAATGTAATTTTCTAAGAGTTTGGCCAAC<br>AACGGGATCAAACAAGTAGTAAATATCCGAAGTGCTACTTTTCATTAAATTTTTTTTTTCC<br>ATTATTGACAAATCTTTTTCTTTGCACAAACAGTTCCATTTTTAAAGCATCAGGAGCAAGA | |

TABLE 7-continued

CENs sequences

| Sequence | SEQ ID NO |
|---|---|
| ACTCTTTAGCCGCTGCTTTTCAGGAGGCTGCAGAAATTTGTTACTGTTCTTGGTTAAATGA<br>AGTACACTAATTTCAAACGAGGAGACCTAGTTCAAAGAATTACTATTATTGAAACTGTTCA<br>ATGTACATAGCTTTTGCCCTTTATATCGTACTGTACATTTGCAAAGTTTTCAAACTAGGAA<br>GCAGACCGTCTCTTGACTCTGTTTACAAAACCCGAAGCTATCTTTTTTAATTTTCCTTTTA<br>TGCGTAATACAAAACCTGGAAAAATAACGAGAAGTTTTTACAATATTCGAAACTTTGCAAA<br>TTAACCCGGTCTGCAATATTTTTTGAGCAGCTTTTCACTGTTAGCTTTACTCTCTTCATTT<br>TTGTAAACATAATGTTTTGAATGACTAGAAGGGGAACTTGTTATTATCGTAGCGCCACTTA<br>TCTCTACTGTATTTCAGTAGTGAAACTTTAGGCCAGCCAAAATTGTCCTAAAGCTTTGGGA<br>TTTGTTAAAATCCCCTTTGAATTTCGTTTAACTATAAGTAATTATCCGAAGTCTACATTTA<br>CTATCATCCATTTTTATATTGCCAAATACTTGATAGAAACTATAGATAGCTATGAAGTTTT<br>CAACAAATCGATTTTTCCTCATAGCTTTCTTAATAAATTGCTGTTATATATTGTAATCCC<br>AAAATATGAAATTGTTGATTATAGCGCCCGGCTTCAAAGCCCTGACAAATATACTCGAAAT<br>GATGCGTAAACCTTCAGCTTTGTTTTGAGGAGCTTCCTTTTGTTCTTTAGAATAAAAGGAA<br>ATAACCGTTTATATTATTCTTAACGGAAGGAAAAAGAAAGAGTTGTCAACGCGTACATATT<br>TGTATAATAAAAGCTACGTTTCAATAAACGTCTAAGGCGGAACTGATAGTATATTTATGCT<br>TGAAATAATTATTTTCGGGCTATTTCCGTCCATAAAGCGTCTCTAGAGGCCAGCATTTAAC<br>TTCTTATAAAATCAAAAATTGGATTACTCTTACGTGATTTAATCACCAGCTCATGGAGGTC<br>TTTTTTTTTCAATTGGGTGCTGTTTAGTAAAAAAAGTTAAGTTATATTTCCAGGCGACTTT<br>AAGAAGGCTTCGCCTACCAAACACTAACTAAAACAAATAACAGAGACATAGACCAGCAGTA<br>TTCTCTCTTTTGCCTTATGCGTGAATCACTTAACCTTGCCTCGATGTAAGCTCTATCCTTT<br>TGAACATGTTTTTTTATGTTTTTACACAGACCCAATTTAATAAACTATAACTATATGTACA<br>CTTTATAAGCCATTGATTTTAGTGTAAACGAGATCGAAAAAGAAACAGATGCTCCTCGGTA<br>ATTTCACAGAAGTCAATATCTGTTTTTTTTGTACAACAATCAAGGAAAAAGTGGTTCACCG<br>GTTTCAAATTATATGAAGTTAGGTAATTCTAAAAAGTCCTTTTGCAAAATTAAGTATGAGC<br>TTCCAAAGTACTTTGAGAATAACATTTAGCATCGTGCAGAAACACTGACAGTAATATTCAA<br>ATATTCATCAACTAGTTTAAATGCTTCTTGTAAACCCGACTTAAAACTGCACTATCCCTAG<br>AAGGGTTTTTCAAAAAAAAGTTTTGAAAAAATACTCAAACTTAAAGTTCAACGCCTGAAA<br>AAACCTCTCACTTTTAAATCACTATGTCGTTGGCATTAATTTTAGAATGTAATAATTACCT<br>CTGATGAAATAACATCATGGAAAATGACTTATGTATATGTGTATTATCTCGACTGGTCTAG<br>GTTTTGCTAGATGGAACAAAGAACTTATTGTTTATAAACTAAATAGGGTATTTTCCAAATT<br>TCTCCTCCTGCGTGTAAGTTGGCGTACACAAAGCTTTCCTCATTTCCCACAAACCCCACAT<br>GTACTGTCCTTAGAGAAAAACAAATCTACGTGCCTTTCAGTTGCAGCCCATGGATGATCAG<br>TAAGTAAAAGTTTGCTTTTTCGGGTTGCAAGCTCACATCAGTCTTTGATTTTGAACTTCAG<br>TCTAAGGTATTCAAAATTCACATATGTATTTTGAATTAATTATATTAAATAAATTATAATA<br>TATAAAGTGCATAAGCAGTATAATCAATAAATAAATGACATAAAACAAAAAAGCTATAAGT<br>AATGTCTAGTCGAAATTCTGCCAGTAACACTTACAACTGCTAGTATCGGAGGTTTTAGGGT<br>CCAAGAGACCAATAAAGAGATTTTCGAAGTGAAAGCGATGAACGCAGGCTCCAACTTAGTG<br>CTACTAGGCTTAAAAATGTTTTTCAAATGTAACAAAGAAATATAGGCGCTTGTCATAACAT<br>TTGTTAATAGATTGGATACCAATTTTAAGCTACAGAAATGGATTAGAAAGCAAGTCACGTA<br>CTTTTCCTAGTTTGGAGATGGAGGTATTAGTCCTTGTTGAATCGGTCCTTACTTGGTATAC<br>TAACAAATAAAGTATTTTCAATGTAAGCACTACTTTTATGGTTTCATTTTGCTAAACGCTTA<br>AAGGTGGTTTCGCCCCCAGAATTCAGATAGAGAAGCAAAACTAAGGATTTTGATTTTATTA<br>AGAAAACTCTGTCTCGCAATAGAAGAGATTTTGAAAGAGAGACTGTTTAGGTATTCTGTTG<br>CTTTAGTTGATGACAGCGCGCCAAGAAACATTAAGGATTATGTATTTGTTAGGTTACATCC<br>ATGAGAGAGTTTTTCAAAGTCTACTAGATTTGAAGTTGTTATATCCGCTAATAAGAAAGCA<br>ATTACACATAGAGCTAAATTGATTTTAAGACCGCAACTTGTTTTAAAATATAATGGGCGCA<br>ATAAAGACAACAAATGTTTGCTTTTGAAGAATACCAATCATAAAATAATTTTCAGTCTCCT<br>CTTTATTAAAGATTATAGGGCTAAGGATGATCGAAAGAGAAATAAAAAGAATTAGTGGCG<br>CTAGAAGCTCTACTTTTTGAAGAAGAATTAAGGTTACGGGATATATATTAACTTAGAGAGT<br>ACTTGCAAAACAATTAATGATAATGAAAAAATTGAAGAGACAAAAAAATGAACTTATAGG<br>TATCAACTCCATGCGTGCAGTTAGAAGAAATTTAAAGAATGTTGATAATTATCCATTATTA<br>CTGTTTGTGCAGTCAGTTGAAGTAAAAGAAAATAATAATGTTTTAGAAGAACCTTACGATG<br>GTGTTGATGGAATTAGAAATAAAATTCATGAAGAATTTAGAGATGTGGTGACCAATGACCA<br>ACCTACCAGTTTACCTCCCCAAAGGGATTTGACTCACAGAATTATACTCATTGAACCTACC<br>AAGAGTACATACAGACGCCAGTACAAATCAAGCTATTCAGAGAAACAAGACTGAATAAAC<br>AGGTTGATGAACTGTTGAAACTAGCCTTTATCAAGTCTGCCCCTAGTTCTTTCAATAGTTT<br>TTTGTTACTTGTTCCAGAAGAAAGATGGTAGTATGAAAATGTGTGTTGACTATGGGTTACT<br>GAATAACAATACGGTAAAAGACAAGTTCTCAATACCACGAATCGACAAATTAATCACATGT<br>TTTGGAGGAGCTTCAGTATTTTCCAAGTTGGATTTGATGTCAGGTTACTTTCAAGTCAGAA<br>TCGCAGAAGATGATATTGAAAAAACAGCATTTTCCACAGATTACGGTCACTTTGAGTGGGT<br>TGTGATGCCTTTCGGTTTAACCAACGCCCCTAGTACTTTCCAAAGAATGATGAATAGGATT<br>CTAGCACCTTATTTGAACCAATTTGTTCAGGTGTACCTGGATGATATTATTTACTCAA<br>AGACTGTTGAAGAACACTACAGTCACATTAGAAAAATATTGGAATTGCTCAGGAGAAATAA<br>GCTGATTGCGAAGAAAAAGAAATGCTCATTTTACTTCAAAACCTTAGGTTTCTTAGGACAT<br>CTCATTTCAAGCAGAGGTATCCAGACTGACCCTGCTAAGATAGACAAAATCAAGAGCTGGC<br>CAATTCCGAAAAACGCCAAAGATGCTCAATCATTCCTAGGATTAGCTGATTACGAATTCAC<br>AATTCAATACTTGAGGTCCTACTAATTCAGTAGCAGACGCTTTGTCTAGGTACCCCTACGA<br>GGAAAATGAAGTTGGTATCAACACAATAGAATCGGTGTTAACACCAAATCAGGAACTTCTA<br>GAACGGATCATTAAGTCGTACGATGAAGACAACGAAACTAAGGAGATATACGACATTTTAA<br>AAGAGAATTTGCCGATCCCGAAGTCAATCCATAACCACATCAAACATTATTCAATTGAGGA<br>TAATTTACTATATTTCTCAGTGGTTAAAGGAGGAAATGATCGAAGAATTGTAGTCTCCCCT<br>AAGTCTAAGTTGGCTCAGGAAATTATTGGTAACGCTCATGACGGTAACTCTGCTGGTCATT<br>TTGGGTATTTCAAAACATACATGAGACTTCACCCTATGTTCTACTGGCCAATTATGCTAAA<br>AAGCGTGAAGAGATATTGTCAAAGATGTACGGTTTGCCAGAAAACCAAACCCGAGACAACT<br>GGTCAAAGAGGATTATTTTCCCCTCTTCCAATTCCTGAAGGAAGATGGACAGACATCAGTT | |

TABLE 7-continued

CENs sequences

| Sequence | SEQ ID NO |
|---|---|
| TGGATTTCGTCACAGGTGTTCCCAGATGCAAAAATGGACACGATATGATTTTGGTAGTGGT GGATAGATTCACGAAGATGGCACATTTCATCCCCACTAGGAAAACTGCAACCGCAGAGCAA TGTGCAAAATTGATAGTAGACAATTGTTTTAAATTACATTGGATTCCAAAAAGAATGGTTT CAGATAATGGCATAGAATTCTTGGTACATCATCACTCTTCTCAACCACTAATCACCCTCAA ACAGATGGTCAAACGGAAAGAACGAACAGAATCTTAAACCAATAACAGAGACATTATGATA GTAACGATCTCTACAGTTGGGACAAATGGTTGTCAATGGCCGAATTTGCCTACAATAGTTC CCATCAAGTCTCGATAGGTTCATCACCATTTGAAGTTTGCTATGGTTACTTACCAGACTCG CCAATGTTTATTTCTAGCAGTCGTGTTTCAAGTAGAAGGTACAGCAATAAAGCTGAAGAAT TCGCATTAAAAATGAAAGTCATCATGGAAAATGTGAAAGAAAACATGATTGAAGCGCAAAG AAGTCAGGAAACACAGCATAATAAGTCGAGAGTGTACGAAACATTTGAAGCTGGAGATTGG ATATTATTACACAAAGATGTATATGGTAGTGATAGATTGTATTACAAAATACAACCGGTAT ACTACGGACCCTACAAGGTTGTCAAAAAGATATCAGACAACGCTTACGAAGTTGATTTACC GAAAACGAATAAAAAGGATAGAGTAATCAATGTCAGATGGCTTAGAAGATTCTTACAAACG GATAAACAGTTTCCCAAGGTACCCCAAGAACAATAGCTGAAGCAAGAAGTAGACTGACCGA GATTATCGGTATAGCTGGTATCGACGAAACAAACGATACATTGGATGTCTACTGGAAAGAT TGTGACCCTTGTCATAGTTCAAGCATCCCATATTCATTATTTTTAGAGATCCCAGAAGATT TACAGAAAACTTTATGGGATAATGCAAAAGCAATTGATAATGATAATAAACTCCGGGACGA AGTTTCTAAAGCGGCGGGGTAATGTAAAAGATCAGACAAAGGACTATCTCTCTATTTCCTA ATCGGGTAATCATATAGAAAGTTAAAAAGAAGTTCTAGAAGATAATTAAATCCCTCAAAAT GCTATTTTTAAATTAAAGAATTACTATTTAAATAGAGGACATTCCATATATGTTCTCAGAG AATTAACATATAAAATATATAAGATATAACAATCAATAATCAGATTCTAAAGTACGTACCA CCAGAAACACTTTTAAGTCAAAGTTTGACTGGATGGCCAAGTTGGTTAAGGCGTGCGACTG TTAATCGCAAGATCGTGAGTTCAACCCTCACTCTGGTCGTTTTTTTAACGGTTGCCTTCGT GATTTAGTTGATACAAGTAACTAACCATGTGGAAAGGTATTAGTCACACTTCGAATATTTT TACAAAATGTAAGGAATACATGTAGGCTTCAATATATTTCTCTTAGAGTCACGTTCGAACT CTTCACCATTTACCGCACCATTAATATTTTCGTGGATTCTACTTGTATCAGTTTTGCTGAC CTTAACCTATTCATGTTTATCTTTGAACCTATTCAAGTACCTTACGGAATTTCTCCTGATG GCGCCTTTACCAGTCTTTCCAAAGTCACTCATTGTAGATATAATGTCTTTACTATTTTTCG TTGTCTATTTATAGTATTTCTCTAGATATATGTGGTTGTATTGTTCTGCTTCAATGAGTAA TCTTTGTACAAGGTGAAAAGTCTTTAACATTTCTTTTACCTTTTTCTCACGAGTCAAGATT TTTCCATACAATATGATGTCATGGATATATTTTTATTTCGCATAGGATTGAACCCCTATGG AAAAAATCTTATATAAAAAGGGATCAAAAACGAACTGAAAAAAAGGAAATGACCTCTTTCTG ATAAGAAATATCAGATGTCTATTTAGCTGGACATATAGGTGGACTCACTTTTGAAGAATGA GAAAGGTAGACTTAACTATATGAACTAGAAAATAGTTAAATCCTTGTTCTAAAATCTTGGC TAAGTCGGCTAGATCGACCCCATCAGGATTGTTAAGGATGTTTGTAGTTTGATTGGTTATG GTTTTACTCAGCTGTTCTACCAGACGTATATTTTGCAGGGTTTGGGGCCAGAGTTTCTTTT TTATTTTCTTTGAGCTACAAACCATTACTCTAATTACCATATTCTTCGTTTTGTTCAAAGC TGATTTCGCTTTAGTGTGGAATCATGTGTATTGTGTGTATAAGATTTTGTTTGAATAGCAT CTAATAGAGAAAGTTACATGTAGCATAGTAGTACAAAGGATAGTATGAACGTCCGTAAGTT CAATAATAGGCAATATAAATGCTATGCCATAATTACTTTTTATGTAGCAATTCATTCCCTG TTAGAATCGCAACTATAATGAGAAAGTGAATTGTGAGTTGGGGTGAGTCGATAACCAAGTA AAGATTCTCTCATCCTAATCCTTTGAAGTTACTCCTATTCCTTTATATAAATCTCGATTTT TTTCCCCATCAAGACAAGTATGGAAACTTTATGTAATTAAAGAACATTAATTTATGAAATC AACTTATACAAGAGGAATAAGATTTTTTTCTTTACTAATTAATTTTAATTTTTTGTGGTT TTGCAAAGAGATTGATCAGTTGTTATATGGCTTTGCTTTTAGAGATAAAACCTTAATTTTA TTTTGTGCTCTTTTGGTTTCCCTGTTTTCATTTTCACAAGTGACAGTAAAGTGATATAGCC ACCAGATATAAAGGTAGCGCGGCGTTCTATATAATACATTTTTATATAACCCACTGATAGT TAAATACCTGCCTACAGCAGAACCATTTATGATATAAATTTTGGATCAGTGTTTAAAGATG CTTTGAATGATCTAAAACTTATTTCTGCCAATCTAAATGAAAAATCCGCCATATTATAGTT GAGTGACAGCCTAGTCCTTAAATCGCGTCTTTAAGTTTCTTCACATTTTTTGCCTTCACAA ATATAAGCACATCATTTCACCGTATGTTTTTTGTTCAAAATACTGAGTCGTGCTGCAGGGA ATTCATCTACAATCCTAACAATCTAAGTTTGTTAACTCCTATATACTATTCCATTCGTTAA TTTTATTTTATTTTTTCTAAAACATATTAGACGGTGCGTAAACGATGTTTATCTTAGGAAA TGGCTAATCAAAAGTATCTTATTTGCATTAAATAGAAAAAGTTTAGGAAATTATTTAAAC TTCGTTCATAGACAAGCTATATGTTCTTATTTATGTAGAGAAGTTATAAGCTAATTATTTT TTTCAGCCATTATAAGTTTAAGCATATAACTGTGTTGAAAGCCACTAAATAAGTGATAAAA AAATCAAAAGACCTACTAGTATACAGAGTTAATTCTACACTTGCTACCCTAATTATAAAAA GAAACTATCGATGTATTTCTGTATTTCTTCTGAACAATTGGGGTTTTAAGTCTACCAACTT CTGAACCTTGATCATAGATACAATAGGTGCACAACACATACACGGTGTGTGGTATATTATG AGCAGCCAATTCACCATTTTGAAAAGCTAAAACTCTGTACCATAACTTTCAGTGGGATCCG TATTATCAAACTATATTAATAATCCTATGTGCTAACTAAAGCCTGGAAGCTATATATAT ATAATTTAGTTTTAATTCATAAAGTTTTTCATTGGACTGCCGGAATGTCATGGGCCTTTA AAACATTCACTGCTTAACTGGTGTAGATTCTTTGTTACACTGTGCATTGCTACTCGTCTTT CGTGTGAATTTCCCATCTCTATTCTAATACCTGTATTTTTCTGTTTAGATTTTGGACATTG AGTTACACTACTCGCTTATGTTTGTTGTAGCTAGTTTGAACTGAATCCTGGAAGTTTATTA TCTTTTTGTGTTCTCACACCACTTGCCAAGGGACTTGAGCCTGAAAAAAAGAATGAGTTGA AAAAAATGTAGGTTTTACACAATTTTAATCATTTTTCTTAAGTATGAATATCAGCTGTCTT GTAAGATGTTTCCATCAATAAGCTGAACTCACTTTATAGAGCACTGAATTTCATTTTTGT ATAACAATTGGTTATTTCCTTTCAGTCTGGCACTCGCTTTTATTCATTTTCCTAATAAATA GCTAATTCTGTTTCGATCAGGACTTCTAACTGTAGTGTGTACAAGATCTAATTCTGAAAAG GGTATTCTCACTTCCTAGTTAAGATGTGTATCATATTCTTTTATAAAACTAAAAGCACCTA GCCTATTGAGTTTATAATACTGAAAGTCTACTGAACTAGTCATCTTTGTACACTTCTTTAG ACTTAGATCCAATCTTGTTGCTTTAGTTTATTTTCTATATAGTTATTTGAATTAATCACAA GTAGCTAACAAAAGGTCCATACTTACCGATTTGTGTATTAGGATTTTTCTTCTATTTCTTT GTAGGTAGTAGTGTTTCTAGGGGTAACCTTTCAAATTGGCCCTTCTGAGTCTATTCTAGTT | |

TABLE 7-continued

CENs sequences

| Sequence | SEQ ID NO |
|---|---|
| TGAAAAGAAAATTTCTCGCTAAATAACACATATTAATAATAGTCTTTGCTATGGAACTAAT | |
| TATTTCTTGATCTAAACTATTTTTGCTCCTGAATAGAAGGACCTAGTTATTTTTTATATTA | |
| GGGCAGAAGAAATCAAAGAAAGAAGTTGAATAAAGAATAGGTATATTTGTACTAAAGTTTG | |
| CTAAAAGCGATTTAGGTGGAGCTTCTATTTATTTAAAAACCCCAATAATCTTAATAACAAT | |
| AAAGGTCTTCCTGTAAACTTTTGAAAAATGTACCGGAGTATTTAAGTTAAGTCCAAACCAC | |
| GAGAATAGGTCAAAAGCTGCTACTTAGTTTATGTTTCATTGCCTTTTCAGTATCTCGAGAC | |
| TTCTCCGCTGTTAATAATAAACAGTTGTCTAGTTATTTTGTTTAGGTTGGATAAAAACCTA | |
| CGGAAAGACAATAGGAGCTTAGGCTATCTATTGATAGATCAATTATTTGTTTTAAGAACTA | |
| TAGAATTAAAAACAAGGCAGTAGTTGTAGATTTTAAAGATTATTTAGAGTAGATAGTAAAG | |
| GCTGTACTGAATATCAATGAGGATTTGCGGAACCAACAAGTGGCCTGCATCAAGCTATTTA | |
| AGTGATTCTATTGGTATTTTACTAGAAAAGGAAAGCTAATCATTTTTCCAATGACGGTTCA | |
| TATAATCCAAGTTTTAAATGGTTTGCATCATCATAATAGGGGTATCTAAAAGGCATAAATC | |
| GACGAAAGTGATAAAAATTACTTATTAAACGACGTATTTACATCCACGTTTTTGTTGGAAG | |
| TACTGAATCTGCCTACTGCTAGTTTGGGGAAGACAATAATACACAAATAAAGACGATAAT | |
| GAAGATTCCAGTTTTTTTAAAGATAAAAAAATAGATATATATGTATAATTGTATGAATAG | |
| TTTTAATAATAACTTATGTTGCTATTTTGATAGCAATTCATTTTACTATTGAAAAGATTAC | |
| CTAGGCAAATAATATGTTTAGCACATCAGATTTTGCACTAATAATAATATAGACTTATGTT | |
| ATAACGTCTGGCAATACCTATGTGTATAGCGAAATAGTAAAGGGCGGGTTGTAAATCGTAT | |
| GTTTTCACTACTCAGACTCATACGACATGTCTAGAAGCCCAAGCAATGAATTAGAAGACTG | |
| TTTGGTACCAATATTCAGTCACCTTGGGTGTAACAAAACTATTTAAAGAGATACTAGAAGA | |
| TATAACCAAATATCATGCACAAAATATAAATGTATAAGTGAAAGTAATGTATTGACACATT | |
| TTGTTTCGGGCACGTGCGCATTAACAGATTCCGTATAAGGTTGATAATTATAGTACCTGGT | |
| GAAGAAGCATTATTCAGAAAGGTTGTAGCCCAACTAGATGTTGAAGTGGACCTTCTAATTT | |
| CCTTAAATACAATAGAAGCAAAATAGGTGTTTCACCTATCACAAACACGATGAGTATTTTC | |
| TCGCTTTGCTTTAGTCTAATAGAACTAATTAGAAAATCCTTTGATATTTGATGCCATGGCT | |
| GGAACAAACTCAAAAACATCTTTCTGGATTATATTTTTCTAGTAATATTAGGAAAATAAGA | |
| AACAGTTACCCAGAAATAAATGGGATTAATAAACAACCGTAACATTTTTCATCTTTTCATG | |
| CGATTTACTCGAGCTCTACATTTTCTATTACCTCAAGAACTAAATTTGTGTAGCATTTATT | |
| TGACGTATAATTTTTATTTAGCTCATCACTAAAGAATACTTGTTATTAAGAGATTCTACCA | |
| TTAATAAAGTACGCAAATCTAGCTTCTCTTAATATTCATGAGTATCCATCTTGTAAAGGCC | |
| TCTGTAAAGCAATAACCTTATATTTCGCTAAATCCAGTAGTCAAAAAATAGATAGCAAGCT | |
| TGAGCAAGATTCTTTTCATTAGCTCCATTATGATTATATAAATATATTGCGCCAGGAAGAA | |
| CTTGGGAGATTTAACTAATGTCGAGAGTACAATGAGGTATAATAAATTTTCATGTTTAATAT | |
| ATCTGATAGAGCATATTTACATGGGAAGCCACTCAAACTAATTCCGTCAATTTTTTTAC | |
| AAATCTAATTTATTATTCCAATCATTAAGTCAAGATAAAAAAAACCCTGAAAAAAGTATAG | |
| ATTCTTAGCTACTTTACCATTCAGGCAAACAAACTCATTCTCCATAAATATGTCTAAGAGT | |
| ACTCTTGAGAAAAATTCTTCTTTTATATTATAACACGATTAAATTTCCTGAGCAAAAACAA | |
| AAATGAATCAGACTCTCCCAGAAAAATAGTGAATGCAACTTTTGTTTTATTAGTAAGAGGA | |
| TTAGGAATATCTTTATAAAGCTGTCTCTGAGTCGATAAACTTATTTATGGCATAATTTCAA | |
| TTTACCAAATGAATTTAGGAATGTTACTGTATACAGAAAACTAAAACAATAACTTCAAGTA | |
| TATTTATAAGTTCTGTTCATTGAGAACCAAATAGTGAGAATTATGCAATATCCTTTTTAAT | |
| GGATTTATAAGTTATTCAATATCAACAATAAATAAACAACATTGATATATATGTAAATAAA | |
| ACGATAGAACCTAAAAAATAATTTATATAATGGAAAACTTCCAGCGAAGTATGATGATATT | |
| CAGAATATATGCGGATAACTATCGAATAAGCACATTAATAGTAATGATATACATGTAAAAG | |
| GTCTTGGGAGACAAATTAATCAATTTTATGATAGTAAAACAAATTTCTTTGCAAACAGCGC | |
| GAACAAAATAAGAAATGATATTTTATATAAAAAATACTAGATGAGTTGACATTGGAGAACA | |
| GTGGTTAAGGAATAGCGTTATGCCACAATGTAGATATTTATAGTAGCTGTAAATTCTATAA | |
| AAACTGGTGTTCAAGAGGCACAATTCCTGACGTGATGCCCATATTTAGTCCAGCAGCTGGA | |
| TAACTTAAAAAGAATCCACAAATTATATAGATCGATATCAATAGATTCAGTTGGAGTTGAA | |
| CTGGTTTCTTATTAATCTTTGTTTTGGTGCCATGATGACTGAGGGTGTCTTCCATAACTAA | |
| TGCTGATATAAATTTTAATCGTTATTTCTGTGCTTAACTCAGAACATAGGTCTAAATATAG | |
| CTGTCAAACAATCAGAAATAAATACTGATCCTGAAATTGGCCTATTGTTAACTATCTACAG | |
| TGTTGAATCTGATAACGAAACTATGCCGGATCAATCATGAAAGATGTTCAAGCGTTAAAAA | |
| GAATCGTACTCTTTTGGTTTAAACGCACCTGTACTATAGTTTGCTTCGAATAAAACCATC | |
| GCCAGTTACCCAACTTTAAGTGAGCACTATTTCTGAAAGTGACATCACATCTTAGTATCTA | |
| ATCTTACCCTCTAGGTAATTGTAAAAATTACCCTCAGCACTGTTTCGACATAGCACTCTTT | |
| AGTGAAAATTTGCAACGTGATCTAAACATGAAAATCCGAGAAATTGCCGGATACGCATAAG | |
| GTGCAAACTTTTCTTGCTGGTCGATAGATCACTTCGTAATGTTCCATTTGCACCTATTGAT | |
| TGATTTTTCGTTGACGTCAACTTCTTATATATGAGCCCTTACAGAAATGATTTTATGGATG | |
| CACGATATTCCTGTTTAAAACAGCCGGCGTTTACTATCCTATAACAAGAGGCTTACATGAC | |
| TCCCACATGAAATATAAACTAAGCGAACCACGAATTCGACTTTGCCGCAAAACGTTTTCTG | |
| AAACATACTGTTTAAATAAGTTCAGGAAAAGGCATAACAGTCATACATAATTGTCTGTATA | |
| GAGTTTTGACATTTATTATAACTCTCTAAGAAAATGTTTGGTAGATTAGACTGTGGAGAGA | |
| AAGAAAAAGAAGAGTGTCTATAAAAACTATAGCTTGACAAATATTTTGATAAAGTTTAGA | |
| AAGAAGCACATGTTTTTTCTGATTTATTCCTACAGAATGGATCAATGAAACCTTTTGGGT | |
| GTTTTTTTTAGAAATTATCAAGATTACATTATTGCATTACAAAAATTGTATGTTTTTGATT | |
| TGAGTTTCGTGCGGCAAAAGATCGGAAATGGAAGCTATCCAATATTACAAATAATATTGTC | |
| GTAGAAATGTTTCTTTAGGGATATCAAAAGTTTGTTAGACGGCTATTACTCTTCTGTTTT | |
| CAACCCGTACATATTTTAAACTGGGAAAATGCAGGATCTTAGAGGGTTCTAGTTTTACCAA | |
| GTACTGTATTTATGGAAGATTCATCCAATACACACAGTAAAATTAAGTTTGAAAATTTGAA | |
| TAGTAAAGACGTACTTCCAGATTATTACGTTCTTCTTATACATATAATTAAATACTTGGTC | |
| TCGAAATTCAGATTCACCAGTAGAAAAGTCCAACAAAAAATTATAAGGACGTACGTTTCC | |
| AGTCGGACCAAACTAGCTGAAAAGCCAATAGTTTCACGATGTAGCTAAATTTTAAGTAGCT | |
| GTTTGAAAAGCTACTTGTTTTTATGTACAAAAAGGTTGTATGTGTTAGTTGAATAGTGTT | |
| TCTTTTTTTTTTGCAATTTCAAGATCAGCGACTTTAAATATTGGTCATTGTGACATGAAAA | |

TABLE 7-continued

CENs sequences

| Sequence | SEQ ID NO |
|---|---|
| AAAAACAGTTACCTTTGAGAACTAAATGACTCTTTTCTTGCTAGACCTTATCGATCTATCT TTTAGCTCATCACAAATATTAGGCGAAAAAGAATACACTAATCTAAGAAAGCTATTTATAT ATTATTTTTTTGATGGAAAAAAAAACTCCAATGTGTGGGATAATGTTGAAATTAGCGTTAT GTTTATTAAGCATGGTGAGTCAGCCCTGATAGAGGGACCATTGAACTGAGAGTACAAACAA GTTGGTGATTAGAACCTATTATTTAAGCATCCTTTAGACAGTGCTGTTTTAACGGGGGTCT CATATATTTAAATCATGTACTATAAGAGGAATAGTCACACACGGATTTCTTTTGATGAAAA TGCTCAAGGACGGGTAGGTAACGAACAAATAAATGAAAAGAAAAAAACTGGAACATAAGGG ACAGCAATCACATAGTCCAAAGCTGAATCCAGAAAAGGCTGCAGAGACTCCGTCATTTGAT GCAAAGCATAAGGGTAAACGGTTAGACGTTGCTGAAGTTAGTAGAAACGTATACTAAGAAA ATCCAACACATGGAATTCAAGCAGCTGCTAAGGGTAGTCATGTGAGTGAATAACCGCTTAA TTTAGTAGAATGCAACAAAAGGATTTATGTATTACATTGCTAATGATTGTTCCACAATAAC AGGCAAAATGCTTTTGATAATTAAGAGGCTAGTCCTCTGCAAACAACCAGAACTCTTCTGA ATTATCAGAGCATTGTTGTGTTATTGGCCCAAATAGCTATTTGCAAGATTGTTAGGCCGAC CTTTAAGAGCACAAGTTTTTTTTCTATAAGAGTTTAATGTATTTTGCGTATGTATAAGGG CGTGCAACTTACCATTTGCTCTGAGAGCAAAAAAACAATAATTTATAAGGTTTACTTATTG TTTATACTAAGTTTTTTTGTTGAAATCTAGCTAACTTTCCAGCTAACGTTGTCGATTATGA TCTAGTTTAGTTTATGTAAGTCAATGTACTAGGGTCTTTTTCAGGTCAATGTTGAATTTCT CAACATAAACATAACACTAAGTTTCTTCTTTAACTCTCAACAATTCTAAGTCCCCTAATGG CAAGAAAAACTTGACCTTACATAACCTTAAGCTGCTTACAGAACAACCCTAAAATGATGCT CCAAGTGGTAAAAAAAGTAGCTTTTACACGGTAAACATTCGGGCAACAAGATTTAGGCTAA CTTTAGGATAAACATAATAGGTTCTCTTCTTATCTTAACCAAATAACAAACACTCCTGCAC GAACAAAATTCAAGCAAACGCGTTATCTGTACTTGTAGAGCTTATATAACAGCATATAACA TGAGAATAGTTGCAGAATTTTATAGCTCTATACGGTTCATCAAATCCTAAATACCCTACTC TCCCTGAGCATAAAGCATGGTCACATGATATATTGCAGATGAATGACATGCTGATGCAT CTTAAAAGCTCCAGAGGTGATTTCCAAAGTTCAAGAATCCTTAGAATGTTGTACTATAAAC CGCCATATAGTTATAGAAAAAGTATATTCAAGCAATGCTGCTTAACAATGACTAATATTAA CGATAGCAACCAAATTATGGCAGGGAACAACCCAACATTATAGACGTAAATAACACATTTC TTTCTATACCCAATAAACACACTGTCCAATTTCCATTGATCTGGAACTATAGACTTTGGCT CCAACAATATAATTTCAAATAAATCTCTGCTTCTAATACCAGTAACTCTTTTCTTTTGAGT GTTTTGACTTTTCAATGGATGGATGCTGGTGGCCGTCTTTGGTCTCAACAACTGCTCGTAC CCAATATCTTTTACTTCGTTTTTAAGCACATCTATAATCCCGTGTTCTATATAGTATAGTG TCAGTTGTCTGAGATAAATATCCGTCTTTTTTAATTGGTCTGATCAATCTCAACATTTCCA GTGGTTTCTTCGACCTCTTCCATCTCTTGAATTTAAGTAATTTAAAGTAAGGTTTTTACAT TAAAAACTGGTTCGATATCAGCCCTTAACGATATAGGTAACATACTGTCAAAGCTTAGATT AATAGTCTTTTCTTTTCCATCTCGCCACATACAAGATATAATAGATACTGTCAAATATATC CCGATCATTGACAAGTAAAACATTATCAAATATGGGGTGTATGATGGAGAGACAAAACTGT TTGCTGCGGTTTACACTTCATAATATTTCTTTCTCACCTAAACCTTGTCAATGTGTCAACA CCAACACAATCGAGATTTTTTTCAAGGTTGATAGTTTTGTGCCGTAGACACTTTACAGCAG CAACTCTATTAGGTCAAAATTGTCTTGCAAGACTTTTGTGTGAAGTTTCAAAACCATCTAA AAAATGTAACGCTATTGTGGCAAAAGCTCATCTTAGAAAGATCTCTTGAGCAGTTCACTTA ATTTCGTAATACAAATACCATAATTACCTGCTGATTTATTTTGCAGAAATAACCATACTCA ACAATGGATTTTTCGTTTATGTCATTCATATATACATCTGTCATAGATTTGAAATATTGG CATGTTGTCACATTGAATACAGCATCAACTCCAGAAACATACTGACTGGATAAGCTCTACA ATTAAACCATGAATTTGGGCGGACTGTGTGACTTTGTTCACAATTTCCGGATATAACACAA TCTCAATATCTTCTTCCCTTCTTTTTTTACTACAAACGCTACCTTTACTTTTCCAAAAGGTT AAGCGAAGGTGCCACATCGTGTTCTTAAGAGGAGTGCTGTTGTTTTGCCATTGTCTTTGTA AACACTCAAATGGTTGATGTGATCTCTTCCGTTCGAGTTAACAATATATGCATAATGGGAT ATCCTTTTATCTTTCTAGTATAATATGTCTTAATAACTACGGCCGTAAACGATTCGGGCCT AATAATCACATTGATGAAGAAATCAAAAACAATGCTGGATTTTTCCAAACAGCTTGTTCGT TGACTTCCGAGCTAGAACATGGCTGATACAAACCAAAACTATAGGTTACTTTCTCTTTAAC CTTTCCATCATAACGGAGCACGGAACTGCGTTAATCCTTAAAAACACATTAATGTTTTTAA GGTTGGCGACATCGAGCAAAACTGAGCAAATTTGTAGCACAAGCCCACTACCAATCCTATT AGCTCACAGTGGATCCTTGAATCCTAAAATCTATAGAATAATATACGTGAGTAACTCCCC CAAAGATGTTCTGTCACTCTGAAAGATGCACCGTGTCTATAAACTGAATATTTAAAAGATG CTCTTAGTCTGGTAAAAGGCCCATATGGTTTCTTGTGTTTCCACCGATATGTTACAGGTGC ATCATTCCATCCACGTCAAAACCTTTCCTTAACGAACACTCCTGTATATTGTAACAAAAGG GAATTTCCGTGCTTGCTAAAAATGTATTGTAATCCGAAACAATACATTTACAGAAGAGCTT TGTAAAACCTATATTTCACCTTTTTAATCAATTGGGGCCTGTAAATAGATTTTAGTAGAC TTTATCTTTTTGTCAAACCTGGATGTCTCAAGAACTTTTCCGTAGAGCCGTTCCCACAAAA GCTACCATGAAAGGCCTTTAATTTATCAGCAAAAATGTAAAATCGCAAGAAGTCATCATCC TTTCTCCGTCCAAGTGGTGGGCGTTCGAAATGAGTATCCACAAGGTTTTCAAGATACTTCC AAAAAGACGGTCTGAATTCTCCTTATCAGGGAAAAATACCTCTCCAATTTTAGCAACAAAA GCTTTACAACAAACCTTCAAGTGCCAGATCTGTTGCTGTGTCTGTGGTTTATCAGATGACA CATGTTGGTGGTGGTAAACATTTTATATCCCAATTAATGGCAGTATAACATCAAAACTATA CAGTGCAACCTCACATCAAGTTACACATTTTATCACAACAAACCGGCAACGTTGGTTGTGT ATTTGAAAGTTGTAATTTTCAGCTACAGTAGTTAATTTATACACTAAAATATAACTCTTGG AGAGCAATATGGATGACTAGGTCCGATCAATCAGCTATTGATGGTACGATATCCATATTTA GTTCGACACTTGATTACTAAGGGATTTCTAAATAATATGCGTATTAAAAGCTACAGTAAGA GCGGAGTTACCTCTCTTATCAATTGTCGGTTTGGCGCCACAATAAATAATGATATCATCTC TAACTAAACGCAAAACATATTACTAGTTGTCATTAGCTAGTTGCCATCAGTGCATATGTG AGTCGACATACCTGCTGTATCACATGATATCAATAAAGGTTGTAGATTATTTTCTTTTCCT TGGGTTCTTTTTATGTGGTATTTTGAAGTAACTCTTTTAAACGTTCAATCTATAACGTGTA ACATGGTTATCTGAAGTAGAATTAGGGCACGTCAAGGCAGTATTGTATTTGCTTGACATGT ATTTATTGGCTGCTTTTAGAAACTAAACTATATTGAATATTTGCATTTTGGCCAATGGTAA AACAGTTTATCTTATTGTCTTATATGATTGCAATGGGAGAAGAATAACTAGCGGATTTATC | |

TABLE 7-continued

CENs sequences

| Sequence | SEQ ID NO |
|---|---|
| AAAGCTAAATCGATAAAACGAGAACAAAACTCAACTATGTTCAATGCAGAATAAAATTATA | |
| CAAAACCACCCAACTTCTCTGATTAATTTCAGACTAGAAAGGCCCCGGATTTCCATTACTG | |
| GATATAAGGGCTAGAGGCATAGAATGGTCAGCAAACATTGGAAGAGAATTTGCTACATATG | |
| GGCTACCAGATGTCAGAAAAATTATAAGGGCTGTTGCAGGTTCGAAAAATAACGAACGTAA | |
| ATTACACACTTCTCAAATGCATATGAACTAGCAAATACTGGATTTTAGTCGGTCTAAATTT | |
| GAAGATAGATTCTGAAACGCTTTGTTCCTGTCGACAAAGACAGAGACTCTGTGGTGAATAT | |
| TGTCAAGTAATTGTGTCGATTGAAACCAGGTCAATCGATGAGAGGCTATAAAGAAAACTTT | |
| AAAGTGTCTATGTACGTCGCTATTTCTGACATTAAGAGTTGACCACTATTCCTTGATGGCC | |
| TTACCGATATTGAGCAGTTAATGGGGGTGAGATTGTTGCAGTCTAACATAAAAGCTTGATG | |
| TGTGTTTTAACCATGTTGAGGCGAGTCTATTGGAGATATACACATGCAAGAAGTTACATGG | |
| GCACTTATACAATCATTTAAATGGTTTCCCTTATAGAACAAAGTCCGCCAAAGAACTCAAT | |
| TTATTTCATGCCTTTTCAGCCATCGGTAACCTAATGTATCATGGATAATTTCATGTTCCTT | |
| TATTCAAATAGTATTTATAAGAGGATGTTAAAGGGCATGATAATGATGCGAAATACGAAAA | |
| GGAACTTTCATAGTAAGTATAAATGTCCAAAAAATGAGTGGATGCCATCCCACACTCACAT | |
| TATGACCATCCCAAAAAAGAAAAACCAAAATTAATTTGTGGTGTCGTTTATATCAAATATG | |
| CAGATGACATTTTGGTTGCTCCAGAACCACTTTTACAGTTATTAATAAAACTGTTGAGGAA | |
| GTTCATGTGTTTAGCAAAAGGCCAAGCTCGATGGATCAATAACAGTAAAGATTATCGGAAA | |
| CTCTGGTGTTGCTATCGCAGACGTAATTGTCCCATTTGAGGTAGTCAAAGAAACTATCAGT | |
| ATAAGTGAGGTTAGGTCATTTTAAATGTTTGATACTGAGCATGTGGTATTCATGTTGGGAA | |
| ACCCATTTATCAAGAGGCAATTTAGTGATCTAACTTTAAGGTATTTAGTAAGTCCCGATAA | |
| CGATAAAGCCAAAGCTGATTTAAATATCGGCCCCTAGACGCAAATCATGCAAGAGGATTGA | |
| AAAAGGAAACACTTGAAAAGTTTACTTGAGATCCACCAACTGAACTACCGCCAAAGAAAAG | |
| ATGCGGGCATATGTTGCCTTGTCTTACCCTAATGAGTTCTCTTTGGAAAAAACAATACCCA | |
| TTAAGCTTCTCTGAGAAACTGGAACTAACAAAACAAGTTGAAGTTTTAATCAAACAAGGTT | |
| TCATCAAAACTAGTTCCAAACCTTTTAACAGTCCAGTGCTATTTGTTAAAAAGAAAGATGG | |
| TACTATGCGTATGTGTGTTGATTATAGGATTTTAAACAATAATGCTGTTAAGAACAAGTTT | |
| CCACTTCCAGATATTGATCAATTGATTTCAAGATTTGGTAAGACAAAAGTCTATTCTAAGT | |
| TAGAGTTGATGCCTGGTTACTACCAAGTGAGAATTGCGGATGAAGATGTCGAAAAGACGGC | |
| TTTTTTTACTCTGGCCATTATGAATGGATGGTAATGCCGGCTGGACTAACAAGTGCATCTG | |
| CGACTTTTCCACAGATGATGAATAATGTCTTGTCTAAAAAATAAATGGATTTGTCCAAGT | |
| GTATTTAGACGACATTTTTATATACTCCAAGATGTTGAAACTCACGGTAAGCACGTGAAA | |
| GAAGTTTTGTCGACACTAAGAAAACATAAACTAATTACGAAGAAGTCGAAATGCAGATTCT | |
| TTTATCAAGAATTTAGGTTCTTAGGACATGTTGTTACACCCAATTTGTATTCAAACCGCTCT | |
| CGAGAAAATTAAAAAGGTAAAGAGTTGGCCAACGCTAAACAAGATCAAAGAAGCACAAAGT | |
| TTTATTGGTTTAACTTCGTTTTATAGAAGGTTTATCAAAGGGCATTCCAAAATTGCTAATC | |
| CAATTCATAAGTTCATGACAAAACAAAGTAAATGGACAAGTGAACAAGACGAAGCCTTCAA | |
| CAAACTAAAGAAAGCTTTGATATCAAGTCCCATCTTGGTGCACCCAAGCTGGTCAGGCAAT | |
| TGTAAATTTGTTCTAAATACCGATGCGTGTGGAGTATCATTAGGTTATACTCTAGAAAAGT | |
| TGGACGAGACAGGTAAATGACGAGGTGTGATTTCTTACGGTTCAAAGAAGCTAGTTGGAAG | |
| TCAACTGAATCATGGAATATATGATCGTGAATTTTTGGCTGTTGTTGAAGCATTAAGAACA | |
| TGAAGATATTATCTCATGGGAAGACATGTCATTGTTATGACGGATCACAAAAGTTTAATTT | |
| ACTTAAAAAACCAAAATCTTATAGACTCCACTAGAGTGGCTAGATGGATGGACTTTTTACC | |
| ACAATTTGATTTTGATATTTGTTACTTACAGGGAAAGAACAATTCTGCCGCTGATGCGTTA | |
| TCTAGATACCCATATAACCACGAAAACAACTTAACGCTAACCAAATCGAATTGGCGTTGC | |
| TGGAATTGACGTAAAAGAGGAGCATGAAACACAGATACATTCTTTGACACTAGGTATTAT | |
| CGAAGCCCATCAAGATTTAAAAAAAGAAATTATTACGGGTTATAAAAAAGATACTAATTAT | |
| GCCTTGATATTCAGAACTTTGAGAGATAAAACAAAAGTTCCAGTTGAGATAAAAAATCAAA | |
| TCAAACATTTCTGTTATCAAGATGAGGTACGTTATTATAAGACATTAGAGTCTCAAGATTT | |
| CTTTAGAGTAGTTATTCCAAACTACAAGAAACTACCGTATAGAATATTCAAAATGCACACG | |
| ATTCCAAAGATGCTTGTCACTTTGGTGCATGGAAAACTTATTTGAATCTTAAAGATAGTTT | |
| TTAATGGTCATCTATGTTGAGACAAATCAAAATGGGTAGAAACCTGCCATATCTGTCAAC | |
| AACACAACACCAACACTGAGGAAGACAAGGGTGGTTTTCCCCTTTACCAATCCCAACAGGT | |
| CGCTGGACCGACATTACGATGGATTTCATTACAGGTTTACCTAGATCGGGAACAGGTTACG | |
| ATATGATCATGGTTGTTATTGATCGCTTTTCAAAAATGGCACATTTTATACCAGCGCACA | |
| AAGACTTAATGCTGCAGCATGTGCTCGTTTGTTTAGTGACAATGTTATCAAGTTACACGGT | |
| GTCCCACAAAGAATAGTTAGTGACAAAGATATTCGGTTTATGAATAAGTTCTGGCAAACAT | |
| TACATTATCTCAATGGTAGTTCTCTACTATTTTCGACTACTAATCATCCAGAAACTGATGG | |
| TCAAACCGAAAGAGTCAACTAGATCGTTAATCAGTTACTTCGGAAATATTCTTCAAACGAT | |
| CAATTATTCTGGGATGAACATCTATCTATGTGTAAACTTAGTTACAATTCAACGTACCAAG | |
| ATTCCATTAAAGCAAGTCCTTTTGAAATCGCCTACGGGTATGAATCGAACATGATTAGAAA | |
| AGTAAATAGCTGGGATTTGGAGGATAACAGATATTCACCTAACGCAGAAGAATTTGTGAGA | |
| CGTGTGAAATTGATTTTACAGCACACTGGATAATATTGTAAAGCACAAGGGCGACAGGAA | |
| AACACCATAATAGAAAAAGAAGATACTTTGAATATAAAGTTGGTGACTTAGTGTTAGTGCA | |
| TCAAGATGCCTTTGGTGTGAATATAAGGTACACAAAAATTCAACCAGTATGATATGGGCCA | |
| TACAGACTAGTCGAGAAAATAAACGGCAATGCTTATAAAGTCGATTTACCGGTTATTAATT | |
| TGAAGGATCGTGAATCAAATGTACAGTGGATTAAATACTATAAAGAAAACCCCAATATTTA | |
| CCAGGAACCGCCTAGAACAGAGCGTGAAATGTTGGCACGAATCAATGAAATGACTGGTATC | |
| GGTGGATGGTCAGAAGAATCAGGCAAAGAAAAGACTTATGATGTCTTCTGGAAAGACTGTG | |
| ATCAAACTCTAGCAAGAAAGGTGCCTGAAAGAATATTCAACCAAGCAGATTTGTCACTACG | |
| TCAAAGCCTAATGCACAATGCCAAATCGATCCAAAAAAACAACAAGCTTGGATACATCCAA | |
| AGTAATCATGATTATAATATATAGAACGTTCCTATTTGTCTCTCAGCTGAAGAAAAAAAT | |
| ACAGATATTGCTCCTACCAAAACACAAAACATATTGTTTTTGATTGAAATAAGTTAGCCA | |
| CTCTCGATTTAAAAAAATACAAATTGAGCTCATAAAAAAATTATTGTTACTGCCAGGATCC | |
| ACCTACATTTATTATTCTAATCTGTTTAATGTTTGCAGTTCATTGGTTCAGTGCCCCCA | |
| TCCGGGATTATCCAGTTATTTTGTTGCACCGTTTTGAGGAACATCGGGGCGATGTTTCCCA | |

TABLE 7-continued

CENs sequences

| Sequence | SEQ ID NO |
|---|---|
| AGAGCCGGGGTAGTGAAAGGGATTTTTCAGGATGTGTTCCAAAAAAGGAAGTGCCAGTAGA<br>TAGACGATAACATACTGATGTTAAGGTTTCGATTTTAGAATAAGGGAAGTTAACAAGGGTC<br>AAGTATCCGGAGTAGGAAGCAAAGAGAGTTAGTCCCGTTGATCATGTAGAGAATAGGCATA<br>GAGAAGCCGTCGGAGACACTGTCATTGGCATAAATTAATTATCATTCATCAACGGGCTATG<br>ACAGGACTGGCACAGTAAAAAATAAAGACCTAAAACGTAATAAGCTCGTACAGGAGTCTGC<br>TATACGAAAAAGAGTAGCAACTGAGGGTGATTCCAGGTTGCGGGCGTGAGTATATCAGACA<br>GACGATATTCCGTTATATAGAATTGATATAGCTGATATAGGTCCTAATCGGGAGTGGAAGC<br>AGCAGAAGGAGGAAGAGAGAAATAGATTACTACTTCTACTACGACTAACTTCCACTACGCC<br>CATTGTCTACTCGTGCGATTATACACCTATTGCGTACTTACTAATACGTGTATCACAATTA<br>TCATTGTTATAAACAATACTGTAACTATGGATAAGGCTATGATTGCTTTTTTGATAAAAGA<br>TTTAACCATAGAAACATCCAGAACTAGGAAATGATTTTGACACCTTACACCTAGTTCTTTG<br>CACAAACATAACAAGCGCAAGTGGTTTAGTGGTAAAATTCAACGTTGCCATCGTTGAGCCC<br>CTGGTTCGATTCCGGGCTTGCGCATCTATCCGAGATAGTTTAGTGGCTAGAATTTCCGCTT<br>GTCACGCGGGAGACCCGGGTTCAATTCCCGGTCTCGGAGATTTTTTTTGTTTTCCAATGCA<br>TTTGTTGTGTCCGTTGAGGCACTTACGATTTCTAAAAAAGTTTTACTATATATTCTAATCG<br>TCTATCAAATATATTTCTAAAATTATTAAATACACAAT | |

Figure 14:
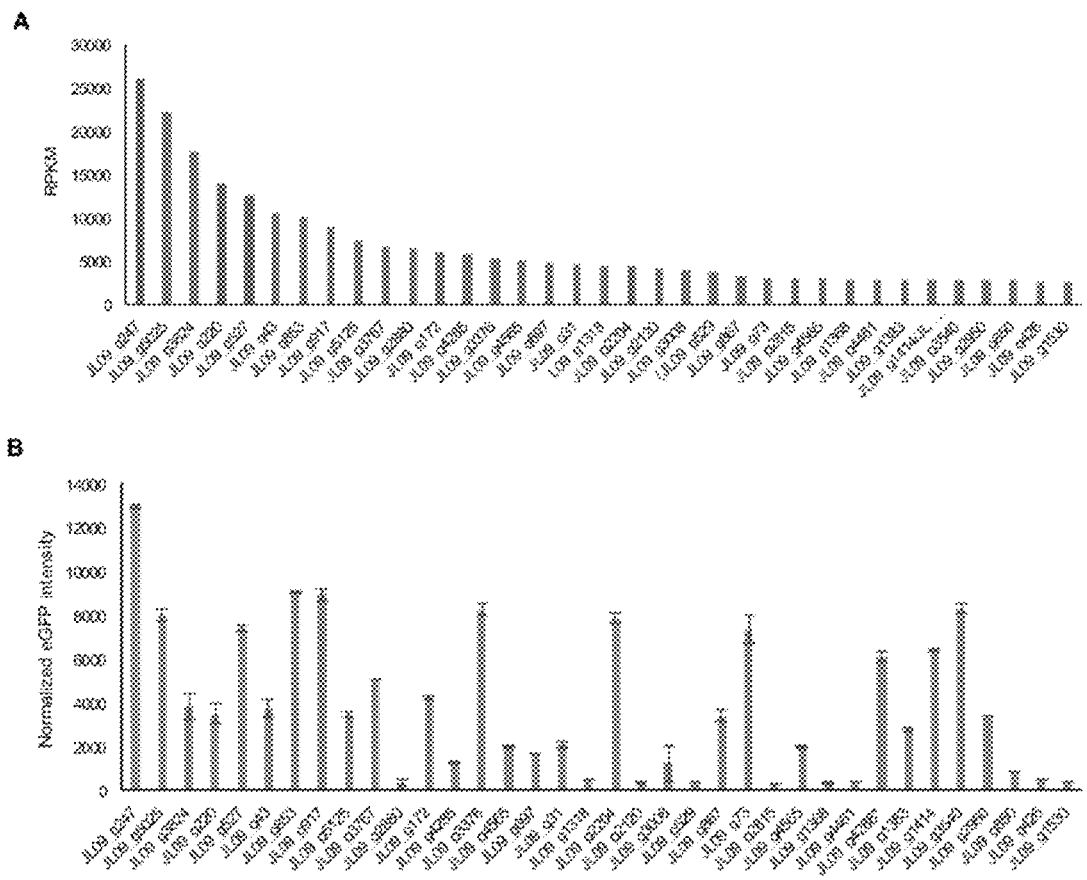
FIG. 14 panel A discloses a plot showing the expression levels of the most highly expressed genes based on RNA-Seq analysis. Panel B discloses GFP expression driven by selected promoters. JL09_g527 (fba1) gene, was used as a positive control.

Example 8. Evaluation of Various Promoters Efficiency to Induce Gene Transcription A few promoters such as TDH3p, PGK1p, TEF1p, and FBA1p were used to create an *I. orientalis* strain capable of producing 11.63 g/L succinic acid. However, so far, no comparative and systematic approach has been adopted for the characterization of a panel of constitutive promoters in *I. orientalis*. Therefore a panel of strong, moderate, and weak constitutive promoters based on the RNA-sequencing data was established. A total number of 5141 genes was expressed, and they were ranked from the most highly expressed to the least expressed based on their Reads Per Kilobase of transcript, per Million mapped reads (RPKM) values. Functional annotation of the genes was performed based on the homology with the *S. cerevisiae* proteins. The genes which fell in 1% cutoff of the most highly expressed genes based on RPKM values were selected and narrowed down the collection to 52 gene. Out of 52, only 36 genes were mapped to the *Saccharomyces* database as listed in Table 8. RNA-Seq data has revealed that the topmost expressed transcript is about ten-fold higher than most of the expressed genes, as shown in FIG. 14A.

TABLE 8

Selected 36 promoters from *I. orientalis* SD108

| Chr_locus | Locus Tag (*I. orientalis*) | CDS_product | Threshold value |
|---|---|---|---|
| 1 | JL09_g247 | glyceraldehyde-3-phosphate dehydrogenase (TDH3) | 0.04 |
| 1 | JL09_g5025 | SED1 | 0.06 |
| 3 | JL09_g3824 | Enolase | 0.08 |
| 1 | JL09_g220 | PGK | 0.12 |
| 3 | JL09_g527 | FBA1 | 0.16 |
| 1 | JL09_g43 | RTC3 | 0.18 |
| 5 | JL09_g853 | GPM1 | 0.19 |
| 1 | JL09_g917 | indolepyruvate decarboxylase 6 | 0.21 |
| 1 | JL09_g5125 | triose-phosphate isomerase TPI1 | 0.27 |
| 2 | JL09_g3767 | thioredoxin peroxidase TSA1 | 0.29 |
| 2 | JL09_g2880 | heat shock protein HSP150 | 0.33 |
| 1 | JL09_g172 | RCF2 | 0.35 |
| 1 | JL09_g4285 | pyruvate kinase CDC19 | 0.37 |
| 2 | JL09_g3376 | inositol-3-phosphate synthase INO1 | 0.39 |
| 5 | JL09_g4565 | ubiquitin | 0.41 |
| 5 | JL09_g697 | RGI1 | 0.43 |
| 2 | JL09_g31 | peptidylprolyl isomerase CPR1 | 0.47 |
| 5 | L09_g1318 | ribosomal 60S subunit protein L10 | 0.51 |
| 2 | JL09_g2204 | translation elongation factor EF-1 alpha | 0.53 |
| 2 | JL09_g2120 | amino acid transporter AGC1 | 0.56 |
| 4 | JL09_g3008 | pyridoxamine-phosphate oxidase PDX3 | 0.58 |
| 3 | JL09_g529 | alcohol dehydrogenase ADH3 | 0.62 |
| 1 | JL09_g867 | PBI2 | 0.68 |
| 1 | JL09_g73 | low-affinity Cu transporter | 0.70 |
| 2 | JL09_g2815 | ribosomal 40S subunit protein S30A | 0.72 |
| 2 | JL09_g4565 | ubiquitin-ribosomal 40S subunit protein S31 fusion protein | 0.76 |
| 5 | JL09_g1368 | NADPH dehydrogenase | 0.78 |
| 4 | JL09_g4461 | hexose transporter HXT6 | 0.80 |
| 2 | JL09_g1383 | cytochrome c isoform 2 | 0.86 |
| 2 | JL09_g1414 | hexose transporter HXT2 | 0.89 |
| 1 | JL09_g3540 | lipid-binding protein HSP12 | 0.91 |

TABLE 8-continued

Selected 36 promoters from *I. orientalis* SD108

| Chr_locus | Locus Tag (*I. orientalis*) | CDS_product | Threshold value |
|---|---|---|---|
| 4 | JL09_g2950 | cytochrome c oxidase subunit VII | 0.93 |
| 5 | JL09_g850 | ubiquinol--cytochrome-c reductase subunit 8 | 0.95 |
| 3 | JL09_g426 | thioredoxin TRX1 | 0.97 |
| 2 | JL09_g1530 | amino acid starvation-responsive transcription factor GCN4 | 1.01 |

Figure 15:
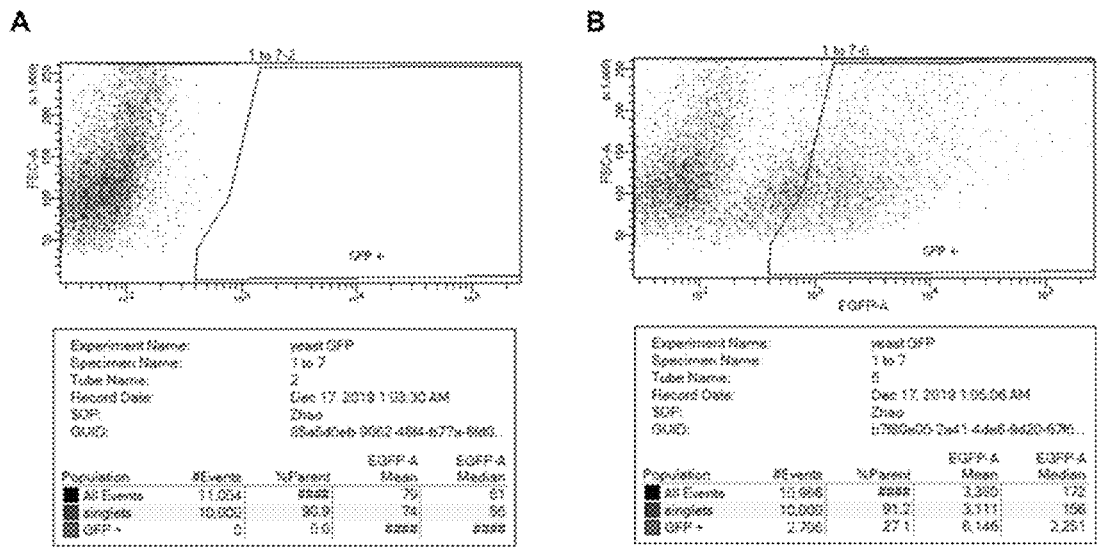
FIG. 15 panel A discloses GFP expression profile of cells transformed with GFP vector without promoter. Panel B discloses GFP expression profile of cells transformed with GFP vector with FBA promoter. Cells were inoculated in the YNB medium with 2% glucose and grown aerobically at 30° C. Fluorescence was measured at 48 h.
Figure 16:
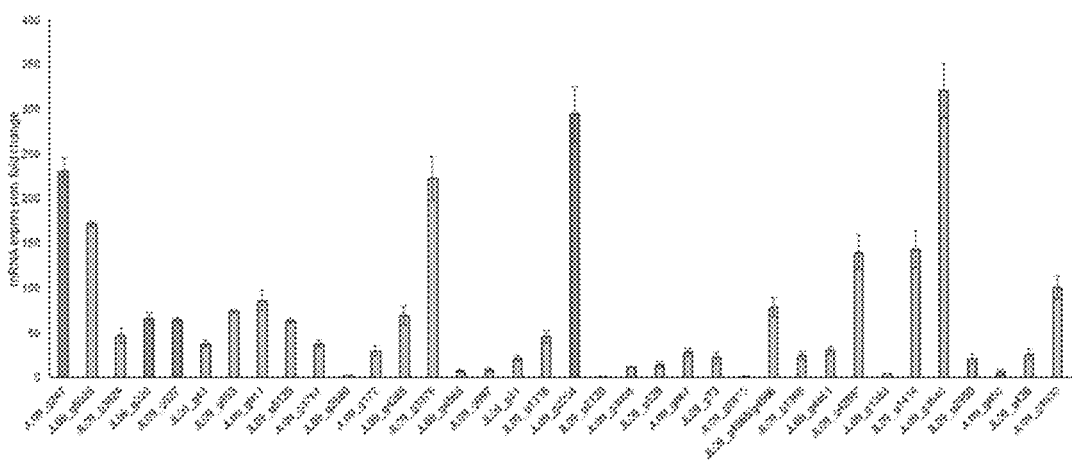
FIG. 16 discloses qPCR expression analysis of the genes corresponding to selected promoters. mRNA from wild type *I. orientalis* strain grown in YPD medium was used for making a cDNA template. The values are the mean of biological triplicates±standard deviations.
Figure 17:
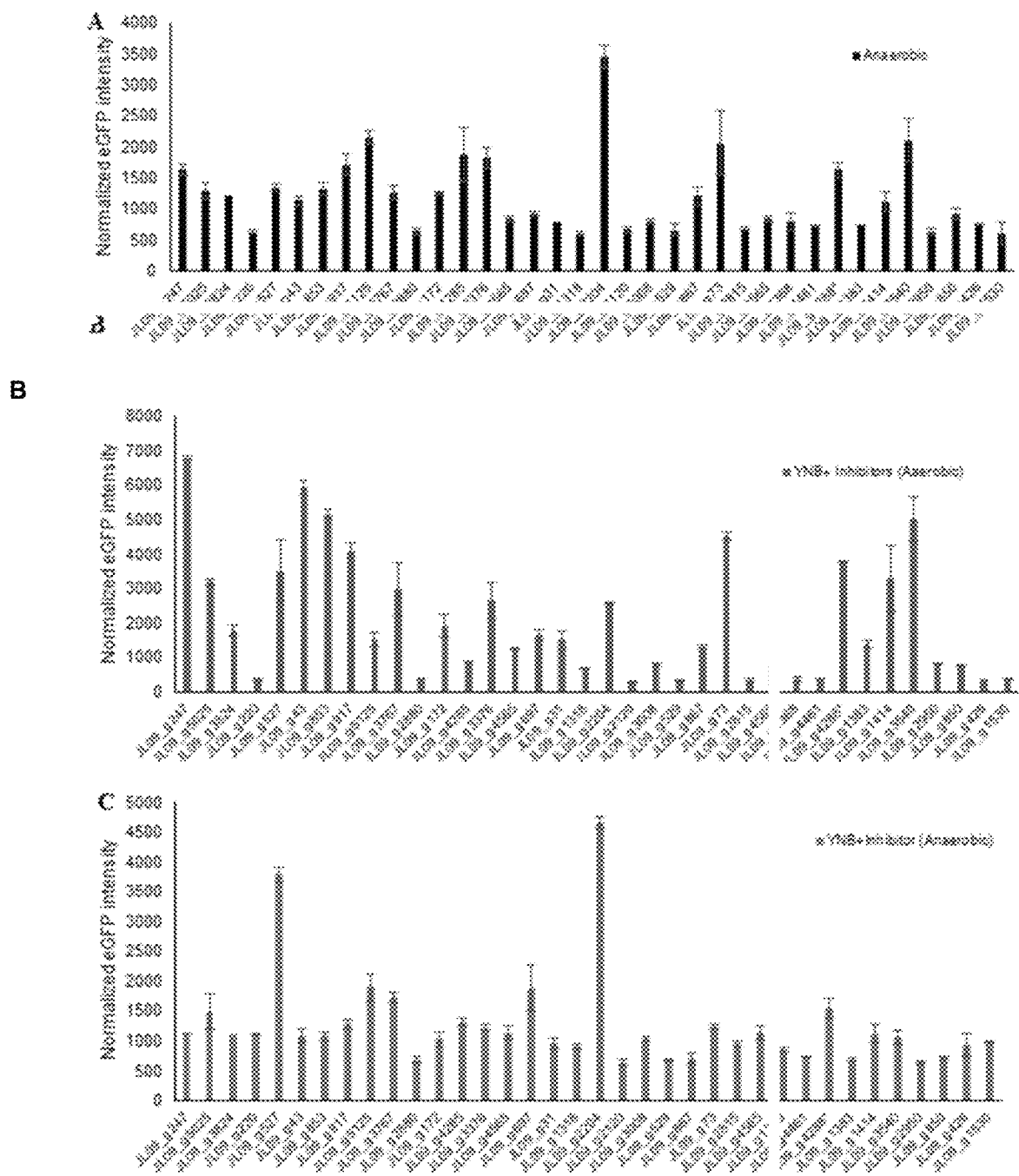
FIG. 17 panel A discloses promoter activity analysis using GFP fluorescence measurement in YNB and anaerobic condition. Panel B discloses promoter activity analysis using GFP fluorescence measurement in YNB medium with lignocellulosic biomass under aerobic condition. Panel C discloses promoter activity analysis using GFP fluorescence measurement in YNB medium with lignocellulosic biomass under anaerobic condition. All values are the mean of biological duplicates±standard deviations.
Figure 18:
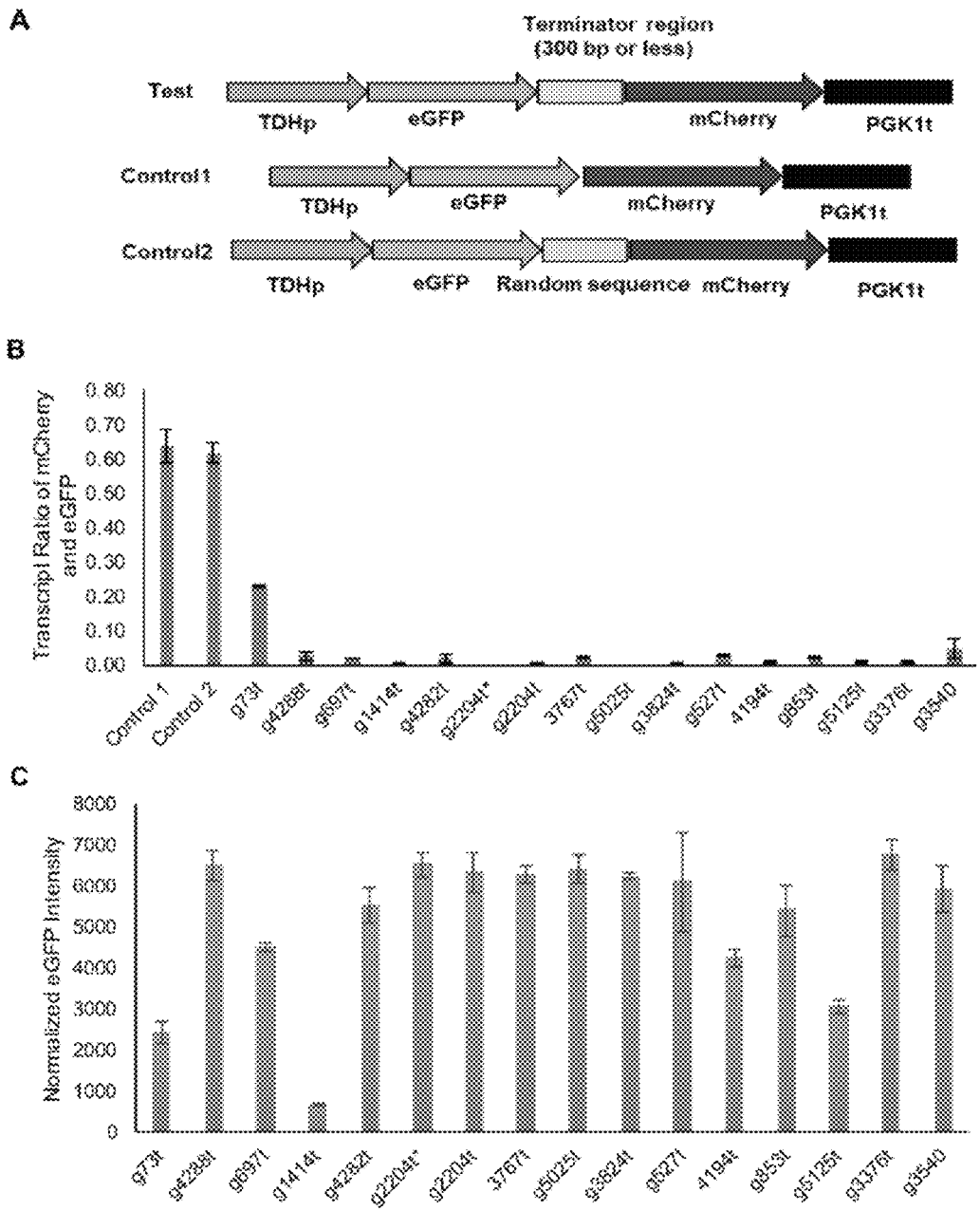
FIG. 18 panel A discloses the construction used to characterized terminators efficiency; terminators were cloned between two reporter genes, GFP and mCherry (Test) whereas either a random sequence (Control 2) or no sequence were inserted between the reporter genes (Control 1). Panel B discloses termination efficiency of the selected terminators calculated at the transcriptional level by determining the ratio of mCherry transcripts to GFP transcripts. Error bars represent standard deviations of two biological replicates. Panel C discloses terminator characterization based on GFP fluorescence intensity. Error bars represent standard deviations of two biological replicates.

To quantify the strength of the promoters, the intensity of GFP fluorescence of the corresponding reporter strains was measured using flow cytometry. Cells carrying the constructs were grown in four equivalent conditions as used for cultivation of the cells for RNA-Seq analysis. Results of GFP fluorescence for YNB minimal medium were mostly consistent with the qPCR results (FIG. 15). In comparison to the positive control (g527, belongs to FBA1p), seven promoters (g247, g5025, g853, g917, g3376, g2204, and g3504) had led to strong expression (FIG. 14B) and the analysis very closely correlated with the qPCR results (FIG. 16). Some, which showed quite similar fluorescence values with that enabled by g527p were included in the list of moderate promoters (g3824, g43, g3767, g172, g973, and g4288), whereas others were included in the list of weak promoters. Surprisingly, the activity of a few promoters such as g2880p, g529p, and g2815p was not detected and the results were also supported by the qPCR data. This reflected that either these promoters were not functional at all in the minimal medium or may require a different inducer. These inducers could be a stress induced by an anaerobic condition, inhibitors present in lignocellulosic biomass or both. To test this hypothesis, the fluorescence in YNB medium in anaerobic condition (FIG. 17) or in YNB medium supplemented with inhibitory compounds present in lignocellulosic hydrolysate such as furfural, HMF, NaCl, and acetic acid was measured, and grown in aerobic as well as in anaerobic condition. These molecules have been shown to hamper the growth and fermentation ability of *S. cerevisiae*. Comparing the GFP expression driven by the g2880p, g529p, and g2815p did not show a noticeable difference when compared in the aerobic and anaerobic condition in YNB medium (FIG. 17A), or with lignocellulosic hydrolysate inhibitors under aerobic and anaerobic (FIGS. 17B and 18C). Interestingly, the identified strong promoters listed in Table 9 were concluded to be constitutive promoters because they were expressed at similar levels in all the culture conditions. Moreover, comparing the promoter strength in YNB and stress-inducing medium has led to the identification of a few different promoters such as g5025p and g3767p in aerobic condition, and g5025p, g3767p, g697, and g4194p in anaerobic condition (Table 9). By comparative analysis, a few strong, medium, and weak constitutive promoters were identified, which can be used to express a long biosynthetic pathway in *I. orientalis*. Sequences of these promoters are listed in Table 10.

TABLE 9

Top 10 promoters from four different conditions

| Aerobic | Aerobic + IN | Anaerobic | Anaerobic + IN |
|---|---|---|---|
| g247 | g247 | g2204 | g2204 |
| g853 | g853 | g5125 | g527 |
| g917 | g3540 | g73 | g5125 |
| g3540 | g917 | g3540 | g697 |
| g3376 | g4288 | g4282 | g3767 |
| g5025 | g527 | g3376 | g4288 |
| g527 | g1414 | g247 | g5025 |
| g2204 | g5025 | g917 | g4282 |
| g1414 | g3767 | g4288 | g4194 |
| g4288 | g3376 | g527 | g917 |

TABLE 10

Promoter sequences

| Promot-er Gene_ID | Sequences | SEQ ID NO |
|---|---|---|
| INO1p | CAACGGTGTAATCAGAGAGAAAATTGCTCTTGCACAGCAACAGCAGCAACAGCAGC<br>AGCAGCAAGCCCAACAAGAGAAAGCTGGAACCCAACAGGACGCATAACTATACTCC<br>AGCCACAAGTTTCTGTAGCTTCTACTTTGGTATATCATTAGTAAACAATAACAATA<br>ACTCACCAATAACCATTATAACGGCAAATCATTTTCACGTGCCGGCGCATTCGCCG<br>TGAGCCCACGCATATACTCGGCAAAAACACCGAAACAGCAGCAACTGGGCTGTCCC<br>AAAGGGGAAATTTCTGCCGTGGACCCCGGGGCCATATCGGCAAACTCGCCGAGACG<br>CTTGTAGTTTATTGGTCAATTGGACAAAGTTGCCAATTTTAGGTGAAAGGAGGAGT<br>AAATTATGGACAGGGTGGCCTGTTGTCATTGGAAAGTCGGCAAATAGAGTCAATTT<br>AGAATATTTTAGAAGGATTGGAGACACCAAAGAGGTGGCCATTGGAGGTAGCATAA<br>AAGGAGGACCATTTCCTGCCAAGTGGAGAGGTACTGTAAAGCCATGTTTTTAACTT<br>TCATCTCATCAAAGCAGAGCAAACTAAAAAAACGAATATA | SEQ ID NO: 17 |
| GPMp | CGAAAAATGCACCACACCCGGAGAAAAAGAGGCCGATAGTCACCGCGTTTTCTGTG<br>GAGTGTGGCCCGGGTGGAGTAATGGTTATAAAAGGAACATTTTCCCACCCAGGGGG<br>TCTTCAATTGGTTTCTCCTTCTTGGGCTTTCAAAGAATCACGTACAATTGTATATC<br>TTAAAACACACACACAAA | SEQ ID NO: 18 |

TABLE 10-continued

Promoter sequences

| Promot-er Gene_ID | Sequences | SEQ ID NO |
|---|---|---|
| JL09_g247 (TDH3p) | TATGGATATGGAGATGAATTTGAATTTAGATTTGGGTCTTGATTTGGGGTTGGAAT TAAAAGGGGATAACAATGAGGGTTTTCCTGTTGATTTAAACAATGGACGTGGGAGG TGATTGATTTAACCTGATCCAAAAGGGGTATGTCTATTTTTTAGAGAGTGTTTTTG TGTCAAATTATGGTAGAATGTGTAAAGTAGTATAAACTTTCCTCTCAAATGACGAG GTTTAAAACACCCCCGGGTGAGCCGAGCCGAGAATGGGGCAATTGTTCAATGTGA AATAGAAGTATCGAGTGAGAAACTTGGGTGTTGGCCAGCCAAGGGGGGGGGGGGA AGGAAAATGGCGCGAATGCTCAGGTGAGATTGTTTTGGAATTGGGTGAAGCGAGGA AATGAGCGACCCGGAGGTTGTGACTTTAGTGGCGGAGGAGGACGGAGGAAAAGCCA AGAGGGAAGTGTATATAAGGGGAGCAATTTGCCACCAGGATAGAATTGGATGAGTT ATAATTCTACTGTATTTATTGTATAATTTATTTCTCCTTTTGTATCAAACACATTA CAAAACACACAAAACACACAAACAAACACAATTACAAAAA | SEQ ID NO: 19 |
| JL09_g5025 | AATACACGAGAGATTATAGCAATACACGAGAAACCATAAGATACTAAGGTAAATCA TGGCAAATCATATTAACTATTGACCTCTGACAAACAGTTATGGCCCTTTAAAGAAG GTAAACGTGGGAAGCCTTGGGACAGGAAAAAAAAAAACCTTCTCTCTCAATG AGCCAACTTTTCATTACATCATCATCGTCCACAATTTAATTGGACAATAGGAAAAT GCAAAACAAATAAAGCTGAGTAAAGAGCGGCAAAAATATGCAAAGAGACAAAGAT TTGCCAAAGAGGCAAAGATCTGCAGAAATGGGAAAAAAAACTGCATAAATTGCAAA ACGCGCTTCTATTTTTAGTACATTCGCCAGCGGCCGTGCTGCTGTTTATCTTTTGCCGTC TTACGGAAGGCGCGCGCCGCCGGTGGCTGTTTTCTGGTAAAGTGACTGTTCCACGG GGGGAAGCTATAAAAAGCGTGAAATCCCTCCCACATTTTCTAATCCCAGTGGTAAA CCCAACTTCTTTTCTATAGTTTTTTTAGCTTTATTCTTTCTCACTTATCAACTTTT ATCGTTCATAGTCTCTCGCTTACAAACTAACACAATAAAA | SEQ ID NO: 20 |
| JL09_g3524 | CAGGGAGGATCCACTCCTAACGTCTCTCCATAATGTCTCTGTTGGCCCATGTCTCT GTCGTTGACACCGTAACCACACCAACCAACCCGTCCATTGTACTGGGATGGTCGTC CATAGACACCTCTCCAACGGGGAACGCCTCATTCGTAAACCGCCAAGGTTACCGTT CCTCCTGACTCGCCCCGTTGTTGATGCTGCGCACCTGTGGTTGCCCAACATGGTTG TATATCGTGTAACCACACCAACACATGTGCAGCACATGTGTTTAAAAGAGTGTCAT GGAGGTGGATCATGATGGAAGTGGACTTTACCACTTGGGAACTGTCTCCACTCCCG GGAAGAAAAGACCCGGCGTATCACGCGGTTGCCTCAATGGGGCAATTTGGAAGGAG AAATATAGGGAAAATCACGTCGCTCTCGGACGGGGAAGAGTTCCAGACTATGAGGG GGGGGGTGGTATATAAAGACAGGAGATGTCCACCCCCAGAGAGAGGAAGAAGTTGG AACTTTAGAAGAGAGAGATAACTTTCCCCAGTGTCCATCAATACACAACCAAACAC AAACTCTATATTTACACATATAACCCCCTCCAACCAAACA | SEQ ID NO: 21 |
| JL09_g220 | CATATTCGACGACTCCGGGGAGTCTAGTAAAGGCGGGTTTTGTCTTTGCCAGTTGA TGTTGCTGAGAGGACTTGTTTGTCCGTTTCTTCCGATTTAATAGTATAGAATCAAC CTACTGTTAATTACACTACGTTATACTAACACAAACAAAAACAAAACAACGACAAC ANNNNNNNNNNNNNNNNNNNNTTCAGGTTGTGTCACTCCGACGGACCATAGTTGGG TAATCGTGCATTCTGAGAGAGTCGCGAGAAGTGAGGACCCCGACCTACGTAAACTA CCTCGGACGGGGCGAGTGGAGGAGTGGGGCGATGGAGGAGTGGGGCGATGGAGTG AGTGGAGGAGTGGGGGGGGGGGGCGGAAAAATAGGTAGCGAAAGGACCCGCTAT CACCCCACCCGGAGAACTCGTTGCCGGGAAGTCATATTTCGACACTCCGGGGAGTC TATAAAAGGCGGGTTTTGTCTTTTGCCAGTTGATGTTGCTGAGAGGACTTGTTTGC CGTTTCTTCCGATTTAATAGTATAGAATCAACCACTGTTAATTACACACGTTATAC TAACACAACAAAAACAAAAACAACGACAACAACAACAACA | SEQ ID NO: 22 |
| JL09_g527 | ATGCCATATTGTATGTGTATTGTATTAAGTGTGTATTGTCTTAAGTGTGTAAGAGA CATTTATTTGTGTCAACAATAGCGACGCCACTGAAAACCTCAAATATCGTATTTAT TAATCCCCTTCCCCCCAGCGCAGATCGTCCCGTCGATTTCTATTGTTTGGGCATTA TCAGCGACGCGACGGCGACGCGCAAGCGGCGATAATGGGCGACGGTCACAAGATGGAAC GAGAAAACAGTTTTTTTCGGATAGGACTCATTTTCCAGGTGAGAATGGGGTGACCC CGGGGAGAAACCTTCCGCGAGTGGAGTGCGAGTGGAGTGGGAAATGTGGCCCCCCC CCCCCTTGTGGGCCATGAGGTTGACAAATACCGTGTGGCCCGGTGATGGAGTGAGA AAGAGAGGGAAATGATAATGGGAAAACAAGGAGAGGCCCGTTTCCCGGGATTTATA TAAAGAGGTGTCTCTATCCCAGTTGAAGTAGAGATTTGTTGATGTAGTTGTTCCTT CCAATAAATTTGTTCAATCAGTACACAGCTAATACTATTATTACAGCTACTACTAA TACTACTACTACTATTACTACCACCCCCAACACAAACACA | SEQ ID NO: 23 |
| JL09_g43 | TCTACCTGTTTTTTTGTTAATCCTACACAAGAAGCCCCTCCTATCTTTGTCTTTAG TTGAATAAGCCTCTTAGGAGATGCCATTAAACCAATTTCATGTCGCCACCAGAGCC TGCAATGGCAGACGTTTGCGCCACGTCATAATGTGGAAGGGGAAGGAGGGGAAGGG GGTGGCAAACCCCAGGAACTGTAAATAATAGCCTGATTGTAAACCACGCGTGTGGC GCATGCGCGCTTTTCCCCTTTTGAGCCCCTCCAACCTATCCCTGATGACCCCCTCGC TGAGCCACATTGGTTACGTATTATGAACCGGTCCTTTTAAAGAATAACGACTGGGA AGGTGGCAAGTATGGGAGGCAAATCAAACTCCAAATATAAATAGCCACCAATATCC TGCTTGTTTTGGGATAATTGGAATCAAACAATGTTTGTAGAAACCAACTAACAAG AGCATAGAACCTCTGCATACAACAATCAAGCACAAACGGACATTATAAATCGTTAA ACACAAATCGTTAAAAGCAAATCTTACAATACAAATCGTTAAAAGCAAATCTTACA ATACAAATCGTTAAAAACAAATCGTACAATACAAACAAAC | SEQ ID NO: 24 |
| JL09_g853 | CGAAAAATGCACCACACCCGGAGAAAAAGAGGCCGATAGTCACCGCGTTTTCTGTG GAGTGTGGCCCGGGTGGAGTAATGGTTATAAAAGGAACATTTTCCCACCCAGGGGG | SEQ ID NO: 25 |

TABLE 10-continued

Promoter sequences

| Promot-er Gene_ID | Sequences | SEQ ID NO |
|---|---|---|
|  | TCTTCAATTGGTTTCTCCTTCTTGGGCTTTCAAAGAATCACGTACAATTGTATATC<br>TTAAAACACACACACAAA |  |
| JL09_g917 | CCTCTATCGTATCGTATCGTAGCGTATCGTACCGTACCGTATCACAGTATAGTCTA<br>ATATTCCGTATCTTATTGTATCCTATCCTATTCGATCCTATTGTATTTCTGTGCAC<br>CATTTTAATTTCTATTGCTATAATGTCCTTATTAGTTGCCACTGTGAGGTGACCAA<br>TGGACGAGGGCGAGCCGTTCAGAAGCCGCGAAGGGTGTTCTTCCCATGAATTTCTT<br>AAGGAGGGCGGCTCAGCTCCGAGAGTGAGGCGAGACGTCTCGGTTAGCGTATCCCC<br>CTTCCTCGGCTTTTACAAATGATGCGCTCTTAATAGTGTGTCGTTATCCTTTTGGC<br>ATTGACGGGGAGGGAAATTGATTGAGCGCATCCATATTTTGGCGGACTGCTGAGG<br>ACAATGGTGGTTTTTCCGGGTGGCGTGGGCTACAAATGATACGATGGTTTTTTTCT<br>TTTCGGAAGGCGTATAAAAAGGACACGGAGAACCCATTTATTCTAATAACAGTT<br>GAGCTTCTTTAATTATTTGTTAATATAATATTCTATTATTATATATTTTCTTCCCA<br>ATAAAACAAAATAAAACAAAACACAGCAAAACACAAAAT | SEQ ID NO: 26 |
| JL09_g5125 | CTCTCTTCTTTCCCTCCACAGTAGAAACCAAATCAAACACCGTTTTGTCGTTAACA<br>CCGTGTTGTCGTTAACACCGTGCTGCTCTTCCCTATCTGTCTACACACACCCGTAC<br>ACCAGAACTTTCTTTACACACACCCCACTAGTCCTTCTTCCCCCCCCCCCACCGGA<br>GACTTTCCGAATTGGGAGCGTCTGCTGACCGCCGGGTCTTTTGTGTTCCGGAATCC<br>TCATCATTTGGATTGTTGCCCAAAGTGGAGTGAGCCCGGAGTATCTTACCATACAG<br>TGAGAGGCACATTAAGTGTACAATAGGTATATATAGATATAACTATATATAGGGGG<br>GACCTTGCTACTAGTGCAGTATAGAAAGTCAGTAGATACTTTCCCCCAATTTGGG<br>CTTATTTTTTCTTCAGGCTGTATAACATCCAACACACACACACACACACATACAC<br>ACACACACCTACTCATATATATATAACTCTTACA | SEQ ID NO: 27 |
| JL09_g3767 | TAGAGCAGAAATTCTACAATACGTTAGATATACTCTCATGGGCCCTTGTATGCTAC<br>AATCGACAGATCTACAATGAATCGGGAGAAGTGATTCTGGATAATCGCCGTTTACG<br>TGAAAATCAGGGTGCAAGTTTTATTATGCACATAGTGGAGATAATACAGCAAATTG<br>TCCAAGACCTTATTTTGCTTGTTTTGACTTTGTTCCCACCATTTTCGGATTCTGTG<br>AAACGTGTACGTGTACGTGCCGCTGCTGTTGTAGATTCTAATGCCAATGCCAATCC<br>GAATGCCATGGCAATGGTGATGTTGATAACAATGGCAATGGCAATGGCAATGGCA<br>ATGGTGATGCAGCTGTGCTGGCGCCAATGGTTGACAACCAGTAAAGTCTAGGTTTT<br>GGTGGGATTGATAAGCTTCATACGGTTTACTAATCTCCAGCGAGAAGCGAGACCGT<br>CTCGTGTGCTCGAAGATTCTATACCGCGAGTATAAAAGGAGAGTAGTTGTCGCCAC<br>CGTTGGCCTTTTATATGGTGGAGGTTATCTTTTGTTTGTATAGCAGTTAGATCAAG<br>CAAGAGTTTATCCAGTTACTCAATTACCCAATAATCTACA | SEQ ID NO: 28 |
| JL09_g2880 | GTGCTTTGAGCATCTGCACTATGGTGACCTCCATCAAATGAAAGTAAAAACGTTCC<br>TTTCCCATACTTGTTGTCGTTGACGTCTGGGAATGTCACCCAAAATAAGTGTGTTG<br>AATGTTGTCACTTGAATAAACACATGCTACTGACTATTGGCACTTTATTATTGCAG<br>TGTTGACTTTCACTACGCGACGTTCATGAAAAACCACGGAGCTGTTGGTAGCTAGA<br>ACAACTTTTTATCGATTCGACACGTTACTACTCTATTTTGCCACACATTTTCTGTG<br>GGCGGTATCTTTAGTGGGGACAAAATGTGTTACTCTAGTTCTCCGCGTGCTCAAAA<br>GAAAACATAATTGTGGGAAAATACCCCACTGGTGGCTGTTTTGGAGGCGGAAATAGA<br>ACCACAGCATACGCAATTGCTATTAGGCATAAAAAACATTTTGGAGTAGGCTGGAC<br>ACAAGAAAACTGTTTATGAATGTGCGTTTTAGGATACTCGAAAACCAGCCATCTGT<br>ATAGTCATATTTACTGTTTGGAAGGCTGGTATGAAGAGGTCATGATAATTCAACGA<br>CTCTTAACAGGGGTGATGTGTTGGAATTTGTATAAAGGGA | SEQ ID NO: 29 |
| JL09_g172 | AGCCCTGGGTTTTTTTTCGACCTTCTAAGCAGTAGAATAATTTCTTGGTGTAGTT<br>CTTGACAAATTACTCATTGCATTGCTTTCTATTGCATTTTTCATGTTGAGAGTCCT<br>GCAACGGCAGTTTATATGAAAAAAAAGAAAAAAAAAGAAAAAAAACGAAAAAAGAA<br>AGAACAAGGTAGCACGGTAGCACGGTAGCATGGTAGCACAACAATGGTGAGAAATC<br>TTTGTTTTTTAAGAGTTTTCAGCCGTTTGCAATCGCCAATTGGAAGAGACAAGCGG<br>TAGCACGCATGTTGCCCAGTGAAATTCCAGCTTGGCCCCAGAAACGCGGATCTCCC<br>CCCCCCGGTCGTTCCGAGTGTTTTCAAGAAACCCGAGTGGGCCCATATTTTTTACA<br>CACTTCCTTCCCTTTCCACCCGTTGCAAAGCCCGCGCAAAGGCCGTCGTATATGAT<br>AAGTATTTAAAAGGCACCTCGTATCCAAACGATGGAGGGCATGGTTAGGAGGTTCT<br>CCTTTGAAGGATTTCCTGTCAGTTCAAATAGTGTTACAAGTACAAGTACAAGTACA<br>AGTACATAGAAGTGAAATATAGCCGAATACAAAAACAAGA | SEQ ID NO: 30 |
| JL09_g4285 | ACTGTGATCCTTGATGCTTTACTGTGATCTCTGATACTCTCTGATACTCTTTGATA<br>CTCTTTTCCATGCATGTTTCGCTTTGCCCTCAGCTACTGCTTCACCTCCCCTCCCC<br>TCTCCCCCTTCTTTCTCCCGTTTCTGCGTTCAACTTCTTTATAGACCCACTAACCC<br>CCAACACTGTATTTAACACATCCCCATTGACCTTCATTGACCCTCCCCCACCAGCG<br>TATTTCTCTTTTCTCTCCCCATTCTCTCTGCTCTTCTCGGCTCGTTGTCGCTCGCG<br>GTCATTTTTTTTCGCCCTTCTTTTCCCGCATTTCCCGTAGCTGGTGTAGTCCGAAA<br>CTGTGCTGATCTTCTTCCTCATATGGGACCATCTGGGTAGAGCTCCTCTATTTATT<br>ATCCGACCCTATTCCACCTTCCTTGCTTGGTTGACAATTTAAGATGAAGTTCCTCC<br>CATTTCTTTTGTACTCCTTTTCTCCTCTTTGTACTTTTGTCTACTTTTCTTGTTT<br>CTTCCCTCTGTAAGCCATCCAAAGAACAGAACCCATCTTTCTCGTGCTGCTTAAAC<br>TAAACCGAACCCACACGCAATCTTAAAAGAACCATAAAAC | SEQ ID NO: 31 |
| JL09_g3376 | CAACGGTGTAATCAGAGAGAAAATTGCTCTTGCACAGCAACAGCAGCAACAGCAGC<br>AGCAGCAAGCCCAACAAGAGAAAGCTGGAACCCAACAGGACGCATAACTATACTCC | SEQ ID NO: 32 |

TABLE 10-continued

Promoter sequences

| Promot-er Gene_ID | Sequences | SEQ ID NO |
|---|---|---|
| | AGCCACAAGTTTCTGTAGCTTCTACTTTGGTATATCATTAGTAAACAATAACAATA ACTCACCAATAACCATTATAACGGCAAATCATTTTCACGTGCCGGCGCATTCGCCG TGAGCCCACGCATATACTCGGCAAAAACACCGAAACAGCAGCAACTGGGCTGTCCC AAAGGGGAAATTTCTGCCGTGGACCCCGGGGCCATATCGGCAAACTCGCCGAGACG CTTGTAGTTTATTGGTCAATTGGACAAAGTTGCCAATTTTAGGTGAAAGGAGGAGT AAATTATGGACAGGGTGGCCTGTTGTCATTGGAAAGTCGGCAAATAGAGTCAATTT AGAATATTTTAGAAGGATTGGAGACACCAAAGAGGTGGCCATTGGAGGTAGCATAA AAGGAGGACCATTTCCTGCCAAGTGGAGAGGTACTGTAAAGCCATGTTTTTAACTT TCATCTCATCAAAGCAGAGCAAACTAAAAAAACGAATATA | |
| JL09_g4565 | TATGTGTATAACTGGACGAACCATAAAAGGGCAAATGCTGTTTGGAAACAGCCTGC AAAGCAAAAAATTTACACTTATAAATGCTCACTCTTGATTAAAAATAACTAGATAAT AAAGCGTTTTGTTTACATATTAATTTATTTTTCTTATTCTTCCCACTAAAGCTAGC ACATGTGAGTAAAAAATAAATTTTAAAAAGTATTTTCACAGAATGAGAATACTTTT TGATATTTAACACCAAAAGTTACATAGCACTGATTTCCGATATAGTGTAACGGCTA TCACGGTCCGCTTTCACCGGGCAGACCCGGGTTCGACTCCCGGTATCGGAATATTT TTTTACTTTTCCTCTTGATTGTTGTCACGTGTTATACACTAGGGCTAGTAGTAACC CTAATTACTGTCTTCGGAACTTGCGCGTTTTTTGTTCTCCTTGGTCTGGCATCAA TCCCCTCTCTGTAGCTGAATATTTTTCCATGTATTTTAGATAAGTGTAAATTATTA AGACGATAAATTTTTCTGTTTACTTTCACTTCTTTCCTTTCATTTGGCACTCAAAA GTTAGGTAAGAAAGAAGCATTTTTTGCAGACGATCCTAAG | SEQ ID NO: 33 |
| JL09_g697 | CATAATTCCATTTACTGAAGCACGAGTTTTTCATCTTGAAGACTCTCGTAGACAGA CCTGACCAACGTTCCGTCAGCTGGAATCCCTAGTAAGGTATCTTATCTGTAGCTG TCTTCAGTAACAAATCGAAGTGCTTACACATTGAACGAAATCGAAAGACTCGGGCA ATTAGGAGATGCCGAAACCCACACCACCAGGCAGTGTGGACATGACTGGATGAATA CTACAACAAACCAACCACAAGTTCAGATGACCACTGAAAAATCCAAAGACATGTAA CACCAGGGTAAGCATCAATTAAAGTTGGTCTCTCCACCCCACCTCTGCAATTCAG TAACGTTATCCGGAACCTCAAAGGAAAAATCGAGTGATAATTTTTCCTTTGTTTCC TCCGCGTCGGATAAAAGCTTCTCCGGACTATTAGAGAGAAATCAGTATATAAGGGA CATGTTTTCTTCATTGGAAGCAGACGAGTTGCTGTTGGGTGGGTTCTCTTTCTACA TTAGACAAGCAAATACTATAAGCAACAAATACATCAGTGTTTTAATAAACAAGAAA ACAGACGGCGAAAGTCCATTCAAAACAAATAAACCAAACA | SEQ ID NO: 34 |
| JL09_g31 | AAGTTTGTCGAGTTTAGAAAAAAACCCTTCAAAAATGACAAATTTGCCACTGCCTT CGGAGTTTATGCGCCAACGGGAATAGGAATTTGACCTTTTTTTTTTACACCCTCAA TCTATTTTATTTTTATTTTCATTTTTATTTGGTTATTTACCAACTCCATCCAATGG TGGACGAGAACGTCAGAGGATTGACGTATTTGCCAACCAAAGCGGTTTTGCCTCTC TACATTTCATTTGGTTCTGGCGCTGTTGAGCAACAACTAAGTACACACAAAGTCAT ACACGTACTTGAGTATACACTCCTCATACATACACGTACACATAAATAACT | SEQ ID NO: 35 |
| JL09_g1318 | CTGTAGTGGAGGTGAGGTTGCAATTCTGGAAAGGGAACAGTCCATGGTTCCCAAA TGCTAGTATTAATCATATTTTTCATTTGGGTCGACACTGGTTTAGAAATCCATTTA CCGAAACCCTTAACCAAAGAACGTATGTACAACATGAGACAGACAACAAAAATAGA TGATATTCATTTACTTAGGGGAGGAAACTGGTGATTAAGGGACGACGATTATTT CAAGTTTAACTCTTGAAATAATCCCAAGGTAATAATTAACTTGACTAAAGTGTTAT TAAGAAGTTACAATAGCCAAATAATTGTTTCAAACGAATAATGGTGCTAGGGTGAT TTCATATCAAGTGTTTAGTTTTATTTTACTTGCCGTAAATATTGTGGCTATTTGCA AAAAAGGGACAATTAGTAATCAATTCAGCAGAAAAAATAATTGAAGAGTTTTTTT TTAATAACCACTTTTTACCAACCTGTCTCCATTAGGATATAAGAAGGAAGTCTTCT CCATAGTTTTTGATTATTAATCTATTTTGCCTTTTCCATTACTTAACTGGTTACTAA CAACATCAACTATTCTTTTATCTCTATAGATTAATACAAG | SEQ ID NO: 36 |
| JI_09_g2204 | TTTGAAACATCATGAAAACTGTTTCACCCTCTGTGAAGCATAAACACTAGAAAGCC AATGAAGAGCTCTACAAGCCTCATATGGGTTCAATGGGTCTGCAATGACCGCATAC GGGCTTGGACAATTACCTTCTATTGAATTTCTGAGAAGAGATACATCTGACCAGCA ATGTAAGCAGACAATCCCAATTCTGTAAACAACCTCTTTGTCCATAATTCCCCATC AGAAGAGTGAAAAATGCCCTCAAAATGCATGCGCCACACCCACCTCTCAACTGCAC TGCGCCACATCTGAGGGTCCTTTCAGGGGTCGACTACCCCGGACACCTCGCAGAGG AGCGACGTCACGTACTTTTAAAATGGCAGAGACGCGCAGTTTCTTGAAGAAAGGAT AAAAATGAAATGGTGCGGAAATGCGAAAATGATGAAAATTTTCTTGGTGGCGAGG AAATTGAGTGCAATAATTGGCACGAGGTTGTTGCCACCCGAGTGTGAGTATATATC CTAGTTTCTGCACTTTTCTTCTTCTTTTCTTTACGTTTTCTTTTCAACTTTTTTTT ACTTTTTCCTTCAACAGACAAATCTAACTTATATATCACA | SEQ ID NO: 37 |
| JL09_g3008 | TGTCTATCCAAAAATACCACAAGGCAATACCCAAGAACAACAGATACTCCAATAAT CAAGGAAATAGTATACTTTCCAGTTATAAACTACTGATAAGAATTCACAATTTCCA GGAAATTAATCGACACCAGCCATTGAGATAGCGACTCTTGCCAATTTTGAATATCA AAACAATAGACCATTATGGAGGGGGGGGGCTCTATACGTCCTATTCCATTCTCATA CCTTTCGCATTATAAAAGAAATTCAATTGATGTGTATAGACTTACTAAACCATAAA CAGAAACAAGCATTTGATAGAGAACTTGTTTGGAGTTGGGCAATTTGGAAGAACA CCTTCAAACCTGATCTTCAATAGCCACTTTGTTCAGATATCCGATAGATCACGCTA TAGAATGGGAAATCAGTCATTGTTACATTTCTCGCTCTTATAAATAGACAAGGTTG TTCATCAAATCTGGAAATGCTGTCTACACCAACAGACAGCAAGACCTATACCTATT | SEQ ID NO: 38 |

TABLE 10-continued

Promoter sequences

| Promot-er Gene_ID | Sequences | SEQ ID NO |
|---|---|---|
| | TATTAGTTGATCTCTACACAAACAACTCAACGAGGTTTAGCAACATCCAAGGAGAG AGAGAAAAAAAATAGTACCAAG | |
| JL09_g529 | GGCCGAGTCCTCTTGCACGGAGTGTGTCCGAAAAGGGCAGCTCTGCAGTGGGGAG AGGAGGTCGCACGTCTATGCGGTGTTGGCATGGCCTGTGCGTGTACCTGTCCCCTC CCTGGGCATCCCCCACTGCGCGCCTTCTCCATTGGGCGCTGCGGGCACTCCGCGCC GTTAATACAGGAGGGGGGGGAAAGCTTAAGATTAGAGCGGGTACAGTCAGTGGGT GTATTGACCCCATTTCTGTCAGTATAAACCCCCCGTTGAGCCGCCGGTTTGGTTGT TTATGGATAAAATTTTTTTTCCCCGCATGGAGAAGATTGAGGGGGAGAAGGAATG GGAAAAAGGCCAGAGCCATCTCCACAGCGGAATCCGACCGTTAATGGGGTGAAACA CCCCCACCAGGTAGAGCAGGAAGAATGGGGAAACAAGGTGGAGAGATGGTCATTGT TGGGAATAGTGGGAAAATGAGGGGGAAGAGAATGACTATAAAATGGGAAGGGGGTC CAAGTTATCCAAGCAGTCCAGTTAGAGAAGGGAAAATAAAGCTATAGATAGAAACC AACCAAACAACCAAACAATTAAACAAACAATTAAACGAAC | SEQ ID NO: 39 |
| JL09_g867 | GGTTGTGCTTGATGCAAGAATCCGTCGTATGAAAAGAATAACAAAAACTTGCTGG ATAAAATGAATAATAGAAGACTCAACAACAGTGAACTTGAGAATCAGTTCAAGAGA ATCATTGCGCTCTGCATCAATACTGATCCTGAAAATATTGATGATAAACTACTTTC AAGTTTGCTTATGTCTGTAGAAAACGATCCTGATCCAGAAATCGGGCAAATCAGAA AAGTCCTTAAAATAGTGGGTGATCTAGATGGGGAACCTAAACAAGATCAACACATC TCAAACCCTGCATCTGTTTCTGCTTCCTCCCATACACCACTAGCCTCTGCATCCGT CGCCACAGGTTCTTCTTCGGCATCCAAATCCGCTTCTATAGCTAAGTAACCCCTGA TGTTCTATTTTTGTATACTTGAAAATAACAACCGTGTCTGAATTTACCGGAGCGGG CTATGCACATAAATTTGATTAGGTACAATGAGGGCGAATATCTTCGCAAAGGTTCT TATCACGCAGCCACTCTCATTTTTCCCCGCTATCAATACATTCTTTTCTTGTCCTA TTCCTCTGTCCCCGTGATCCTACAACACAACTAAACAAAA | SEQ ID NO: 40 |
| JL09_g73 | ACACCTTTAAAAGAGTTGCATCATCCAAGTGTTGTAAGATGCTTGTCCAGCTACTG TAGTTAATCAGCTCAAGTTTCAGAACAGTTTCAGAGCCTATCTTCATGACATCACT CATCTGTGCTTAACCTTACAAACATCGGCAATCGGAGATTGATCATGAGCACATTA TTTGAGCTGTTGCTTTATTAGGCATCATATTCCCGATAAATCCAATCGGGCTTTGA ATGATGACTATACTATCGAGCCATACCTTCTTAAATCAACTATATATAACTGGTAA TACTTCTGTCTGATAGCTATCAATATCTGAGTGGGGTTTTTAACTTCCTTTTCCCT TCCACATCCGCAATCAAGAACAGATAAA | SEQ ID NO: 41 |
| JL09_g2815 | GCACTAGATGGTCCATTTTGTAACGCATGTGTAAACCGATAGAGGACAACTTTTCG ACCGATAAGAGACGTTTAAAAAAAAAATGAGACTGGGGAATTCTGAAGGGTGGG GTGTCTAAGTTTAAATTCTAGGTGTAAACTGAACAGTGTAAAGTCTTCTACTATAA TTGTATAGCTTTCAGCTCGAAGGTGAAGACAGTGTGGTGTGCTCTGTACTTTGTTG ATGGGAATCGGGTATA | SEQ ID NO: 42 |
| JL09_g4565 | TATGTGTATAACTGGACGAACCATAAAAGGGCAAATGCTGTTTGGAAACAGCCTGC AAAGCAAAAAATTTACACTTATAAATGCTCACTCTTGATTAAAAAAACTAGATAAT AAAGCGTTTTGTTTACATATTAATTTATTTTTCTTATTCTTCCCACTAAAGCTAGC ACATGTGAGTAAAAAATAAATTTTAAAAAGTATTTTCACAGAATGAGAATACTTTT TGATATTTAACACCAAAAGTTACATAGCACTGATTTCCGATATAGTGTAACGGCTA TCACGGTCCGCTTTCACCGGGCAGACCCGGGTTCGACTCCCGGTATCGGAATATTT TTTTACTTTTCCTCTTGATTGTTGTCACGTGTTATACACTAGGGCTAGTAGTAACC CTAATTACTGTCTTCGGAACTTGCGCGTTTTTTTGTTCTCCTTGGTCTGGCATCAA TCCCCTCTCTGTAGCTGAATATTTTTCCATGTATTTTAGATAAGTGTAAATTATTA AGACGATAAATTTTTCTGTTTACTTTCACTTCTTTCCTTTCATTTGGCACTCAAAA GTTAGGTAAGAAAGAAGCATTTTTTGCAGACGATCCTAAG | SEQ ID NO: 43 |
| JL09_g1368 | CAATAAGGATTTATGTCCAGGAGGAGAAAAAGAATTAGCAAACGTGTCTGATTTA CCAATTATAGCAGGGGAAACAACAAATAACGAAGAATAAAGCTTTAATAAGAACTT ATAACTATGCAATTAAGAGAAGCACTGGGAAAGAACTGCCCTTTTTCTAATTTGGA AAGGAAAATAAGGGGAGGAAAAGCAAGCGTGGAAGCACCAGTATTTGATCTCTTCA TCGAGCAAGTAACCCTTTGCAAGATTTGAGGGAAATGGAGAACTCAAGTGTTTAATT AAGGCGTCAATTTCTTCCGAAAGAAGCAATCCTTCCTAATTAGGAAATGACGCGAA AGACGTCTTGCAAAGGAAGGCGTACGGTGGAGGAGTTTTGGAAGAGGAAGGTGTGC AGTGGGGGATCGTTCGGCATTATTAATCACATCATTTCCACGGAAAAAATCACTCA TCACGGCTCAGCTGTAACCGAAAGTTGATTTGTAAGCAAGGGACCCCTAGAGAAGA CTATAAATAGTCAGGACACCCCTATTTCAGGGTTCTTGTACTTTTTAGTTAGGGT GACCATTACGATACATAGACAACAAGATATACAGCAAGAA | SEQ ID NO: 44 |
| JL09_g4461 | TTGATAGTTCCAGTTGTTCCTGTCTTTACTCAAACTAACTTGACAATTAAGATCTC AAGAGCAGCTTCTTCAGCTATGTAAATATTACCCACTTTTACATACCAATATCGTC TTCTCCTCCCTTTAATAAAAGGGAGAAGTCTAAAGTGCAAAGTAACGTGTTCCCTA GCATATGCCACTCGCAAGTTTGTAAACCTAAACTACCTGAAAGTCTATTAAGCTGA AATTGAAAAGCAGAAAGAAACAGAGTTTTATTGTCCGCTCTTTACCACCCACCCT TATGCTTTGTTGTAACAATTTCAAAAATAGCTTCTTTTTTTTTGCGGAAAAAATAC GGGGAACCTGTCTATTTCGGCTATTTCATCATTGTGTGATTTTTAGTCAAACGGAA ACCACTTATAGGAGGTGAGTTTTCTATTTCATGGAGAAACTAGATTGTATTTAAAT | SEQ ID NO: 45 |

TABLE 10-continued

Promoter sequences

| Promot-er Gene_ID | Sequences | SEQ ID NO |
|---|---|---|
| | TCCTTGCTCTCTCTCTCCCTAAATTCCACTTTTCTCCGAATCAGCACATTCTTGAT TTTCCTTTTTTACTTTTTTCTTATTCTTTTACCATCCTTAGTCATAGTATCCCAAA TTACTTAAACTTAACTTGAATTTAGAAAATTATTCAAAAG | |
| JL09_g4288* | AATATGTTCTGAGCGGAAACCCCCGTGTTTTTATTATTTTCCAGTAGGAACGCCGT GTCTCCCCACAAGTTTGACAGCATGCTGTTTCTAATTGAACCTGTGTTTACTAATG GCTGCAGCAAGATAATGATGTATGTCCAACAAGAGATGTGCCTTTAATGGATGGTT GCTTGATGTCCATGAGGGCAATTTGTTTCCCTGGGTTCCCCCGTCAGGAGGTTTAC CACAAGGGCAAGACTCCAGAACTTGACCAATTGCAGGTACAATGCAATTTTTTTTC CGCTCTCGCCGTTCAGACATGCTCCATTTTTGCTGACTCGGACTAAGTATGTGTG AGGCCGCATTTTCCTGTTTTTCCAACATTGGGTGATTTTGTATAGTCGAACACAAG GGTTTTTCCATTGCATATATTAATCCCATAGCTGGAAAGACGGGTATTTAAACCTC CTAGTTTCCACCCTGGATATCTCTCAACAGACCTAAGTTCAACCTTTTTTTTTCCA AATTTCCTCTTCAACCACAAACAAATATACACTCACATATTCTAATACTATTTGTT TAAAAACAAAAGAAAGTACAAAAAAAAATTCACACAAAAG | SEQ ID NO: 46 |
| JL09_g1383 | TGGTTGCAGTAGAAAAGCTCTTTCAAGAGGTATAAACTAATGATCTCTCAATAGTG AAACGCCACCAGAAAATGTGCTCAGCTGGTTTGAGTTATGTCACTTGCGGTGACCA ACTACTATTTCTCTCACTTGGAACGAGGCGCGTCTGCAAAACATGTCGTGTCGCAG CAGGCTATTAGTTGTAGCACAAACACAACTGCCGTCTAAGTCGCGCCACAACAGAG GAGAATGATGCACCGAGTACGGATTTCCCCTTACGGATGAGTTTACTTCCGGCCAA TCGTGTGCGAGAAAATTGCAATTTTGTCGGCGCGGGCTTTTTTTCGTATGTGTTTG GGGGATTTATAGTTGTCAGCGGACCCACTTTGGAGAGGAACCACTTGGGAGACCTG TTTATCCAATTCTTTCTTCTGAATACCTGTTTGTCTCTTTCCTTGATTTCCCCTTT CTTCCTATTTTCTTTGATTTTCCTATAGACTAACAATCAAATAGAATATTCTAACA | SEQ ID NO: 47 |
| JL09_g1414 | ATGTAGGAGCAGTGCCTGAGAGAGGTGTCAAGGTAAACGTTATCGGTAGGAGCATG GCTGGAGTGGAAACGCGAGGAACGCCTTCTGGCTAGTCCCTCCCTATTTTTCCTCT CCCCCCCCCGCATTAAGAATCGAGATATTAGCTCCTCAGGATGTATCGGAAGAAGC GAGGCATACATTTGTGTGGAGGCTCGGGATCCGAATATGGCTATTCTGTTCAGTGA AAAGGGGGGGAGGGAAGATTTGCCTATTCTTGTTATAACCCGCACCAGTGGCGGT GAGTTTCCGTTCTCCCGTTGGAAAAAAAAAGAAAAGTGGTGTGCCGGATTAACTT GGTGGTCCGGGTAAACTTGCGCGTTTCTTTTTCCAAGACTGTACTGGAGTTTTTCC ATTTGCTTGCAGATGCGGAAAAATGGTGTGGACATGCTTCTCCTTCTTGTTGAAAA ATGTATTTAAGTCCCCACAAATCCCCCAACTTTCTCCACTTTTTTCACCTTCTGTC TTAGCTTCTCTTTTGATTTTAATTTTTATCTTCTTTCAGCATCCAAACACTTTAAA AAAATCACTTATAATATATATAGCATAGCACATTCAAGAG | SEQ ID NO: 48 |
| JL09_g3540 | GCGGGACAGGTACATACACCTGTAGAGGAGGCTAACGGTGACTTTAGATGTGGAAG TTTAATGTCTCTATGGCGTCTACGTGAATATTTCCAACGAGGAGCAGTATACTATA AAAGGACAAGTGTTTCTCCCACTGTTTGTAATGTGTTGGTGGTAGTTTTATCCCCC ATATATTTTCTACAAGACAAGACAACCCAATACCTTATACATTCACAACATATAAC A | SEQ ID NO: 49 |
| JL09_g2950 | CTAGACAGGGAGGATGAGACCACGGAAAAAAGAGCCGACAGGTCTCTGGATGCCGC TGAAAATCATACCTCGCATGAACACTTTAGCTACGAAAACGGTAATGGCTTAACAA AGGACTCATCCCTTCCCTCTAGATGGGCTTGAAGGCGTAGTACATTATATAAGCCT GTGTAGACAAACAAATACTTCTATGAGGTTACAACCCGAGTTCCGACTACTCAATT AGGAAACTATTTCTGTAACGTTGATTCATGTAGCTGTCTGTCAGCGCGCATGCCTA ATTGGGAAAAACACCATAATTCTCAATTTTCATTGGCCAGCCCTTTAATGTGGGTC GTTTTTCATACAATTTCGCCTTTCGCTTAGCATTAAAAAACTAAACTTCTACTCAC TGGACGTGGTGTGTATTTTGTTTCTGACAAGGTAGAGGTGTCGACAAACAAGAAGG TATGTATAAAGG | SEQ ID NO: 50 |
| JL09_g850 | TGATAAACTTTGGTTTCTTTCAAAACGTTAGGCAGTTCTTTTGCTAAAACCTTTCC AAGTGATGTTGGAACTATAGAATTTATTAATGTAGCCAAAGATATCAGTCGTAAAG CCCATTGCCTCATAAAATTTGATAAATATATAGACGGTAATGACAACAGCAAAGAA CCTATACATGTACGTTTGACAGCTCCTGGAAAATACATGTGATCAAATGAATCCAG ACTGTCTATCCCCAGGTTTATAAAGTCATGAATGGCTTGAACATTAAATGATTCCT CTACTTTGGTGTATGGAGCAACCAATAACATATACGTTATTGATGTAAACAATGTC AGATCCAACAAATGCTGTAGTGTGCTTGTTGTCATCAATCCTTGGATAACGAGATA TAGAGAAAGATTAACCATACGTTGAAACGAAGAAGGACGTAAGAGAAGAACGTAA GGAGTACACGCTATACTCGTGCCCTCACATTTTTCTAGTCCAACTAAATTTTATAT TTTGTTTGATCTTTTCATTGACCTTTTAGCTAGTCTTGCCTTCTCCTTTGCTTCT TTTTTGTGAGTATAGGAGCACACCAAAAGAACAGTAAGTG | SEQ ID NO: 51 |
| JL09_g426 | AAGGGTACGTATAGTTATAAGAGTGGATATAGTAATATGGCCTTAGTAATATGGCC TTAGTAGTGTTGGCCATGGTGTAAATTATGGTATTAACATTAGTACAAGTGGTGGC GAGAACAACAGCAATAGCAGGGGTATTACGACGTGGGTTGACAAAGCAATGCCTAA AGCGGAAAGAGGCAAGTTTGAGAGGAAAAAAGAGAGTCCTATTAATTTATACCATT ATTAACAAAACGCCTTCGACGGCATCGACGCGTCGCTGACGCATATTGTGCGCGGG CCACGTGTCAGCGACGCGTCGACGACGGGTTTAATTCCATTTAAGATTAATTTAT TCAAGCTATAGGAGAACAAAAGAAGCTTATTAAACACAAGAAAGGGGAGCGATTTC CCCCCATTTTATGTCTTCTCCCTCTCGACTCCAATTTCTGACAAATACAGAAAATC TAATCTCACTTATGCAGCGTGAGGTTTTAAATATGTAATGGAAGATTTGAAGCGTC | SEQ ID NO: 52 |

TABLE 10-continued

Promoter sequences

| Promoter Gene_ID | Sequences | SEQ ID NO |
|---|---|---|
| | AAGTGTCCACAGTGAGAATTTCGGGTTTCCATATAAAGTCGCCACCCCCCGCCCAT<br>TAATTGTAGAAATTAGCTGAACTTAACCAATGCAGTATTA | |
| JL09_g1530 | CGTCAAAGGAACTCAACACTGTCAACGGTATCACTAATGGGAAGTTTAATAATATC<br>TACTTTTATTTCCTTTAAATTTTTTTTGTTTCATCTTTTAATTAAACAACAGGACT<br>TTTAATAACAAACACTTACAGCAACTGCTTCTACAAACAAATCATTTACACTACTA<br>CTACGTTTTTGGAACCAAGAGAATTATCATATACTCCAGAAATGTCTGCTTAAATC<br>ATTTGTTTGATCAAGAATTATATTCATAAAATATTATAAATTAAGTTATCGTTTGT<br>TCCTACCCACGATTTTTTTCTAAACATTTGTTCACTATCGAATTAGAAAAAATACT<br>CACTTTAAAAGTCTATTTTTTATCAACCCCTTATTAAAAAAAGTCCTTCAATATGT<br>CCCCGTAAATTAAATACTATTAAGAAACCGACCATTATGGCGTTCCACTTTTACCC<br>CCCTCCTTTAACTTATTAATTCAAGAAAAAAAAATTAATTGTCACATATTAAAGTC<br>TATCTCTACTATCACTATTATCCACCCTTTATTACAATCTCATTAGAAATTATTAC<br>AACAGTCACTGCAACTAATAAATTAACCAAATTGTCTGAA | SEQ ID NO: 53 |

Example 9. Evaluation of Various Terminators Efficiency to Terminate Gene Transcription The corresponding putative terminators of the 16 above-identified strong promoters were selected for characterization (Table 11). Furthermore, the strength of these terminators at both transcriptional and translation levels was demonstrated. Out of the 16 targets, only 14 terminators were included, since the terminators of the pdc6 and tdh3 genes had been used previously for the expression of the succinic acid pathway. These terminators were amplified from either the intergenic sequences or the 300-bp sequences downstream of the target genes following a similar approach described previously, and then cloned between the two reporter genes, gfp, and mCherry (FIG. 18A). Notably, it was found that the 300 bp sequence of the TEF1 terminator also included the promoter region and therefore we also selected the first 150 bp of this terminator for further study (g2204t*).

As shown in FIG. 18A, the two reporter genes (gfp and mCherry) shared a single promoter (TDH3p, g247) and the terminator of the pgk1 gene was placed after the mCherry gene, whereas the target terminators were placed between the two reporter genes. The same design was used to discover new terminators. Additionally, 2 controls were included, one with no terminator sequence inserted between the reporter genes (Control 1) and the other where a random sequence of 300 bp that does not correspond to any promoter and terminator region inserted between the reporter genes (Control 2). In both the cases, the transcriptional ratio of mCherry and GFP was calculated to be approximately 0.64-0.62 (FIG. 18B). Interestingly, except for the terminator of the g73 gene that had a transcriptional ratio of 0.23, the rest of the terminators had a transcriptional ratio ranging from 0.03 to 0, and therefore were concluded to be strong terminators.

To further investigate the effect of the selected terminators on gene expression efficiency, their corresponding GFP fluorescence intensities were measured by flow cytometry, which have shown that changing the terminator has changed the expression level of GFP. Interestingly, terminators from strong promoters have shown similar fluorescence intensities (FIG. 18C). This clearly demonstrates that tuning of strong promoters along with the terminators plays an important role in the modulation of gene expression and can help in designing optimized metabolic pathways for production of chemicals and fuels.

TABLE 11

Terminator sequences

| Terminators | Sequences | SEQ ID NO |
|---|---|---|
| PFK1t | TATTCGAGAAGGTTTCTACTGACGTCTTGGATAATTCTTCTTTGACCTTCTATATTCTA<br>TCTTAATTTTTCCCTTGTTATTTATTTGTTGTCTCTTTCTTCTTTTACTGTCCTTTTCT<br>TTCTTTGCTGTCCTTTTGTTTCTTTTTTTTCCTTCCCTCTCAAAAAAGGAAACTGGGC<br>CTATTTTTTTTTTTTCTGACGTATGTTAAGATGCAATGTTATAATGAAATTTAAATTA<br>TTATTTATGTTAATGAAAAAAAAAACAGCAAAAACGTGTGACTATTTCTGCCTGCATGT<br>TATTATGTTATTGTAGAAGTAAATAGTACCTTCGATGGGAAATCAAACCAGTTTTCAAT<br>CCGTTTTCACCGAAAGAGCTCGAATTGTGCGTAATTTTGTGGTCTGTACGGCGATTATT<br>TGCAAATCGGGAATGGTGTGCGAAAACTAACAAAATTAATGTATGCTCTAAATATGTCC<br>CATCAGCTGGAAGGAGAACAATAGACGG | SEQ ID NO: 54 |
| MDH1t | AGGTGAAACACAACAACCTCCTTTTTAGCTTGAAAGAGACAAATTCTAAACAAAAAAA<br>CCGAATAAAAACACTGAACAAAACTGGAAAAAAAAAACATTAGACAAAGCTGCGCTGAA<br>TTGGCTCTAATACATTATGCTCTATCTTATATATAGTACATATGGACACGTTTTCCATT<br>TCACCCTTTACATATAAGTAAAGAGAGGATAACACCAATAAACTTACACCTTATTCAAT<br>CTTACGATTATTTTATATTTATTTAGCTATTTATTGATAACTTAAATATCTAACTACAT<br>ATTTATCTATTCATTTATTTCTTGATTCATTTATTGAAGCATTTACAAAATCACTTATA<br>CATTCTTTTGGCTCAAAAAGGTAAGCTACTTTAGATGCTCCTCTGAACAACTTTATAAC<br>CCTGTACG | SEQ ID NO: 55 |

TABLE 11-continued

Terminator sequences

| Terminators | Sequences | SEQ ID NO |
|---|---|---|
| PDC1t | TGACATCTGAATGTAAAATGAACATTAAAATGAATTACTAAACTTTACGTCTACTTTAC<br>AATCTATAAACTTTGTTTAATCATATAACGAAATACACTAATACACAATCCTGTACGTA<br>TGTAATACTTTTATCCATCAAGGATTGAGAAAAAAAAGTAATGATTCCCTGGGCCATTA<br>AAACTTAGACCCCCAAGCTTGGATAGGTCACTCTCTATTTTCGTTTCTCCCTTCCCTGA<br>TAGAAGGGTGATATGTAATTAAGAATAATATATAATTTTATAATAAAAAGTTTAAAC | SEQ ID NO: 56 |
| 853t | ATACTTAAATGATTAGACGAATAAACTACTCTATATAACGTTTTATAATGTTAATGTTC<br>ATGCTTTGATAGTCTCTCCCGGAGAATGTACTCTGCGCTTCATAGTTCTCTTGATTTTG<br>CTCCGTATAAGGTGCACAGGTTTAGACCTTTTTTTTTTTCAGAGGTACTTGCATGAAAA<br>CCTAGAGTGAATATTTCTTGTAGTGGATCTGTCACAATCTAAATCCCCTCGTAGTACTC<br>CTCAAACAACAGCAGGAGCTCTCCGAAGGATTAATAATTTGTCGTATCCATTTTGGTCA<br>TCTAC | SEQ ID NO: 57 |
| 3540t | GCGGGACAGGTACATACACCTGTAGAGGAGGCTAACGGTGACTTTAGATGTGGAAGTTT<br>AATGTCTCTATGGCGTCTACGTGAATATTTCCAACGAGGAGCAGTATACTATAAAAGGA<br>CAAGTGTTTCTCCCACTGTTTGTAATGTGTTGGTGGTAGTTTTATCCCCCATATATTTT<br>CTACAAGACAAGCAACCCAATACCTTATACATTCACAACATATAACA | SEQ ID NO: 58 |
| 3376t | CTACAACAAGATGTTTGTTCAAGGGGAGCAACTTGTCCCTCGTTAAATAATTTGTAAGA<br>AAAACTTCTTCCTTTTATCTCTTTCTTTTTTTCTTTTTAAAAAACTATCTAGTAAGGA<br>AATATACACAATTTACTTTGTACGCTGTCTCTCTTTCTCTTTCTCTCTATGTCTATC<br>TCTCCCTATCGCTCTGTATGTATGTACATTACCGTCTTCCCAAATGGCTCAACCCGAC<br>TGCGAGAAGACTTCAAAACACTCAATTATGGTCTTTAGATTTTCCAGTACGTTGTTGAC<br>AGATA | SEQ ID NO: 59 |
| 5025t | GTGGATTAGGTTACTGCTCTTTCTTTTGGTAATTTATAATTTAAACAAGTTTATTTAAT<br>TTGAAACTCTTATTTACTTAGATTAGATTTTAAACTTACATACTTTTAATAACTCTGGG<br>ATATCCTATTTAATATAACTAATAGCTAATTTGTTCTTTTTCAGTTGAATCTTTTGGCG<br>ATTCTCTCTCTCCCTTTCCTGTTCTTTACCATCTTTACCGTAAAGTATTGGAATAAAGT<br>AATGTTTGCAATTAGGGAGGTCCATAAAAATATCGACCCGTCGCCTTTTCCTTTATTCT<br>TACCC | SEQ ID NO: 60 |
| 527t | ATGTCTAACGTCTAGCATGTGGCGTCTAACGTCAGTCTGTTATAGTTGAATGATTATT<br>TACTTGTATACTTTAGCTTAAAGTAATGATGAAATGTTTTTTTTGTCTTGTCCTTTTT<br>GGCCGTGACTTTCCAGTTTCAACGGTTTTAGAGTTTCCAATCAAGATGTTCATGAGGTG<br>GTGAACACTGTGTTGGTGACTCCGGGGTGTAAAAGAAAGTTCTTTTGGAGGGGAATTGC<br>TTATGTCTGTGATTCCCAATCACTCATTATACTATA | SEQ ID NO: 61 |
| 2204t (Tef1at) | GTATAGCCATATAGTTTAATTCCTTTATACTTTTTATAACTATTTCTTACACTAATTAT<br>TATTATCAATTATTTATTGTAGAATTTGACTCTTGCGTCGATCACCATGACAGGGCTAT<br>CTTAACAAGGGGTAATTTTTGTTGATGGAGTCAAGTAGCATTCCGACGGGAAGTGTCGA<br>TGCCTCTGAACGAAATCTTCCGATTAGCTCTGCAAAGAAGTGGAAATTGTCAGCGCATT<br>ATTATAATTGCAAGTTGGAGAGATAGCGATTAAGCTTTTGACTTCTACTCATATACAAA<br>CTTTT | SEQ ID NO: 62 |
| s2204t* | GTATAGCCATATAGTTTAATTCCTTTATACTTTTTATAACTATTTCTTACACTAATTAT<br>TATTATCAATTATTTATTGTAGAATTTGACTCTTGCGTCGATCACCATGACAGGGCTAT<br>CTTAACAAGGGGTAATTTTTGTTGATGGAGTC | SEQ ID NO: 63 |
| 1414t | AATAAATGAAACTTTACTAAACTAATGACCAATCTATATATCCTTTATGAATTTAATTT<br>TATGTAATGACTAGAACAATATTATTTTTTGTGTACGAATGATTAACTAGAATTTGCA<br>ATAGATACGACTTCAAAATTGAACAATACGATTTATCGCTTAGCTATGCTTTTATTGAG<br>AAATC | SEQ ID NO: 64 |
| 4288t | ATCACTTTCTGTCAATTGTCTTAATTATTTTAATATGGTATTTTTATTTGAAATACTAA<br>AGCACATTTTCCTTTCCACATTTAATTTCTTAATGAACTTTATTTCTTTATGATTTCTA<br>GATCTATACTTCTATTTGTCAACTAACTAGATTAATTTTAACACTTACATTTCTTTTTT<br>AAAACTATGAATCATAACATGCTTGATAGCTCTTATTTGTTTTTTTTTACAGATCAAAA<br>AACACCTTTTGTAGAAGTAATTGGTCTGGTTTGTATGTGACATTAATACTATTTTCTTT<br>GGAAG | SEQ ID NO: 65 |
| 3767t | ATTCTGAGGCGAACTATAGAATGAATAACGAATGGTATACTGTGGCTATCTTCCACCTT<br>ACCTCTATTTTTTTTTGGAAAAACATCTAAAGAATCCCATTTTTATACTGTGTAGTTA<br>ATTGAATTCTTAAGTTTC | SEQ ID NO: 66 |
| 5125t | TAATTCAAAGTGTCCCTCATTCTTCTTAATGTCTAACGTCTATACTTTTGTACTGTACA<br>ATGAAAATAAATGATTATCCATCCGTCCATTATTTTACTGTTTTTTTATATATAGATC<br>TATATGTTACACTGCACAGAAACAT | SEQ ID NO: 67 |
| 73t | ATGTCCTATTCCTATTTTTCTTTCTATACATGCTTCAGATACTTCTCCGTTTATCATAT<br>TTATACTAGCGCTTTTCATTC | SEQ ID NO: 68 |
| 4282t | AGGTATAGTCTCATCTACTGACAATTACCTGTGTATAGTAACATTTAATATTTAACGAT<br>TAATACTTTATGAACAGTGCCAGAACTATACTAATTAACGATTTTCTGATGAGAATTAC | SEQ ID NO: 69 |

TABLE 11-continued

Terminator sequences

| Terminators | Sequences | SEQ ID NO |
|---|---|---|
| | AAGGTATGACTCATTTGGTGTTATATTTTATAATGGAGTAAGCAGTACATTTTCCTCCG<br>GTAAACGGCTGTCCTTATTTAATCATACGCTTAAATATGAGGGCATAATATGGTGTCTA<br>ATCCCATTTCTAGAAATAGTATGCTTTCCAATTAGGCTGGACTTTGTTATCGAACTGCG<br>GTCAT | |
| 697t | AGGTATAGTCTCATCTACTGACAATTACCTGTGTATAGTAACATTTAATATTTAACGAT<br>TAATACTTTATGAACAGTGCCAGAACTATACTAATTAACGATTTTCTGATGAGAATTAC<br>AAGGTATGACTCATTTGGTGTTATATTTTATAATGGAGTAAGCAGTACATTTTCCTCCG<br>GTAAACGGCTGTCCTTATTTAATCATACGCTTAAATATGAGGGCATAATATGGTGTCTA<br>ATCCCATTTCTAGAAATAGTATGCTTTCCAATTAGGCTGGACTTTGTTATCGAACTGCG<br>GTCAT | SEQ ID NO: 70 |
| 4194t | TTTGAATCAACTTTTCCCCTAAGGTTTAATACATGCCCATGATTTTTAACGACTTTTAT<br>TATAAATAACGACTTTATAGCTTTATGATTACTAAATTATTACTACTACGACAATATTC<br>AGGGTATGCATAATAACATTAATTTTAAAACATGAGGCATTCCTTGAATTTATGCCTTT<br>ACAAGTATCAACAATAGCTTAAAAAAGCTTTTTTCGCATCATGCCGAGCCTCCTAAAAT<br>TAGATACCGCGCTGCCCTTAGGGAAAAAAAAACCCCAAAACTCCTCTTGTTGGGAGGGC<br>CGTCA | SEQ ID NO: 71 |
| Random sequence | AACTGTTTCACCCTCTGTGAAGCATAAACACTAGAAAGCCAATGAAGAGCTCTACAAGC<br>CTCATATGGGTTCAATGGGTCTGCAATGACCGCATACGGGCTTGGACAATTACCTTCTA<br>TTGAATTTCTGAGAAGAGATACATCTGACCAGCAATGTAAGCAGACAATCCCAATTCTG<br>TAAACAACCTCTTTGTCCATAATTCCCCATCAGAAGAGTGAAAAATGCCCTCAAAATGC<br>ATGCGCCACACCCACCTCTCAACTGCACTGCGCCACATCTGAGGGTCCTTTCAGGGGTC<br>GACTA | SEQ ID NO: 72 |

Example 10. Method for DNA Assembly in *I. Orientalis*

Figure 19:
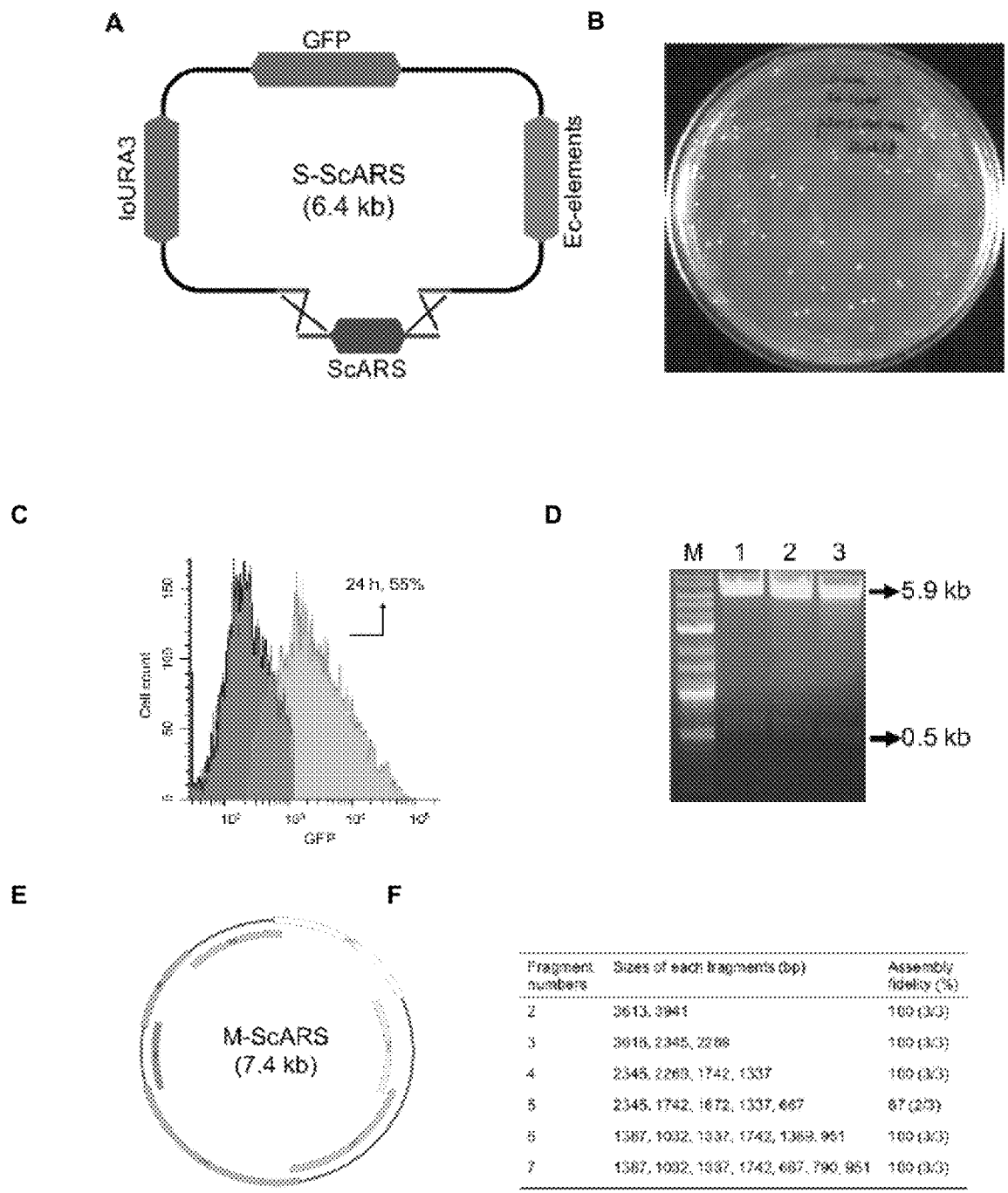
FIG. 19 panel A discloses a shortened ScARS plasmid (S-ScARS) assembled by 6 kb backbone and 0.4 kb ScARS. Panel B discloses heat-shock transformation of two fragments with 50 ng amount for each on SC-URA solid medium. Panel C discloses GFP expression profiles of randomly picked colony containing S-SCARS at 24 h. Panel D discloses the restriction digestion analysis of randomly picked colonies by PpuMI and KpnI. M represents 1 kb plus DNA ladder. Panel E discloses the modified ScARS plasmid (M-ScARS) used for in vivo assembly of various numbers of fragments, picturing only fragment number 7. Panel F discloses the various numbers of fragments, their sizes, and assembly fidelity. Panel G discloses restriction digestion analysis of assembled plasmids from different fragments by HindIII and XhoI, showing 3013 bp, 2014 bp, 860 bp, 860 bp, and 675 bp bands. Three colonies were picked for each assembly test.

Rapid plasmid construction is regarded critical in metabolic engineering, especially for large biochemical pathway assembly in one-step fashion. Since *I. orientalis* employs the homologous recombination mechanism for double-stranded DNA repair, an in vivo DNA assembly method in *I. orientalis* for fast and reliable pathway construction was developed. The usage of the helper elements corresponding to *S. cerevisiae*, which would save at least 3 days in generating a construct was skipped. As proof of concept, the assembly of a shortened version of the ScARS plasmid (S-ScARS, 6.4 kb) containing loURA3, ScARS and GFP cassettes, by co-transforming the linearized ScARS plasmid backbone (digested by PpuMI+ApaI, ~6 kb) lacking ScARS and the amplified 0.4 kb ScARS with 40 bp overlaps at two sides into *I. orientalis* was performed (FIG. 19A). As shown in FIG. 19B, only the successfully assembled plasmid containing ScARS could grow on SC-URA plate, and three randomly picked colonies were chosen for GFP fluorescence analysis by flow cytometry and plasmid digestion by PpuMI+KpnI. The results showed that the GFP expression profile from S-ScARS was the same as that from the ScARS plasmid, with ~55% cells expressing GFP at 24 h (FIG. 19C), and two bands (5.9 kb, 0.5 kb) were observed on the agarose DNA gel for the digested S-ScARS plasmid (FIG. 19D), indicating 100% assembly fidelity for two-fragment assembly.

In vivo assembly of a modified plasmid ScARS (M-ScARS, Sed1 promoter for GFP expression, ~7.4 kb, FIG. 11C) was then performed using multiple fragments. 2~7 fragments (2F~7F) were PCR-amplified from the previously constructed M-ScARS backbone (FIG. 19E-F) and cotransformed to *I. orientalis*. Plasmid digestion showed that all of the three randomly picked colonies from the 2, 3, 4, 6 and 7-fragment assembly groups were correctly assembled (3/3, 100%), while 5-fragment (5F) assembly showed 67% efficiency (2/3) (FIG. 19G). Notably, 12-fragment assembly of M-ScARS was also successful with 100% fidelity (3/3), providing the foundation for assembling large biochemical pathways in *I. orientalis*.

Figure 21:
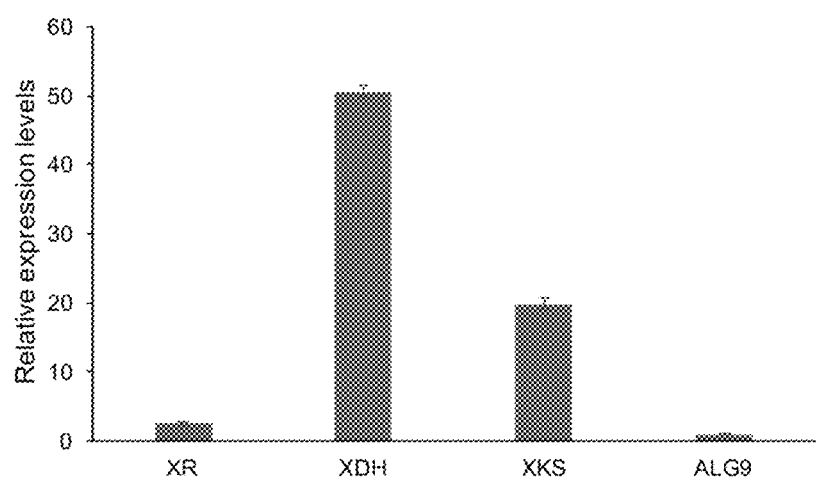
FIG. 21 discloses qPCR analysis of XR, XDH, and XKS expressions. ALG9 was used as the reference gene. Error bars represent standard deviations of biological duplicates.

The in vivo assembly and the aforementioned tools were extended to a longer pathway, the xylose utilization pathway. This pathway included three genes, XR, XDH, and XKS, which encode for xylose reductase, xylitol dehydrogenase, and xylulokinase, respectively. First, three helper plasmids by assembling the ScARS/CEN-L backbone (digested by ApaI and NotI) with the URA3 expression cassette, XR, XDH, and XKS genes were constructed, and the constitutive promoters and terminators characterized above (FIG. 20A). After obtaining the helper plasmids, the plasmid containing the xylose utilization pathway (ScARS/CEN-L-Xylose, FIG. 11D) were then constructed by assembling the backbone, the URA3 cassette, and the three individual gene expression cassettes, TDH3p-XR-MDH1t, HSP12p-XDH-PDC1t, and INO1p-XKS-PFK1t. For in vivo assembly, 100 ng of each fragment, with 70-80 overlaps (40 bp overlap with backbone) were co-transformed to *I. orientalis* and the resultant plasmids were confirmed by restriction digestion and DNA sequencing. As shown in FIG. 20B, the correct clones of XR helper plasmid exhibited three bands with sizes of 6127, 2561 and 1217, while XDH helper plasmid exhibited four bands with sizes of 4044, 2561, 1861 and 1217; XKS helper plasmid, exhibited three bands with sizes of 7224, 2561 and 1217; and the combined XR-XDH-XKS xylose pathway plasmid (ScARS/CEN-L-Xylose) exhibited four bands with sizes of 7016, 3736, 2561 and 1217. The results showed 100% fidelity was achieved for the assembly of the 6.5 kb xylose utilization pathway with an 8 kb plasmid backbone. The function of the assembled xylose utilization pathway was analyzed by growing the recombinant *I. orientalis* strain containing xylose utilization pathway in SC-URA medium supplemented with xylose instead of glucose. The recombinant *I. orientalis* strain carrying the whole xylose utilization pathway grew faster than the control strain containing the ScARS/CEN-L plasmid in xylose medium (FIG. 20C), and the residual xylose at 144 h were 16.1 g/L and 17.6 g/L in the media of engineered and control strains (FIG. 20D), respectively, indicating that the assembled xylose utilization pathway was successfully expressed. (FIG. 21). qPCT was used to verify the expression levels of the three pathway genes, and the results showed that XR was poorly expressed while XDH and XKS were expressed. This could explain the slow growth rate of the recombinant *I. orientalis* strain.

Pathway engineering is an important strategy for producing value-added bioproducts with high yield and productivity especially for long biosynthetic pathways. HR-based DNA assembler has been proved to be efficient for assembling large biochemical pathways in *S. cerevisiae*. However, limited attempts were reported to apply HR-based assembly in other yeast hosts for rapid pathway engineering, even though some yeast species exhibit much more attractive capacities, such as the high acid tolerant *I. orientalis*. Here, in vivo DNA assembly was performed in *I. orientalis*, and very high fidelity was achieved when a 14.5 kb-plasmid carrying a xylose utilization pathway from 5 fragments of different sizes was assembled. Although the pathway did not function well (the strain grew slowly), which may be due to the codon bias or the imbalance of the promoter/terminator strengths, it still demonstrated that the DNA assembly could be adopted for efficient construction of biochemical pathways in *I. orientalis*.

Example 11. Materials and Methods

All the materials and methods used in Examples 7-10 are provided herein.

Strains, Media, and Chemicals.

All strains used in Examples 7-10 are listed in Table 12. *E. coli* DH5a was used to maintain and amplify plasmids. *I. orientalis* SD108 and *S. cerevisiae* YSG50 were propagated in YPAD medium consisting of 1% yeast extract, 2% peptone, 0.01% adenine hemisulphate, and 2% glucose. Recombinant *I. orientalis* strains were grown in Synthetic Complete (SC) dropout medium lacking uracil (SC-URA). LB broth, bacteriological grade agar, yeast extract, peptone, yeast nitrogen base (w/o amino acid and ammonium sulfate), ammonium sulfate, and D-xylose were obtained from Difco (BD, Sparks, MD), while complete synthetic medium was purchased from MP Biomedicals (Solon, OH). All restriction endonucleases, Q5 DNA polymerase and Phusion polymerase were purchased from New England Biolabs (Ipswich, MA). cDNA synthesis kit and SYBR Green PCR master mix were purchased from Bio-Rad (Hercules, CA). The QIAprep spin mini-prep kit and RNA isolation mini kit were purchased from Qiagen (Valencia, CA), whereas Zymoclean Gel DNA Recovery Kit and Zymoprep Yeast Plasmid Miniprep Kits were purchased from Zymo Research (Irvine, CA). All other chemicals and consumables were purchased from Sigma (St. Louis, MO), VWR (Radnor, PA), and Fisher Scientific (Pittsburgh, PA). Oligonucleotides including gBlocks and primers were all synthesized by Integrated DNA Technologies (IDT, Coralville, IA). DNA sequencing was performed by ACGT, Inc. (Wheeling, IL).

TABLE 12

Strains and plasmids used in this study

| Strains/Plasmids | Features | Sources |
|---|---|---|
| Strains | | |
| *E. coli* DH5α | Cloning host | NEB |
| *I. orientalis* SD108 | ura3Δ, host for plasmids in this study | (Xiao et al., 2014) |
| *S. cerevisiae* YSG50 | ade2-1, ade3Δ22, ura3-1, his3-11, 15, trp1-1, leu2-3, 112, can 1-100, used for plasmid assembly | (Shao et al., 2009) |
| Plasmids | | |
| pScARS | Also reported as plo-UG, derived from pRS415, containing *E. coli* elements, ScARS, ScLEU2, IoURA3 and GFP cassette | Present disclosure |
| pVT15b-epi | CRISPR/Cas9 plasmid, containing ScARS, IoURA3, iCas9, RPR1 promoter, and sgRNA scaffold. Used for PCR of iCas9 and sgRNA cassettes | Present disclosure |
| pScARS/CEN-0.8 kb | Derived from pScARS by integrating the conserved 0.8 kb sequence from predicted CEN1~5 | Present disclosure |
| pScARS/CEN-L | Also mentioned as pScARS-CEN-0.8 kb-2, the screened centromere-like sequence with improved pScARS stability | Present disclosure |
| pScARS-Cas9-ade2 | Derived from pScARS by changing GFP cassette to Cas9 cassette, also containing sgRNA targeting ade2 | Present disclosure |
| pScARS/CEN-L-Cas9-ade2 | Derived from pScARS/CEN-L by changing GFP cassette to Cas9 cassette, also containing sgRNA targeting ade2 | Present disclosure |
| pUG6-TDH3-Lm.ldhA-CYC1 | Used for amplifying ldhD gene | (Baek et al., 2017) |
| pScARS-LDH | Derived from pScARS by changing GFP cassette to LDH cassette | Present disclosure |

TABLE 12-continued

Strains and plasmids used in this study

| Strains/Plasmids | Features | Sources |
| --- | --- | --- |
| pScARS/CEN-L-LDH | Derived from pScARS/CEN-L by changing GFP cassette to LDH cassette | Present disclosure |
| pS-ScARS | The shortened version of pScARS by removing ScLeu2 element | Present disclosure |
| pM-ScARS | The modified version of pScARS by replacing GFP promoter from TDH3p to SED1p_g5025 | Present disclosure |
| pRS416Xyl-Zea_A_EVA | Used for amplifying xylose utilization pathway genes, XR, XDH, and XKS | (Shao et al., 2009) |
| pScARS/CEN-L-Xylose | Derived from pScARS/CEN-L, containing xylose utilization pathway genes, XR, XDH, and XKS | Present disclosure |
| Plasmid-64324 | pU6-(BbsI) CBh-Cas9-T2A-mCherry, for mCherry amplification | Addgene |
| p247_GFP | Modified version of pScARS by replacing GFP promoter with g247 (TDH3) promoter | Present disclosure |
| pX_GFP | Modified version of pScARS by replacing GFP promoter with X promoter, and X represents g853 (GPM1), g917, g3540, g3376, g5025, g527, g2204, g1414, g4288, g3767, g5125, g73, g4282, g697, g4194, and other tested promoters | Present disclosure |
| p247_mCherry | The modified version of p247_GFP by replacing GFP with mCherry gene and ENO2t terminator with PGK1t | Present disclosure |
| p247_GFP_mCherry | The modified version of p247_GFP, where mCherry added after ENO2t terminator, and PGK1t after mCherry | Present disclosure |
| pControl1 | The modified version of p247_GFP_mCherry where mCherry are cloned in continuity of GFP, removed ENO2t terminator | Present disclosure |
| pControl2 | The modified version of p247_GFP_mCherry, where ENO2t terminator sequence were replaced by random 300 bp sequence | Present disclosure |
| pZF_ter | The modified version of p247_GFP_mCherry, where ENO2t terminator sequence were replaced by different putative terminator sequence | Present disclosure |

TABLE 13

Genetic elements/DNA sequences

| Genetic elements/ DNA | Sequences | SEQ ID NO |
| --- | --- | --- |
| ScARS | GATCGCCAACAAATACTACCTTTTATCTTGCTCTTCCTGCTCTCAGGTATTAATGCCG AATTGTTTCATCTTGTCTGTGTAGAAGACCCACACACGAAAATCCTGTGATTTTACATT TTACTTATCGTTAATCGAATGTATATCTATTTAATCTGCTTTTCTTGTCTAATAAATA TATATGTAAAGTACGCTTTTTGTTGAAATTTTTAAACCTTTGTTTATTTTTTTTTCT TCATTCCGTAACTCTTCTACCTTCTTTATTTACTTTCTAAAATCCAAATACAAAACAT AAAAATAAATAAACACAGAGTAAATTCCCAAATTATTCCATCATTAAAAGATACGAGG CGCGTGTAAGTTACAGGCAAGCGATC | SEQ ID NO: 73 |
| CEN-0.8kb-2 (CEN-L) | TCTAGCTATTTTGTTTAGGTTGGGTAAAAACCTACGGAAAGACAATTGGAGCTTAGGC TATCTATTGATAGATCAATTATTTGTTTTAAGAACTATAGAATTAAAAACAAGGCAGT AGTTGTAGATTTTAAAGATTATTTAGAGTAGATAGTAAAGGCTGTACTGAATATCAAT GAGGATTTGCAGAACCAACAAGTGGCCTGCATCAAGCTATTTAAGTGATTCTATTGGT ATTTTACTAGAAAAGGAAGGCTAATCATTTTTCCAATGACGGTTCATATAATCCAAGT TTTAAATGGTTTGCATCATCATAATAGGGGTATCTAAAAGGCATAAATCGACGAAAGT GATAAAAATTACTTATTAAACGACGTATTTACATCCACGTTTTTGCTGGAAGTACTGA ATCTGCCTACTGCTAGTTTGGGGAAGACAATAATACACAAAATAAAGACGATGATGAA GATTCCAGTTTTTTTTAAAGATAAAAAAATAGATATATATGTATAATTGTATGAATAG TTTTAATAATAACTTATGTTGCTATTTTGATAGCAATTCATTTTACTATTGAAAAGGT TACCCAGGCAAATAATATGTTTAGCACATCAGATTCTGTACTAATAATAATATAGAGT TATGTTATAACGTCAGGCAATACTTATGTGTATAGCGAAATAGTAAATGGCAGATTGT AAACCGTATGTTTTCACTACTCAGACTCATACGATATGTCTAGAAGCCCAACCAATGA ATTAGAGGACTGTTTGATATCAACATCCAGTCACTTTGAGTGTAATAAAACTATTTA | SEQ ID NO: 74 |
| ade2-gblock | CTTTGGTCTCCTGCAGAATTCGCAGTTGCAGACTCTGTTAGCGTTGAAAGCACCGAGA CAGCATTGCAAATGAAATTTGGTTTCCCATTTATGCTGAAGTCCAAAACTGAAGCAT ATGATGAGACAGCATTGCAAAATGTGTTTGGAGACCTTTC (UNDERLINED IS N20 FOR ADE2 KNOCKOUT) | SEQ ID NO: 75 |

TABLE 13-continued

Genetic elements/DNA sequences

| Genetic elements/ DNA | Sequences | SEQ ID NO |
|---|---|---|
| ldhD | ATGAAGATTTTTGCTTACGGCATTCGTGATGATGAAAAGCCATCACTTGAAGAATGGA AAGCGGCTAACCCAGAGATTGAAGTGGACTACACAAGAGCTATTGACACCTGAAAC AGTTAAGTTGGCTGAGGGATCAGATTCAGCTGTTGTTTACCAACAACTGGACTATACA CGTGAAACATTGACAGCTTTAGCTAACGTTGGTGTTACTAACTTGTCATTGCGTAACG TTGGTACAGATAACATTGATTTTGATGCAGCACGTGAATTTAACTTTAACATTTCAAA TGTTCCTGTTTATTCACCAAATGCTATTGCAGAACACTCAATGATTCAATTATCTCGT TTGCTACGTCGCACGAAAGCATTGGATGCCAAAATTGCTAAGCACGACTTGCGCTGGG CACCAACAATTGGACGTGAAATGCGTATGCAAACAGTTGGTGTATTGGTACAGGCCA TATTGGCCGTGTTGCTATTAACATTTTGAAAGGCTTTGGGGCAAAGGTTATTGCTTAT GATAAGTACCCAAATGCTGAATTGCAAGCAGAAGGTTTGTACGTTGACACATTAGACG AATTATATGCACAAGCTGATGCAATTTCATTGTATGTTCCTGGTGTGCCTGAAAACCA TCATCTAATCAATGCAGAGGCTATTGCTAAGATGAAGGATGGCGTGGTTATCATGAAT GCTGCGCGTGGTAATTTGATGGACATTGATGCTATTATTGATGGTTTGAATTCTGGTA AGATTTCAGACTTCGGTATGGACGTTTATGAAAATGAAGTTGGCTTGTTCAATGAAGA TTGGTCTGGTAAAGAATTCCCAGATGCTAAGATTGCTGACTTGATTTCACGCGAAAAT GTATTGGTTACGCCACATACCGGCTTTCTATACAACTAAAGCTGTTCTAGAAATGGTTC ACCAATCATTTGATGCAGCAGTTGCTTTCGCCAAAGGTGAGAAGCCAGCTATTGCTGT TGAATATTAA | SEQ ID NO: 76 |
| XR | ATGGTTCCTGCTATCAAGCTCAACTCCGGCTTCGACATGCCCCAGGTCGGCTTCGGCC TCTGGAAGGTCGACGGCTCCATCGCTTCCGATGTCGTCTACAACGCTATCAAGGCAGG CTACCGCCTCTTCGATGGTGCCTGCGACTACGGCAACGAGGTTGAGTGCGGCCAGGGT GTAGCCCGCGCCATCAAGGAGGGCATCGTCAAGCGCGAGGAGCTCTTCATCGTCTCCA AGCTCTGGAACACCTTCCACGACGGCGACCGCTCGAGCCCATCGTCCGCAAGCAGCT TGCCGACTGGGGTCTCGAGTACTTCGATCTCTACCTGATCCACTTCCCCGTCGCCCTC GAGTACGTCGACCCCTCGGTCCGCTACCCTCCCGGCTGGCACTTTGATGGCAAGAGCG AGATCCGCCCCTCAAAGGCCACCATCCAAGAGACCTGGACGGCCATGGAGTCGCTCGT CGAGAAGGGTCTCTCCAAGAGCATTGGCGTCTCCAACTTCCAGGCCCAGCTCCTGTAC GACCTCCTGCGCTACGCCAAGGTCCGCCCCGCCACTCTCCAGATCGAGCACCACCCCT ACCTCGTCCAGCAGAACCTCCTCAACCTTGCCAAGGCTGAGGGCATCGCCGTGACCGC CTACTCCTCCTTCGGCCCTGCTTCTTTCCGCGAGTTCAACATGGAGCACGCCCAGAAG CTCCAGCCTCTCCTCGAGGACCCCACCATCAAGGCTATTGGTGACAAGTACAACAAGG ATCCTGCCCAGGTCCTCCTCCGTTGGGCCACCCAGCGCGGCCTGGCCATCATCCCCAA GTCTAGCCGCGAGGCCACCATGAAGTCCAACCTCAACTCTCTTGATTTCGATCTCTCC GAGGAGGACATCAAGACCATCTCTGGTTTCGACCGCGGCATCCGCTTCAACCAGCCCA CCAACTACTTCTCCGCTGAGAACCTCTGGATTTTCGGTTAG | SEQ ID NO: 77 |
| XDH | ATGGCTACCGACGGCAAGTCTAACCTCTCCTTCGTCCTTAACAAGCCCCTCGACGTCT GCTTCCAGGACAAGCCCGTCCCCAAGATCAACTCCCCCCATGACGTACTCGTCGCCGT CAACTACACCGGCATCTGCGGCTCCGATGTCCACTACTGGCTCCATGGCGCTATCGGC CACTTTGTTGTGAAGGACCCCATGGTTCTCGGCCACGAGTCCGCCGGTACTATTGTTG CCGTCGGCGATGCCGTCAAGACTCTTTCCGTCGGCGACCGTGTCGCCCTCGAGCCCGG CTACCCCTGCCGCCGCTGCGTCCACTGCCTTTCCGGCCACTACAACCTCTGCCCCGAA ATGCGGTTCGCCGCCACCCCTCCTTACGACGGCACCCTGACCGGCTTCTGGACCGCCC CCGCCGACTTCTGCTACAAGCTCCCCGAGACCGTCTCGCTCCAGGAGGGTGCCCTGAT CGAGCCCCTCGCTGTCGCCGTCCACATCACCAAGCAGGCCAAGATCCAGCCCGGTCAG ACCGTGGTCGTTATGGGCGCCGGCCCCGTCGGCCTCCTCTGTGCGCCGCGTTGCCAAGG CCTACGGCGCCTCCAAGGTTGTCTCGGTCGACATTGTCCCCTCCAAGCTCGAGTTCGC CAAGTCGTTCGCCGCCACCCACACCTACCTCGCAGCGCGTGTCGCCCGAGGAGAAC GCGCGCAACATTATCGCGGCCGCCGACCTTGCGAGGGTGCCGATGCCGTCATTGACG CCAGCGGCGCTGAGCCCTCCATCCAGGCGGCACTCCACGTCGTCGTCAGGGCGGCCA CTACGTCCAGGGCGGTATGGGCAAGGACAACATCATCTTCCCCATTATGGCGCTCTGC ATCAAGGAGGTCACGGCTAGCGGCTCGTTCCGCTACGGCAGCGGTGACTACAGGCTGG CTATTCAGCTTGTTGAGCAGGGCAAGGTTGATGTCAAGAAGCTCGTCAACGGCGTTGT TCCCTTCAAGAATGCCGAGGAGGCTTTTCAAGAAGGTTAAGGAGGGTGAGGTTATCAAG ATCCTCATTGCTGGCCCTAACGAGGATGTCGAGGGTAGTCTTGATACTACTGTTGATG AGAAGAAGCTGAATGAGGCCAAGGCTTGCGGTGGTTCTGGCTGCTGCTAA | SEQ ID NO: 78 |
| XKS | ATGACCACTACCCCATTTGATGCTCCAGATAAGCTCTTCCTCGGGTTCGATCTTTCGA CTCAGCAGTTGAAGATCATCGTCACCGATGAAAACCTCGCTGCTCTCAAAACCTACAA TGTCGAGTTCGATAGCATCAACAGCTCTGTCCAGAAGGGTGTCATTGCTATCAACGAC GAAATCAGCAAGGGTGCCATTATTCCCCGTTTACATGTGGTTGGATGCCCTTGACC ATGTTTTTGAAGACATGAAGAAGGACGGATTCCCCTTCAACAAGGTTGTTGGTATTTC CGGTTCTTGTCAACAGCACGGTTCGGTATACTGGTCTAGAACGGCCGAGAAGGTCTTG TCCGAATTGGACGCTGAATCTTCGTTATCGAGCCAGATGAGATCTGCTTTCACCTTCA AGCACGCTCCAAACTGGCAGGATCACTCTACCGGTAAAGAGCTTGAAGAGTTCGAAAG AGTGATTGGTGCTGATGCCTTGGCTGATATCTCTGGTTCCAGAGCCCATTACAGATTC ACAGGGCTCCAGATTAGAAAGTTGTCTACCAGATTCAAGCCCGAAAAGTACAACAGAA CTGCTCGTATCTCTTTAGTTTCGTCATTTGTTGCCAGTGTGTTGCTTGGTAGAATCAC CTCCATTGAAGAAGCCGATGCTTGTGGAATGAACTTGTACGATATCGAAAGCGCGAG TTCAACGAAGAGCTCTTGGCCATCGCTGCTGGTGTCCACCCTGAGTTGGATGGTGTAG AACAAGACGGTGAAATTTACAGAGCTGGTATCAATGAGTTGAAGAGAAAGTTGGGTCC TGTCAAACCTATAACATACGAAAGCGAAGGTGACATTGCCTCTTACTTTGTCACCAGA | SEQ ID NO: 79 |

TABLE 13-continued

Genetic elements/DNA sequences

| Genetic elements/ DNA | Sequences | SEQ ID NO |
|---|---|---|
| | TACGGCTTCAACCCCGACTGTAAAATCTACTCGTTCACCGGAGACAATTTGGCCACGA TTATCTCGTTGCCTTTGGCTCCAAATGATGCTTTGATCTCATTGGGTACTTCTACTAC AGTTTTAATTATCACCAAGAACTACGCTCCTTCTTCTCAATACCATTTGTTTAAACAT CCAACCATGCCTGACCACTACATGGGCATGATCTGCTACTGTAACGGTTCCTTGGCCA GAGAAAAGGTTAGAGACGAAGTCAACGAAAAGTTCAATGTAGAAGACAAGAAGTCGTG GGACAAGTTCAATGAAATCTTGGACAAATCCACAGACTTCAACAACAAGTTGGGTATT TACTTCCCACTTGGCGAAATTGTCCCTAATGCCGCTGCTCAGATCAAGAGATCGGTGT TGAACAGCAAGAACGAAATTGTAGACGTTGAGTTGGGCGACAAGAACTGGCAACCTGA AGATGATGTTTCTTCAATTGTAGAATCACAGACTTTGTCTTGTAGATTGAGAACTGGT CCAATGTTGAGCAAGAGTGGAGATTCTTCTGCTTCCAGCTCTGCCTCACCTCAACCAG AAGGTGATGGTACAGATTTGCACAAGGTCTACCAAGACTTGGTTAAAAAGTTTGGTGA CTTGTTCACTGATGGAAAGAAGCAAACCTTTGAGTCTTTGACCGCCAGACCTAACCGT TGTTACTACGTCGGTGGTGCTTCCAACAACGGCAGCATTATCCSCAAGATGGGTTCCA TCTTGGCTCCCGTCAACGGAAACTACAAGGTTGACATTCCTAACGCCTGTGCATTGGG TGGTGCTTACAAGGCCAGTTGGAGTTACGAGTGTGAAGCCAAGAAGGAATGGATCGGA TACGATCAGTATATCAACAGATTGTTTGAAGTAAGTGACGAGATGAATCTGTTCGAAG TCAAGGATAAATGGCTCGAATATGCCAACGGGTTGGAATGTTGGCCAAGATGGAAAG TGAATTGAAACACTAA | |
| gfp | ATGAGTAAAGGAGAAGAACTTTTCACTGGAGTTGTCCCAATTCTTGTTGAATTAGATG GTGATGTTAATGGGCACAAATTTTCTGTCAGTGGAGAGGGTGAAGGTGATGCAACATA CGGAAAACTTACCCTTAAATTTATTTGCACTACTGGAAAACTACCTGTTCCATGGCCA ACACTTGTCACTACTTTCTCTTATGGTGTTCAATGCTTTTCAAGATACCCAGATCATA TGAAACGGCATGACTTTTTCAAGAGTGCCATGCCCGAAGGTTATGTACAGGAAAGAAC TATATTTTTCAAAGATGACGGGAACTACAAGACACGTGCTGAAGTCAAGTTTGAAGGT GATACCCTTGTTAATAGAATCGAGTTAAAAGGTATTGATTTTAAAGAAGATGGAAACA TTCTTGGACACAAATTGGAATACAACTATAACTCACACAATGTATACATCATGGCAGA CAAACAAAAGAATGGAATCAAAGTTAACTTCAAAATTAGACACAACATTGAAGATGGA AGCGTTCAACTAGCAGACCATTATCAACAAAATACTCCAATTGGCGATGGCCCTGTCC TTTTACCAGACAACCATTACCTGTCCACACAATCTGCCCTTTCGAAAGATCCCAACGA AAAGAGAGACCACATGGTCCTTCTTGAGTTTGTAACAGCTGCTGGGATTACACATGGC ATGGATGAACTATACAAATAG | SEQ ID NO: 80 |
| mCherry | ATGGTGAGCAAGGGCGAGGAGGATAACATGGCCATCATCAAGGAGTTCATGCGCTTCA AGGTGCACATGGAGGGCTCCGTGAACGGCCACGAGTTCGAGATCGAGGGCGAGGGCGA GGGCCGCCCCTACGAGGGCACCCAGACCGCCAAGCTGAAGGTGACCAAGGGTGGCCCC CTGCCCTTCGCCTGGGACATCCTGTCCCCTCAGTTCATGTACGGCTCCAAGGCCTACG TGAAGCACCCCGCCGACATCCCCGACTACTTGAAGCTGTCCTTCCCCGAGGGCTTCAA GTGGGAGCGCGTGATGAACTTCGAGGACGGCGGCGTGGTGACCGTGACCCAGGACTCC TCCCTGCAGGACGGCGAGTTCATCTACAAGGTGAAGCTGCGCGGCACCAACTTCCCCT CAGACGGCCCCGTAATGCAGAAGAAAACCATGGGCTGGGAGGCCTCCTCCGAGCGGAT GTACCCCGAGGACGGCGCCCTGAAGGGCGAGATCAAGCAGAGGCTGAAGCTGAAGGAC GGCGGCCACTACGACGCTGAGGTCAAGACCACCTACAAGGCCAAGAAGCCCGTGCAGC TGCCCGGCGCCTACAACGTCAACATCAAGTTGGACATCACCTCCCACAACGAGGACTA CACCATCGTGGAACAGTACGAACGCGCCGAGGGCCGCCACTCCACCGGCGGCATGGAC GAGCTGTACAAGTAA | SEQ ID NO: 81 |

Plasmid Construction.

Most of the plasmid construction was carried out by the in vivo DNA assembly method in *I. orientalis*, while the rest were carried out either by the DNA assembler method in *S. cerevisiae* or Gibson assembly in *E. coli*. Briefly, 50~100 ng of PCR-amplified fragments and restriction enzyme digested backbone were cotransformed into *I. orientalis* SD108 via a lithium acetate-mediated method. The colonies formed on SC-URA plates were randomly picked for functional characterization, and the confirmed target cells were then used to extract plasmids for *E. coli* transformation to enrich the plasmids. The plasmids were verified by restriction digestion or DNA sequencing. If needed, the correctly assembled plasmids can be retransformed into *I. orientalis* SD108 for further characterization. The constructed plasmids were shown in Table 12, and the designed primers were listed in Table 14.

TABLE 14

Primers

| Primers | Sequences (5' to 3') | SEQ ID NO |
|---|---|---|
| CEN-0.8kb-F | TAACTGCGGTCAAGATATTTCTTGAATCAGGCGCCTCTA GCTATTTTGTTTAGGTTGGGT | SEQ ID NO: 82 |
| CEN-0.8kb-R | ATTCTGATATTATCCAAAGATGTTGAGGGCCCTAAATAGT TTTATTACACTCAAAGTGAC | SEQ ID NO: 83 |
| ade2-seq-F | TGAACACATTGATGGTTCATTC | SEQ ID NO: 84 |

TABLE 14 -continued

Primers

| Primers | Sequences (5' to 3') | SEQ ID NO |
|---|---|---|
| ade2-seq-R | TCTTTTACAACATAGTTACCTCTAC | SEQ ID NO: 85 |
| GFP-qPCR-F | GATGGTGATGTTAATGGGCAC | SEQ ID NO: 86 |
| GFP-qPCR-R | GGGTAAGTTTTCCGTATGTTGC | SEQ ID NO: 87 |
| TRP1-qPCR-F | TCCCCGTTATTTCAAGGTTCG | SEQ ID NO: 88 |
| TRP1-qPCR-R | CTTGTCCCCAAACGAACTTG | SEQ ID NO: 89 |
| Assembly-ScARS-F | GCGCACATTTCCCCGAAAAGTGCCACCTGGGTCCCTCG AGGATCGCCAACAAATACTACC | SEQ ID NO: 90 |
| Assembly-ScARS-R | ATGAGACAATGATTGCCGCTAGACAATGTCAACCTGCAG GATCGCTTGCCTGTAACTTAC | SEQ ID NO: 91 |
| 1387F-F | AAGGACTTAAATATTTGTACAAACATGTTCCATCTAGAGC CACCTGGGTC | SEQ ID NO: 92 |
| 1387F-R | ATCGCTGAGATAGGTGCCTCACTGATTAAGCATTGGTAA CTGTCAGACCAAGTTTACTC | SEQ ID NO: 93 |
| 1032F-F | ATCTAAAGTATATATGAGTAAACTTGGTCTGACAGTTACC AATGCTTAATCAGTGAG | SEQ ID NO: 94 |
| 1032F-R | AACACCCGCTGACGCGCCCTGACGGGCTTGTCGCGGAA CCCCTATTTGTT | SEQ ID NO: 95 |
| 1337F-F | GAATGTATTTAGAAAAATAAACAAATAGGGGTTCCGCGA CAAGCCCGTCAGGGCG | SEQ ID NO: 96 |
| 1337F-R | CGCTAGACAATGTCAACCTTCCCTGTTTACGCGTCTCGA GCCTGATGCGGTA | SEQ ID NO: 97 |
| 1742F-F | TAAGGAGAAAATACCGCATCAGGCTCGAGACGCGTAAAC AGGGAAGGT | SEQ ID NO: 98 |
| 1742F-R | GGTTTCTCGTGTATTGCTATAATCTCTCGTGTATTCGTCT GTAGAGTAAAGAAACT | SEQ ID NO: 99 |
| 667F-F | TAAGATGAACGAGAAGTTTCTTTACTCTACAGACGAATAC ACGAGAGATTATAGCAA | SEQ ID NO: 100 |
| 667F-R | ACTCCAGTGAAAAGTTCTTCTCCTTTACTCATTTTTATTGT GTTAGTTTGTAAGC | SEQ ID NO: 101 |
| 790F-F | TTCATAGTCTCTCGCTTACAAACTAACACAATAAAAATGA GTAAAGGAGAAGAACTTT | SEQ ID NO: 102 |
| 790F-R | AATTGTACTAGATATTTAGTAAAAGCATTAGTTAGATCTAT TTGTATAGTTCATCCATG | SEQ ID NO: 103 |
| 951F-F | GATTACACATGGCATGGATGAACTATACAAATAGATCTAA CTAATGCTTTTACTAAAT | SEQ ID NO: 104 |
| 951F-R | TATAGCACGTGATGAAAAGGACCCAGGTGGCTCTAGATG GAACATGTTTGTACAAATATT | SEQ ID NO: 105 |
| XR-cassette-F | TCTAACCTAAGGACTTAAATATTTGTACAAACATGTTCCA TTGATTTAACCTGATCCA | SEQ ID NO: 106 |
| XR-cassette-R | TGACTATCGGCCTCTTTTTCTCCGGGTGTGGTGCATTTTT CGCGTACAGGGTTATAAAGT | SEQ ID NO: 107 |
| XDH-cassette-F | ACTTTAGATGCTCCTCTGAACAACTTTATAACCCTGTACG CGAAAAATGCACCACACC | SEQ ID NO: 108 |
| XDH-cassette-R | TTGCTGTGCAAGAGCAATTTCTCTCTGATTACACCGTTG GTTCATCTTATTCTTTAGC | SEQ ID NO: 109 |
| XKS-cassette-F | ATAATAAAAGTTTAAACTTGGCTAAAGAATAAGATGAAC CAACGGTGTAATCAGAGAG | SEQ ID NO: 110 |
| XKS-cassette-R | CCTCACTAAAGGGAACAAAAGCTGGAGCTCCACCGCGG TGGCCCGTCTATTGTTCTCCTT | SEQ ID NO: 111 |

TABLE 14 -continued

Primers

| Primers | Sequences (5' to 3') | SEQ ID NO |
|---|---|---|
| URA3-cassette-F | CAACATCCAGTCACTTTGAGTGTAATAAAACTATTTAGGGCCGTTGACATTGTCTAGCGG | SEQ ID NO: 112 |
| URA3-cassette-R | TAAAAAATAGACATACCCCTTTTGGATCAGGTTAAATCAATGGAACATGTTTGTACAA | SEQ ID NO: 113 |
| qPCR-XR-F | AGGCTATTGGTGACAAGTACAA | SEQ ID NO: 114 |
| qPCR-XR-R | CCTCGGAGAGATCGAAATCAAG | SEQ ID NO: 115 |
| qPCR-XDH-F | GTGACTACAGGCTGGCTATTC | SEQ ID NO: 116 |
| qPCR-XDH-R | CCCTGCTCAACAAGCTGAATA | SEQ ID NO: 117 |
| qPCR-XKS-F | GATTCACAGGGCTCCAGATTAG | SEQ ID NO: 118 |
| qPCR-XKS-R | CAACACACTGGCAACAAATGA | SEQ ID NO: 119 |
| Promoter assembly | | |
| En02t_CEN/ARS_Fwd | AAGGACTTAAATATTTGTACAAACATGTTCCATCTAGAGCCACCTGGGTC | SEQ ID NO: 120 |
| En02t_CEN/ars_Rev | TATAGCACGTGATGAAAAGGACCCAGGTGGCTCTAGATGGAACATGTTTGTACAAATATT | SEQ ID NO: 121 |
| FBAp_GFP_Fwd | CTACTACTACTATTACTACCACCCCAACACAAACACAATGAGTAAAGGAGAAGAACTTT | SEQ ID NO: 122 |
| FBAp_GFP_Rev | GGACAACTCCAGTGAAAAGTTCTTCTCCTTTACTCATTGTGTTTGTGTTGGGGGTGG | SEQ ID NO: 123 |
| scUra_Fwd | GAATGTATTTAGAAAAATAAACAAATAGGGGTTCCGCGACAAGCCCGTCAGGGCG | SEQ ID NO: 124 |
| scURA_Ura3p_Rev | CGCTAGACAATGTCAACCTTCCCTGTTTACGCGTCTCGAGCCTGATGCGGTA | SEQ ID NO: 125 |
| TEF1t_FBAp_Fwd | AAGAATAAGATGAACGAGAAGTTTCTTTACTCTACAGACGATGCCATATTGTATGTGTATTG | SEQ ID NO: 126 |
| Tef1t_FBAp_Rev | TACACACTTAATACAATACACATACAATATGGCATCGTCTGTAGAGTAAAGAAACT | SEQ ID NO: 127 |
| Ura_Ura3p_Fwd | TAAGGAGAAAATACCGCATCAGGCTCGAGACGCGTAAACAGGGAAGGT | SEQ ID NO: 128 |
| CEN/ARS/Amp_Rev | AACACCCGCTGACGCGCCCTGACGGGCTTGTCGCGGAACCCCTATTTGTT | SEQ ID NO: 129 |
| Terminator assembly | | |
| 4194t_mcherry_Fwd | AAAAACCCCAAAACTCCTCTTGTTGGGAGGGCCGTCAATGGTGAGCAAGGGCGAG | SEQ ID NO: 131 |
| 4194t_mcherry_rev | TGATGGCCATGTTATCCTCCTCGCCCTTGCTCACCATTGACGGCCCTCCCAACAA | SEQ ID NO: 132 |
| Ura_Ura3p_Fwd | TTAGAAAAATAAACAAATAGGGGTTCCGCGCTCGAGACGCGTAAACAGGGAAGGT | SEQ ID NO: 133 |
| Amp_Ura3p_IO_Rev | AATGTCAACCTTCCCTGTTTACGCGTCTCGAGCGCGGAACCCCTATTTGTTTATT | SEQ ID NO: 134 |
| GFP_4194t_Fwd | ATTACACATGGCATGGATGAACTATACAAATAGTTTGAATCAACTTTTCCCCTAA | SEQ ID NO: 135 |
| GFP_4194_Rev | TGTATTAAACCTTAGGGGAAAAGTTGATTCAAACTATTTGTATAGTTCATCCATG | SEQ ID NO: 136 |
| mcherry_pgk1t_Fwd | CCACCGGCGGCATGGACGAGCTGTACAAGTAAATCAAACATAGATCAACGTAATG | SEQ ID NO: 137 |

TABLE 14 -continued

Primers

| Primers | Sequences (5' to 3') | SEQ ID NO |
|---|---|---|
| mcherry_pgk1t_Rev | TTATATTAAATTCATTACGTTGATCTATGTTTGATTTACTTGTACAGCTCGTCCA | SEQ ID NO: 138 |
| PDC1t_TDH3p_Fwd | GAATAATATATAATTTTATAATAAAAAGTTTAAACTATGGATATGGAGATGAATTTG | SEQ ID NO: 139 |
| PDC1t_TDH3p_Rev | TCTAAATTCAAATTCATCTCCATATCCATAGTTTAAACTTTTTATTATAAAATTATATA | SEQ ID NO: 140 |
| PGKt_ARS_Fwd | TTATTATTATTATTATTATTATTATCATATCTAGAGCCACCTGGGTC | SEQ ID NO: 141 |
| PGK1t_CEN/ARS_Rev | ACGTGATGAAAAGGACCCAGGTGGCTCTAGATATGATAATAATAATAATAATAATAA | SEQ ID NO: 142 |

Centromere-Like Sequence Prediction and Isolation.

The centromere regions were predicted using in silico GC3 analysis. In brief, the whole genome sequence of *I. orientalis* was downloaded from NCBI (www.ncbi.nlm.nih.gov/) along with their annotations. The coding sequences (CDS) were then extracted from the genome using BED-Tools (v2.20.1). CodonW (v1.4.4) (codonw.sourceforge.net/) was used to calculate the GC3 percentage for each CDS sequence and a line graph was generated with a moving average of 15 genes corresponding to each chromosome. The longest intergenic regions from each chromosome that may locate the centromere sequences were chosen for alignment to achieve the conserved fragment for functional characterization. The conserved sequence (CEN-0.8 kb) was PCR-amplified from *I. orientalis* genomic DNA, and ligated with KasI and ApaI digested ScARS (plo-UG) plasmid backbone, resulting in ScARS/CEN-0.8 kb. After verification by restriction digestion, the ScARS/CEN-0.8 kb plasmid was transformed to *I. orientalis* SD108 through heat-shock and screened on SC-URA solid medium for around 2 days. Then, 10 colonies were randomly picked for GFP measurement from 24 h to 120 h by flow cytometry, and the one exhibiting higher cell ratio of GFP expression than those from ScARS-plasmid was chosen for characterization.

Centromere-Like Sequence Prediction and Isolation.

The function of CEN-L in improving plasmid stability was characterized by evaluating ade2 knockout efficiency and D-lactic acid production. The ScARS/CEN-L-Cas9-ade2 plasmid was constructed by integrating CEN-L to pScARS-Cas9-ade2, which was assembled by cotransforming 100 ng of Cas9 expression cassette (PCR-amplified from pVT15b-epi), single guide RNA targeting ade2, and digested pScARS backbone (XbaI and NotI). After transformation, the ade2 knockout efficiency was calculated by the ratio between pink colonies and total colonies. The pink colonies were also picked for further confirmation by DNA sequencing. To construct D-lactic acid producing strain, the D-lactate dehydrogenase gene (IdhD) from *Leuconostoc mesenteroides* was amplified from pUG6-TDH3-Lm.IdhA-CYC1 and cotransformed to *I. orientalis* together with TDH3 promoter, TEF1 terminator, and digested ScARS and ScARS/CEN-L backbone (Bsu36I+NotI). Three colonies were picked and cultivated in 2 mL SC-URA medium as seed cultures for 2 days and then transferred to new SC-URA medium with the same initial OD. The samples were collected at various time points, and the supernatants were analyzed for lactic acid production by HPLC (Agilent Technologies 1200 Series, Santa Clara, CA). The HPLC was equipped with a Rezex™ ROA-Organic Acid H$^+$ (8%) column (Phenomenex Inc., Torrance, CA) and a refractive index detector (RID). The column was eluted with 0.005 N$_{H2SO4}$ at a flow rate of 0.6 mL/min at 50° C.

Plasmid copy numbers were quantified. Briefly, two sets of primers specific to the GFP gene in plasmids and to the TRP1 reference gene in the *I. orientalis* genomic DNA were designed (Table 14), and a 16-fold serial dilution was applied to construct the standard curves for both GFP and TRP1. qPCR was performed on a QuantStudio 7 Flex Real-Time PCR System (Applied Biosystems, Foster City, CA) using a two-step cycling reaction program. Total DNA (genomic DNA and plasmid DNA) was firstly extracted from *I. orientalis* cells by Zymolase plus freeze-thaw lysis method, and then the cell lysates were centrifuged and the supernatants were diluted appropriately for qPCR. The copy number was determined as the ratio between the calculated molar amounts of gfp and trp1 genes in the total DNA extracts, according to the two standard curves. The sizes of 10.8 Mbp for *I. orientalis* genome and 10 kb for plasmids were used in the calculation.

Promoter Characterization.

For promoter characterization, RNA-Seq analysis was performed in the U.S. Department of Energy's Joint Genomics Institute (JGI) central facility. *I. orientalis* was first grown in YPD broth overnight under 30° C. and 200 rpm on the platform shaker. The overnight culture of *I. orientalis* was pelleted and inoculated into the following four conditions: 1) YNB medium with glucose, aerobic condition; 2) YNB medium with glucose and lignocellulosic biomass inhibitors (1 g/L furfural, 3 g/L hydroxymethylfuran (HMF), 10 g/L NaCl, and 3 g/L acetic acid) in aerobic condition; 3) YNB medium with, anaerobic condition; 4) YNB medium with glucose and lignocellulosic biomass inhibitors in anaerobic condition. The aerobic cultures were grown at 200 rpm on the platform shaker while the anaerobic cultures were grown with a stir bar rotating at 400 rpm. Total RNA was extracted from cells from the above four conditions separately by the RNeasy Kit from QIAGEN and then treated with TURBO DNase from Ambion to remove DNA contaminants. RNA samples were quantified by Qubit RNA BR Assay Kit and were mixed with an equal amount of RNA to make a total 3000 ng mixed RNA sample for library preparation and sequencing. To validate the expression of selected gene in the RNA-Seq data, qPCR was performed. *I. orientalis* cells were inoculated in YPD medium, and culture was grown at 30° C. with constant shaking at 250 rpm for overnight. The next day, cells were inoculated into fresh YNB medium with 2% glucose with the initial OD at 600 nm (OD600) of 0.1 and grown till OD reached to 1. Cells were collected from 1 mL of culture, and total RNA was extracted using the RNeasy mini kit from Qiagen. DNase treatment of RNA was performed in the column during the preparation of RNA using the RNase-Free DNase Set from Qiagen. cDNA synthesis was carried out using the iScript™ Reverse Transcription Supermix and iTaq Universal SYBR Green Supermix from Biorad was used for qPCR. Primers for qPCR were designed using the IDT online tool (Primer Quest). For primer design, the amplicon length was restricted to be around 140 bp and melting temperature (Tm) was set at 58° C. For qPCR reactions. The manufacturer's protocol was followed: 10 µL of 2×SYBR Green supermix, 300 nM of forward and reverse primer, 1 µL of cDNA and further volume were make up to 20 µL with RNAase/DNAse free water. MicroAmp Optical 384 well plates from Applied Biosystems were used for the qPCR reactions which were performed on the Applied Biosystems machine using the following program: 2 min at 50° C. and 5 min at 95° C. for one cycle followed by 15 s at 95° C., 30 s at 60° C., and 30 s at 72° ° C. for 40 cycles, with a final cycle of 5 min at 72° C. The endogenous gene alg9, encoding a mannosyltransferase, involved in N-linked glycosylation, was used as the internal control. Expression of the selected gene for promoter characterization was normalized by the alg9 expression level. Raw data was analyzed using QuantStudio™ Real-time PCR software from Applied Biosystems.

For the cloning of promoters, either the intergenic region or the 600 bp upstream of genes were chosen for characterization. Promoter sequences are shown in Table 10. Putative promoters were cloned with the GFP reporter gene using the in vivo DNA assembly method and later confirmed through restriction digestion with HindIII and Sa/I. Pairs of primers used to amplify the promoter region and other genetic elements including the GFP gene, terminator elements, E. coli part (Col1 region and ampicillin cassette), ura3 gene (auxotrophic marker), promoter and terminator for ura3 gene expression, and ura3 gene from S. cerevisiae along with the promoter and terminator are shown in Table 14. The resultant plasmid is an E. coli/S. cerevisiae/I. orientalis shuttle vector (Table 12).

Terminator Characterization.

A total of 14 terminators was selected, mostly of 300 bp and some of smaller lengths, were amplified from I. orientalis genomic DNA and cloned between the GFP and mCherry genes by using the in vivo DNA assembly method (6 fragment assembly). Primers and DNA sequences of genetic elements and structural genes used in this study are listed in Tables 13 and 14, respectively. A plasmid backbone fragment was PCR-amplified from the p247_GFP plasmid and the mCherry gene was PCR-amplified from plasmid-64324 (Addgene). A random sequence used as a negative control was PCR-amplified from a non-functional region from I. orientalis genomic DNA which does not code for any promoter and terminator and does not contain a stretch of polyT with more than four T's. As a control, another plasmid was constructed without any sequence between the GFP gene and the mCherry gene. The resultant plasmid was verified by restriction digestion using HindIII and XhoI.

Recombinant I. orientalis strains harboring control plasmids or selected terminators were evaluated using qPCR and cDNA libraries and qPCR analysis was performed as previously described. Relative amounts of GFP and mCherry transcripts were determined using the alg9 gene as a control followed by calculation of the ratio of mCherry to GFP transcripts for evaluating the strength of the terminators. Experiments were performed in biological triplicates.

Assembly of a Xylose Utilization Pathway.

Plasmid ScARS/CEN-L was digested with ApaI and NotI to obtain the backbone which was used as a PCR template to obtain the URA3 expression cassette. XR, XDH, and XKS were PCR-amplified from pRS416Xyl-Zea_A_EVA. Promoters and terminators were PCR-amplified from the genomic DNA of I. orientalis (Tables 10 and 11). All overlaps were designed to have 70-80 bp to facilitate in vivo homologous recombination, except for the overlaps between fragments and the backbone (~40 bp). Approximately 100 ng of each fragment was transformed into I. orientalis, and the resultant transformants were spread onto SC-URA plates and incubated at 30° C. Yeast colonies were collected for plasmid extraction, and the resultant plasmids were transformed to E. coli for enrichment. For assembly of a helper plasmid harboring individual XRIXDHIXKS cassette, plasmids were extracted from randomly picked E. coli colonies and were verified by restriction digestion and DNA sequencing. Afterwards, individual cassettes, TDH3p-XR-MDH1t, HSP12p-XDH-PDC1t, and INO1p-XKS-PFK1t, were PCR-amplified from the helper plasmids (primers are listed in Table 12), and mixed with ScARS/CEN-L backbone (digested by ApaI and NotI) and URA3 expression cassette. I. orientalis was transformed with 100 ng of each fragment, spread on a SC-URA plate, and incubated at 30° C. Plasmids were then extracted from I. orientalis and transformed to E. coli. Plasmids were extracted from three different E. coli colonies and were confirmed by restriction digestion and DNA sequencing.

The recombinant I. orientalis carrying the xylose utilization pathway was analyzed by monitoring the cell growth in SC-URA liquid medium supplemented with 2% xylose (SC-URA+XYL) as the sole carbon source. Colonies were picked into 2 mL SC-URA liquid medium supplemented with 2% glucose and grown for 2 days. Cells were spun down and washed with SC-URA+XYL medium twice to remove the remaining glucose and finally resuspended in fresh SC-URA+XYL medium with an initial OD600 of 0.2. Then, the cells were grown at 30° C. for 144 hours and OD600 was measured. The residual xylose was measured through HPLC after diluting the samples by 10-fold.

Flow Cytometry.

The GFP expression was measured by flow cytometry as described elsewhere. In brief, the transformed I. orientalis cells were cultured in SC-URA medium for 24 h to 120 h and then centrifuged for 2 min at 2,000×g to remove the supernatant. The cell pellets were resuspended in 10 mM phosphate-buffered saline (PBS, pH 7.4) and then analyzed by flow cytometry at 488 nm on a BD LSR II flow cytometer analyzer (BD Biosciences, San Jose, CA).

Similarly, for promoter characterization, constructs were transformed into I. orientalis and single colonies were picked from SC-URA plates and inoculated in the SC-URA medium and grown for 24 h. Cells were then inoculated in YNB medium with 2% glucose and YNB with glucose and lignocellulosic hydrolysate (1 g/L furfural, 3 g/L HMF, 3 g/L acetate and 10 g/L NaCl) and cultured under aerobic and anaerobic conditions. Samples after 48 h were taken for GFP fluorescence measurement. For terminator characterization, flow cytometer BD LSR FORTESSA with HTS was used to determine the fluorescence intensities of mCherry at 610 nm and GFP at 488 nm.

Example 12 Development of a Trifunctional CRISPR System Tool for *Issatchenkia orientalis*

An orthogonal and generally applicable tri-functional CRISPR system comprising CRISPRa, CRISPRi, and CRISPRd (CRISPR-AID) was developed for metabolic engineering of *Issatchenkia orientalis*. Due to the modular and multiplex advantages of the CRISPR system, CRISPR-AID can be used to perform a combinatorial optimization of various metabolic engineering targets and explore the synergistic interactions among transcriptional activation, transcriptional interference, and gene deletion in an organism. Three functional Cas proteins are identified that can work orthogonally from the list of 7 sorted cas9 proteins (Table 15).

TABLE 15

Cas protein and their PAM sequence used in the study

| Cas protein | PAM sequence |
|---|---|
| NmCas9 | NNNNGAAT |
| StCas9 | NNAGAAW |
| SaCas9 | NNGRRT |
| SpCas9 | NGG |
| AsCpf1 | TTTN |
| LbCpf1 | TTTN |
| CjCas9 | NNNNACAC or NNNNRYCA |

Evaluation of Various CRISPR Proteins in *I. orientalis*

Figure 22:
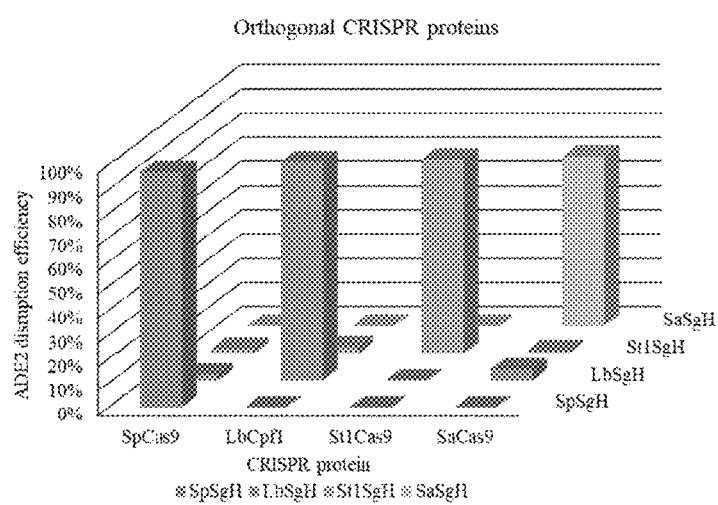
FIG. 22 discloses an orthogonal CRISPR system. The orthogonality was tested by co-transforming the CRISPR proteins (SpCas9, LbCpf1, St1Cas9, and SaCas9) and gRNAs (SpSgH, LbSgH, St1SgH, and SaSgH) with different origins and evaluating ADE2 disruption efficiency.

To develop a genetic toolbox system, a tri-functional CRISPR-AID system was developed. First, three functional CRISPR protein in *I. orientalis* were characterized. We tested the nuclease activity of seven CAS proteins in *I. orientalis* (Table 16) by targeting the ADE2 gene disruption, which results in accumulating red pigment in yeast in adenine deficient synthetic medium. spCas9 was included as a positive control. Initially, we adopted two plasmid systems, where CRISPR proteins were cloned in a plasmid containing URA selection marker and guide RNAs were cloned in Leu containing selection marker plasmid and 500 ng homology donor was provided during transformation. Although it was found that a few of the CRISPR proteins are functional in *I. orientalis*, their efficiency was low. Since the spCas9 activity was also very low (5%), it suggests that the two plasmid system was not maintained well, which led to lower efficiency in CjCas9 (2%), St1Cas9 (3%), SaCas9 (77%), and IbCpf1 (89%) (Table 16). Therefore, we further assembled all the fragments in a single plasmid, including CRISPR protein, gRNA, and 500 bp of homology arm, which led to an improvement in nuclease efficiency in all proteins, including our positive control. We found an increase in CRISPRd efficiency to 75% with St1Sg1, 100% for SaSg3, 100% for LbSg2 and LbSg3, and 97% for SpSg1 (positive control). Therefore, SpCas9, SaCas9, St1Cas9, and LbCpf1 were chosen for further studies (Table 16). Furthermore, the orthogonality of the chosen CRISPR proteins were checked by calculating deletion efficiency using guide RNA of different Cas proteins. Our result suggests that all four Cas nucleases are only efficient with their cognate guide RNA (FIG. 22).

TABLE 16

Nuclease activity of CRISPR protein orthologs in yeast

| Cas protein | gRNA | Double plasmid | Single Plasmid |
|---|---|---|---|
| CjCas9 | CjSg1 | 0 | 0 |
|  | CjSg2 | 0 | 0 |
|  | CjSg3 | 2% | 21% |
| St1Cas9 | St1Sg1 | 0 | 75% |
|  | St1Sg2 | 0 | 16% |
|  | St1Sg3 | 3% | 10% |
| SaCas9 | SaSg1 | 0 | 50% |
|  | SaSg2 | 0 | 0 |
|  | SaSg3 | 77% | 100% |
| LbCpf1 | LbSg1 | 0 | 62.5% |
|  | LbSg2 | 0 | 100% |
|  | LbSg3 | 89% | 100% |
| AsCpf1 | AsSg1 | 0 | 0 |
|  | AsSg2 | 0 | 0 |
|  | AsSg3 | 0 | 0 |
| NmCas9 | NmSg1 | 0 | 0 |
|  | NmSg2 | 0 | 0 |
|  | NmSg3 | 0 | 0 |
| SpCas9 | SpSg | 5% | 97% |
| Repair template |  | PCR product | In plasmid |

Figure 23:
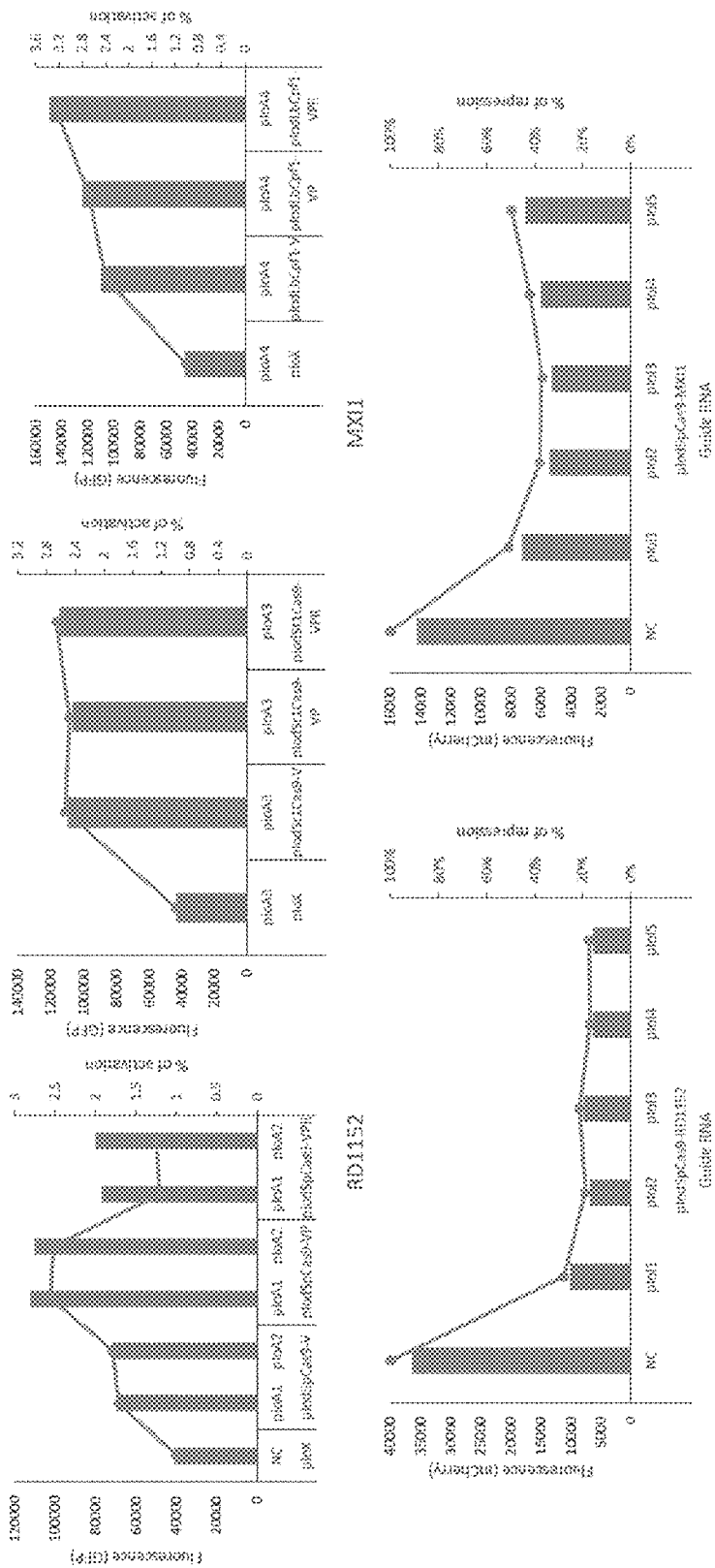
FIG. 23 discloses an evaluation of activation and repression domains. The upper panel shows the activation assay results using V, VP, and VPR repression domains; Lower panel shows the repression assay results using RD1152 and MXI1 domains.

Evaluation of the Activation and Repression Domains for CRISPRa and CRISPRi, Respectively To identify an efficient transcriptional regulation domain, we first generated a few reporter yeast strains, where mCherry driven by high TDHp for CRISPRi and GFP driven by weak (p697, p850) and moderate (p43, p172) promoters for CRISPRa were integrated into the SD108 genome at Leu2 site. All four reporter strains showed mCherry and GFP expression and one of them (GR3) was selected for further study. VP64 (V), VP64-p65AD (VP), and VP64-p65AD Rta (VPR) activation domains were tested in combination with nuclease-deficient CRISPR proteins (dSpCas9, dSt1Cas9, and dLbCpf1) and found that these activation domains have varying activity with different CRISPR proteins. In the case of dSpCas9, the VP domain worked best, whereas in the case of dSt1Cas9 and LbCpf1, all domains have shown a similar activation activity, but activation through VPR was marginally high (FIG. 23). We have selected dst1ca9_VPR (nuclease deficient st1cas9 with VPR activation domain) as activation candidate for our study. We also checked another domain, HSF but did not find comparable activation of GFP.

Several repression domains, such as MXI1 from mammalian cells and RD1152 from *S. cerevisiae*, have shown activity in yeast. We have evaluated the efficiency of these two repression domains in *I. orientalis*, and both MXI1 and RD1152 are functional in *I. orientalis*, but RD1152 domain shows higher CRISPRi efficiency than MXI1 (FIG. 23). dSpCas9-RD1152 demonstrated the highest CRISPRi efficiency and was chosen for further studies. We finalized the tri-functional and orthogonal CRISPR-AID system's optimal design to be LbCpf1 for CRISPRd, dSpCas9-RD1152 for CRISPRi, and dStCas9_VPR for CRISPRa. Further, we integrated these AID systems into the *I. orientalis* genome and confirmed their expression and activity.

Example 13 Development of RNA Interference and cDNA Overexpression Systems for Genome-Wide Gene Knockdown and Gene Overexpression Genome-wide engineering is a powerful tool to facilitate metabolic engineering, generate strains with complex phenotypes, and discover answers to fundamental questions in biology. Trans-acting regulatory RNAs can be employed for genome-scale screening of genetic modifications that help attain desired phenotypes and improve the production of the products of interest. In eukaryotic organisms, RNA interference (RNAi) is a cellular gene silencing mechanism. Dicer (Dcr) cleaves homologous double-stranded RNA (dsRNA) into generate small guide RNAs; Argonaute (Ago) can then use the small guide RNAs to degrade the corresponding mRNA, or to reduce the gene expression. Gene knockdown is a fundamental approach to engineer more efficient microbial cell factories.

Figure 24A:
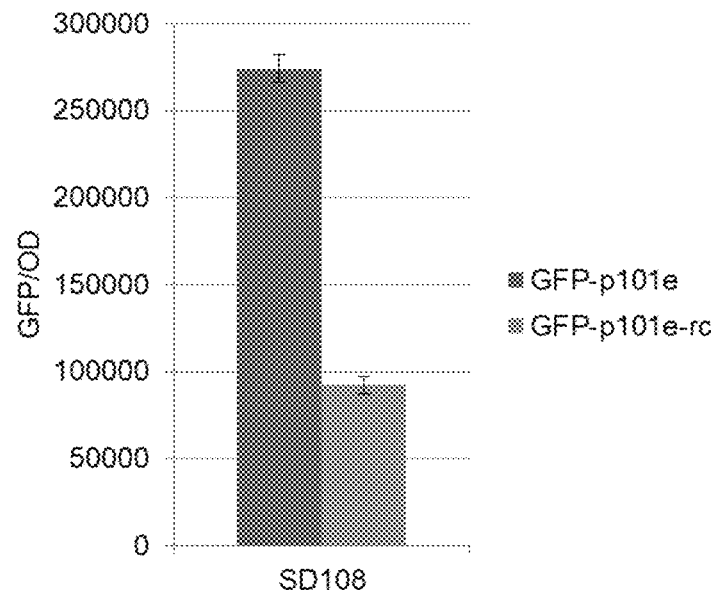
FIG. 24A discloses a graph depicting that the endogenous RNAi machinery is functional. GFP was integrated to the genome. Then, episomal plasmid for overexpression of full-length antisense of GFP was transformed into the GFP-harboring SD108 strain. Repression of GFP was achieved with efficiency of 67%.

We developed an RNA interference system to knock down genes of interest in *I. orientalis*. Based on BLAST analysis, *I. orientalis* may contain 1 endogenous Ago gene (g45) and 2 endogenous Dcr genes (g1046 and g2995). g1046 and g2995 are arbitrarily labeled as Dcr1 and Dcr2. To verify if the endogenous RNAi machinery is functional, GFP was integrated to the genome. Then, episomal plasmid for overexpression of full-length antisense of GFP was transformed into the GFP-harboring SD108 strain. Repression of GFP was achieved with efficiency of 67% (FIG. 24A).

Figure 24B:
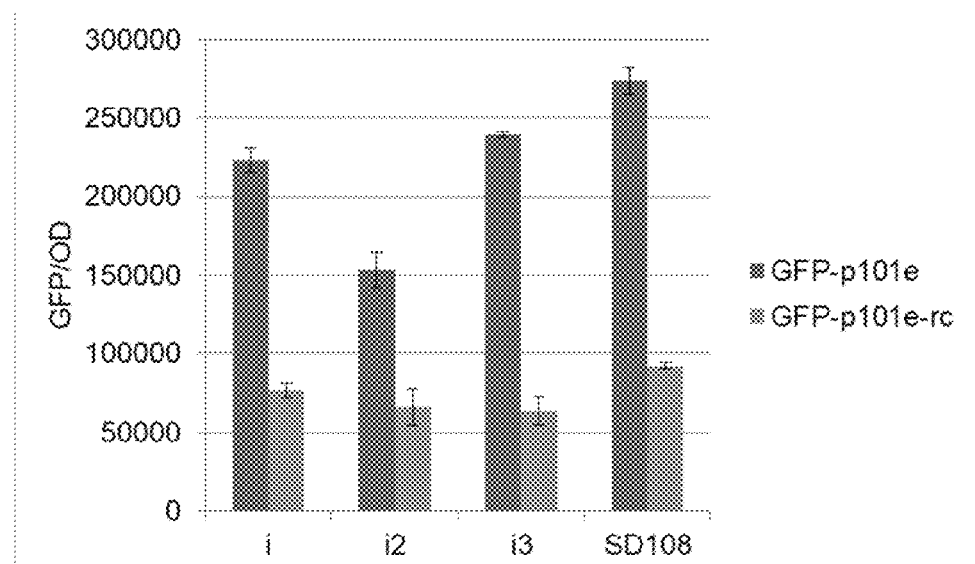
FIG. 24B discloses a graph depicting overexpression of the endogenous RNAi system further improving the knockdown efficiency. 3 different cassettes for overexpression, Ago and Dcr1 (strain i), Ago and Dcr2-lab (strain i2), and Ago and Dcr2-Wolfe (strain i3), were integrated to GFP-carrying SD108 genome. Dcr2 annotation done by Zhao lab is 123 bp shorter than Dcr2 annotation done by Wolfe lab. Overexpression of full-length antisense of GFP in strain i3 increased the GFP repression efficiency up to 73%.

We also checked if overexpression of the endogenous RNAi system could further improve the knockdown efficiency. We integrated to GFP-carrying SD108 genome 3 different cassettes for overexpression of Ago and Dcr1 (strain i), Ago and Dcr2-lab (strain i2), and Ago and Dcr2-Wolfe (strain i3). The Dcr2 annotation done by Zhao lab is 123 bp shorter than the Dcr2 annotation done by Wolfe lab. Overexpression of full-length antisense of GFP in strain i3 increased the GFP repression efficiency up to 73% (FIG. 24B).

Figure 24C:
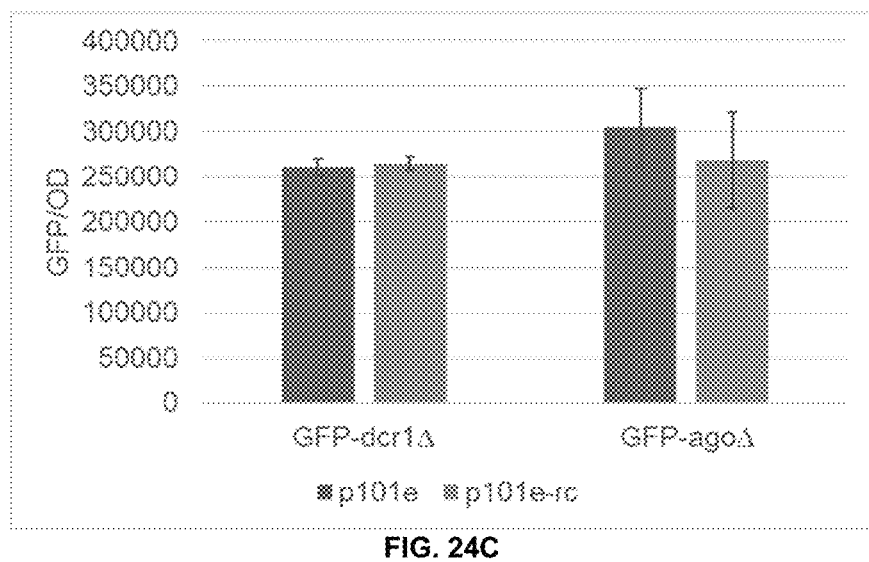
FIG. 24C discloses a graph depicting that endogenous Ago and Dcr genes are necessary for RNAi functionality. Ago and Dcr genes were deleted from GFP-carrying SD108 strain. Deletion of Dcr2 was not possible, which indicate Dcr2 might be an essential gene. GFP repression was not observed for deletion of Dcr1. On the other hand, GFP knockdown efficiency was reduced to 12% for Ago deletion. For strain GFP-dcr1Δ, small guide dsRNAs were not generated due to the knockout of Dcr1, and the intact Ago could not degrade the GFP. On the other hand, for strain GFP-agoΔ, the intact Dcr might cleave the dsRNA formed from GFP and antisense GFP, leading to partial degradation of GFP and a small GFP knockdown efficiency.

To verify that the endogenous Ago and Dcr genes are necessary for RNAi functionality, Ago and Dcr genes were deleted from GFP-carrying SD108 strain. Deletion of Dcr2 was not possible, which indicates Dcr2 might be an essential gene. GFP repression was not observed for deletion of Dcr1. On the other hand, GFP knockdown efficiency was reduced to 12% for Ago deletion. For strain GFP-dcr1Δ, small guide dsRNAs were not generated due to the knockout of Dcr1, and the intact Ago could not degrade the GFP. On the other hand, for strain GFP-agoΔ, the intact Dcr might cleave the dsRNA formed from GFP and antisense GFP, leading to partial degradation of GFP and a small GFP knockdown efficiency (FIG. 24C).

The results indicated *I. orientalis* contains an endogenous RNAi machinery.

All patents, patent applications, and other scientific or technical writings referred to anywhere herein are incorporated by reference herein in their entirety. The compositions and methods illustratively described herein suitably can be practiced in the absence of any element or elements, limitation or limitations that are specifically or not specifically disclosed herein. Thus, for example, in each instance herein any of the terms "comprising", "consisting essentially of", and "consisting of" may be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the claims. Thus, it should be understood that although the present compositions and methods have been specifically disclosed by embodiments, optional features, modifications and variations of the concepts herein disclosed may be resorted to by those skilled in the art, and that such modifications and variations are considered to be within the scope of the methods and compositions as defined by the description and the appended claims.

What is claimed is:

1. A vector comprising a polynucleotide comprising a centromere-like sequence (CEN-L) having 90% or more sequence identity to the sequence set forth in SEQ ID NO:74 or SEQ ID NO:163, wherein the polynucleotide is 50% or less the size of a naturally-occurring CEN polynucleotide, and wherein the vector is a plasmid, a phage, a cosmid, yeast artificial chromosome, yeast integrative plasmid, yeast replicative plasmid, shuttle vector, or a viral vector.

2. The vector of claim 1, further comprising a *Saccharomyces cerevisiae* autonomously replicating sequence (ScARS).

3. The vector of claim 2, wherein the ScARS is set forth in SEQ ID NO:73.

4. An expression cassette comprising:
(i) a guide RNA (gRNA) targeting a polynucleotide and binding a catalytically-active RNA-guided DNA endonuclease protein, wherein the gRNA is operably linked to an RNA polymerase (RNAP) III promoter;
(ii) a polynucleotide encoding a catalytically active RNA-guided DNA endonuclease protein, wherein the polynucleotide is operably linked to a promoter sequence and to a terminator sequence;
(iii) a *Saccharomyces cerevisiae* autonomously replicating sequence (ScARS); and (iv) a centromere-like sequence (CEN-L) having 90% or more sequence identity to the sequence as set forth in SEQ ID NO:74 or SEQ ID NO: 163, wherein the CEN-L sequence is 50% or less the size of a naturally-occurring CEN sequence.

5. A vector comprising the expression cassette of claim 4.

6. The vector of claim 5, wherein the vector is a plasmid or a viral vector.

7. A recombinant yeast comprising the vector of claim 5.

8. A method of altering the expression of one or more gene products in a yeast comprising transforming a yeast with the vector of claim 5, wherein expression of at least one gene product is increased, expression of at least one gene product is decreased, at least one polynucleotide or fragment thereof is deleted, or combinations thereof as compared to a yeast that has not been transformed with the vector.

9. The expression cassette of claim 4, wherein the promoter is g247, g5025, g853, g917, g3376, 92204, g3504, g3824, g43, g3767, g172, g973, or g4288.

10. The expression cassette of claim 4, wherein the terminator is g4288t, g697t, g1414t, g4282t, g2204t, g3767t, g5025t, g3824t, g527t, g4194t, g853t, g5125t, g3376t, or g3540t.

11. An expression cassette comprising:
(i) one or more polynucleotides encoding one or more proteins of interest, wherein the one or more polynucleotides are each operably linked to a promoter sequence and to a terminator sequence;
(ii) a *Saccharomyces cerevisiae* autonomously replicating sequence (ScARS); and
(iii) a centromere-like sequence (CEN-L) having 90% or more sequence identity to the sequence as set forth in SEQ ID NO:74 or SEQ ID NO: 163, wherein the CEN-L sequence is 50% or less the size of a naturally-occurring CEN polynucleotide.

12. A vector comprising the expression cassette of claim 11.

13. A system for targeted genome engineering comprising one or more vectors, each vector comprising:
(i) a guide RNA (gRNA) that binds a target polynucleotide and a catalytically-active RNA-guided DNA endonuclease protein;
(ii) a polynucleotide encoding a catalytically active RNA-guided DNA endonuclease protein that binds to a gRNA, generates a double-stranded nucleic acid break, and induces deletion of a target polynucleotide;
(iii) an RNA polymerase III promoter that induces capping a 5' end of a polynucleotide, and polyadenylation of a 3' end of the polynucleotide;
(iv) a *Saccharomyces cerevisiae* autonomously replicating sequence (ScARS);
(v) a centromere-like sequence (CEN-L) having 90% or more sequence identity to the sequence as set forth in SEQ ID NO:74 or SEQ ID NO: 163, wherein the CEN-L sequence is 50% or less the size of a naturally-occurring CEN sequence; or (vi) a polynucleotide encoding a protein of interest, operably linked to a promoter sequence and to a terminator sequence.

14. A system for targeted genome engineering of a yeast, the system comprising one or more vectors comprising:
(i) a first single guide RNA (sgRNA) that is capable of binding a target nucleic acid and binding a first nuclease-deficient RNA-guided DNA endonuclease protein;
(ii) a second sgRNA that is capable of binding a target nucleic acid and binding a second nuclease-deficient RNA-guided DNA endonuclease protein;
(iii) a third sgRNA that is capable of binding a target nucleic acid and binding a catalytically-active RNA-guided DNA endonuclease protein;
(iv) a polynucleotide encoding the first nuclease-deficient RNA-guided DNA endonuclease protein that binds to the first sgRNA and causes transcriptional activation;
(v) a polynucleotide encoding the second nuclease-deficient RNA-guided DNA endonuclease protein that binds to the second sgRNA and causes transcriptional interference;
(vi) a polynucleotide encoding the catalytically active RNA-guided DNA endonuclease protein that binds to the third sgRNA and causes a double-stranded nucleic acid break and causes gene deletion;
(vii) a *Saccharomyces cerevisiae* autonomously replicating sequence (ScARS); and
(viii) a centromere-like sequence (CEN-L) having 90% or more sequence identity to the sequence as set forth in SEQ ID NO:74 or SEQ ID NO: 163, wherein the CEN-L sequence is 50% or less the size of a naturally-occurring CEN sequence.

15. The system of claim 14, wherein components (i), (ii), (iii), (iv), (v), (vi), (vii), and (viii) are located on same or different vectors of the system.

16. The system of claim 14, wherein the first single guide RNA (sgRNA) is operably linked to an RNA polymerase (RNAP) III promoter.

17. The system of claim 14, wherein the first nuclease-deficient RNA-guided DNA endonuclease protein is functional only when bound to the first sgRNA.

18. The system of claim 14, wherein the second nuclease-deficient RNA-guided DNA endonuclease protein is functional only when bound to the second sgRNA.

19. The system of claim 14, wherein the catalytically active RNA-guided DNA endonuclease protein is functional only when bound to the third sgRNA.

20. A method of altering expression of gene products, the method comprising:
introducing into a yeast cell the system of claim 14, wherein the expression of at least one gene product is increased, the expression of at least one gene product is decreased, and the expression of at least one gene product is deleted relative to a yeast cell that has not been transformed with the system of claim 14.

* * * * *